United States Patent
Kuduk et al.

(10) Patent No.: US 10,987,359 B2
(45) Date of Patent: Apr. 27, 2021

(54) OXADIAZEPINONE DERIVATIVES AND METHODS OF TREATING HEPATITIS B INFECTIONS

(71) Applicant: Novira Therapeutics, Inc., Spring House, PA (US)

(72) Inventors: Scott Kuduk, Harleysville, PA (US); George D. Hartman, Lansdale, PA (US)

(73) Assignee: Novira Therapeutics, Inc., Spring House, PA (US)

(*) Notice: Subject to any disclaimer, the term of this patent is extended or adjusted under 35 U.S.C. 154(b) by 69 days.

(21) Appl. No.: 16/313,984

(22) PCT Filed: Jun. 29, 2017

(86) PCT No.: PCT/US2017/040130
§ 371 (c)(1),
(2) Date: Dec. 28, 2018

(87) PCT Pub. No.: WO2018/005881
PCT Pub. Date: Jan. 4, 2018

(65) Prior Publication Data
US 2020/0197408 A1 Jun. 25, 2020

Related U.S. Application Data

(60) Provisional application No. 62/511,565, filed on May 26, 2017, provisional application No. 62/356,487, filed on Jun. 29, 2016.

(51) Int. Cl.
| | | |
|---|---|---|
| *C07D 498/04* | (2006.01) | |
| *C07D 487/04* | (2006.01) | |
| *C07D 471/04* | (2006.01) | |
| *A61K 31/551* | (2006.01) | |
| *A61K 31/553* | (2006.01) | |
| *A61P 31/12* | (2006.01) | |
| *A61P 31/20* | (2006.01) | |
| *A61K 31/55* | (2006.01) | |
| *A61K 45/06* | (2006.01) | |
| *C07D 471/14* | (2006.01) | |
| *C07D 498/14* | (2006.01) | |

(52) U.S. Cl.
CPC ............ *A61K 31/553* (2013.01); *A61K 31/55* (2013.01); *A61K 45/06* (2013.01); *A61P 31/20* (2018.01); *C07D 471/14* (2013.01); *C07D 498/14* (2013.01)

(58) Field of Classification Search
CPC .. C07D 498/04; C07D 487/04; C07D 471/04; A61K 31/551; A61K 31/553; A61P 31/12
See application file for complete search history.

(56) References Cited

U.S. PATENT DOCUMENTS

| | | |
|---|---|---|
| 4,500,525 A | 2/1985 | Winters et al. |
| 7,531,531 B2 | 5/2009 | Fancelli et al. |
| 8,288,425 B2 | 10/2012 | Edwards et al. |
| 8,309,578 B2 | 11/2012 | Mantegani et al. |
| 9,351,965 B2 | 5/2016 | Shipps, Jr. et al. |

(Continued)

FOREIGN PATENT DOCUMENTS

| | | |
|---|---|---|
| EP | 0086422 A | 8/1983 |
| WO | 2002014314 A1 | 2/2002 |

(Continued)

OTHER PUBLICATIONS

Haiyong et al. (2015) "Recent Advance of the hepatitis B virus inhibitors: a medicinal chemistry overview," Future Medicinal Chemistry, 7 (5): 587-607.

(Continued)

*Primary Examiner* — Bruck Kifle
(74) *Attorney, Agent, or Firm* — Brian Trinque; Lathrop GPM LLP

(57) ABSTRACT

Provided herein are compounds of formula (IA) and (III) useful for the treatment of HBV infection in a subject in need thereof, pharmaceutical compositions thereof, and methods of inhibiting, suppressing, or preventing HBV infection in the subject.

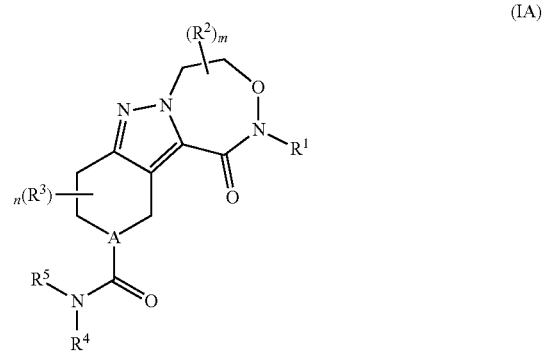

(IA)

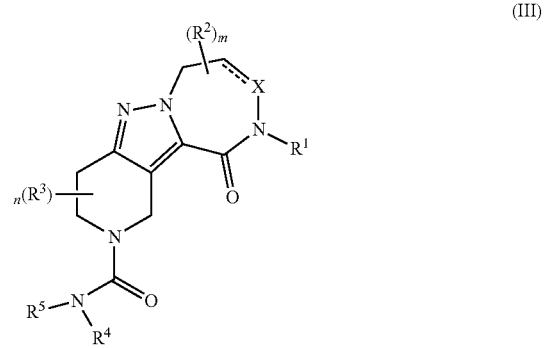

(III)

24 Claims, 1 Drawing Sheet

(56) References Cited

U.S. PATENT DOCUMENTS

| | | |
|---|---|---|
| 9,518,057 B2 | 12/2016 | Hartman et al. |
| 9,527,845 B2 | 12/2016 | Hartman et al. |
| 9,550,779 B2 | 1/2017 | Hartman et al. |
| 9,890,161 B2 | 2/2018 | Hartman et al. |
| 10,077,264 B2 | 9/2018 | Hartman et al. |
| 10,093,669 B2 | 10/2018 | Hartman et al. |
| 10,189,835 B2 | 1/2019 | Hartman et al. |
| 10,538,519 B2 | 1/2020 | Hartman et al. |
| 10,544,141 B2 | 1/2020 | Hartman et al. |
| 10,556,904 B2 | 2/2020 | Hartman et al. |
| 2015/0132258 A1 | 5/2015 | Hartman |
| 2020/0181142 A1 | 6/2020 | Hartman et al. |
| 2020/0181144 A1 | 6/2020 | Kuduk et al. |

FOREIGN PATENT DOCUMENTS

| | | |
|---|---|---|
| WO | 2003070236 A2 | 8/2003 |
| WO | 2004014374 A1 | 2/2004 |
| WO | 2008005511 A1 | 1/2008 |
| WO | 2012036997 A1 | 3/2012 |

OTHER PUBLICATIONS

Samala, G. et al. Eur. J. Med. Chem. 2013, 69, 356-364.

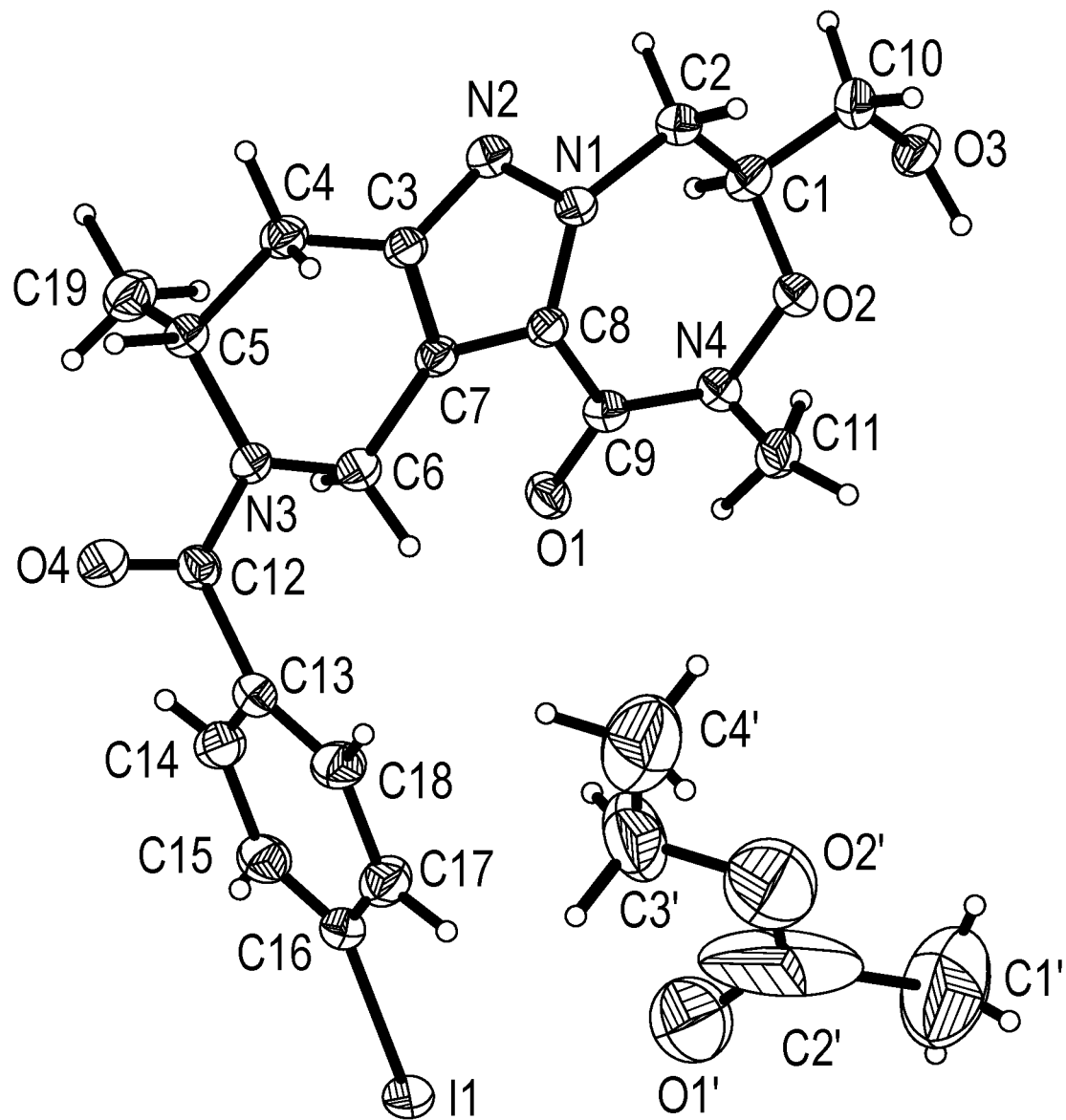

OXADIAZEPINONE DERIVATIVES AND METHODS OF TREATING HEPATITIS B INFECTIONS

RELATED APPLICATIONS

This application is a 35 U.S.C. § 371 filing of International Application No. PCT/US2017/040130, filed Jun. 29, 2017, which claims the benefit of U.S. provisional patent application No. 62/356,487, filed Jun. 29, 2016; and U.S. provisional patent application No. 62/511,565, filed May 26, 2017; the entire contents of each of which are incorporated herein by reference.

BACKGROUND

Chronic hepatitis B virus (HBV) infection is a significant global health problem, affecting over 5% of the world population (over 350 million people worldwide and 1.25 million individuals in the U.S.).

Despite the availability of a prophylactic HBV vaccine, the burden of chronic HBV infection continues to be a significant unmet worldwide medical problem, due to suboptimal treatment options and sustained rates of new infections in most parts of the developing world. Current treatments do not provide a cure and are limited to only two classes of agents (interferon alpha and nucleoside analogues/inhibitors of the viral polymerase); drug resistance, low efficacy, and tolerability issues limit their impact. The low cure rates of HBV are attributed at least in part to the fact that complete suppression of virus production is difficult to achieve with a single antiviral agent. However, persistent suppression of HBV DNA slows liver disease progression and helps to prevent hepatocellular carcinoma. Current therapy goals for HBV-infected patients are directed to reducing serum HBV DNA to low or undetectable levels, and to ultimately reducing or preventing the development of cirrhosis and hepatocellular carcinoma.

The HBV capsid protein plays essential functions during the viral life cycle. HBV capsid/core proteins form metastable viral particles or protein shells that protect the viral genome during intercellular passage, and also play a central role in viral replication processes, including genome encapsidation, genome replication, and virion morphogenesis and egress. Capsid structures also respond to environmental cues to allow un-coating after viral entry. Consistently, the appropriate timing of capsid assembly and disassembly, the appropriate capsid stability and the function of core protein have been found to be critical for viral infectivity.

There is a need in the art for therapeutic agents that can increase the suppression of virus production and that can treat, ameliorate, or prevent HBV infection. Administration of such therapeutic agents to an HBV infected patient, either as monotherapy or in combination with other HBV treatments or ancillary treatments, will lead to significantly reduced virus burden, improved prognosis, diminished progression of the disease and enhanced seroconversion rates.

SUMMARY

Provided herein are compounds useful for the treatment of HBV infection in a subject in need thereof. Thus, in an aspect, provided herein is a compound of Formula Ia:

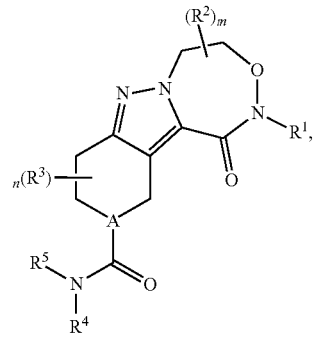

or a pharmaceutically acceptable salt thereof, wherein

A is N or C(H);

$R^1$ is H, $C_1$-$C_6$-alkyl, $C_1$-$C_6$-alkenyl, or $C_1$-$C_6$-alkyl-OH;

$R^2$ is, at each occurrence, independently selected from —OH, halo, $C_1$-$C_6$-alkyl, $C_1$-$C_6$-alkylene, $C_0$-$C_6$-alkyl-$C_3$-$C_6$-cycloalkyl, $C_0$-$C_6$-alkyl-$C_2$-$C_6$-heterocycloalkyl, $C_0$-$C_6$-alkyl-$OR^6$, $C_0$-$C_6$-alkyl-$N(R^7)_2$, $C_0$-$C_6$-alkyl-$S(O)R^8$, $C_0$-$C_6$-alkyl-$S(O)_2R^8$, $C_0$-$C_6$-alkyl-$C(O)OR^9$, $C_0$-$C_6$-alkyl-$OC(O)R^9$, $C_0$-$C_6$-alkyl-$OC(O)OR^9$, $C_0$-$C_6$-alkyl-$OC(O)N(R^7)_2$, and $C_0$-$C_6$-alkyl-$C(O)N(R^7)_2$, wherein alkyl, cycloalkyl, and heterocycloalkyl are optionally substituted with 1, 2, or 3 groups, each independently selected from —OH and halo;

$R^3$ is, at each occurrence, independently selected from —OH, halo, $C_1$-$C_6$-alkyl, $C_1$-$C_6$-haloalkyl, —O—$C_1$-$C_6$-alkyl, and $C_1$-$C_6$-alkyl-OH;

$R^4$ is selected from $(CR^aR^b)_p$—$C_1$-$C_9$-heteroaryl, $(CR^aR^b)_p$—$C_6$-$C_{12}$-aryl, $(CR^aR^b)_p$—$C_3$-$C_7$-cycloalkyl, and $(CR^aR^b)_p$—$C_2$-$C_6$-heterocycloalkyl, wherein heteroaryl, aryl, cycloalkyl, and heterocycloalkyl are optionally substituted with 1, 2, 3, or 4 groups, each independently selected from —OH, halo, —CN, —$SF_5$, $C_1$-$C_6$-alkyl, $C_1$-$C_6$-haloalkyl, —O—$C_1$-$C_6$-alkyl, and $C_1$-$C_6$-alkyl-OH;

$R^5$ is selected from H, $C_1$-$C_6$-alkyl, and $C_1$-$C_6$-alkyl-OH;

$R^6$ is selected from H, $C_1$-$C_6$-alkyl, $C_1$-$C_6$-haloalkyl, $C_1$-$C_6$-alkenyl, and $C_0$-$C_6$-alkyl-$C_3$-$C_6$-cycloalkyl;

$R^7$ is selected from H, $C_1$-$C_6$-alkyl, $C_1$-$C_6$-haloalkyl, $C_1$-$C_6$-alkyl-$OR^{10}$, —$C(O)C_1$-$C_6$-alkyl, —$C(O)C_1$-$C_6$-haloalkyl, —$C(O)C_1$-$C_6$-alkyl-$OR^{10}$, —$C(O)C_1$-$C_6$-alkyl-CN, —$C(O)C_3$-$C_7$-cycloalkyl, —$C(O)O$—$C_1$-$C_6$-alkyl, —$C(O)O$—$C_1$-$C_6$-haloalkyl, —$C(O)O$—$C_3$-$C_7$-cycloalkyl, —$C(O)N(R^{10})_2$, —$S(O)_2C_1$-$C_6$-alkyl, —$S(O)_2C_1$-$C_6$-haloalkyl and —$S(O)_2C_3$-$C_7$-cycloalkyl;

or wherein two $R^7$ groups together with the N to which they are attached form a $C_2$-$C_6$ heterocycle, wherein the $C_2$-$C_6$ heterocycle is further independently and optionally substituted with 1 or 2 oxo or halogen substituents;

$R^8$ is selected from H and $C_1$-$C_6$-alkyl;

$R^9$ is selected from H and $C_1$-$C_6$-alkyl;

$R^{10}$ is selected from H and $C_1$-$C_6$-alkyl;

$R^a$ is, at each occurrence, independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH;

$R^b$ is, at each occurrence, independently selected from H and $C_1$-$C_6$-alkyl;

m is 0, 1, 2, 3, or 4;

n is 0, 1, 2, 3, or 4; and p is 0, 1, 2, 3, or 4.

In another aspect, provided herein is a compound of Formula I:

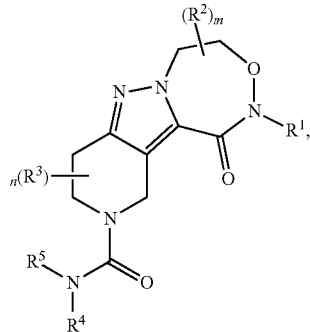

or a pharmaceutically acceptable salt thereof, wherein $R^1$ is H, $C_1$-$C_6$-alkyl, $C_1$-$C_6$-alkenyl, or $C_1$-$C_6$-alkyl-OH;

$R^2$ is, at each occurrence, independently selected from —OH, halo, $C_1$-$C_6$-alkyl, $C_1$-$C_6$-alkylene, $C_0$-$C_6$-alkyl-$C_3$-$C_6$-cycloalkyl, $C_0$-$C_6$-alkyl-$C_2$-$C_6$-heterocycloalkyl, $C_0$-$C_6$-alkyl-$OR^6$, $C_0$-$C_6$-alkyl-$N(R^7)_2$, $C_0$-$C_6$-alkyl-$SR^8$, $C_0$-$C_6$-alkyl-$S(O)R^8$, $C_0$-$C_6$-alkyl-$S(O)_2R^8$, $C_0$-$C_6$-alkyl-$C(O)OR^9$, $C_0$-$C_6$-alkyl-$OC(O)R^9$, $C_0$-$C_6$-alkyl-$OC(O)OR^9$, $C_0$-$C_6$-alkyl-$OC(O)N(R^7)_2$, and $C_0$-$C_6$-alkyl-$C(O)N(R^7)_2$, wherein alkyl, cycloalkyl, and heterocycloalkyl are optionally substituted with 1, 2, or 3 groups, each independently selected from —OH and halo;

$R^3$ is, at each occurrence, independently selected from —OH, halo, $C_1$-$C_6$-alkyl, $C_1$-$C_6$-haloalkyl, —O—$C_1$-$C_6$-alkyl, and $C_1$-$C_6$-alkyl-OH;

$R^4$ is selected from $(CR^aR^b)_p$—$C_1$-$C_9$-heteroaryl, $(CR^aR^b)_p$—$C_6$-$C_{12}$-aryl, $(CR^aR^b)_p$—$C_3$-$C_7$-cycloalkyl, and $(CR^aR^b)_p$—$C_2$-$C_6$-heterocycloalkyl, wherein heteroaryl, aryl, cycloalkyl, and heterocycloalkyl are optionally substituted with 1, 2, 3, or 4 groups, each independently selected from —OH, halo, —CN, —$SF_5$, $C_1$-$C_6$-alkyl, $C_1$-$C_6$-haloalkyl, —O—$C_1$-$C_6$-alkyl, and $C_1$-$C_6$-alkyl-OH;

$R^5$ is selected from H, $C_1$-$C_6$-alkyl, and $C_1$-$C_6$-alkyl-OH;

$R^6$ is selected from H, $C_1$-$C_6$-alkyl, $C_1$-$C_6$-haloalkyl, $C_1$-$C_6$-alkenyl, and $C_0$-$C_6$-alkyl-$C_3$-$C_6$-cycloalkyl;

$R^7$ is selected from H, $C_1$-$C_6$-alkyl, and $C_1$-$C_6$-alkyl-OH;

$R^8$ is selected from H and $C_1$-$C_6$-alkyl;

$R^9$ is selected from H and $C_1$-$C_6$-alkyl;

$R^a$ is, at each occurrence, independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH;

$R^b$ is, at each occurrence, independently selected from H and $C_1$-$C_6$-alkyl;

m is 0, 1, 2, 3, or 4;

n is 0, 1, 2, 3, or 4; and p is 0, 1, 2, 3, or 4.

In an embodiment, the compound of Formula Ia has the structure of Formula II:

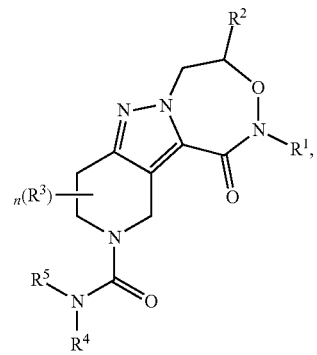

or a pharmaceutically acceptable salt thereof.

In another aspect, provided herein is a compound of Formula III:

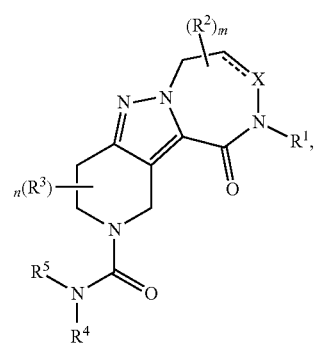

or a pharmaceutically acceptable salt thereof, wherein

------ is a single or double bond;

X is N—$R^c$;

$R^1$ is H, $C_1$-$C_6$-alkyl, $C_1$-$C_6$-alkenyl, or $C_1$-$C_6$-alkyl-OH;

$R^2$ is, at each occurrence, independently selected from —OH, halo, $C_1$-$C_6$-alkyl, $C_1$-$C_6$-alkylene, $C_0$-$C_6$-alkyl-$C_3$-$C_6$-cycloalkyl, $C_0$-$C_6$-alkyl-$C_2$-$C_6$-heterocycloalkyl, $C_0$-$C_6$-alkyl-$OR^6$, $C_0$-$C_6$-alkyl-$N(R^7)_2$, $C_0$-$C_6$-alkyl-$SR^8$, $C_0$-$C_6$-alkyl-$S(O)R^8$, $C_0$-$C_6$-alkyl-$S(O)_2R^8$, $C_0$-$C_6$-alkyl-$C(O)OR^9$, $C_0$-$C_6$-alkyl-$OC(O)R^9$, $C_0$-$C_6$-alkyl-$OC(O)OR^9$, $C_0$-$C_6$-alkyl-$OC(O)N(R^7)_2$, and $C_0$-$C_6$-alkyl-$C(O)N(R^7)_2$, wherein alkyl, cycloalkyl, and heterocycloalkyl are optionally substituted with 1, 2, or 3 groups, each independently selected from —OH and halo;

$R^3$ is, at each occurrence, independently selected from —OH, halo, $C_1$-$C_6$-alkyl, $C_1$-$C_6$-haloalkyl, —O—$C_1$-$C_6$-alkyl, and $C_1$-$C_6$-alkyl-OH;

$R^4$ is selected from $(CR^aR^b)_p$—$C_1$-$C_9$-heteroaryl, $(CR^aR^b)_p$—$C_6$-$C_{12}$-aryl, $(CR^aR^b)_p$—$C_3$-$C_7$-cycloalkyl, and $(CR^aR^b)_p$—$C_2$-$C_6$-heterocycloalkyl, wherein heteroaryl, aryl, cycloalkyl, and heterocycloalkyl are optionally substituted with 1, 2, 3, or 4 groups, each independently selected from —OH, halo, —CN, —$SF_5$, $C_1$-$C_6$-alkyl, $C_1$-$C_6$-haloalkyl, —O—$C_1$-$C_6$-alkyl, and $C_1$-$C_6$-alkyl-OH;

$R^5$ is selected from H, $C_1$-$C_6$-alkyl, and $C_1$-$C_6$-alkyl-OH;

$R^6$ is selected from H, $C_1$-$C_6$-alkyl, $C_1$-$C_6$-haloalkyl, $C_1$-$C_6$-alkenyl, and $C_0$-$C_6$-alkyl-$C_3$-$C_6$-cycloalkyl;

$R^7$ is selected from H, $C_1$-$C_6$-alkyl, $C_1$-$C_6$-haloalkyl, $C_1$-$C_6$-alkyl-$OR^{10}$, —$C(O)C_1$-$C_6$-alkyl, —$C(O)C_1$-$C_6$-haloalkyl, —$C(O)C_1$-$C_6$-alkyl-$OR^{10}$, —$C(O)C_1$-$C_6$-alkyl-CN, —C(O)C$_3$-C$_7$-cycloalkyl, —C(O)O—C$_1$-C$_6$-alkyl, —C(O)O—C$_1$-C$_6$-haloalkyl, —C(O)O—C$_3$-C$_7$-cycloalkyl, —C(O)N(R$^{10}$)$_2$, —S(O)$_2$C$_1$-C$_6$-alkyl, —S(O)$_2$C$_1$-C$_6$-haloalkyl and —S(O)$_2$C$_3$-C$_7$-cycloalkyl;

or wherein two R$^7$ groups together with the N to which they are attached form a C$_2$-C$_6$ heterocycle, wherein the C$_2$-C$_6$ heterocycle is further independently and optionally substituted with 1 or 2 oxo or halogen substituents;

R$^8$ is selected from H and C$_1$-C$_6$-alkyl;
R$^9$ is selected from H and C$_1$-C$_6$-alkyl;
R$^{10}$ is selected from H and C$_1$-C$_6$-alkyl;
R$^a$ is, at each occurrence, independently selected from H, —OH, halo, C$_1$-C$_6$-alkyl, C$_1$-C$_6$-haloalkyl, —O—C$_1$-C$_6$-alkyl, and C$_1$-C$_6$-alkyl-OH;
R$^b$ is, at each occurrence, independently selected from H and C$_1$-C$_6$-alkyl;
R$^c$ is absent, H, C$_1$-C$_6$-alkyl, C$_1$-C$_6$-alkenyl, C$_1$-C$_6$-haloalkyl, or C$_1$-C$_6$-alkyl-OH;
m is 0, 1, 2, 3, or 4;
n is 0, 1, 2, 3, or 4; and
p is 0, 1, 2, 3, or 4.

In another aspect, provided herein is a pharmaceutical composition comprising at least one compound of Formula Ia, Formula I, Formula II, or Formula III, or a pharmaceutically acceptable salt thereof, together with a pharmaceutically acceptable carrier.

In another aspect, provided herein is a pharmaceutical composition comprising at least one disclosed compound, together with a pharmaceutically acceptable carrier. In another aspect, provided herein is a method of treating an HBV infection in an individual in need thereof, comprising administering to the individual a therapeutically effective amount of a compound of Formula Ia, Formula I, Formula II, or Formula III, or a pharmaceutically acceptable salt thereof.

In another aspect, provided herein is a method of inhibiting or reducing the formation or presence of HBV DNA-containing particles or HBV RNA-containing particles in an individual in need thereof, comprising administering to the individual a therapeutically effective amount of a compound of Formula Ia, Formula I, Formula II, or Formula III, or a pharmaceutically acceptable salt thereof.

In an embodiment, any of the methods provided herein can further comprising administering to the individual at least one additional therapeutic agent selected from the group consisting of an HBV polymerase inhibitor, immunomodulatory agents, interferon, viral entry inhibitor, viral maturation inhibitor, capsid assembly modulator, reverse transcriptase inhibitor, a cyclophilin/TNF inhibitor, a TLR-agonist, an HBV vaccine, and any combination thereof.

BRIEF DESCRIPTION OF THE DRAWINGS

FIG. 1 shows the X-ray crystal structure of the iodobenzoic acid analogue of Intermediate 18, also referred to as compound 215.

DETAILED DESCRIPTION

Provided herein are compounds, e.g., the compounds of Formula Ia, Formula I, Formula II, or Formula III, or pharmaceutically acceptable salts thereof, that are useful in the treatment and prevention of HBV infection in subject.

Without being bound to any particular mechanism of action, these compounds are believed to modulate or disrupt HBV assembly and other HBV core protein functions necessary for HBV replication or the generation of infectious particles. In addition, or alternatively, the compounds may disrupt HBV capsid assembly to induce production of defective viral particles with greatly reduced infectivity or replication capacity. In other words, the compounds provided herein may act as capsid assembly modulators by modulating (e.g., accelerating, delaying, inhibiting, disrupting or reducing) normal viral capsid assembly or disassembly, binding capsids, and/or altering metabolism of cellular polyproteins and precursors. The modulation may occur when the capsid protein is mature, or during viral infectivity. The disclosed compounds can be used in methods of modulating the activity or properties of HBV cccDNA, or the generation or release of HBV RNA particles from within an infected cell.

In one embodiment, the compounds described herein are suitable for monotherapy and are effective against natural or native HBV strains and against HBV strains resistant to currently known drugs. In another embodiment, the compounds described herein are suitable for use in combination therapy.

Definitions

Listed below are definitions of various terms used to describe this invention. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e. to at least one) of the grammatical object of the article. By way of example, "an element" means one element or more than one element. Furthermore, use of the term "including" as well as other forms, such as "include", "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, including ±5%, ±1%, and ±0.1% from the specified value, as such variations are appropriate to perform the disclosed methods.

As used herein, the term "capsid assembly modulator" refers to a compound that disrupts or accelerates or inhibits or hinders or delays or reduces or modifies normal capsid assembly (e.g., during maturation) or normal capsid disassembly (e.g., during infectivity) or perturbs capsid stability, thereby inducing aberrant capsid morphology and function. In one embodiment, a capsid assembly modulator accelerates capsid assembly or disassembly, thereby inducing aberrant capsid morphology. In another embodiment, a capsid assembly modulator interacts (e.g. binds at an active site, binds at an allosteric site, modifies or hinders folding and the like) with the major capsid assembly protein (CA), thereby disrupting capsid assembly or disassembly. In yet another embodiment, a capsid assembly modulator causes a perturbation in structure or function of CA (e.g., ability of CA to assemble, disassemble, bind to a substrate, fold into a suitable conformation, or the like), which attenuates viral infectivity or is lethal to the virus.

As used herein, the term "treatment" or "treating" is defined as the application or administration of a therapeutic agent, i.e., a disclosed compound (alone or in combination with another pharmaceutical agent), to a patient, or application or administration of a therapeutic agent to an isolated tissue or cell line from a patient (e.g., for diagnosis or ex vivo applications), who has an HBV infection, a symptom of HBV infection or the potential to develop an HBV infection, with the purpose to cure, heal, alleviate, relieve, alter, remedy, ameliorate, improve or affect the HBV infection, the symptoms of HBV infection, or the potential to develop an HBV infection. Such treatments may be specifically tailored or modified, based on knowledge obtained from the field of pharmacogenomics.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "patient," "individual" or "subject" refers to a human or a non-human mammal. Non-human mammals include, for example, livestock and pets, such as ovine, bovine, porcine, canine, feline and murine mammals. Preferably, the patient, subject, or individual is human.

As used herein, the terms "effective amount," "pharmaceutically effective amount," and "therapeutically effective amount" refer to a nontoxic but sufficient amount of an agent to provide the desired biological result. That result may be reduction or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary, and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference. As used herein, the term "alkyl," by itself or as part of another substituent means, unless otherwise stated, a straight or branched chain hydrocarbon having the number of carbon atoms designated (i.e., $C_0$-$C_6$-alkyl means null or an alkyl having one to six carbon atoms) and includes straight and branched chains. Examples include methyl, ethyl, propyl, isopropyl, butyl, isobutyl, tert-butyl, pentyl, neopentyl, and hexyl. Other examples of $C_1$-$C_6$-alkyl include ethyl, methyl, isopropyl, isobutyl, n-pentyl, and n-hexyl.

As used herein, the term "alkenyl," denotes a monovalent group derived from a hydrocarbon moiety containing at least two carbon atoms and at least one carbon-carbon double bond. The double bond may or may not be the point of attachment to another group. Alkenyl groups (e.g., $C_2$-$C_8$- alkenyl) include, but are not limited to, for example, ethenyl, propenyl, prop-1-en-2-yl, butenyl, 1-methyl-2-buten-1-yl, heptenyl, octenyl and the like.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "haloalkyl" refers to alkl radicals wherein any one or more of the alkyl carbon atoms is substituted with halo as defined above. Haloalkyl embraces monohaloalkyl, dihaloalkyl, and polyhaloalkyl radicals. The term "haloalkyl" includes, but is not limited to, fluoromethyl, difluoromethyl, trifluoromethyl, chloromethyl, dichloromethyl, trichloromethyl, and pentafluoroethyl.

As used herein, the term "cycloalkyl" refers to a mono cyclic or polycyclic non-aromatic radical, wherein each of the atoms forming the ring (i.e., skeletal atoms) is a carbon atom. In one embodiment, the cycloalkyl group is saturated or partially unsaturated. In another embodiment, the cycloalkyl group is fused with an aromatic ring. Cycloalkyl groups include groups having 3 to 10 ring atoms ($C_3$-$C_{10}$-cycloalkyl), groups having 3 to 8 ring atoms ($C_3$-$C_8$-cycloalkyl), groups having 3 to 7 ring atoms ($C_3$-$C_7$-cycloalkyl), and groups having 3 to 6 ring atoms ($C_3$-$C_6$-cycloalkyl). Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene. Polycyclic cycloalkyls include adamantine and norbornane. The term cycloalkyl includes unsaturated nonaromatic cyclic groups, which contain at least one carbon carbon double bond or one carbon carbon triple bond.

As used herein, the term "heterocycloalkyl" or "heterocyclyl" refers to a heteroalicyclic group containing one to four ring heteroatoms each selected from O, S, and N. In one embodiment, each heterocyclyl group has from 3 to 10 atoms in its ring system, with the proviso that the ring of said group does not contain two adjacent O or S atoms. Heterocyclyl substituents may be alternatively defined by the number of carbon atoms, e.g., $C_2$-$C_8$-heterocyclyl indicates the number of carbon atoms contained in the heterocyclic group without including the number of heteroatoms. For example, a $C_2$-$C_8$-heterocyclyl will include an additional one to four heteroatoms. Preferably, the heterocyclyl group has less than three heteroatoms. More preferably, the heterocyclyl group has one to two heteroatoms. In another embodiment, the heterocycloalkyl group is fused with an aromatic ring. In one embodiment, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure.

An example of a 3-membered heterocyclyl group includes, and is not limited to, aziridine. Examples of 4-membered heterocycloalkyl groups include, and are not limited to, azetidine and a beta lactam. Examples of 5-membered heterocyclyl groups include, and are not limited to, pyrrolidine, oxazolidine and thiazolidinedione. Examples of 6-membered heterocycloalkyl groups include, and are not limited to, piperidine, morpholine, and piperazine.

Other non-limiting examples of heterocyclyl groups include monocyclic groups such as aziridine, oxirane, thiirane, azetidine, oxetane, thietane, pyrrolidine, pyrroline, pyrazolidine, imidazoline, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

As used herein, the term "aromatic" refers to a carbocycle or heterocycle with one or more polyunsaturated rings and having aromatic character, i.e., having (4n+2) delocalized π (pi) electrons, where n is an integer.

As used herein, the term "aryl," employed alone or in combination with other terms, means, unless otherwise stated, a carbocyclic aromatic system containing one or more rings (typically one, two, or three rings), wherein such rings may be attached together in a pendent manner, such as a biphenyl, or may be fused, such as naphthalene. Examples of aryl groups include phenyl, anthracyl, and naphthyl. Preferred examples are phenyl (e.g., $C_6$-aryl) and biphenyl (e.g., $C_{12}$-aryl). In some embodiments, aryl groups have from six to sixteen carbon atoms. In some embodiments, aryl groups have from six to twelve carbon atoms (e.g., $C_6$-$C_{12}$-aryl). In some embodiments, aryl groups have six carbon atoms (e.g., $C_6$-aryl).

As used herein, the term "heteroaryl" or "heteroaromatic" refers to a heterocycle having aromatic character. Heteroaryl substituents may be defined by the number of carbon atoms, e.g., $C_1$-$C_9$-heteroaryl indicates the number of carbon atoms contained in the heteroaryl group without including the number of heteroatoms. For example, a $C_1$-$C_9$-heteroaryl will include an additional one to four heteroatoms. Preferably, the heteroaryl group has less than three heteroatoms. More preferably, the heteroaryl group has one to two heteroatoms. A polycyclic heteroaryl may include one or more rings that are partially saturated. Non-limiting examples of heteroaryls include pyridyl, pyrazinyl, pyrimidinyl (including, e.g., 2- and 4-pyrimidinyl), pyridazinyl, thienyl, furyl, pyrrolyl (including, e.g., 2-pyrrolyl), imidazolyl, thiazolyl, oxazolyl, pyrazolyl (including, e.g., 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Non-limiting examples of polycyclic heterocycles and heteroaryls include indolyl (including, e.g., 3-, 4-, 5-, 6- and 7-indolyl), indolinyl, quinolyl, tetrahydroquinolyl, isoquinolyl (including, e.g., 1- and 5-isoquinolyl), 1,2,3,4-tetrahydroisoquinolyl, cinnolinyl, quinoxalinyl (including, e.g., 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (including, e.g., 3-, 4-, 5-, 6- and 7-benzofuryl), 2,3-dihydrobenzofuryl, 1,2-benzisoxazolyl, benzothienyl (including, e.g., 3-, 4-, 5-, 6-, and 7-benzothienyl), benzoxazolyl, benzothiazolyl (including, e.g., 2-benzothiazolyl and 5-benzothiazolyl), purinyl, benzimidazolyl (including, e.g., 2-benzimidazolyl), benzotriazolyl, thioxanthinyl, carbazolyl, carbolinyl, acridinyl, pyrrolizidinyl, and quinolizidinyl.

As used herein, the term "substituted" means that an atom or group of atoms has replaced hydrogen as the substituent attached to another group.

As used herein, the terminology "selected from . . . " (e.g., "$R^4$ is selected from A, B and C") is understood to be equivalent to the terminology "selected from the group consisting of . . . " (e.g., "$R^4$ is selected from the group consisting of A, B and C").

Compounds

Provided herein are compounds having the structure of Formula Ia:

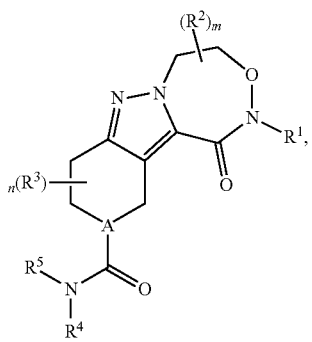

or a pharmaceutically acceptable salt thereof.

A may be N or C(H). In embodiments, A is N. In embodiments, A is C(H).

$R^1$ may be H, $C_1$-$C_6$-alkyl, $C_1$-$C_6$-alkenyl, or $C_1$-$C_6$-alkyl-OH. In embodiments, $R^1$ is H. In embodiments, $R^1$ is $C_1$-$C_6$-alkyl. In embodiments, $R^1$ is $C_1$-$C_6$-alkenyl. In embodiments, $R^1$ is $C_1$-$C_6$-alkyl-OH.

In embodiments, there may be 0, 1, 2, 3, or 4 $R^2$ substituents: m is 0, 1, 2, 3, or 4. Each $R^2$ may be independently selected from —OH, halo, $C_1$-$C_6$-alkyl, $C_1$-$C_6$-alkylene, $C_0$-$C_6$-alkyl-$C_3$-$C_6$-cycloalkyl, $C_0$-$C_6$-alkyl-$C_2$-$C_6$-heterocycloalkyl, $C_0$-$C_6$-alkyl-$OR^6$, $C_0$-$C_6$-alkyl-$N(R^7)_2$, $C_0$-$C_6$-alkyl-$S(O)R^8$, $C_0$-$C_6$-alkyl-$S(O)_2R^8$, $C_0$-$C_6$-alkyl-C(O)$OR^9$, $C_0$-$C_6$-alkyl-OC(O)$R^9$, $C_0$-$C_6$-alkyl-OC(O)$OR^9$, $C_0$-$C_6$-alkyl-OC(O)$N(R^7)_2$, or $C_0$-$C_6$-alkyl-C(O)$N(R^7)_2$. In certain embodiments, m is 0 and there is no $R^2$ substitution. In certain embodiments, m is 1 and there is one $R^2$ substitution. In certain embodiments, m is 2 and there are two $R^2$ substitutions. In certain embodiments, m is 3 and there are three $R^2$ substitutions. In certain embodiments, m is 4 and there are four $R^2$ substitutions. In embodiments, there may be 0, 1, 2, 3, or 4 $R^3$ substituents: n is 0, 1, 2, 3, or 4. In certain embodiments, n is 0 and there is no $R^3$ substitution. In certain embodiments, n is 1 and there is one $R^3$ substitution. In certain embodiments, n is 2 and there are two $R^3$ substitutions. In certain embodiments, n is 3 and there are three $R^3$ substitutions. In certain embodiments, n is 4 and there are four $R^3$ substitutions.

In certain embodiments, $R^2$ may be $C_1$-$C_6$-alkyl optionally substituted with 1, 2, or 3 halo groups. In certain embodiments, $R^2$ may be $C_0$-$C_6$-alkyl-$OR^6$, wherein $R^6$ is $C_1$-$C_6$-haloalkyl. In certain embodiments, $R^2$ may be $(CH_2)_{1-2}$—O—$C_1$-$C_3$-alkyl, wherein $C_1$-$C_3$-alkyl is optionally substituted with 1, 2, or 3 halo groups. In certain embodiments, m is 1 or 2.

Each $R^3$ may be independently selected from —OH, halo, $C_1$-$C_6$-alkyl, $C_1$-$C_6$-haloalkyl, —O—$C_1$-$C_6$-alkyl, and $C_1$-$C_6$-alkyl-OH. In certain embodiments, at least one $R^3$ is —OH. In certain embodiments, at least one $R^3$ is halo. In certain embodiments, at least one $R^3$ is $C_1$-$C_6$-alkyl. In certain embodiments, at least one $R^3$ is $C_1$-$C_6$-haloalkyl. In certain embodiments, at least one $R^3$ is —O—$C_1$-$C_6$-alkyl. In certain embodiments, at least one $R^3$ is $C_1$-$C_6$-alkyl-OH.

$R^4$ is selected from $(CR^aR^b)_p$—$C_1$-$C_9$-heteroaryl, $(CR^aR^b)_p$—$C_6$-$C_{12}$-aryl, $(CR^aR^b)_p$—$C_3$-$C_7$-cycloalkyl, and $(CR^aR^b)_p$—$C_2$-$C_6$-heterocycloalkyl, wherein heteroaryl, aryl, cycloalkyl, and heterocycloalkyl are optionally substituted with 1, 2, 3, or 4 groups, each independently selected from —OH, halo, —CN, —$SF_5$, $C_1$-$C_6$-alkyl, $C_1$-$C_6$-haloalkyl, —O—$C_1$-$C_6$-alkyl, and $C_1$-$C_6$-alkyl-OH. In certain embodiments, $R^4$ is $(CR^aR^b)_p$—$C_1$-$C_9$-heteroaryl optionally substituted with 1, 2, 3, or 4 groups, each independently selected from —OH, halo, —CN, —$SF_5$, $C_1$-$C_6$-alkyl, $C_1$-$C_6$-haloalkyl, —O—$C_1$-$C_6$-alkyl, and $C_1$-$C_6$-alkyl-OH. In certain embodiments, $R^4$ is $(CR^aR^b)_p$—$C_6$-$C_{12}$-aryl optionally substituted with 1, 2, 3, or 4 groups, each independently selected from —OH, halo, —CN, —$SF_5$, $C_1$-$C_6$-alkyl, $C_1$-$C_6$-haloalkyl, —O—$C_1$-$C_6$-alkyl, and $C_1$-$C_6$-alkyl-OH. In certain embodiments, $R^4$ is $(CR^aR^b)_p$—$C_3$-$C_7$-cycloalkyl optionally substituted with 1, 2, 3, or 4 groups, each independently selected from —OH, halo, —CN, —$SF_5$, $C_1$-$C_6$-alkyl, $C_1$-$C_6$-haloalkyl, —O—$C_1$-$C_6$-alkyl, and $C_1$-$C_6$-alkyl-OH. In certain embodiments, $R^4$ is $(CR^aR^b)_p$—$C_2$-$C_6$-heterocycloalkyl optionally substituted with 1, 2, 3, or 4 groups, each independently selected from —OH, halo, —CN, —$SF_5$, $C_1$-$C_6$-alkyl, $C_1$-$C_6$-haloalkyl, —O—$C_1$-$C_6$-alkyl, and $C_1$-$C_6$-alkyl-OH. In certain embodiments, $R^4$ is phenyl or pyridyl, wherein said phenyl or pyridyl is optionally substituted with 1, 2, 3, or 4 groups, each independently selected from halo, —CN, $C_1$-$C_6$-alkyl and $C_1$-$C_6$-haloalkyl. In a particular embodiment, $R^4$ is phenyl, wherein the phenyl is substituted with 1, 2, 3, or 4 groups, each independently selected from halo, —CN, $C_1$-$C_6$-alkyl and $C_1$-$C_6$-haloalkyl. In another particular embodiment, $R^4$ is pyridyl, wherein the pyridyl is substituted with 1, 2, 3, or 4 groups, each independently selected from halo, —CN, $C_1$-$C_6$-alkyl and $C_1$-$C_6$-haloalkyl.

$R^5$ may be selected from H, $C_1$-$C_6$-alkyl, and $C_1$-$C_6$-alkyl-OH. In a particular embodiment, $R^5$ is H.

$R^6$ may be selected from H, $C_1$-$C_6$-alkyl, $C_1$-$C_6$-haloalkyl, $C_1$-$C_6$-alkenyl, and $C_0$-$C_6$-alkyl-$C_3$-$C_6$-cycloalkyl. In a particular embodiment, $R^6$ is selected from H, $C_1$-$C_6$-alkyl, and $C_1$-$C_6$-haloalkyl.

$R^7$ may be independently selected from H, $C_1$-$C_6$-alkyl, $C_1$-$C_6$-haloalkyl, $C_1$-$C_6$-alkyl-$OR^{10}$, —C(O)$C_1$-$C_6$-alkyl, —C(O)$C_1$-$C_6$-haloalkyl, —C(O)$C_1$-$C_6$-alkyl-$OR^{10}$, —C(O)$C_1$-$C_6$-alkyl-CN, —C(O)$C_3$-$C_7$-cycloalkyl, —C(O)O—$C_1$-$C_6$-alkyl, —C(O)O—$C_1$-$C_6$-haloalkyl, —C(O)O—$C_3$-$C_7$-cycloalkyl, —C(O)$N(R^{10})_2$, —$S(O)_2C_1$-$C_6$-alkyl, —$S(O)_2C_1$-$C_6$-haloalkyl and —$S(O)_2C_3$-$C_7$-cycloalkyl;

or wherein two $R^7$ groups together with the N to which they are attached form a $C_2$-$C_6$ heterocycle, wherein the $C_2$-$C_6$ heterocycle is further independently and optionally substituted with 1 or 2 oxo or halogen substituents. In an embodiment, $R^7$ is, at each occurrence, independently selected from H and $C_1$-$C_6$-alkyl. In a further embodiment, $R^7$ is, at each occurrence, independently selected from H, $C_1$-$C_6$-haloalkyl, $C_1$-$C_6$-alkyl-$OR^{10}$, —C(O)$C_1$-$C_6$-alkyl, —C(O)$C_1$-$C_6$-haloalkyl, —C(O)$C_1$-$C_6$-alkyl-$OR^{10}$, —C(O)$C_1$-$C_6$-alkyl-CN, —C(O)$C_3$-$C_7$-cycloalkyl, —C(O)O—$C_1$-$C_6$-alkyl, —C(O)O—$C_1$-$C_6$-haloalkyl, —C(O)O—$C_3$-$C_7$-cycloalkyl, —C(O)$N(R^{10})_2$, —$S(O)_2C_1$-$C_6$-alkyl, —$S(O)_2C_1$-$C_6$-haloalkyl or —$S(O)_2C_3$-$C_7$-cycloalkyl. In an embodiment, $R^7$ is, at each occurrence, independently selected from $C_1$-$C_6$-alkyl, $C_1$-$C_6$-haloalkyl, —C(O)$C_1$-$C_6$-alkyl, —C(O)$C_1$-$C_6$-haloalkyl, —C(O)$C_1$-$C_6$-alkyl-$OR^{10}$, —C(O)$C_1$-$C_6$-alkyl-CN, —C(O)$C_3$-$C_7$-cycloalkyl, —C(O)O—$C_1$-$C_6$-alkyl, —C(O)O—$C_1$-$C_6$-haloalkyl, —C(O)O—$C_3$-$C_7$-cycloalkyl, —C(O)$N(R^{10})_2$, —$S(O)_2C_1$-$C_6$-alkyl, —$S(O)_2C_1$-$C_6$-haloalkyl or —$S(O)_2C_3$-$C_7$-cycloalkyl.

$R^8$ may be selected from H and $C_1$-$C_6$-alkyl.

$R^9$ may be selected from H and $C_1$-$C_6$-alkyl.

$R^{10}$ may be selected from H and $C_1$-$C_6$-alkyl.

$R^a$ may be independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH.

$R^b$ may be independently selected from H and $C_1$-$C_6$-alkyl.

m may be 0, 1, 2, 3, or 4.
n may be 0, 1, 2, 3, or 4.
p may be 0, 1, 2, 3, or 4.

In another aspect, provided herein are compounds having the structure of Formula I:

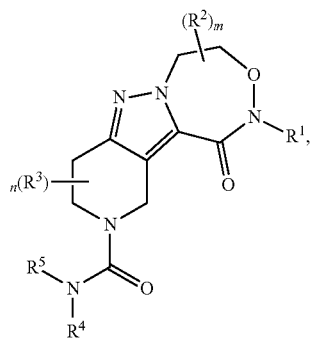

or a pharmaceutically acceptable salt thereof.

$R^1$ may be H, $C_1$-$C_6$-alkyl, $C_1$-$C_6$-alkenyl, or $C_1$-$C_6$-alkyl-OH. In embodiments, $R^1$ is H. In embodiments, $R^1$ is $C_1$-$C_6$-alkyl. In embodiments, $R^1$ is $C_1$-$C_6$-alkenyl. In embodiments, $R^1$ is $C_1$-$C_6$-alkyl-OH.

In embodiments, there may be 0, 1, 2, 3, or 4 $R^2$ substituents: m is 0, 1, 2, 3, or 4. Each $R^2$ may be independently selected from —OH, halo, $C_1$-$C_6$-alkyl, $C_1$-$C_6$-alkylene, $C_0$-$C_6$-alkyl-$C_3$-$C_6$-cycloalkyl, $C_0$-$C_6$-alkyl-$C_2$-$C_6$-heterocycloalkyl, $C_0$-$C_6$-alkyl-$OR^6$, $C_0$-$C_6$-alkyl-$N(R^7)_2$, $C_0$-$C_6$-alkyl-$SR^8$, $C_0$-$C_6$-alkyl-$S(O)R^8$, $C_0$-$C_6$-alkyl-$S(O)_2R^8$, $C_0$-$C_6$-alkyl-$C(O)OR^9$, $C_0$-$C_6$-alkyl-$OC(O)R^9$, $C_0$-$C_6$-alkyl-$OC(O)OR^9$, $C_0$-$C_6$-alkyl-$OC(O)N(R^7)_2$, or $C_0$-$C_6$-alkyl-$C(O)N(R^7)_2$. In certain embodiments, m is 0 and there is no $R^2$ substitution. In certain embodiments, m is 1 and there is one $R^2$ substitution. In certain embodiments, m is 2 and there are two $R^2$ substitutions. In certain embodiments, m is 3 and there are three $R^2$ substitutions. In certain embodiments, m is 4 and there are four $R^2$ substitutions. In embodiments, there may be 0, 1, 2, 3, or 4 $R^3$ substituents: n is 0, 1, 2, 3, or 4. In certain embodiments, n is 0 and there is no $R^3$ substitution. In certain embodiments, n is 1 and there is one $R^3$ substitution. In certain embodiments, n is 2 and there are two $R^3$ substitutions. In certain embodiments, n is 3 and there are three $R^3$ substitutions. In certain embodiments, n is 4 and there are four $R^3$ substitutions.

In certain embodiments, $R^2$ may be $C_1$-$C_6$-alkyl optionally substituted with 1, 2, or 3 halo groups. In certain embodiments, $R^2$ may be $C_0$-$C_6$-alkyl-$OR^6$, wherein $R^6$ is $C_1$-$C_6$-haloalkyl. In certain embodiments, $R^2$ may be $(CH_2)_{1-2}$—O—$C_1$-$C_3$-alkyl, wherein $C_1$-$C_3$-alkyl is optionally substituted with 1, 2, or 3 halo groups. In certain embodiments, m is 1 or 2.

Each $R^3$ may be independently selected from —OH, halo, $C_1$-$C_6$-alkyl, $C_1$-$C_6$-haloalkyl, —O—$C_1$-$C_6$-alkyl, and $C_1$-$C_6$-alkyl-OH. In certain embodiments, at least one $R^3$ is —OH. In certain embodiments, at least one $R^3$ is halo. In certain embodiments, at least one $R^3$ is $C_1$-$C_6$-alkyl. In certain embodiments, at least one $R^3$ is $C_1$-$C_6$-haloalkyl. In certain embodiments, at least one $R^3$ is —O—$C_1$-$C_6$-alkyl. In certain embodiments, at least one $R^3$ is $C_1$-$C_6$-alkyl-OH.

$R^4$ is selected from $(CR^aR^b)_p$—$C_1$-$C_9$-heteroaryl, $(CR^aR^b)_p$—$C_6$-$C_{12}$-aryl, $(CR^aR^b)_p$—$C_3$-$C_7$-cycloalkyl, and $(CR^aR^b)_p$—$C_2$-$C_6$-heterocycloalkyl, wherein heteroaryl, aryl, cycloalkyl, and heterocycloalkyl are optionally substituted with 1, 2, 3, or 4 groups, each independently selected from —OH, halo, —CN, —$SF_5$, $C_1$-$C_6$-alkyl, $C_1$-$C_6$-haloalkyl, —O—$C_1$-$C_6$-alkyl, and $C_1$-$C_6$-alkyl-OH. In certain embodiments, $R^4$ is $(CR^aR^b)_p$—$C_1$-$C_9$-heteroaryl optionally substituted with 1, 2, 3, or 4 groups, each independently selected from —OH, halo, —CN, —$SF_5$, $C_1$-$C_6$-alkyl, $C_1$-$C_6$-haloalkyl, —O—$C_1$-$C_6$-alkyl, and $C_1$-$C_6$-alkyl-OH. In certain embodiments, $R^4$ is $(CR^aR^b)_p$—$C_6$-$C_{12}$-aryl optionally substituted with 1, 2, 3, or 4 groups, each independently selected from —OH, halo, —CN, —$SF_5$, $C_1$-$C_6$-alkyl, $C_1$-$C_6$-haloalkyl, —O—$C_1$-$C_6$-alkyl, and $C_1$-$C_6$-alkyl-OH. In certain embodiments, $R^4$ is $(CR^aR^b)_p$—$C_3$-$C_7$-cycloalkyl optionally substituted with 1, 2, 3, or 4 groups, each independently selected from —OH, halo, —CN, —$SF_5$, $C_1$-$C_6$-alkyl, $C_1$-$C_6$-haloalkyl, —O—$C_1$-$C_6$-alkyl, and $C_1$-$C_6$-alkyl-OH. In certain embodiments, $R^4$ is $(CR^aR^b)_p$—$C_2$-$C_6$-heterocycloalkyl optionally substituted with 1, 2, 3, or 4 groups, each independently selected from —OH, halo, —CN, —$SF_5$, $C_1$-$C_6$-alkyl, $C_1$-$C_6$-haloalkyl, —O—$C_1$-$C_6$-alkyl, and $C_1$-$C_6$-alkyl-OH. In certain embodiments, $R^4$ is phenyl or pyridyl, wherein said phenyl or pyridyl is optionally substituted with 1, 2, 3, or 4 groups, each independently selected from halo, —CN, $C_1$-$C_6$-alkyl and $C_1$-$C_6$-haloalkyl. In a particular embodiment, $R^4$ is phenyl, wherein the phenyl is substituted with 1, 2, 3, or 4 groups, each independently selected from halo, —CN, $C_1$-$C_6$-alkyl and $C_1$-$C_6$-haloalkyl. In another particular embodiment, $R^4$ is pyridyl, wherein the pyridyl is substituted with 1, 2, 3, or 4 groups, each independently selected from halo, —CN, $C_1$-$C_6$-alkyl and $C_1$-$C_6$-haloalkyl.

$R^5$ may be selected from H, $C_1$-$C_6$-alkyl, and $C_1$-$C_6$-alkyl-OH. In a particular embodiment, $R^5$ is H.

$R^6$ may be selected from H, $C_1$-$C_6$-alkyl, $C_1$-$C_6$-haloalkyl, $C_1$-$C_6$-alkenyl, and $C_0$-$C_6$-alkyl-$C_3$-$C_6$-cycloalkyl. In a particular embodiment, $R^6$ is selected from H, $C_1$-$C_6$-alkyl, and $C_1$-$C_6$-haloalkyl.

$R^7$ may be independently selected from H, $C_1$-$C_6$-alkyl, and $C_1$-$C_6$-alkyl-OH. In a particular embodiment, $R^7$ is, at each occurrence, independently selected from H, and $C_1$-$C_6$-alkyl.

$R^8$ may be selected from H and $C_1$-$C_6$-alkyl.
$R^9$ may be selected from H and $C_1$-$C_6$-alkyl.
$R^a$ may be independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH.
$R^b$ may be independently selected from H and $C_1$-$C_6$-alkyl.

m may be 0, 1, 2, 3, or 4.
n may be 0, 1, 2, 3, or 4.
p may be 0, 1, 2, 3, or 4.

In another aspect, provided herein are compounds having the structure of Formula III:

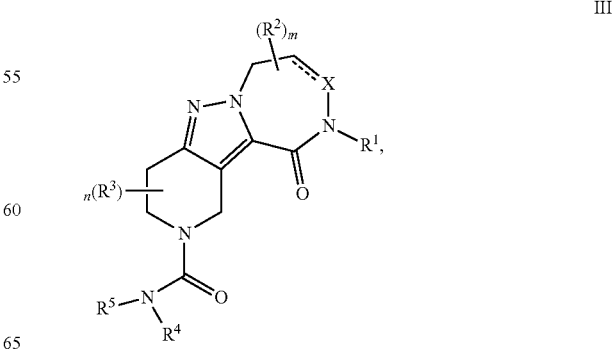

or a pharmaceutically acceptable salt thereof.

----- may be a single bond or a double bond. In embodiments, ----- is a single bond. In embodiments, ----- is a double bond.

X is N—$R^c$.

$R^1$ may be H, $C_1$-$C_6$-alkyl, $C_1$-$C_6$-alkenyl, or $C_1$-$C_6$-alkyl-OH. In embodiments, $R^1$ is H. In embodiments, $R^1$ is $C_1$-$C_6$-alkyl. In embodiments, $R^1$ is $C_1$-$C_6$-alkenyl. In embodiments, $R^1$ is $C_1$-$C_6$-alkyl-OH.

In embodiments, there may be 0, 1, 2, 3, or 4 $R^2$ substituents: m is 0, 1, 2, 3, or 4. Each $R^2$ may be independently selected from —OH, halo, $C_1$-$C_6$-alkyl, $C_1$-$C_6$-alkylene, $C_0$-$C_6$-alkyl-$C_3$-$C_6$-cycloalkyl, $C_0$-$C_6$-alkyl-$C_2$-$C_6$-heterocycloalkyl, $C_0$-$C_6$-alkyl-$OR^6$, $C_0$-$C_6$-alkyl-$N(R^7)_2$, $C_0$-$C_6$-alkyl-$SR^8$, $C_0$-$C_6$-alkyl-$S(O)R^8$, $C_0$-$C_6$-alkyl-$S(O)_2R^8$, $C_0$-$C_6$-alkyl-$C(O)OR^9$, $C_0$-$C_6$-alkyl-$OC(O)R^9$, $C_0$-$C_6$-alkyl-$OC(O)OR^9$, $C_0$-$C_6$-alkyl-$OC(O)N(R^7)_2$, or $C_0$-$C_6$-alkyl-$C(O)N(R^7)_2$. In certain embodiments, m is 0 and there is no $R^2$ substitution. In certain embodiments, m is 1 and there is one $R^2$ substitution. In certain embodiments, m is 2 and there are two $R^2$ substitutions. In certain embodiments, m is 3 and there are three $R^2$ substitutions. In certain embodiments, m is 4 and there are four $R^2$ substitutions. In embodiments, there may be 0, 1, 2, 3, or 4 $R^3$ substituents: n is 0, 1, 2, 3, or 4. In certain embodiments, n is 0 and there is no $R^3$ substitution. In certain embodiments, n is 1 and there is one $R^3$ substitution. In certain embodiments, n is 2 and there are two $R^3$ substitutions. In certain embodiments, n is 3 and there are three $R^3$ substitutions. In certain embodiments, n is 4 and there are four $R^3$ substitutions.

Each $R^3$ may be independently selected from —OH, halo, $C_1$-$C_6$-alkyl, $C_1$-$C_6$-haloalkyl, —O—$C_1$-$C_6$-alkyl, and $C_1$-$C_6$-alkyl-OH. In certain embodiments, at least one $R^3$ is —OH. In certain embodiments, at least one $R^3$ is halo. In certain embodiments, at least one $R^3$ is $C_1$-$C_6$-alkyl. In certain embodiments, at least one $R^3$ is $C_1$-$C_6$-haloalkyl. In certain embodiments, at least one $R^3$ is —O—$C_1$-$C_6$-alkyl. In certain embodiments, at least one $R^3$ is $C_1$-$C_6$-alkyl-OH.

$R^4$ is selected from $(CR^aR^b)_p$—$C_1$-$C_9$-heteroaryl, $(CR^aR^b)_p$—$C_6$-$C_{12}$-aryl, $(CR^aR^b)_p$—$C_3$-$C_7$-cycloalkyl, and $(CR^aR^b)_p$—$C_2$-$C_6$-heterocycloalkyl, wherein heteroaryl, aryl, cycloalkyl, and heterocycloalkyl are optionally substituted with 1, 2, 3, or 4 groups, each independently selected from —OH, halo, —CN, —$SF_5$, $C_1$-$C_6$-alkyl, $C_1$-$C_6$-haloalkyl, —O—$C_1$-$C_6$-alkyl, and $C_1$-$C_6$-alkyl-OH. In certain embodiments, $R^4$ is $(CR^aR^b)_p$—$C_1$-$C_9$-heteroaryl optionally substituted with 1, 2, 3, or 4 groups, each independently selected from —OH, halo, —CN, —$SF_5$, $C_1$-$C_6$-alkyl, $C_1$-$C_6$-haloalkyl, —O—$C_1$-$C_6$-alkyl, and $C_1$-$C_6$-alkyl-OH. In certain embodiments, $R^4$ is $(CR^aR^b)_p$—$C_6$-$C_{12}$-aryl optionally substituted with 1, 2, 3, or 4 groups, each independently selected from —OH, halo, —CN, —$SF_5$, $C_1$-$C_6$-alkyl, $C_1$-$C_6$-haloalkyl, —O—$C_1$-$C_6$-alkyl, and $C_1$-$C_6$-alkyl-OH. In certain embodiments, $R^4$ is $(CR^aR^b)_p$—$C_3$-$C_7$-cycloalkyl optionally substituted with 1, 2, 3, or 4 groups, each independently selected from —OH, halo, —CN, —$SF_5$, $C_1$-$C_6$-alkyl, $C_1$-$C_6$-haloalkyl, —O—$C_1$-$C_6$-alkyl, and $C_1$-$C_6$-alkyl-OH. In certain embodiments, $R^4$ is $(CR^aR^b)_p$—$C_2$-$C_6$-heterocycloalkyl optionally substituted with 1, 2, 3, or 4 groups, each independently selected from —OH, halo, —CN, —$SF_5$, $C_1$-$C_6$-alkyl, $C_1$-$C_6$-haloalkyl, —O—$C_1$-$C_6$-alkyl, and $C_1$-$C_6$-alkyl-OH. In certain embodiments, $R^4$ is phenyl or pyridyl, wherein said phenyl or pyridyl is optionally substituted with 1, 2, 3, or 4 groups, each independently selected from halo, —CN, $C_1$-$C_6$-alkyl and $C_1$-$C_6$-haloalkyl. In a particular embodiment, $R^4$ is phenyl, wherein the phenyl is substituted with 1, 2, 3, or 4 groups, each independently selected from halo, —CN, $C_1$-$C_6$-alkyl and $C_1$-$C_6$-haloalkyl. In another particular embodiment, $R^4$ is pyridyl, wherein the pyridyl is substituted with 1, 2, 3, or 4 groups, each independently selected from halo, —CN, $C_1$-$C_6$-alkyl and $C_1$-$C_6$-haloalkyl.

$R^5$ may be selected from H, $C_1$-$C_6$-alkyl, and $C_1$-$C_6$-alkyl-OH. In a particular embodiment, $R^5$ is H.

$R^6$ may be selected from H, $C_1$-$C_6$-alkyl, $C_1$-$C_6$-haloalkyl, $C_1$-$C_6$-alkenyl, and $C_0$-$C_6$-alkyl-$C_3$-$C_6$-cycloalkyl. In a particular embodiment, $R^6$ is selected from H, $C_1$-$C_6$-alkyl, and $C_1$-$C_6$-haloalkyl.

$R^7$ may be independently selected from H, $C_1$-$C_6$-alkyl, and $C_1$-$C_6$-alkyl-OH. In a particular embodiment, $R^7$ is, at each occurrence, independently selected from H, and $C_1$-$C_6$-alkyl.

$R^8$ may be selected from H and $C_1$-$C_6$-alkyl.

$R^9$ may be selected from H and $C_1$-$C_6$-alkyl.

$R^a$ may be independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH.

$R^b$ may be independently selected from H and $C_1$-$C_6$-alkyl.

$R^c$ may be selected from absent, H, $C_1$-$C_6$-alkyl, $C_1$-$C_6$-alkenyl, $C_1$-$C_6$-haloalkyl, or $C_1$-$C_6$-alkyl-OH.

m may be 0, 1, 2, 3, or 4.

n may be 0, 1, 2, 3, or 4.

p may be 0, 1, 2, 3, or 4.

In an embodiment of the compound of Formula III, n is 0, 1, or 2; and each $R^3$ is independently $C_1$-$C_6$-alkyl.

In another embodiment of the compound of Formula III, $R^4$ is phenyl, pyridinyl, or cyclohexyl, wherein $R^4$ is optionally substituted with 1, 2, or 3 groups, each independently selected from —F, —Br, —Cl, —I, —CN, —$CH_3$, —$CH_2CH_3$, —$CF_3$, —$CHF_2$, and —$SF_5$. In yet another embodiment of the compound of Formula III, $R^1$ is $CH_3$;

$R^2$ is selected from the group consisting of: H, $C_{1-4}$haloalkyl, OH, $C_{1-4}$alkyl, $CH_2OH$, $CH(OH)CH_3$, $CH(OH)CH_2CH_3$, $CH(OH)$cyclopropyl, and $CH_2OCH_2CHF_2$;

$R^3$ is H or $CH_3$;

$R^4$ is

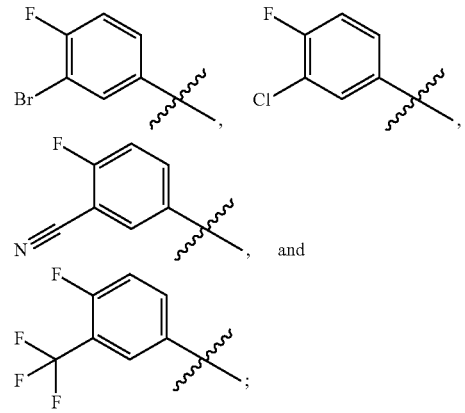

$R^5$ is H;

$R^c$ is absent, H, $C_{1-4}$alkyl, $CH_2CH=CH_2$, $CH_3CHF_2$, $CH_2CH_2OH$, $CH_2CH_2CH_2OH$, or $CH_2CH(OH)CH_3$;

m is 0, 1, or 2; and n is 0 or 1.

In an embodiment of the compound of Formula Ia, $R^1$ is $C_1$-$C_6$-alkyl, or $C_1$-$C_6$-alkenyl.

In another embodiment of the compound of Formula Ia, $R^1$ is —CH$_3$, —CH$_2$CH$_3$, —CH$_2$CH$_2$CH$_3$, —CH$_2$CH=CH$_2$, or —CD$_3$.

In an embodiment of the compound of Formula Ia, m is 1 or 2; and each $R^2$ is independently selected from C$_1$-C$_6$-alkyl, C$_1$-C$_6$-haloalkyl, C$_0$-C$_6$-alkyl-OR$^6$; C$_1$-C$_6$-alkyl-N(R$^7$)$_2$, C$_0$-C$_6$-alkyl-S(O)R$^8$, C$_0$-C$_6$-alkyl-S(O)$_2$R$^8$, C$_0$-C$_6$-alkyl-C(O)OR$^9$, C$_0$-C$_6$-alkyl-OC(O)R$^9$, C$_0$-C$_6$-alkyl-OC(O)OR$^9$, C$_0$-C$_6$-alkyl-OC(O)N(R$^7$)$_2$, and C$_0$-C$_6$-alkyl-C(O)N(R$^7$)$_2$.

In an embodiment of the compound of Formula I, $R^1$ is C$_1$-C$_6$-alkyl, or C$_1$-C$_6$-alkenyl.

In another embodiment of the compound of Formula I, $R^1$ is —CH$_3$, —CH$_2$CH$_3$, —CH$_2$CH$_2$CH$_3$, —CH$_2$CH=CH$_2$, or —CD$_3$.

In an embodiment of the compound of Formula I, m is 1 or 2; and each $R^2$ is independently selected from C$_1$-C$_6$-alkyl, C$_1$-C$_6$-haloalkyl, C$_0$-C$_6$-alkyl-OR$^6$; C$_1$-C$_6$-alkyl-N(R$^7$)$_2$, C$_0$-C$_6$-alkyl-S(O)R$^8$, C$_0$-C$_6$-alkyl-S(O)$_2$R$^8$, C$_0$-C$_6$-alkyl-C(O)OR$^9$, C$_0$-C$_6$-alkyl-OC(O)R$^9$, C$_0$-C$_6$-alkyl-OC(O)OR$^9$, C$_0$-C$_6$-alkyl-OC(O)N(R$^7$)$_2$, and C$_0$-C$_6$-alkyl-C(O)N(R$^7$)$_2$.

In an embodiment, the compound of Formula Ia has the structure of Formula II:

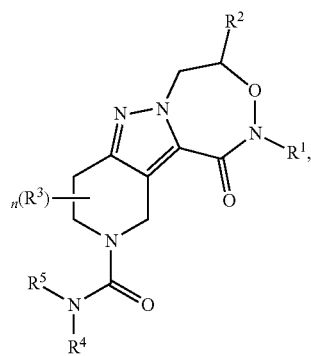

II or a pharmaceutically acceptable salt thereof.

In an embodiment of the compound of Formula Ia or Formula II, $R^2$ is C$_0$-C$_6$-alkyl-OR$^6$, C$_0$-C$_6$-alkyl-C(O)N(R$^7$)$_2$ and C$_1$-C$_6$-alkyl-N(R$^7$)$_2$.

In an embodiment of the compound of Formula Ia or Formula II, $R^2$ is selected from the group consisting of —CH$_2$OH, —CH$_2$OCF$_3$, —C(O)-3,3-difluoroazetidine, —C(O)-3,3-difluoropyrrolidine, —C(O)N(CH$_3$)(CH$_2$CHF$_2$), —C(O)N(CH$_3$)(CH$_2$CF$_3$), —C(O)N(H)(CH$_2$CHF$_2$), —C(O)N(H)(CH$_3$), —C(O)N(H)(CH$_2$CF$_3$), —CH$_2$N(H)(C(O)CH$_3$), —CH$_2$N(H)(C(O)CF$_3$), —CH$_2$N(H)(C(O)OCH$_3$), —CH$_2$N(H)(S(O)$_2$CH$_3$), —CH$_2$N(H)(S(O)$_2$CF$_3$), —CH$_2$-pyrrolidin-2-one, —CH$_2$N(H)(C(O)CH$_2$CH$_3$), —CH$_2$N(H)(C(O)-cyclopropyl), —CH$_2$N(H)(C(O)CH$_2$CF$_3$), —CH$_2$N(H)(C(O)CH(CH$_3$)$_2$), —CH$_2$N(H)(C(O)C(CH$_3$)$_3$), —CH$_2$N(H)(C(O)OCH$_2$CH$_3$), —CH$_2$N(H)(C(O)O-cyclopropyl), —CH$_2$N(H)(C(O)N(CH$_3$)$_2$), —CH$_2$N(H)(C(O)CH$_2$CN), —CH$_2$N(H)(C(O)CH$_2$OH), —CH$_2$N(H)(C(O)OCH$_2$CF$_3$), —CH$_2$N(H)(S(O)$_2$CH$_2$CH$_3$), CH$_2$N(H)(S(O)$_2$CH$_2$CF$_3$) and —CH$_2$N(H)(S(O)$_2$-cyclopropyl).

In an embodiment of the compound of Formula Ia or Formula II, $R^2$ is selected from the group consisting of —CH$_3$, —CH$_2$OH, —CH$_2$F, —CH$_2$OCH$_3$, —CH$_2$OCH$_2$CH$_3$, —CH$_2$OCH$_2$CH$_2$CH$_3$, —CH$_2$OCH$_2$-cyclopropyl, —CH$_2$OCH$_2$CHF$_2$, —CH$_2$OCH$_2$CF$_3$, —CH$_2$OCH$_2$CH=CH$_2$, —CH$_2$SCH$_3$, —CH$_2$S(O)CH$_3$, —CH$_2$—S(O)$_2$CH$_3$, —CH$_2$OC(O)OCH$_3$, —CH$_2$OC(O)OCH(CH$_3$)$_2$, —CH$_2$OC(O)OC(CH$_3$)$_3$, —CH$_2$OC(O)OCH$_2$CH$_3$, —CH$_2$OC(O)CH$_3$, —CH$_2$OC(O)C(CH$_3$)$_3$, —C(O)OH, —C(O)OCH$_3$, —CH$_2$OC(O)NH$_2$, —CH$_2$OC(O)N(CH$_3$)$_2$, —C(O)NH$_2$, —C(O)NHCH$_3$, —C(O)N(CH$_3$)$_2$, and —CH$_2$N(CH$_3$)$_2$.

In an embodiment of the compound of Formula Ia or Formula II, $R^2$ is C$_1$-C$_6$-alkyl optionally substituted with 1, 2, or 3 halo groups. In an embodiment of the compound of Formula Ia or Formula II, $R^2$ is C$_0$-C$_6$-alkyl-OR$^6$, wherein $R^6$ is C$_1$-C$_6$-haloalkyl. In certain embodiments, $R^2$ is (CH$_2$)$_{1-2}$—O—C$_1$-C$_3$-alkyl, wherein C$_1$-C$_3$-alkyl is optionally substituted with 1, 2, or 3 halo groups. In certain embodiments, m is 1 or 2.

In an embodiment of the compound of Formula Ia or Formula II, n is 0, 1, or 2; and each $R^3$ is independently C$_1$-C$_6$-alkyl.

In an embodiment of the compound of Formula Ia or Formula II, each $R^3$ is independently C$_1$-C$_3$-alkyl. In a further embodiment of the compound of Formula I or Formula II, $R^3$ is independently —CH$_3$.

In an embodiment of the compound of Formula Ia or Formula II, n is 1, and $R^3$ is in the following position:

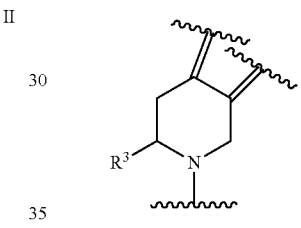

In an embodiment of the compound of Formula Ia or Formula II, $R^4$ is (CR$^a$R$^b$)$_p$—C$_1$-C$_5$-heteroaryl, (CR$^a$R$^b$)$_p$—C$_6$-aryl, or (CR$^a$R$^b$)$_p$—C$_3$-C$_7$-cycloalkyl, wherein heteroaryl, aryl, and cycloalkyl are optionally substituted with 1, 2, or 3 groups, each independently selected from —OH, halo, —CN, —SF$_5$, C$_1$-C$_6$-alkyl, C$_1$-C$_6$-haloalkyl, —O—C$_1$-C$_6$-alkyl, and C$_1$-C$_6$-alkyl-OH;

$R^a$ is H or C$_1$-C$_6$-alkyl;

$R^b$ is H or C$_1$-C$_6$-alkyl; and p is 0 or 1.

In an embodiment of the compound of Formula I or Formula II, $R^2$ is selected from the group consisting of —CH$_3$, —CH$_2$OH, —CH$_2$F, —CH$_2$OCH$_3$, —CH$_2$OCH$_2$CH$_3$, —CH$_2$OCH$_2$CH$_2$CH$_3$, —CH$_2$OCH$_2$-cyclopropyl, —CH$_2$OCH$_2$CHF$_2$, —CH$_2$OCH$_2$CF$_3$, —CH$_2$OCH$_2$CH=CH$_2$, —CH$_2$SCH$_3$, —CH$_2$S(O)CH$_3$, —CH$_2$—S(O)$_2$CH$_3$, —CH$_2$OC(O)OCH$_3$, —CH$_2$OC(O)OCH(CH$_3$)$_2$, —CH$_2$OC(O)OC(CH$_3$)$_3$, —CH$_2$OC(O)OCH$_2$CH$_3$, —CH$_2$OC(O)CH$_3$, —CH$_2$OC(O)C(CH$_3$)$_3$, —C(O)OH, —C(O)OCH$_3$, —CH$_2$OC(O)NH$_2$, —CH$_2$OC(O)N(CH$_3$)$_2$, —C(O)NH$_2$, —C(O)NHCH$_3$, —C(O)N(CH$_3$)$_2$, and —CH$_2$N(CH$_3$)$_2$. In an embodiment of the compound of Formula I or Formula II, n is 0, 1, or 2; and each $R^3$ is independently C$_1$-C$_6$-alkyl. In an embodiment of the compound of Formula I or Formula II, each $R^3$ is independently C$_1$-C$_3$-alkyl. In a further embodiment of the compound of Formula I or Formula II, $R^3$ is independently —CH$_3$.

In another embodiment of the compound of Formula Ia or Formula II, $R^4$ is C$_1$-C$_5$-heteroaryl, C$_6$-aryl, or C$_3$-C$_7$-cycloalkyl any of which is optionally substituted with 1, 2, or 3 groups, each independently selected from —OH, halo, —CN, —SF$_5$, C$_1$-C$_6$-alkyl, and C$_1$-C$_6$-haloalkyl.

In an embodiment of the compound of Formula Ia or Formula II, R$^4$ is phenyl, pyridinyl, or cyclohexyl, any of which is optionally substituted with 1, 2, or 3 groups, each independently selected from —F, —Br, —Cl, —I, —CN, —CH$_3$, —CH$_2$CH$_3$, —CF$_3$, —CHF$_2$, and —SF$_5$.

In an embodiment of the compound of Formula Ia or Formula II, R$^4$ is selected from the group consisting of:

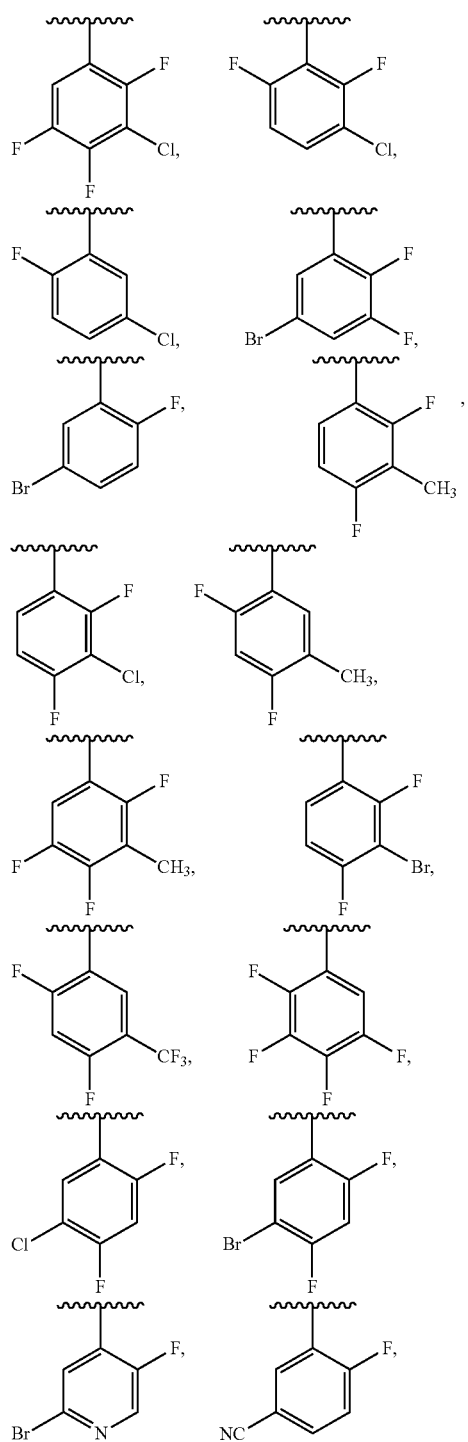

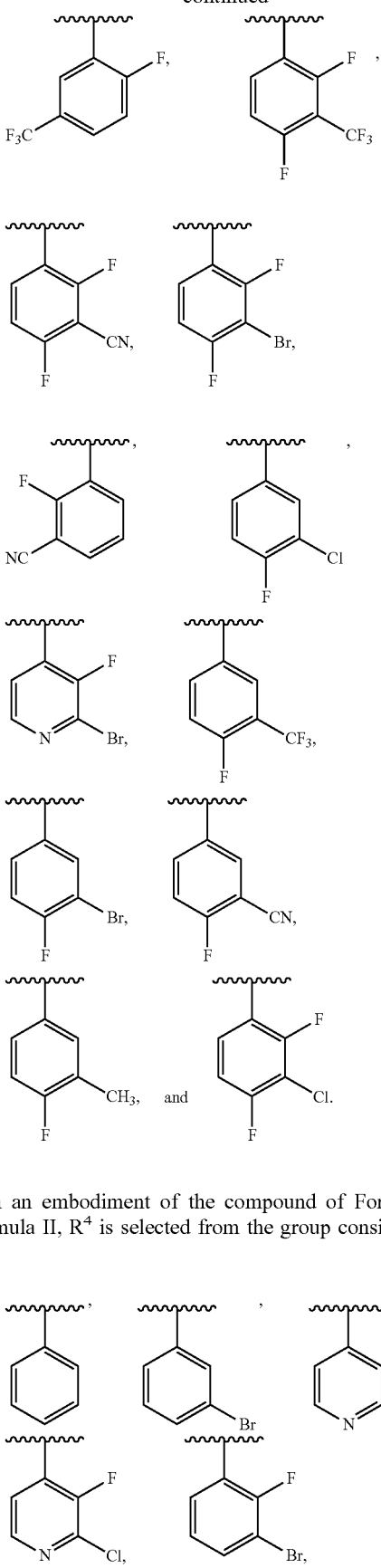

In an embodiment of the compound of Formula Ia or Formula II, R$^4$ is selected from the group consisting of:

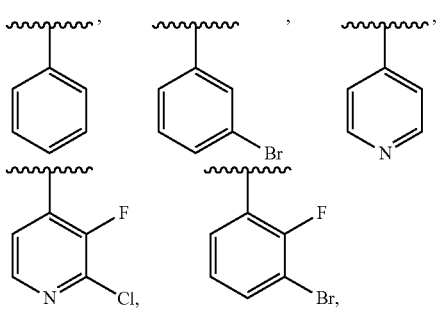

-continued
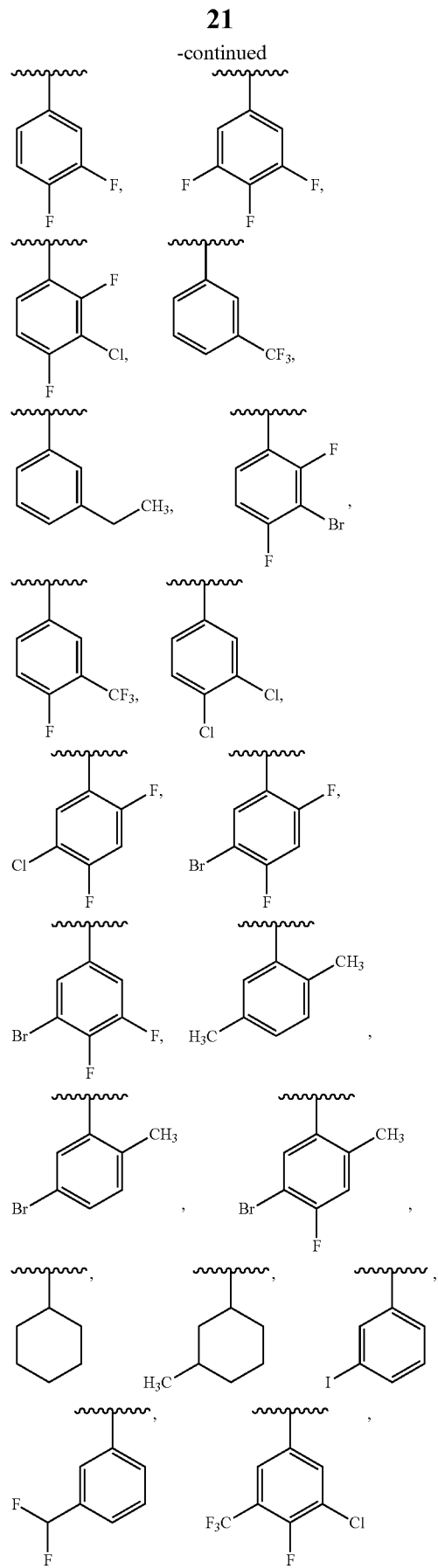
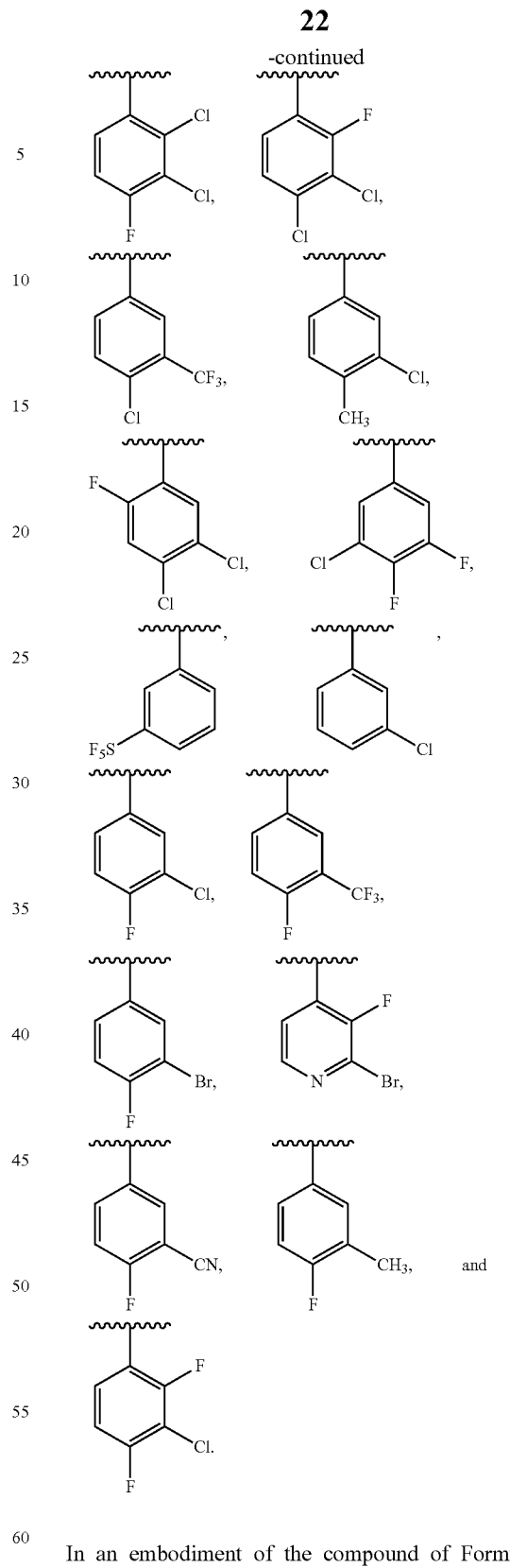
In an embodiment of the compound of Formula I or Formula II, $R^4$ is $(CR^aR^b)_p$—$C_1$-$C_5$-heteroaryl, $(CR^aR^b)_p$—$C_6$-aryl, or $(CR^aR^b)_p$—$C_3$-$C_7$-cycloalkyl, wherein heteroaryl, aryl, and cycloalkyl are optionally substituted with 1, 2, or 3 groups, each independently selected from —OH, halo, —CN, —SF$_5$, $C_1$-$C_6$-alkyl, $C_1$-$C_6$-haloalkyl, —O—$C_1$-$C_6$-alkyl, and $C_1$-$C_6$-alkyl-OH;

$R^a$ is H or $C_1$-$C_6$-alkyl;

$R^b$ is H or $C_1$-$C_6$-alkyl; and p is 0 or 1. In another embodiment of the compound of Formula I or Formula II, $R^4$ is $C_1$-$C_5$-heteroaryl, $C_6$-aryl, or $C_3$-$C_7$-cycloalkyl, any of which is optionally substituted with 1, 2, or 3 groups, each independently selected from —OH, halo, —CN, —$SF_5$, $C_1$-$C_6$-alkyl, and $C_1$-$C_6$-haloalkyl. In an embodiment of the compound of Formula I or Formula II, $R^4$ is phenyl, pyridinyl, or cyclohexyl, any of which is optionally substituted with 1, 2, or 3 groups, each independently selected from —F, —Br, —Cl, —I, —CN, —$CH_3$, —$CH_2CH_3$, —$CF_3$, —$CHF_2$, and —$SF_5$.

In an embodiment of the compound of Formula I or Formula II, $R^4$ is selected from the group consisting of:

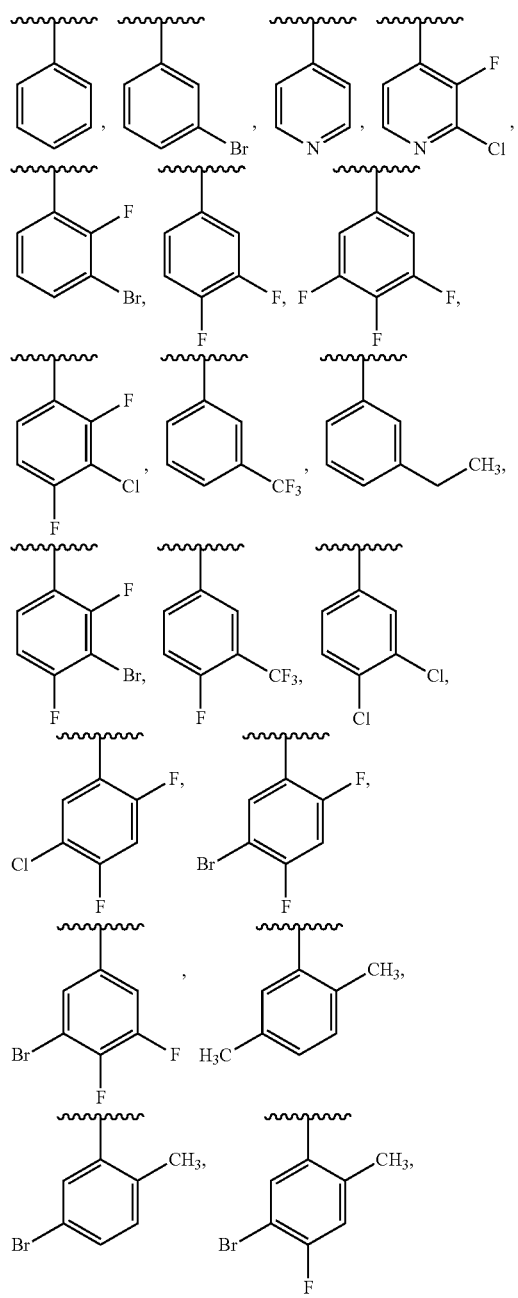

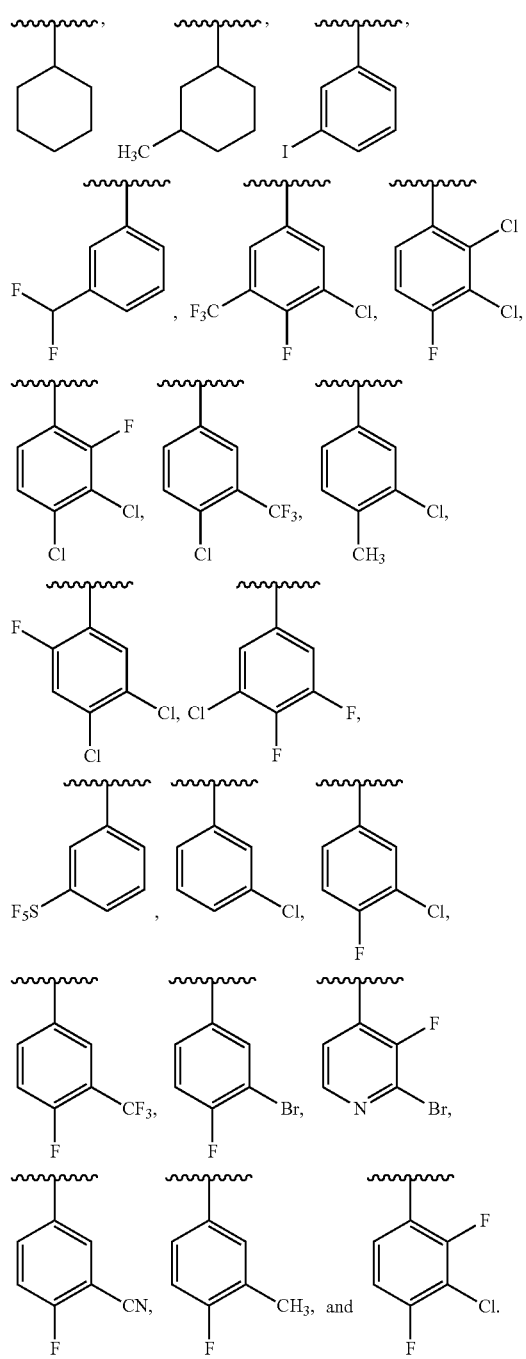

In another embodiment of the compound of Formula Ia or Formula II, $R^4$ is

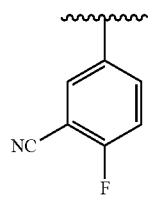

In another embodiment of the compound of Formula Ia or Formula II, $R^5$ is H or —$CH_3$.

In an embodiment of the compound of Formula Ia or Formula II, $R^5$ is H or $C_1$-$C_6$-alkyl. In an embodiment of the compound of Formula I or Formula II, $R^5$ is H or $C_1$-$C_6$-alkyl. In another embodiment of the compound of Formula I or Formula II, $R^5$ is H or —$CH_3$.

In another embodiment of the compound of Formula Ia,

A is N or C(H)

$R^1$ is $C_1$-$C_6$-alkyl;

$R^2$ is, independently selected from the group consisting of $C_1$-$C_6$-alkyl, $C_1$-$C_6$-haloalkyl, $C_0$-$C_6$-alkyl-$OR^6$, $C_1$-$C_6$-alkyl-$N(R^7)_2$, $C_0$-$C_6$-alkyl-$SR^8$, $C_0$-$C_6$-alkyl-$S(O)R^8$, $C_0$-$C_6$-alkyl-$S(O)_2R^8$, $C_0$-$C_6$-alkyl-$C(O)OR^9$, $C_0$-$C_6$-alkyl-$OC(O)R^9$, $C_0$-$C_6$-alkyl-$OC(O)OR^9$, $C_0$-$C_6$-alkyl-$OC(O)N(R^7)_2$, and $C_0$-$C_6$-alkyl-$C(O)N(R^7)_2$;

$R^3$ is, at each occurrence, independently selected from $C_1$-$C_6$-alkyl;

$R^4$ is selected from $(CR^aR^b)_p$—$C_1$-$C_9$-heteroaryl and $(CR^aR^b)_p$—$C_6$-$C_{12}$-aryl, wherein the heteroaryl or aryl is optionally substituted with 1, 2, 3, or 4 groups, each independently selected from halo, —CN, —$SF_5$, $C_1$-$C_6$-alkyl, and $C_1$-$C_6$-haloalkyl;

$R^5$ is H or $C_1$-$C_6$-alkyl;

$R^6$ is selected from H, $C_1$-$C_6$-alkyl, $C_1$-$C_6$-haloalkyl, $C_1$-$C_6$-alkenyl, and $C_0$-$C_6$-alkyl-$C_3$-$C_6$-cycloalkyl;

$R^7$ is selected from H, $C_1$-$C_6$-alkyl, and $C_1$-$C_6$-alkyl-OH;

$R^8$ is selected from H and $C_1$-$C_6$-alkyl;

$R^9$ is selected from H and $C_1$-$C_6$-alkyl;

$R^a$ is, at each occurrence, independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH;

$R^b$ is, at each occurrence, independently selected from H and $C_1$-$C_6$-alkyl;

m is 0, 1 or 2;

n is 0, 1 or 2; and p is 0 or 1. In another embodiment of the compound of Formula Ia, $R^1$ is $C_1$-$C_6$-alkyl;

$R^2$ is, at each occurrence, independently selected from —$CH_2OH$, —$CH_2OCF_3$, —C(O)-3,3-difluoroazetidine, —C(O)-3,3-difluoropyrrolidine, —$C(O)N(CH_3)$($CH_2CHF_2$), —$C(O)N(CH_3)$($CH_2CF_3$), —$C(O)N(H)$($CH_2CHF_2$), —$C(O)N(H)(CH_3)$, —$C(O)N(H)(CH_2CF_3)$, —$CH_2N(H)(C(O)CH_3)$, —$CH_2N(H)(C(O)CF_3)$, —$CH_2N(H)(C(O)OCH_3)$, —$CH_2N(H)(S(O)_2CH_3)$, —$CH_2N(H)(S(O)_2CF_3)$, —$CH_2$-pyrrolidin-2-one, —$CH_2N(H)(C(O)CH_2CH_3)$, —$CH_2N(H)(C(O)$-cyclopropyl), —$CH_2N(H)(C(O)CH_2CF_3)$, —$CH_2N(H)(C(O)CH(CH_3)_2)$, —$CH_2N(H)(C(O)C(CH_3)_3)$, —$CH_2N(H)(C(O)OCH_2CH_3)$, —$CH_2N(H)(C(O)O$-cyclopropyl), —$CH_2N(H)(C(O)N(CH_3)_2)$, —$CH_2N(H)(C(O)CH_2CN)$, —$CH_2N(H)(C(O)CH_2OH)$, —$CH_2N(H)(C(O)OCH_2CF_3)$, —$CH_2N(H)(S(O)_2CH_2CH_3)$, —$CH_2N(H)(S(O)_2CH_2CF_3)$ and —$CH_2N(H)(S(O)_2$-cyclopropyl);

$R^3$ is, at each occurrence, independently selected from $C_1$-$C_6$-alkyl;

$R^4$ is selected from $(CR^aR^b)_p$—$C_1$-$C_9$-heteroaryl and $(CR^aR^b)_p$—$C_6$-$C_{12}$-aryl, wherein the heteroaryl or aryl is optionally substituted with 1, 2, 3, or 4 groups, each independently selected from halo, —CN, —$SF_5$, $C_1$-$C_6$-alkyl, and $C_1$-$C_6$-haloalkyl;

$R^5$ is H;

m is 0, 1 or 2;

n is 0, 1 or 2; and p is 0.

In further embodiment of the compound of Formula Ia, $R^1$ is $C_1$-$C_6$-alkyl;

$R^2$ is, at each occurrence, independently selected from —$CH_3$, —$CH_2OH$, —$CH_2F$, —$CH_2OCH_3$, —$CH_2OCH_2CH_3$, —$CH_2OCH_2CH_2CH_3$, —$CH_2OCH_3$, —$CH_2OCH_2$-cyclopropyl, —$CH_2OCH_2CHF_2$, —$CH_2OCH_2CF_3$, —$CH_2OCH_2CH=CH_2$, —$CH_2SCH_3$, —$CH_2S(O)CH_3$, —$CH_2$—$S(O)_2CH_3$, —$CH_2OC(O)OCH_3$, —$CH_2OC(O)OCH(CH_3)_2$, —$CH_2OC(O)OC(CH_3)_3$, —$CH_2OC(O)OCH_2CH_3$, —$CH_2OC(O)CH_3$, —$CH_2OC(O)C(CH_3)_3$, —C(O)OH, —C(O)$OCH_3$, —$CH_2OC(O)NH_2$, —$CH_2OC(O)N(CH_3)_2$, —$C(O)NH_2$, —$C(O)NHCH_3$, —$C(O)N(CH_3)_2$, and —$CH_2N(CH_3)_2$;

$R^3$ is, at each occurrence, independently selected from $C_1$-$C_6$-alkyl;

$R^4$ is selected from $(CR^aR^b)_p$—$C_1$-$C_9$-heteroaryl and $(CR^aR^b)_p$—$C_6$-$C_{12}$-aryl, wherein the heteroaryl or aryl is optionally substituted with 1, 2, 3, or 4 groups, each independently selected from halo, —CN, —$SF_5$, $C_1$-$C_6$-alkyl, and $C_1$-$C_6$-haloalkyl;

$R^5$ is H;

m is 0, 1 or 2;

n is 0, 1 or 2; and p is 0.

In another embodiment of the compound of Formula I, $R^1$ is $C_1$-$C_6$-alkyl;

$R^2$ is, at each occurrence, independently selected from —$CH_3$, —$CH_2OH$, —$CH_2F$, —$CH_2OCH_3$, —$CH_2OCH_2CH_3$, —$CH_2OCH_2CH_2CH_3$, —$CH_2OCH_2$-cyclopropyl, —$CH_2OCH_2CHF_2$, —$CH_2OCH_2CF_3$, —$CH_2OCH_2CH=CH_2$, —$CH_2SCH_3$, —$CH_2S(O)CH_3$, —$CH_2$—$S(O)_2CH_3$, —$CH_2OC(O)OCH_3$, —$CH_2OC(O)OCH(CH_3)_2$, —$CH_2OC(O)OC(CH_3)_3$, —$CH_2OC(O)OCH_2CH_3$, —$CH_2OC(O)CH_3$, —$CH_2OC(O)C(CH_3)_3$, —C(O)OH, —$C(O)OCH_3$, —$CH_2OC(O)NH_2$, —$CH_2OC(O)N(CH_3)_2$, —$C(O)NH_2$, —$C(O)NHCH_3$, —$C(O)N(CH_3)_2$, and —$CH_2N(CH_3)_2$;

$R^3$ is, at each occurrence, independently selected from $C_1$-$C_6$-alkyl;

$R^4$ is selected from $(CR^aR^b)_p$—$C_1$-$C_9$-heteroaryl and $(CR^aR^b)_p$—$C_6$-$C_{12}$-aryl, wherein the heteroaryl or aryl is optionally substituted with 1, 2, 3, or 4 groups, each independently selected from halo, —CN, —$SF_5$, $C_1$-$C_6$-alkyl, and $C_1$-$C_6$-haloalkyl;

$R^5$ is H;

m is 0, 1 or 2;

n is 0, 1 or 2; and p is 0.

In a particular embodiment, $R^1$ is methyl and $R^4$ is 3-chloro-4-fluorophenyl.

In another particular embodiment, $R^1$ is methyl, $R^2$ is —$CH_2OH$ and m is 1.

In yet another particular embodiment, $R^1$ is methyl, $R^2$ is —$CH_2F$ and m is 1.

Provided herein are compounds according to the following embodiments:

In a particular embodiment of Formula I, $R^1$ is $C_1$-$C_6$-alkyl, $R^2$ is —$CH_3$, $R^4$ is phenyl, wherein the phenyl is substituted with at least one halogen, $R^5$ is H, m is 1 and n is 0.

In another particular embodiment of Formula I, $R^1$ is $C_1$-$C_6$-alkyl, $R^2$ is —$CH_3$, $R^4$ is phenyl, wherein the phenyl is substituted with at least one halogen, $R^5$ is H, m is 2 and n is 0.

In another particular embodiment of Formula I, $R^1$ is $C_1$-$C_6$-alkyl, $R^2$ is —$CH_2F$, $R^4$ is phenyl or pyridyl, wherein the phenyl or pyridyl is substituted with 1-3 groups independently selected from halo, —CN, —$SF_5$, $C_1$-$C_6$-alkyl, and $C_1$-$C_6$-haloalkyl, $R^5$ is H, and n is 0.

In another particular embodiment of Formula Ia, $R^1$ is $C_1$-$C_6$-alkyl, $R^2$ is —$CH_2OCH_2CHF_2$, $R^4$ is phenyl or pyridyl, wherein the phenyl or pyridyl is substituted with 1-3 groups independently selected from halo, —CN, —$SF_5$, $C_1$-$C_6$-alkyl, and $C_1$-$C_6$-haloalkyl, $R^5$ is H, n is 1, and $R^3$ is $C_1$-$C_6$-alkyl.

In another particular embodiment of Formula I, $R^1$ is $C_1$-$C_6$-alkyl; $R^2$ is $C_1$-$C_6$-alkyl or $C_0$-$C_6$-alkyl-$OR^6$, wherein alkyl is substituted with halo, and $R^6$ is H or $C_1$-$C_6$-haloalkyl; $R^3$ is $C_1$-$C_6$-alkyl; $R^4$ is phenyl substituted with 1 or 2 groups, each independently selected from halo and —CN; $R^5$ is H; m is 1; and n is 1.

In another particular embodiment of Formula I, $R^1$ is methyl; $R^2$ is —$CH_2F$ or $CH_2$—O—$CH_2CHF_2$; $R^3$ is methyl; $R^4$ is phenyl substituted with 1 or 2 groups, each independently selected from F and —CN; $R^5$ is H; m is 1; and n is 1.

In a particular embodiment of Formula II, $R^1$ is $C_1$-$C_6$-alkyl, $R^2$ is —$CH_2OH$, $R^4$ is phenyl or pyridyl, wherein the phenyl or pyridyl is substituted with 1-3 groups independently selected from halo, —CN, —$SF_5$, $C_1$-$C_6$-alkyl, and $C_1$-$C_6$-haloalkyl, $R^5$ is H, and n is 0.

In a particular embodiment of Formula II, $R^1$ is —$CD_3$, $R^2$ is —$CH_2OH$, $R^4$ is phenyl, wherein the phenyl is substituted with at least one halogen, $R^5$ is H, and n is 0.

In another particular embodiment of Formula II, $R^1$ is $C_1$-$C_6$-alkyl, $R^2$ is —$CH_2F$, $R^4$ is phenyl or pyridyl, wherein the phenyl or pyridyl is substituted with 1-3 groups independently selected from halo, —CN, —$SF_5$, $C_1$-$C_6$-alkyl, and $C_1$-$C_6$-haloalkyl, $R^5$ is H, and n is 0.

In another particular embodiment of Formula II, $R^1$ is $C_1$-$C_6$-alkyl, $R^2$ is —$CH_2OCH_2CHF_2$, $R^4$ is phenyl or pyridyl, wherein the phenyl or pyridyl is substituted with 1-3 groups independently selected from halo, —CN, —$SF_5$, $C_1$-$C_6$-alkyl, and $C_1$-$C_6$-haloalkyl, $R^5$ is H, n is 1, and $R^3$ is $C_1$-$C_6$-alkyl.

In another particular embodiment of Formula II, $R^1$ is $C_1$-$C_6$-alkyl, $R^2$ is —$CH_2OH$, $R^3$ is $C_1$-$C_6$-alkyl, $R^4$ is phenyl, wherein the phenyl is substituted with at least one halogen, $R^5$ is H, and n is 1.

In another particular embodiment of Formula II, $R^1$ is $C_1$-$C_6$-alkyl, $R^2$ is —$CH_2S(O)_2CH_3$, $R^4$ is phenyl, wherein the phenyl is substituted with at least one halogen, $R^5$ is H, and n is 0.

In another particular embodiment of Formula II, $R^1$ is $C_1$-$C_6$-alkyl, $R^2$ is —$CH_2OC(O)O$—$C_1$-$C_6$-alkyl, $R^4$ is phenyl, wherein the phenyl is substituted with at least one halogen, $R^5$ is H, and n is 0.

In another particular embodiment of Formula II, $R^1$ is $C_1$-$C_6$-alkyl, $R^2$ is —$CH_2OC(O)NH_2$, $R^4$ is phenyl, wherein the phenyl is substituted with at least one halogen, $R^5$ is H, and n is 0.

In another particular embodiment of Formula II, $R^1$ is $C_1$-$C_6$-alkyl, $R^2$ is —$C(O)NH_2$, —$C(O)NHCH_3$, or —$C(O)N(CH_3)_2$, $R^4$ is phenyl, wherein the phenyl is substituted with at least one halogen, $R^5$ is H, and n is 0.

In another particular embodiment of Formula II, $R^1$ is $C_1$-$C_6$-alkyl, $R^2$ is —$CH_2OC(O)N(CH_3)_2$, $R^4$ is phenyl, wherein the phenyl is substituted with at least one halogen, $R^5$ is H, and n is 0.

In another particular embodiment of Formula I, $R^1$ is $C_1$-$C_6$-alkyl, $R^4$ is phenyl, wherein the phenyl is substituted with at least one halogen, $R^5$ is H, m is 0 and n is 0.

In another particular embodiment of Formula I, $R^1$ is $C_1$-$C_6$-alkyl, $R^3$ is $C_1$-$C_6$-alkyl, $R^4$ is phenyl or pyridyl, wherein the phenyl or pyridyl is substituted with 1-3 groups independently selected from halo, —CN, $C_1$-$C_6$-alkyl, and $C_1$-$C_6$-haloalkyl, $R^5$ is H, m is 0 and n is 1. In a more particular embodiment, $R^3$ is (R)-methyl.

In another particular embodiment of Formula II, $R^1$ is $C_1$-$C_6$-alkyl, $R^2$ is —$CH_2F$, $R^3$ is $C_1$-$C_6$-alkyl, $R^4$ is phenyl or pyridyl, wherein the phenyl or pyridyl is substituted with 1-3 groups independently selected from halo, —CN, $C_1$-$C_6$-alkyl, and $C_1$-$C_6$-haloalkyl, $R^5$ is H, and n is 1. In a more particular embodiment, $R^3$ is (R)-methyl.

In another particular embodiment of Formula II, $R^1$ is $C_1$-$C_6$-alkyl, $R^2$ is —$CH_2N(CH_3)_2$, $R^3$ is $C_1$-$C_6$-alkyl, $R^4$ is phenyl or pyridyl, wherein the phenyl or pyridyl is substituted with 1-3 groups independently selected from halo, —CN, $C_1$-$C_6$-alkyl, and $C_1$-$C_6$-haloalkyl, $R^5$ is H, and n is 1. In a more particular embodiment, $R^3$ is (R)-methyl. In another particular embodiment of Formula II, $R^1$ is $C_1$-$C_6$-alkyl, $R^2$ is selected from —$CH_2OCH_3$, —$CH_2OCH_2CH_3$, —$CH_2OCH_2CH$=$CH_2$, —$CH_2OCH_2CH_2CH_3$, —$CH_2OCH_2$-cyclopropyl, —$CH_2OCH_2CHF_2$, and —$CH_2OCH_2CF_3$, $R^4$ is phenyl, wherein the phenyl is substituted with at least one halogen, $R^5$ is H, and n is 0.

In another particular embodiment of Formula Ia, $R^1$ is $C_1$-$C_6$-alkyl, $R^4$ is phenyl, wherein the phenyl is substituted with at least one halogen, $R^5$ is H, m is 0 and n is 0.

In another particular embodiment of Formula Ia, $R^1$ is $C_1$-$C_6$-alkyl, $R^3$ is $C_1$-$C_6$-alkyl, $R^4$ is phenyl or pyridyl, wherein the phenyl or pyridyl is substituted with 1-3 groups independently selected from halo, —CN, $C_1$-$C_6$-alkyl, and $C_1$-$C_6$-haloalkyl, $R^5$ is H, m is 0 and n is 1. In a more particular embodiment, $R^3$ is (R)-methyl.

In an embodiment of Formula II, $R^1$ is $C_1$-$C_6$-alkyl, $R^2$ is $C_0$-$C_6$-alkyl-$OR^6$, $R^4$ is phenyl, wherein the phenyl is substituted with at least one halogen, $R^5$ is H, $R^6$ is H, and n is 0.

In an embodiment of Formula II, $R^1$ is $C_1$-$C_6$-alkyl, $R^2$ is $C_0$-$C_6$-alkyl-$OR^6$, $R^4$ is phenyl, wherein the phenyl is substituted with at least one halogen, $R^5$ is H, $R^6$ is $C_1$-$C_6$-haloalkyl, and n is 0.

In another embodiment of Formula II, $R^1$ is $C_1$-$C_6$-alkyl, $R^2$ is $C_0$-$C_6$-alkyl-$C(O)N(R^7)_2$, wherein two $R^7$ groups together form a $C_2$-$C_6$ heterocycle with the N to which they are attached, wherein the $C_2$-$C_6$ heterocycle is further independently and optionally substituted with 1 or 2 oxo or halogen substituents, $R^4$ is phenyl, wherein the phenyl is substituted with at least one halogen, $R^5$ is H, and n is 0.

In another embodiment of Formula II, $R^1$ is $C_1$-$C_6$-alkyl, $R^2$ is $C_0$-$C_6$-alkyl-$C(O)N(C_1$-$C_6$-alkyl)($C_1$-$C_6$-haloalkyl), $R^4$ is phenyl, wherein the phenyl is substituted with at least one halogen,
$R^5$ is H, and n is 0.

In another embodiment of Formula II, $R^1$ is $C_1$-$C_6$-alkyl, $R^2$ is $C_0$-$C_6$-alkyl-$C(O)N(H)(C_1$-$C_6$-haloalkyl), $R^4$ is phenyl, wherein the phenyl is substituted with at least one halogen, $R^5$ is H, and n is 0.

In another embodiment of Formula II, $R^1$ is $C_1$-$C_6$-alkyl, $R^2$ is $C_0$-$C_6$-alkyl-$C(O)N(H)(C_1$-$C_6$-alkyl), $R^4$ is phenyl, wherein the phenyl is substituted with at least one halogen, $R^5$ is H, and n is 0.

In yet another embodiment of Formula II, $R^1$ is $C_1$-$C_6$-alkyl, $R^2$ is $C_1$-$C_6$-alkyl-$N(R^7)_2$, is phenyl, wherein the phenyl is substituted with at least one halogen, $R^5$ is H, wherein two $R^7$ groups together form a $C_2$-$C_6$ heterocycle with the N to which they are attached, wherein the $C_2$-$C_6$ heterocycle is further independently and optionally substituted with 1 or 2 oxo or halogen substituents, and n is 0.

In yet another embodiment of Formula II, $R^1$ is $C_1$-$C_6$-alkyl, $R^2$ is $C_1$-$C_6$-alkyl-$N(H)(C_1$-$C_6$-alkyl), $R^4$ is phenyl, wherein the phenyl is substituted with at least one halogen, $R^5$ is H, and n is 0.

In yet another embodiment of Formula II, $R^1$ is $C_1$-$C_6$-alkyl, $R^2$ is $C_1$-$C_6$-alkyl-N(H)($C_1$-$C_6$-haloalkyl), $R^4$ is phenyl, wherein the phenyl is substituted with at least one halogen, $R^5$ is H, and n is 0.

In yet another embodiment of Formula II, $R^1$ is $C_1$-$C_6$-alkyl, $R^2$ is $C_1$-$C_6$-alkyl-N(H)(—C(O)$C_1$-$C_6$-alkyl), $R^4$ is phenyl, wherein the phenyl is substituted with at least one halogen, $R^5$ is H, and n is 0.

In yet another embodiment of Formula II, $R^1$ is $C_1$-$C_6$-alkyl, $R^2$ is $C_1$-$C_6$-alkyl-N(H)(—C(O)$C_1$-$C_6$-haloalkyl), $R^4$ is phenyl, wherein the phenyl is substituted with at least one halogen, $R^5$ is H, and n is 0.

In yet another embodiment of Formula II, $R^1$ is $C_1$-$C_6$-alkyl, $R^2$ is $C_1$-$C_6$-alkyl-N(H)(—C(O)$C_1$-$C_6$-alkyl-OH), $R^4$ is phenyl, wherein the phenyl is substituted with at least one halogen, $R^5$ is H, and n is 0.

In yet another embodiment of Formula II, $R^1$ is $C_1$-$C_6$-alkyl, $R^2$ is $C_1$-$C_6$-alkyl-N(H)(—C(O)$C_1$-$C_6$-alkyl-CN), $R^4$ is phenyl, wherein the phenyl is substituted with at least one halogen, $R^5$ is H, and H, and n is 0.

In yet another embodiment of Formula II, $R^1$ is $C_1$-$C_6$-alkyl, $R^2$ is $C_1$-$C_6$-alkyl-N(H)(—C(O)$C_3$-$C_7$-cycloalkyl), $R^4$ is phenyl, wherein the phenyl is substituted with at least one halogen, $R^5$ is H, and n is 0.

In yet another embodiment of Formula II, $R^1$ is $C_1$-$C_6$-alkyl, $R^2$ is $C_1$-$C_6$-alkyl-N(H)(—C(O)O—$C_1$-$C_6$-alkyl), $R^4$ is phenyl, wherein the phenyl is substituted with at least one halogen, $R^5$ is H, and n is 0.

In yet another embodiment of Formula II, $R^1$ is $C_1$-$C_6$-alkyl, $R^2$ is $C_1$-$C_6$-alkyl-N(H)(—C(O)O—$C_1$-$C_6$-haloalkyl), $R^4$ is phenyl, wherein the phenyl is substituted with at least one halogen, $R^5$ is H, and n is 0.

In yet another embodiment of Formula II, $R^1$ is $C_1$-$C_6$-alkyl, $R^2$ is $C_1$-$C_6$-alkyl-N(H)(—C(O)O—$C_3$-$C_7$-cycloalkyl), $R^4$ is phenyl, wherein the phenyl is substituted with at least one halogen, $R^5$ is H, and n is 0.

In yet another embodiment of Formula II, $R^1$ is $C_1$-$C_6$-alkyl, $R^2$ is $C_1$-$C_6$-alkyl-N(H)(—C(O)N($C_1$-$C_6$-alkyl)$_2$), $R^4$ is phenyl, wherein the phenyl is substituted with at least one halogen, $R^5$ is H, and n is 0.

In yet another embodiment of Formula II, $R^1$ is $C_1$-$C_6$-alkyl, $R^2$ is $C_1$-$C_6$-alkyl-N(H)(—S(O)$_2$$C_1$-$C_6$-alkyl), $R^4$ is phenyl, wherein the phenyl is substituted with at least one halogen, $R^5$ is H, and n is 0.

In yet another embodiment of Formula II, $R^1$ is $C_1$-$C_6$-alkyl, $R^2$ is $C_1$-$C_6$-alkyl-N(H)(—S(O)$_2$$C_1$-$C_6$-haloalkyl), $R^4$ is phenyl, wherein the phenyl is substituted with at least one halogen, $R^5$ is H, and n is 0.

In yet another embodiment of Formula II, $R^1$ is $C_1$-$C_6$-alkyl, $R^2$ is $C_1$-$C_6$-alkyl-N(H)(—S(O)$_2$$C_3$-$C_7$-cycloalkyl), $R^4$ is phenyl, wherein the phenyl is substituted with at least one halogen, $R^5$ is H, $R^7$ is —S(O)$_2$$C_3$-$C_7$-cycloalkyl, and H, and n is 0.

In another particular embodiment of Formula II, $R^1$ is $C_1$-$C_6$-alkyl, $R^2$ is selected from —CH$_2$OH, —CH$_2$OCF$_3$, —C(O)-3,3-difluoroazetidine, —C(O)-3,3-difluoropyrrolidine, —C(O)N(CH$_3$)(CH$_2$CHF$_2$), —C(O)N(CH$_3$)(CH$_2$CF$_3$), —C(O)N(H)(CH$_2$CHF$_2$), —C(O)N(H)(CH$_3$), —C(O)N(H)(CH$_2$CF$_3$), —CH$_2$N(H)(C(O)CH$_3$), —CH$_2$N(H)(C(O)CF$_3$), —CH$_2$N(H)(C(O)OCH$_3$), —CH$_2$N(H)(S(O)$_2$ CH$_3$), —CH$_2$N(H)(S(O)$_2$CF$_3$), —CH$_2$-pyrrolidin-2-one, —CH$_2$N(H)(C(O)CH$_2$CH$_3$), —CH$_2$N(H)(C(O)-cyclopropyl), —CH$_2$N(H)(C(O)CH$_2$CF$_3$), —CH$_2$N(H)(C(O)CH(CH$_3$)$_2$), —CH$_2$N(H)(C(O)C(CH$_3$)$_3$), —CH$_2$N(H)(C(O)OCH$_2$CH$_3$), —CH$_2$N(H)(C(O)O-cyclopropyl), —CH$_2$N(H)(C(O)N(CH$_3$)$_2$), —CH$_2$N(H)(C(O)CH$_2$CN), —CH$_2$N(H)(C(O)CH$_2$OH), —CH$_2$N(H)(C(O)OCH$_2$CF$_3$), —CH$_2$N(H)(S(O)$_2$CH$_2$CH$_3$), —CH$_2$N(H)(S(O)$_2$CH$_2$CF$_3$) and —CH$_2$N(H)(S(O)$_2$-cyclopropyl), $R^4$ is phenyl, wherein the phenyl is substituted with at least one halogen, $R^5$ is H, and n is 0.

In an embodiment of Formula II, $R^1$ is $C_1$-$C_6$-alkyl, $R^2$ is $C_0$-$C_6$-alkyl-OR$^6$, $R^3$ is $C_1$-$C_6$-alkyl, $R^4$ is phenyl, wherein the phenyl is substituted with at least one halogen, $R^5$ is H, $R^6$ is H, and n is 1. In a more particular embodiment, $R^3$ is (R)-methyl.

In another embodiment of Formula II, $R^1$ is $C_1$-$C_6$-alkyl, $R^2$ is $C_0$-$C_6$-alkyl-C(O)N($C_1$-$C_6$-haloalkyl)($C_1$-$C_6$-alkyl), $R^3$ is $C_1$-$C_6$-alkyl, $R^4$ is phenyl, wherein the phenyl is substituted with at least one halogen, $R^5$ is H, and n is 1. In a more particular embodiment, $R^3$ is (R)-methyl.

In another embodiment of Formula II, $R^1$ is $C_1$-$C_6$-alkyl, $R^2$ is $C_0$-$C_6$-alkyl-C(O)N($C_1$-$C_6$-haloalkyl)(H), $R^3$ is $C_1$-$C_6$-alkyl, $R^4$ is phenyl, wherein the phenyl is substituted with at least one halogen, $R^5$ is H, and n is 1. In a more particular embodiment, $R^3$ is (R)-methyl.

In another embodiment of Formula II, $R^1$ is $C_1$-$C_6$-alkyl, $R^2$ is $C_0$-$C_6$-alkyl-C(O)N($C_1$-$C_6$-alkyl)(H), $R^3$ is $C_1$-$C_6$-alkyl, $R^4$ is phenyl, wherein the phenyl is substituted with at least one halogen, $R^5$ is H, and n is 1. In a more particular embodiment, $R^3$ is (R)-methyl.

In yet another embodiment of Formula II, $R^1$ is $C_1$-$C_6$-alkyl, $R^2$ is $C_1$-$C_6$-alkyl-N(—C(O)$C_1$-$C_6$-alkyl)(H), $R^3$ is $C_1$-$C_6$-alkyl, $R^4$ is phenyl, wherein the phenyl is substituted with at least one halogen, $R^5$ is H, and n is 1. In a more particular embodiment, $R^3$ is (R)-methyl.

In yet another embodiment of Formula II, $R^1$ is $C_1$-$C_6$-alkyl, $R^2$ is $C_1$-$C_6$-alkyl-N(—S(O)$_2$$C_1$-$C_6$-alkyl)(H), $R^3$ is $C_1$-$C_6$-alkyl, $R^4$ is phenyl, wherein the phenyl is substituted with at least one halogen, $R^5$ is H, and n is 1. In a more particular embodiment, $R^3$ is (R)-methyl.

In yet another embodiment of Formula II, $R^1$ is $C_1$-$C_6$-alkyl, $R^2$ is $C_1$-$C_6$-alkyl-N(—C(O)O—$C_1$-$C_6$-alkyl)(H), $R^3$ is $C_1$-$C_6$-alkyl, $R^4$ is phenyl, wherein the phenyl is substituted with at least one halogen, $R^5$ is H, and n is 1. In a more particular embodiment, $R^3$ is (R)-methyl.

In another particular embodiment of Formula II, $R^1$ is $C_1$-$C_6$-alkyl, $R^2$ is selected from —CH$_2$OH, —C(O)N(CH$_3$)(CH$_2$CHF$_2$), —C(O)N(H)(CH$_2$CHF$_2$), —C(O)N(H)(CH$_3$), —CH$_2$N(H)(C(O)CH$_3$), —CH$_2$N(H)(C(O)OCH$_3$), —CH$_2$N(H)(S(O)$_2$CH$_3$), $R^3$ is $C_1$-$C_6$-alkyl, $R^4$ is phenyl, wherein the phenyl is substituted with at least one halogen, $R^5$ is H, and n is 1. In a more particular embodiment, $R^3$ is (R)-methyl.

In an embodiment of Formula III, $R^1$ is $C_1$-$C_6$-alkyl, $R^3$ is $C_1$-$C_6$-alkyl, $R^4$ is phenyl, wherein the phenyl is substituted with at least one halogen, $R^5$ is H, $R^c$ is H, $C_{1-4}$alkyl, CH$_2$CH=CH$_2$, CH$_3$CHF$_2$, CH$_2$CH$_2$OH, CH$_2$CH$_2$CH$_2$OH, or CH$_2$CH(OH)CH$_3$, m is 0, and n is 1. In a more particular embodiment, $R^3$ is (R)-methyl.

In an embodiment of Formula III, $R^1$ is $C_1$-$C_6$-alkyl, $R^2$ is selected from —$C_{1-4}$haloalkyl, OH, $C_{1-4}$alkyl, CH$_2$OH, CH(OH)CH$_3$, CH(OH)CH$_2$CH$_3$, CH(OH)cyclopropyl, CH$_2$OCH$_2$CHF$_2$, $R^3$ is $C_1$-$C_6$-alkyl, $R^4$ is phenyl, wherein the phenyl is substituted with at least one halogen, $R^5$ is H, $R^c$ is H, $C_{1-4}$alkyl, CH$_2$CH=CH$_2$, CH$_3$CHF$_2$, CH$_2$CH$_2$OH, CH$_2$CH$_2$CH$_2$OH, CH$_2$CH(OH)CH$_3$, and n is 1. In a more particular embodiment, $R^3$ is (R)-methyl.

In an embodiment of Formula III, $R^1$ is $C_1$-$C_6$-alkyl, $R^3$ is $C_1$-$C_6$-alkyl, $R^4$ is phenyl, wherein the phenyl is substituted with at least one halogen, $R^5$ is H, $R^c$ is absent, m is 0, and n is 1. In a more particular embodiment, $R^3$ is (R)-methyl.

In an embodiment of Formula III, $R^1$ is $C_1$-$C_6$-alkyl, $R^2$ is selected from —$C_{1-4}$haloalkyl, OH, $C_{1-4}$alkyl, CH$_2$OH, CH(OH)CH$_3$, CH(OH)CH$_2$CH$_3$, CH(OH)cyclopropyl, CH$_2$OCH$_2$CHF$_2$, $R^3$ is $C_1$-$C_6$-alkyl, $R^4$ is phenyl, wherein the phenyl is substituted with at least one halogen, $R^5$ is H, $R^c$ is absent, and n is 1. In a more particular embodiment, $R^3$ is (R)-methyl.
Certain embodiments of Formulas I and II are shown below in Table 1.
TABLE 1
001
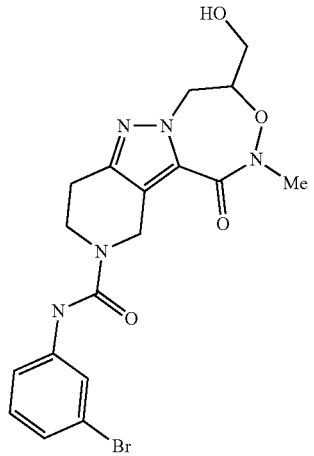 [SMILES: CN1OC(CO)Cn2nc3c(c2C1=O)CN(C(=O)Nc1cccc(Br)c1)CC3]
002
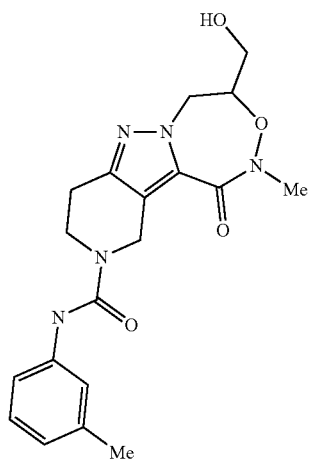 [SMILES: Cc1cccc(NC(=O)N2CCc3nn4c(c3C2)C(=O)N(C)OC(CO)C4)c1]
003
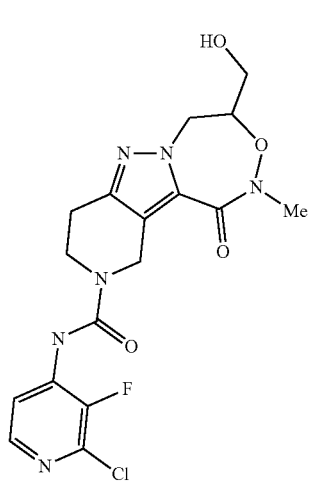 [SMILES: CN1OC(CO)Cn2nc3c(c2C1=O)CN(C(=O)Nc1ccnc(Cl)c1F)CC3]
TABLE 1-continued
004
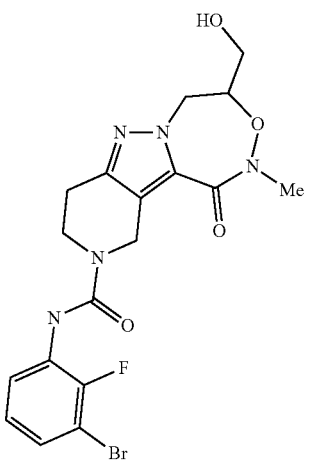 [SMILES: CN1OC(CO)Cn2nc3c(c2C1=O)CN(C(=O)Nc1cccc(Br)c1F)CC3]
005
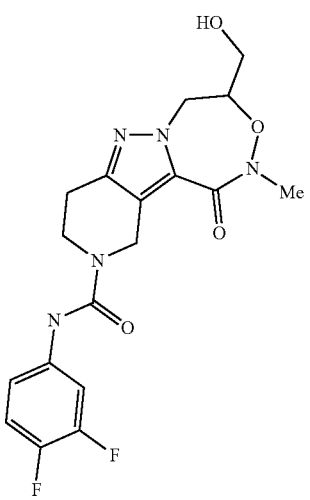 [SMILES: CN1OC(CO)Cn2nc3c(c2C1=O)CN(C(=O)Nc1ccc(F)c(F)c1)CC3]
006
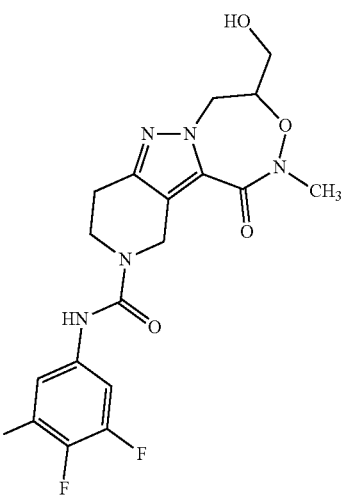

TABLE 1-continued
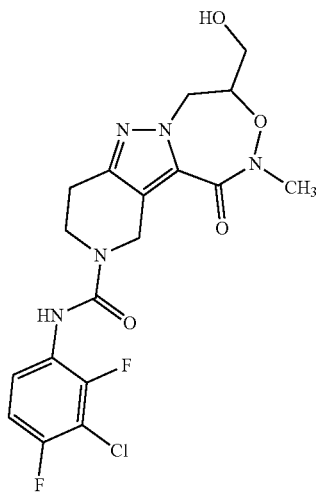 [SMILES: CN1OC(CO)Cn2nc3c(c2C1=O)CN(C(=O)Nc1ccc(F)c(Cl)c1F)CC3] 007
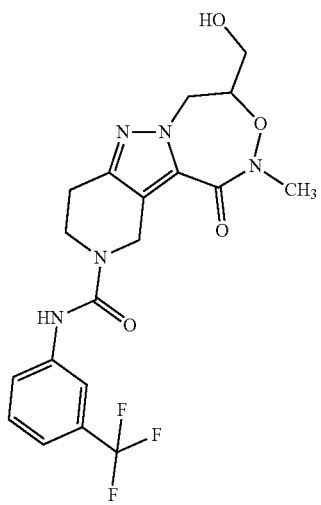 [SMILES: CN1OC(CO)Cn2nc3c(c2C1=O)CN(C(=O)Nc1cccc(C(F)(F)F)c1)CC3] 008
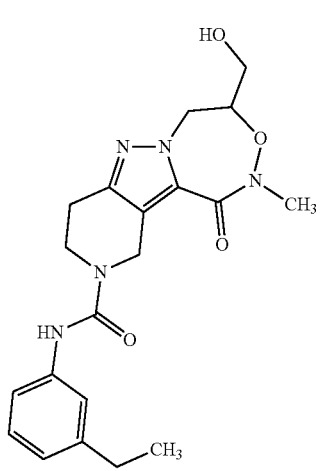 [SMILES: CCc1cccc(NC(=O)N2CCc3nn4c(c3C2)C(=O)N(C)OC(CO)C4)c1] 009
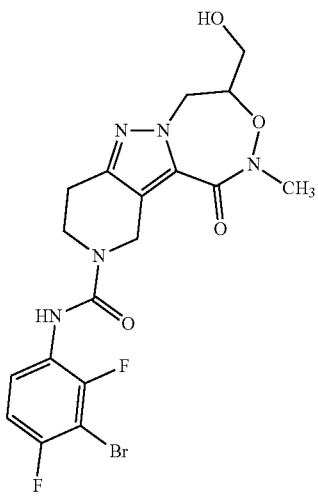 [SMILES: CN1OC(CO)Cn2nc3c(c2C1=O)CN(C(=O)Nc1ccc(F)c(Br)c1F)CC3] 010
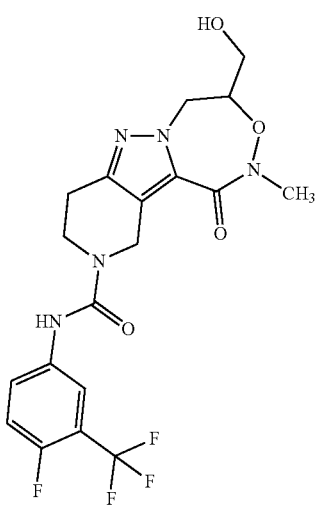 [SMILES: CN1OC(CO)Cn2nc3c(c2C1=O)CN(C(=O)Nc1ccc(F)c(C(F)(F)F)c1)CC3] 011
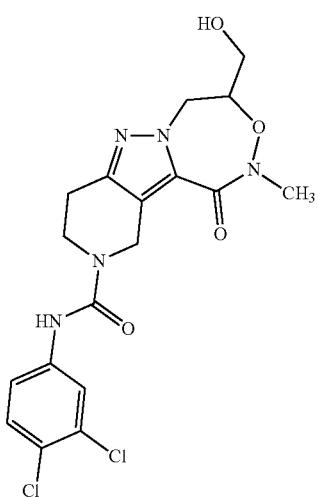 [SMILES: CN1OC(CO)Cn2nc3c(c2C1=O)CN(C(=O)Nc1ccc(Cl)c(Cl)c1)CC3] 012

TABLE 1-continued
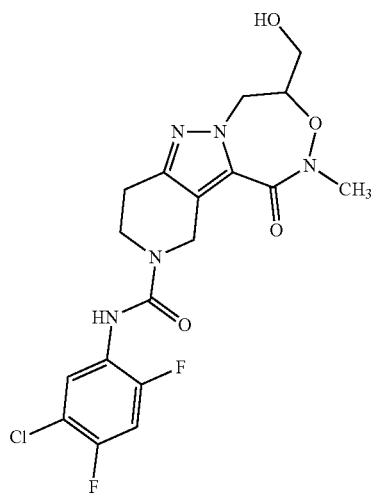 013
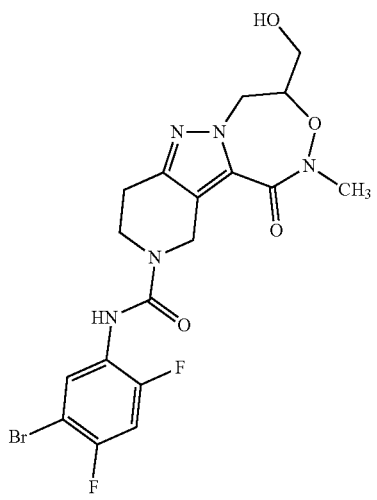 [SMILES: CN1OC(CO)Cn2nc3c(c2C1=O)CN(C(=O)Nc1cc(Cl)c(F)cc1F)CC3] 014
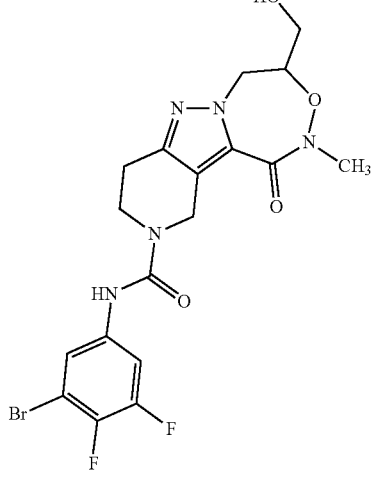 015
TABLE 1-continued
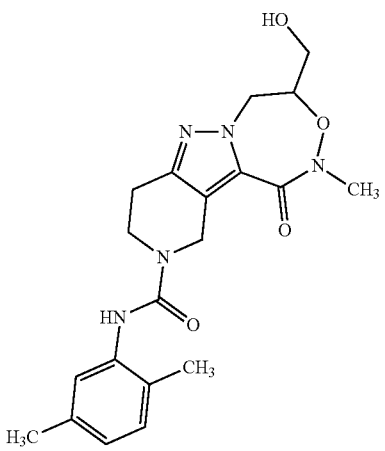 016
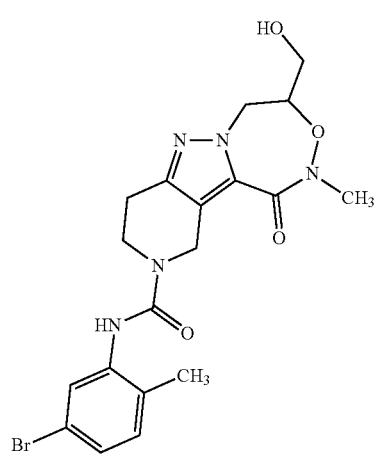 [SMILES: Cc1ccc(Br)cc1NC(=O)N1CCc2nn3c(c2C1)C(=O)N(C)OC(CO)C3] 017
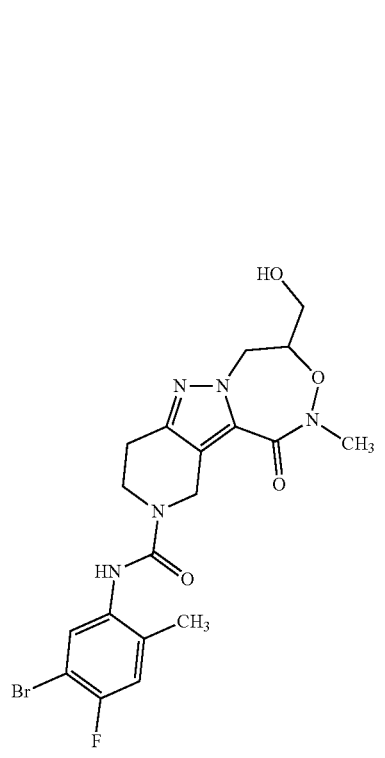 018

TABLE 1-continued
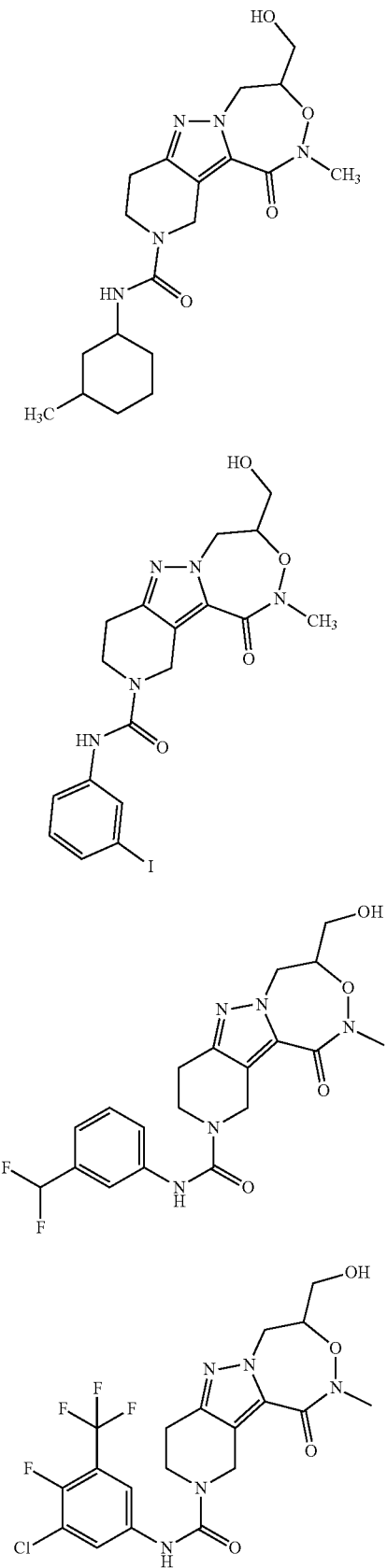
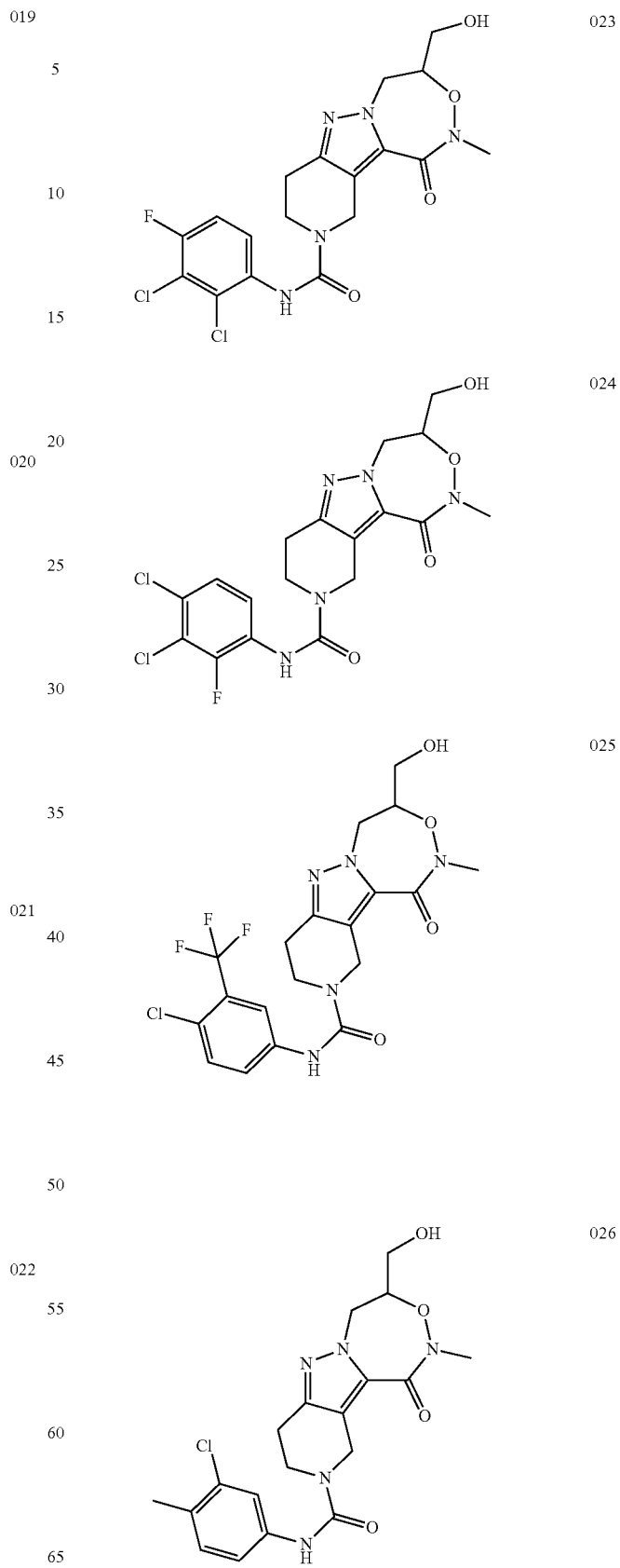

TABLE 1-continued
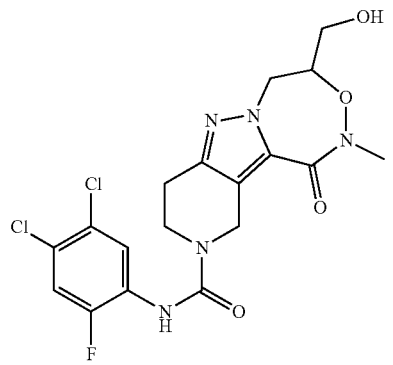 [SMILES: CN1OC(CO)Cn2nc3c(c2C1=O)CN(C(=O)Nc1cc(Cl)c(Cl)cc1F)CC3] 027
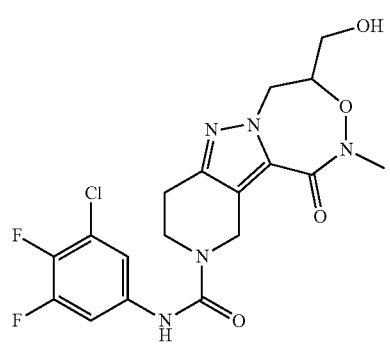 [SMILES: CN1OC(CO)Cn2nc3c(c2C1=O)CN(C(=O)Nc1cc(F)c(F)c(Cl)c1)CC3] 028
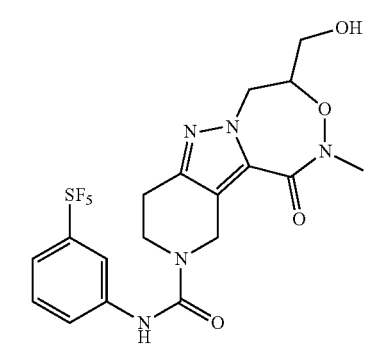 029
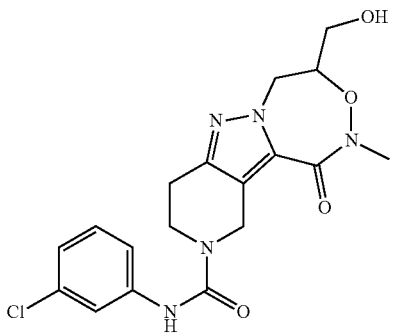 [SMILES: CN1OC(CO)Cn2nc3c(c2C1=O)CN(C(=O)Nc1cccc(Cl)c1)CC3] 030
TABLE 1-continued
031
106
032
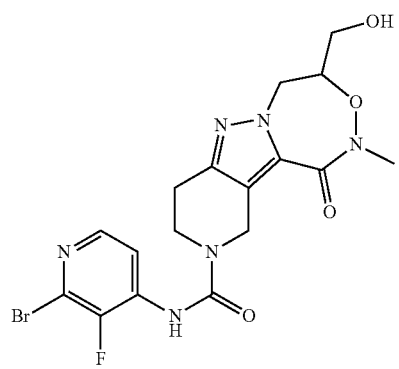 [SMILES: CN1OC(CO)Cn2nc3c(c2C1=O)CN(C(=O)Nc1ccnc(Br)c1F)CC3] 033

TABLE 1-continued
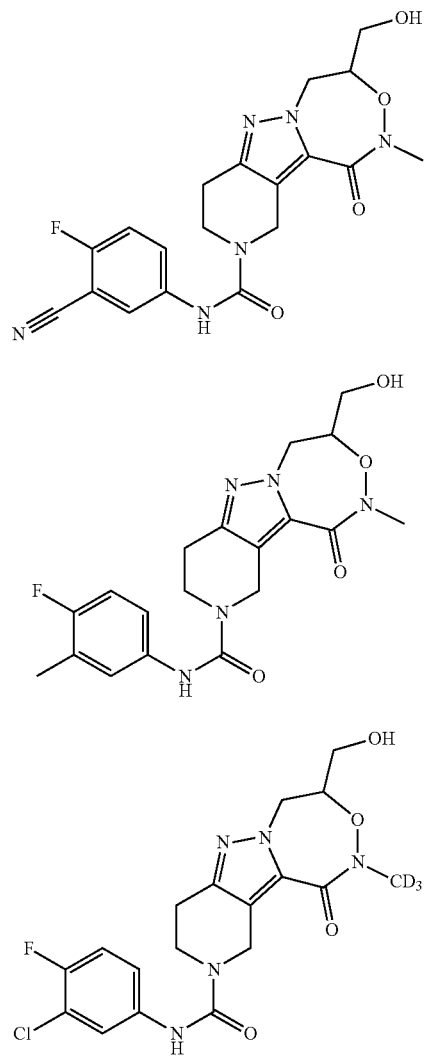
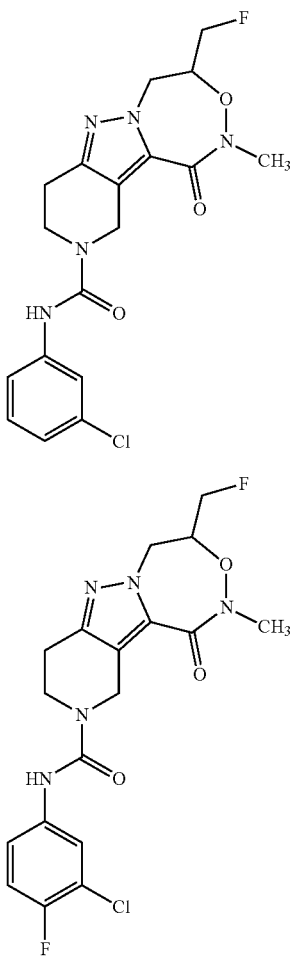

TABLE 1-continued

| | |
|---|---|
| 040 | 043 |
| 041 | 044 |
| 042 | 045 |

TABLE 1-continued
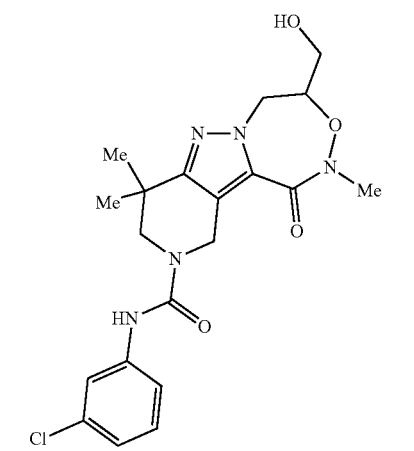 [SMILES: CN1OC(CO)Cn2nc3c(c2C1=O)CN(C(=O)Nc1cccc(Cl)c1)CC3(C)C]
046
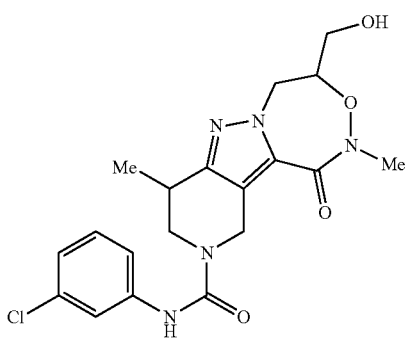 [SMILES: CC1CN(C(=O)Nc2cccc(Cl)c2)Cc2c1nn1c2C(=O)N(C)OC(CO)C1]
047
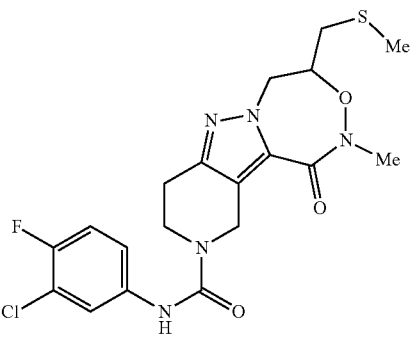 [SMILES: CSCC1Cn2nc3c(c2C(=O)N(C)O1)CN(C(=O)Nc1ccc(F)c(Cl)c1)CC3]
048
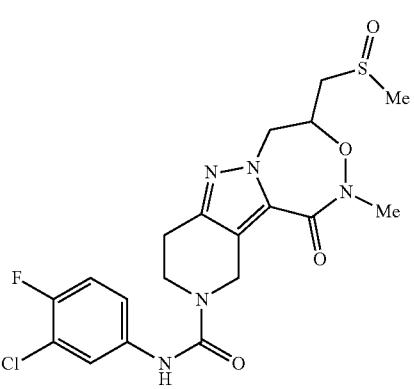 [SMILES: CN1OC(CS(C)=O)Cn2nc3c(c2C1=O)CN(C(=O)Nc1ccc(F)c(Cl)c1)CC3]
049
TABLE 1-continued
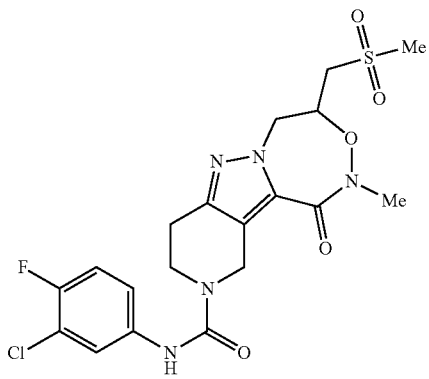 [SMILES: CN1OC(CS(C)(=O)=O)Cn2nc3c(c2C1=O)CN(C(=O)Nc1ccc(F)c(Cl)c1)CC3]
050
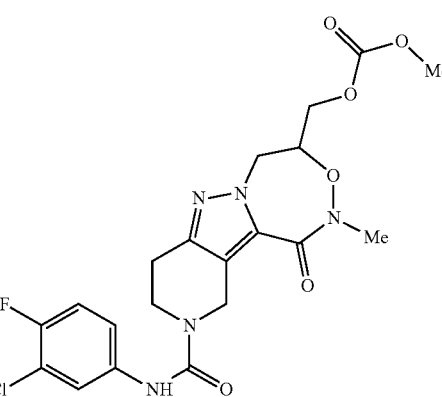
051
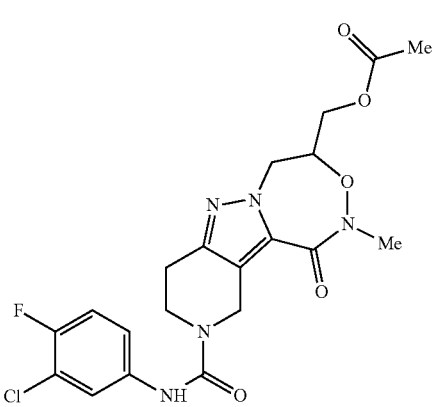 [SMILES: CC(=O)OCC1Cn2nc3c(c2C(=O)N(C)O1)CN(C(=O)Nc1ccc(F)c(Cl)c1)CC3]
052
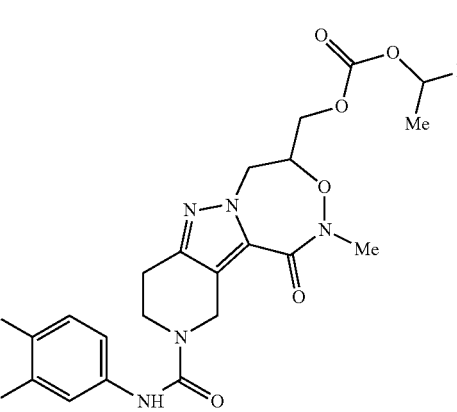
053

TABLE 1-continued
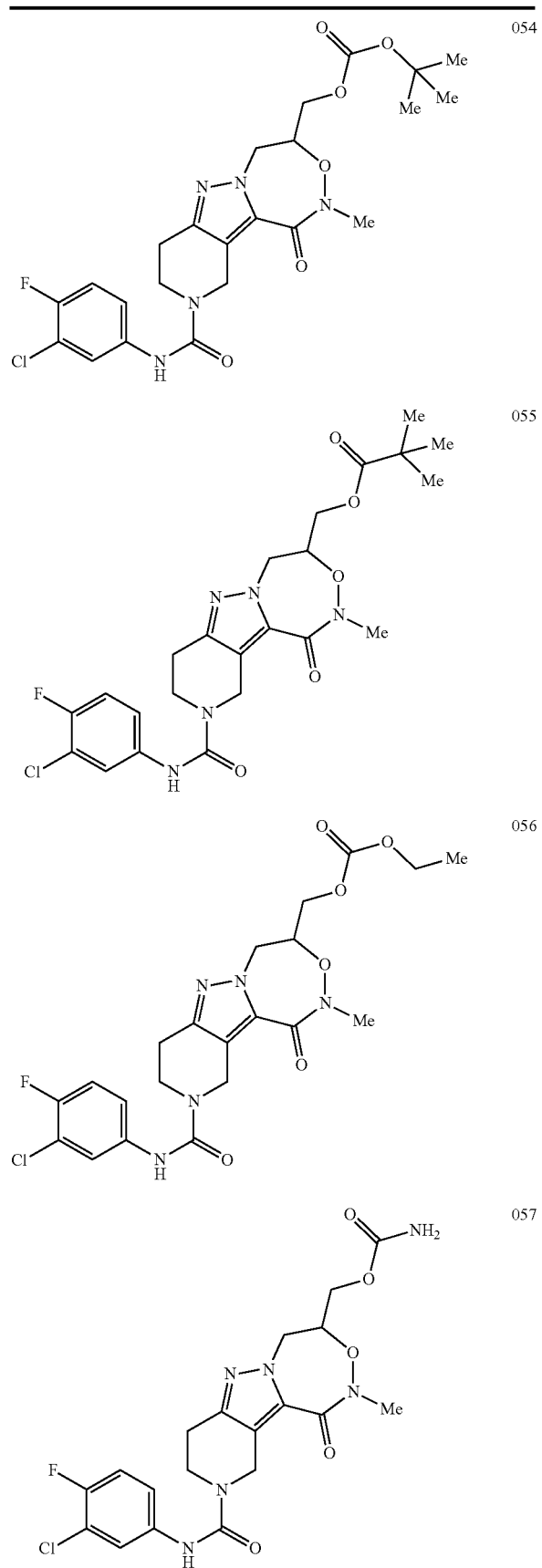
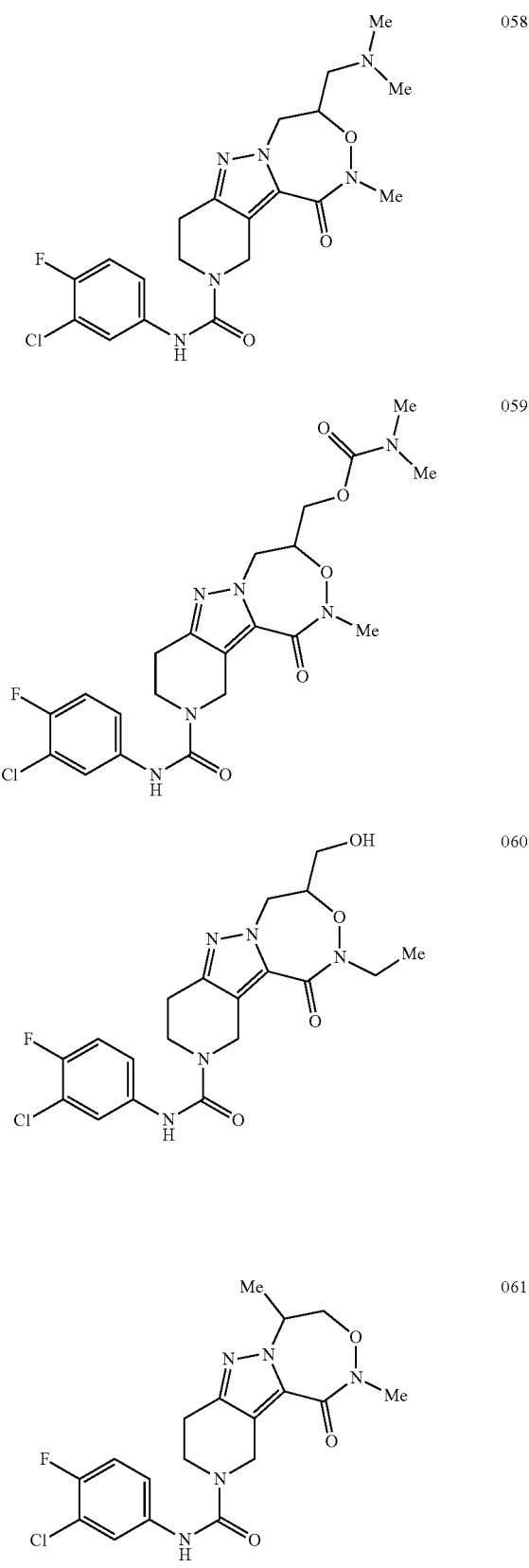

TABLE 1-continued
| | |
|---|---|
| 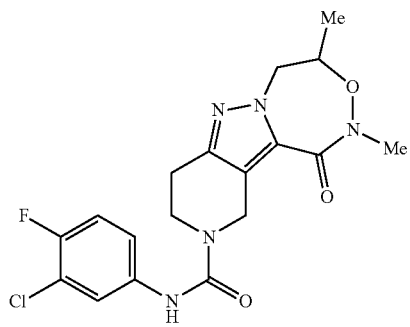 [SMILES: CC1Cn2nc3c(c2C(=O)N(C)O1)CN(C(=O)Nc1ccc(F)c(Cl)c1)CC3] 062 | 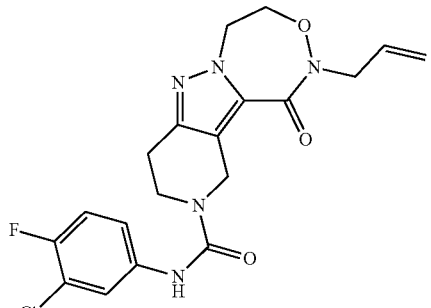 067 |
| 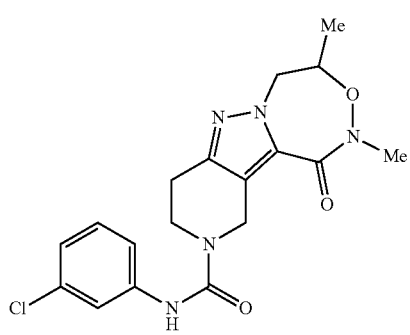 [SMILES: CC1Cn2nc3c(c2C(=O)N(C)O1)CN(C(=O)Nc1cccc(Cl)c1)CC3] 063 | 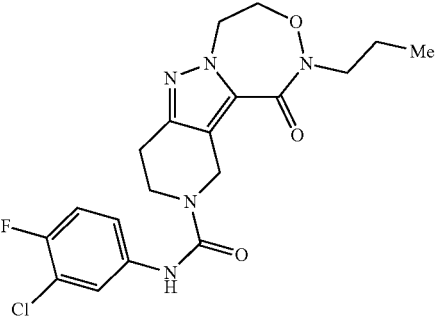 068 |
| 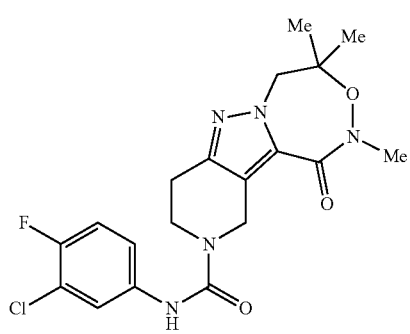 [SMILES: CN1OC(C)(C)Cn2nc3c(c2C1=O)CN(C(=O)Nc1ccc(F)c(Cl)c1)CC3] 064 | 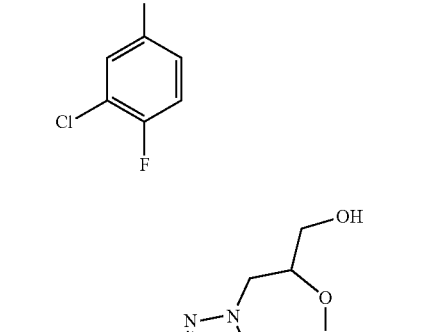 069 |
| 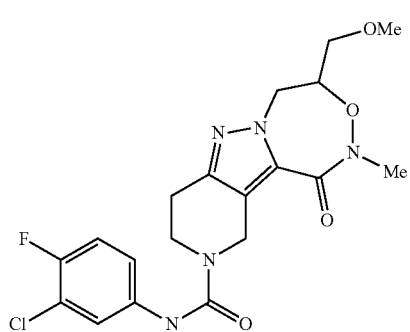 065 | 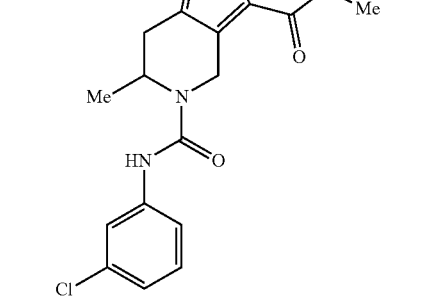 070 |
| 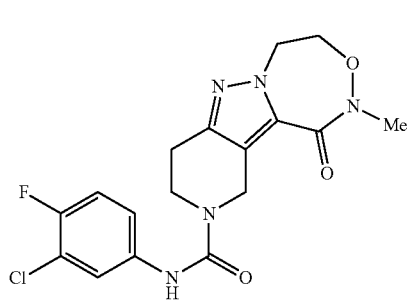 [SMILES: CN1OCCn2nc3c(c2C1=O)CN(C(=O)Nc1ccc(F)c(Cl)c1)CC3] 066 | |

| | |
|---|---|
| 071 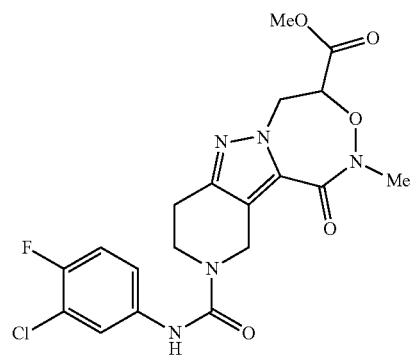 [SMILES: COC(=O)C1Cn2nc3c(c2C(=O)N(C)O1)CN(C(=O)Nc1ccc(F)c(Cl)c1)CC3] | 075 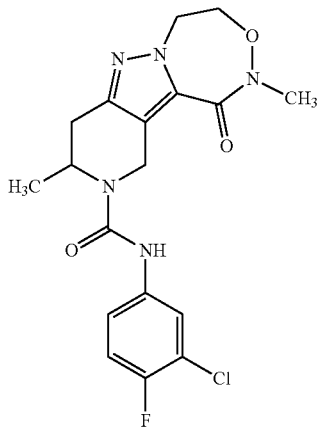 |
| 072 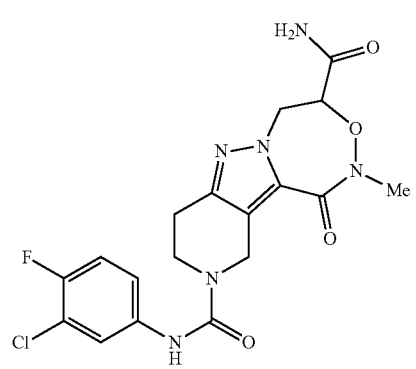 [SMILES: CN1OC(C(N)=O)Cn2nc3c(c2C1=O)CN(C(=O)Nc1ccc(F)c(Cl)c1)CC3] | 076 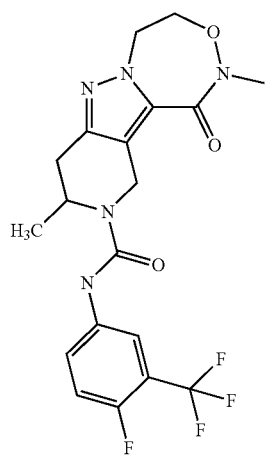 |
| 073 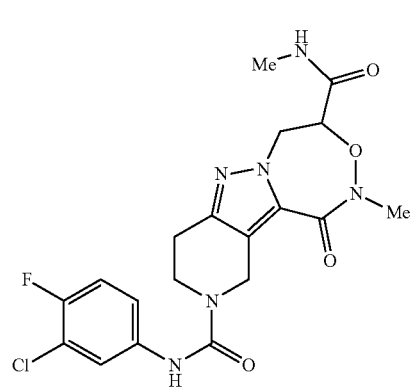 [SMILES: CNC(=O)C1Cn2nc3c(c2C(=O)N(C)O1)CN(C(=O)Nc1ccc(F)c(Cl)c1)CC3] | 077 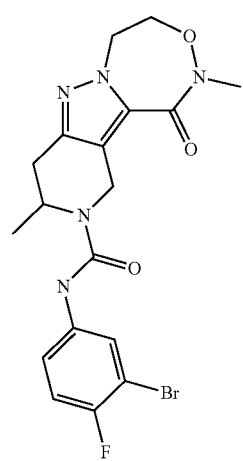 |
| 074 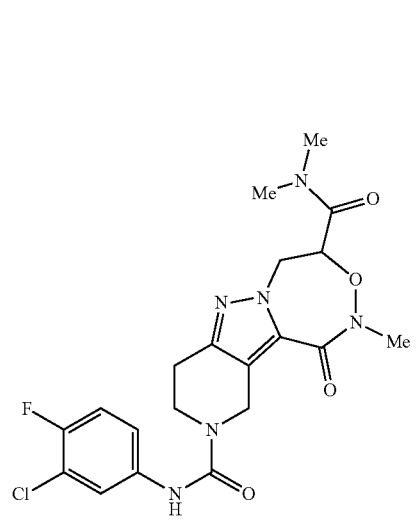 [SMILES: CN(C)C(=O)C1Cn2nc3c(c2C(=O)N(C)O1)CN(C(=O)Nc1ccc(F)c(Cl)c1)CC3] | |

TABLE 1-continued
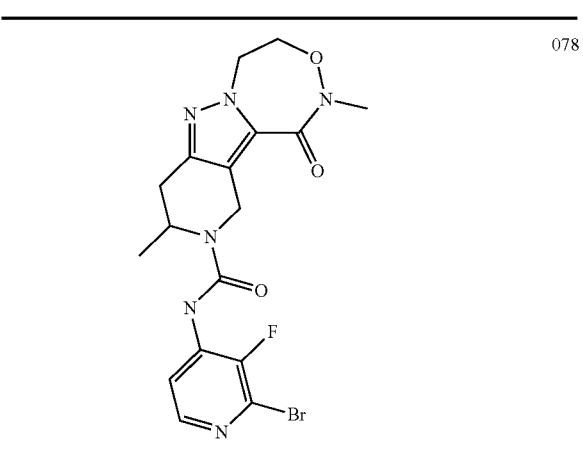
078
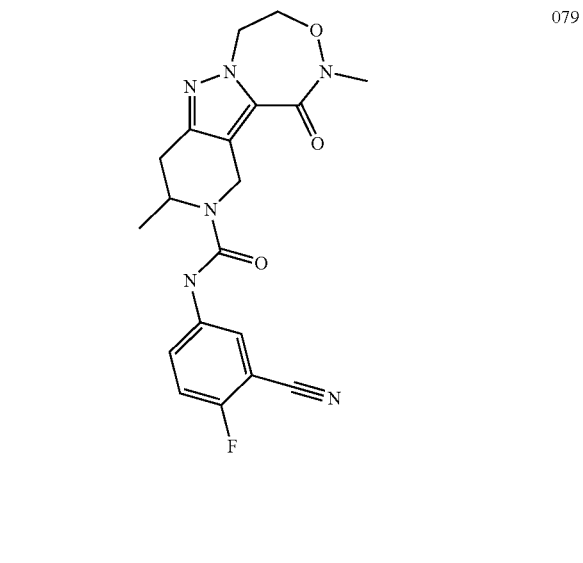
079
080
TABLE 1-continued
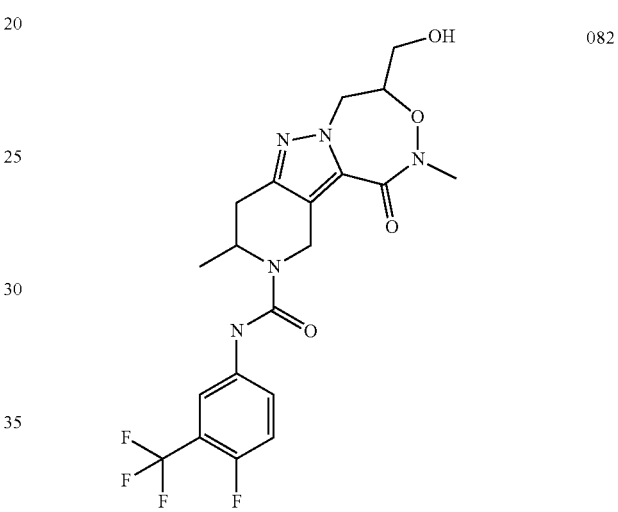
081
082
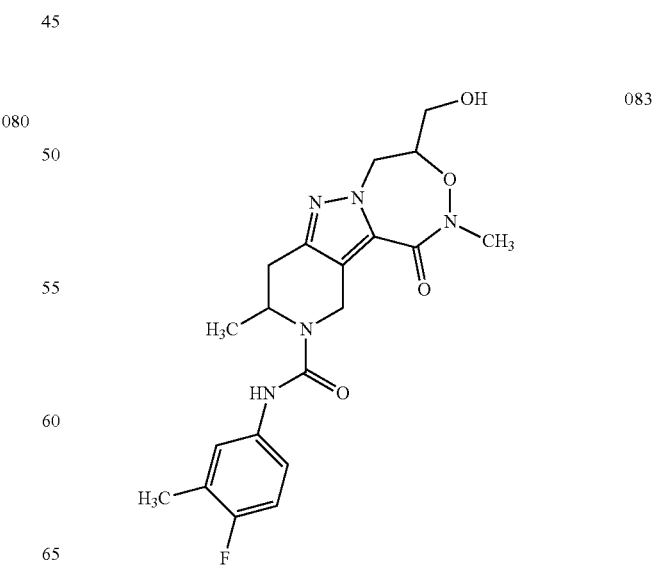
083

TABLE 1-continued
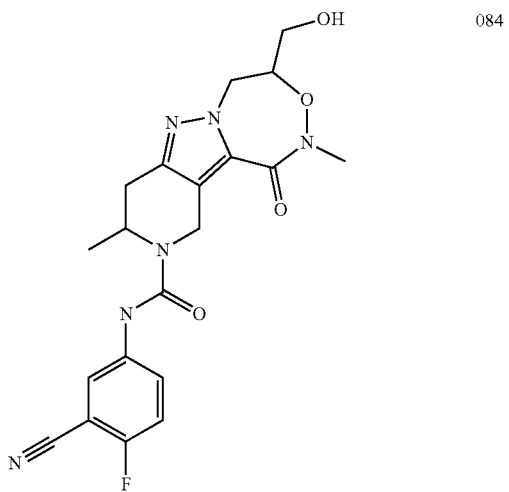
084
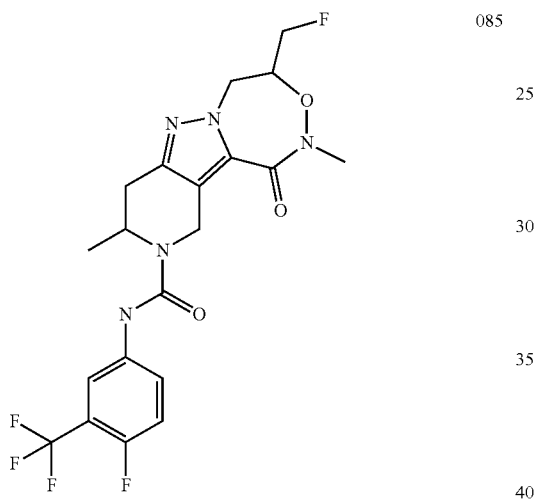
085
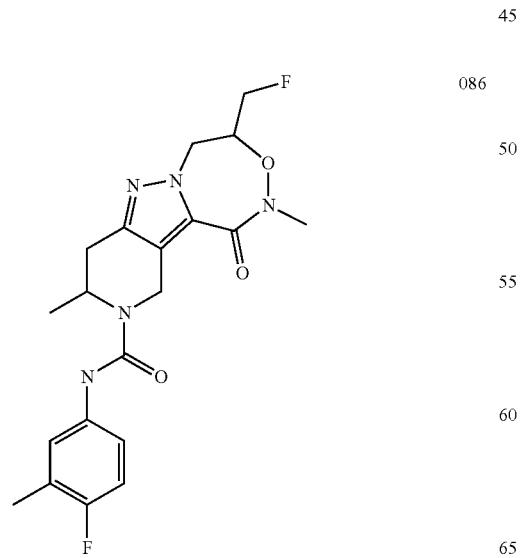
086
TABLE 1-continued
087
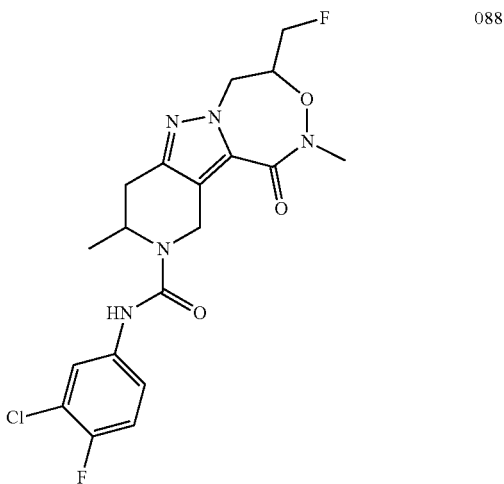
088
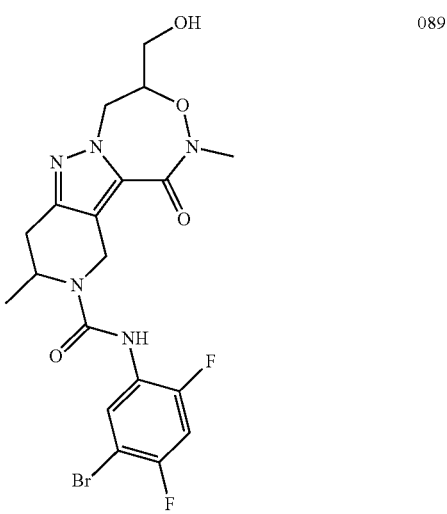
089

TABLE 1-continued
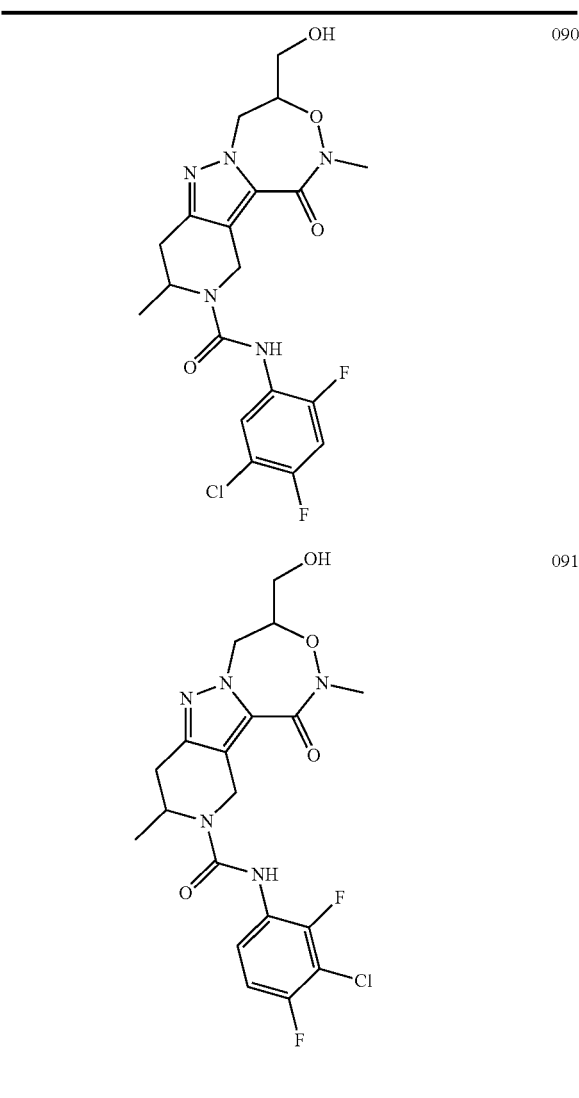
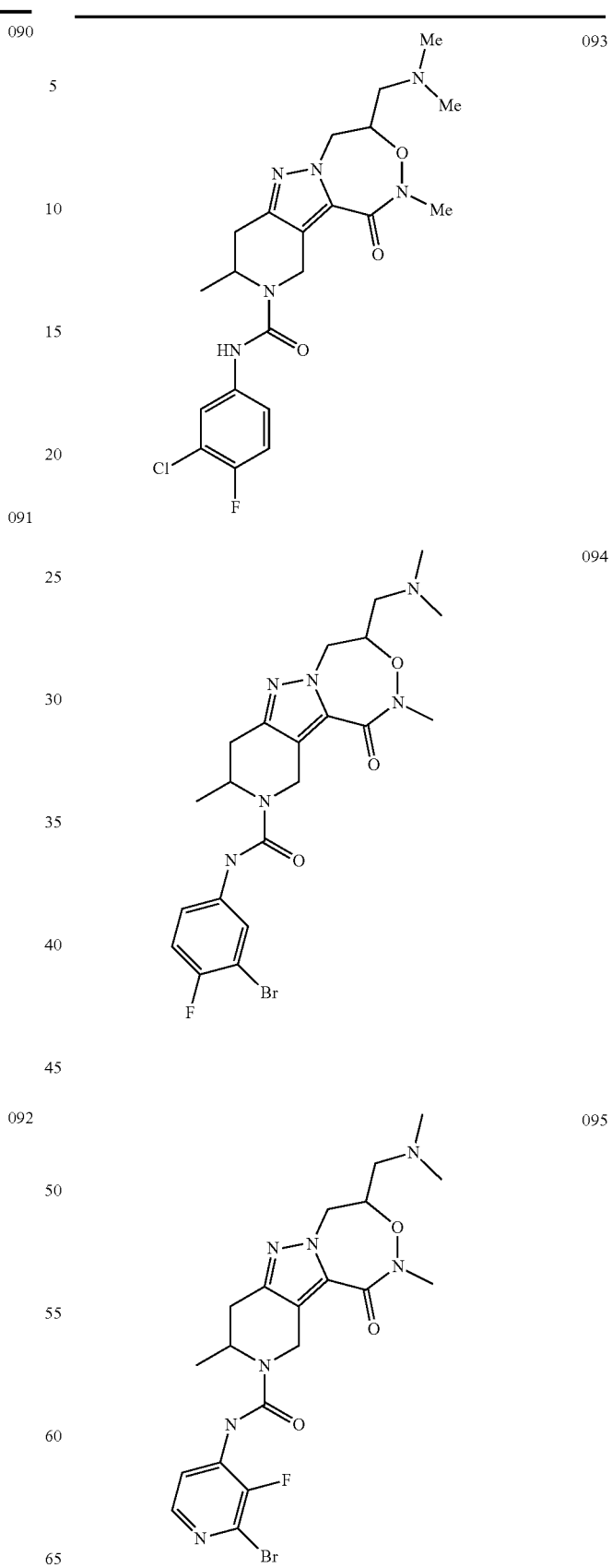

TABLE 1-continued
096 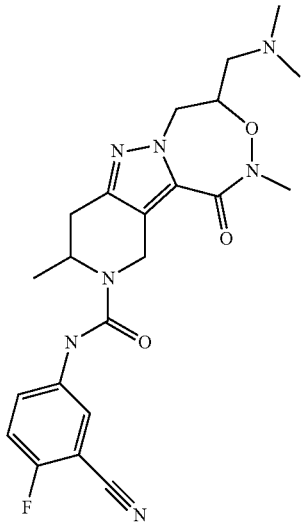 [SMILES: CC1Cc2nn3c(c2CN1C(=O)Nc1ccc(F)c(C#N)c1)C(=O)N(C)OC(CN(C)C)C3]
097 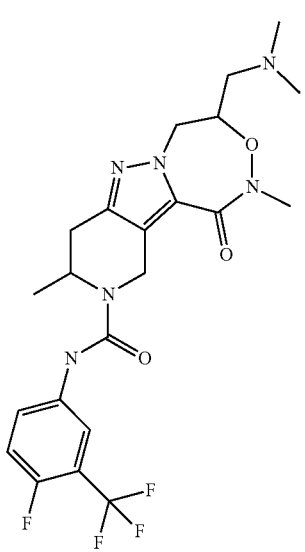 [SMILES: CC1Cc2nn3c(c2CN1C(=O)Nc1ccc(F)c(C(F)(F)F)c1)C(=O)N(C)OC(CN(C)C)C3]
098 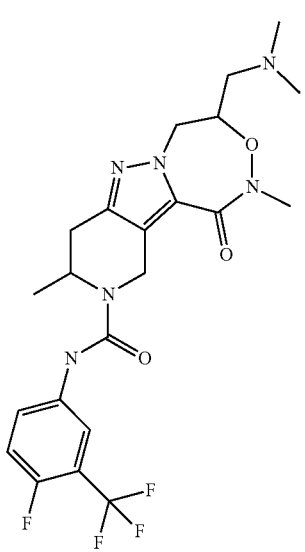 [SMILES: CC1Cc2nn3c(c2CN1C(=O)Nc1ccc(F)c(C(F)(F)F)c1)C(=O)N(C)OC(CN(C)C)C3]
099 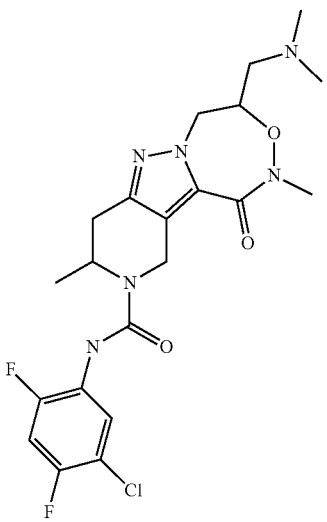 [SMILES: CC1Cc2nn3c(c2CN1C(=O)Nc1cc(Cl)c(F)cc1F)C(=O)N(C)OC(CN(C)C)C3]
100 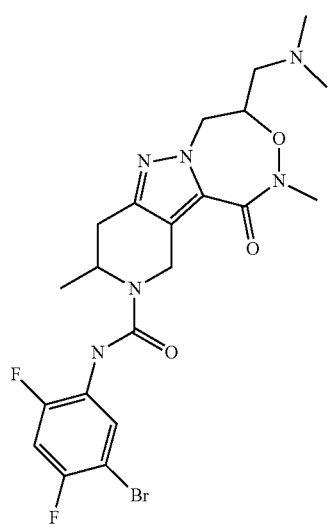 [SMILES: CC1Cc2nn3c(c2CN1C(=O)Nc1cc(Br)c(F)cc1F)C(=O)N(C)OC(CN(C)C)C3]
101 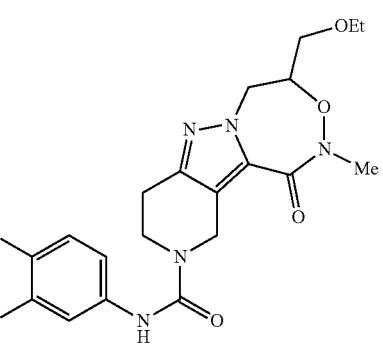

TABLE 1-continued

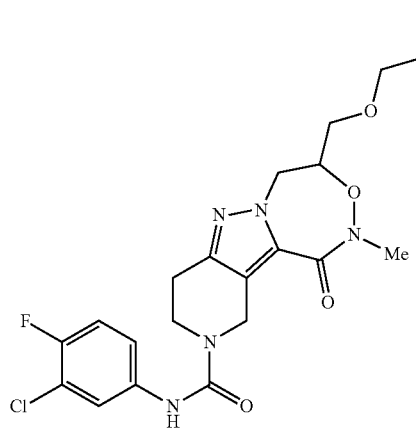
102

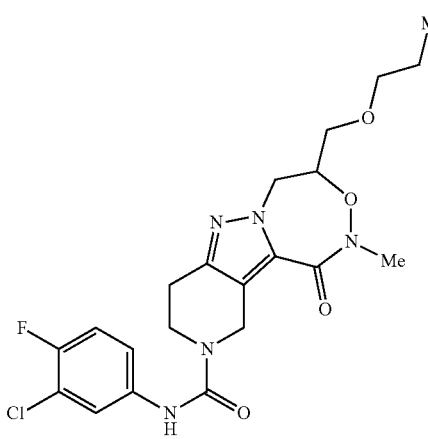
103

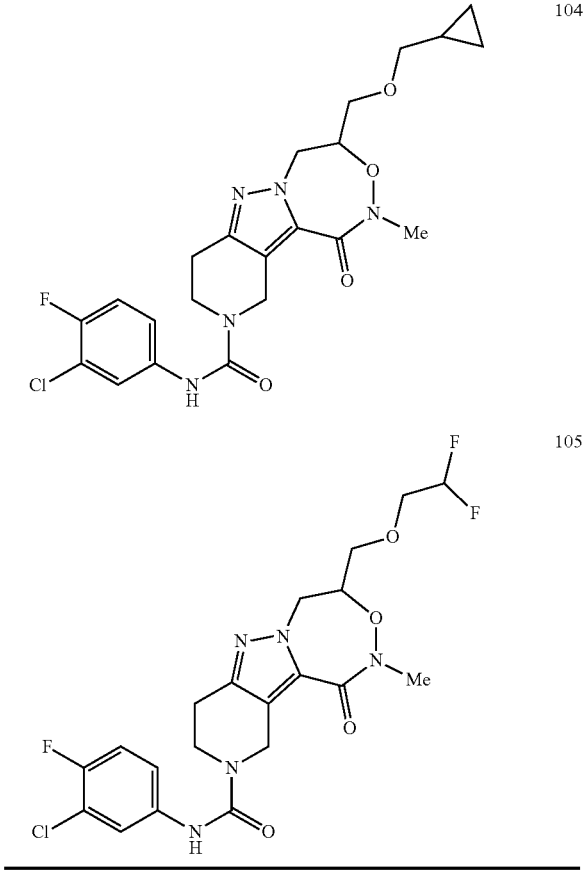
104

105

In an embodiment, compounds of Formulas I and II are selected from:

| Compound ID | Compound Name |
|---|---|
| 001 | N-(3-bromophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |
| 002 | 4-(hydroxymethyl)-2-methyl-1-oxo-N-(m-tolyl)-1,4,5,8,9,11-hexahydropyrido[4',3':3,4]pyrazolo[5,1-d][1,2,5]oxadiazepine-10(2H)-carboxamide |
| 003 | N-(2-chloro-3-fluoropyridin-4-yl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |
| 004 | N-(3-bromo-2-fluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |
| 005 | N-(3,4-difluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |
| 006 | 4-(hydroxymethyl)-2-methyl-1-oxo-N-(3,4,5-trifluorophenyl)-1,4,5,8,9,11-hexahydropyrido[4',3':3,4]pyrazolo[5,1-d][1,2,5]oxadiazepine-10(2H)-carboxamide |
| 007 | N-(3-chloro-2,4-difluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |
| 008 | 4-(hydroxymethyl)-2-methyl-1-oxo-N-(3-(trifluoromethyl)phenyl)-1,4,5,8,9,11-hexahydropyrido[4',3':3,4]pyrazolo[5,1-d][1,2,5]oxadiazepine-10(2H)-carboxamide |
| 009 | N-(3-ethylphenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |
| 010 | N-(3-bromo-2,4-difluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |

-continued

| Compound ID | Compound Name |
|---|---|
| 011_E1 | (S*)-N-(4-fluoro-3-(trifluoromethyl)phenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |
| 011_E2 | (R*)-N-(4-fluoro-3-(trifluoromethyl)phenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |
| 012 | N-(3,4-dichlorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |
| 013 | N-(5-chloro-2,4-difluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |
| 014 | N-(5-bromo-2,4-difluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |
| 015 | N-(3-bromo-4,5-difluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |
| 016 | N-(2,5-dimethylphenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |
| 017 | N-(5-bromo-2-methylphenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |
| 018 | N-(5-bromo-4-fluoro-2-methylphenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |
| 019 | 4-(hydroxymethyl)-2-methyl-N-(3-methylcyclohexyl)-1-oxo-1,4,5,8,9,11-hexahydropyrido[4',3':3,4]pyrazolo[5,1-d][1,2,5]oxadiazepine-10(2H)-carboxamide |
| 020 | 4-(hydroxymethyl)-N-(3-iodophenyl)-2-methyl-1-oxo-1,4,5,8,9,11-hexahydropyrido[4',3':3,4]pyrazolo[5,1-d][1,2,5]oxadiazepine-10(2H)-carboxamide |
| 021 | N-(3-(difluoromethyl)phenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |
| 022 | N-(3-chloro-4-fluoro-5-(trifluoromethyl)phenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |
| 023 | N-(2,3-dichloro-4-fluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |
| 024 | N-(3,4-dichloro-2-fluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |
| 025 | N-(4-chloro-3-(trifluoromethyl)phenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |
| 026 | N-(3-chloro-4-methylphenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |
| 027 | N-(4,5-dichloro-2-fluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |
| 028_E1 | (S*)-N-(3-chloro-4,5-difluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |
| 029 | 4-(hydroxymethyl)-2-methyl-1-oxo-N-(3-(pentafluoro-16-sulfanyl)phenyl)-1,4,5,8,9,11-hexahydropyrido[4',3':3,4]pyrazolo[5,1-d][1,2,5]oxadiazepine-10(2H)-carboxamide |
| 030 | N-(3-chlorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |
| 031_E1 | (S*)-N-(3-chloro-4-fluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |
| 031_E2 | (R*)-N-(3-chloro-4-fluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |
| 032_E1 | (S*)-N-(3-bromo-4-fluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |
| 033_E1 | (S*)-N-(2-bromo-3-fluoropyridin-4-yl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |

-continued

| Compound ID | Compound Name |
|---|---|
| 034_E1 | (S*)-N-(3-cyano-4-fluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |
| 035_E1 | (S*)-N-(4-fluoro-3-methylphenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |
| 036 | 4-(fluoromethyl)-2-methyl-1-oxo-N-(3-(trifluoromethyl)phenyl)-1,4,5,8,9,11-hexahydropyrido[4',3':3,4]pyrazolo[5,1-d][1,2,5]oxadiazepine-10(2H)-carboxamide |
| 037_E1 | (S*)-N-(3-chlorophenyl)-4-(fluoromethyl)-2-methyl-1-oxo-1,4,5,8,9,11-hexahydropyrido[4',3':3,4]pyrazolo[5,1-d][1,2,5]oxadiazepine-10(2H)-carboxamide |
| 038_E1 | (S*)-N-(3-chloro-4-fluorophenyl)-4-(fluoromethyl)-2-methyl-1-oxo-1,4,5,8,9,11-hexahydropyrido[4',3':3,4]pyrazolo[5,1-d][1,2,5]oxadiazepine-10(2H)-carboxamide |
| 039_E1 | (S*)-N-(4-fluoro-3-(trifluoromethyl)phenyl)-4-(fluoromethyl)-2-methyl-1-oxo-1,4,5,8,9,11-hexahydropyrido[4',3':3,4]pyrazolo[5,1-d][1,2,5]oxadiazepine-10(2H)-carboxamide |
| 040_E1 | (S*)-N-(3-bromo-4-fluorophenyl)-4-(fluoromethyl)-2-methyl-1-oxo-1,4,5,8,9,11-hexahydropyrido[4',3':3,4]pyrazolo[5,1-d][1,2,5]oxadiazepine-10(2H)-carboxamide |
| 041_E1 | (S*)-N-(2-bromo-3-fluoropyridin-4-yl)-4-(fluoromethyl)-2-methyl-1-oxo-1,4,5,8,9,11-hexahydropyrido[4',3':3,4]pyrazolo[5,1-d][1,2,5]oxadiazepine-10(2H)-carboxamide |
| 042_E1 | (S*)-N-(3-cyano-4-fluorophenyl)-4-(fluoromethyl)-2-methyl-1-oxo-1,4,5,8,9,11-hexahydropyrido[4',3':3,4]pyrazolo[5,1-d][1,2,5]oxadiazepine-10(2H)-carboxamide |
| 043_E1 | (S*)-N-(4-fluoro-3-methylphenyl)-4-(fluoromethyl)-2-methyl-1-oxo-1,4,5,8,9,11-hexahydropyrido[4',3':3,4]pyrazolo[5,1-d][1,2,5]oxadiazepine-10(2H)-carboxamide |
| 044_E1 | (S*)-N-(3-chloro-4,5-difluorophenyl)-4-(fluoromethyl)-2-methyl-1-oxo-1,4,5,8,9,11-hexahydropyrido[4',3':3,4]pyrazolo[5,1-d][1,2,5]oxadiazepine-10(2H)-carboxamide |
| 045 | N-(3-chloro-4-fluorophenyl)-4-(hydroxymethyl)-N,2-dimethyl-1-oxo-1,4,5,8,9,11-hexahydropyrido[4',3':3,4]pyrazolo[5,1-d][1,2,5]oxadiazepine-10(2H)-carboxamide |
| 046 | N-(3-chlorophenyl)-4-(hydroxymethyl)-2,8,8-trimethyl-1-oxo-1,4,5,8,9,11-hexahydropyrido[4',3':3,4]pyrazolo[5,1-d][1,2,5]oxadiazepine-10(2H)-carboxamide |
| 047 | N-(3-chlorophenyl)-4-(hydroxymethyl)-2,8-dimethyl-1-oxo-1,4,5,8,9,11-hexahydropyrido[4',3':3,4]pyrazolo[5,1-d][1,2,5]oxadiazepine-10(2H)-carboxamide |
| 048 | N-(3-chloro-4-fluoro-phenyl)-2-methyl-4-(methylsulfanylmethyl)-1-oxo-5,8,9,11-tetrahydro-4H-pyrido[2,3]pyrazolo[2,4-d][1,2,5]oxadiazepine-10-carboxamide |
| 049_E1 | (S*)-N-(3-chloro-4-fluorophenyl)-2-methyl-4-(((S*)-methylsulfinyl)methyl)-1-oxo-1,4,5,8,9,11-hexahydropyrido[4',3':3,4]pyrazolo[5,1-d][1,2,5]oxadiazepine-10(2H)-carboxamide |
| 049_E2 | (S*)-N-(3-chloro-4-fluorophenyl)-2-methyl-4-(((R*)-methylsulfinyl)methyl)-1-oxo-1,4,5,8,9,11-hexahydropyrido[4',3':3,4]pyrazolo[5,1-d][1,2,5]oxadiazepine-10(2H)-carboxamide |
| 049_E3 | (R*)-N-(3-chloro-4-fluorophenyl)-2-methyl-4-(((R*)-methylsulfinyl)methyl)-1-oxo-1,4,5,8,9,11-hexahydropyrido[4',3':3,4]pyrazolo[5,1-d][1,2,5]oxadiazepine-10(2H)-carboxamide |
| 049_E4 | (R*)-N-(3-chloro-4-fluorophenyl)-2-methyl-4-(((S*)-methylsulfinyl)methyl)-1-oxo-1,4,5,8,9,11-hexahydropyrido[4',3':3,4]pyrazolo[5,1-d][1,2,5]oxadiazepine-10(2H)-carboxamide |
| 050 | N-(3-chloro-4-fluorophenyl)-2-methyl-4-((methylsulfonyl)methyl)-1-oxo-1,4,5,8,9,11-hexahydropyrido[4',3':3,4]pyrazolo[5,1-d][1,2,5]oxadiazepine-10(2H)-carboxamide |
| 051 | (10-((3-chloro-4-fluorophenyl)carbamoyl)-2-methyl-1-oxo-1,2,4,5,8,9,10,11-octahydropyrido[4',3':3,4]pyrazolo[5,1-d][1,2,5]oxadiazepin-4-yl)methyl methyl carbonate |
| 052 | (10-((3-chloro-4-fluorophenyl)carbamoyl)-2-methyl-1-oxo-1,2,4,5,8,9,10,11-octahydropyrido[4',3':3,4]pyrazolo[5,1-d][1,2,5]oxadiazepin-4-yl)methyl acetate |
| 053 | (10-((3-chloro-4-fluorophenyl)carbamoyl)-2-methyl-1-oxo-1,2,4,5,8,9,10,11-octahydropyrido[4',3':3,4]pyrazolo[5,1-d][1,2,5]oxadiazepin-4-yl)methyl isopropyl carbonate |
| 054 | tert-butyl((10-((3-chloro-4-fluorophenyl)carbamoyl)-2-methyl-1-oxo-1,2,4,5,8,9,10,11-octahydropyrido[4',3':3,4]pyrazolo[5,1-d][1,2,5]oxadiazepin-4-yl)methyl) carbonate |
| 055 | (10-((3-chloro-4-fluorophenyl)carbamoyl)-2-methyl-1-oxo-1,2,4,5,8,9,10,11-octahydropyrido[4',3':3,4]pyrazolo[5,1-d][1,2,5]oxadiazepin-4-yl)methyl pivalate |

-continued

| Compound ID | Compound Name |
|---|---|
| 056 | (10-((3-chloro-4-fluorophenyl)carbamoyl)-2-methyl-1-oxo-1,2,4,5,8,9,10,11-octahydropyrido[4',3':3,4]pyrazolo[5,1-d][1,2,5]oxadiazepin-4-yl)methyl ethyl carbonate |
| 057 | (10-((3-chloro-4-fluorophenyl)carbamoyl)-2-methyl-1-oxo-1,2,4,5,8,9,10,11-octahydropyrido[4',3':3,4]pyrazolo[5,1-d][1,2,5]oxadiazepin-4-yl)methyl carbamate |
| 058 | N-(3-chloro-4-fluoro-phenyl)-4-[(dimethylamino)methyl]-2-methyl-1-oxo-5,8,9,11-tetrahydro-4H-pyrido[2,3]pyrazolo[2,4-d][1,2,5]oxadiazepine-10-carboxamide |
| 059 | [10-[(3-chloro-4-fluoro-phenyl)carbamoyl]-2-methyl-1-oxo-5,8,9,11-tetrahydro-4H-pyrido[2,3]pyrazolo[2,4-d][1,2,5]oxadiazepin-4-yl]methyl N,N-dimethylcarbamate |
| 060_E1 | (S*)-N-(3-chloro-4-fluorophenyl)-2-ethyl-4-(hydroxymethyl)-1-oxo-1,4,5,8,9,11-hexahydropyrido[4',3':3,4]pyrazolo[5,1-d][1,2,5]oxadiazepine-10(2H)-carboxamide |
| 060_E2 | (R*)-N-(3-chloro-4-fluorophenyl)-2-ethyl-4-(hydroxymethyl)-1-oxo-1,4,5,8,9,11-hexahydropyrido[4',3':3,4]pyrazolo[5,1-d][1,2,5]oxadiazepine-10(2H)-carboxamide |
| 061 | N-(3-chloro-4-fluoro-phenyl)-2,5-dimethyl-1-oxo-5,8,9,11-tetrahydro-4H-pyrido[2,3]pyrazolo[2,4-d][1,2,5]oxadiazepine-10-carboxamide |
| 062 | N-(3-chloro-4-fluorophenyl)-2,4-dimethyl-1-oxo-1,4,5,8,9,11-hexahydropyrido[4',3':3,4]pyrazolo[5,1-d][1,2,5]oxadiazepine-10(2H)-carboxamide |
| 063 | N-(3-chlorophenyl)-2,4-dimethyl-1-oxo-1,4,5,8,9,11-hexahydropyrido[4',3':3,4]pyrazolo[5,1-d][1,2,5]oxadiazepine-10(2H)-carboxamide |
| 064 | N-(3-chloro-4-fluoro-phenyl)-2,4,4-trimethyl-1-oxo-5,8,9,11-tetrahydropyrido[2,3]pyrazolo[2,4-d][1,2,5]oxadiazepine-10-carboxamide |
| 065 | N-(3-chloro-4-fluoro-phenyl)-4-(methoxymethyl)-2-methyl-1-oxo-5,8,9,11-tetrahydro-4H-pyrido[2,3]pyrazolo[2,4-d][1,2,5]oxadiazepine-10-carboxamide |
| 066 | N-(3-chloro-4-fluoro-phenyl)-2-methyl-1-oxo-5,8,9,11-tetrahydro-4H-pyrido[2,3]pyrazolo[2,4-d][1,2,5]oxadiazepine-10-carboxamide |
| 067 | 2-allyl-N-(3-chloro-4-fluoro-phenyl)-1-oxo-5,8,9,11-tetrahydro-4H-pyrido[2,3]pyrazolo[2,4-c][1,2,5]oxadiazepine-10-carboxamide |
| 068 | N-(3-chloro-4-fluoro-phenyl)-1-oxo-2-propyl-5,8,9,11-tetrahydro-4H-pyrido[2,3]pyrazolo[2,4-c][1,2,5]oxadiazepine-10-carboxamide |
| 069_E1 | (4S*,9S*)-N-(3-chloro-4-fluorophenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 069_E2 | (4R*,9S*)-N-(3-chloro-4-fluorophenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 069_E3 | (4R*,9R*)-N-(3-chloro-4-fluorophenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 069_E4 | (4S*,9R*)-N-(3-chloro-4-fluorophenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 070 | N-(3-chloro-4-fluoro-phenyl)-4-(hydroxymethyl)-2,9-dimethyl-1-oxo-5,8,9,11-tetrahydro-4H-pyrido[2,3]pyrazolo[2,4-d][1,2,5]oxadiazepine-10-carboxamide |
| 071 | methyl 10-[(3-chloro-4-fluoro-phenyl)carbamoyl]-2-methyl-1-oxo-5,8,9,11-tetrahydro-4H-pyrido[2,3]pyrazolo[2,4-d][1,2,5]oxadiazepine-4-carboxylate |
| 072 | N10-(3-chloro-4-fluoro-phenyl)-2-methyl-1-oxo-5,8,9,11-tetrahydro-4H-pyrido[2,3]pyrazolo[2,4-d][1,2,5]oxadiazepine-4,10-dicarboxamide |
| 073 | N10-(3-chloro-4-fluoro-phenyl)-N4,2-dimethyl-1-oxo-5,8,9,11-tetrahydro-4H-pyrido[2,3]pyrazolo[2,4-d][1,2,5]oxadiazepine-4,10-dicarboxamide |
| 074 | N10-(3-chloro-4-fluoro-phenyl)-N4,N4,2-trimethyl-1-oxo-5,8,9,11-tetrahydro-4H-pyrido[2,3]pyrazolo[2,4-d][1,2,5]oxadiazepine-4,10-dicarboxamide |
| 075 | (9R)-N-(3-chloro-4-fluoro-phenyl)-2,9-dimethyl-1-oxo-5,8,9,11-tetrahydro-4H-pyrido[2,3]pyrazolo[2,4-d][1,2,5]oxadiazepine-4,10-carboxamide |
| 076 | (R)-N-(4-fluoro-3-(trifluoromethyl)phenyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 077 | (R)-N-(3-bromo-4-fluorophenyl)-2,9-dimethyl-1-oxo-1,4,5,8,9,11-hexahydropyrido[4',3':3,4]pyrazolo[5,1-d][1,2,5]oxadiazepine-10(2H)-carboxamide |

-continued

| Compound ID | Compound Name |
|---|---|
| 078 | (R)-N-(2-bromo-3-fluoropyridin-4-yl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 079 | (R)-N-(3-cyano-4-fluorophenyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 080 | (R)-N-(4-fluoro-3-methylphenyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 081 | (R)-N-(3-chloro-4,5-difluorophenyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 082_E1 | (4S*,9R)-N-(4-fluoro-3-(trifluoromethyl)phenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 082_E2 | (4R*,9R)-N-(4-fluoro-3-(trifluoromethyl)phenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 083_E1 | (4S*,9R)-N-(4-fluoro-3-methylphenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 083_E2 | (4R*,9R)-N-(4-fluoro-3-methylphenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 084_E1 | (4S*,9R)-N-(3-cyano-4-fluorophenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 08_4E2 | (4R*,9R)-N-(3-cyano-4-fluorophenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 085_E1 | (4S*,9R)-N-(4-fluoro-3-(trifluoromethyl)phenyl)-4-(fluoromethyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 085_2 | (4R*,9R)-N-(4-fluoro-3-(trifluoromethyl)phenyl)-4-(fluoromethyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 086_E1 | (4S*,9R)-N-(4-fluoro-3-methylphenyl)-4-(fluoromethyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 086_E2 | (4R*,9R)-N-(4-fluoro-3-methylphenyl)-4-(fluoromethyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 087_E1 | (4S*,9R)-N-(3-cyano-4-fluorophenyl)-4-(fluoromethyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 087_E2 | (4R*,9R)-N-(3-cyano-4-fluorophenyl)-4-(fluoromethyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 088_E1 | (4S*,9R)-N-(3-chloro-4-fluorophenyl)-4-(fluoromethyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 088 | (4R*,9R)-N-(3-chloro-4-fluorophenyl)-4-(fluoromethyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 089_E1 | (4S*,9R)-N-(5-bromo-2,4-difluorophenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 089_E2 | (4R*,9R)-N-(5-bromo-2,4-difluorophenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 090_E1 | (4S*,9R)-N-(5-chloro-2,4-difluorophenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 090_E2 | (4R*,9R)-N-(5-chloro-2,4-difluorophenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 091_E1 | (4S*,9R)-N-(3-chloro-2,4-difluorophenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 091_E2 | (4R*,9R)-N-(3-chloro-2,4-difluorophenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 092_E1 | (4S*,9R)-N-(3-bromo-2,4-difluorophenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide |

-continued

| Compound ID | Compound Name |
| --- | --- |
| 092_E2 | (4R*,9R)-N-(3-bromo-2,4-difluorophenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 093_D1 | (4S*,9R)-N-(3-chloro-4-fluorophenyl)-4-((dimethylamino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 093_D2 | (4R*,9R)-N-(3-chloro-4-fluorophenyl)-4-((dimethylamino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 094_D1 | (4S*,9R)-N-(3-bromo-4-fluorophenyl)-4-((dimethylamino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 094_D2 | (4R*,9R)-N-(3-bromo-4-fluorophenyl)-4-((dimethylamino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 095_D1 | (4S*,9R)-N-(2-bromo-3-fluoropyridin-4-yl)-4-((dimethylamino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide 10(2H)-carboxamide |
| 095_D2 | (4R*,9R)-N-(2-bromo-3-fluoropyridin-4-yl)-4-((dimethylamino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 096_D1 | (4S*,9R)-N-(3-cyano-4-fluorophenyl)-4-((dimethylamino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 096_D2 | (4R*,9R)-N-(3-cyano-4-fluorophenyl)-4-((dimethylamino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 097_D1 | (4S*,9R)-4-((dimethylamino)methyl)-N-(4-fluoro-3-methylphenyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 097_D2 | (4R*,9R)-4-((dimethylamino)methyl)-N-(4-fluoro-3-methylphenyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 098_D1 | (4S*,9R)-4-((dimethylamino)methyl)-N-(4-fluoro-3-(trifluoromethyl)phenyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 098_D2 | (4R*,9R)-4-((dimethylamino)methyl)-N-(4-fluoro-3-(trifluoromethyl)phenyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 099_D1 | (4S*,9R)-N-(5-chloro-2,4-difluorophenyl)-4-((dimethylamino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 099_D2 | (4R*,9R)-N-(5-chloro-2,4-difluorophenyl)-4-((dimethylamino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 100_D1 | (4S*,9R)-N-(5-bromo-2,4-difluorophenyl)-4-((dimethylamino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 100_D2 | (4R*,9R)-N-(5-bromo-2,4-difluorophenyl)-4-((dimethylamino)methyl)-2,9-dimethyl-1-oxo-1,4,5,8,9,11-hexahydropyrido[4',3':3,4]oxadiazepine-10(2H)-carboxamide |
| 101 | N-(3-chloro-4-fluoro-phenyl)-4-(ethoxymethyl)-2-methyl-1-oxo-5,8,9,11-tetrahydro-4H-pyrido[2,3]pyrazolo[2,4-d][1,2,5]oxadiazepine-10-carboxamide |
| 102 | 4-(allyloxymethyl)-N-(3-chloro-4-fluoro-phenyl)-2-methyl-1-oxo-5,8,9,11-tetrahydro-4H-pyrido[2,3]pyrazolo[2,4-d][1,2,5]oxadiazepine-10-carboxamide |
| 103 | N-(3-chloro-4-fluoro-phenyl)-2-methyl-1-oxo-4-(propoxymethyl)-5,8,9,11-tetrahydro-4H-pyrido[2,3]pyrazolo[2,4-d][1,2,5]oxadiazepine-10-carboxamide |
| 104 | N-(3-chloro-4-fluoro-phenyl)-4-(cyclopropylmethoxymethyl)-2-methyl-1-oxo-5,8,9,11-tetrahydro-4H-pyrido[2,4-d][1,2,5]oxadiazepine-10-carboxamide |
| 105 | N-(3-chloro-4-fluoro-phenyl)-4-(2,2-difluoroethoxymethyl)-2-methyl-1-oxo-5,8,9,11-tetrahydro-4H-pyrido[2,3]pyrazolo[2,4-d][1,2,5]oxadiazepine-10-carboxamide |
| 106 | N-(3-chloro-4-fluoro-phenyl)-2-methyl-1-oxo-4-(2,2,2-trifluoroethoxymethyl)-5,8,9,11-tetrahydro-4H-pyrido[2,3]pyrazolo[2,4-d][1,2,5]oxadiazepine-10-carboxamide |
| 107 | N-(3-chloro-4-fluoro-phenyl)-4-(hydroxymethyl)-1-oxo-2-(trideuteriomethyl)-5,8,9,11-tetrahydro-4H-pyrido[2,3]pyrazolo[2,4-d][1,2,5]oxadiazepine-10-carboxamide |

*Pure but unknown enantiomer or diastereomer.

and pharmaceutically acceptable salts thereof.
Certain embodiments of Formulae I and II are shown below in Table 2.
TABLE 2
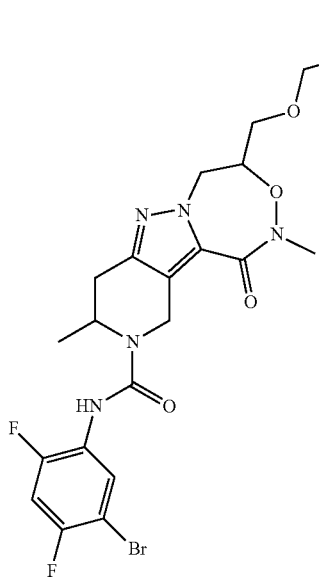 108
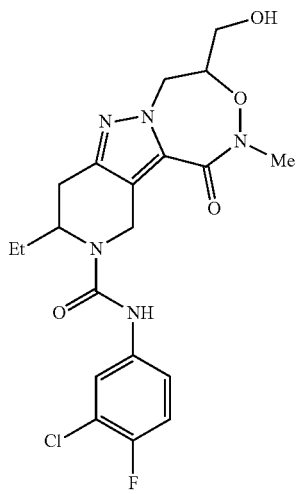 109
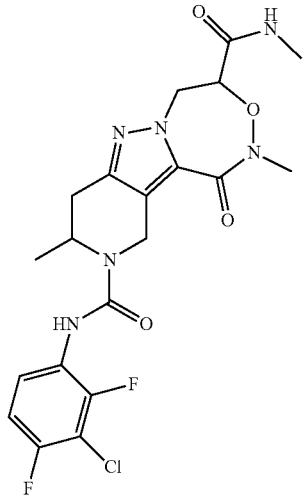 [SMILES: CNC(=O)C1Cn2nc3c(c2C(=O)N(C)O1)CN(C(=O)Nc1ccc(F)c(Cl)c1F)C(C)C3] 110
TABLE 2-continued
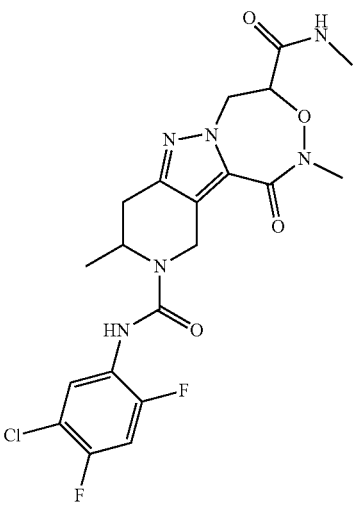 [SMILES: CNC(=O)C1Cn2nc3c(c2C(=O)N(C)O1)CN(C(=O)Nc1cc(Cl)c(F)cc1F)C(C)C3] 111
 112
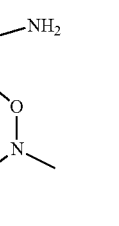 113

TABLE 2-continued
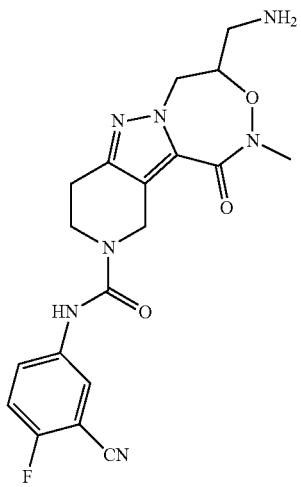 [SMILES: CN1OC(CN)Cn2nc3c(c2C1=O)CN(C(=O)Nc1ccc(F)c(C#N)c1)CC3]
114
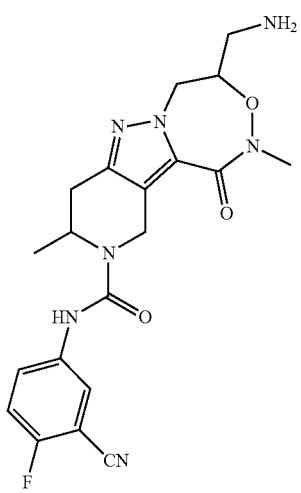 [SMILES: CC1Cc2nn3c(c2CN1C(=O)Nc1ccc(F)c(C#N)c1)C(=O)N(C)OC(CN)C3]
115
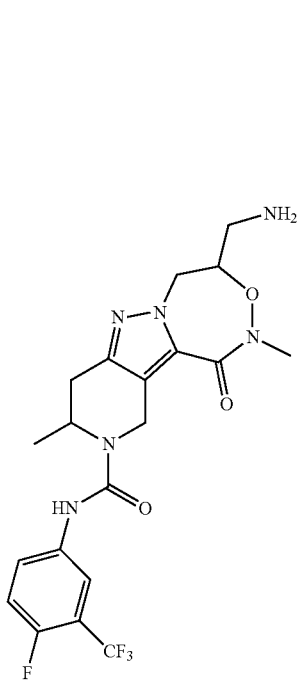 [SMILES: CC1Cc2nn3c(c2CN1C(=O)Nc1ccc(F)c(C(F)(F)F)c1)C(=O)N(C)OC(CN)C3]
116
TABLE 2-continued
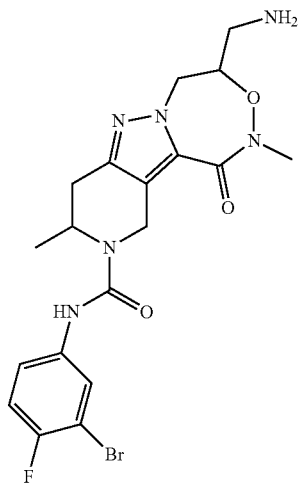 [SMILES: CC1Cc2nn3c(c2CN1C(=O)Nc1ccc(F)c(Br)c1)C(=O)N(C)OC(CN)C3]
117
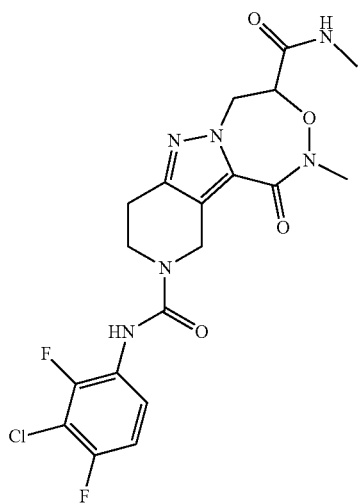 [SMILES: CNC(=O)C1Cn2nc3c(c2C(=O)N(C)O1)CN(C(=O)Nc1ccc(F)c(Cl)c1F)CC3]
118
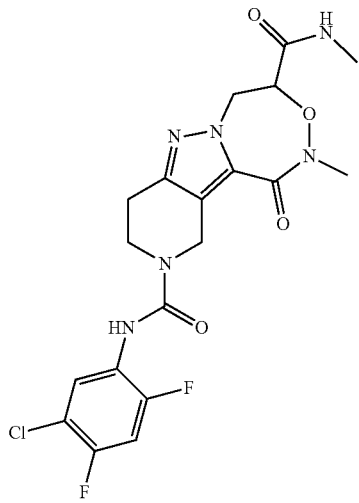 [SMILES: CNC(=O)C1Cn2nc3c(c2C(=O)N(C)O1)CN(C(=O)Nc1cc(Cl)c(F)cc1F)CC3]
119

TABLE 2-continued
120
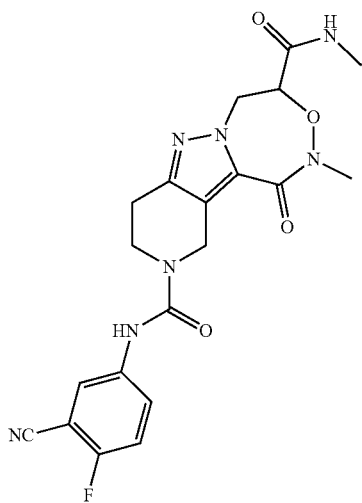 [SMILES: CNC(=O)C1Cn2nc3c(c2C(=O)N(C)O1)CN(C(=O)Nc1ccc(F)c(C#N)c1)CC3]
121
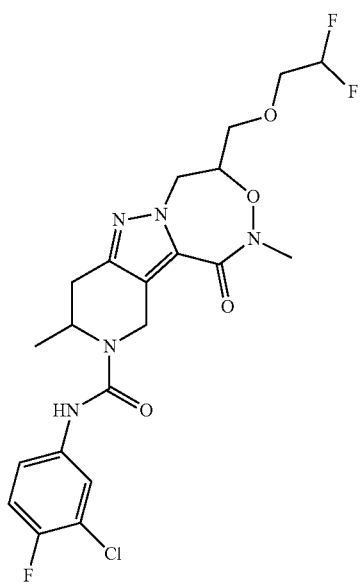 [SMILES: CC1Cc2nn3c(c2CN1C(=O)Nc1ccc(F)c(Cl)c1)C(=O)N(C)OC(COCC(F)F)C3]
TABLE 2-continued
122
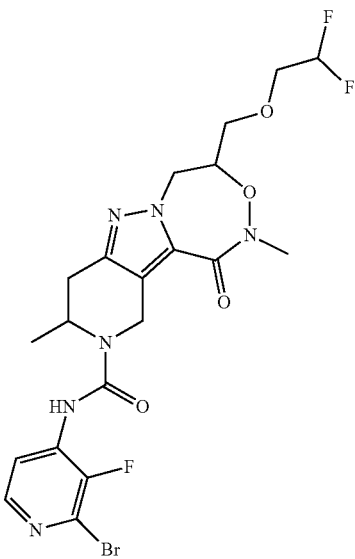 [SMILES: CC1Cc2nn3c(c2CN1C(=O)Nc1ccnc(Br)c1F)C(=O)N(C)OC(COCC(F)F)C3]
123

TABLE 2-continued

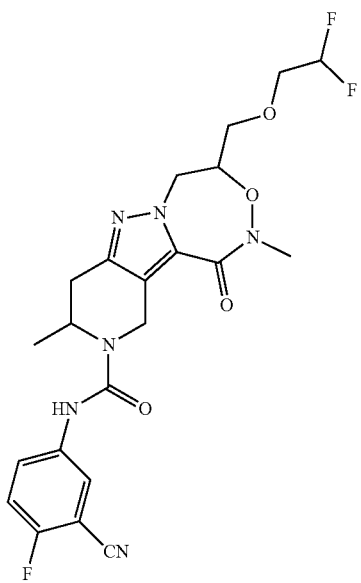 [SMILES: CC1Cc2nn3c(c2CN1C(=O)Nc1ccc(F)c(C#N)c1)C(=O)N(C)OC(COCC(F)F)C3]

124

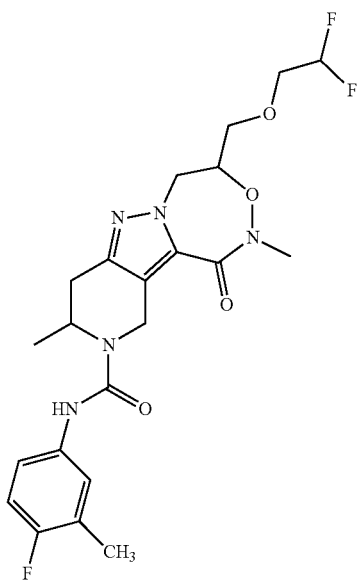 [SMILES: Cc1cc(NC(=O)N2Cc3c(nn4c3C(=O)N(C)OC(COCC(F)F)C4)CC2C)ccc1F]

125

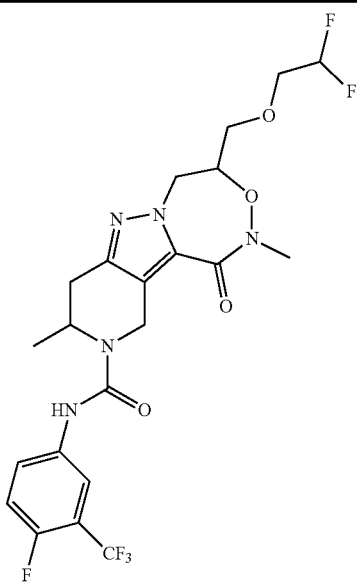

126

127

In an embodiment, compounds of Formulae I and II are selected from:

| Compound ID | Compound Name |
| --- | --- |
| 108_D1 | (4S*,9R)-N-(5-bromo-2,4-difluorophenyl)-4-((2,2-difluoroethoxy)methyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 108_D2 | (4R*,9R)-N-(5-bromo-2,4-difluorophenyl)-4-((2,2-difluoroethoxy)methyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 109_D1 | (4S*,9S*)-N-(3-chloro-4-fluorophenyl)-9-ethyl-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |
| 109_D2 | (4S*,9R*)-N-(3-chloro-4-fluorophenyl)-9-ethyl-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |

| Compound ID | Compound Name |
| --- | --- |
| 109_D3 | (4R*,9R*)-N-(3-chloro-4-fluorophenyl)-9-ethyl-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |
| 109_D4 | (4R*,9S*)-N-(3-chloro-4-fluorophenyl)-9-ethyl-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |
| 110_D1 | (4S*,9R)-N10-(3-chloro-2,4-difluorophenyl)-N4,2,9-trimethyl-1-oxo-1,4,5,8,9,11-hexahydropyrido[4',3':3,4]pyrazolo[5,1-d][1,2,5]oxadiazepine-4,10(2H)-diacarboxamide |
| 110_D2 | (4R*,9R)-N10-(3-chloro-2,4-difluorophenyl)-N4,2,9-trimethyl-1-oxo-1,4,5,8,9,11-hexahydropyrido[4',3':3,4]pyrazolo[5,1-d][1,2,5]oxadiazepine-4,10(2H)-diacarboxamide |
| 111_D1 | (4S*,9R)-N10-(5-chloro-2,4-difluorophenyl)-N4,2,9-trimethyl-1-oxo-1,4,5,8,9,11-hexahydropyrido[4',3':3,4]pyrazolo[5,1-d][1,2,5]oxadiazepine-4,10(2H)-diacarboxamide |
| 111_D2 | (4R*,9R)-N10-(5-chloro-2,4-difluorophenyl)-N4,2,9-trimethyl-1-oxo-1,4,5,8,9,11-hexahydropyrido[4',3':3,4]pyrazolo[5,1-d][1,2,5]oxadiazepine-4,10(2H)-diacarboxamide |
| 112_D1 | (4S*,9R)-N10-(3-cyano-4-fluorophenyl)-N4,2,9-trimethyl-1-oxo-1,4,5,8,9,11-hexahydropyrido[4',3':3,4]pyrazolo[5,1-d][1,2,5]oxadiazepine-4,10(2H)-diacarboxamide |
| 112_D2 | (4R*,9R)-N10-(3-cyano-4-fluorophenyl)-N4,2,9-trimethyl-1-oxo-1,4,5,8,9,11-hexahydropyrido[4',3':3,4]pyrazolo[5,1-d][1,2,5]oxadiazepine-4,10(2H)-diacarboxamide |
| 113 | 4-(aminomethyl)-N-(3-chloro-4-fluoro-phenyl)-2-methyl-1-oxo-5,8,9,11-tetrahydro-4H-pyrido[2,3]pyrazolo[2,4-d][1,2,5]oxadiazepine-10-carboxamide |
| 114_E1 | (S*)-4-(aminomethyl)-N-(3-cyano-4-fluoro-phenyl)-2-methyl-1-oxo-5,8,9,11-tetrahydro-4H-pyrido[2,3]pyrazolo[2,4-d][1,2,5]oxadiazepine-10-carboxamide |
| 115_D1 | (4S*,9R)-4-(aminomethyl)-N-(3-cyano-4-fluorophenyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 115_D2 | (4R*,9R)-4-(aminomethyl)-N-(3-cyano-4-fluorophenyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 116_D1 | (4S*,9R)-4-(aminomethyl)-N-(4-fluoro-3-(trifluoromethyl)phenyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 116_D2 | (4R*,9R)-4-(aminomethyl)-N-(4-fluoro-3-(trifluoromethyl)phenyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 117_D1 | (4S*,9R)-4-(aminomethyl)-N-(3-bromo-4-fluorophenyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 117_D2 | (4R*,9R)-4-(aminomethyl)-N-(3-bromo-4-fluorophenyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 118 | N10-(3-chloro-2,4-difluorophenyl)-N4,2-dimethyl-1-oxo-1,4,5,8,9,11-hexahydropyrido[4',3':3,4]pyrazolo[5,1-d][1,2,5]oxadizepine-4,10(2H)-dicarboxamide |
| 119 | N10-(5-chloro-2,4-difluorophenyl)-N4,2-dimethyl-1-oxo-1,4,5,8,9,11-hexahydropyrido[4',3':3,4]pyrazolo[5,1-d][1,2,5]oxadizepine-4,10(2H)-dicarboxamide |
| 120 | N10-(3-cyano-4-fluorophenyl)-N4,2-dimethyl-1-oxo-1,4,5,8,9,11-hexahydropyrido[4',3':3,4]pyrazolo[5,1-d][1,2,5]oxadizepine-4,10(2H)-dicarboxamide |
| 121_D1 | (4S*,9R)-N-(3-chloro-4-fluorophenyl)-4-((2,2-difluoroethoxy)methyl)-2,9-dimethyl-1-oxo-1,4,5,8,9,11-hexahydropyrido[4',3':3,4]pyrazolo[5,1-d][1,2,5]oxadiazepine-10(2H)-carboxamide |

-continued

| Compound ID | Compound Name |
|---|---|
| 121_D2 | (4R*,9R)-N-(3-chloro-4-fluorophenyl)-4-((2,2-difluoroethoxy)methyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 122_D1 | (4S*,9R)-N-(3-bromo-4-fluorophenyl)-4-((2,2-difluoroethoxy)methyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 122_D2 | (4R*,9R)-N-(3-bromo-4-fluorophenyl)-4-((2,2-difluoroethoxy)methyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 123_D1 | (4S*,9R)-N-(2-bromo-3-fluoropyridin-4-yl)-4-((2,2-difluoroethoxy)methyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 123_D2 | (4R*,9R)-N-(2-bromo-3-fluoropyridin-4-yl)-4-((2,2-difluoroethoxy)methyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 124_D1 | (4S*,9R)-N-(3-cyano-4-fluorophenyl)-4-((2,2-difluoroethoxy)methyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 124_D2 | (4R*,9R)-N-(3-cyano-4-fluorophenyl)-4-((2,2-difluoroethoxy)methyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 125_D1 | (4S*,9R)-4-((2,2-difluoroethoxy)methyl)-N-(4-fluoro-3-methylphenyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 125_D2 | (4R*,9R)-4-((2,2-difluoroethoxy)methyl)-N-(4-fluoro-3-methylphenyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 126_D1 | (4S*,9R)-4-((2,2-difluoroethoxy)methyl)-N-(4-fluoro-3-(trifluoromethyl)phenyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 126_D2 | (4R*,9R)-4-((2,2-difluoroethoxy)methyl)-N-(4-fluoro-3-(trifluoromethyl)phenyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 127_D1 | (4S*,9R)-N-(5-chloro-2,4-difluorophenyl)-4-((2,2-difluoroethoxy)methyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 127_D2 | (4R*,9R)-N-(5-chloro-2,4-difluorophenyl)-4-((2,2-difluoroethoxy)methyl)-2,9-dimethyl-1-oxo-1,4,5,8,9,11-hexahydropyrido[4',3':3,4]pyrazolo[5,1-d][1,2,5]oxadiazepine-10(2H)-carboxamide |

*Pure but unknown enantiomer or diastereomer.

and pharmaceutically acceptable salts thereof.

Certain embodiments of Formula Ia and Formula II are shown below in Table 3.

TABLE 3

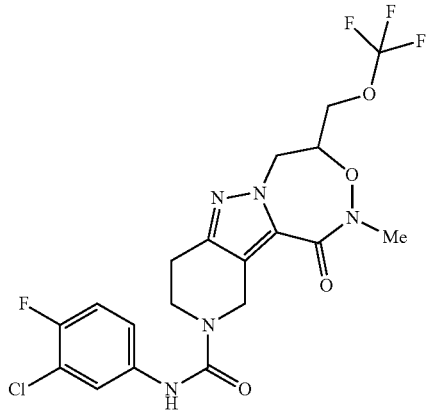 [SMILES: CN1OC(COC(F)(F)F)Cn2nc3c(c2C1=O)CN(C(=O)Nc1ccc(F)c(Cl)c1)CC3]

128

TABLE 3-continued

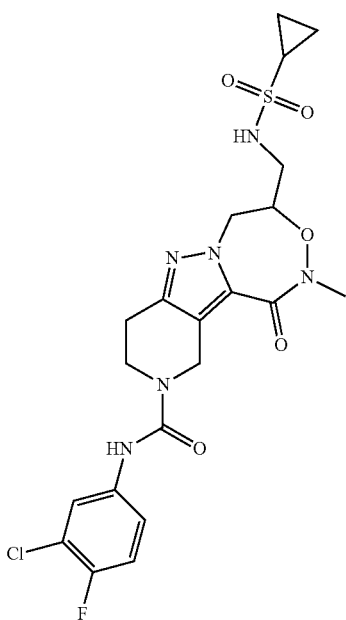 [SMILES: CN1OC(CNS(=O)(=O)C2CC2)Cn2nc3c(c2C1=O)CN(C(=O)Nc1ccc(F)c(Cl)c1)CC3]

129

TABLE 3-continued
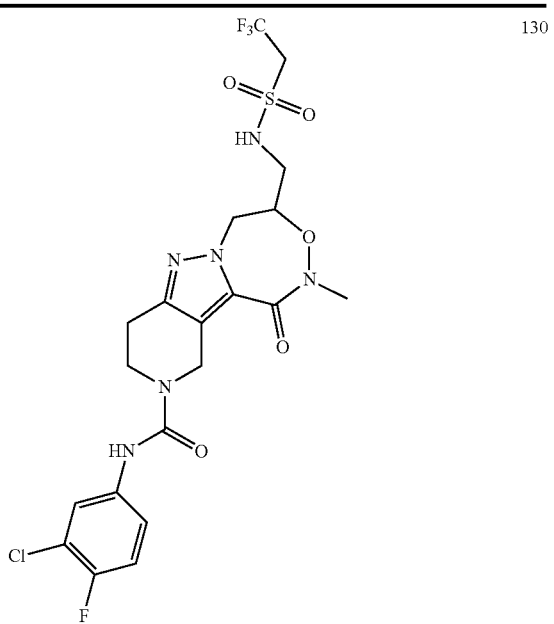
130
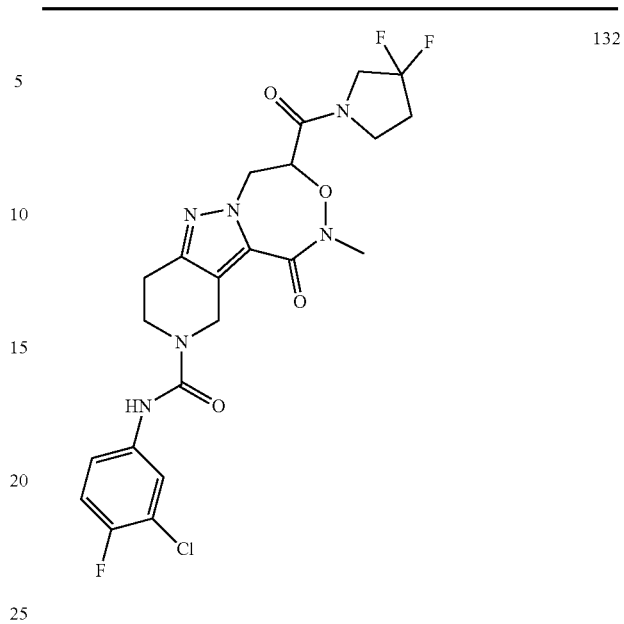
132
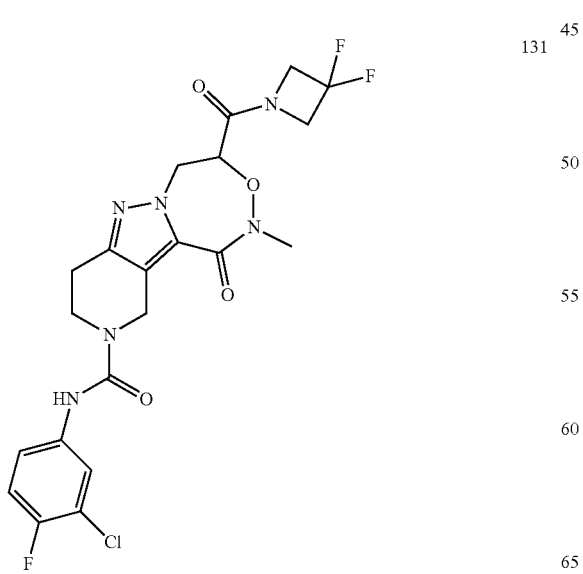
131
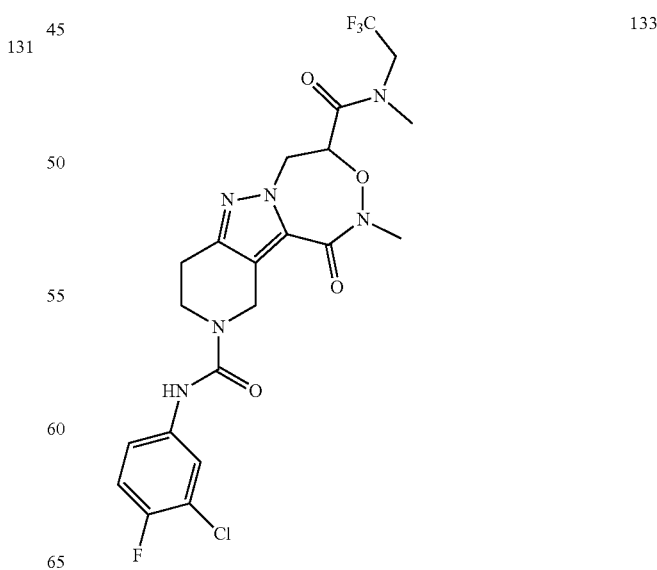
133

TABLE 3-continued
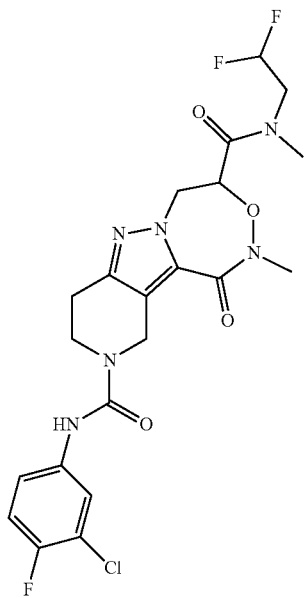 [SMILES: CN(CC(F)F)C(=O)C1Cn2nc3c(c2C(=O)N(C)O1)CN(C(=O)Nc1ccc(F)c(Cl)c1)CC3]
134
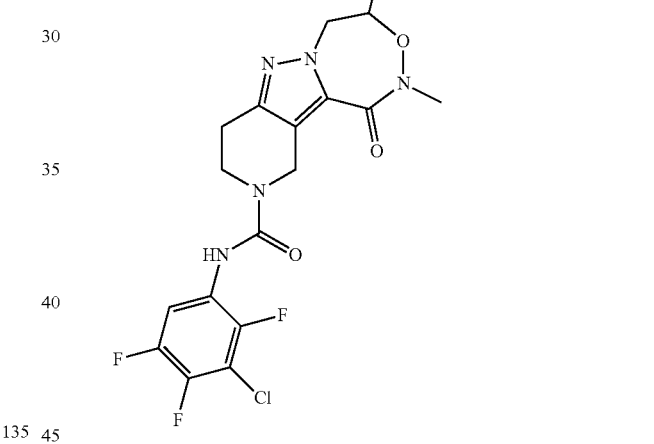
136
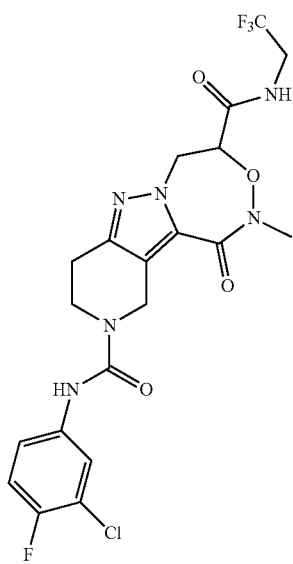 [SMILES: CN1OC(C(=O)NCC(F)(F)F)Cn2nc3c(c2C1=O)CN(C(=O)Nc1ccc(F)c(Cl)c1)CC3]
135
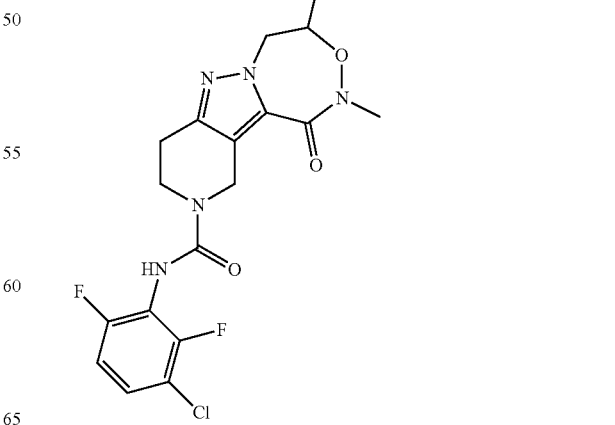
137
138

TABLE 3-continued
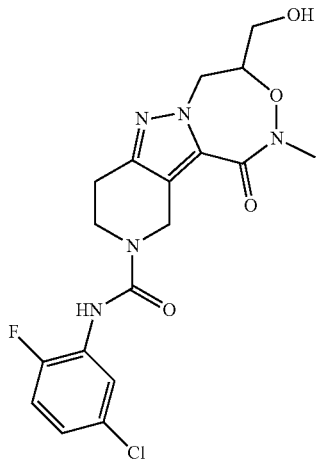 [SMILES: CN1OC(CO)Cn2nc3c(c2C1=O)CN(C(=O)Nc1cc(Cl)ccc1F)CC3]
139
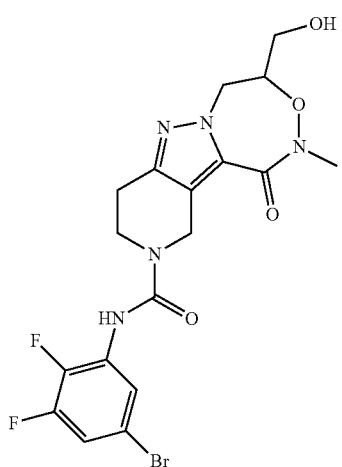 [SMILES: CN1OC(CO)Cn2nc3c(c2C1=O)CN(C(=O)Nc1cc(Br)cc(F)c1F)CC3]
140
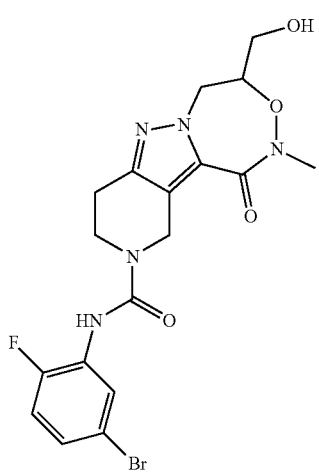 [SMILES: CN1OC(CO)Cn2nc3c(c2C1=O)CN(C(=O)Nc1cc(Br)ccc1F)CC3]
141
TABLE 3-continued
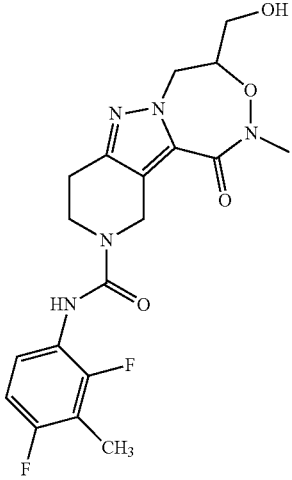
142
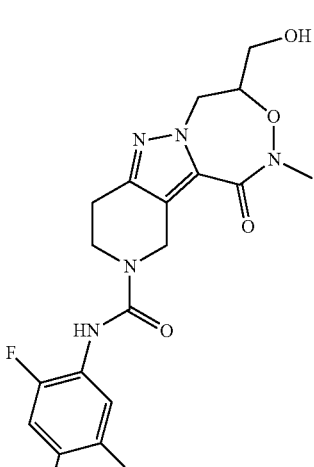
143
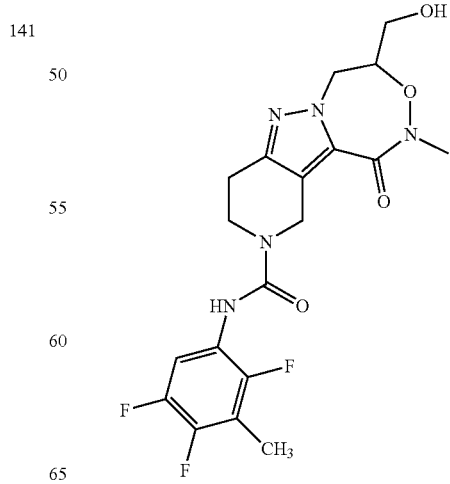
144

TABLE 3-continued
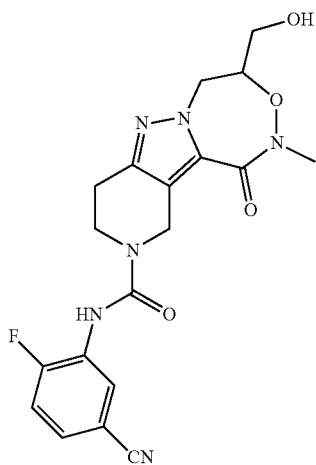 [SMILES: CN1OC(CO)Cn2nc3c(c2C1=O)CN(C(=O)Nc1cc(C#N)ccc1F)CC3]
145
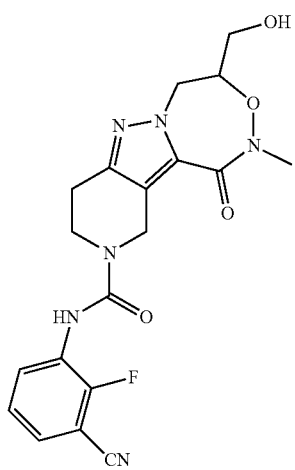 [SMILES: CN1OC(CO)Cn2nc3c(c2C1=O)CN(C(=O)Nc1cccc(C#N)c1F)CC3]
146
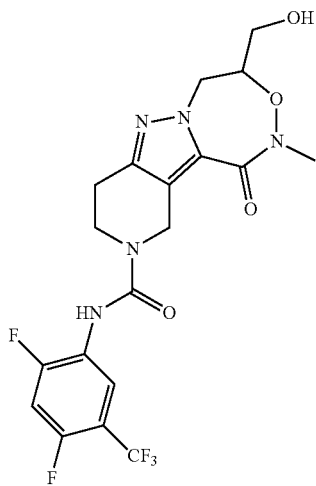 [SMILES: CN1OC(CO)Cn2nc3c(c2C1=O)CN(C(=O)Nc1cc(C(F)(F)F)c(F)cc1F)CC3]
147
TABLE 3-continued
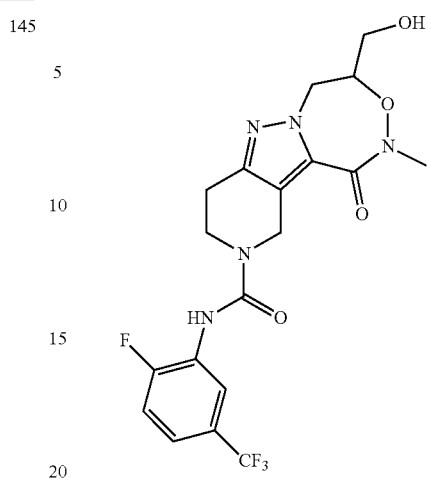
148
149
150

TABLE 3-continued
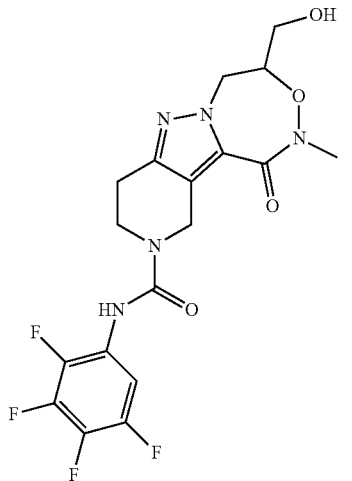 [SMILES: CN1OC(CO)Cn2nc3c(c2C1=O)CN(C(=O)Nc1cc(F)c(F)c(F)c1F)CC3] 151
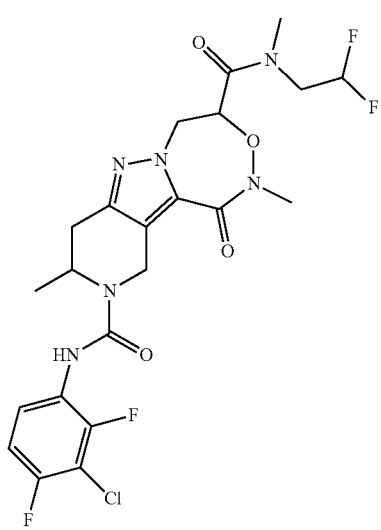 [SMILES: CC1Cc2nn3c(c2CN1C(=O)Nc1ccc(F)c(Cl)c1F)C(=O)N(C)OC(C(=O)N(C)CC(F)F)C3] 152
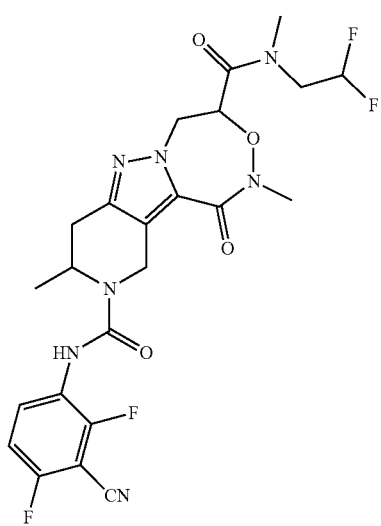 [SMILES: CC1Cc2nn3c(c2CN1C(=O)Nc1ccc(F)c(C#N)c1F)C(=O)N(C)OC(C(=O)N(C)CC(F)F)C3] 153
TABLE 3-continued
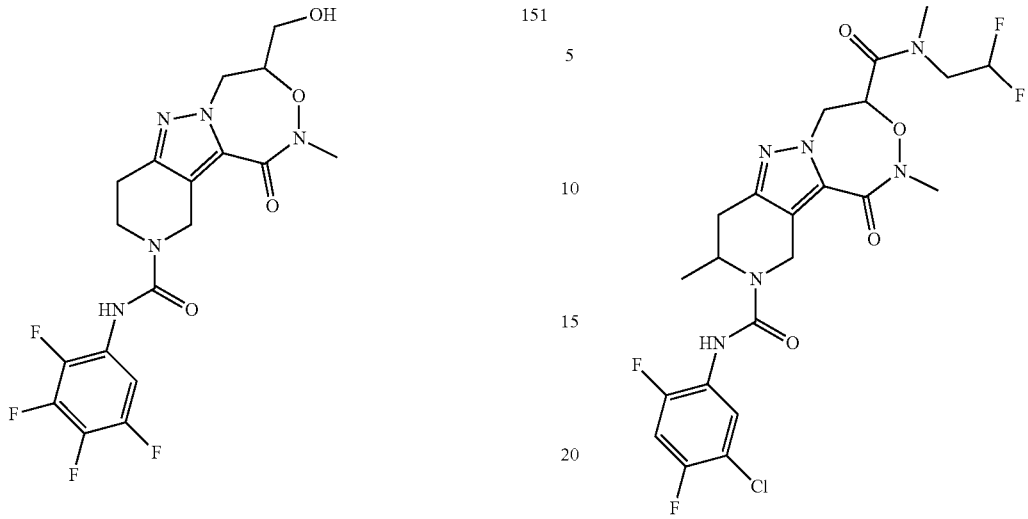 154
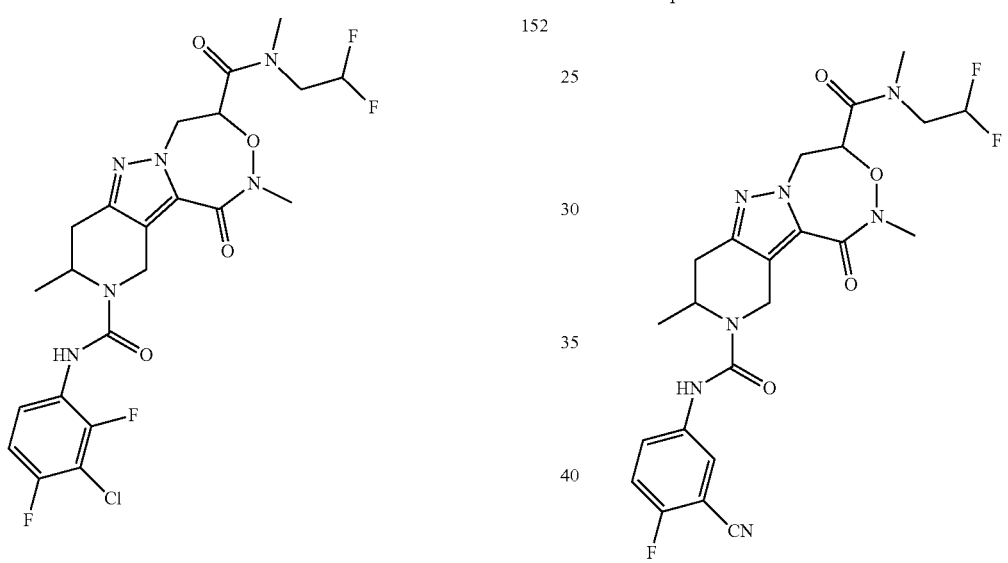 155
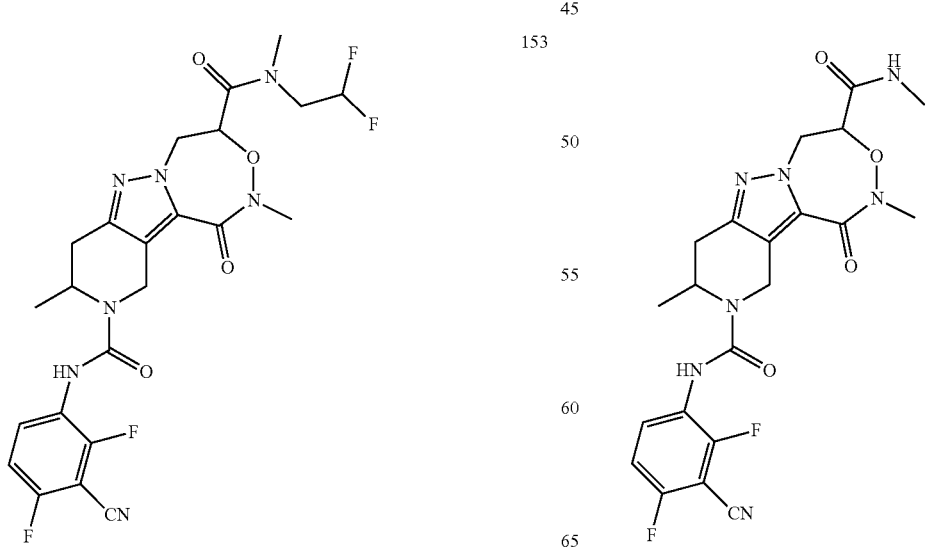 156

TABLE 3-continued
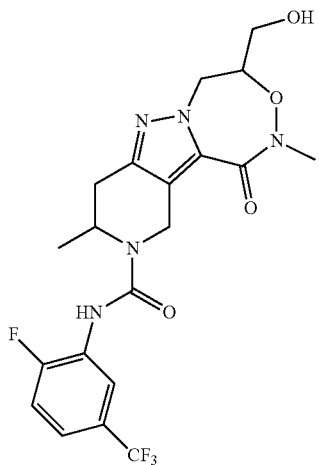 [SMILES: CC1Cc2nn3c(c2CN1C(=O)Nc1cc(C(F)(F)F)ccc1F)C(=O)N(C)OC(CO)C3]
157
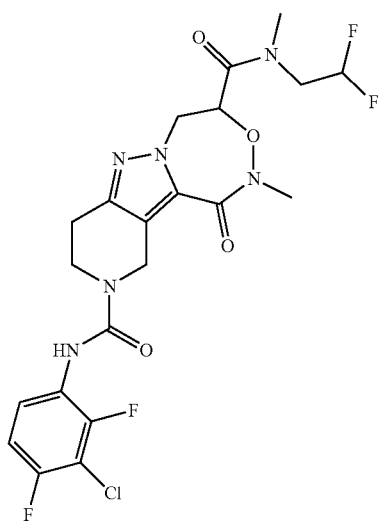 [SMILES: CN(CC(F)F)C(=O)C1Cn2nc3c(c2C(=O)N(C)O1)CN(C(=O)Nc1ccc(F)c(Cl)c1F)CC3]
158
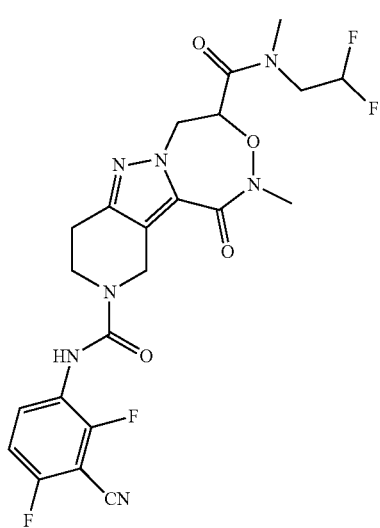 [SMILES: CN(CC(F)F)C(=O)C1Cn2nc3c(c2C(=O)N(C)O1)CN(C(=O)Nc1ccc(F)c(C#N)c1F)CC3]
159
TABLE 3-continued
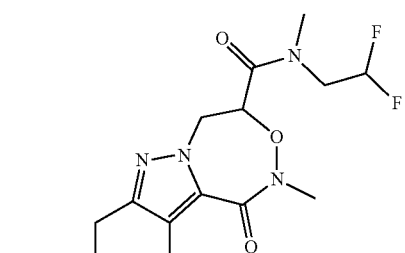
160
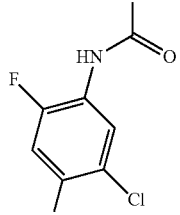
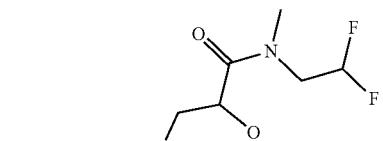
161
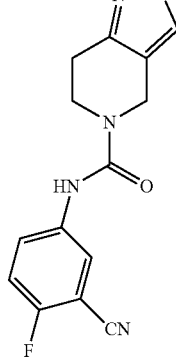
162
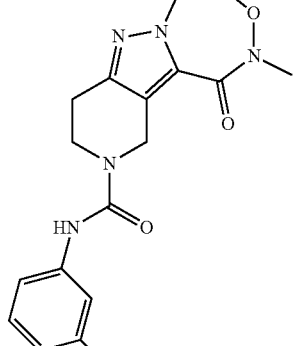

TABLE 3-continued
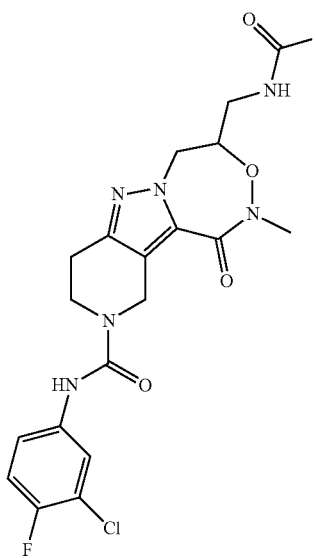
163
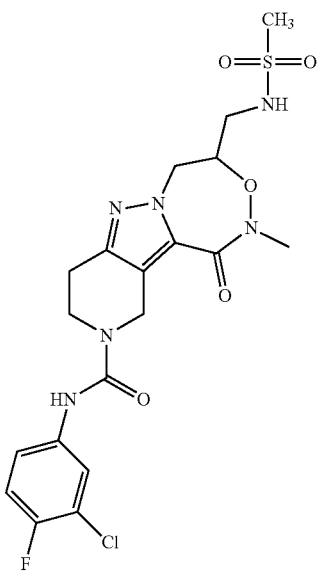
165
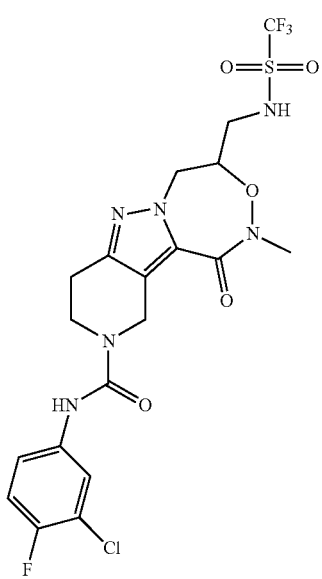 [SMILES: CN1OC(CNS(=O)(=O)C(F)(F)F)Cn2nc3c(c2C1=O)CN(C(=O)Nc1ccc(F)c(Cl)c1)CC3]
164
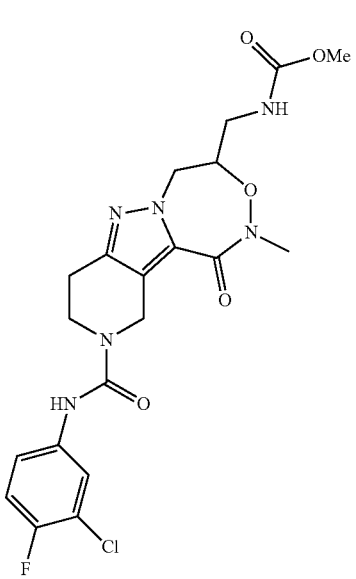 [SMILES: COC(=O)NCC1Cn2nc3c(c2C(=O)N(C)O1)CN(C(=O)Nc1ccc(F)c(Cl)c1)CC3]
166

TABLE 3-continued
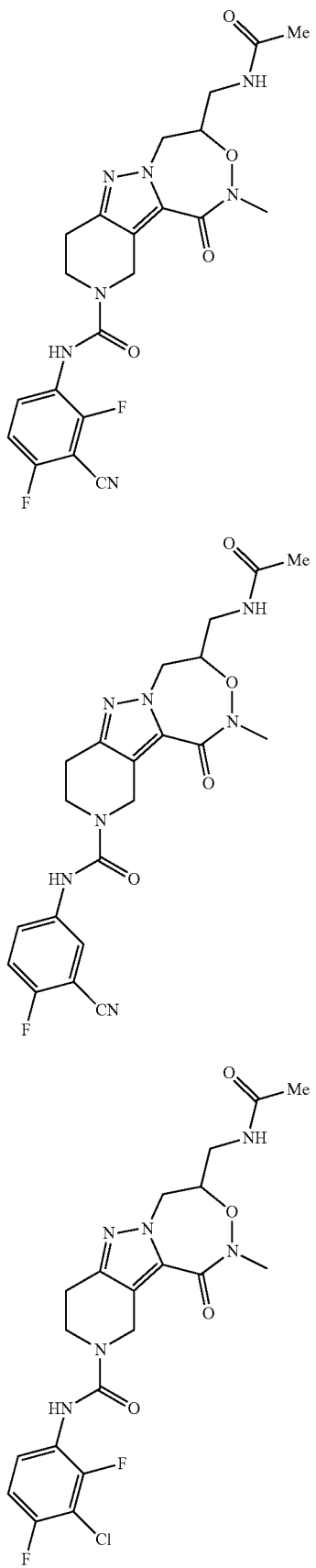

TABLE 3-continued
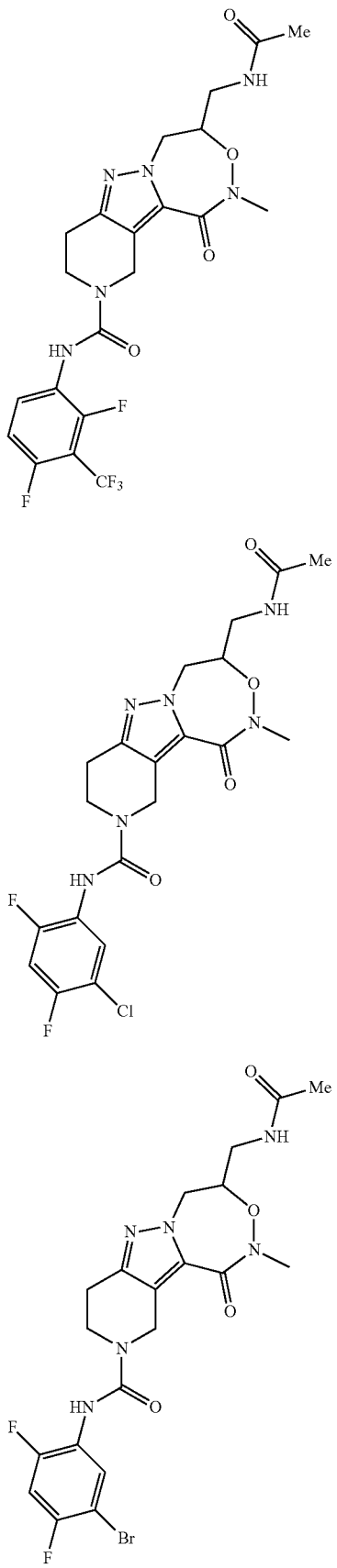
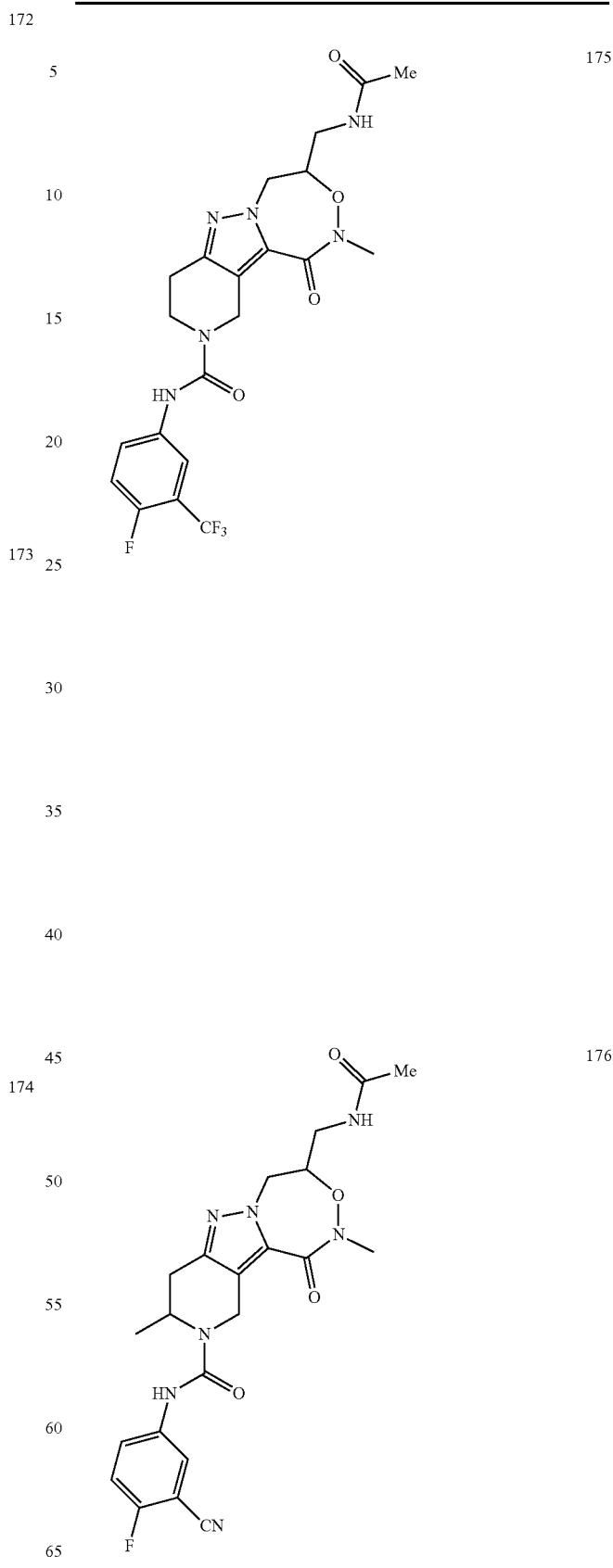

TABLE 3-continued
| 177 | 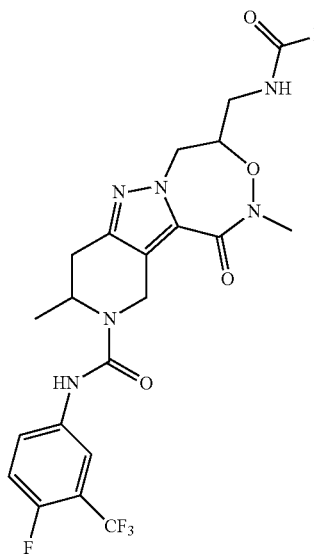 |
| 178 | 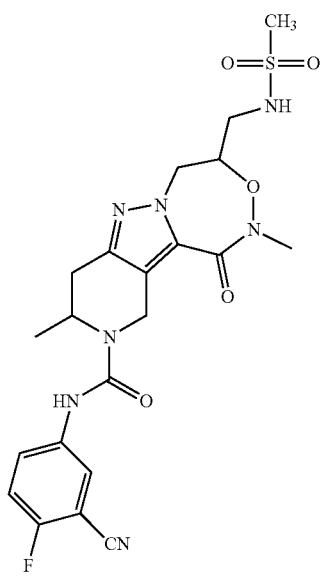 [SMILES: CC1Cc2nn3c(c2CN1C(=O)Nc1ccc(F)c(C#N)c1)C(=O)N(C)OC(CNS(C)(=O)=O)C3] |
| 179 | 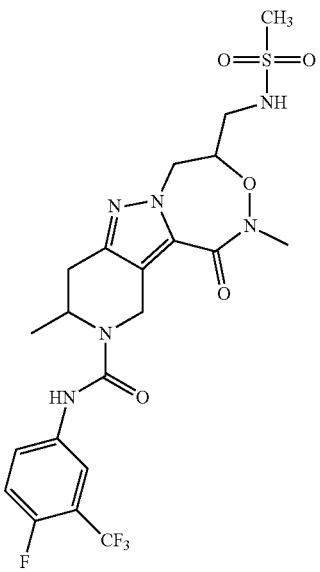 [SMILES: CC1Cc2nn3c(c2CN1C(=O)Nc1ccc(F)c(C(F)(F)F)c1)C(=O)N(C)OC(CNS(C)(=O)=O)C3] |
| 180 | 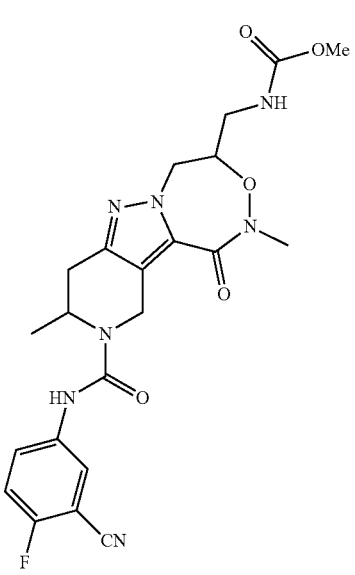 |

TABLE 3-continued
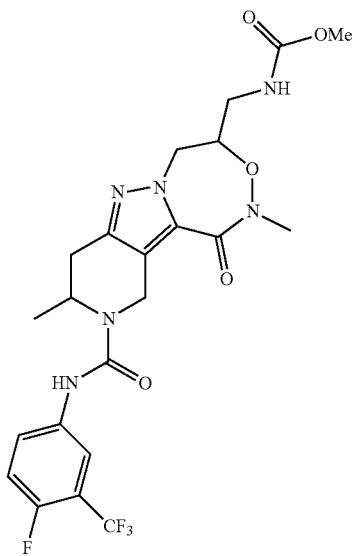 [SMILES: COC(=O)NCC1Cn2nc3c(c2C(=O)N(C)O1)CN(C(=O)Nc1ccc(F)c(C#N)c1)C(C)C3]
181
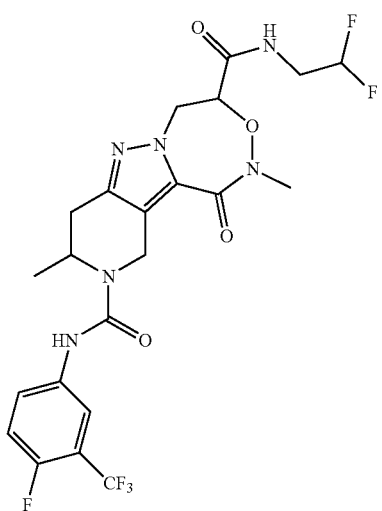 [SMILES: CC1Cc2nn3c(c2CN1C(=O)Nc1ccc(F)c(C(F)(F)F)c1)C(=O)N(C)OC(C(=O)NCC(F)F)C3]
182
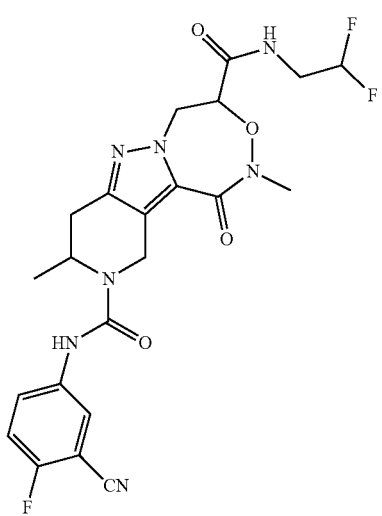 [SMILES: CC1Cc2nn3c(c2CN1C(=O)Nc1ccc(F)c(C#N)c1)C(=O)N(C)OC(C(=O)NCC(F)F)C3]
183
TABLE 3-continued
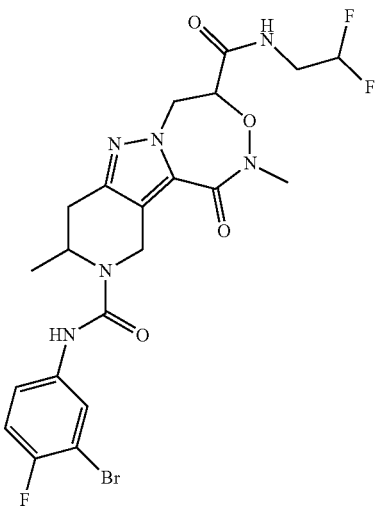 [SMILES: CC1Cc2nn3c(c2CN1C(=O)Nc1ccc(F)c(Br)c1)C(=O)N(C)OC(C(=O)NCC(F)F)C3]
184
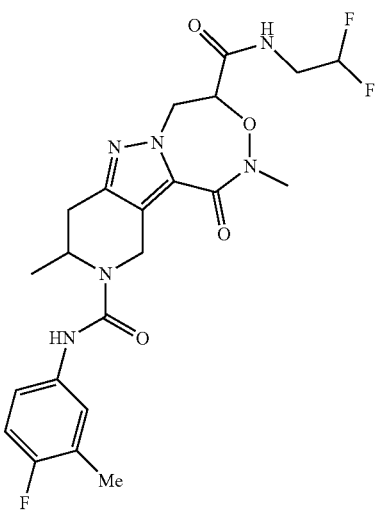 [SMILES: Cc1cc(NC(=O)N2Cc3c(nn4c3C(=O)N(C)OC(C(=O)NCC(F)F)C4)CC2C)ccc1F]
185
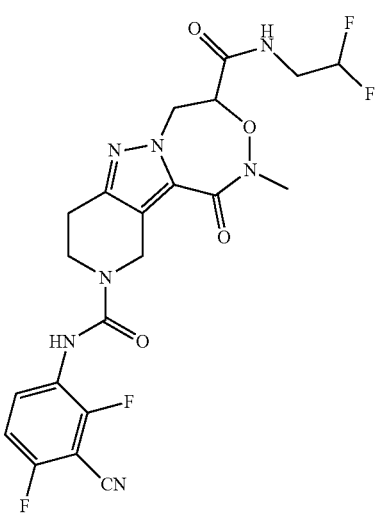 [SMILES: CN1OC(C(=O)NCC(F)F)Cn2nc3c(c2C1=O)CN(C(=O)Nc1ccc(F)c(C#N)c1F)CC3]
186

TABLE 3-continued
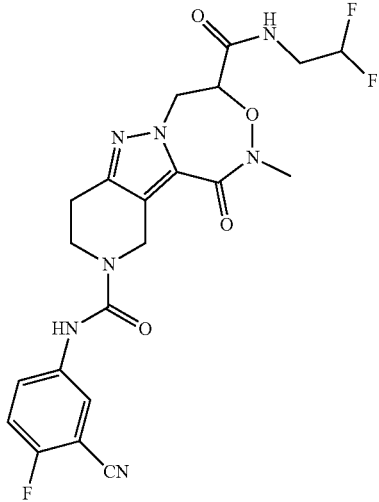 [SMILES: CN1OC(C(=O)NCC(F)F)Cn2nc3c(c2C1=O)CN(C(=O)Nc1ccc(F)c(C#N)c1)CC3]
187
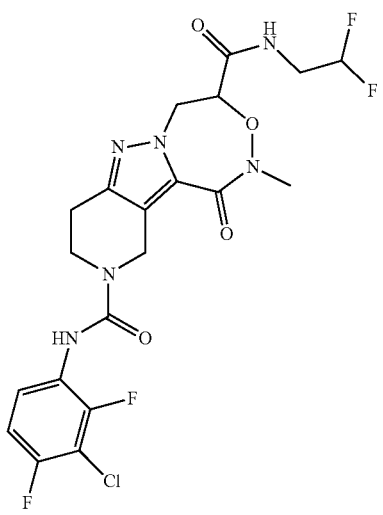
188
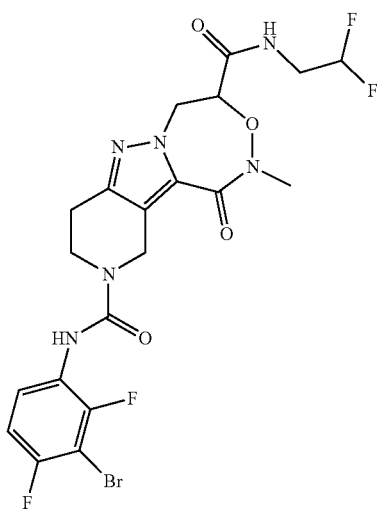 [SMILES: CN1OC(C(=O)NCC(F)F)Cn2nc3c(c2C1=O)CN(C(=O)Nc1ccc(F)c(Cl)c1F)CC3]
189
TABLE 3-continued
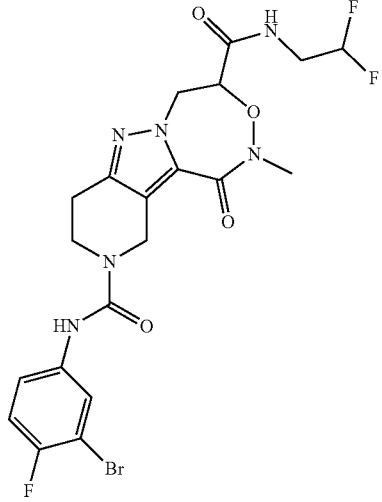 [SMILES: CN1OC(C(=O)NCC(F)F)Cn2nc3c(c2C1=O)CN(C(=O)Nc1ccc(F)c(Br)c1)CC3]
190
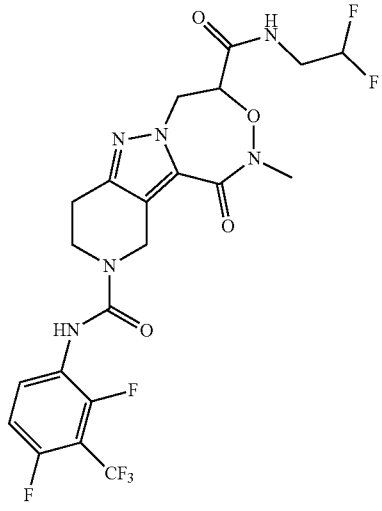
191
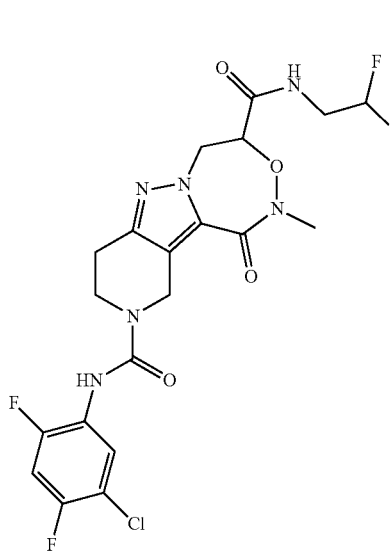
192

TABLE 3-continued
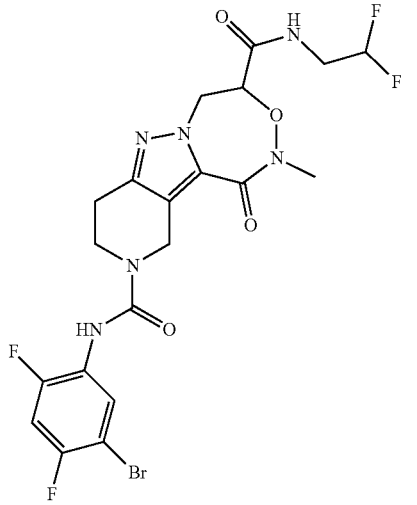 [SMILES: CN1OC(C(=O)NCC(F)F)Cn2nc3c(c2C1=O)CN(C(=O)Nc1cc(Br)c(F)cc1F)CC3]
193
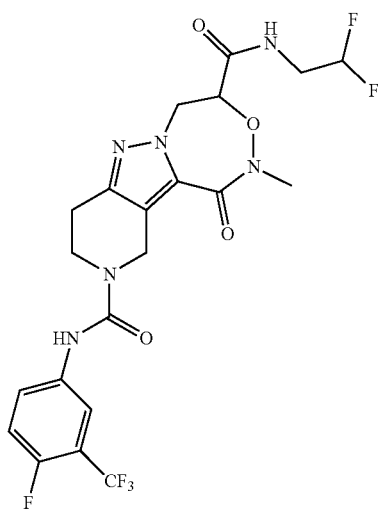
194
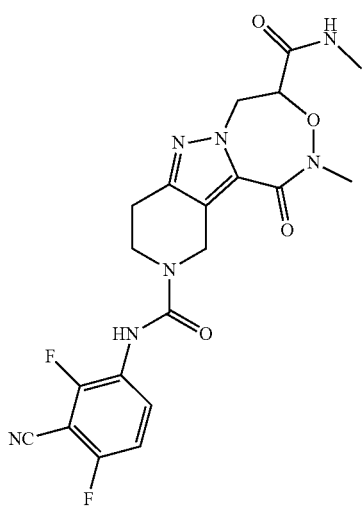 [SMILES: CNC(=O)C1Cn2nc3c(c2C(=O)N(C)O1)CN(C(=O)Nc1ccc(F)c(C#N)c1F)CC3]
195
TABLE 3-continued
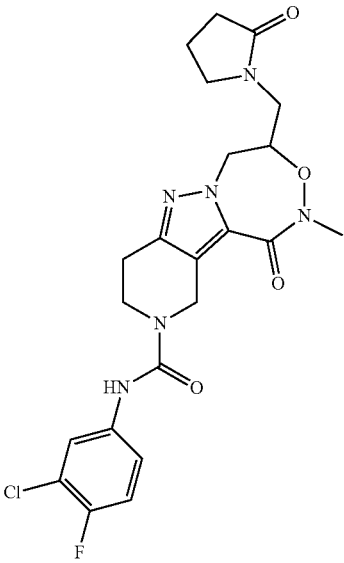 [SMILES: CN1OC(CN2CCCC2=O)Cn2nc3c(c2C1=O)CN(C(=O)Nc1ccc(F)c(Cl)c1)CC3]
196
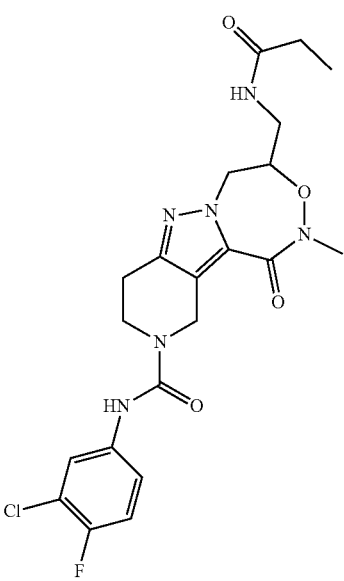 [SMILES: CCC(=O)NCC1Cn2nc3c(c2C(=O)N(C)O1)CN(C(=O)Nc1ccc(F)c(Cl)c1)CC3]
197

TABLE 3-continued
| 198 | 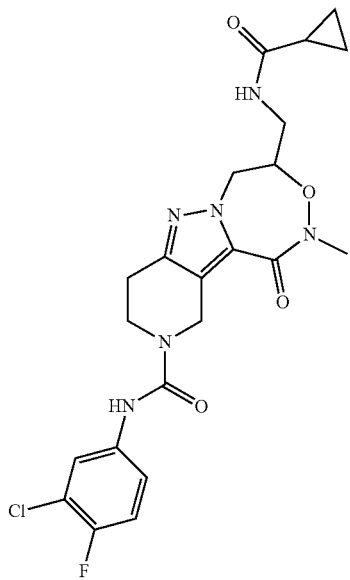 [SMILES: CN1OC(CNC(=O)C2CC2)Cn2nc3c(c2C1=O)CN(C(=O)Nc1ccc(F)c(Cl)c1)CC3] |
| 199 | 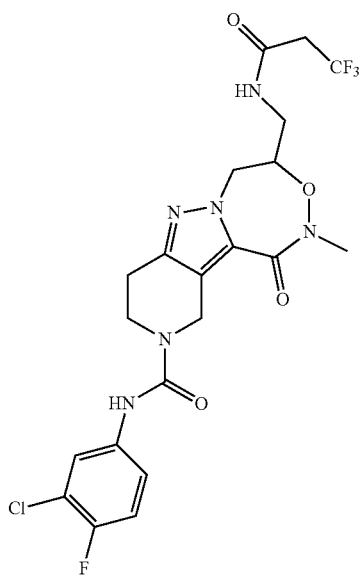 [SMILES: CN1OC(CNC(=O)CC(F)(F)F)Cn2nc3c(c2C1=O)CN(C(=O)Nc1ccc(F)c(Cl)c1)CC3] |
| 200 | 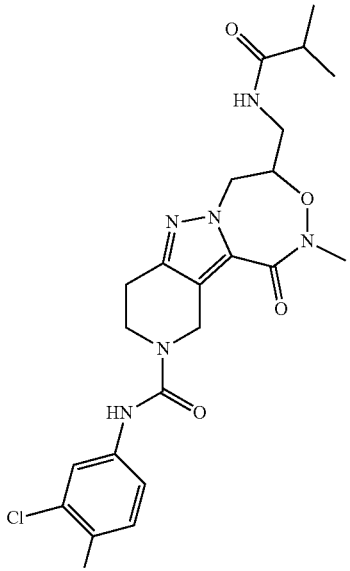 |
| 201 | |

TABLE 3-continued
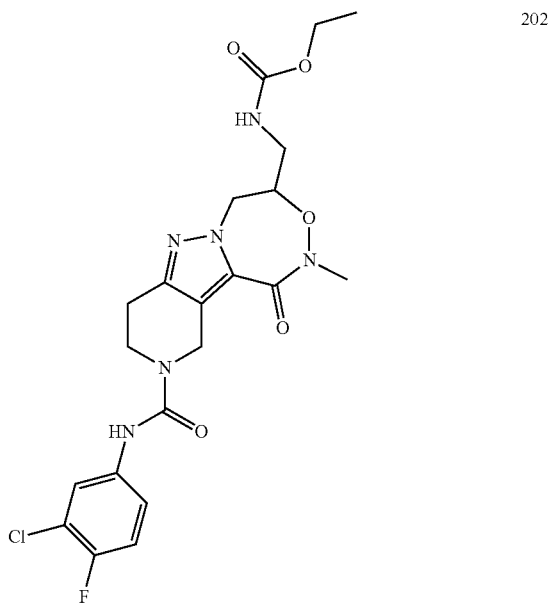
202
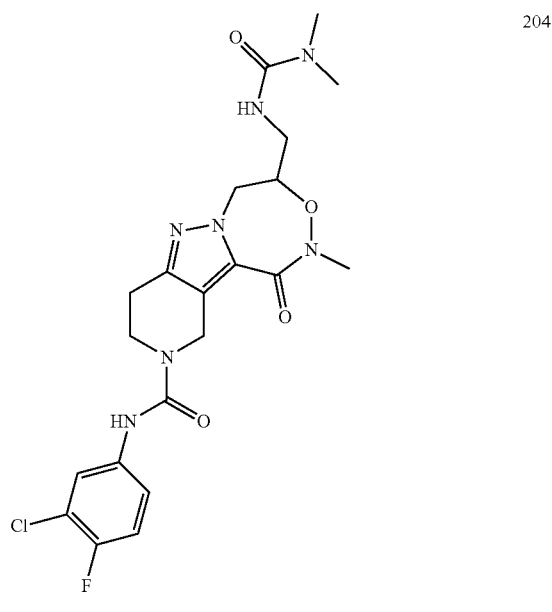
204
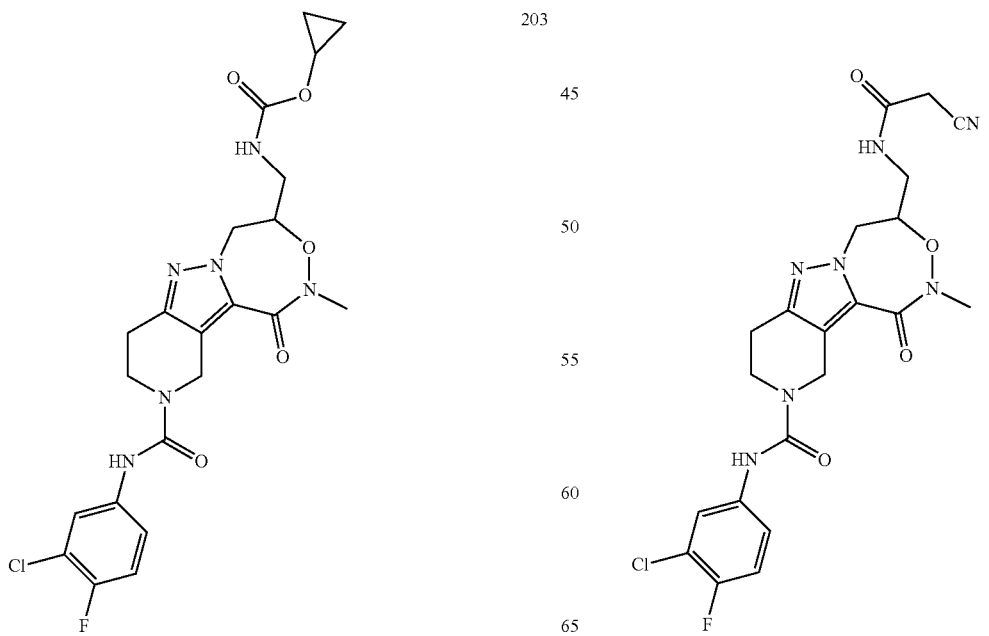
203
205

TABLE 3-continued

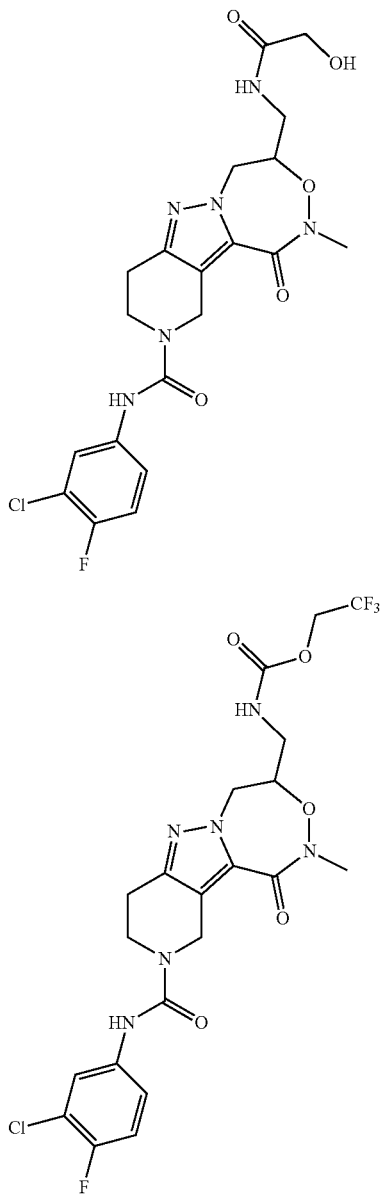

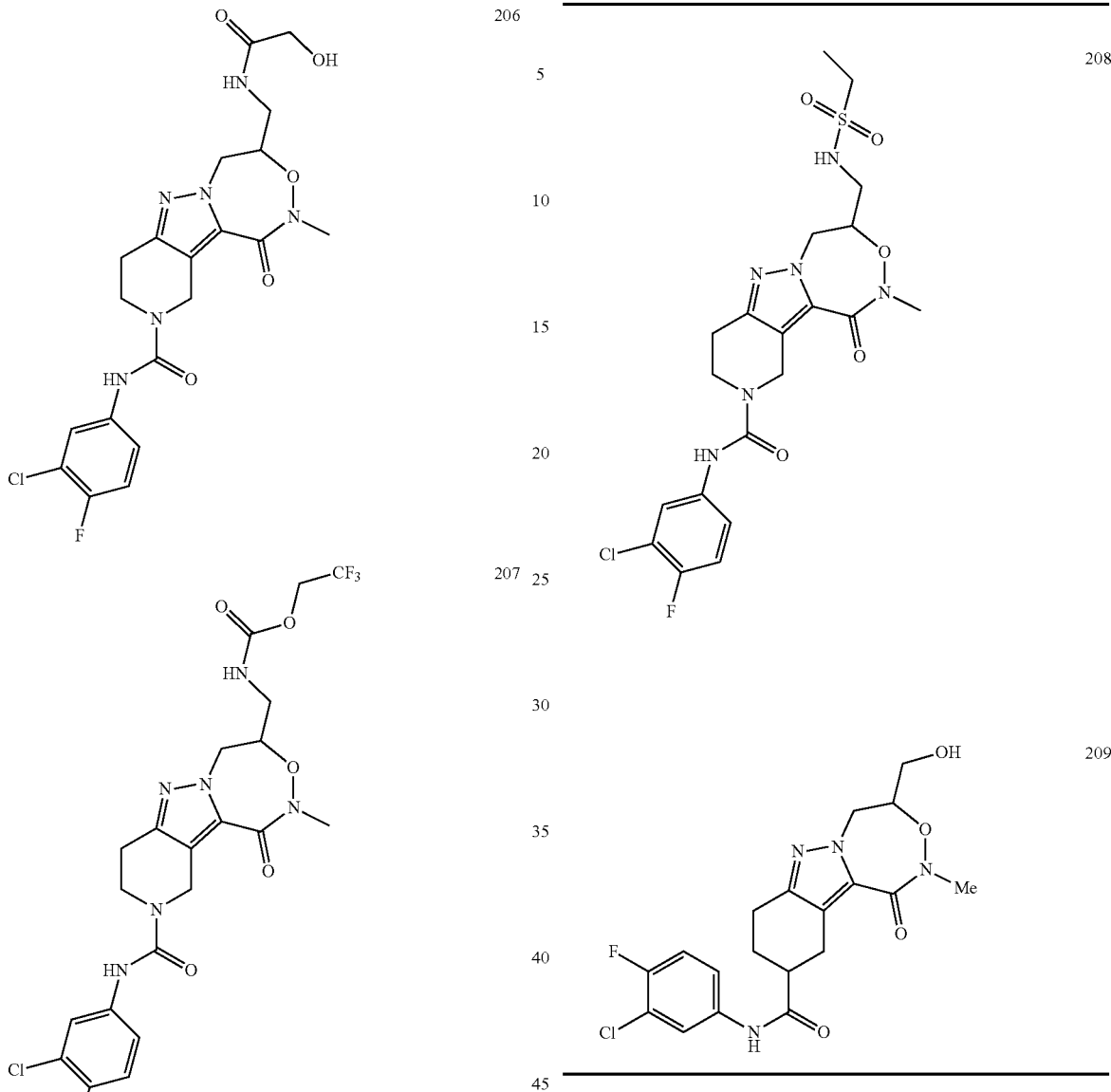

In an embodiment, compounds of Formulas Ia and II are selected from:

| Compound ID | Compound Name |
|---|---|
| 128 | N-(3-chloro-4-fluoro-phenyl)-2-methyl-1-oxo-4-(trifluoromethoxymethyl)-5,8,9,11-tetrahydro-4H-pyrido[2,3]pyrazolo[2,4-d][1,2,5]oxadiazepine-10-carboxamide |
| 129 | N-(3-chloro-4-fluorophenyl)-4-(ethylsulfonamidomethyl)-2-methyl-1-oxo-1,4,5,8,9,11-hexahydropyrido[4',3':3,4]pyrazolo[5,1-d][1,2,5]oxadiazepine-10(2H)-carboxamide |
| 130 | N-(3-chloro-4-fluorophenyl)-2-methyl-1-oxo-4-(((2,2,2-trifluoroethyl)sulfonamido)methyl)-1,4,5,8,9,11-hexahydropyrido[4',3':3,4]pyrazolo[5,1-d][1,2,5]oxadiazepine-10(2H)-carboxamide |
| 131 | N-(3-chloro-4-fluorophenyl)-4-(3,3-difluoroazetidine-1-carbonyl)-2-methyl-1-oxo-1,4,5,8,9,11-hexahydropyrido[4',3':3,4]pyrazolo[5,1-d][1,2,5]oxadiazepine-10(2H)-carboxamide |
| 132 | N-(3-chloro-4-fluorophenyl)-4-(3,3-difluoropyrrolidine-1-carbonyl)-2-methyl-1-oxo-1,4,5,8,9,11-hexahydropyrido[4',3':3,4]pyrazolo[5,1-d][1,2,5]oxadiazepine-10(2H)-carboxamide |
| 133 | N10-(3-chloro-4-fluorophenyl)-N4,2-dimethyl-1-oxo-N4-(2,2,2-trifluoroethyl)-1,4,5,8,9,11-hexahydropyrido[4',3':3,4]pyrazolo[5,1-d][1,2,5]oxadiazepine-4,10(2H)-dicarboxamide |

-continued

| Compound ID | Compound Name |
|---|---|
| 134 | N10-(3-chloro-4-fluorophenyl)-N4-(2,2-difluoroethyl)-N4,2-dimethyl-1-oxo-1,4,5,8,9,11-hexahydropyrido[4',3':3,4]pyrazolo[5,1-d][1,2,5]oxadiazepine-4,10(2H)-dicarboxamide |
| 135 | N10-(3-chloro-4-fluorophenyl)-2-methyl-1-oxo-N4-(2,2,2-trifluoroethyl)-1,4,5,8,9,11-hexahydropyrido[4',3':3,4]pyrazolo[5,1-d][1,2,5]oxadiazepine-4,10(2H)-dicarboxamide |
| 136 | N10-(3-chloro-4-fluorophenyl)-N4-(2,2-difluoroethyl)-2-methyl-1-oxo-1,4,5,8,9,11-hexahydropyrido[4',3':3,4]pyrazolo[5,1-d][1,2,5]oxadiazepine-4,10(2H)-dicarboxamide |
| 137_E1 | (S*)-N-(3-chloro-2,4,5-trifluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |
| 138_E1 | (S*)-N-(3-chloro-2,6-difluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |
| 139_E1 | (S*)-N-(5-chloro-2-fluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |
| 140_E1 | (S*)-N-(5-bromo-2,3-difluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |
| 141_E1 | (S*)-N-(5-bromo-2-fluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |
| 142_E1 | (S*)-N-(2,4-difluoro-3-methylphenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |
| 143_E1 | (S*)-N-(2,4-difluoro-5-methylphenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |
| 144_E1 | (S*)-4-(hydroxymethyl)-2-methyl-1-oxo-N-(2,4,5-trifluoro-3-methylphenyl)-1,4,5,8,9,11-hexahydropyrido[4',3':3,4]pyrazolo[5,1-d][1,2,5]oxadiazepine-10(2H)-carboxamide |
| 145_E1 | (S*)-N-(5-cyano-2-fluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |
| 146_E1 | (S*)-N-(3-cyano-2-fluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |
| 147_E1 | (S*)-N-(2,4-difluoro-5-(trifluoromethyl)phenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |
| 148_E1 | (S*)-N-(2-fluoro-5-(trifluoromethyl)phenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |
| 149_E1 | (S*)-N-(2,4-difluoro-3-(trifluoromethyl)phenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |
| 150_E1 | (S*)-N-(2-bromo-5-fluoropyridin-4-yl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide |
| 151_E1 | (S*)-4-(hydroxymethyl)-2-methyl-1-oxo-N-(2,3,4,5-tetrafluorophenyl)-1,4,5,8,9,11-hexahydropyrido[4',3':3,4]pyrazolo[5,1-d][1,2,5]oxadiazepine-10(2H)-carboxamide |
| 152_D1 | (4S*,9R)-N10-(3-chloro-2,4-difluorophenyl)-N4-(2,2-difluoroethyl)-N4,2,9-trimethyl-1-oxo-1,4,5,8,9,11-hexahydropyrido[4',3':3,4]pyrazolo[5,1-d][1,2,5]oxadiazepine-4,10(2H)-carboxamide |
| 152_D2 | (4R*,9R)-N10-(3-chloro-2,4-difluorophenyl)-N4-(2,2-difluoroethyl)-N4,2,9-trimethyl-1-oxo-1,4,5,8,9,11-hexahydropyrido[4',3':3,4]pyrazolo[5,1-d][1,2,5]oxadiazepine-4,10(2H)-carboxamide |
| 153_D1 | (4S*,9R)-N10-(3-cyano-2,4-difluorophenyl)-N4-(2,2-difluoroethyl)-N4,2,9-trimethyl-1-oxo-1,4,5,8,9,11-hexahydropyrido[4',3':3,4]pyrazolo[5,1-d][1,2,5]oxadiazepine-4,10(2H)-carboxamide |
| 153_D2 | (4R*,9R)-N10-(3-cyano-2,4-difluorophenyl)-N4-(2,2-difluoroethyl)-N4,2,9-trimethyl-1-oxo-1,4,5,8,9,11-hexahydropyrido[4',3':3,4]pyrazolo[5,1-d][1,2,5]oxadiazepine-4,10(2H)-carboxamide |
| 154_D1 | (4S*,9R)-N10-(5-chloro-2,4-difluorophenyl)-N4-(2,2-difluoroethyl)-N4,2,9-trimethyl-1-oxo-1,4,5,8,9,11-hexahydropyrido[4',3':3,4]pyrazolo[5,1-d][1,2,5]oxadiazepine-4,10(2H)-carboxamide |
| 154_D2 | (4R*,9R)-N10-(5-chloro-2,4-difluorophenyl)-N4-(2,2-difluoroethyl)-N4,2,9-trimethyl-1-oxo-1,4,5,8,9,11-hexahydropyrido[4',3':3,4]pyrazolo[5,1-d][1,2,5]oxadiazepine-4,10(2H)-carboxamide |
| 155_D1 | (4S*,9R)-N10-(3-cyano-4-fluorophenyl)-N4-(2,2-difluoroethyl)-N4,2,9-trimethyl-1-oxo-1,4,5,8,9,11-hexahydropyrido[4',3':3,4]pyrazolo[5,1-d][1,2,5]oxadiazepine-4,10(2H)-carboxamide |

-continued

| Compound ID | Compound Name |
| --- | --- |
| 155_D2 | (4R*,9R)-N10-(3-cyano-4-fluorophenyl)-N4-(2,2-difluoroethyl)-N4,2,9-trimethyl-1-oxo-1,4,5,8,9,11-hexahydropyrido[4',3':3,4]pyrazolo[5,1-d][1,2,5]oxadiazepine-4,10(2H)-carboxamide |
| 156_D1 | (4S*,9R)-N10-(3-cyano-2,4-difluorophenyl)-N4,2,9-trimethyl-1-oxo-1,4,5,8,9,11-hexahydropyrido[4',3':3,4]pyrazolo[5,1-d][1,2,5]oxadiazepine-4,10(2H)-dicarboxamide |
| 156_D2 | (4R*,9R)-N10-(3-cyano-2,4-difluorophenyl)-N4,2,9-trimethyl-1-oxo-1,4,5,8,9,11-hexahydropyrido[4',3':3,4]pyrazolo[5,1-d][1,2,5]oxadiazepine-4,10(2H)-dicarboxamide |
| 157_D1 | (4S*,9R)-N-[2-fluoro-5-(trifluoromethyl)phenyl]-4-(hydroxymethyl)-2,9-dimethyl-1-oxo-5,8,9,11-tetrahydro-4H-pyrido[2,3]pyrazolo[2,4-d][1,2,5]oxadiazepine-10(2H)-carboxamide |
| 157_D2 | (4R*,9R)-N-[2-fluoro-5-(trifluoromethyl)phenyl]-4-(hydroxymethyl)-2,9-dimethyl-1-oxo-5,8,9,11-tetrahydro-4H-pyrido[2,3]pyrazolo[2,4-d][1,2,5]oxadiazepine-10(2H)-carboxamide |
| 158 | N10-(3-chloro-2,4-difluorophenyl)-N4-(2,2-difluoroethyl)-N4,2-dimethyl-1-oxo-1,4,5,8,9,11-hexahydropyrido[4',3':3,4]pyrazolo[5,1-d][1,2,5]oxadiazepine-4,10(2H)-carboxamide |
| 159 | N10-(5-chloro-2,4-difluorophenyl)-N4-(2,2-difluoroethyl)-N4,2-dimethyl-1-oxo-1,4,5,8,9,11-hexahydropyrido[4',3':3,4]pyrazolo[5,1-d][1,2,5]oxadiazepine-4,10(2H)-carboxamide |
| 160 | N10-(3-cyano-4-fluorophenyl)-N4-(2,2-difluoroethyl)-N4,2-dimethyl-1-oxo-1,4,5,8,9,11-hexahydropyrido[4',3':3,4]pyrazolo[5,1-d] 4,10(2H)-dicarboxamide |
| 161 | N10-(3-cyano-2,4-difluorophenyl)-N4-(2,2-difluoroethyl)-N4,2-dimethyl-1-oxo-1,4,5,8,9,11-hexahydropyrido[4',3':3,4]pyrazolo[5,1-d][1,2,5]oxadiazepine-4,10(2H)-carboxamide |
| 162 | 4-(acetamidomethyl)-N-(3-chloro-4-fluorophenyl)-2-methyl-1-oxo-1,4,5,8,9,11-hexahydropyrido[4',3':3,4]pyrazolo[5,1-d][1,2,5]oxadiazepine-10(2H)-carboxamide |
| 163 | N-(3-chloro-4-fluorophenyl)-2-methyl-1-oxo-4-((2,2,2-trifluoroacetamido)methyl)-1,4,5,8,9,11-hexahydropyrido[4',3':3,4]pyrazolo[5,1-d][1,2,5]oxadiazepine-10(2H)-carboxamide |
| 164 | N-(3-chloro-4-fluorophenyl)-2-methyl-1-oxo-4-(((trifluoromethyl)sulfonamido)methyl)-1,4,5,8,9,11-hexahydropyrido[4',3':3,4]pyrazolo[5,1-d][1,2,5]oxadiazepine-10(2H)-carboxamide |
| 165 | N-(3-chloro-4-fluorophenyl)-2-methyl-4-(methylsulfonamidomethyl)-1-oxo-1,4,5,8,9,11-hexahydropyrido[4',3':3,4]pyrazolo[5,1-d][1,2,5]oxadiazepine-10(2H)-carboxamide |
| 166 | methyl ((10-(3-chloro-4-fluorophenyl)carbamoyl)-2-methyl-1-oxo-1,2,4,5,8,9,10,11-octahydropyrido[4',3':3,4]pyrazolo[5,1-d][1,2,5]oxadiazaepin-4-yl)methyl)carbamate |
| 167_E1 | (S*)-4-(acetamidomethyl)-N-(3-cyano-2,4-difluorophenyl)-2-methyl-1-oxo-1,4,5,8,9,11-hexahydropyrido[4',3':3,4]pyrazolo[5,1-d][1,2,5]oxadiazepine-10(2H)-carboxamide |
| 168_E1 | (S*)-4-(acetamidomethyl)-N-(3-cyano-4-fluorophenyl)-2-methyl-1-oxo-1,4,5,8,9,11-hexahydropyrido[4',3':3,4]pyrazolo[5,1-d][1,2,5]oxadiazepine-10(2H)-carboxamide |
| 169_E1 | (S*)-4-(acetamidomethyl)-N-(3-chloro-2,4-difluorophenyl)-2-methyl-1-oxo-1,4,5,8,9,11-hexahydropyrido[4',3':3,4]pyrazolo[5,1-d][1,2,5]oxadiazepine-10(2H)-carboxamide |
| 170_E1 | (S*)-4-(acetamidomethyl)-N-(3-bromo-2,4-difluorophenyl)-2-methyl-1-oxo-1,4,5,8,9,11-hexahydropyrido[4',3':3,4]pyrazolo[5,1-d][1,2,5]oxadiazepine-10(2H)-carboxamide |
| 171_E1 | (S*)-4-(acetamidomethyl)-N-(3-bromo-4-fluorophenyl)-2-methyl-1-oxo-1,4,5,8,9,11-hexahydropyrido[4',3':3,4]pyrazolo[5,1-d][1,2,5]oxadiazepine-10(2H)-carboxamide |
| 172_E1 | (S*)-4-(acetamidomethyl)-N-(2,4-difluoro-3-(trifluoromethyl)phenyl)-2-methyl-1-oxo-1,4,5,8,9,11-hexahydropyrido[4',3':3,4]pyrazolo[5,1-d][1,2,5]oxadiazepine-10(2H)-carboxamide |
| 173_E1 | (S*)-4-(acetamidomethyl)-N-(5-chloro-2,4-difluorophenyl)-2-methyl-1-oxo-1,4,5,8,9,11-hexahydropyrido[4',3':3,4]pyrazolo[5,1-d][1,2,5]oxadiazepine-10(2H)-carboxamide |
| 174_E1 | (S*)-4-(acetamidomethyl)-N-(5-bromo-2,4-difluorophenyl)-2-methyl-1-oxo-1,4,5,8,9,11-hexahydropyrido[4',3':3,4]pyrazolo[5,1-d][1,2,5]oxadiazepine-10(2H)-carboxamide |
| 175_E1 | (S*)-4-(acetamidomethyl)-N-(4-fluoro-3-(trifluoromethyl)phenyl)-2-methyl-1-oxo-1,4,5,8,9,11-hexahydropyrido[4',3':3,4]pyrazolo[5,1-d][1,2,5]oxadiazepine-10(2H)-carboxamide |
| 176_D1 | (4S*,9R)-4-(acetamidomethyl)-N-(3-cyano-4-fluorophenyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 176_D2 | (4R*,9R)-4-(acetamidomethyl)-N-(3-cyano-4-fluorophenyl)-2,9-dimethyl-1-oxo-1,4,5,8,9,11-hexahydropyrido[4',3':3,4]pyrazolo[5,1-d][1,2,5]oxadiazepine-10(2H)-carboxamide |

| Compound ID | Compound Name |
| --- | --- |
| 177_D1 | (4S*,9R)-4-(acetamidomethyl)-N-(4-fluoro-3-(trifluoromethyl)phenyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 177_D2 | (4R*,9R)-4-(acetamidomethyl)-N-(4-fluoro-3-(trifluoromethyl)phenyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 178_D1 | (4S*,9R)-N-(3-cyano-4-fluorophenyl)-2,9-dimethyl-4-(methylsulfonamidomethyl)-1-oxo-1,4,5,8,9,11-hexahydropyrido[4',3':3,4]pyrazolo[5,1-d][1,2,5]oxadiazepine-10(2H)-carboxamide |
| 178_D2 | (4R*,9R)-N-(3-cyano-4-fluorophenyl)-2,9-dimethyl-4-(methylsulfonamidomethyl)-1-oxo-1,4,5,8,9,11-hexahydropyrido[4',3':3,4]pyrazolo[5,1-d][1,2,5]oxadiazepine-10(2H)-carboxamide |
| 179_D1 | (4S*,9R)-N-(4-fluoro-3-(trifluoromethyl)phenyl)-2,9-dimethyl-4-(methylsulfonamidomethyl)-1-oxo-1,4,5,8,9,11-hexahydropyrido[4',3':3,4]pyrazolo[5,1-d][1,2,5]oxadiazepine-10(2H)-carboxamide |
| 179_D2 | (4R*,9R)-N-(4-fluoro-3-(trifluoromethyl)phenyl)-2,9-dimethyl-4-(methylsulfonamidomethyl)-1-oxo-1,4,5,8,9,11-hexahydropyrido[4',3':3,4]pyrazolo[5,1-d][1,2,5]oxadiazepine-10(2H)-carboxamide |
| 180_D1 | methyl (((4S*,9R)-10-((3-cyano-4-fluorophenyl)carbamoyl)-2,9-dimethyl-1-oxo-1,2,4,5,8,9,10,11-octahydropyrido[4',3':3,4]pyrazolo[5,1-d][1,2,5]oxadiazepin-4-yl)methyl)carbamate |
| 180_D2 | methyl (((4R*,9R)-10-((3-cyano-4-fluorophenyl)carbamoyl)-2,9-dimethyl-1-oxo-1,2,4,5,8,9,10,11-octahydropyrido[4',3':3,4]pyrazolo[5,1-d][1,2,5]oxadiazepin-4-yl)methyl)carbamate |
| 181_D1 | methyl (((4S*,9R)-10-((4-fluoro-3-(trifluoromethyl)phenyl)carbamoyl)-2,9-dimethyl-1-oxo-1,2,4,5,8,9,10,11-octahydropyrido[4',3':3,4]pyrazolo[5,1-d][1,2,5]oxadiazepin-4-yl)methyl)carbamate |
| 181_D2 | methyl (((4R*,9R)-10-((4-fluoro-3-(trifluoromethyl)phenyl)carbamoyl)-2,9-dimethyl-1-oxo-1,2,4,5,8,9,10,11-octahydropyrido[4',3':3,4]pyrazolo[5,1-d][1,2,5]oxadiazepin-4-yl)methyl)carbamate |
| 182_D1 | (4S*,9R)-4-(((2,2-difluoroethyl)amino)methyl)-N-(4-fluoro-3-(trifluoromethyl)phenyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 182_D2 | (4R*,9R)-4-(((2,2-difluoroethyl)amino)methyl)-N-(4-fluoro-3-(trifluoromethyl)phenyl)-2,9-dimethyl-1-oxo-1,4,5,8,9,11-hexahydropyrido[4',3':3,4]pyrazolo[1,2,5]oxadiazepine-10(2H)-carboxamide |
| 183_D1 | (4S*,9R)-N-(3-cyano-4-fluorophenyl)-4-(((2,2-difluoroethyl)amino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 183_D2 | (4R*,9R)-N-(3-cyano-4-fluorophenyl)-4-(((2,2-difluoroethyl)amino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 184_D1 | (4S*,9R)-N-(3-bromo-4-fluorophenyl)-4-(((2,2-difluoroethyl)amino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 184_D2 | (4R*,9R)-N-(3-bromo-4-fluorophenyl)-4-(((2,2-difluoroethyl)amino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 185_D1 | (4S*,9R)-4-(((2,2-difluoroethyl)amino)methyl)-N-(4-fluoro-3-methylphenyl)-2,9-dimethyl-1-oxo-1,4,5,8,9,11-hexahydropyrido[4',3':3,4]pyrazolo[5,1-d][1,2,5]oxadiazepine-10(2H)-carboxamide |
| 185_D2 | (4R*,9R)-4-(((2,2-difluoroethyl)amino)methyl)-N-(4-fluoro-3-methylphenyl)-2,9-dimethyl-1-oxo-1,4,5,8,9,11-hexahydropyrido[4',3':3,4]pyrazolo[5,1-d][1,2,5]oxadiazepine-10(2H)-carboxamide |

| Compound ID | Compound Name |
|---|---|
| 186_E1 | (S*)-N-(3-cyano-2,4-difluorophenyl)-4-(((2,2-difluoroethyl)amino)methyl)-2-methyl-1-oxo-1,4,5,8,9,11-hexahydropyrido[4',3':3,4]pyrazolo[5,1-d][1,2,5]oxadiazepine-10(2H)-carboxamide |
| 187_E1 | (S*)-N-(3-cyano-4-fluorophenyl)-4-(((2,2-difluoroethyl)amino)methyl)-2-methyl-1-oxo-1,4,5,8,9,11-hexahydropyrido[4',3':3,4]pyrazolo[5,1-d][1,2,5]oxadiazepine-10(2H)-carboxamide |
| 188_E1 | (S*)-N-(3-chloro-2,4-difluorophenyl)-4-(((2,2-difluoroethyl)amino)methyl)-2-methyl-1-oxo-1,4,5,8,9,11-hexahydropyrido[4',3':3,4]pyrazolo[5,1-d][1,2,5]oxadiazepine-10(2H)-carboxamide |
| 189_E1 | (S*)-N-(3-bromo-2,4-difluorophenyl)-4-(((2,2-difluoroethyl)amino)methyl)-2-methyl-1-oxo-1,4,5,8,9,11-hexahydropyrido[4',3':3,4]pyrazolo[5,1-d][1,2,5]oxadiazepine-10(2H)-carboxamide |
| 190_E1 | (S*)-N-(3-bromo-4-fluorophenyl)-4-(((2,2-difluoroethyl)amino)methyl)-2-methyl-1-oxo-1,4,5,8,9,11-hexahydropyrido[4',3':3,4]pyrazolo[5,1-d][1,2,5]oxadiazepine-10(2H)-carboxamide |
| 191_E1 | (S*)-N-(2,4-difluoro-3-(trifluoromethyl)phenyl)-4-(((2,2-difluoroethyl)amino)methyl)-2-methyl-1-oxo-1,4,5,8,9,11-hexahydropyrido[4',3':3,4]pyrazolo[5,1-d][1,2,5]oxadiazepine-10(2H)-carboxamide |
| 192_E1 | (S*)-N-(5-chloro-2,4-difluorophenyl)-4-(((2,2-difluoroethyl)amino)methyl)-2-methyl-1-oxo-1,4,5,8,9,11-hexahydropyrido[4',3':3,4]pyrazolo[5,1-d][1,2,5]oxadiazepine-10(2H)-carboxamide |
| 193_E1 | (S*)-N-(5-bromo-2,4-difluorophenyl)-4-(((2,2-difluoroethyl)amino)methyl)-2-methyl-1-oxo-1,4,5,8,9,11-hexahydropyrido[4',3':3,4]pyrazolo[5,1-d][1,2,5]oxadiazepine-10(2H)-carboxamide |
| 194_E1 | (S*)-4-(((2,2-difluoroethyl)amino)methyl)-N-(4-fluoro-3-(trifluoromethyl)phenyl)-2-methyl-1-oxo-1,4,5,8,9,11-hexahydropyrido[4',3':3,4]pyrazolo[5,1-d][1,2,5]oxadiazepine-10(2H)-carboxamide |
| 195 | N10-(3-cyano-2,4-difluorophenyl)-N4,2-dimethyl-1-oxo-1,4,5,8,9,11-hexahydropyrido[4',3':3,4]pyrazolo[5,1-d][1,2,5]oxadiazepine-4,10(2H)-dicarboxamide |
| 196 | N-(3-chloro-4-fluoro-phenyl)-2-methyl-1-oxo-4-[(2-oxopyrrolidin-1-yl)methyl]-5,8,9,11-tetrahydro-4H-pyrido[2,3]pyrazolo[2,4-d][1,2,5]oxadiazepine-10-carboxamide |
| 197 | N-(3-chloro-4-fluorophenyl)-2-methyl-1-oxo-4-(propionamidomethyl)-1,4,5,8,9,11-hexahydropyrido[4',3':3,4]pyrazolo[5,1-d][1,2,5]oxadiazepine-10(2H)-carboxamide |
| 198 | N-(3-chloro-4-fluorophenyl)-4-(cyclopropanecarboxamidomethyl)-2-methyl-1-oxo-1,4,5,8,9,11-hexahydropyrido[4',3':3,4]pyrazolo[5,1-d][1,2,5]oxadiazepine-10(2H)-carboxamide |
| 199 | N-(3-chloro-4-fluorophenyl)-2-methyl-1-oxo-4-((3,3,3-trifluoropropanamido)methyl)-1,4,5,8,9,11-hexahydropyrido[4',3':3,4]pyrazolo[5,1-d][1,2,5]oxadiazepine-10(2H)-carboxamide |
| 200 | N-(3-chloro-4-fluorophenyl)-4-(isobutyramidomethyl)-2-methyl-1-oxo-1,4,5,8,9,11-hexahydropyrido[4',3':3,4]pyrazolo[5,1-d][1,2,5]oxadiazepine-10(2H)-carboxamide |
| 201 | N-(3-chloro-4-fluorophenyl)-2-methyl-1-oxo-4-(pivalamidomethyl)-1,4,5,8,9,11-hexahydropyrido[4',3':3,4]pyrazolo[5,1-d][1,2,5]oxadiazepine-10(2H)-carboxamide |
| 202 | ethyl ((10-((3-chloro-4-fluorophenyl)carbamoyl)-2-methyl-1-oxo-1,2,4,5,8,9,10,11-octahydropyrido[4',3':3,4]pyrazolo[5,1-d][1,2,5]oxadiazepin-4-yl)methyl)carbamate |
| 203 | cyclopropyl ((10-((3-chloro-4-fluorophenyl)carbamoyl)-2-methyl-1-oxo-1,2,4,5,8,9,10,11-octahydropyrido[4',3':3,4]pyrazolo[5,1-d][1,2,5]oxadiazepin-4-yl)methyl)carbamate |
| 204 | N-(3-chloro-4-fluorophenyl)-4-((3,3-dimethylureido)methyl)-2-methyl-1-oxo-1,4,5,8,9,11-hexahydropyrido[4',3':3,4]pyrazolo[5,1-d][1,2,5]oxadiazepine-10(2H)-carboxamide |
| 205 | N-(3-chloro-4-fluorophenyl)-4-((2-cyanoacetamido)methyl)-2-methyl-1-oxo-1,4,5,8,9,11-hexahydropyrido[4',3':3,4]pyrazolo[5,1-d][1,2,5]oxadiazepine-10(2H)-carboxamide |
| 206 | N-(3-chloro-4-fluorophenyl)-4-((2-hydroxyacetamido)methyl)-2-methyl-1-oxo-1,4,5,8,9,11-hexahydropyrido[4',3':3,4]pyrazolo[5,1-d][1,2,5]oxadiazepine-10(2H)-carboxamide |
| 207 | 2,2,2-trifluoroethyl ((10-((3-chloro-4-fluorophenyl)carbamoyl)-2-methyl-1-oxo-1,2,4,5,8,9,10,11-octahydropyrido[4',3':3,4]pyrazolo[5,1-d][1,2,5]oxadiazepine-4-yl)methyl)carbamate |
| 208 | N-(3-chloro-4-fluorophenyl)-4-(ethylsulfonamidomethyl)-2-methyl-1-oxo-1,4,5,8,9,11-hexahydropyrido[4',3':3,4]pyrazolo[5,1-d][1,2,5]oxadiazepine-10(2H)-carboxamide |
| 209 | N-(3-chloro-4-fluoro-phenyl)-4-(hydroxymethyl)-2-methyl-1-oxo-4,5,8,9,10,11-hexahydro-[1,2,5]oxadiazepino[5,4-b]indazole-10-carboxamide | and pharmaceutically acceptable salts thereof.

Certain embodiments of Formula Ia are shown below in Table 4.
TABLE 4
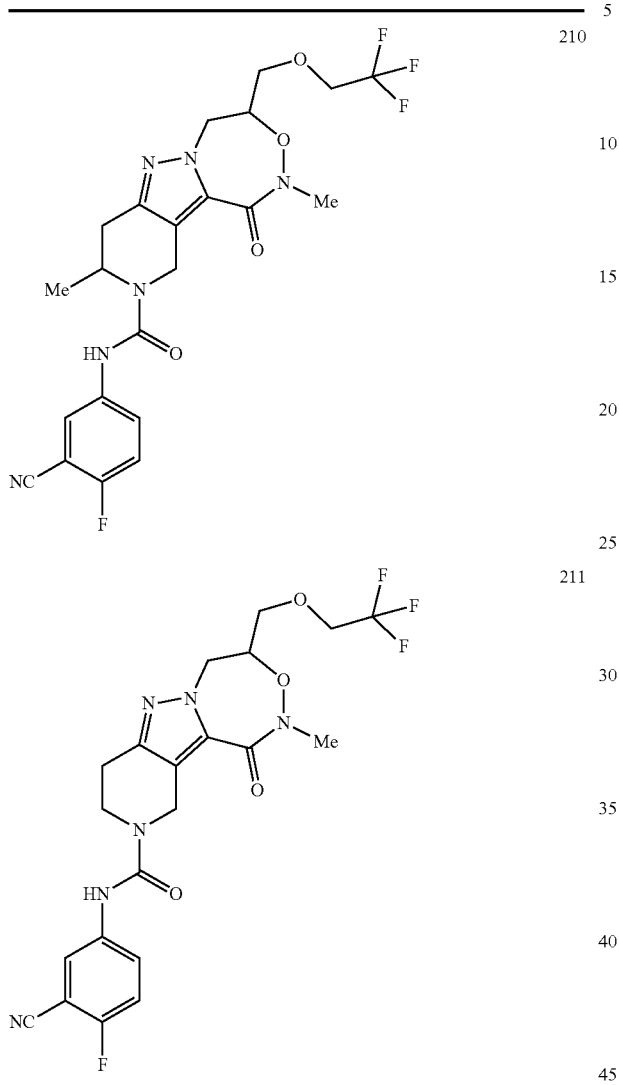
TABLE 4-continued
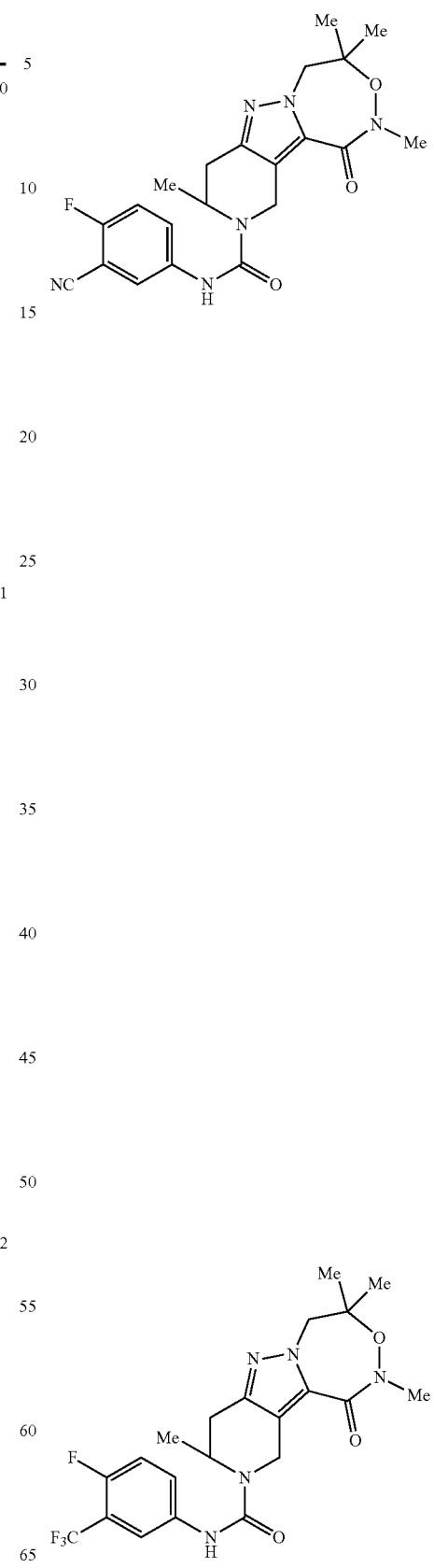

In an embodiment, compounds of Formula Ia are selected from:

| Compound ID | Compound Name |
|---|---|
| 210 | (4S*,9R)-N-(3-cyano-4-fluorophenyl)-2,9-dimethyl-1-oxo-4-((2,2,2-trifluoroethoxy)methyl)-1,4,5,8,9,11-hexahydropyrido[4',3':3,4]pyrazolo[5,1-d][1,2,5]oxadiazepine-10(2H)-carboxamide |
| 211 | (S*)-N-(3-cyano-4-fluorophenyl)-4-((2,2-difluoroethoxy)methyl)-2-methyl-1-oxo-1,4,5,8,9,11-hexahydropyrido[4',3':3,4]pyrazolo[5,1-d][1,2,5]oxadiazepine-10(2H)-carboxamide |
| 212 | (S*)-4-((2,2-difluoroethoxy)methyl)-N-(4-fluoro-3-(trifluoromethyl)phenyl)-2-methyl-1-oxo-1,4,5,8,9,11-hexahydropyrido[4',3':3,4]pyrazolo[5,1-d][1,2,5]oxadiazepine-10(2H)-carboxamide |
| 213 | (R)-N-(3-cyano-4-fluorophenyl)-2,4,4,9-tetramethyl-1-oxo-1,4,5,8,9,11-hexahydropyrido[4',3':3,4]pyrazolo[5,1-d][1,2,5]oxadiazepine-10(2H)-carboxamide |
| 214 | (R)-N-(4-fluoro-3-(trifluoromethyl)phenyl)-2,4,4,9-tetramethyl-1-oxo-1,4,5,8,9,11-hexahydropyrido[4',3':3,4]pyrazolo[5,1-d] 10(2H)-carboxamide |

*Pure but unknown enantiomer or diastereomer.

and pharmaceutically acceptable salts thereof.

Certain embodiments of Formula III are shown below in Table 5.

TABLE 5

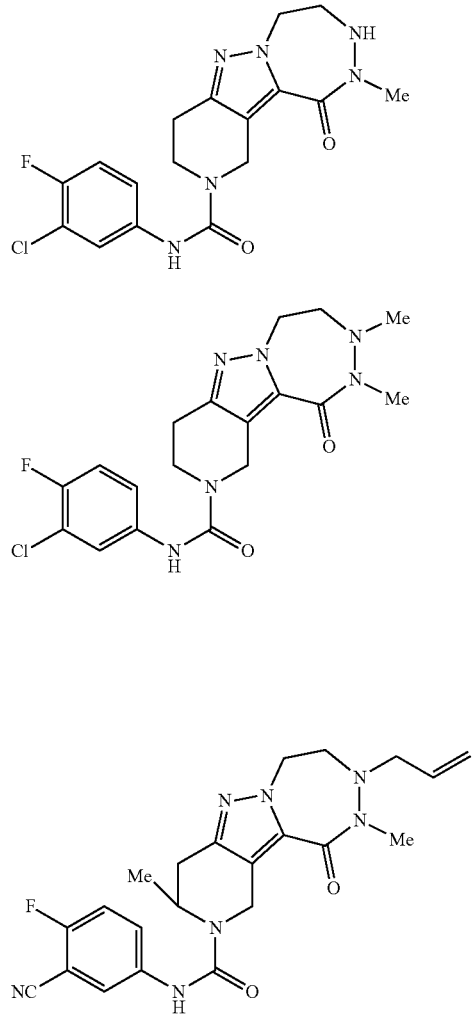

TABLE 5-continued

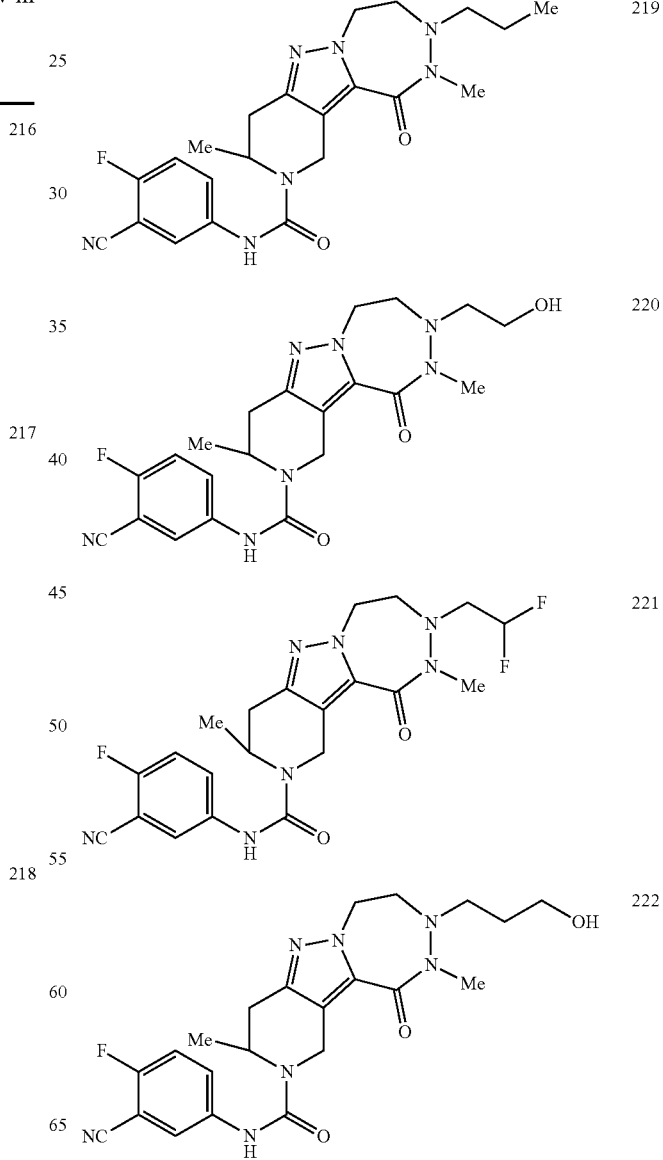

TABLE 5-continued
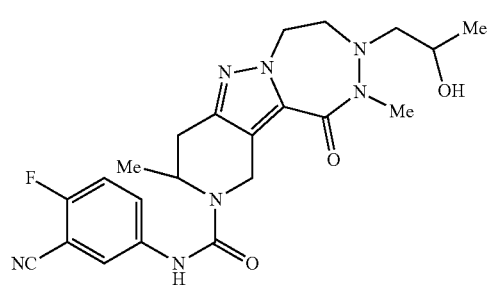 [SMILES: CC(O)CN1CCn2nc3c(c2C(=O)N1C)CN(C(=O)Nc1ccc(F)c(C#N)c1)C(C)C3] 223
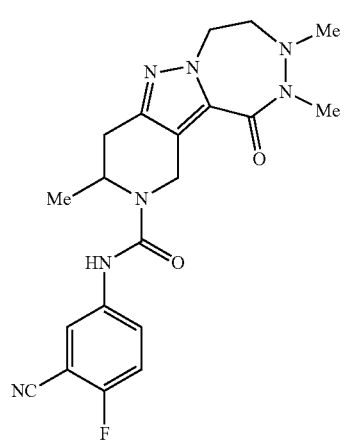 224
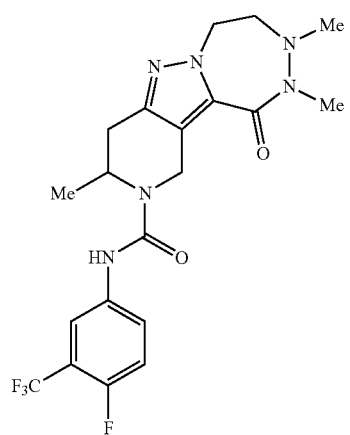 [SMILES: CC1Cc2nn3c(c2CN1C(=O)Nc1ccc(F)c(C(F)(F)F)c1)C(=O)N(C)N(C)CC3] 225
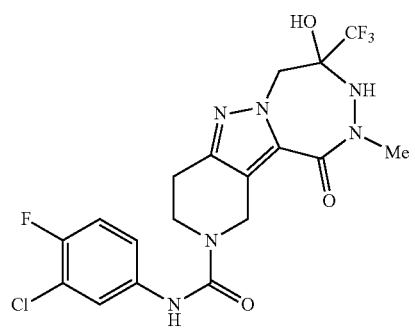 [SMILES: CN1NC(O)(C(F)(F)F)Cn2nc3c(c2C1=O)CN(C(=O)Nc1ccc(F)c(Cl)c1)CC3] 226
TABLE 5-continued
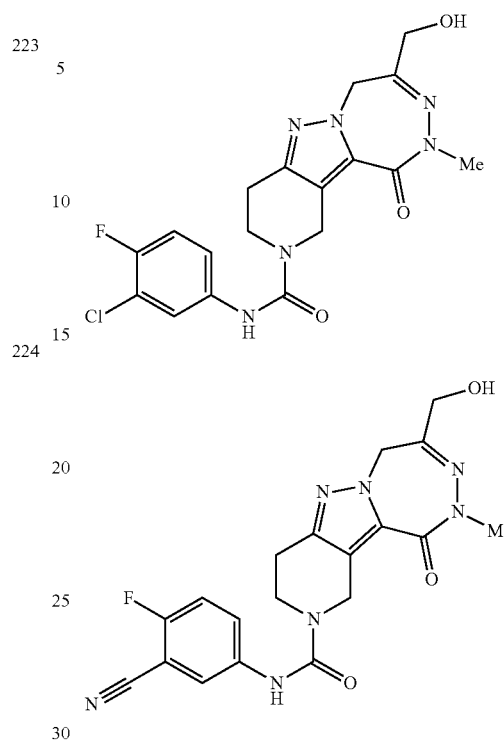 227
228
229
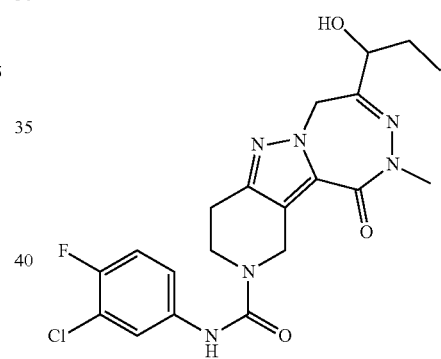 
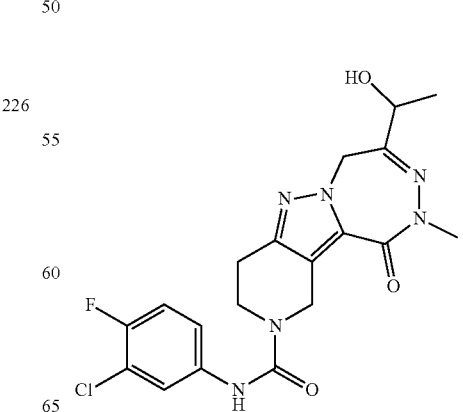 230

TABLE 5-continued
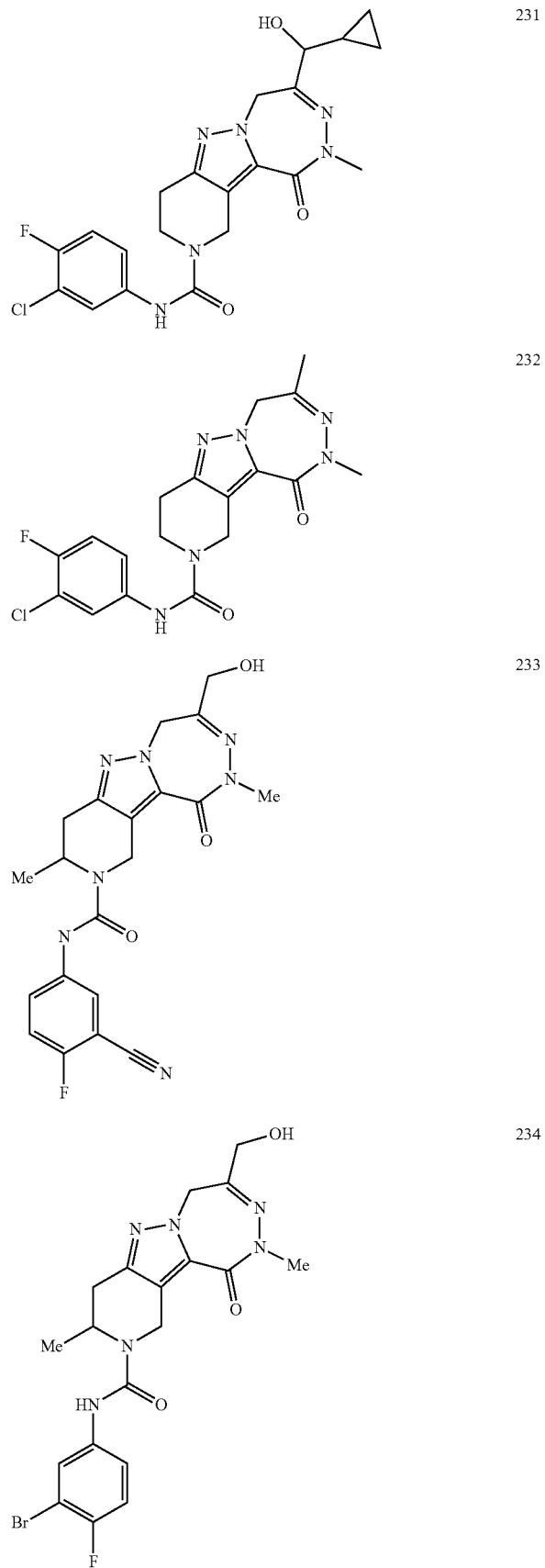
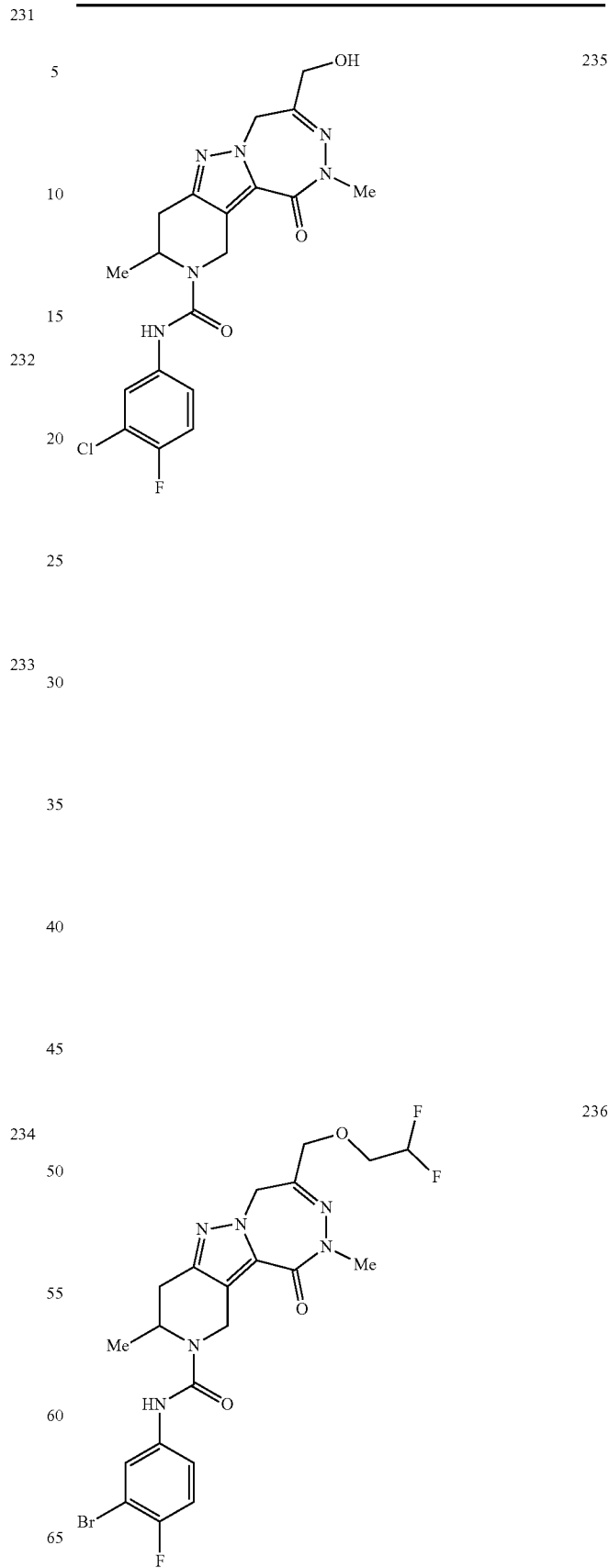

TABLE 5-continued

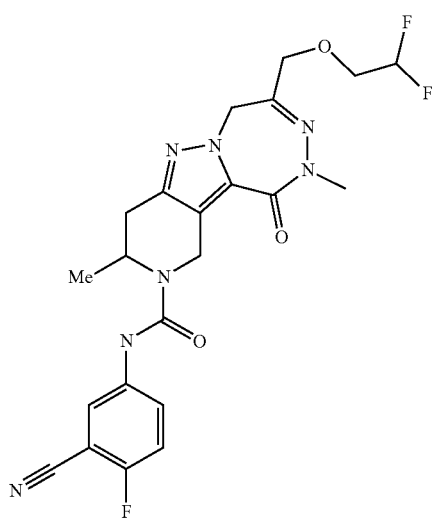 [SMILES: CC1Cc2nn3c(c2CN1C(=O)Nc1ccc(F)c(C#N)c1)C(=O)N(C)N=C(COCC(F)F)C3]

237

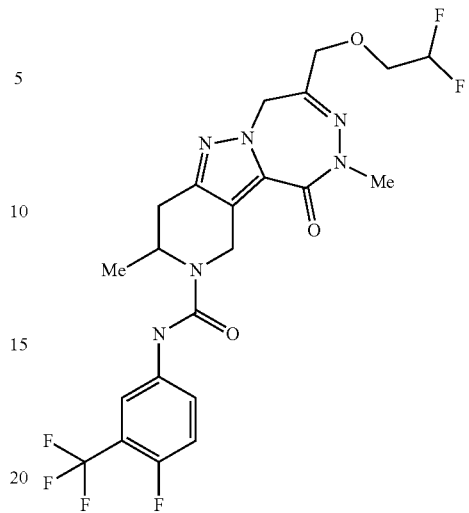

238

In an embodiment, compounds of Formula III are selected from:

| Compound ID | Compound Name |
|---|---|
| 216 | N-(3-chloro-4-fluorophenyl)-2-methyl-1-oxo-1,2,3,4,5,8,9,11-octahydro-10H-pyrido[4',3':3,4]pyrazolo[5,1-d][1,2,5]triazepine-10-carboxamide |
| 217 | N-(3-chloro-4-fluorophenyl)-2,3-dimethyl-1-oxo-1,2,3,4,5,8,9,11-octahydro-10H-pyrido[4',3':3,4]pyrazolo[5,1-d][1,2,5]triazepine-10-carboxamide |
| 218 | (R)-3-allyl-N-(3-cyano-4-fluorophenyl)-2,9-dimethyl-1-oxo-1,2,3,4,5,8,9,11-octahydro-10H-pyrido[4',3':3,4]pyrazolo[5,1-d][1,2,5]triazepine-10-carboxamide |
| 219 | (R)-N-(3-cyano-4-fluorophenyl)-3-(2,2-difluoroethyl)-2,9-dimethyl-1-oxo-1,2,3,4,5,8,9,11-octahydro-10H-pyrido[4',3':3,4]pyrazolo[5,1-d][1,2,5]triazepine-10-carboxamide |
| 220 | (R)-N-(3-cyano-4-fluorophenyl)-3-(2-hydroxyethyl)-2,9-dimethyl-1-oxo-1,2,3,4,5,8,9,11-octahydro-10H-pyrido[4',3':3,4]pyrazolo[5,1-d][1,2,5]triazepine-10-carboxamide |
| 221 | (R)-N-(3-cyano-4-fluorophenyl)-2,9-dimethyl-1-oxo-3-propyl-1,2,3,4,5,8,9,11-octahydro-10H-pyrido[4',3':3,4]pyrazolo[5,1-d][1,2,5]triazepine-10-carboxamide |
| 222 | (R)-N-(3-cyano-4-fluorophenyl)-3-(3-hydroxypropyl)-2,9-dimethyl-1-oxo-1,2,3,4,5,8,9,11-octahydro-10H-pyrido[4',3':3,4]pyrazolo[5,1-d][1,2,5]triazepine-10-carboxamide |
| 223 | (9R)-N-(3-cyano-4-fluorophenyl)-3-(2-hydroxypropyl)-2,9-dimethyl-1-oxo-1,2,3,4,5,8,9,11-octahydro-10H-pyrido[4',3':3,4]pyrazolo[5,1-d][1,2,5]triazepine-10-carboxamide |
| 224 | (R)-N-(3-cyano-4-fluorophenyl)-2,3,9-trimethyl-1-oxo-1,2,3,4,5,8,9,11-octahydro-10H-pyrido[4',3':3,4]pyrazolo[5,1-d][1,2,5]triazepine-10-carboxamide |
| 225 | (R)-N-(4-fluoro-3-(trifluoromethyl)phenyl)-2,3,9-trimethyl-1-oxo-1,2,3,4,5,8,9,11-octahydro-10H-pyrido[4',3':3,4]pyrazolo[5,1-d][1,2,5]triazepine-10-carboxamide |
| 226 | N-(3-chloro-4-fluorophenyl)-4-hydroxy-2-methyl-1-oxo-4-(trifluoromethyl)-1,2,3,4,5,8,9,11-octahydro-10H-pyrido[4',3':3,4]pyrazolo[5,1-d][1,2,5]triazepine-10-carboxamide |
| 227 | N-(3-chloro-4-fluorophenyl)-4-(hydroxymethyl)-2-methyl-1-oxo-1,2,5,8,9,11-hexahydro-10H-pyrido[4',3':3,4]pyrazolo[5,1-d][1,2,5]triazepine-10-carboxamide |
| 228 | N-(3-cyano-4-fluorophenyl)-4-(hydroxymethyl)-2-methyl-1-oxo-1,2,5,8,9,11-hexahydro-10H-pyrido[4',3':3,4]pyrazolo[5,1-d][1,2,5]triazepine-10-carboxamide |
| 229 | N-(3-chloro-4-fluorophenyl)-4-(1-hydroxypropyl)-2-methyl-1-oxo-1,2,5,8,9,11-hexahydro-10H-pyrido[4',3':3,4]pyrazolo[5,1-d][1,2,5]triazepine-10-carboxamide |
| 230 | N-(3-chloro-4-fluorophenyl)-4-(1-hydroxyethyl)-2-methyl-1-oxo-1,2,5,8,9,11-hexahydro-10H-pyrido[4',3':3,4]pyrazolo[5,1-d][1,2,5]triazepine-10-carboxamide |
| 231 | N-(3-chloro-4-fluorophenyl)-4-(cyclopropyl(hydroxy)methyl)-2-methyl-1-oxo-1,2,5,8,9,11-hexahydro-10H-pyrido[4',3':3,4]pyrazolo[5,1-d][1,2,5]triazepine-10-carboxamide |

-continued

| Compound ID | Compound Name |
|---|---|
| 232 | N-(3-chloro-4-fluorophenyl)-2,4-dimethyl-1-oxo-1,2,5,8,9,11-hexahydro-10H-pyrido[4',3':3,4]pyrazolo[5,1-d][1,2,5]triazepine-10-carboxamide |
| 233 | (R)-N-(3-cyano-4-fluorophenyl)-4-(hydroxymethyl)-2,9-dimethyl-1-oxo-1,2,5,8,9,11-hexahydro-10H-pyrido[4',3':3,4]pyrazolo[5,1-d][1,2,5]triazepine-10-carboxamide |
| 234 | (R)-N-(3-bromo-4-fluorophenyl)-4-(hydroxymethyl)-2,9-dimethyl-1-oxo-1,2,5,8,9,11-hexahydro-10H-pyrido[4',3':3,4]pyrazolo[5,1-d][1,2,5]triazepine-10-carboxamide |
| 235 | (R)-N-(3-chloro-4-fluorophenyl)-4-(hydroxymethyl)-2,9-dimethyl-1-oxo-1,2,5,8,9,11-hexahydro-10H-pyrido[4',3':3,4]pyrazolo[5,1-d][1,2,5]triazepine-10-carboxamide |
| 236 | (R)-N-(3-bromo-4-fluorophenyl)-4-((2,2-difluoroethoxy)methyl)-2,9-dimethyl-1-oxo-1,2,5,8,9,11-hexahydro-10H-pyrido[4',3':3,4]pyrazolo[5,1-d][1,2,5]triazepine-10-carboxamide |
| 237 | (R)-N-(3-cyano-4-fluorophenyl)-4-((2,2-difluoroethoxy)methyl)-2,9-dimethyl-1-oxo-1,2,5,8,9,11-hexahydro-10H-pyrido[4',3':3,4]pyrazolo[5,1-d][1,2,5]triazepine-10-carboxamide |
| 238 | (R)-4-((2,2-difluoroethoxy)methyl)-N-(4-fluoro-3-(trifluoromethyl)phenyl)-2,9-dimethyl-1-oxo-1,2,5,8,9,11-hexahydro-10H-pyrido[4',3':3,4]pyrazolo[5,1-d][1,2,5]triazepine-10-carboxamide |

*Pure but unknown enantiomer or diastereomer.

and pharmaceutically acceptable salts thereof.

The disclosed compounds may possess one or more stereocenters, and each stereocenter may exist independently in either the R or S configuration. In one embodiment, compounds described herein are present in optically active or racemic forms. It is to be understood that the compounds described herein encompass racemic, optically-active, regioisomeric and stereoisomeric forms, or combinations thereof that possess the therapeutically useful properties described herein.

Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomer is utilized as the disclosed compound described herein. In another embodiment, compounds described herein contain one or more chiral centers. These compounds are prepared by any means, including stereoselective synthesis, enantioselective synthesis or separation of a mixture of enantiomers or diastereomers. Resolution of compounds and isomers thereof is achieved by any means including, by way of non-limiting example, chemical processes, enzymatic processes, fractional crystallization, distillation, and chromatography.

In one embodiment, the disclosed compounds may exist as tautomers. All tautomers are included within the scope of the compounds presented herein.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In one embodiment, isotopically-labeled compounds are useful in drug or substrate tissue distribution studies. In another embodiment, substitution with heavier isotopes such as deuterium affords greater metabolic stability (for example, increased in vivo half-life or reduced dosage requirements).

In yet another embodiment, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In one embodiment, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey and Sundberg, Advanced Organic Chemistry 4th Ed., Vols. A and B (Plenum 2000, 2001), and Green and Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

Methods

Provided herein is a method of treating an HBV infection in an individual in need thereof, comprising administering to the individual a therapeutically effective amount of a disclosed compound.

Also provided herein is a method of eradicating an HBV infection in an individual in need thereof, comprising administering to the individual a therapeutically effective amount of a disclosed compound.

Provided herein is a method of reducing viral load associated with an HBV infection in an individual in need thereof, comprising administering to the individual a therapeutically effective amount of a disclosed compound.

Further, provided herein is a method of reducing reoccurrence of an HBV infection in an individual in need thereof, comprising administering to the individual a therapeutically effective amount of a disclosed compound.

Provided herein is a method of inhibiting or reducing the formation or presence of HBV DNA-containing particles or HBV RNA-containing particles in an individual in need thereof, comprising administering to the individual a therapeutically effective amount of a disclosed compound.

In certain aspects, the methods and/or compositions described herein are effective for inhibiting or reducing the formation or presence of HBV-associated particles in vitro or in vivo (e.g., in a cell, in a tissue, in an organ (e.g., in the liver), in an organism or the like). HBV-associated particles may contain HBV DNA (i.e., linear and/or covalently closed circular DNA (cccDNA)) and/or HBV RNA (i.e., pre-genomic RNA and/or sub-genomic RNA). Accordingly, HBV-associated particles include HBV DNA-containing particles or HBV RNA-containing particles.

As used herein, "HPV-associated particles" refer to both infectious HBV virions (i.e., Dane particles) and non-infectious HBV subviral particles (i.e., HBV filaments and/or HBV spheres). HBV virions comprise an outer envelope including surface proteins, a nucleocapsid comprising core proteins, at least one polymerase protein, and an HBV genome. HBV filaments and HBV spheres comprise HBV surface proteins, but lack core proteins, polymerase and an HBV genome. HBV filaments and HBV spheres are also known collectively as surface antigen (HBsAg) particles. HBV spheres comprise middle and small HBV surface proteins. HBV filaments also include middle, small and large HBV surface proteins.

HBV subviral particles can include the nonparticulate or secretory HBeAg, which serves as a marker for active replication of HBV.

Provided herein is a method of reducing an adverse physiological impact of an HBV infection in an individual in need thereof, comprising administering to the individual a therapeutically effective amount of a disclosed compound.

Also provided herein is a method of reducing, slowing, or inhibiting an HBV infection in an individual in need thereof, comprising administering to the individual a therapeutically effective amount of a disclosed compound.

Provided herein is a method of inducing reversal of hepatic injury from an HBV infection in an individual in need thereof, comprising administering to the individual a therapeutically effective amount of a disclosed compound.

Provided herein is a method of reducing the physiological impact of long-term antiviral therapy for HBV infection in an individual in need thereof, comprising administering to the individual a therapeutically effective amount of a disclosed compound.

Provided herein is a method of prophylactically treating an HBV infection in an individual in need thereof, wherein the individual is afflicted with a latent HBV infection, comprising administering to the individual a therapeutically effective amount of a disclosed compound.

In one embodiment, the individual is refractory to other therapeutic classes of HBV drugs (e.g, HBV polymerase inhibitors, interferons, viral entry inhibitors, viral maturation inhibitors, literature-described capsid assembly modulators, antiviral compounds of distinct or unknown mechanism, and the like, or combinations thereof). In another embodiment, the disclosed method reduces viral load in an individual suffering from an HBV infection to a greater extent or at a faster rate compared to the extent that other therapeutic classes of HBV drugs reduce viral load in the individual.

In one embodiment, the administering of a disclosed compound, or a pharmaceutically acceptable salt thereof, allows for administering of the at least one additional therapeutic agent at a lower dose or frequency as compared to the administering of the at least one additional therapeutic agent alone that is required to achieve similar results in prophylactically treating an HBV infection in an individual in need thereof.

In one embodiment, the administering of a disclosed compound, or a pharmaceutically acceptable salt thereof, reduces the viral load in the individual to a greater extent or at a faster rate compared to the administering of a compound selected from the group consisting of an HBV polymerase inhibitor, interferon, viral entry inhibitor, viral maturation inhibitor, distinct capsid assembly modulator, antiviral compounds of distinct or unknown mechanism, and any combination thereof.

In one embodiment, the disclosed method reduces viral load in an individual suffering from an HBV infection, thus allowing lower doses or varying regimens of combination therapies to be used.

In one embodiment, the disclosed method causes a lower incidence of viral mutation or viral resistance compared to other classes of HBV drugs, thereby allowing for long term therapy and minimizing the need for changes in treatment regimens.

In one embodiment, the administering of a compound the invention, or a pharmaceutically acceptable salt thereof, causes a lower incidence of viral mutation or viral resistance than the administering of a compound selected from the group consisting of an HBV polymerase inhibitor, interferon, viral entry inhibitor, viral maturation inhibitor, distinct capsid assembly modulator, antiviral compounds of distinct or unknown mechanism, and combination thereof.

In one embodiment, the disclosed method increases the seroconversion rate from HBV infected to non-HBV infected or from detectable HBV viral load to non-detectable HBV viral load beyond that of current treatment regimens. As used herein, "seroconversion" refers to the period of time during which HBV antibodies develop and become detectable.

In one embodiment, the disclosed method increases or normalizes or restores normal health, elicits full recovery of normal health, restores life expectancy, or resolves the viral infection in the individual in need thereof.

In one embodiment, the disclosed method eliminates or decreases the number of HBV RNA particles that are released from HBV infected cells thus enhancing, prolonging, or increasing the therapeutic benefit of the disclosed compounds.

In one embodiment, the disclosed method eradicates HBV from an individual infected with HBV, thereby obviating the need for long term or life-long treatment, or shortening the duration of treatment, or allowing for reduction in dosing of other antiviral agents.

In another embodiment, the disclosed method further comprises monitoring or detecting the HBV viral load of the subject, and wherein the method is carried out for a period of time including until such time that the HBV virus is undetectable.

Accordingly, in one embodiment, provided herein is a method of treating an HBV infection in an individual in need thereof, comprising administering to the individual a therapeutically effective amount of a compound of Formula Ia, or a pharmaceutically acceptable salt thereof.

Accordingly, in one embodiment, provided herein is a method of treating an HBV infection in an individual in need thereof, comprising administering to the individual a therapeutically effective amount of a compound of Formula I, or a pharmaceutically acceptable salt thereof.

In another embodiment, provided herein is a method of treating an HBV infection in an individual in need thereof, comprising administering to the individual a therapeutically effective amount of a compound of Formula II, or a pharmaceutically acceptable salt thereof.

In another embodiment, provided herein is a method of treating an HBV infection in an individual in need thereof, comprising administering to the individual a therapeutically effective amount of a compound of Formula III, or a pharmaceutically acceptable salt thereof.

In another embodiment, provided herein is a method of treating an HBV infection in an individual in need thereof, comprising administering to the individual a therapeutically effective amount of a compound of Table 1, or a pharmaceutically acceptable salt thereof.

In another embodiment, provided herein is a method of treating an HBV infection in an individual in need thereof, comprising administering to the individual a therapeutically effective amount of a compound of Table 2, or a pharmaceutically acceptable salt thereof.

In another embodiment, provided herein is a method of treating an HBV infection in an individual in need thereof, comprising administering to the individual a therapeutically effective amount of a compound of Table 3, or a pharmaceutically acceptable salt thereof.

In another embodiment, provided herein is a method of treating an HBV infection in an individual in need thereof, comprising administering to the individual a therapeutically effective amount of a compound of Table 4, or a pharmaceutically acceptable salt thereof.

In another embodiment, provided herein is a method of treating an HBV infection in an individual in need thereof, comprising administering to the individual a therapeutically effective amount of a compound of Table 5, or a pharmaceutically acceptable salt thereof.

In an embodiment of any of the methods provided herein, the method can further comprise monitoring the HBV viral load of the subject, wherein the method is carried out for a period of time such that the HBV virus is undetectable.

Combination Therapies

The disclosed compounds may be useful in combination with one or more additional compounds useful for treating HBV infection. These additional compounds may comprise other disclosed compounds and/or compounds known to treat, prevent, or reduce the symptoms or effects of HBV infection. Such compounds include, but are not limited to, HBV polymerase inhibitors, interferons, viral entry inhibitors, viral maturation inhibitors, literature-described capsid assembly modulators, reverse transcriptase inhibitors, immunomodulatory agents, TLR-agonists, and other agents with distinct or unknown mechanisms that affect the HBV life cycle or affect the consequences of HBV infection.

In non-limiting examples, the disclosed compounds may be used in combination with one or more drugs (or a salt thereof) selected from the group comprising:

HBV reverse transcriptase inhibitors, and DNA and RNA polymerase inhibitors including, but not limited to, lamivudine (3TC, Zeffix, Heptovir, Epivir, and Epivir-HBV), entecavir (Baraclude, Entavir), adefovir dipivoxil (Hepsara, Preveon, bis-POM PMEA), tenofovir disoproxil fumarate (Viread, TDF or PMPA);

interferons including, but not limited to, interferon alpha (IFN-α), interferon beta (IFN-β), interferon lambda (IFN-λ), and interferon gamma (IFN-γ);

viral entry inhibitors;

viral maturation inhibitors;

literature-described capsid assembly modulators, such as, but not limited to, BAY 41-4109;

reverse transcriptase inhibitors;

immunomodulatory agents such as TLR-agonists; and agents of distinct or unknown mechanisms, such as but not limited to AT-61 ((E)-N-(1-chloro-3-oxo-1-phenyl-3-(piperidin-1-yl)prop-1-en-2-yl)benzamide), AT-130 ((E)-N-(1-bromo-1-(2-methoxyphenyl)-3-oxo-3-(piperidin-1-yl) prop-1-en-2-yl)-4-nitrobenzamide), and similar analogs.

In one embodiment, the additional therapeutic agent is an interferon. The term "interferon" or "IFN" refers to any member of the family of highly homologous species-specific proteins that inhibit viral replication and cellular proliferation and modulate immune response. Human interferons are grouped into three classes: Type I, which includes interferon-alpha (IFN-α), interferon-beta (IFN-β), and interferon-omega (IFN-ω), Type II, which includes interferon-gamma (IFN-γ), and Type III, which includes interferon-lambda (IFN-λ). Recombinant forms of interferons that have been developed and are commercially available are encompassed by the term "interferon" as used herein. Subtypes of interferons, such as chemically modified or mutated interferons, are also encompassed by the term "interferon" as used herein. Chemically modified interferons may include pegylated interferons and glycosylated interferons. Examples of interferons also include, but are not limited to, interferon-alpha-2a, interferon-alpha-2b, interferon-alpha-n1, interferon-beta-1a, interferon-beta-1b, interferon-lamda-1, interferon-lamda-2, and interferon-lamda-3. Examples of pegylated interferons include pegylated interferon-alpha-2a and pegylated interferon alpha-2b.

Accordingly, in one embodiment, the compounds of Formula Ia, Formula I, or Formula II can be administered in combination with an interferon selected from the group consisting of interferon alpha (IFN-α), interferon beta (IFN-β), interferon lambda (IFN-λ), and interferon gamma (IFN-γ). In one specific embodiment, the interferon is interferon-alpha-2a, interferon-alpha-2b, or interferon-alpha-n1. In another specific embodiment, the interferon-alpha-2a or interferon-alpha-2b is pegylated. In a preferred embodiment, the interferon-alpha-2a is pegylated interferon-alpha-2a (PEGASYS).

In another embodiment, the additional therapeutic agent is selected from immune modulator or immune stimulator therapies, which includes biological agents belonging to the interferon class.

Further, the additional therapeutic agent may be an agent of distinct or unknown mechanism including agents that disrupt the function of other essential viral protein(s) or host proteins required for HBV replication or persistence.

In another embodiment, the additional therapeutic agent is an antiviral agent that blocks viral entry or maturation or targets the HBV polymerase such as nucleoside or nucleotide or non-nucleos(t)ide polymerase inhibitors. In a further embodiment of the combination therapy, the reverse transcriptase inhibitor or DNA or RNA polymerase inhibitor is Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, PMPA, cidofovir, Efavirenz, Nevirapine, Delavirdine, or Etravirine.

In an embodiment, the additional therapeutic agent is an immunomodulatory agent that induces a natural, limited immune response leading to induction of immune responses against unrelated viruses. In other words, the immunomodulatory agent can effect maturation of antigen presenting cells, proliferation of T-cells and cytokine release (e.g., IL-12, IL-18, IFN-alpha, -beta, and -gamma and TNF-alpha among others), In a further embodiment, the additional therapeutic agent is a TLR modulator or a TLR agonist, such as a TLR-7 agonist or TLR-9 agonist. In further embodiment of the combination therapy, the TLR-7 agonist is selected from the group consisting of SM360320 (9-benzyl-8-hydroxy-2-(2-methoxy-ethoxy)adenine) and AZD 8848 (methyl [3-({[3-(6-amino-2-butoxy-8-oxo-7,8-dihydro-9H-purin-9-yl)propyl][3-(4-morpholinyl)propyl]amino}methyl)phenyl] acetate).

In any of the methods provided herein, the method may further comprise administering to the individual at least one HBV vaccine, a nucleoside HBV inhibitor, an interferon or any combination thereof. In an embodiment, the HBV vaccine is at least one of RECOMBIVAX HB, ENGERIX-B, ELOVAC B, GENEVAC-B, or SHANVAC B.

In one embodiment, the methods described herein further comprise administering at least one additional therapeutic agent selected from the group consisting of nucleotide/nucleoside analogs, entry inhibitors, fusion inhibitors, and any combination of these or other antiviral mechanisms.

In another aspect, provided herein is method of treating an HBV infection in an individual in need thereof, comprising reducing the HBV viral load by administering to the individual a therapeutically effective amount of a disclosed compound alone or in combination with a reverse transcriptase inhibitor; and further administering to the individual a therapeutically effective amount of HBV vaccine. The reverse transcriptase inhibitor may be at least one of Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, PMPA, cidofovir, Efavirenz, Nevirapine, Delavirdine, or Etravirine.

In another aspect, provided herein is a method of treating an HBV infection in an individual in need thereof, comprising reducing the HBV viral load by administering to the individual a therapeutically effective amount of a disclosed compound alone or in combination with a antisense oligonucleotide or RNA interference agent that targets HBV nucleic acids; and further administering to the individual a therapeutically effective amount of HBV vaccine. The antisense oligonucleotide or RNA interference agent possesses sufficient complementarity to the the target HBV nucleic acids to inhibit replication of the viral genome, transcription of viral RNAs, or translation of viral proteins.

In another embodiment, the disclosed compound and the at least one additional therapeutic agent are co-formulated. In yet another embodiment, the disclosed compound and the at least one additional therapeutic agent are co-administered.

For any combination therapy described herein, synergistic effect may be calculated, for example, using suitable methods such as the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

In an embodiment of any of the methods of administering combination therapies provided herein, the method can further comprise monitoring or detecting the HBV viral load of the subject, wherein the method is carried out for a period of time including until such time that the HBV virus is undetectable.

Administration/Dosage/Formulations

In another aspect, provided herein is a pharmaceutical composition comprising at least one disclosed compound, or a pharmaceutically acceptable salt thereof, together with a pharmaceutically acceptable carrier.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could begin administration of the pharmaceutical composition to dose the disclosed compound at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited to unitary dosages for the patients to be treated; each unit containing a predetermined quantity of the disclosed compound calculated to produce the desired therapeutic effect in association with the required pharmaceutical vehicle. The dosage unit forms of the invention are dictated by and directly dependent on (a) the unique characteristics of the disclosed compound and the particular therapeutic effect to be achieved, and (b) the limitations inherent in the art of compounding/formulating such a disclosed compound for the treatment of HBV infection in a patient.

In one embodiment, the compositions of the invention are formulated using one or more pharmaceutically acceptable excipients or carriers. In one embodiment, the pharmaceutical compositions of the invention comprise a therapeutically effective amount of a disclosed compound and a pharmaceutically acceptable carrier.

In some embodiments, the dose of a disclosed compound is from about 1 mg to about 2,500 mg. In some embodiments, a dose of a disclosed compound used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., another drug for HBV treatment) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a disclosed compound, alone or in combination with a second pharmaceutical agent; and instructions for using the compound to treat, prevent, or reduce one or more symptoms of HBV infection in a patient.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For parenteral administration, the disclosed compounds may be formulated for injection or infusion, for example, intravenous, intramuscular or subcutaneous injection or infusion, or for administration in a bolus dose or continuous infusion. Suspensions, solutions or emulsions in an oily or aqueous vehicle, optionally containing other formulatory agents such as suspending, stabilizing or dispersing agents may be used.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (Ia). Reactions may be performed between the melting point and the reflux temperature of the solvent, and preferably between 0° C. and the reflux temperature of the solvent. Reactions may be heated employing conventional heating or microwave heating. Reactions may also be conducted in sealed pressure vessels above the normal reflux temperature of the solvent.

Abbreviations and acronyms used herein include the following:

TABLE 6

| Term | Acronym |
| --- | --- |
| Acetonitrile | ACN or MeCN |
| Aqueous | aq |
| Atmosphere | atm |
| tert-Butylcarbamoyl | Boc |
| Boron-dipyrromethene | BODIPY |
| Benzyl | Bn |
| Broad | br |
| Capside assembly | CA |
| Carboxybenzyl | CBz |
| Diatomaceous Earth | Celite ® |
| 1,1'-Carbonyldiimidazole | CDI |
| Doublet of doublets | dd |

TABLE 6-continued

| Term | Acronym |
| --- | --- |
| Diethylaminosulfur trifluoride | DAST |
| Di-tert-butyl azodicarboxylate | DBAD |
| 1,8-Diazabicyclo[5.4.0]undec-7-ene | DBU |
| Dichloroethane | DCE |
| Dichloromethane | DCM |
| Bis(2-methoxyethyl)aminosulfur trifluoride | Deoxo-Fluor ® |
| Diethyl azodicarboxylate | DEAD |
| Diisopropyl azodicarboxylate | DIAD |
| Diisopropylethylamine | DIPEA, DIEA, or Hunig's base |
| 4-Dimethylaminopyridine | DMAP |
| 1,2-Dimethoxyethane | DME |
| N,N-Dimethylformamide | DMF |
| Dimethyl sulfide | DMS |
| Dimethylsulfoxide | DMSO |
| Deoxyribonucleic Acid | DNA |
| 1-Ethyl-3-(3-dimethylaminopropyl)carbodiimide | EDCI, EDAC, or EDC |
| Diethyl ether | Ether, Et$_2$O |
| Ethyl Acetate | EtOAc, or EA |
| Ethanol | EtOH |
| Electrospray ionization | ESI |
| Normal-phase silica gel chromatography | FCC |
| Grams | g |
| Hours | h or hr |
| (1-[Bis(dimethylamino)methylene]-1H-1,2,3-triazolo[4,5-b]pyridinium 3-oxid hexafluorophosphate) | HATU |
| Hepatitis B Virus | HBV |
| Acetic acid | HOAc |
| 1-Hydroxy-7-azabenzotriazole | HOAt |
| Hydroxybenzotriazole | HOBt |
| High-pressure liquid chromatography | HPLC |
| Hertz | Hz |
| Isopropyl alcohol | iPrOH, IPA |
| Potassium tert-butoxide | KOtBu |
| Lithium aluminum hydride | LAH |
| Liquid chromatography and mass spectrometry | LCMS |
| Lithium diisopropylamide | LDA |
| Lithium bis(trimethylsilyl)amide | LHMDS |
| Molar | M |
| multiplet | m |
| Mass to charge ratio | m/z |
| meta-Chloroperoxybenzoic acid | mCPBA |
| Methyl Iodide | MeI |
| Methanol | MeOH |
| Milligrams | mg |
| Megahertz | MHz |
| Minute | min |
| Milliliter | mL |
| Microliter | uL |
| Millimole | mmol |
| Micromole | µmol |
| Mass spectrometry | MS |
| Mesityl chloride | MsCl |
| Normal | N |
| Sodium acetate | NaOAc |
| Sodium tert-butoxide | NaOt-Bu |
| N-Methylmorpholine N-oxide | NMO |
| Nuclear magnetic resonance | NMR |
| CF3SO3-or triflate | OTf |
| Polymerase chain reaction | PCR |
| Petroleum ether | PE |
| Palladium (II) acetate | Pd(OAc)$_2$ |
| Palladium(II)bis(triphenylphosphine) dichloride | Pd(PPh$_3$)$_2$Cl$_2$ |
| Tetrakis(triphenylphosphine)palladium(0) | Pd(PPh$_3$)$_4$ |
| [1,1'-Bis(di-tert-butylphosphino)ferrocene] dichloropalladium(II) | PdCl$_2$(dtbpf) or Pd(dtbpf)$_2$Cl$_2$ |
| [1,1'-Bis(diphenylphosphino)ferrocene] dichloropalladium(II) | PdCl$_2$(dppf) or Pd(dppf)$_2$Cl$_2$ |
| 9-(2-Phosphonyl-methoxypropyly)adenine | PMPA |
| Parts per million | ppm |
| Precipitate | ppt |
| Polytetrafluoroethylene | PTFE |
| Pyridine | Py |
| Benzotriazol-1-yl-oxytripyrrolidinophosphonium hexafluorophosphate | PyBOP |
| Retention time | R$_t$ |
| Ribonucleic Acid | RNA |
| Room temperature | rt |
| singlet | s |
| Saturated | sat |
| 1-Chloromethyl-4-fluoro-1,4-diazoniabicyclo[2.2.2]octane bis(tetrafluoroborate) | Selectfluor ® |
| [2-(Trimethylsilyl)ethoxy]methyl acetal | SEM |
| Supercritical Fluid Chromatography | SFC |
| Temperature | T |
| triplet | t |
| Propylphosphonic anhydride | T$_3$P |
| Tert-Butyl alcohol | tBuOH, t-BuOH |
| Tetra-n-butylammonium fluoride | TBAF |
| Tetra-n-butylammonium iodide | TBAI |
| Tert-butyldiphenylsilyl chloride | TBDP SCl |
| Triethylamine | TEA |
| Trifluoroacetic acid | TFA |
| Tetrahydrofuran | THF |
| Thin layer chromatography | TLC |
| Toll-like receptor | TLR |
| Tumor necrosis factor | TNF |
| Tetrapropylammonium perruthenate | TPAP |
| Volume in milliliters of solvent per gram of substrate | V, or volumes |
| (Diethylamino)difluorosulfonium tetrafluoroborate | XtalFluor ® |

PREPARATIVE EXAMPLES

Exemplary compounds useful in methods of the invention will now be described by reference to the illustrative synthetic schemes for their general preparation below and the specific examples to follow.

SCHEME 1

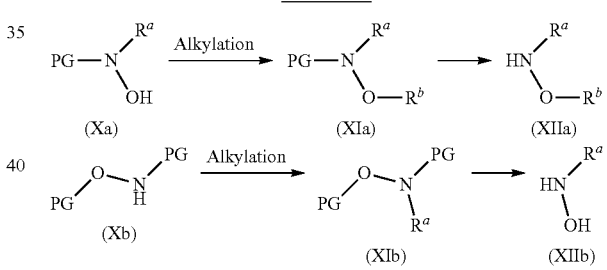

According to SCHEME 1, a commercially available or synthetically accessible compound of formula (Xa), where $R^a$ is —$C_{1-6}$alkyl, $C_{1-6}$haloalkyl, or $C_{1-6}$alkenyl, and PG is a suitable nitrogen protecting group such as BOC, Bn, and the like, is alkylated with an alkylating agent such as methyl 2-bromo-2-methylpropanoate, and the like, to provide a compound of formula (XIa), where $R^b$ is $C_{1-6}$alkyl optionally substituted with CO$_2$Me. A compound of formula (Xb), where PG is a suitable nitrogen protecting group such as BOC, Bn, and the like, is alkylated under conditions known to one skilled in the art, for example, reaction with or without a base such as NaH, Cs$_2$CO$_3$, K$_2$CO$_3$, and the like, in a suitable solvent such as THF, DMF and the like, with an alkylating agent such as deuterium methyl iodide, allyl bromide, and the like, to provide a compound of formula (XIb), where $R^a$ is $C_{1-6}$alkyl, $C_{1-6}$haloalkyl, or $C_{1-6}$alkenyl.

Deprotection of the nitrogen protecting group, employing conditions known to one skilled in the art provides a compound of formula (XIIa) and (XIIb). For example, the BOC protecting group is removed with acid such as TFA, HCl, and the like, in a suitable solvent such as DCM, and the like.

SCHEME 2

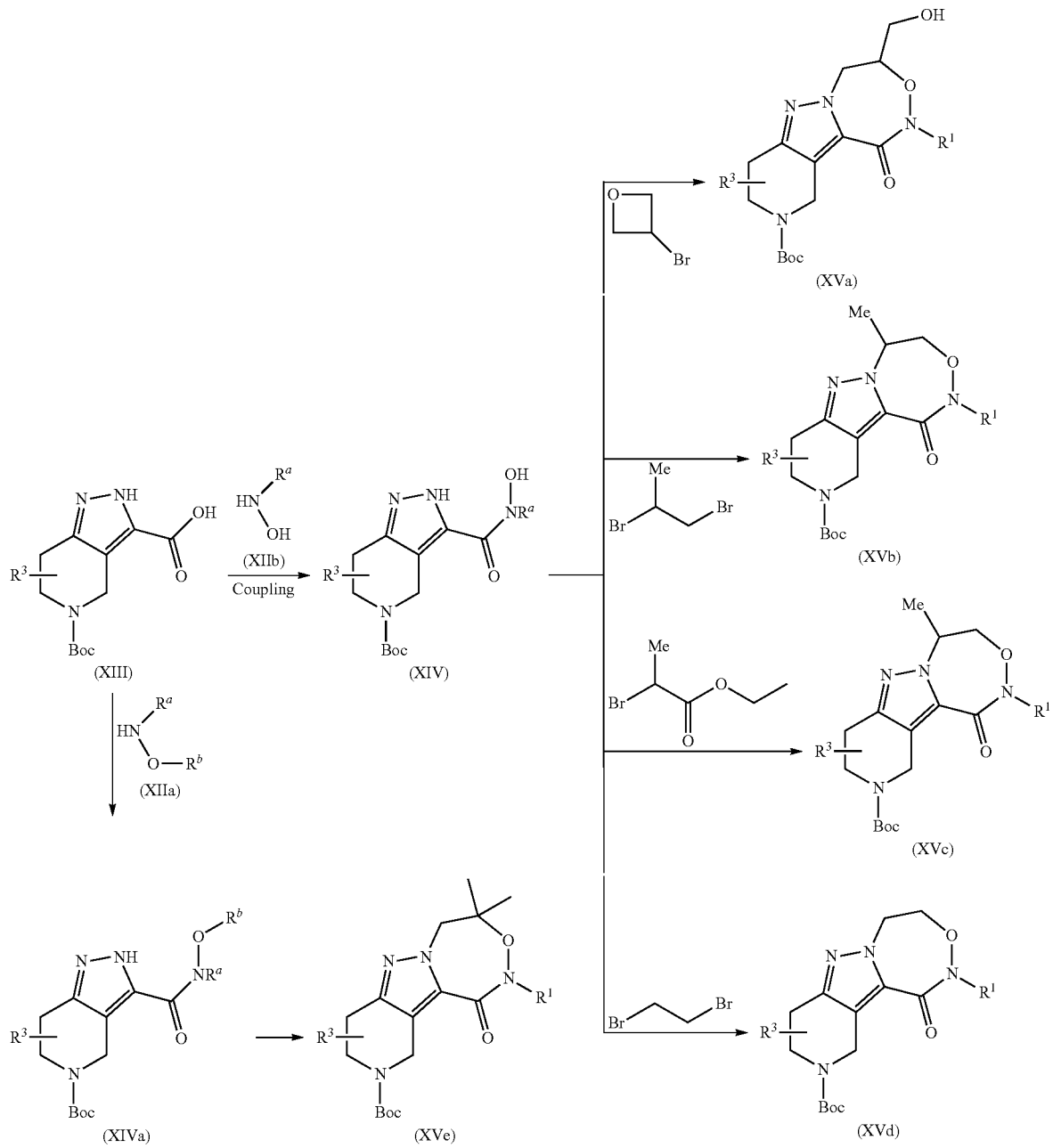

According to SCHEME 2, a commercially available or synthetically accessible compound of Formula (XIII), where $R^3$ is H or $C_{1-6}$alkyl, is coupled with a compound of Formula (XIIb), where $R^a$ is $C_{1-6}$alkyl, $C_{1-6}$haloalkyl, or $C_{1-6}$alkenyl, under amide bond coupling conditions to provide a compound of Formula (XIV). For example, an acid compound of Formula (XIII) is reacted with an amine of Formula (XII), in the presence of a dehydrating agent such as HOBt/EDAC, CDI, PyBOP, HATU, HOAT, propylphosphonic anhydride (T₃P), a suitably selected base such as DIPEA, TEA, and the like, in a solvent such as toluene, MeCN, EtOAc, DMF, THF, DCM, or a mixture thereof, to afford a compound of Formula (XIV).

A compound of Formula (XIV), where $R^3$ is H or $C_{1-6}$alkyl, $R^a$ is $C_{1-6}$alkyl, $C_{1-6}$haloalkyl, or $C_{1-6}$alkenyl, is reacted with oxetane bromide, with a base such as cesium carbonate, with a phase transfer catalyst such as TBAI, in a solvent such as DMF, at a temperature of about 60-80° C. for a period of 5-6 h provides a compound of Formula (XVa) where $R^3$ is H or $C_{1-6}$alkyl and $R^1$ is $C_{1-6}$alkyl, $C_{1-6}$haloalkyl, or $C_{1-6}$alkenyl.

A compound of Formula (XIV), where $R^3$ is H or $C_{1-6}$alkyl, $R^a$ is $C_{1-6}$alkyl, $C_{1-6}$haloalkyl, or $C_{1-6}$alkenyl, is reacted with 1-methyl-dibromoethane, with a base such as potassium carbonate, solvent such as DMF, at a temperature of about 20° C. provides a compound of Formula (XVb) where $R^3$ is H or $C_{1-6}$alkyl and $R^1$ is $C_{1-6}$alkyl, $C_{1-6}$haloalkyl, or $C_{1-6}$alkenyl.

A compound of Formula (XIV), where $R^3$ is H or $C_{1-6}$alkyl, $R^a$ is $C_{1-6}$alkyl, $C_{1-6}$haloalkyl, or $C_{1-6}$alkenyl, is reacted with ethyl 2-bromopropanoate, with a base such as cesium carbonate, with a phase transfer catalyst such as TBAI, in a solvent such as DMF, at a temperature of about 40-60° C. for a period of 14-18 h provides a compound of Formula (XVc) where $R^3$ is H or $C_{1-6}$alkyl and $R^1$ is $C_{1-6}$alkyl, $C_{1-6}$haloalkyl, or $C_{1-6}$alkenyl.

A compound of Formula (XIV), where $R^3$ is H or $C_{1-6}$alkyl, $R^a$ is $C_{1-6}$alkyl, $C_{1-6}$haloalkyl, or $C_{1-6}$alkenyl, is reacted with 1-methyl-dibromoethane, with a base such as cesium carbonate, with a phase transfer catalyst such as TBAI, solvent such as DMF, at a temperature of about 20° C. provides a compound of Formula (XVd) where $R^3$ is H or $C_{1-6}$alkyl and $R^1$ is $C_{1-6}$alkyl, $C_{1-6}$haloalkyl, or $C_{1-6}$alkenyl.

A commercially available or synthetically accessible compound of Formula (XIII), where $R^3$ is H or $C_{1-6}$alkyl, is coupled with a compound of Formula (XIIa), where $R^a$ is $C_{1-6}$alkyl, $C_{1-6}$haloalkyl, or $C_{1-6}$alkenyl, and $R^b$ is $C_{1-6}$alkyl optionally substituted with $CO_2Me$, under amide bond coupling conditions to provide a compound of Formula (XIVa). For example, an acid compound of Formula (XIII) is reacted with an amine of Formula (XIaI), in the presence of a dehydrating agent such as HOBt/EDAC, CDI, PyBOP, HATU, HOAT, propylphosphonic anhydride ($T_3P$), a suitably selected base such as DIPEA, TEA, and the like, in a solvent such as toluene, MeCN, EtOAc, DMF, THF, DCM, or a mixture thereof, to afford a compound of Formula (XIVa).

A compound of Formula (XIV), where $R^3$ is H or $C_{1-6}$alkyl, $R^a$ is $C_{1-6}$alkyl, $C_{1-6}$haloalkyl, or $C_{1-6}$alkenyl, and $R^b$ is $C_{1-6}$alkyl optionally substituted with $CO_2Me$ is reacted with a trialkyl phosphate such as tributyl phosphate, a coupling reagent such as DIAD, solvent such as THF, at a temperature of about reflux provides a compound of Formula (XVe) where $R^3$ is H or $C_{1-6}$alkyl and $R^1$ is $C_{1-6}$alkyl, $C_{1-6}$haloalkyl, or $C_{1-6}$alkenyl.

SCHEME 3

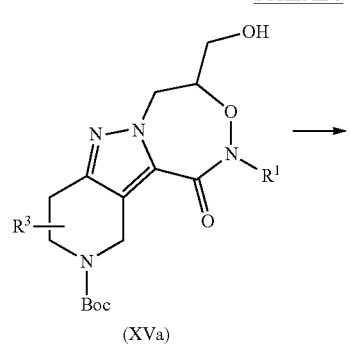

(XVa)

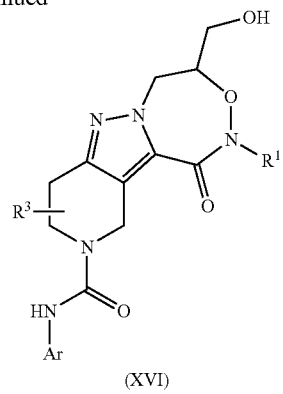

(XVI)

According to SCHEME 3, a compound of Formula (XVI) where Ar is an optionally substituted aryl ring, $R^3$ is H or $C_{1-6}$alkyl, and $R^1$ is $C_{1-6}$alkyl, $C_{1-6}$haloalkyl, or $C_{1-6}$alkenyl, can be prepared in two steps. For example, a compound of Formula (XVa) is reacted with an acid such as TFA, in a solvent such as DCM, at a temperature of about about 15° C. for about 30 minutes to provide a compound of Formula (XVI) where the Boc group has been removed. The resulting product can then be reacted with an optionally substituted N-aryl phenyl carbamate such as phenyl (3-chloro-4-fluorophenyl)carbamate and a base such as TEA in a solvent such as DCM to provide a compound of Formula (XVI) where Ar is an optionally substituted aryl ring.

SCHEME 4

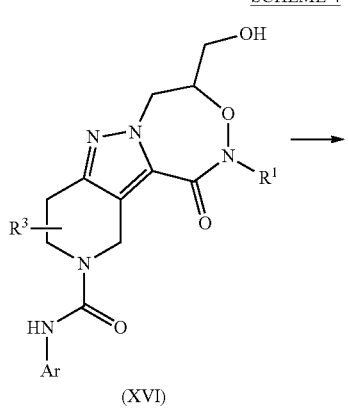

(XVI)

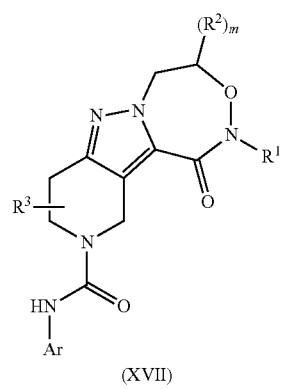

(XVII)

According to SCHEME 4, a compound of Formula (XVI) where Ar is an optionally substituted aryl ring, $R^3$ is H or $C_{1-6}$alkyl, and $R^1$ is $C_{1-6}$alkyl, $C_{1-6}$haloalkyl, or $C_{1-6}$alkenyl is reacted with a fluorinating reagent such as DAST, in a solvent such as DCM to provide a compound of Formula (XVII) where $R^2$ is $CH_2F$.

A compound of Formula (XVII) where Ar is an optionally substituted aryl ring, $R^3$ is H or $C_{1-6}$alkyl, $R^1$ is $C_{1-6}$alkyl, $C_{1-6}$haloalkyl, or $C_{1-6}$alkenyl, $R^2$ is $CH_2SC_1$-$C_6$alkyl, and m is 1 was prepared in two steps. First, a compound of Formula (XVI) was coupled with a sulfonating reagent such as MsCl, in presence of a base such as TEA, in a solvent such as DCM, at a temperature of about 25° C. for about 2 h to provide a compound of Formula (XVII) where $R^2$ is $CH_2OMs$ and m is 1. Second, adding a sulfide nucleophile such as sodium methyl sulfide, in a solvent such as DMF, at a temperature of about 15° C. for about 16 h to provide a compound of Formula (XVII) where $R^2$ is $CH_2SC_1$-$C_6$alkyl, and m is 1.

A compound of Formula (XVII) where Ar is an optionally substituted aryl ring, $R^3$ is H or $C_{1-6}$alkyl, $R^1$ is $C_{1-6}$alkyl, $C_{1-6}$haloalkyl, or $C_{1-6}$alkenyl, $R^2$ is $CH_2SC_1$-$C_6$alkyl, and m is 1 is reacted with an oxidant such as m-CPBA, in a solvent such as DCM, at a temperature of about 30° C. for about 16 h to provide a compound of Formula (XVII) where $R^2$ is $CH_2S(O)C_1$-$C_6$alkyl or $CH_2SO_2C_1$-$C_6$alkyl and m is 1.

A compound of Formula (XVI) where Ar is an optionally substituted aryl ring, $R^3$ is H or $C_{1-6}$alkyl, and $R^1$ is $C_{1-6}$alkyl, $C_{1-6}$haloalkyl, or $C_{1-6}$alkenyl is reacted with NaOCN, with an acid such as TFA, in a solvent such as DCM, at a temperature of about 25° C. for about 32 h to provide a compound of Formula (XVII) where $R^2$ is $CH_2O(O)NH_2$.

A compound of Formula (XVII) where Ar is an optionally substituted aryl ring, $R^3$ is H or $C_{1-6}$alkyl, $R^1$ is $C_{1-6}$alkyl, $C_{1-6}$haloalkyl, or $C_{1-6}$alkenyl, $R^2$ is COOH, and m is 1 is reacted with an $N(C_{1-6}alkyl)_{0-2}$ such as methyl amine or dimethyl amine, using a coupling agent such as HATU, with a base such as DIPEA, in a solvent such as DMF to provide a compound of Formula (XVII) where $R^2$ is $C(O)N(C_{1-6}alkyl)_{0-2}$ and m is 1.

A compound of Formula (XVII) where Ar is an optionally substituted aryl ring, $R^3$ is H or $C_{1-6}$alkyl, $R^1$ is $C_{1-6}$alkyl, $C_{1-6}$haloalkyl, or $C_{1-6}$alkenyl, $R^2$ is $C_{3-6}$lactam, and m is 1 is prepared in 2 steps. First, a compound of Formula (XVII) where $R^2$ is $CH_2NH_2$ is reacted with haloalkyl acid chloride such as $C_1CH_2CH_2CH_2C(O)Cl$, with a base such as TEA, in a solvent such as DCM to provide a compound of Formula (XVII) where $R^2$ is $CH_2NHC(O)CH_2CH_2CH_2Cl$ and m is 1. Second, reacting with a strong base such as NaH, in a solvent such as THF to provide a compound of Formula (XVII) $R^2$ is $C_{3-6}$lactam, and m is 1.

A compound of Formula (XVII) where Ar is an optionally substituted aryl ring, $R^3$ is H or $C_{1-6}$alkyl, $R^1$ is $C_{1-6}$alkyl, $C_{1-6}$haloalkyl, or $C_{1-6}$alkenyl, $R^2$ is $CH_2N_3$, and m is 1 is reacted with with a phosphine such as triphenyl phosphine, in a solvent such a THF, water, or a mixture of both to provide a compound of Formula (XVII) where $R^2$ is $CH_2NH_2$.

SCHEME 5

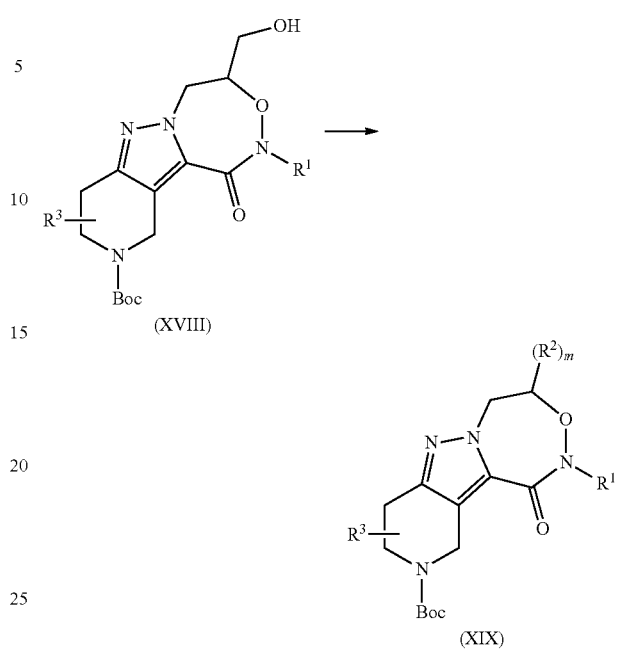

According to SCHEME 5, a compound of Formula (XIX) where $R^3$ is H or $C_{1-6}$alkyl, $R^1$ is $C_{1-6}$alkyl, $C_{1-6}$haloalkyl, or $C_{1-6}$alkenyl, $R^2$ is $CH_2N(C_{1-6}alkyl)_{0-2}$ or $C(O)N(C_{1-6}alkyl)_{0-2}$, and m is 1 is prepared in two steps. First, a compound of Formula (XVIII) is reacted with a sulfonating reagent such as MsCl, with a base such as TEA, in a solvent such as DCM to provide a compound of Formula (XIX) where $R^2$ is $CH_2OH$. Second, reacting with an amine such as $N(C_{1-6}alkyl)_{0-2}$, with a base such as potassium carbonate, in a solvent such as DMF, at a temperature of about 80° C. for about 24 h to provide a compound of (XIX) where $R^2$ is $CH_2N(C_{1-6}alkyl)_{0-2}$ or $C(O)N(C_{1-6}alkyl)_{0-2}$, and m is 1.

A compound of Formula (XVIII) where $R^3$ is H or $C_{1-6}$alkyl, and $R^1$ is $C_{1-6}$alkyl, $C_{1-6}$haloalkyl, or $C_{1-6}$alkenyl is reacted with a $C_{1-6}$alkyl halide, $C_{1-6}$alkenyl halide, $C_{1-6}$haloalkyl triflate or halo-$C_{1-6}$alkyl-$C_{1-6}$cycloalkyl such as MeI, EtI, n-propyliodide, allylbromide, $CHF_2CH_2OTf$, $CF_3CH_2OTf$ or c-$PrCH_2Br$ with a strong base such as NaH, in a solvent such as DMF to provide a compound of Formula (XIX) where $R^2$ is $CH_2OC_{1-6}$alkyl, $CH_2OC_{1-6}$alkenyl, $CH_2OC_{1-6}$haloalkyl, or $CH_2OC_{1-6}$alkyl-$C_{1-6}$cycloalkyl.

A compound of Formula (XIX) where $R^3$ is H or $C_{1-6}$alkyl, $R^1$ is $C_{1-6}$alkyl, $C_{1-6}$haloalkyl, or $C_{1-6}$alkenyl, $R^2$ is $COOC_{1-6}$alkyl, and m is 1 is prepared in 2 steps. First, a compound of Formula (XVIII) is reacted with an oxidant such as TPAP, a co-oxidant such as NMO, in a solvent such as MeCN to provide a compound of Formula (XIX) where $R^2$ is COOH. Second, reacting with a $C_{1-6}$alkyl-halide such as Met with a base such as potassium carbonate, in a solvent such as MeCN to provide a compound of (XIX) where $R^2$ is $COOC_{1-6}$alkyl, and m is 1.

A compound of Formula (XVIII) where $R^3$ is H or $C_{1-6}$alkyl, and $R^1$ is $C_{1-6}$alkyl, $C_{1-6}$haloalkyl, or $C_{1-6}$alkenyl is reacted with a silane such as $TMSCF_3$, a triflate salt such as silver triflate, a base such as 2-fluropyridine, a desilation reagent such as potassium fluoride, a fluorinating reagent suc has Selectfluor®, in a solvent such as Ethyl Acetate to provide a compound of Formula (XIX) where $R^2$ is $CH_2OCF_3$ and m is 1.

A compound of Formula (XIX) where $R^3$ is H or $C_{1-6}$alkyl, $R^1$ is $C_{1-6}$alkyl, $C_{1-6}$haloalkyl, or $C_{1-6}$alkenyl, $R^2$ is $CH_2OMs$, and m is 1 is reacted with an amine such as $N(C_{1-6}alkyl)_{0-2}$ or $N(C_{1-6}haloalkyl)_{0-2}$, a base such as potassium carbonate, in a solvent such as MeCN, at a temperature of about 80° C. for about 16 h to provide a compound of Formula (XIX) where $R^2$ is $CH_2N(C_{1-6}alkyl)_{0-2}$ or $N(C_{1-6}haloalkyl)_{0-2}$ and m is 1.

A compound of Formula (XIX) where $R^3$ is H or $C_{1-6}$alkyl, $R^1$ is $C_{1-6}$alkyl, $C_{1-6}$haloalkyl, or $C_{1-6}$alkenyl, $R^2$ is COOH, and m is 1 is reacted with an amine such as $N(C_{1-6}alkyl)_{0-2}$, $N(C_{1-6}haloalkyl)_{0-2}$, or $N(C_{1-6}alkyl)(C_{1-6}haloalkyl)$, a base such as 3-picoline, a sulfonating reagent such as MsCl, in a solvent such as MeCN, at a temperature of about 0° C. to 30° C. for about 1 h to provide a compound of Formula (XIX) where $R^2$ is $C(O)N(C_{1-6}alkyl)_{0-2}$, $C(O)N(C_{1-6}haloalkyl)_{0-2}$, or $C(O)N(C_{1-6}alkyl)(C_{1-6}haloalkyl)$ and m is 1.

A compound of Formula (XIX) where $R^3$ is H or $C_{1-6}$alkyl, $R^1$ is $C_{1-6}$alkyl, $C_{1-6}$haloalkyl, or $C_{1-6}$alkenyl, $R^2$ is $CH_2NHC(O)C_{1-6}alkyl$, and m is 1 is prepared in three steps. First, a compound of Formula (XIX) where $R^2$ is $CH_2OMs$ and m is 1 is reacted with a nucleophilic azide such as sodium azide, in a solvent such as DMF, at a temperature of about 70° C. for about 16 h to provide a compound of Formula (XIX) where $R^2$ is $CH_2N_3$. Second, reacting with a phosphine such as triphenyl phosphine, in a solvent such a THF, water, or a mixture of both to provide a compound of Formula (XIX) where $R^2$ is $CH_2NH_2$. Third, reacting with a $C_{1-6}$alkyl anhydride such as acetic anhydride, a base such as TEA, in a solvent such as DCM to provide a compound of Formula (XIX) where $R^2$ is $CH_2NHC(O)C_{1-6}alkyl$.

A compound of Formula (XIX) where $R^3$ is H or $C_{1-6}$alkyl, $R^1$ is $C_{1-6}$alkyl, $C_{1-6}$haloalkyl, or $C_{1-6}$alkenyl, $R^2$ is $CH_2NH_2$, and m is 1 is reacted with a $C_{1-6}$alkyl-$SO_2$-halide such as MsCl, a base such as TEA, in a solvent such as DCM to provide a compound of Formula (XIX) where $R^2$ is $CH_2NH(SO_2C_{1-6}alkyl)$, and m is 1.

SCHEME 6

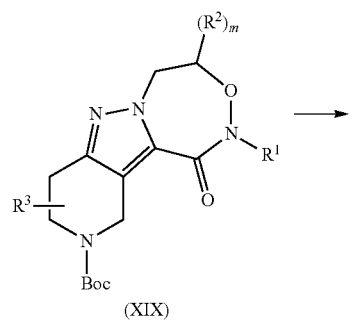

(XIX)

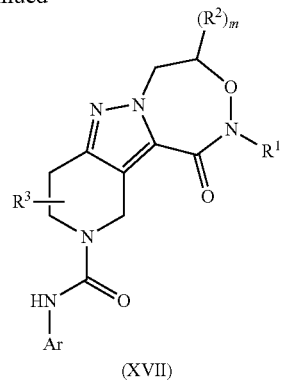

(XVII)

Method A:

According to SCHEME 6, a compound of Formula (XVII) where Ar is an optionally substituted aryl ring, $R^3$ is H or $C_{1-6}$alkyl, $R^1$ is $C_{1-6}$alkyl, $C_{1-6}$haloalkyl, or $C_{1-6}$alkenyl, $R^2$ is as described in any of the examples above, and m is 1 is prepared in 2 steps. First, a compound of Formula (XIX) is reacted with an acid such as TFA, in a solvent such as DCM, at a temperature of about 15° C. for about 30 min to provide a compound of Formula (XIX) where the Boc has been removed. Second, adding a reagent useful for forming an isocyanate such as triphosgene, an optionally substituted aryl amine such as analine, a base such as TEA, in a solvent such as DCM, at a temperature of about 25° C. for about 15 min to provide a compound of Formula (XVII) where Ar is an optionally substituted aryl ring.

Method B:

a compound of Formula (XVII) where Ar is an optionally substituted aryl ring, $R^3$ is H or $C_{1-6}$alkyl, $R^1$ is $C_{1-6}$alkyl, $C_{1-6}$haloalkyl, or $C_{1-6}$alkenyl, $R^2$ is as described in any of the examples above, and m is 1 is prepared in 2 steps. First, a compound of Formula (XIX) is reacted with an acid such as TFA, in a solvent such as DCM, at a temperature of about about 15° C. for about 30 min to provide a compound of Formula (XIX) where the Boc has been removed. Second, adding an optionally substituted N-aryl phenyl carbamate such as phenyl (3-chloro-4-fluorophenyl)carbamate, as base such as TEA, in a solvent such as DCM to provide a compound of Formula (XVII) where Ar is an optionally substituted aryl ring.

SCHEME 7

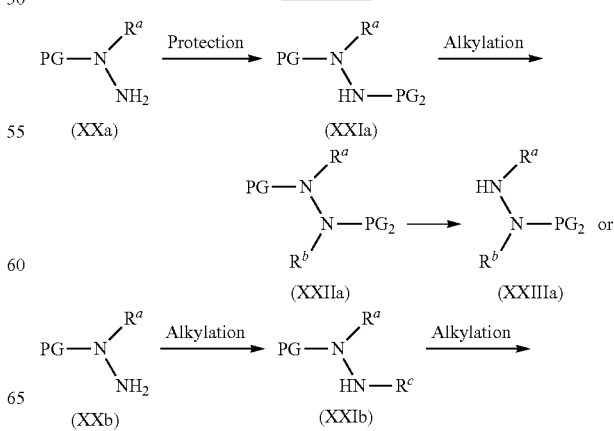

-continued

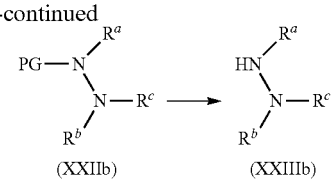

According to SCHEME 7, a commercially available or synthetically accessible compound of formula (XXa), where $R^a$ is $C_{1-6}$alkyl, and PG is a suitable nitrogen protecting group such as BOC, Bn, and the like, is protected with an a suitable nitrogen protecting group such as carboxybenzyl (Cbz), and the like, to provide a compound of formula (XXIa), where $PG_2$ is a suitable nitrogen protecting group such as carboxybenzyl (Cbz), and the like.

A compound of formula (XXIIa), where $R^a$ is $C_{1-6}$alkyl, PG is a suitable nitrogen protecting group such as BOC, Bn, and the like, $PG_2$ is a suitable nitrogen protecting group such as carboxybenzyl (Cbz), and the like, and $R^b$ is $CH_2CH_2OH$ is prepared in two steps from (XXIa). First, (XXIa) is alkylated under conditions known to one skilled in the art, for example, reaction with or without a base such as NaH, $Cs_2CO_3$, $K_2CO_3$, and the like, in a suitable solvent such as THF, DMF and the like, with an alkylating agent such as 1-bromo-methyl acetate, and the like, to provide a compound of formula (XXIIa) where $R^b$ is $CH_2(O)OMe$. Second, reduction under conditions known to one skilled in the art, for example, reduction using lithium borohydride, and the like, in a suitable solvent such as THF, and the like to provide a compound of formula (XXIIa), where $R^a$ is $C_{1-6}$alkyl, PG is a suitable nitrogen protecting group such as BOC, Bn, and the like, $PG_2$ is a suitable nitrogen protecting group such as carboxybenzyl (Cbz), and the like, and $R^b$ is $CH_2CH_2OH$.

A commercially available or synthetically accessible compound of formula (XXb), where $R^a$ is $C_{1-6}$alkyl, and PG is a suitable nitrogen protecting group such as BOC, Bn, and the like, is alkylated under conditions known to one skilled in the art, for example, reaction with or without a base such as diisopropyl ethyl amine, NaH, $Cs_2CO_3$, $K_2CO_3$, and the like, in a suitable solvent such as THF, DMF and the like, with an alkylating agent such as (2-bromoethoxy)(tert-butyl)dimethylsilane, and the like, to provide a compound of formula (XXIb), where $R^c$ is $CH_2CH_2OTBS$, and the like.

A compound of formula (XXIIb), where $R^a$ is $C_{1-6}$alkyl, PG is a suitable nitrogen protecting group such as BOC, Bn, and the like, $R^b$ is Me or $CH_2CH=CH_2$, and $R^c$ is a $CH_2CH_2OH$, and the like, is prepared in two steps. First, alkylating under conditions known to one skilled in the art, for example, reaction with or without a base such as diisopropyl ethyl amine, NaH, $Cs_2CO_3$, $K_2CO_3$, and the like, in a suitable solvent such as THF, DMF and the like, with an alkylating agent such as allyl bromide, methyl iodide, and the like, to provide a compound of formula (XXIIb) where $R^b$ is Me or $CH_2CH=CH_2$. Second, deprotection under conditions known to one skilled in the art, for example, deprotection using hydrochloric acid, and the like, in a suitable solvent such as ethyl acetate, and the like to provide a compound of formula (XXIIb), where $R^a$ is $C_{1-6}$alkyl, PG is a suitable nitrogen protecting group such as BOC, Bn, and the like, $R^c$ is $CH_2CH_2OH$ and $R^b$ is Me or $CH_2CH=CH_2$.

Deprotection of the nitrogen protecting group, employing conditions known to one skilled in the art provides a compound of formula (XXIIIa) and (XXIIIb). For example, the BOC protecting group is removed with acid such as TFA, HCl, and the like, in a suitable solvent such as DCM, and the like.

Any of the above alkylation steps are optional. In absence of alkylation, a proton is understood to be in the place of $R^b$ or $R^c$.

SCHEME 8

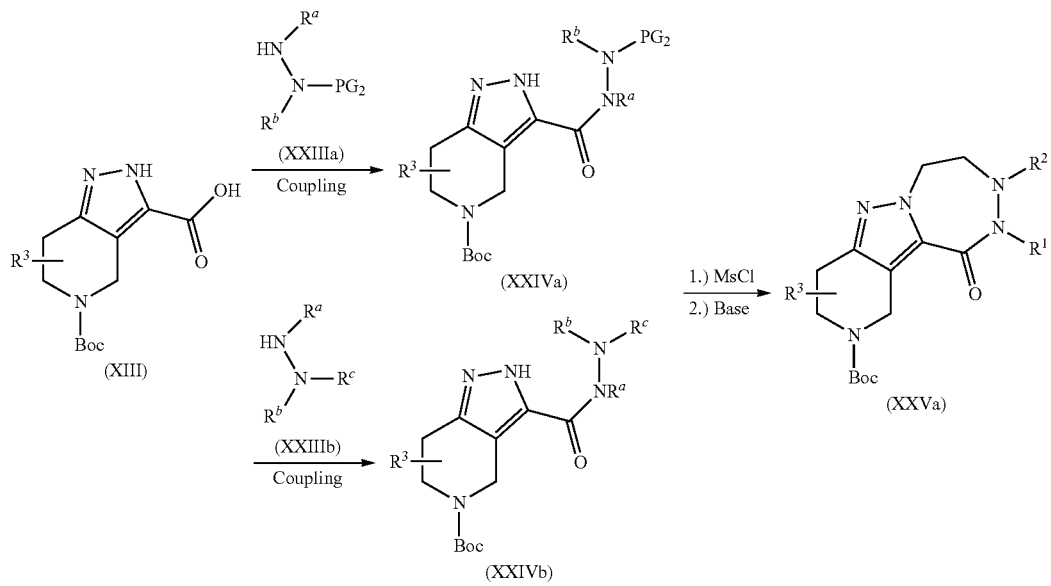

According to SCHEME 8, a commercially available or synthetically accessible compound of Formula (XIII), where $R^3$ is H or $C_{1-6}$alkyl, is coupled with a compound of Formula (XXIIIa), where $R^a$ is $C_{1-6}$alkyl, $PG_2$ is a suitable nitrogen protecting group such as carboxybenzyl (Cbz), and the like, and $R^b$ is 2-ethanol, under amide bond coupling conditions to provide a compound of Formula (XXIVa). For example, an acid compound of Formula (XIII) is reacted with an amine of Formula (XXIIIa), in the presence of a dehydrating agent such as HOBt/EDAC, CDI, PyBOP, HATU, HOAT, propylphosphonic anhydride (T$_3$P), a suitably selected base such as DIPEA, TEA, and the like, in a solvent such as toluene, MeCN, EtOAc, DMF, THF, DCM, or a mixture thereof, to afford a compound of Formula (XXIVa).

A commercially available or synthetically accessible compound of Formula (XIII), where R$^3$ is H or C$_{1-6}$alkyl, is coupled with a compound of Formula (XXIIIb), where R$^a$ is C$_{1-6}$alkyl, R$^c$ is CH$_2$CH$_2$OH and R$^b$ is Me or CH$_2$CH=CH$_2$, under amide bond coupling conditions to provide a compound of Formula (XXIVb). For example, an acid compound of Formula (XIII) is reacted with an amine of Formula (XXIIIb), in the presence of a dehydrating agent such as HOBt/EDAC, CDI, PyBOP, HATU, HOAT, propylphosphonic anhydride (T$_3$P), a suitably selected base such as DIPEA, TEA, and the like, in a solvent such as toluene, MeCN, EtOAc, DMF, THF, DCM, or a mixture thereof, to afford a compound of Formula (XXIVb).

A compound of Formula (XXIVa), where R$^3$ is H or C$_{1-6}$alkyl, where R$^a$ is C$_{1-6}$alkyl, PG$_2$ is a suitable nitrogen protecting group such as carboxybenzyl (Cbz), and the like, and R$^b$ is 2-ethanol, is reacted with MsCl, with a base such as triethyl amine, in a solvent such as DCM, to provide a compound of Formula (XXVa) where R$^3$ is H or C$_{1-6}$alkyl and R$^1$ is C$_{1-6}$alkyl, and R$^2$ is a suitable nitrogen protecting group such as carboxybenzyl (Cbz).

A compound of Formula (XXIVb), where R$^3$ is H or C$_{1-6}$alkyl, where R$^a$ is C$_{1-6}$alkyl, R$^c$ is CH$_2$CH$_2$OH and R$^b$ is Me or CH$_2$CH=CH$_2$, is reacted with MsCl, with a base such as triethyl amine, in a solvent such as DCM, to provide a compound of Formula (XXVa) where R$^3$ is H or C$_{1-6}$alkyl and R$^1$ is C$_{1-6}$alkyl, and R$^2$ is Me or CH$_2$CH=CH$_2$.

Deprotection of the nitrogen protecting group, employing conditions known to one skilled in the art provides a compound of formula (XXVa) where R$^2$ is H. For example, the Cbz protecting group is removed with hydrogen and palladium over carbon, and the like, in a suitable solvent such as MeOH, and the like.

SCHEME 9

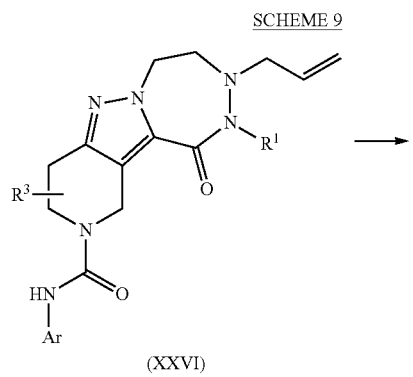

(XXVI)

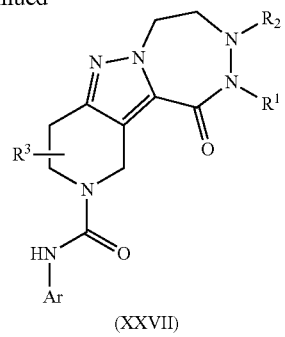

(XXVII)

According to SCHEME 9, a compound of Formula (XXVI) where Ar is an optionally substituted aryl ring, R$^3$ is H or C$_{1-6}$alkyl, and R$^1$ is C$_{1-6}$alkyl, is reacted with a reducing reagent such as hydrogen and palladium over carbon, in a solvent such as MeOH to provide a compound of Formula (XXVII) where R$^2$ is CH$_2$CH$_2$CH$_3$.

A compound of Formula (XXVII) where Ar is an optionally substituted aryl ring, R$^3$ is H or C$_{1-6}$alkyl, R$^1$ is C$_{1-6}$alkyl, and R$^2$ is CH$_2$CH$_2$OH, was prepared in two steps. First, a compound of Formula (XXVI) was oxidized with a reagent such as OsO$_4$, in presence of NaIO$_4$, in a solvent such as THF and water mixture, to provide a compound of Formula (XXVII) where R$^2$ is CH$_2$CH=O. Second, adding a reducing reagent such as sodium borohydride, in a solvent such as a THF and ethanol mixture, to provide a compound of Formula (XXVII) where R$^2$ is CH$_2$CH$_2$OH.

A compound of Formula (XXVII) where Ar is an optionally substituted aryl ring, R$^3$ is H or C$_{1-6}$alkyl, R$^1$ is C$_{1-6}$alkyl, and R$^2$ is CH$_2$CHF$_2$, was prepared in two steps. First, a compound of Formula (XXVI) was oxidized with a reagent such as OsO$_4$, in presence of NaIO$_4$, in a solvent such as THF and water mixture, to provide a compound of Formula (XXVII) where R$^2$ is CH$_2$CH=O. Second, adding a fluorinating agent such as DAST, in a solvent such as DCM, to provide a compound of Formula (XXVII) where R$^2$ is CH$_2$CHF$_2$.

SCHEME 10

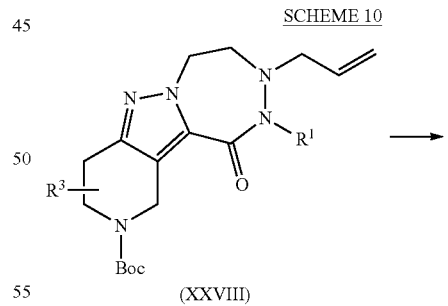

(XXVIII)

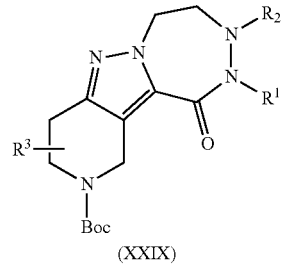

(XXIX)

According to SCHEME 9, a compound of Formula (XXVIII) where $R^3$ is H or $C_{1-6}$alkyl, and $R^1$ is $C_{1-6}$alkyl, is reacted under hydroboration conditions, using reagents such as $BH_3$-DMS, in a solvent such as THF, followed by a base such as sodium hydroxide, and an oxidant such as hydrogen peroxide to provide a compound of Formula (XXIX) where $R^2$ is $CH_2CH_2CH_2OH$.

A compound of Formula (XXVIII) where $R^3$ is H or $C_{1-6}$alkyl, and $R^1$ is $C_{1-6}$alkyl, is reacted under hydroboration conditions, using reagents such as $BH_3$-DMS, in a solvent such as THF, followed by a base such as sodium hydroxide, and an oxidant such as hydrogen peroxide to provide a compound of Formula (XXIX) where $R^2$ is $CH_2CHOHCH_3$.

SCHEME 11

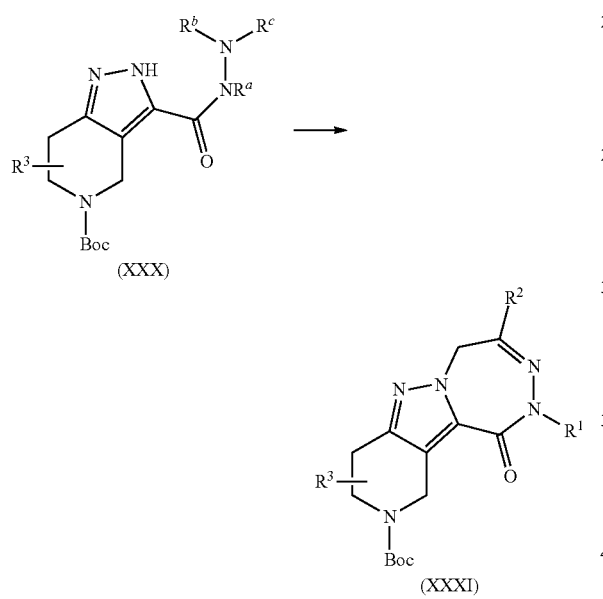

(XXX)

(XXXI)

A compound of Formula (XXXI) where $R^3$ is H or $C_{1-6}$alkyl, $R^1$ is $C_{1-6}$alkyl, and $R^2$ is $CH_2OH$, was prepared in three steps. First, a compound of Formula (XXX) was coupled with a reagent such as 3-chloro-2-oxopropyl acetate, in presence of a suitable acid such as p-toluenesulfonic acid, in a solvent such as DCM. Second, adding a reagent such as MsCl, in presence of a suitable base such as pyridine, in a solvent such as DCM. Third, adding a suitable base such as sodium hydride, in a solvent such as THF, to provide a compound of Formula (XXXI) where $R^3$ is H or $C_{1-6}$alkyl, $R^1$ is $C_{1-6}$alkyl, and $R^2$ is $CH_2OH$.

A compound of Formula (XXXI) where $R^3$ is H or $C_{1-6}$alkyl, $R^1$ is $C_{1-6}$alkyl, and $R^2$ is Me, was prepared in three steps. First, a compound of Formula (XXX) was coupled with a reagent such as 1-hydroxypropan-2-one, in presence of a suitable acid such as p-toluenesulfonic acid, in a solvent such as DCM. Second, adding a reagent such as MsCl, in presence of a suitable base such as pyridine, in a solvent such as DCM. Third, adding a suitable base such as sodium hydride, in a solvent such as THF, to provide a compound of Formula (XXXI) where $R^3$ is H or $C_{1-6}$alkyl, $R^1$ is $C_{1-6}$alkyl, and $R^2$ is Me.

SCHEME 12

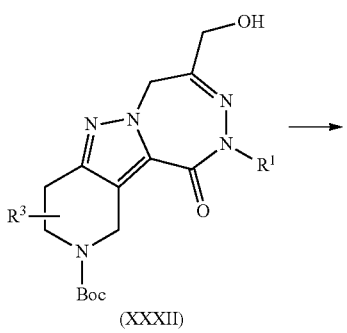

(XXXII)

(XXXI)

A compound of Formula (XXXI) where $R^3$ is H or $C_{1-6}$alkyl, $R^1$ is $C_{1-6}$alkyl, and $R^2$ is CH(Et)OH, CH(Me)OH, or CH(cPr)OH was prepared in two steps. First, a compound of Formula (XXXII) was oxidized with a reagent such as DMP, in a solvent such as DCM. Second, adding a Grignard reagent such as EtMgBr, MeMgBr, or cPrMgBr, in a solvent such as THF to provide a compound of Formula (XXXI) where $R^3$ is H or $C_{1-6}$alkyl, $R^1$ is $C_{1-6}$alkyl, and $R^2$ is CH(Et)OH, CH(Me)OH, or CH(cPr)OH.

SCHEME 13

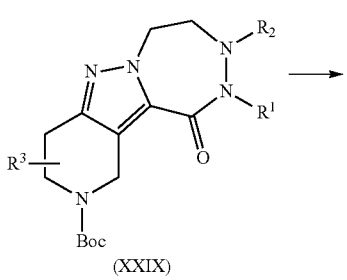

(XXIX)

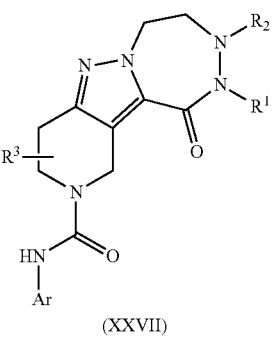

(XXVII)

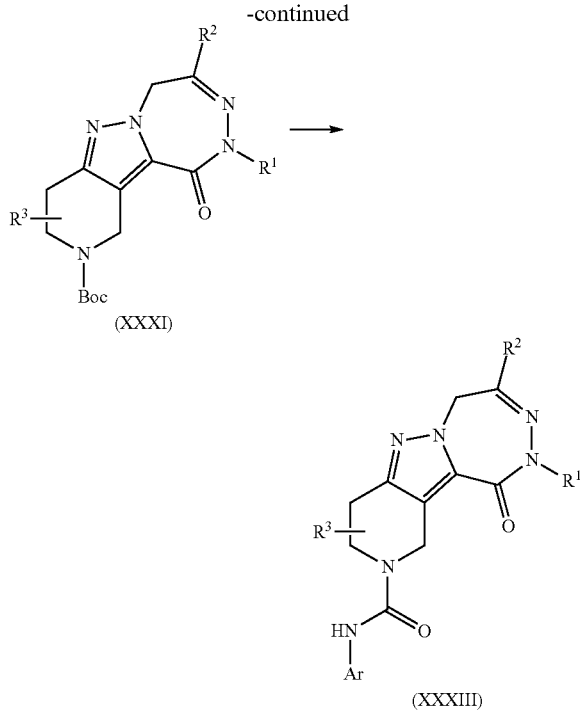

(XXXI)

(XXXIII)

Method A:

According to SCHEME 13, a compound of Formula (XXXIII) or Formula (XXVII) where Ar is an optionally substituted aryl ring, $R^3$ is H or $C_{1-6}$alkyl, $R^1$ is $C_{1-6}$alkyl, and $R^2$ is as described in any of the examples above is prepared in 2 steps. First, a compound of Formula (XXXI) or Formula (XXIX) is reacted with an acid such as TFA, in a solvent such as DCM, at a temperature of about 15° C. for about 30 min to provide a compound of Formula (XXXI) or Formula (XXIX) where the Boc has been removed. Second, adding a reagent useful for forming an isocyanate such as triphosgene, an optionally substituted aryl amine such as analine, a base such as TEA, in a solvent such as DCM, at a temperature of about 25° C. for about 15 min to provide a compound of Formula (XXXIII) or Formula (XXVII) where Ar is an optionally substituted aryl ring.

Method B:

A compound of Formula (XXXIII) or Formula (XXVII) where Ar is an optionally substituted aryl ring, $R^3$ is H or $C_{1-6}$alkyl, $R^1$ is $C_{1-6}$alkyl, $C_{1-6}$haloalkyl, or $C_{1-6}$alkenyl, $R^2$ is as described in any of the examples above, and m is 1 is prepared in 2 steps. First, a compound of Formula (XXXI) or Formula (XXIX) is reacted with an acid such as TFA, in a solvent such as DCM, at a temperature of about 15° C. for about 30 min to provide a compound of Formula (XXXI) or Formula (XXIX) where the Boc has been removed. Second, adding an optionally substituted N-aryl phenyl carbamate such as phenyl (3-chloro-4-fluorophenyl)carbamate, as base such as TEA, in a solvent such as DCM to provide a compound of Formula (XXXIII) or Formula (XXVII) where Ar is an optionally substituted aryl ring.

Intermediate 1. tert-butyl 4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxylate Step 1. Preparation of tert-butyl 3-(2-ethoxy-2-oxoacetyl)-4-oxo-piperidine-1-carboxylate. To LiHMDS (1 M, 652.44 mL, 1.30 eq) was added a solution of tert-butyl 4-oxopiperidine-1-carboxylate (100.00 g, 501.88 mmol, 1.00 eq) in THF (1.00 L) was added dropwise at −78° C. under $N_2$. The reaction mixture was stirred at −78° C. for 30 minutes under $N_2$. Diethyl oxalate (95.35 g, 652.44 mmol, 1.30 eq) was added dropwise. After addition, the reaction mixture was warmed to 15° C. over a period of 30 minutes and stirred at 15° C. for another 2 hours. TLC showed the reaction was completed. The reaction was quenched with aqueous saturated $NH_4Cl$ (1.5 L) and then neutralized with dilute hydrochloric acid, the aqueous layer was extracted with EtOAc (800 mL*3). The combined organic phase was dried over anhydrous $Na_2SO_4$, filtered and concentrated in vacuum to give the title compound (165.00 g, crude) as a yellow oil and used directly for next step.

Step 2. Preparation of 5-tert-butyl-3-ethyl 1,4,6,7-tetrahydropyrazolo [4,3-c]pyridine-3,5-dicarboxylate. A mixture of tert-butyl 3-(2-ethoxy-2-oxo-acetyl)-4-oxo-piperidine-1-carboxylate (165.00 g, 551.25 mmol, 1.00 eq) and $NH_2NH_2·H_2O$ (35.71 g, 606.37 mmol, 1.10 eq) in AcOH (1.00 L) was degassed and purged with $N_2$ for 3 times. Then the mixture was stirred at 80° C. for 1 hour under $N_2$ atmosphere. TLC and LCMS showed the reaction was completed. The mixture was concentrated under reduced pressure. The residue was dissolved in EtOAc (800 mL) and washed with $Na_2CO_3$ (1 N, 1.2 L). The aqueous phase was extracted with ethyl acetate (800 mL*2). The combined organic phase was washed with brine (1 L*2), dried with anhydrous $Na_2SO_4$, filtered and concentrated in vacuum to give the title compound (130.00 g, 440.19 mmol, 79.85% yield) as a yellow solid. $^1$H NMR (400 MHz, METHANOL-$d_4$) δ=4.57-4.65 (m, 2H), 4.36 (d, J=7.03 Hz, 2H), 3.67-3.74 (m, 2H), 2.75 (t, J=5.65 Hz, 2H), 1.49 (s, 9H), 1.36-1.40 (m, 3H). LCMS: 296 [M+1]

Step 3. Preparation of tert-butyl 3-[hydroxy(methyl)carbamoyl]-1,4,6,7-tetrahydropyrazolo[4,3-c]pyridine-5-carboxylate. Sodium metal (7.78 g, 338.60 mmol, 8.02 mL, 10.00 eq) was added to MeOH (100.00 mL) portionwise at 0° C., and the mixture was stirred at 15° C. for 0.5 hr under $N_2$. Then N-methylhydroxylamine (8.48 g, 101.58 mmol, 3.00 eq, HCl) was added to the mixture and the mixture was stirred at 15° C. for 0.5 hr under $N_2$. Then 5-tert-butyl 3-ethyl 1,4,6,7-tetrahydropyrazolo[4,3-c]pyridine-3,5-dicarboxylate (10.00 g, 33.86 mmol, 1.00 eq) was added, the mixture was stirred at 70° C. for 16 hr under $N_2$ atmosphere.

TLC showed the starting material was consumed completely and a new spot was detected mainly. The mixture was poured into ice-water (300 mL) and stirred at 5 min. Then the mixture was concentrated in vacuum to give the residue. The pH of the aqueous phase was adjusted to around 6 with diluted hydrochloride acid (1 N) and extracted with ethyl acetate (100 mL*3). The combined organic phase was washed with brine (300 mL), dried with anhydrous $Na_2SO_4$, filtered and concentrated in vacuum to give the title compound (8.00 g, 27.00 mmol, 79.73% yield) as a yellow solid. $^1$H NMR (400 MHz, METHANOL-$d_4$) δ=4.62 (brs, 2H) 3.70 (t, J=5.52 Hz, 2H) 3.31-3.58 (m, 3H) 2.74 (s, 2H) 1.48 (s, 9H). LCMS: 297 [M+1]

Step 4. Preparation of tert-butyl 4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxylate. A mixture of tert-butyl 3-[hydroxy(methyl)carbamoyl]-1,4,6,7-tetrahydroPyrazolo [4,3-c]pyridine-5-carboxylate (8.00 g, 27.00 mmol, 1.00 eq), 3-bromooxetane (4.07 g, 29.70 mmol, 1.10 eq), TBAI (997.22 mg, 2.70 mmol, 0.10 eq) and $Cs_2CO_3$ (13.19 g, 40.50 mmol, 1.50 eq) in DMF (80.00 mL) was degassed and purged with $N_2$ for 3 times, and then the mixture was stirred at 70° C. for 3 hr under $N_2$ atmosphere. TLC showed the starting material was consumed completely, desired product was major. The mixture was poured into water (200 mL) and stirred for 5 min. The aqueous phase was extracted with ethyl acetate (100 mL*3). The combined organic phase was washed with brine (300 mL*2), dried with anhydrous $Na_2SO_4$, filtered and concentrated in vacuum. The residue was purified by column chromatography ($SiO_2$, Petroleum ether/Ethyl acetate=100/1 to 1/2) to give the title compound (4.50 g, 12.39 mmol, 45.88% yield, 97% purity) as a yellow solid. $^1$H NMR (400 MHz, CHLOROFORM-d) δ=4.62 (brs, 2H) 4.53 (brs, 2H) 4.32-4.42 (m, 1H) 3.57-3.88 (m, 4H) 3.29 (br. s., 3H) 2.68-2.79 (m, 2H) 1.41-1.53 (m, 9H). LCMS: 353 [M+1].

The racemate of tert-butyl 4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxylate (2.6 g) was separated by SFC to get both enantiomers E1 (1.2 g, the first peak one) and E2 (1.3 g, the second one) (SFC separation condition: Column: Chiralpak AD-3 100×4.6 mm I.D., 3 um Mobile phase: methanol (0.05% DEA) in $CO_2$ from 5% to 40% Flow rate: 3 mL/min Wavelength: 220 nm). Each of the enantiomers were separately used to prepare the urea targets with the two sequential Boc protection and urea formation steps.

Intermediate 2. 3-chloro-4-fluoro-N-methylaniline

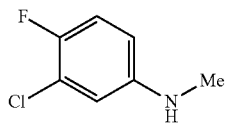

Step 1. Preparation of tert-butyl N-(3-chloro-4-fluorophenyl)carbamate. To a mixture of 3-chloro-4-fluoro-aniline (1.00 g, 6.87 mmol, 1.00 eq) and $(Boc)_2O$ (3.00 g, 13.74 mmol, 3.16 mL, 2.00 eq) in $H_2O$ (10.00 mL) was added TEA (2.09 g, 20.61 mmol, 2.86 mL, 3.00 eq) dropwise at 15° C. under $N_2$. The mixture was stirred at 10-20° C. for 3 h. LCMS showed 3.6% starting material remained and 93.2% desired product was generated. The reaction mixture was extracted with DCM (10 mL*2). The combined organic phase was dried with ydrous $Na_2SO_4$, filtered and concentrated in vacuum. The residue was rinsed with PE (2 mL). The solid was collected by filtration, and dried in high vacuo to give the title compound (1.10 g, 4.48 mmol, 65.21% yield) as white solid. $^1$H NMR (400 MHz, DMSO-$d_6$) δ 9.59 (br s, 1H), 7.60-7.81 (m, 1H), 7.23-7.44 (m, 2H), 3.33 (s, 2H), 2.37-2.60 (m, 11H), 1.47 (s, 9H).

Step 2. Preparation of tert-butyl N-(3-chloro-4-fluorophenyl)-N-methyl-carbamate. To a mixture of tert-butyl N-(3-chloro-4-fluoro-phenyl)carbamate (600.00 mg, 2.44 mmol, 1.00 eq) in DMF (5.00 mL) was added NaH (195.38 mg, 4.88 mmol, 60% purity, 2.00 eq) at 0-5° C. under $N_2$. The resulting mixture was stirred at 20° C. for 1 hr. Then $CH_3I$ (1.04 g, 7.32 mmol, 455.70 µL, 3.00 eq) was added dropwise at 15-20° C. The resulting mixture was stirred for 2 hr. LCMS showed starting material consumed and 98.55% desired product formed. The mixture was poured into water (20 mL), and extracted with EtOAc (3*5 mL). The combined organic phase was dried over anhydrous $Na_2SO_4$, filtered and concentrated under reduced pressure to give the title compound (500.00 mg, 1.93 mmol, 78.91% yield) as yellow oil, which was used directly in next step. $^1$H NMR (400 MHz, CHLOROFORM-d) δ 7.30 (dd, J=2.01, 6.53 Hz, 1H), 7.26 (s, 1H), 7.04-7.14 (m, 2H), 3.22 (s, 3H), 1.39-1.52 (m, 9H)

Step 3. Preparation of 3-chloro-4-fluoro-N-methyl-aniline. To a solution of HCl in dioxane (4 M, 5.00 mL, 11.56 eq), was added tert-butyl N-(3-chloro-4-fluoro-phenyl)-N-methyl-carbamate (450.00 mg, 1.73 mmol, 1.00 eq) below 0° C. The resulted mixture was stirred at 0-5° C. for 1 h, then warmed naturally to 15-20° C. and stirred at 15-20° C. for 2 hr. LCMS showed the starting material was consumed and 98% desired product was formed. The resulting mixture was concentrated under reduced pressure to give the title compound (240.00 mg, 1.22 mmol, 70.76% yield, HCl) as white solid which was used directly in the next step without further purification.

Intermediate 3. tert-butyl 4-(hydroxymethyl)-2,8,8-trimethyl-1-oxo-1,4,5,8,9,11-hexahydropyrido[4',3':3,4]pyrazolo[5,1-d][1,2,5]oxadiazepine-10(2H)-carboxylate

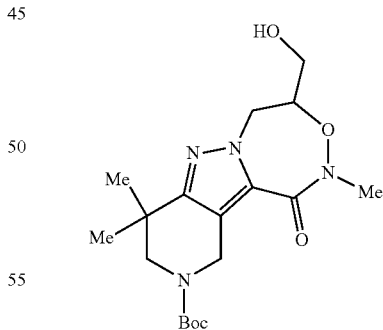

Step 1. Preparation of tert-butyl-5-(2-ethoxy-2-oxo-acetyl)-3,3-dimethyl-4-oxo-piperidine-1-carboxylate. To LiHMDS (1 M, 5.72 mL, 1.30 eq) was added a solution of tert-butyl 3,3-dimethyl-4-oxo-piperidine-1-carboxylate (1.00 g, 4.40 mmol, 1.00 eq) in THF (10.00 mL) at −78° C. under $N_2$. The reaction mixture was stirred at −78° C. for 30 minutes. Diethyl oxalate (835.82 mg, 5.72 mmol, 781.14 µL 1.30 eq) was added dropwise. After addition, the reaction mixture was warmed to 15° C. and stirred for another 2 hours. TLC indicated starting material was consumed completely, and a major new spot with larger polarity was detected. The reaction was quenched with diluted HCl (1N, 40 mL) and then extracted with EtOAc (100 mL*3). The combined organic phase was dried over anhydrous $Na_2SO_4$, filtered and concentrated in vacuum to afford the title compound (1.00 g, crude) as yellow oil. The product was used in the next step without purification.

Step 2. Preparation of 5-(tert-butyl) 3-ethyl 7,7-dimethyl-1,4,6,7-tetrahydro-5H-pyrazolo[4,3-c]pyridine-3,5-dicarboxylate. To a solution of tert-butyl 5-(2-ethoxy-2-oxo-acetyl)-3,3-dimethyl-4-oxo-piperidine-1-carboxylate (800.00 mg, 2.44 mmol, 1.00 eq) in EtOH (10.00 mL) was added $NH_2NH_2.H_2O$ (143.70 mg, 2.44 mmol, 139.51 µL 85% purity, 1.00 eq). The reaction mixture was stirred at 15° C. for 2 hours. TLC indicated the starting material was consumed completely, and one major new spot with larger polarity was detected. The reaction mixture was diluted with EtOAc (150 mL) and washed with water (80 mL*2), the organic phase was dried with anhydrous $Na_2SO_4$, filtered and concentrated in vacuum. The residue was purified by silica gel chromatography to afford the title compound (760.00 mg, 2.23 mmol, 91.50% yield, 95% purity) as yellow solid. $^1H$ NMR (400 MHz, METHANOL-$d_4$) δ=4.61 (s, 2H) 4.33-4.38 (q, J=7.11 Hz, 2H) 3.44 (brs, 2H) 1.49 (s, 9H) 1.37-1.40 (t, J=7.09 Hz, 3H) 1.28 (s, 6H). LCMS: 324 [M+1].

Step 3. Preparation of 5-tert-butoxycarbonyl-7,7-dimethyl-4,6-dihydro-1H-pyrazolo[4,3-c]pyridine-3-carboxylic acid. To a solution of 5-(tert-butyl) 3-ethyl 7,7-dimethyl-1,4,6,7-tetrahydro-5H-pyrazolo[4,3-c]pyridine-3,5-dicarboxylate (900.00 mg, 2.78 mmol, 1.00 eq) in THF (10.00 mL) was added a solution of NaOH (222.64 mg, 5.57 mmol, 2.00 eq) in $H_2O$ (2.00 mL), the reaction mixture was warmed to 50° C. and stirred at 50° C. for 5 hours. TLC showed the reaction was completed. The pH of the reaction mixture was adjusted to around 6 by adding diluted hydrochloride acid (2N, 10 mL), then extracted with EtOAc (100 mL*4) and water (20 mL), the organic phase was dried over anhydrous $Na_2SO_4$, filtered and concentrated in vacuum to afford the title compound (780.00 mg, 2.59 mmol, 93.10% yield, 98% purity) as white solid. The product was used in the next step directly without further purification. LCMS: 296 [M+1].

Step 4. Preparation of tert-butyl 3-[hydroxy(methyl)carbamoyl]-7,7-dimethyl-4,6-dihydro-1H-pyrazolo[4,3-c]pyridine-5-carboxylate. To a mixture of 5-tert-butoxycarbonyl-7,7-dimethyl-4,6-dihydro-1H-pyrazolo[4,3-c] pyridine-3-carboxylic acid (200.00 mg, 677.21 µmol, 1.00 eq) in THF (5.00 mL) was added $T_3P$ (1.72 g, 2.71 mmol, 1.61 mL, 50% purity, 4.00 eq) and TEA (342.63 mg, 3.39 mmol, 469.36 µL 5.00 eq), followed by N-methylhydroxylamine (113.12 mg, 1.35 mmol, 2.00 eq, HCl), the reaction mixture was stirred at 40° C. for 16 hours. LCMS showed the starting material was consumed completely and one main peak with desired MS was detected. The reaction mixture was diluted with EtOAc (80 mL) and washed with water (50 mL*2), the organic phase was dried with anhydrous $Na_2SO_4$, filtered and concentrated in vacuum. The residue was purified by silica gel chromatography to afford the title compound (70.00 mg, 215.80 µmol, 31.87% yield) as white solid. $^1H$ NMR (400 MHz, CHLOROFORM-d) δ=4.64 (s, 2H) 3.39 (brs, 5H) 1.47 (s, 9H) 1.27 (s, 6H). LCMS: 269 [M+1-56].

Step 5. Preparation of tert-butyl 4-(hydroxymethyl)-2,8,8-trimethyl-1-oxo-1,2,4,5,8,9-hexahydro pyrido[4',3':3,4] pyrazolo[5,1-d][1,2,5]oxadiazepine-10(11H)-carboxylate. To a mixture of tert-butyl 3-[hydroxy(methyl)carbamoyl]-7,7-dimethyl-4,6-dihydro-1H-pyrazolo[4,3-c]pyridine-5-carboxylate (70.00 mg, 215.80 µmol, 1.00 eq) and 3-bromooxetane (35.47 mg, 258.96 µmol, 1.20 eq) in DMF (2.00 mL) was added $Cs_2CO_3$ (105.47 mg, 323.70 µmol, 1.50 eq) and TBAI (7.97 mg, 21.58 µmol, 0.10 eq), the reaction mixture was warmed to 75° C. and stirred at 75° C. for 3 hours. LCMS showed 50% of the starting material was remained. The reaction mixture was stirred at 75° C. for another 3 hours. LCMS showed the starting material was consumed completely and one main peak with desired MS was detected. The reaction mixture was diluted with EtOAc (100 mL) and washed with water (50 mL*3), the organic phase was dried with anhydrous $Na_2SO_4$, filtered and concentrated in vacuum to afford the title compound (53.00 mg, crude) as yellow oil. The product was used in the next step directly without further purification. LCMS: 381 [M+1].

Intermediate 4. tert-butyl 4-(hydroxymethyl)-2,8-dimethyl-1-oxo-1,4,5,8,9,11-hexahydropyrido[4',3':3,4]pyrazolo[5,1-d][1,2,5]oxadiazepine-10(2H)-carboxylate

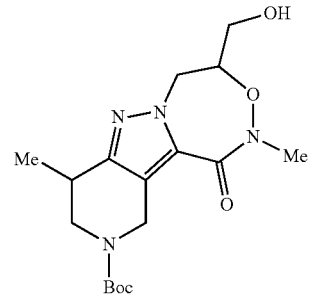 [SMILES: CC1CN(C(=O)OC(C)(C)C)Cc2c1nn1c2C(=O)N(C)OC(CO)C1]

Step 1. Preparation of tert-butyl 3-methyl-4-oxo-piperidine-1-carboxylate. To a solution of 1-benzyl-3-methyl-piperidin-4-one (2.00 g, 9.84 mmol, 1.00 eq) and $Boc_2O$ (2.15 g, 9.84 mmol, 2.26 mL, 1.00 eq) in MeOH (50.00 mL) was added Pd/C (9.84 mmol, 1.00 eq) under $N_2$. The suspension was degassed under vacuum and purged with $H_2$ several times. The mixture was stirred under $H_2$ (50 psi) at 20° C. for 16 hours. TLC (PE:EA=5:1) showed the reaction was completed. The mixture was filtered. The filtrate was concentrated in vacuum. The residue was purified by column chromatography (PE:EA=0%~15%) to afford the title compound (2.00 g, 9.38 mmol, 95.33% yield) as colorless oil. $^1H$ NMR (400 MHz, CHLOROFORM-d) δ=4.16-4.24 (m, 1H), 3.22-3.33 (m, 1H), 2.86 (brs, 1H), 2.38-2.61 (m, 3H), 1.51 (s, 9H), 1.06 (d, J=6.7 Hz, 3H).

Step 2. Preparation of tert-butyl 3-(2-ethoxy-2-oxo-acetyl)-5-methyl-4-oxo-piperidine-1-carboxylate. To a solution of tert-butyl 3-methyl-4-oxo-piperidine-1-carboxylate (2.00 g, 9.38 mmol, 1.00 eq) in THF (40.00 mL) was added LiHMDS (1 M, 11.26 mL, 1.20 eq) dropwise at −60° C. The mixture was stirred at −60° C. for 30 min. Diethyl oxalate (1.51 g, 10.32 mmol, 1.41 mL, 1.10 eq) was added dropwise at −60° C. Then the mixture was stirred at 20° C. for 1 hr. TLC (PE:EA=5:1) showed the reaction was completed. The reaction was quenched by saturated $NH_4Cl$ (20 mL) and extracted with EtOAc (60 mL*2). The combined organic layer was dried over $Na_2SO_4$, filtrated. The filtrate was concentrated in vacuum to afford the title compound (2.00 g, crude) as yellow oil.

Step 3. Preparation of 5-(tert-butyl) 3-ethyl 7-methyl-1,4,6,7-tetrahydro-5H-pyrazolo[4,3-c]pyridine-3,5-dicarboxylate. To a solution of tert-butyl 3-(2-ethoxy-2-oxoacetyl)-5-methyl-4-oxo-piperidine-1-carboxylate (2.00 g, 6.38 mmol, 1.00 eq) in EtOH (40.00 mL) was added NH₂NH₂.H₂O (394.59 mg, 6.70 mmol, 383.10 μL85% purity, 1.05 eq). The mixture was stirred at 20° C. for 16 hr. Major desired product was detected via LCMS. The mixture was concentrated in vacuum. The residue was diluted with EtOAc (80 mL) and H₂O (30 mL). The organic phase was dried over Na₂SO₄, filtrated. The filtrate was concentrated in vacuum. The residue was purified by column chromatography (PE:EA:10%~50%) to afford the title compound (1.00 g, 3.23 mmol, 50.61% yield) as white solid. ¹H NMR (400 MHz, CHLOROFORM-d) δ=1.30-1.34 (m, 3H) 1.41 (t, J=7.09 Hz, 3H) 1.49-1.55 (m, 9H) 2.98-3.38 (m, 2H) 3.74-4.08 (m, 1H) 4.40 (q, J=6.78 Hz, 2H) 4.47-4.68 (m, 1H) 4.78 (d, J=17.19 Hz, 1H).

Step 4. Preparation of 5-tert-butoxycarbonyl-7-methyl-1,4,6,7-tetrahydropyrazolo[4,3-c]pyridine-3-carboxylic acid. To a solution of 5-(tert-butyl) 3-ethyl 7-methyl-1,4,6,7-tetrahydro-5H-pyrazolo[4,3-c]pyridine-3,5-dicarboxylate (1.00 g, 3.23 mmol, 1.00 eq) in THF (10.00 mL) was added a solution of NaOH (258.40 mg, 6.46 mmol, 2.00 eq) in H₂O (2.00 mL). The mixture was stirred at 40° C. for 16 hr. TLC (PE:EA=1:1) showed the reaction was completed and one major spot appeared. Adjusted the pH of the mixture to 5-6 with 1N HCl (10 mL) and extracted with EtOAc (20 mL*2). The combined organic layer was dried over Na₂SO₄, filtrated. The filtrate was concentrated in vacuum to afford the title compound (850.00 mg, 2.95 mmol, 91.21% yield, 97.5% purity) as white solid. LCMS: 282 [M+1].

Step 5. Preparation of tert-butyl 3-[hydroxy(methyl)carbamoyl]-7-methyl-1,4,6,7-tetrahydropyrazolo[4,3-c]pyridine-5-carboxylate. To a solution of 5-tert-butoxycarbonyl-7-methyl-1,4,6,7-tetrahydropyrazolo[4,3-c] pyridine-3-carboxylic acid (200.00 mg, 710.96 μmol, 1.00 eq) and N-methylhydroxylamine (237.52 mg, 2.84 mmol, 4.00 eq, HCl) in THF (5.00 mL) was added T₃P (1.81 g, 2.84 mmol, 1.69 mL, 50% purity, 3.99 eq) followed by TEA (575.54 mg, 5.69 mmol, 788.41 μL8.00 eq). The mixture was heated to 40° C. for 16 hr. TLC (DCM:MeOH=10:1) showed two main spots appeared. The mixture was extracted with EtOAc (20 mL*2) and H₂O (20 mL). The combined organic layer was dried over Na₂SO₄, filtrated. The filtrate was concentrated. The residue was purified by column chromatography (PE:EA=50%~100%) to afford the title compound (66.00 mg, 212.66 μmol, 29.91% yield) as white solid. LCMS: 312 [M+1].

Step 6. Preparation of tert-butyl 4-(hydroxymethyl)-2,8-dimethyl-1-oxo-1,2,4,5,8,9-hexahydropyrido[4',3':3,4]pyrazolo[5,1-d][1,2,5]oxadiazepine-10(11H)-carboxylate. To a solution of tert-butyl 3-[hydroxy(methyl)carbamoyl]-7-methyl-1,4,6,7-tetra hydropyrazolo[4,3-c]pyridine-5-carboxylate (60.00 mg, 193.33 μmol, 1.00 eq) in DMF (2.00 mL) was added Cs₂CO₃ (188.97 mg, 579.99 μmol, 3.00 eq) followed by 3-bromooxetane (31.78 mg, 232.00 μmol, 1.20 eq). The mixture was stirred at 75° C. for 4 hr. LCMS showed the reaction was completed, major desired product was detected. The mixture was diluted with EtOAc (60 mL) and H₂O (30 mL). Separated the organic layer and washed with H₂O (30 mL*3), dried over Na₂SO₄, filtrated. The filtrate was concentrated in vacuum to afford the title compound (60.00 mg, crude) as yellow oil. LCMS: 367 [M+1].

Intermediate 5. tert-butyl 2-ethyl-4-(hydroxymethyl)-1-oxo-1,4,5,8,9,11-hexahydropyrido[4',3':3,4]pyrazolo[5,1-d][1,2,5]oxadiazepine-10(2H)-carboxylate

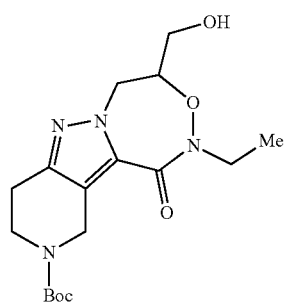 [SMILES: CCN1OC(CO)Cn2nc3c(c2C1=O)CN(C(=O)OC(C)(C)C)CC3]

Step 1. Preparation of tert-butyl 3-[ethyl(hydroxy)carbamoyl]-2,4,6,7-tetrahydropyrazolo[4,3-c] pyridine-5-carboxylate. To a solution of 5-tert-butoxycarbonyl-2,4,6,7-tetrahydropyrazolo[4,3-c]pyridine-3-carboxylic acid (100.00 mg, 374.14 μmol, 1.00 eq) in DMF (3.00 mL) was added HATU (184.94 mg, 486.38 μmol, 1.30 eq), DIPEA (241.77 mg, 1.87 mmol, 326.72 μL5.00 eq) and N-ethylhydroxylamine (109.48 mg, 1.12 mmol, 3.00 eq, HCl). The mixture was stirred at 80° C. for 16 hr. LCMS showed the desired product was detected and ~20% starting material was remained. The mixture was poured into water (20 mL), and extracted with DCM (20 mL*2). The organic layer was washed with brine (30 mL*3), dried over anhydrous Na₂SO₄ and concentrated in vacuum. The crude was purified by Prep-TLC (Dichloromethane:Methanol=10:1) to give the title compound (36.00 mg, 115.65 μmol, 30.91% yield, 99.7% purity) as colorless oil. LCMS: 311[M+1].

Step 2. Preparation of tert-butyl 2-ethyl-4-(hydroxymethyl)-1-oxo-1,4,5,8,9,11-hexahydropyrido[4',3':3,4]pyrazolo[5,1-d][1,2,5]oxadiazepine-10(2H)-carboxylate. To a solution of tert-butyl 3-[ethyl(hydroxy)carbamoyl]-2,4,6,7-tetrahydropyrazolo [4,3-c]pyridine-5-carboxylate (36.00 mg, 116.00 μmol, 1.00 eq) and 3-bromooxetane (19.07 mg, 139.20 μmol, 1.20 eq) in DMF (2.00 mL) was added Cs₂CO₃ (45.35 mg, 139.20 μmol, 1.20 eq) and TBAI (4.28 mg, 11.60 μmol, 0.10 eq). The mixture was stirred at 75° C. for 3 hr. LCMS showed about 40% starting material 2 was remained. The mixture was stirred at 75° C. for another 3 hr. The mixture was diluted with ethyl acetate (40 mL), washed with brine (30 mL*3). The organic layer was dried over anhydrous Na₂SO₄, concentrated in vacuum. The crude was purified by prep-TLC (100% Ethyl acetate). The title compound (25.00 mg, 68.23 μmol, 58.82% yield) was obtained as the colorless oil.

Intermediate 6. tert-butyl 3-(hydroxy(methyl)carbamoyl)-2,4,6,7-tetrahydro-5H-pyrazolo[4,3-c]pyridine-5-carboxylate

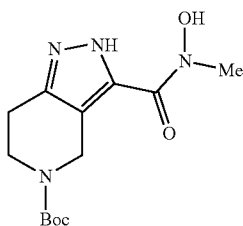 [SMILES: CN(O)C(=O)c1[nH]nc2c1CN(C(=O)OC(C)(C)C)CC2]

Step 1. Preparation of tert-butyl 3-(2-ethoxy-2-oxo-acetyl)-4-oxo-piperidine-1-carboxylate. To LiHMDS (1 M, 652.44 mL, 1.30 eq) was added a solution of tert-butyl 4-oxopiperidine-1-carboxylate (100.00 g, 501.88 mmol, 1.00 eq) in THF (1.00 L) dropwise at −78° C. under $N_2$. The reaction mixture was stirred at −78° C. for 30 minutes under $N_2$. Then diethyl oxalate (95.35 g, 652.44 mmol, 1.30 eq) was added dropwise. After addition, the reaction mixture was warmed to 15° C. over a period of 30 minutes and stirred at 15° C. for another 2 hours. TLC (PE/EA=3/1) showed the reaction was completed. The reaction was quenched with $NH_4Cl$ (sat. aq, 1.5 L) and then neutralized with diluted hydrochloric acid, the aqueous layer was extracted with EtOAc (800 mL×3). The combined organic phase was dried over anhydrous $Na_2SO_4$, filtered and concentrated in vacuum to afford the title compound (165.00 g, crude) as yellow oil and used directly for next step.

Step 2. Preparation of 5-tert-butyl 3-ethyl 1,4,6,7-tetrahydropyrazolo [4,3-c]pyridine-3,5-dicarboxylate. A mixture of tert-butyl 3-(2-ethoxy-2-oxo-acetyl)-4-oxo-piperidine-1-carboxylate (165.00 g, crude, 551.25 mmol, 1.00 eq) and $NH_2NH_2.H_2O$ (35.71 g, 606.37 mmol, 1.10 eq) in AcOH (1.00 L) was degassed and purged with $N_2$ for 3 times. Then the mixture was stirred at 80° C. for 1 hour under $N_2$ atmosphere. TLC (PE/EA=1/1) and LCMS showed the reaction was completed. The mixture was concentrated under reduced pressure. The residue was dissolved in EtOAc (800 mL) and washed with $Na_2CO_3$ (1 N, 1.2 L). The aqueous phase was extracted with ethyl acetate (800 mL×2). The combined organic phase was washed with brine (1 L×2), dried with anhydrous $Na_2SO_4$, filtered and concentrated in vacuum to afford the title compound (130.00 g, 440.19 mmol, 79.85% yield) as a yellow solid. LCMS: 296 [M+1]. $^1$H NMR (400 MHz, METHANOL-$d_4$) δ=4.57-4.65 (m, 2H), 4.36 (d, J=7.03 Hz, 2H), 3.67-3.74 (m, 2H), 2.75 (t, J=5.65 Hz, 2H), 1.49 (s, 9H), 1.36-1.40 (m, 3H).

Step 3. Preparation of 5-tert-butoxycarbonyl-1,4,6,7-tetrahydropyrazolo[4,3-c]pyridine-3-carboxylic acid. A mixture of 5-tert-butyl 3-ethyl 1,4,6,7-tetrahydropyrazolo[4,3-c]pyridine-3,5-dicarboxylate (10.00 g, 33.86 mmol, 1.00 eq) and NaOH (2.03 g, 50.79 mmol, 1.50 eq) in THF (100.00 mL) and $H_2O$ (20.00 mL) was degassed and purged with $N_2$ for 3 times, and then the mixture was stirred at 40° C. for 16 hr under $N_2$ atmosphere. Then the mixture was stirred at 50° C. for 4 hr, LCMS showed the reaction was completed. The mixture was diluted in water (100 mL) and extracted with EA (50 mL×2). The aqueous phase was separated and adjusted the pH~6 by adding diluted hydrochloride acid (1 N), solid was precipitated out. The mixture was filtered and the cake was concentrated in vacuum to afford the title compound (8.00 g, 29.93 mmol, 88.40% yield, 100% purity) as a yellow solid. LCMS: 268 [M+1]

Step 4. Preparation of tert-butyl 3-(hydroxy(methyl)carbamoyl)-2,4,6,7-tetrahydro-5H-pyrazolo[4,3-c]pyridine-5-carboxylate. A mixture of 5-tert-butoxycarbonyl-1,4,6,7-tetrahydropyrazolo[4,3-c]pyridine-3-carboxylic acid (3.00 g, 11.22 mmol, 1.00 eq), N-methylhydroxylamine (1.41 g, 16.83 mmol, 1.50 eq, HCl), $T_3P$ (17.86 g, 56.10 mmol, 16.69 mL, 5.00 eq) and TEA (11.35 g, 112.20 mmol, 15.55 mL, 10.00 eq) in THF (30.00 mL) was degassed and purged with $N_2$ for 3 times, and then the mixture was stirred at 50° C. for 16 hour under $N_2$ atmosphere. LCMS showed the reaction was completed. The mixture was poured into water (80 mL), the aqueous layer was adjusted pH~4 by 1N HCl, then the aqueous layer was extracted with DCM (40 mL×3), the combined organic layer was dried with anhydrous $Na_2SO_4$, filtered and concentrated in vacuum. The residue was purified by column chromatography ($SiO_2$, PE/EA=100/1 to 1/1) to give the crude product which was rinsed with EtOAc to afford the title compound (1.30 g, 4.39 mmol, 39.10% yield, 100% purity) as a white solid. LCMS: 319 [M+23].

Intermediate 7. tert-butyl 2,5-dimethyl-1-oxo-1,4,5,8,9,11-hexahydropyrido[4',3':3,4]pyrazolo[5,1-d][1,2,5]oxadiazepine-10(2H)-carboxylate

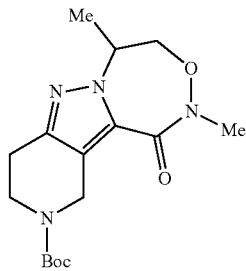 [SMILES: CC1CON(C)C(=O)c2c3c(nn21)CCN(C(=O)OC(C)(C)C)C3]

To a solution of tert-butyl 3-(hydroxy(methyl)carbamoyl)-2,4,6,7-tetrahydro-5H-pyrazolo[4,3-c]pyridine-5-carboxylate (Intermediate 6, 50.00 mg, 168.74 µmol, 1.00 eq) in DMF (2.00 mL) was added TBAI (6.23 mg, 16.87 µmol, 0.10 eq). The reaction mixture was stirred at 15° C. for 3 hr. LCMS showed ~77% of the starting material remained and ~8.5% of desired product was detected. The reaction mixture was stirred at 50° C. for another 24 hr. TLC indicated the starting material remained and two new spots formed. The reaction mixture was quenched by water (20 mL) and extracted with EtOAc (30 mL×3). The combined organic layers were washed with saturated $NH_4Cl$. The residue was purified by prep-TLC (PE/EA, 1/3) to give the title compound (10.00 mg, 29.73 µmol, 17.62% yield) was obtained as a white solid. LCMS: 337 [M+1]. $^1$H NMR (400 MHz, CHLOROFORM-d) (pilot run EW4043-68) δ 4.60-4.76 (m, 3H), 4.48 (dd, J=5.52, 11.42 Hz, 1H), 3.88-4.04 (m, 1H), 3.73-3.85 (m, 1H), 3.66 (s, 1H), 3.31 (s, 3H), 2.79 (s, 2H), 1.62 (d, J=6.65 Hz, 3H), 1.49 (s, 9H).

Intermediate 8. tert-butyl 2,4-dimethyl-1-oxo-1,4,5,
8,9,11-hexahydropyrido[4',3':3,4]pyrazolo[5,1-d][1,
2,5]oxadiazepine-10(2H)-carboxylate

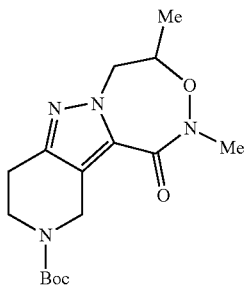 [SMILES: CC1Cn2nc3c(c2C(=O)N(C)O1)CN(C(=O)OC(C)(C)C)CC3]

Step 1. Preparation of tert-butyl 3-[(2-ethoxy-1-methyl-2-oxo-ethoxy)-methyl-carbamoyl]-2,4,6,7-tetrahydropyrazolo[4,3-c]pyridine-5-carboxylate. To a solution of tert-butyl 3-(hydroxy(methyl)carbamoyl)-2,4,6,7-tetrahydro-5H-pyrazolo[4,3-c]pyridine-5-carboxylate (Intermediate 6, 400.00 mg, 1.35 mmol, 1.00 eq) in THF (20.00 mL) was added t-BuOK (151.50 mg, 1.35 mmol, 1.00 eq) under $N_2$. The reaction mixture was stirred at 0° C. for 1 hr. Then ethyl 2-bromopropanoate (232.00 mg, 1.28 mmol, 166.91 μL 0.95 eq) in THF (4.00 mL) was added dropwise under $N_2$. After addition, the reaction mixture was stirred at 15° C. for 2 hr. TLC (PE/EA, 1/2) indicated the starting material was consumed completely and two new spots formed. The reaction mixture was quenched by sat. aq. $NH_4Cl$ (15 mL) and extracted with EtOAc (30 mL×3). The combined organic layers were washed with water (15 mL) and brine (20 mL), dried with anhydrous $Na_2SO_4$, filtered and concentrated in vacuo. The residue was purified by column chromatography (PE/EA, 2/1 to 1/1) to give the title compound (510.00 mg, 1.29 mmol, 95.29% yield) as a white solid.

Step 2. Preparation of tert-butyl 3-[(2-hydroxy-1-methyl-ethoxy)-methyl-carbamoyl]-2,4,6,7-tetra hydropyrazolo[4,3-c]pyridine-5-carboxylate. To a solution of tert-butyl 3-[(2-ethoxy-1-methyl-2-oxo-ethoxy)-methyl-carbamoyl]-2,4,6,7-tetrahydropyrazolo[4,3-c]pyridine-5-carboxylate (400.00 mg, 706.29 μmol, 1.00 eq) in THF (5.00 mL) was added $NaBH_4$ (26.72 mg, 706.29 μmol, 1.00 eq) followed by MeOH (200.00 μL at −10° C. The mixture was stirred at 10° C. for 2 hr. TLC showed the starting material was consumed and three spots appeared. The mixture was quenched by saturated $NH_4Cl$ (10 mL) and extracted with EtOAc (20 mL*2). The combined organic layer was dried over $Na_2SO_4$, filtrated. The filtrate was concentrated in vacuum. The residue was purified by prep-TLC (EA:MeOH=10:1) to get the title compound (80.00 mg, 225.73 μmol, 31.96% yield) as colorless oil.

Step 3. Preparation of tert-butyl 2,4-dimethyl-1-oxo-1,4,5,8,9,11-hexahydropyrido[4',3':3,4]pyrazolo[5,1-d][1,2,5]oxadiazepine-10(2H)-carboxylate. To a solution of tert-butyl 3-[(2-hydroxy-1-methyl-ethoxy)-methyl-carbamoyl]-2,4,6,7-tetrahydropyrazolo[4,3-c]pyridine-5-carboxylate (70.00 mg, 197.52 μmol, 1.00 eq) in THF (4.00 mL) was added tributylphosphane (79.92 mg, 395.04 μmol, 97.46 μL 2.00 eq) followed by DIAD (79.88 mg, 395.04 μmol, 76.81 μL 2.00 eq) under $N_2$. The mixture was heated to 60° C. for 16 hr. TLC showed the starting material consumed and one main spot appeared. The mixture was extracted with EtOAc (30 mL*2) and $H_2O$ (20 mL). The combined organic layer was dried over $Na_2SO_4$, filtrated. The filtrate was concentrated in vacuum. The residue was purified by prep-TLC (PE:EA=1:2) to get the title compound (42.00 mg, 124.86 μmol, 63.21% yield) as colorless oil.

Intermediate 9. tert-butyl 2,4,4-trimethyl-1-oxo-1,4,5,8,9,11-hexahydropyrido[4',3':3,4]pyrazolo[5,1-d][1,2,5]oxadiazepine-10(2H)-carboxylate

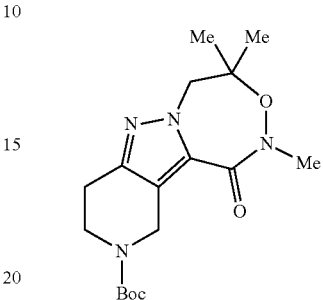

Step 1. Preparation of methyl-2-[tert-butoxycarbonyl(methyl)amino]oxy-2-methyl-propanoate. To a solution of $CH_3ONa$ (587.78 mg, 10.88 mmol, 1.00 eq) in MeOH (20.00 mL) was added methyl 2-bromo-2-methyl-propanoate (1.97 g, 10.88 mmol, 1.41 mL, 1.00 eq) and tert-butyl N-hydroxy-N-methyl-carbamate (1.60 g, 10.88 mmol, 1.00 eq) at 15° C. The mixture was heated to 60° C. with stirring for 16 h. TLC (PE:EtOAc=5:1) showed that starting material was consumed completely and one main new spot formed. The mixture was evaporated to remove the solvent and get the residue. The residue was purified by column chromatography ($SiO_2$, Petroleum ether/Ethyl acetate=100/1 to 20/1) to obtain the title compound (2.30 g, 9.30 mmol, 85.49% yield) as off-white liquid. $^1H$ NMR (400 MHz, CHLOROFORM-d) δ=3.74 (s, 3H), 3.11 (s, 3H), 1.48 (d, J=4.9 Hz, 15H).

Step 2. Preparation of tert-butyl N-(2-hydroxy-1,1-dimethyl-ethoxy)-N-methyl-carbamate. $LiBH_4$ (704.60 mg, 32.35 mmol, 4.00 eq) was charged to a cooled three-necked round bottom flask at −78° C. under $N_2$, then a solution of methyl 2-[tert-butoxycarbonyl(methyl)amino]oxy-2-methyl-propanoate (2.00 g, 8.09 mmol, 1.00 eq) in THF (20.00 mL) was added dropwise. After addition, the reaction mixture was warmed to 0° C. and stirred at 0° C. for 2 hours. TLC (PE:EtOAc=2:1) showed that reactant 3 was consumed completely and one main spot formed. The mixture was quenched with 20 mL of water and filtered to get the filtrate. The filtrate was extracted with EtOAc (20 mL*3) and the organic phases were combined. The combined organic phase was dried over anhydrous $Na_2SO_4$, filtered and concentrated to get the residue. The residue was purified by column chromatography ($SiO_2$, Petroleum ether/Ethyl acetate=1/0 to 15/1) to obtain the title compound (1.30 g, 5.93 mmol, 73.32% yield) as off-white liquid. $^1H$ NMR (400 MHz, CHLOROFORM-d) δ=4.60 (brs, 1H), 3.59 (br d, J=12.35 Hz, 1H), 3.01-3.21 (m, 4H), 1.49 (s, 9H), 1.15-1.33 (m, 6H).

Step 3. Preparation of 2-methyl-2-(methylaminooxy)propan-1-ol. To a solution of tert-butyl N-(2-hydroxy-1,1-dimethyl-ethoxy)-N-methyl-carbamate (1.30 g, 5.93 mmol, 1.00 eq) in dioxane (2.00 mL) was added HCl/dioxane (4 M, 6.00 mL, 4.05 eq) under stirring at 15° C. for 2 h. TLC (PE:EtOAc=3:1) showed that the starting material was consumed completely and one main spot formed. The mixture was directly evaporated to get the title compound (1.10 g, crude, HCl) as yellow oil. ¹H NMR (400 MHz, METHANOL-d₄) δ=3.75 (s, 2H), 2.95 (s, 3H), 1.37 (s, 6H).

Step 4. Preparation of tert-butyl 3-[(2-hydroxy-1,1-dimethyl-ethoxy)-methyl-carbamoyl]-2,4,6,7-tetrahydropyrazolo[4,3-c]pyridine-5-carboxylate. To a solution of 5-tert-butoxycarbonyl-2,4,6,7-tetrahydropyrazolo[4,3-c]pyridine-3-carboxylic acid (800.00 mg, 2.99 mmol, 1.00 eq) and 2-methyl-2-(methylaminooxy)propan-1-ol (604.89 mg, 3.89 mmol, 1.30 eq, HCl) in THF (8.00 mL) was added T₃P (3.81 g, 5.98 mmol, 3.56 mL, 50% purity, 2.00 eq) and TEA (2.42 g, 23.92 mmol, 3.32 mL, 8.00 eq). The mixture was stirred at 30° C. for 2 hr. LCMS showed 30% desired product and 40% byproduct with MS+1=747. The mixture was diluted with saturated NH₄Cl (50 mL) and extracted with EtOAc (50 mL*2). The combined organic layer was dried over Na₂SO₄, filtrated. The filtrate was concentrated in vacuum. The residue was purified by column chromatography (PE:EA:30%~100%) to get the title compound (200.00 mg, 542.84 μmol, 18.16% yield) as white solid. ¹H NMR (400 MHz, CHLOROFORM-d) δ=4.70 (brs, 2H), 3.60-3.77 (m, 4H), 3.50 (brs, 3H), 2.77 (t, J=5.32 Hz, 2H), 1.49 (s, 9H), 1.36 (s, 6H).

Step 5. Preparation of tert-butyl 2,4,4-trimethyl-1-oxo-1,4,5,8,9,11-hexahydropyrido[4',3':3,4]pyrazolo[5,1-d][1,2,5]oxadiazepine-10(2H)-carboxylate. To a solution of tert-butyl 3-[(2-hydroxy-1,1-dimethyl-ethoxy)-methyl-carbamoyl]-2,4,6,7-tetrahydropyrazolo[4,3-c]pyridine-5-carboxylate (200.00 mg, 542.84 μmol, 1.00 eq) in THF (2.00 mL) was added tributylphosphane (219.66 mg, 1.09 mmol, 267.87 μL2.00 eq) followed by DIAD (219.54 mg, 1.09 mmol, 211.09 μL2.00 eq) under N₂. The mixture was heated to 80° C. for 16 hr. TLC (PE:EA=0:1) showed the starting material was consumed and one main spot appeared. The mixture was extracted with EtOAc (10 mL*2) and H₂O (10 mL). The combined organic layer was dried over Na₂SO₄, filtrated. The filtrate was concentrated in vacuum. The residue was purified by prep-TLC (PE:EA=0:1) to give the title compound (150.00 mg, 428.07 μmol, 78.86% yield) as colorless oil.

Intermediate 10. tert-butyl 2-methyl-1-oxo-1,4,5,8,9,11-hexahydropyrido[4',3':3,4]pyrazolo[5,1-d][1,2,5]oxadiazepine-10(2H)-carboxylate

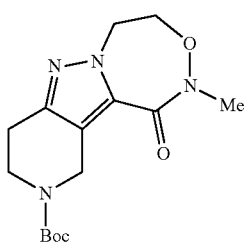 [SMILES: CN1OCCn2nc3c(c2C1=O)CN(C(=O)OC(C)(C)C)CC3]

To a mixture of tert-butyl 3-(hydroxy(methyl)carbamoyl)-2,4,6,7-tetrahydro-5H-pyrazolo[4,3-c]pyridine-5-carboxylate (Intermediate 6, 100.00 mg, 337.47 μmol, 1.00 eq) and K₂CO₃ (93.28 mg, 674.94 μmol, 2.00 eq) in DMF (3.00 mL) was added 1,2-dibromoethane (69.74 mg, 371.22 μmol, 28.01 μL1.10 eq) in one portion at 15° C. The mixture was stirred at 15° C. for 36 hours. LCMS and TLC (dichloromethane:methanol=10:1) showed the reaction was completed. The mixture was poured into water (15 mL) and stirred for 2 min. The aqueous phase was extracted with ethyl acetate (15 mL*2). The combined organic phase was washed with brine (10 mL*2), dried with anhydrous Na₂SO₄, filtered and concentrated in vacuum. The residue was purified by prep-TLC (dichloromethane:methanol=10:1) to afford the title compound (55.00 mg, 170.62 μmol, 50.56% yield, 100% purity) as a yellow solid. LCMS: 323 [M+1].

Intermediate 11. N-allylhydroxylamine

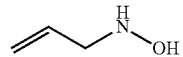

Step 1. Preparation of [allyl(tert-butoxycarbonyl)amino] tert-butyl carbonate. To a solution of (tert-butoxycarbonylamino) tert-butyl carbonate (5.50 g, 23.58 mmol, 1.00 eq) in DMF (30.00 mL) was added K₂CO₃ (6.52 g, 47.16 mmol, 2.00 eq) and 3-bromoprop-1-ene (3.71 g, 30.65 mmol, 1.30 eq) under N₂, the reaction mixture was stirred at 50° C. for 12 hr. TLC indicated the starting material was consumed completely and one new spot formed. The reaction mixture was filtered and the filter cake was washed with EtOAc (100 mL×3), the organic layer was added water (200 mL) and extracted with EtOAc (200 mL×3), the combined layers were washed with water (50 mL×3) and brine (150 mL), dried with anhydrous Na₂SO₄, filtered and concentrated in vacuum. The residue was purified by column chromatography to give the title compound (5.20 g, 19.03 mmol, 80.68% yield) as colorless oil. ¹H NMR (400 MHz, CHLOROFORM-d) δ=5.76-6.00 (m, 1H) 5.18-5.31 (m, 2H) 4.19 (d, J=5.77 Hz, 2H) 1.52 (s, 9H) 1.49 (s, 9H).

Step 2. Preparation of N-allylhydroxylamine. To a solution of [allyl(tert-butoxycarbonyl)amino] tert-butyl carbonate (1.90 g, 6.95 mmol, 1.00 eq) in DCM (35.00 mL) was added TFA (53.90 g, 472.74 mmol, 35.00 mL, 68.02 eq), the reaction mixture was stirred at 15° C. for 3 hr. TLC indicated the starting material was consumed completely and one new spot formed. The reaction mixture was concentrated in vacuum to give the title compound (1.31 g, crude, TFA) as a light yellow oil.

Intermediate 12. tert-butyl 2-allyl-1-oxo-1,4,5,8,9,11-hexahydropyrido[4',3':3,4]pyrazolo[5,1-d][1,2,5]oxadiazepine-10(2H)-carboxylate

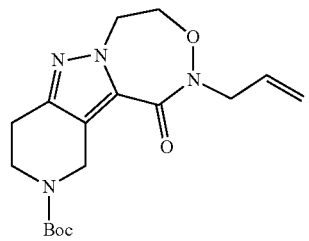 [SMILES: C=CCN1OCCn2nc3c(c2C1=O)CN(C(=O)OC(C)(C)C)CC3]

Step 1. Preparation of tert-butyl3-[allyl(hydroxy)carbamoyl]-2,4,6,7-tetrahydropyrazolo[4,3-c]pyridine-5-carboxylate. To a solution of N-allylhydroxylamine (Intermediate 11, 1.05 g, 5.61 mmol, 1.50 eq, TFA) and TEA (3.07 g, 30.29 mmol, 4.20 mL, 8.10 eq) in THF (50.00 mL) was added T₃P (9.64 g, 15.15 mmol, 9.01 mL, 50% purity, 4.05 eq) and 5-tert-butoxycarbonyl-2,4,6,7-tetrahydropyrazolo[4,3-c]

pyridine-3-carboxylic acid (1.00 g, 3.74 mmol, 1.00 eq), the reaction mixture was stirred at 30° C. for 40 min. LCMS showed the starting material was consumed completely and a peak (about 69%) with desired MS was detected. The reaction mixture was quenched with water (40 mL) and extracted with EtOAc (40 mL×3), the combined organic layers were washed with water (50 mL×3) and brine (50 mL), filtered, dried with anhydrous $Na_2SO_4$ and concentrated in vacuum to give the title compound (900.00 mg, 2.29 mmol, 61.21% yield, 82% purity) as a light yellow solid. $^1$H NMR (400 MHz, CHLOROFORM-d) δ=5.90 (s, 1H) 5.20-5.35 (m, 2H) 4.23-4.77 (m, 4H) 3.67 (s, 2H) 2.71 (s, 2H) 1.48 (s, 9H). LCMS: 323 [M+1].

Step 2. Preparation of tert-butyl 2-allyl-1-oxo-5,8,9,11-tetrahydro-4H-pyrido[2,3]pyrazolo[2,4-c] [1,2,5]oxadiazepine-10-carboxylate. To a mixture of tert-butyl 3-[allyl(hydroxy)carbamoyl]-2,4,6,7-tetrahydropyrazolo [4,3-c] pyridine-5-carboxylate (80.00 mg, 248.17 μmol, 1.00 eq) and 1,2-dibromoethane (69.93 mg, 372.25 μmol, 28.08 μL1.50 eq) in DMF (2.00 mL) was added $Cs_2CO_3$ (242.58 mg, 744.51 μmol, 3.00 eq) and TBAI (9.17 mg, 24.82 μmol, 0.10 eq), the reaction mixture was stirred at 30° C. for 16 hours. LCMS showed the starting material was consumed completely and about 60% of desired compound was detected. The reaction mixture was diluted with EtOAc (80 mL) and washed with water (50 mL*2), the organic phase was dried with anhydrous $Na_2SO_4$, filtered and concentrated in vacuum. The residue was purified by silica gel chromatography to give the title compound (53.00 mg, 136.91 μmol, 55.17% yield, 90% purity) as yellow oil. LCMS: 349 [M+1].

Intermediate 13. 5-(tert-butoxycarbonyl)-6-methyl-4,5,6,7-tetrahydro-1H-pyrazolo[4,3-c]pyridine-3-carboxylic acid

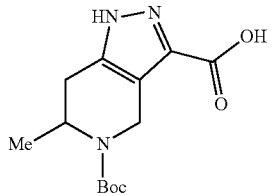

Step 1. Preparation of ethyl 3-aminobutanoate. $SOCl_2$ (28.84 g, 242.43 mmol, 17.59 mL, 2.50 eq) was added to EtOH (100.00 mL) dropwise at 0° C. under $N_2$. The mixture was stirred at 0° C. for 0.5 hr under $N_2$. Then 3-aminobutanoic acid (10.00 g, 96.97 mmol, 1.00 eq) was added to the mixture and the mixture was stirred at 25° C. for 1.5 hr under $N_2$. And then the mixture was stirred at 50° C. for 1 hr under $N_2$ atmosphere. TLC (DCM/MeOH=10/1) showed the reaction was completed. The mixture was concentrated in vacuum to afford the title compound (16.00 g, 95.45 mmol, 98.43% yield, HCl) as black brown oil. $^1$H NMR (400 MHz, METHANOL-$d_4$) δ=2.66 (d, J=7.15 Hz, 2H), 2.09-2.19 (m, 1H), 1.17 (d, J=6.53 Hz, 2H), −0.18 (d, J=6.65 Hz, 3H), −0.27 (s, 3H)

Step 2. Preparation of ethyl 3-[(3-ethoxy-3-oxo-propyl)amino]butanoate. To a solution of ethyl 3-aminobutanoate (10.00 g, 59.66 mmol, 11.24 mL, 1.00 eq, HCl) in EtOH (100.00 mL) was added NaOH (2.51 g, 62.64 mmol, 1.05 eq) followed by ethyl prop-2-enoate (7.17 g, 71.59 mmol, 7.79 mL, 1.20 eq). The mixture was heated to 80° C. and stirred at 80° C. for 16 hr. TLC (DCM:MeOH=10:1) showed the starting material remained and a new spot was appeared. The pH of the mixture was adjusted to 4 with HCl (1N) and extracted with EA (200 mL). The aqueous phase was adjust to pH~8 with $Na_2CO_3$ (sat. aq) and then extracted with EA (200 mL×2). The combined organic layer was dried over $Na_2SO_4$, filtered and concentrated to afford the title compound (9.00 g, 38.91 mmol, 65.22% yield) as colorless oil.

Step 3. Preparation of ethyl 3-[tert-butoxycarbonyl-(3-ethoxy-3-oxo-propyl)amino]butanoate. To a mixture of ethyl 3-[(3-ethoxy-3-oxo-propyl)amino]butanoate (9.00 g, 38.91 mmol, 1.00 eq) and TEA (5.51 g, 54.47 mmol, 7.55 mL, 1.40 eq) in THF (50.00 mL) was added $Boc_2O$ (8.49 g, 38.91 mmol, 8.94 mL, 1.00 eq) at 30° C. The mixture was stirred at 30° C. for 12 hours. TLC (PE/EA=5/1) and LCMS showed the reaction was completed. The mixture was poured into water (30 mL) and stirred for 1 min. The aqueous phase was extracted with ethyl acetate (30 mL×2). The combined organic phase was washed with brine (30 mL×2), dried with anhydrous $Na_2SO_4$, filtered and concentrated in vacuum. The residue was purified by silica gel chromatography (PE/EA=10/1) to afford the title compound (7.00 g, 21.12 mmol, 54.29% yield) as yellow oil.

Step 4. Preparation of 1-tert-butyl 3-ethyl 6-methyl-4-oxo-piperidine-1,3-dicarboxylate. To a mixture of ethyl 3-[tert-butoxycarbonyl-(3-ethoxy-3-oxo-propyl)amino] butanoate (7.20 g, 21.73 mmol, 1.00 eq) in THF (200.00 mL) was added t-BuOK (2.68 g, 23.90 mmol, 1.10 eq) in one portion at −40° C. under $N_2$. The mixture was stirred at −40° C. for 1 hr. LCMS showed the reaction was completed. The mixture was poured into water (50 mL) and stirred for 3 min. The aqueous phase was extracted with ethyl acetate (50 mL×2). The combined organic phase was washed with brine (50 mL×2), dried with anhydrous $Na_2SO_4$, filtered and concentrated in vacuum to afford the title compound (5.00 g, 17.52 mmol, 80.64% yield) as yellow oil. LCMS: 186 [M−99].

Step 5. Preparation of tert-butyl 3-hydroxy-6-methyl-1,4,6,7-tetrahydropyrazolo [4,3-c]pyridine-5-carboxylate. To a mixture of 1-tert-butyl 3-ethyl 6-methyl-4-oxo-piperidine-1,3-dicarboxylate (5.00 g, 17.52 mmol, 1.00 eq) in MeOH (30.00 mL) was added $N_2H_4 \cdot H_2O$ (1.03 g, 17.52 mmol, 1.00 mL, 85% purity, 1.00 eq) in one portion at 30° C. under $N_2$. The mixture was stirred at 30° C. for 12 hours. LCMS showed the reaction was completed. The mixture was concentrated in vacuum. The residue was purified by prep-HPLC(FA) to afford the title compound (1.50 g, 5.92 mmol, 33.80% yield) as yellow solid. LCMS: 254 [M+1]. $^1$H NMR (400 MHz, METHANOL-$d_4$) δ 4.70-4.82 (m, 1H), 4.58-4.68 (m, 1H), 3.76-3.89 (m, 1H), 2.75-2.88 (m, 1H), 2.37-2.50 (m, 1H), 1.49 (s, 9H), 1.13 (d, J=6.90 Hz, 3H)

Step 6. Preparation of tert-butyl 6-methyl-3-(trifluoromethylsulfonyloxy)-1,4,6,7-tetrahydropyrazolo [4,3-c]pyridine-5-carboxylate. To a mixture of tert-butyl 3-hydroxy-6-methyl-1,4,6,7-tetrahydropyrazolo[4,3-c] pyridine-5-carboxylate (1.50 g, 5.92 mmol, 1.00 eq) in Py (5.00 mL) was added 1,1,1-trifluoro-N-phenyl-N-(trifluoromethylsulfonyl)methanesulfonamide (3.17 g, 8.88 mmol, 1.50 eq) in one portion under $N_2$. The mixture was stirred at 20° C. for 12 hours. TLC (PE/EA=2/1) showed the reaction was completed. The mixture was concentrated in vacuum. The residue was diluted with ethyl acetate (150 mL) and poured into HCl (0.5 N, 20 mL) and stirred for 1 min. The aqueous phase was extracted with ethyl acetate (100 mL×2). The combined organic phase was washed with brine (100 mL×2), dried with anhydrous $Na_2SO_4$, filtered and concentrated in vacuum. The residue was purified by silica gel chromatography (PE/EA=10/1) to afford the title compound (1.40 g, 3.63 mmol, 61.37% yield) as yellow solid.

Step 7. Preparation of tert-butyl 6-methyl-3-vinyl-1,4,6,7-tetrahydropyrazolo[4,3-c] pyridine-5-carboxylate. To a mixture of tert-butyl 6-methyl-3-(trifluoromethylsulfonyloxy)-1,4,6,7-tetrahydropyrazolo[4,3-c]pyridine-5-carboxylate (200.00 mg, 519.00 μmol, 1.00 eq) and [trifluoro(vinyl)boranyl]potassium (1+) (208.56 mg, 1.56 mmol, 3.00 eq) in dioxane (2.00 mL) and H₂O (200.00 μL) were added XPHOS-Pd-G2 (Chloro(2-dicyclohexylphosphino-2',4',6'-triisopropyl-1,1'-biphenyl)[2-(2'-amino-1,1'-biphenyl)]palladium(II)) (40.83 mg, 51.90 μmol, 0.10 eq) and K₃PO₄ (330.50 mg, 1.56 mmol, 3.00 eq) in one portion under N₂. The reaction vessel was sealed and heated under microwave at 140° C. for 2 hours. TLC (PE/EA=2/1) showed ~10% of the starting material remained, 80% of the title compound was detected. The mixture was poured into water (30 mL) and stirred for 2 min. The aqueous phase was extracted with ethyl acetate (30 mL×2). The combined organic phase was washed with brine (30 mL×2), dried with anhydrous Na₂SO₄, filtered and concentrated in vacuum. The residue was purified by silica gel chromatography (PE/EA=10/1) to afford the title compound (190.00 mg, 656.59 μmol, 42.17% yield, 91% purity) as yellow oil. LCMS: 264 [M+1].

Step 8. Preparation of tert-butyl 3-formyl-6-methyl-1,4,6,7-tetrahydropyrazolo[4,3-c]pyridine-5-carboxylate. To a mixture of tert-butyl 6-methyl-3-vinyl-1,4,6,7-tetrahydropyrazolo[4,3-c]pyridine-5-carboxylate (400.00 mg, 1.52 mmol, 1.00 eq) in THF (40.00 mL) and H₂O (8.00 mL) was added NaIO₄ (1.30 g, 6.08 mmol, 336.79 μL4.00 eq) and OsO₄ (38.62 mg, 152.00 μmol, 7.88 μL0.10 eq) in one portion at 20° C. The mixture was stirred at 20° C. for 3 hours. LCMS showed the reaction was completed. The mixture was quenched with Na₂SO₃ (sat. aq, 20 mL) and stirred for 5 min. The aqueous phase was extracted with ethyl acetate (20 mL×2). The combined organic phase was washed with brine (20 mL×2), dried with anhydrous Na₂SO₄, filtered and concentrated in vacuum to afford the title compound (400.00 mg, crude) as yellow oil.

Step 9. Preparation of 5-tert-butoxycarbonyl-6-methyl-1,4,6,7-tetrahydropyrazolo[4,3-c]pyridine-3-carboxylic acid. To a mixture of tert-butyl 3-formyl-6-methyl-1,4,6,7-tetrahydropyrazolo[4,3-c] pyridine-5-carboxylate (400.00 mg, crude, 1.51 mmol, 1.00 eq) in t-BuOH (20.00 mL) was added 2-methylbut-2-ene (1PD0.56 g, 150.58 mmol, 16.00 mL, 99.72 eq) dropwise at 0° C., then a solution of NaH₂PO₄ (905.85 mg, 7.55 mmol, 5.00 eq) and sodium; chlorite (1.37 g, 15.10 mmol, 10.00 eq) in H₂O (10.00 mL) was added to the above mixture dropwise at 0° C. The mixture was stirred at 0° C. for 2 hours. LCMS showed the reaction was completed. The mixture was adjusted to pH~9 with solid NaHCO₃, the aqueous phase was extracted with ethyl acetate (10 mL×2). The aqueous layer was acidified to pH~4 with 2N HCl and extracted with ethyl acetate (10 mL×2). The combined organic phase was washed with brine (10 mL×2), dried with anhydrous Na₂SO₄, filtered and concentrated in vacuum to afford the title compound (320.00 mg, 910.03 μmol, 60.27% yield, 80% purity) as yellow solid. LCMS: 282 [M+1].

Intermediate 14. tert-butyl 4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxylate

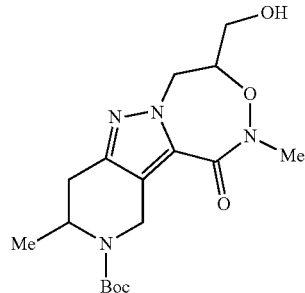 [SMILES: CC1Cc2nn3c(c2CN1C(=O)OC(C)(C)C)C(=O)N(C)OC(CO)C3]

To a mixture of 5-(tert-butoxycarbonyl)-6-methyl-4,5,6,7-tetrahydro-1H-pyrazolo[4,3-c]pyridine-3-carboxylic acid (Intermediate 13, 400.00 mg, 1.42 mmol, 1.00 eq) and N-(oxetan-3-yloxy) methanamine (585.72 mg, 5.68 mmol, 4.00 eq) in THF (5.00 mL) was added T₃P (2.71 g, 4.26 mmol, 2.53 mL, 50% purity, 3.00 eq) and TEA (7.29 g, 72.05 mmol, 9.99 mL, 50.74 eq) in one portion under N₂. The mixture was stirred at 50° C. for 12 hours. LCMS showed the reaction was completed and one peak was detected, whereas TLC (dichloromethane:methanol=10:1) showed three new points. The residue was poured into water (30 mL) and stirred for 2 min. The aqueous phase was extracted with ethyl acetate (30 mL*2). The combined organic phase was washed with brine (20 mL*2), dried with anhydrous Na₂SO₄, filtered and concentrated in vacuum. The residue was purified by silica gel chromatography (Petroleum ether/Ethyl acetate=100/1, 50/1), followed by prep-HPLC(base) to give the title compound (50.00 mg, 136.46 μmol, 9.61% yield) as a white solid. LCMS: 367 [M+1]. ¹H NMR (400 MHz, CHLOROFORM-d) 4.63-5.16 (m, 3H), 4.09-4.61 (m, 4H), 3.60-3.94 (m, 2H), 3.30 (s, 3H), 2.85-3.02 (m, 1H), 2.50-2.66 (m, 1H), 1.48 (s, 9H), 1.13 (dd, J=3.64, 6.78 Hz, 3H).

Intermediate 15. tert-butyl 6-methyl-3-(methyl (oxetan-3-yloxy)carbamoyl)-1,4,6,7-tetrahydro-5H-pyrazolo[4,3-c]pyridine-5-carboxylate

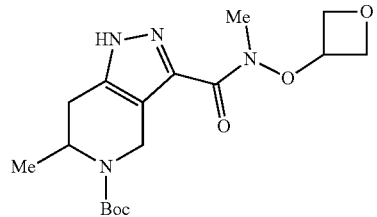 [SMILES: CC1Cc2[nH]nc(C(=O)N(C)OC3COC3)c2CN1C(=O)OC(C)(C)C]

To a mixture of 5-(tert-butoxycarbonyl)-6-methyl-4,5,6,7-tetrahydro-1H-pyrazolo[4,3-c]pyridine-3-carboxylic acid (Intermediate 13, 400.00 mg, 1.42 mmol, 1.00 eq) and N-(oxetan-3-yloxy) methanamine (585.72 mg, 5.68 mmol, 4.00 eq) in THF (5.00 mL) was added T₃P (2.71 g, 4.26 mmol, 2.53 mL, 50% purity, 3.00 eq) and TEA (7.29 g, 72.05 mmol, 9.99 mL, 50.74 eq) in one portion under N₂. The mixture was stirred at 50° C. for 12 hours. LCMS showed the reaction was completed and one peak was detected, whereas TLC (dichloromethane:methanol=10:1) showed three new points. The residue was poured into water (30 mL) and stirred for 2 min. The aqueous phase was extracted with ethyl acetate (30 mL*2). The combined organic phase was washed with brine (20 mL*2), dried with anhydrous $Na_2SO_4$, filtered and concentrated in vacuum. The residue was purified by silica gel chromatography (Petroleum ether/Ethyl acetate=100/1, 50/1), followed by prep-HPLC(base) to give the title compound (160.00 mg, 436.67 μmol, 30.75% yield) as white solid. LCMS: 367 [M+1]. $^1$H NMR (400 MHz, CHLOROFORM-d) δ 5.11 (d, J=5.14 Hz, 2H), 4.86 (d, J=6.15 Hz, 3H), 4.75 (dd, J=5.02, 7.65 Hz, 2H), 4.08-4.26 (m, 1H), 3.48 (br. s., 3H), 2.91-3.05 (m, 1H), 2.52-2.65 (m, 1H), 1.49 (s, 9H), 1.13 (d, J=6.90 Hz, 3H).

Intermediate 16. 10-(tert-butyl) 4-methyl 2-methyl-1-oxo-1,4,5,8,9,11-hexahydropyrido[4',3':3,4]pyrazolo[5,1-d][1,2,5]oxadiazepine-4,10(2H)-dicarboxylate

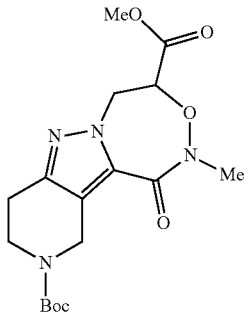 [SMILES: COC(=O)C1Cn2nc3c(c2C(=O)N(C)O1)CN(C(=O)OC(C)(C)C)CC3]

Step 1. Preparation of 10-tert-butoxycarbonyl-2-methyl-1-oxo-5,8,9,11-tetrahydro-4H-pyrido[2,3]pyrazolo[2,4-d][1,2,5]oxadiazepine-4-carboxylic acid. To a mixture of tert-butyl 4-(hydroxymethyl)-2-methyl-1-oxo-5,8,9,11-tetrahydro-4H-pyrido[2,3]pyrazolo[2,4-d][1,2,5]oxadiazepine-10-carboxylate (1.00 g, 2.84 mmol, 1.00 eq) and NMO (2.50 g, 21.30 mmol, 2.25 mL, 7.50 eq) in MeCN (30.00 mL) was added TPAP (199.61 mg, 568.00 μmol, 0.20 eq) in one portion at 0° C. under $N_2$. The mixture was stirred at 0° C. for 2 hr. LCMS showed the reaction was completed. The residue was concentrated in vacuum to afford the title compound (1.04 g, crude) as black brown solid. LCMS: 367 [M+1].

Step 2. Preparation of 10-(tert-butyl) 4-methyl 2-methyl-1-oxo-1,4,5,8,9,11-hexahydropyrido[4',3':3,4]pyrazolo[5,1-d][1,2,5]oxadiazepine-4,10(2H)-dicarboxylate. To a mixture of 10-tert-butoxycarbonyl-2-methyl-1-oxo-5,8,9,11-tetrahydro-4H-pyrido[2,3]pyrazolo[2,4-d][1,2,5]oxadiazepine-4-carboxylic acid (1.04 g, 2.84 mmol, 1.00 eq) and $K_2CO_3$ (1.18 g, 8.52 mmol, 3.00 eq) in MeCN (5.00 mL) was added MeI (1.21 g, 8.52 mmol, 530.70 μL3.00 eq) in one portion at 25° C. under $N_2$. The mixture was stirred at 25° C. 12 hours. LCMS showed the reaction was not reacted. The starting material was recovered from the reaction mixture by extracted with ethyl acetate (20 mL*2) after neutralized with 1N HCl to pH 3. Then reacted again (To a mixture of 10-tert-butoxycarbonyl-2-methyl-1-oxo-5,8,9,11-tetrahydro-4H-pyrido [2,3]pyrazolo[2,4-d][1,2,5]oxadiazepine-4-carboxylic acid (1.04 g, 2.84 mmol, 1.00 eq) and $K_2CO_3$ (1.18 g, 8.52 mmol, 3.00 eq) in MeCN (5.00 mL) was added MeI (1.21 g, 8.52 mmol, 530.70 μL3.00 eq) in one portion at 25° C. under $N_2$. The mixture was stirred at 25° C. for 12 hours). LCMS and TLC (ethyl acetate:petroleum ether=2:1) showed the reaction was completed. The residue was poured into water (20 mL) and stirred for 2 min. The aqueous phase was extracted with ethyl acetate (20 mL*2). The combined organic phase was washed with brine (20 mL*2), dried with anhydrous $Na_2SO_4$, filtered and concentrated in vacuum. The residue was purified by silica gel chromatography (Petroleum ether/Ethyl acetate=10/1, 2/1) to afford the title compound (150.00 mg, 394.33 μmol, 13.88% yield, 100% purity) as yellow oil. LCMS: 381 [M+1]. $^1$H NMR (400 MHz, CHLOROFORM-d) 4.79-4.98 (m, 2H), 4.45-4.75 (m, 3H), 3.88 (s, 3H), 3.54-3.85 (m, 2H), 3.38 (s, 3H), 2.67-2.89 (m, 2H), 1.49 (s, 9H).

Intermediate 17. tert-butyl(R)-2,9-dimethyl-1-oxo-1,4,5,8,9,11-hexahydropyrido[4',3':3,4]pyrazolo[5,1-d][1,2,5]oxadiazepine-10(2H)-carboxylate

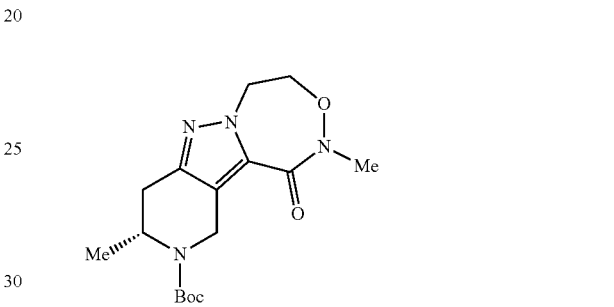

Step 1. Preparation of tert-butyl(2R)-5-(2-ethoxy-2-oxoacetyl)-2-methyl-4-oxo-piperidine-1-carboxylate. To a solution of tert-butyl (2R)-2-methyl-4-oxo-piperidine-1-carboxylate (4.00 g, 18.76 mmol, 1.00 eq) in THF (50.00 mL) was added LiHMDS (1 M, 22.51 mL, 1.20 eq) dropwise at −70° C. The mixture was stirred at −70° C. for 0.5 hr. Then diethyl oxalate (3.56 g, 24.38 mmol, 3.33 mL, 1.30 eq) was added dropwise at −70° C. The mixture was stirred at 10° C. for 1 hr. TLC (petroleum ether:ethyl acetate=5:1) showed the starting material consumed and one new spot appeared. The mixture was quenched by 1N HCl (500 mL) and extracted with ethyl acetate (300 mL*5). The combined organic layer was dried over $Na_2SO_4$, filtrated. The filtrate was concentrated in vacuum to get the title compound (5.00 g, crude) as yellow oil.

Step 2. Preparation of 5-tert-butyl 3-ethyl (6R)-6-methyl-1,4,6,7-tetrahydropyrazolo[4,3-c] Pyridine-3,5-dicarboxylate. To a solution of tert-butyl (2R)-5-(2-ethoxy-2-oxoacetyl)-2-methyl-4-oxo-piperidine-1-carboxylate (5.00 g, 15.96 mmol, 1.00 eq) in EtOH (30.00 mL) was added $NH_2NH_2 \cdot H_2O$ (939.75 mg, 15.96 mmol, 912.38 μL85% purity, 1.00 eq). The mixture was stirred at 10° C. for 1 hr. TLC (petroleum ether (PE):ethyl acetate (EA)=1:1) showed the starting material consumed and one main spot appeared. The reaction mixture was concentrated in vacuum. The residue was purified by column chromatography (PE:EA: 20%~60%) to get the title compound (3.60 g, 11.64 mmol, 72.91% yield) as a yellow solid.

Step 3. Preparation of (6R)-5-tert-butoxycarbonyl-6-methyl-1,4,6,7-tetrahydropyrazolo[4,3-c]pyridine-3-carboxylic acid. To a solution of 5-tert-butyl 3-ethyl (6R)-6-methyl-1,4,6,7-tetrahydropyrazolo [4,3-c]pyridine-3,5-dicarboxylate (3.60 g, 11.64 mmol, 1.00 eq) in THF (30.00 mL) was added a solution of NaOH (930.95 mg, 23.27 mmol, 2.00 eq) in $H_2O$ (7.00 mL). The mixture was stirred at 50° C. for 16 hr. TLC (PE:EA=1:1) showed the starting material consumed and one main spot with higher polarity appeared. The pH of the mixture was adjusted to 5-6 with 1N HCl. The mixture was diluted with ethyl acetate (300 mL) and H$_2$O (100 mL). The organic layer was separated, dried with Ns$_2$SO$_4$, and filtered. The filtrate was concentrated in vacuum to get the title compound (3.00 g, 10.66 mmol, 91.62% yield) as a white solid. $^1$H NMR (400 MHz, METHANOL-d$_4$) δ=4.93 (d, J=17.24 Hz, 1H), 4.68-4.75 (m, 1H), 4.04 (d, J=16.51 Hz, 1H), 2.82 (dd, J=6.05, 15.96 Hz, 1H), 2.52 (d, J=15.89 Hz, 1H), 1.39 (s, 9H), 1.02 (d, J=6.97 Hz, 3H).

Step 4. Preparation of tert-butyl(6R)-3-[hydroxy(methyl)carbamoyl]-6-methyl-1,4,6,7-tetrahydropyrazolo[4,3-c]pyridine-5-carboxylate. To a solution of (6R)-5-tert-butoxycarbonyl-6-methyl-1,4,6,7-tetrahydropyrazolo [4,3-c]pyridine-3-carboxylic acid (2.70 g, 9.60 mmol, 1.00 eq) and N-methylhydroxylamine (2.40 g, 28.79 mmol, 3.00 eq, HCl) in DMF (20.00 mL) was added HOBt (1.95 g, 14.40 mmol, 1.50 eq), PyBOP (7.49 g, 14.40 mmol, 1.50 eq) and DIEA (6.20 g, 47.99 mmol, 8.38 mL, 5.00 eq). The mixture was stirred at 30° C. for 3 hr. TLC (DCM:MeOH=10:1) showed the starting material was consumed and one main spot appeared. The mixture was extracted with ethyl acetate (150 mL*3) and H$_2$O (150 mL). The combined organic layer was washed with H$_2$O (150 mL*2), 1N HCl (80 mL) and saturated Na$_2$CO$_3$ (50 mL). The organic layer was dried with Na$_2$SO$_4$, filtrated. The filtrate was concentrated in vacuum. The residue was purified by column chromatography (petroleum ether:ethyl acetate: 60%~100%) to get the title compound (2.00 g, 6.44 mmol, 67.13% yield) as white solid. $^1$H NMR (400 MHz, METHANOL-d$_4$) δ=5.06 (d, J=13.82 Hz, 1H), 4.78-4.84 (m, 1H), 4.20 (brs, 1H), 3.40 (brs, 3H), 2.93 (dd, J=5.93, 15.71 Hz, 1H), 2.63 (d, J=15.89 Hz, 1H), 1.50 (s, 9H), 1.14 (d, J=6.85 Hz, 3H).

Step 5. Preparation of tert-butyl (R)-2,9-dimethyl-1-oxo-1,4,5,8,9,11-hexahydropyrido[4',3':3,4]pyrazolo[5,1-d][1,2,5]oxadiazepine-10(2H)-carboxylate. To a solution of tert-butyl (6R)-3-[hydroxy(methyl)carbamoyl]-6-methyl-1,4,6,7-tetrahydropyrazolo[4,3-c]pyridine-5-carboxylate (2.00 g, 6.44 mmol, 1.00 eq) in DMF (20.00 mL) was added Cs$_2$CO$_3$ (6.30 g, 19.32 mmol, 3.00 eq) followed by 1,2-dibromoethane (1.81 g, 9.66 mmol, 728.81 µL1.50 eq) and TBAI (238.03 mg, 644.00 µmol, 0.10 eq). The mixture was stirred at 50° C. for 16 hr. TLC (PE:EA=0:1) showed the starting material was consumed and one main spot appeared. The mixture was extracted with ethyl acetate (20 mL*2) and H$_2$O (20 mL). The combined organic layer was washed with H$_2$O (20 mL*2), dried with Na$_2$SO$_4$, filtrated. The filtrate was concentrated in vacuum. The residue was purified by column chromatography (petroleum ether:ethyl acetate=50%~100%) to get the title compound (1.50 g, 4.19 mmol, 65.09% yield, 94% purity) as a white solid. $^1$H NMR (400 MHz, CHLOROFORM-d) δ=4.73-5.06 (m, 1H), 4.38-4.52 (m, 1H), 4.21-4.36 (m, 1H), 4.11 (d, J=17.48 Hz, 1H), 3.21 (s, 3H), 2.84-2.93 (m, 1H), 2.51 (d, J=15.77 Hz, 1H), 1.41 (s, 10H), 1.06 (d, J=6.97 Hz, 3H).

Intermediate 18. tert-butyl(9R)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxylate

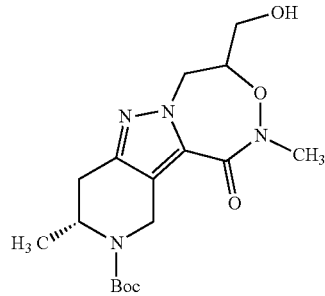

To a solution of (R)-5-(tert-butoxycarbonyl)-6-methyl-4,5,6,7-tetrahydro-1H-pyrazolo[4,3-c]pyridine-3-carboxylic acid (Intermediate 13, 2.30 g, 7.41 mmol, 1.00 eq) in DMF (20.00 mL) was added Cs$_2$CO$_3$ (7.24 g, 22.23 mmol, 3.00 eq) followed by 3-bromooxetane (1.32 g, 9.63 mmol, 1.30 eq) and TBAI (273.74 mg, 741.00 µmol, 0.10 eq). The mixture was stirred at 75° C. for 4 hr. LCMS showed 70% desired product. The mixture was extracted with ethyl acetate (20 mL*2) and H$_2$O (20 mL). The combined organic layer was washed with H$_2$O (20 mL*2), dried with Na$_2$SO$_4$, filtrated. The filtrate was concentrated in vacuum. The residue was purified by column chromatography (Petroleum ether:ethyl acetate=50%~100%) to get 1.8 g desired product with 85% purity. 1.5 g was re-purified by prep-HPLC (FA) to get 1.1 g of pure desired product, which was separated by SFC to afford both diastereomers (420 mg) and (470 mg).

SFC separation condition: Instrument: SFC Thar_80_Q; Column: OD-10 µm; Mobile phase: A for CO$_2$ and B for Isopropanol (0.1% Ammonia); Isocratic: B 20%; Flow rate: 50 mL/min; Back pressure: 100 bar; Column temperature: 35° C.; Wavelength: 220 nm.

Intermediate 19. 2,2-difluoroethyl trifluoromethanesulfonate

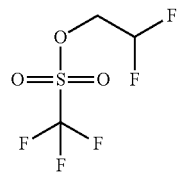

To a solution of 2,2-difluoroethanol (500.00 mg, 6.09 mmol, 1.00 eq) and DIPEA (945.08 mg, 7.31 mmol, 1.28 mL, 1.20 eq) in DCM (5.00 mL) was added Tf$_2$O (1.89 g, 6.70 mmol, 1.11 mL, 1.10 eq) at 0° C. under N$_2$, and the mixture was stirred at 10° C. for 3 h. The starting material have lower boiling point and the reaction was not detected. The mixture was diluted with DCM (10 mL) and washed with water (20 mL*2) and brine (20 mL*1). The organic phase was dried over anhydrous Na$_2$SO$_4$ and filtered. DMF (1 mL) was added. The resulting mixture was concentrated in vacuo to get a DMF solution of (2,2,2-trifluoroethyl trifluoromethanesulfonate (5.68 mmol, 1 mL), which directly used in the next step.

Intermediate 20. 2,2,2-trifluoroethyl trifluoromethanesulfonate

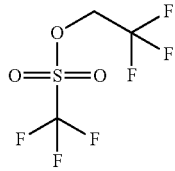

To a solution of 2,2,2-trifluoroethanol (2.09 g, 20.84 mmol, 1.50 mL, 1.00 eq) and DIPEA (3.23 g, 25.01 mmol, 4.36 mL, 1.20 eq) in DCM (10.00 mL) was added Tf$_2$O (6.47 g, 22.92 mmol, 3.78 mL, 1.10 eq) at 0° C. under N$_2$, and the mixture was stirred at 10° C. for 3 h. The starting material have lower boiling point and the reaction was not detected. The mixture was diluted with DCM (10 mL) and washed with water (20 mL*2) and brine (20 mL*1). The organic phase was dried over anhydrous Na$_2$SO$_4$ and filtered. DMF (1.00 mL) was added. The resulting mixture was concentrated in vacuo to get a DMF solution of 2,2,2-trifluoroethyl trifluoromethanesulfonate (14.19 mmol, 1 mL) was obtained, directly used in the next step.

Intermediate 21. tert-butyl 4-(hydroxymethyl)-2-(methyl-d3)-1-oxo-1,4,5,8,9,11-hexahydropyrido[4',3':3,4]pyrazolo[5,1-d][1,2,5]oxadiazepine-10(2H)-carboxylate

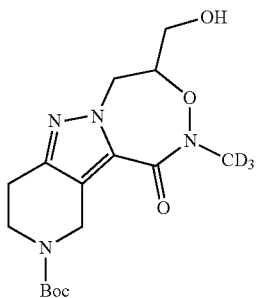

Step 1. Preparation of [tert-butoxycarbonyl (trideuteriomethyl)amino] tert-butyl carbonate. A mixture of (tert-butoxycarbonylamino) tert-butyl carbonate (100.00 mg, 428.71 µmol, 1.00 eq), CD$_3$I (138.04 mg, 857.42 µmol, 2.00 eq) and K$_2$CO$_3$ (88.88 mg, 643.07 µmol, 1.50 eq) in DMF (3.00 mL) was degassed and purged with N$_2$ for 3 times, and then the mixture was stirred at 50° C. for 16 hour under N$_2$ atmosphere. TLC showed the starting material was consumed completely and a new spot appeared. The mixture was poured into water (5 mL) and stirred at 5 min. The aqueous phase was extracted with ethyl acetate (3 mL*3). The combined organic phase was washed with brine (5 mL), dried with anhydrous Na$_2$SO$_4$, filtered and concentrated in vacuum to give the title compound (100.00 mg, 399.50 µmol, 93.19% yield) as a colorless oil, which was used directly for the next step.

Step 2. Preparation of N-(trideuteriomethyl)hydroxylamine. A mixture of [tert-butoxycarbonyl(trideuteriomethyl)amino] tert-butyl carbonate (100.00 mg, 399.50 µmol, 1.00 eq) in DCM (3.00 mL) was added TFA (3.08 g, 27.01 mmol, 2.00 mL, 67.62 eq). The mixture was stirred at 15° C. for 2 hour. TLC showed the starting material was consumed completely and a new spot appeared. The mixture was concentrated in vacuum to give (65.56 mg, 399.51 µmol, 100.00% yield, TFA) as a yellow oil, which was used directly for the next step.

Step 3. Preparation of tert-butyl 3-[hydroxy(trideuteriomethyl)carbamoyl]-2,4,6,7-tetrahydropyrazolo [4,3-c]pyridine-5-carboxylate. A mixture of 5-tert-butoxycarbonyl-2,4,6,7-tetrahydropyrazolo [4,3-c]pyridine-3-carboxylic acid (100.00 mg, 374.14 µmol, 1.00 eq), N-(trideuteriomethyl)hydroxylamine (61.40 mg, 374.14 µmol, 1.00 eq, TFA), T$_3$P (357.13 mg, 1.12 mmol, 333.77 µL3.00 eq) and TEA (189.30 mg, 1.87 mmol, 259.32 µL5.00 eq) in THF (3.00 mL) was degassed and purged with N$_2$ for 3 times, and then the mixture was stirred at 15° C. for 16 hour under N$_2$ atmosphere. LCMS showed the starting material was consumed completely and desired product was major. The mixture was poured into ice-water (5 mL) and stirred at 5 min. Then the mixture was concentrated in vacuum to give the residue. The pH of the aqueous phase was adjusted to around 6 by adding diluted hydrochloride acid (1 N) and extracted with ethyl acetate (3 mL*3). The combined organic phase was washed with brine (5 mL), dried with anhydrous Na$_2$SO$_4$, filtered and concentrated in vacuum to give the title compound (75.00 mg, 238.02 µmol, 63.62% yield, 95% purity) as a white solid. $^1$H NMR (400 MHz, METHANOL-d$_4$) δ 4.62 (s, 2H) 3.71 (d, J=4.16 Hz, 2H) 2.70-2.78 (m, 2H) 1.48 (d, J=3.42 Hz, 9H). LCMS: 300 [M+1].

Step 4. Preparation of tert-butyl 4-(hydroxymethyl)-2-(methyl-d3)-1-oxo-1,4,5,8,9,11-hexahydropyrido[4',3':3,4]pyrazolo[5,1-d][1,2,5]oxadiazepine-10(2H)-carboxylate. A mixture of tert-butyl 3-[hydroxy(trideuteriomethyl)carbamoyl]-2,4,6,7-tetrahydropyrazolo[4,3-c]pyridine-5-carboxylate (75.00 mg, 250.55 µmol, 1.00 eq), 3-bromooxetane (41.18 mg, 300.66 µmol, 1.20 eq), TBAI (9.25 mg, 25.06 µmol, 0.10 eq) and Cs$_2$CO$_3$ (122.45 mg, 375.83 µmol, 1.50 eq) in DMF (3.00 mL) was degassed and purged with N$_2$ for 3 times, and then the mixture was stirred at 70° C. for 3 hour under N$_2$ atmosphere. TLC showed the starting material was consumed completely and two new spots appeared. The mixture was poured into water (10 mL) and stirred at 5 min. The aqueous phase was extracted with ethyl acetate (5 mL*3). The combined organic phase was washed with brine (10 mL), dried with anhydrous Na$_2$SO$_4$, filtered and concentrated in vacuum. The residue was purified by Prep-TLC (DCM/MeOH=10/1) to give the title compound (41.00 mg, 98.06 µmol, 39.14% yield, 85% purity) as a white solid. $^1$H NMR (400 MHz, CHLOROFORM-d) δ 4.47-4.72 (m, 4H) 4.31-4.43 (m, 1H) 3.59-3.95 (m, 4H) 2.77 (br. s., 2H) 1.49 (s, 9H). LCMS: 356 [M+1].

Intermediate 22. 10-(tert-butyl) 4-methyl 2-methyl-1-oxo-1,4,5,8,9,11-hexahydropyrido[4',3':3,4]pyrazolo[5,1-d][1,2,5]oxadiazepine-4,10(2H)-dicarboxylate

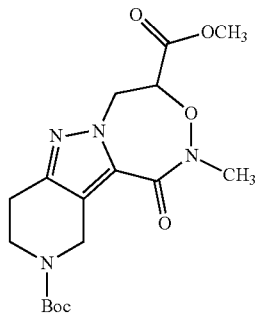 [SMILES: COC(=O)C1Cn2nc3c(c2C(=O)N(C)O1)CN(C(=O)OC(C)(C)C)CC3]

Step 1. Preparation of 10-tert-butoxycarbonyl-2-methyl-1-oxo-5,8,9,11-tetrahydro-4H-pyrido[2,3]pyrazolo[2,4-d][1,2,5]oxadiazepine-4-carboxylic acid. To a mixture of tert-butyl 4-(hydroxymethyl)-2-methyl-1-oxo-5,8,9,11-tetrahydro-4H-pyrido[2,3]pyrazolo[2,4-d][1,2,5]oxadiazepine-10-carboxylate (Intermediate 1, 1.00 g, 2.84 mmol, 1.00 eq) and NMO (2.50 g, 21.30 mmol, 2.25 mL, 7.50 eq) in MeCN (30.00 mL) was added TPAP (199.61 mg, 568.00 µmol, 0.20 eq) in one portion at 0° C. under N₂. The mixture was stirred at 0° C. for 2 hr. LCMS showed the reaction was completed. The mixture was concentrated in vacuum to afford the title compound (1.04 g, crude) as black brown solid. LCMS: 367 [M+1].

Step 2. Preparation of 10-tert-butyl 4-methyl 2-methyl-1-oxo-5,8,9,11-tetrahydro-4H-pyrido[2,3]pyrazolo[2,4-d][1,2,5]oxadiazepine-4,10-dicarboxylate. To a mixture of 10-tert-butoxycarbonyl-2-methyl-1-oxo-5,8,9,11-tetrahydro-4H-pyrido[2,3]pyrazolo[2,4-d][1,2,5]oxadiazepine-4-carboxylic acid (1.04 g, crude, 2.84 mmol, 1.00 eq) and K₂CO₃ (1.18 g, 8.52 mmol, 3.00 eq) in MeCN (20.00 mL) was added MeI (1.21 g, 8.52 mmol, 530.70 µL3.00 eq) in one portion at 25° C. under N₂. The mixture was stirred at 25° C. 12 hours. LCMS showed the reaction didn't react. The starting material was recovered: the reaction mixture was neutralized with HCl (1 N, aq) to pH=3, then extracted with ethyl acetate (20 mL×2). The combined organic layer was dried over Na₂SO₄, filtered and concentrated to dryness. The reaction was performed again. To the recovered starting material and K₂CO₃ (1.18 g, 8.52 mmol, 3.00 eq) in MeCN (20.00 mL) was added MeI (1.21 g, 8.52 mmol, 530.70 µL3.00 eq) in one portion at 25° C. under N₂. The mixture was stirred at 25° C. for 12 hours. LCMS and TLC (EA/PE=2/1) showed the reaction was completed, and 45% of the title compound was detected. The residue was poured into water (20 mL) and stirred for 2 min. The aqueous phase was extracted with ethyl acetate (20 mL×2). The combined organic phase was washed with brine (20 mL×2), dried with anhydrous Na₂SO₄, filtered and concentrated in vacuum. The residue was purified by silica gel chromatography (PE/EA=10/1, 2/1) to afford the title compound (150.00 mg, 394.33 µmol, 13.88% yield, 100% purity) as yellow oil. LCMS: 381 [M+1]. ¹H NMR (400 MHz, CHLOROFORM-d) 4.79-4.98 (m, 2H), 4.45-4.75 (m, 3H), 3.88 (s, 3H), 3.54-3.85 (m, 2H), 3.38 (s, 3H), 2.67-2.89 (m, 2H), 1.49 (s, 9H).

Intermediate 23. tert-butyl 9-ethyl-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxylate

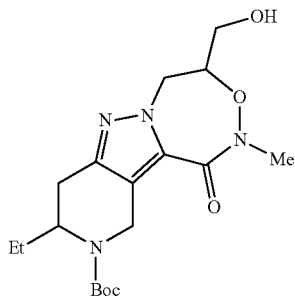 [SMILES: CCC1Cc2nn3c(c2CN1C(=O)OC(C)(C)C)C(=O)N(C)OC(CO)C3]

Step 1. Preparation of tert-butyl 4-oxopyridine-1-carboxylate. To a solution of pyridin-4-ol (5.00 g, 52.58 mmol, 1.00 eq) in t-BuOH (250.00 mL) was added NaH (2.73 g, 68.35 mmol, 60% purity, 1.30 eq) under N₂, and the mixture was warmed to 50° C. in hot water bath until the mixture turned to a slurry. A solution of (Boc)₂O (14.92 g, 68.35 mmol, 15.71 mL, 1.30 eq) in t-BuOH (100.00 mL) was added dropwise, the mixture was stirred at 30° C. for 16 h. TLC indicated 50% of pyridin-4-ol was remained, and one major new spot with lower polarity was detected. The reaction mixture was quenched with water (200 mL), acidified to PH=7 with 10% HCl, and then extracted with ethyl acetate (300 mL*3), the combined organic phase was dried over anhydrous Na₂SO₄, filtered and concentrated in vacuum. The residue was purified by silica gel chromatography. The title compound (2.90 g, 14.86 mmol, 28.25% yield) was obtained as white solid. 1H NMR (400 MHz, CHLOROFORM-d) δ=8.03-8.09 (m, 2H) 6.25-6.33 (m, 2H) 1.61 (s, 9H).

Step 2. Preparation of tert-butyl 4-oxo-2-vinyl-2,3-dihydropyridine-1-carboxylate. To a mixture of tert-butyl 4-oxopyridine-1-carboxylate (5.80 g, 29.71 mmol, 1.00 eq) and TMSCl (9.68 g, 89.13 mmol, 11.26 mL, 3.00 eq) in THF (50.00 mL) was added bromo(vinyl)magnesium (1 M, 44.57 mL, 1.50 eq) dropwise under N₂ at −78° C. The reaction mixture was warmed to 10° C. and stirred at 10° C. for 2 hours. TLC indicated the starting material consumed completely, and one major new spot with lower polarity was detected. The reaction was quenched with aqueous solution of NH₄Cl (120 mL) and then extracted with ethyl acetate (150 mL*3). The combined organic phase was dried over anhydrous Na₂SO₄, filtered and concentrated in vacuum. The residue was purified by silica gel chromatography to give the title compound (4.60 g, 20.19 mmol, 67.96% yield, 98% purity) as yellow oil. LCMS: 224 [M+1].

Step 3. Preparation of tert-butyl 4-oxo-2-vinyl-piperidine-1-carboxylate. To a solution of tert-butyl 4-oxo-2-vinyl-2,3-dihydropyridine-1-carboxylate (4.60 g, 20.60 mmol, 1.00 eq) in AcOH (30.00 mL) was added Zn (6.74 g, 103.00 mmol, 5.00 eq) under N₂, the reaction mixture was stirred at 70° C. for 4 hours. TLC indicated the starting material consumed completely, and two new spots with lower polarity were detected. The reaction mixture was filtered and the filtrate was diluted with ethyl acetate (200 mL) and washed with aqueous solution of NaHCO₃ (100 mL*3), the organic phase was dried with anhydrous Na₂SO₄, filtered and concentrated in vacuum. The residue was purified by silica gel chromatography to afford the title compound (3.05 g, 13.40 mmol, 65.06% yield, 99% purity) as yellow oil. LCMS: 170 [M−56+1].

Step 4. Preparation of tert-butyl 5-(2-ethoxy-2-oxoacetyl)-4-oxo-2-vinyl-piperidine-1-carboxylate. Cooled the three-necked round bottom flask to −78° C., LiHMDS (1 M, 11.54 mL, 1.30 eq) was added under N₂, then a solution of tert-butyl 4-oxo-2-vinyl-piperidine-1-carboxylate (2.00 g, 8.88 mmol, 1.00 eq) in THF (15.00 mL) was added dropwise, the reaction mixture was stirred at −78° C. for 30 minutes under N₂. Then a solution of diethyl oxalate (1.56 g, 10.66 mmol, 1.46 mL, 1.20 eq) in THF (10.00 mL) was added dropwise. After addition, the reaction mixture was stirred at −78° C. for 30 minutes, then at 10° C. for another 2 hours. TLC indicated tert-butyl 4-oxo-2-vinyl-piperidine-1-carboxylate consumed completely, and one major new spot with larger polarity was detected. The reaction mixture was quenched with aqueous solution of NH₄Cl (100 mL) and then extracted with ethyl acetate (150 mL*2). The combined organic phase was dried over anhydrous Na₂SO₄, filtered and concentrated in vacuum to give the title compound (2.00 g, crude) was obtained as yellow oil, which was used in the next step directly without further purification.

Step 5. Preparation of 5-tert-butyl 3-ethyl 6-vinyl-1,4,6,7-tetrahydropyrazolo[4,3-c]pyridine-3,5-dicarboxylate. To a solution of tert-butyl 5-(2-ethoxy-2-oxo-acetyl)-4-oxo-2-vinyl-piperidine-1-carboxylate (2.00 g, 6.15 mmol, 1.00 eq) in EtOH (20.00 mL) was added a solution of $NH_2NH_2 \cdot H_2O$ (289.76 mg, 4.92 mmol, 281.32 µL 85% purity, 0.80 eq) in EtOH (2.00 mL) dropwise. The reaction mixture was stirred at 10° C. for one hour. LCMS showed one main peak with desired MS was detected. The reaction mixture was diluted with ethyl acetate (150 mL) and washed with water (80 mL*2), the organic phase was dried with anhydrous $Na_2SO_4$, filtered and concentrated in vacuum. The residue was purified by silica gel chromatography to give the title compound (1.30 g, 3.92 mmol, 63.74% yield, 97% purity) was obtained as yellow solid. $^1$H NMR (400 MHz, CHLOROFORM-d) δ=5.71 (ddd, J=17.32, 10.54, 4.89 Hz, 1H) 5.04-5.18 (m, 3H) 4.09-4.44 (m, 4H) 2.98-3.05 (m, 2H) 1.51 (s, 9H) 1.38 (t, J=7.09 Hz, 3H); LCMS: 322 [M+1].

Step 6. Preparation of 5-tert-butyl 3-ethyl 6-ethyl-1,4,6,7-tetrahydropyrazolo [4,3-c]pyridine-3,5-dicarboxylate. To a solution of 5-tert-butyl 3-ethyl 6-vinyl-1,4,6,7-tetrahydropyrazolo[4,3-c] pyridine-3,5-dicarboxylate (1.50 g, 4.67 mmol, 1.00 eq) in MeOH (60.00 mL) was added Pd/C (200.00 mg, 10% purity) under $N_2$, The suspension was degassed under vacuum and purged with $H_2$ three times, the mixture was stirred under $H_2$ (15 psi) at 10° C. for 16 hours. LCMS showed the starting material consumed completely and desired product was detected. The reaction mixture was filtered and the filtrate was concentrated to give the title compound (1.42 g, 4.22 mmol, 90.26% yield, 96% purity) as yellow solid, which was combined with another batch (187 mg) to separated by SFC to get a pair of enantiomers (E1: 0.76 g and E2: 0.77 g). SFC separation condition: Instrument: SFC Thar_80_Q; Column: IC-10 µm; Mobile phase: A for $CO_2$ and B for Methanol (0.1% Ammonia); Isocratic: B 25%; Flow rate: 55 mL/min; Back pressure: 100 bar; Column temperature: 35° C.; Wavelength: 220 nm.

E1: 1H NMR (400 MHz, CHLOROFORM-d) δ=4.92-5.25 (m, 1H) 4.47-4.76 (m, 1H) 4.32-4.45 (m, 2H) 3.95-4.18 (m, 1H) 2.95 (dd, J=16.02, 5.99 Hz, 1H) 2.74 (d, J=16.02 Hz, 1H) 1.43-1.54 (m, 11H) 1.39 (t, J=7.09 Hz, 3H) 0.90 (t, J=7.34 Hz, 3H).

E2: 1H NMR (400 MHz, CHLOROFORM-d) δ=4.97-5.25 (m, 1H) 4.46-4.75 (m, 1H) 4.28-4.45 (m, 2H) 3.95-4.18 (m, 1H) 2.89-3.01 (m, 1H) 2.76 (d, J=16.02 Hz, 1H) 1.42-1.57 (m, 11H) 1.38 (t, J=7.09 Hz, 3H) 0.87-0.94 (m, 3H).

Step 7. Preparation of 5-tert-butoxycarbonyl-6-ethyl-1,4,6,7-tetrahydropyrazolo[4,3-c]pyridine-3-carboxylic acid. To a solution of 5-tert-butyl 3-ethyl 6-ethyl-1,4,6,7-tetrahydropyrazolo[4,3-c] pyridine-3,5-dicarboxylate (750.00 mg, 2.32 mmol, 1.00 eq) in MeOH (15.00 mL) was added a solution of NaOH (139.20 mg, 3.48 mmol, 1.50 eq) in $H_2O$ (3.00 mL), the reaction mixture was stirred at 50° C. for 16 hours. LCMS showed one main peak with desired MS was detected. The pH of the reaction mixture was adjusted to around 6 by adding diluted HCl (1N, 15 mL). The resulting mixture was extracted with ethyl acetate (50 mL*3). The combined organic phase was dried over anhydrous $Na_2SO_4$, filtered and concentrated in vacuum to give the title compound (630.00 mg, crude) as white solid used in next step directly without further purification. LCMS: 296 [M+1].

Step 8. Preparation of tert-butyl 6-ethyl-3-[hydroxy(methyl) carbamoyl]-1,4,6,7-tetrahydropyrazolo[4,3-c]pyridine-5-carboxylate. To a mixture of 5-tert-butoxycarbonyl-6-ethyl-1,4,6,7-tetrahydropyrazolo[4,3-c] pyridine-3-carboxylic acid (600.00 mg, 2.03 mmol, 1.00 eq) and N-methylhydroxylamine (339.09 mg, 4.06 mmol, 2.00 eq, HCl) in DMF (8.00 mL) was added PyBOP (1.27 g, 2.44 mmol, 1.20 eq), HOBt (329.15 mg, 2.44 mmol, 1.20 eq) and DIPEA (1.05 g, 8.12 mmol, 1.42 mL, 4.00 eq), the reaction mixture was stirred at 25° C. for 2 hours. LCMS showed about 40% of desired compound was detected. The reaction mixture was diluted with ethyl acetate (100 mL) and washed with water (50 mL*3), the organic phase was dried with anhydrous $Na_2SO_4$, filtered and concentrated in vacuum. The residue was purified by silica gel chromatography to give the title compound (560.00 mg, 1.55 mmol, 76.54% yield, 90% purity) as white solid. LCMS: 325 [M+1].

Step 9. Preparation of tert-butyl 9-ethyl-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxylate. To a mixture of tert-butyl 6-ethyl-3-[hydroxy(methyl) carbamoyl]-1,4,6,7-tetrahydropyrazolo[4,3-c]pyridine-5-carboxylate (500.00 mg, 1.54 mmol, 1.00 eq) and 3-bromooxetane (253.14 mg, 1.85 mmol, 1.20 eq) in DMF (3.00 mL) was added $Cs_2CO_3$ (752.64 mg, 2.31 mmol, 1.50 eq) and TBAI (56.88 mg, 154.00 µmol, 0.10 eq), the reaction mixture was stirred at 55° C. for 4 hours. LCMS showed one main peak with desired MS was detected. The reaction mixture was diluted with ethyl acetate (100 mL) and washed with water (50 mL*3). The organic phase was dried with anhydrous $Na_2SO_4$, filtered and concentrated in vacuum. The residue was purified by silica gel chromatography to give the title compound (430.00 mg, 1.13 mmol, 73.39% yield) as white solid. LCMS: 381 [M+1].

Intermediate 24. (9R)-10-(tert-butoxycarbonyl)-2,9-dimethyl-1-oxo-1,2,4,5,8,9,10,11-octahydropyrido[4',3':3,4]pyrazolo[5,1-d][1,2,5]oxadiazepine-4-carboxylic acid

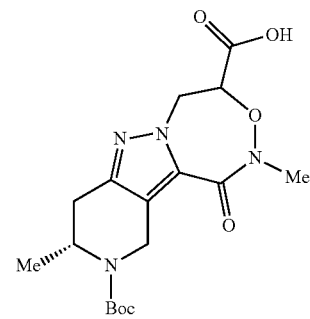 [SMILES: C[C@@H]1Cc2nn3c(c2CN1C(=O)OC(C)(C)C)C(=O)N(C)OC(C(=O)O)C3]

Step 1. Preparation of (9R)-10-tert-butoxycarbonyl-2,9-dimethyl-1-oxo-5,8,9,11-tetrahydro-4H-pyrido[2,3]pyrazolo[2,4-d][1,2,5]oxadiazepine-4-carboxylic acid. To a solution of tert-butyl (9R)-4-(hydroxymethyl)-2,9-dimethyl-1-oxo-5,8,9,11-tetrahydro-4H-pyrido[2,3]pyrazolo[2,4-d][1,2,5]oxadiazepine-10-carboxylate (Intermediate 18, 500.00 mg, 1.36 mmol, 1.00 eq, diastereomer separated by SFC) and NMO (1.19 g, 10.20 mmol, 1.08 mL, 7.50 eq) in MeCN (10.00 mL) was added TPAP (119.49 mg, 340.00 µmol, 0.25 eq). The mixture was stirred at 30° C. for 12 hr. LCMS showed the starting material was consumed completely, desired mass was major. The mixture was poured into water (20 mL) and washed with tert-butyl methyl ether (10 mL), the aqueous layer was acidified by 0.5 N HCl to pH~3, extracted with DCM (20 mL×2), the organic layer was washed with brine (10 mL), dried over anhydrous Na$_2$SO$_4$ and concentrated in vacuum to afford the title compound (520.00 mg, crude) as a black brown solid. LCMS: 381[M+1].

Intermediate 25. tert-butyl(9R)-2,9-dimethyl-4-(methylcarbamoyl)-1-oxo-1,4,5,8,9,11-hexahydropyrido[4',3':3,4]pyrazolo[5,1-d][1,2,5]oxadiazepine-10(2H)-carboxylate

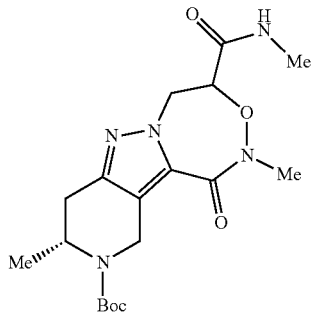 [SMILES: CNC(=O)C1Cn2nc3c(c2C(=O)N(C)O1)CN(C(=O)OC(C)(C)C)[C@H](C)C3]

A mixture of (9R)-10-(tert-butoxycarbonyl)-2,9-dimethyl-1-oxo-1,2,4,5,8,9,10,11-octahydropyrido[4',3':3,4]pyrazolo[5,1-d][1,2,5]oxadiazepine-4-carboxylic acid (Intermediate 24, 256.00 mg, 672.99 μmol, 1.00 eq, diastereomer separated by SFC), methanamine (227.20 mg, 3.36 mmol, 5.00 eq, HCl), T$_3$P (856.53 mg, 1.35 mmol, 800.50 μL 50% purity, 2.00 eq), TEA (681.00 mg, 6.73 mmol, 932.88 μL 10.00 eq) in THF (10.00 mL) was degassed and purged with N$_2$ for 3 times, and then the mixture was stirred at 70° C. for 16 hour under N$_2$ atmosphere. LCMS showed the starting material was consumed completely, desired product was major. The mixture was poured into water (20 mL) and extracted with ethyl acetate (10 mL*2). The combined organic phase was washed with brine (30 mL), dried with anhydrous Na$_2$SO$_4$, filtered and concentrated in vacuum to give the title compound (220.00 mg, 525.62 μmol, 78.10% yield, 94% purity) as a black blown solid. LCMS: 394[M+1].

Intermediate 26. 10-(tert-butoxycarbonyl)-2-methyl-1-oxo-1,2,4,5,8,9,10,11-octahydropyrido[4',3':3,4]pyrazolo[5,1-d][1,2,5]oxadiazepine-4-carboxylic acid

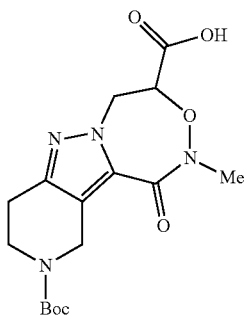 [SMILES: CN1OC(C(=O)O)Cn2nc3c(c2C1=O)CN(C(=O)OC(C)(C)C)CC3]

To a solution of tert-butyl 4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxylate (Intermediate 1, 400.00 mg, 1.14 mmol, 1.00 eq) and NMO (1.00 g, 8.55 mmol, 902.37 μL 7.50 eq) in MeCN (20.00 mL) was added TPAP (100.16 mg, 285.00 μmol, 0.25 eq). The mixture was stirred at 20° C. for 12 h. The mixture was poured into water (40 mL) and washed with tert-butyl methyl ether (20 mL), the aqueous layer was acidified by 0.5 N HCl to pH=3, extracted with DCM (40 mL*2). The organic layer was washed with brine (20 mL), dried over anhydrous Na$_2$SO$_4$ and concentrated in vacuum to afford the title compound (550.00 mg, crude) as brown oil. LCMS: 367 [M+1].

Intermediate 27. tert-butyl 4-((2,2-difluoroethyl)(methyl)carbamoyl)-2-methyl-1-oxo-1,4,5,8,9,11-hexahydropyrido[4',3':3,4]pyrazolo[5,1-d][1,2,5]oxadiazepine-10(2H)-carboxylate

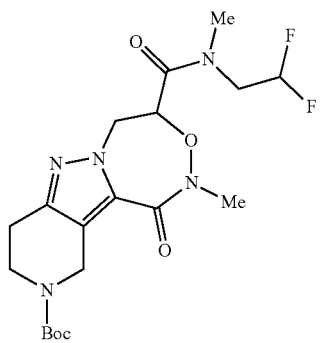 [SMILES: CN(CC(F)F)C(=O)C1Cn2nc3c(c2C(=O)N(C)O1)CN(C(=O)OC(C)(C)C)CC3]

To a mixture of 10-(tert-butoxycarbonyl)-2-methyl-1-oxo-1,2,4,5,8,9,10,11-octahydropyrido[4',3':3,4]pyrazolo[5,1-d][1,2,5]oxadiazepine-4-carboxylic acid (Intermediate 26, 340.00 mg, 928.02 μmol, 1.00 eq), 3-PICOLINE (259.28 mg, 2.78 mmol, 270.08 μL 3.00 eq) and 2,2-difluoro-N-methyl-ethanamine (244.16 mg, 1.86 mmol, 2.00 eq, HCl) in MeCN (10.00 mL) was added MsCl (212.61 mg, 1.86 mmol, 143.66 μL 2.00 eq) at 0° C. The mixture was stirred at 25° C. for 1 h under N$_2$. The mixture was adjusted to pH=6 by 1N HCl, then diluted with H$_2$O (30 mL) and extracted Ethyl acetate (30 mL*2). The combined organic layers was dried over Na$_2$SO$_4$, filtered and concentrated under reduced pressure. The residue was purified by column chromatography (Petroleum ether:Ethyl acetate=1/1) to afford the title compound (290.00 mg, 634.36 μmol, 68.36% yield, 97% purity) as white solid. LCMS: 444 [M+1].

Intermediate 28. tert-butyl 4-(azidomethyl)-2-methyl-1-oxo-1,4,5,8,9,11-hexahydropyrido[4',3':3,4]pyrazolo[5,1-d][1,2,5]oxadiazepine-10(2H)-carboxylate

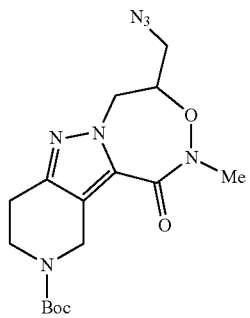 [SMILES: CN1OC(CN=[N+]=[N-])Cn2nc3c(c2C1=O)CN(C(=O)OC(C)(C)C)CC3]

Step 1. Preparation of tert-butyl 2-methyl-4-(methylsulfonyloxymethyl)-1-oxo-5,8,9,11-tetrahydro-4H-pyrido[2,3]pyrazolo[2,4-d][1,2,5]oxadiazepine-10-carboxylate. A mixture of tert-butyl 4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxylate (Intermediate 1, 500.00 mg, 1.42 mmol, 1.00 eq, single enatiomer separated by SFC), TEA (574.76 mg, 5.68 mmol, 787.34 μL 4.00 eq) in DCM (10.00 mL) was added MsCl (487.98 mg, 4.26 mmol, 329.72 μL 3.00 eq) dropwise at 0° C. under N₂, and then the mixture was stirred at 15° C. for 3 hour under N₂ atmosphere. TLC showed the starting material was consumed completely and new spot formed. The mixture was poured into ice-water (40 mL) and stirred at 5 min. The aqueous phase was extracted with DCM (10 mL*2). The combined organic phase was washed with brine (50 mL), dried with anhydrous Na₂SO₄, filtered and concentrated in vacuum to give the title compound (611.00 mg, crude) as a yellow solid. LCMS: 431[M+1]

Step 2. Preparation of tert-butyl 4-(azidomethyl)-2-methyl-1-oxo-1,4,5,8,9,11-hexahydropyrido[4',3':3,4]pyrazolo[5,1-d][1,2,5]oxadiazepine-10(2H)-carboxylate. A mixture of tert-butyl2-methyl-4-(methylsulfonyloxymethyl)-1-oxo-5,8,9,11-tetra hydro-4H-pyrido[2,3]pyrazolo[2,4-d][1,2,5]oxadiazepine-10-carboxylate (611.00 mg, 1.42 mmol, 1.00 eq), NaN₃ (553.63 mg, 8.52 mmol, 6.00 eq) in DMF (10.00 mL) was degassed and purged with N₂ for 3 times, and then the mixture was stirred at 70° C. for 16 hr under N₂ atmosphere. TLC showed the starting material was consumed completely, desired product was major. The mixture was diluted with ethyl acetate (10 mL) and washed with brine (30 mL, *3). The organic phase was dried over Na₂SO₄, filtered and concentrated in vacuo. The residue was purified by column chromatography (Petroleum ether/Ethyl acetate=100/1 to 1:1) to give the title compound (500.00 mg, 1.26 mmol, 88.63% yield, 95% purity) as a colorless oil. LCMS: 378[M+1].

Intermediate 29. tert-butyl(9R)-4-(azidomethyl)-2,9-dimethyl-1-oxo-1,4,5,8,9,11-hexahydropyrido[4',3':3,4]pyrazolo[5,1-d][1,2,5]oxadiazepine-10(2H)-carboxylate

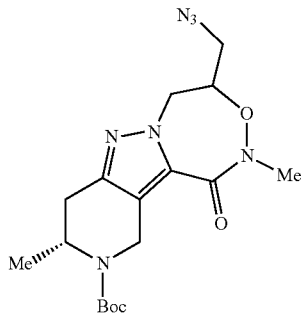 [SMILES: C[C@@H]1Cc2nn3c(c2CN1C(=O)OC(C)(C)C)C(=O)N(C)OC(CN=[N+]=[N-])C3]

Step 1. Preparation of tert-butyl (9R)-2,9-dimethyl-4-(methylsulfonyloxymethyl)-1-oxo-5,8,9,11-tetrahydro-4H-pyrido[2,3]pyrazolo[2,4-d][1,2,5]oxadiazepine-10-carboxylate. A mixture of tert-butyl (9R)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxylate (Intermediate 18, 3.00 g, 8.19 mmol, 1.00 eq), TEA (4.14 g, 40.95 mmol, 5.67 mL, 5.00 eq) in DCM (40.00 mL) was added MsCl (3.75 g, 32.76 mmol, 2.53 mL, 4.00 eq) dropwise at 0° C. under N₂, and then the mixture was stirred at 30° C. for 3 hour under N₂ atmosphere. TLC showed the starting material was consumed completely, a new spot appeared. The mixture was poured into ice-water (50 mL) and stirred at 5 min. The aqueous phase was extracted with DCM (40 mL*2). The combined organic phase was washed with brine (50 mL), dried with anhydrous Na₂SO₄, filtered and concentrated in vacuum. The residue was purified by column chromatography (SiO₂, Petroleum ether/Ethyl acetate=100/1 to 1:2) to give the title compound (3.40 g, 7.34 mmol, 89.66% yield, 96% purity) as a white solid. LCMS: 445 [M+1].

Step 2. Preparation of tert-butyl (9R)-4-(azidomethyl)-2,9-dimethyl-1-oxo-1,4,5,8,9,11-hexahydropyrido[4',3':3,4]pyrazolo[5,1-d][1,2,5]oxadiazepine-10(2H)-carboxylate. A mixture of tert-butyl(9R)-2,9-dimethyl-4-(methylsulfonyloxymethyl)-1-oxo-5,8,9,11-tetrahydro-4H-pyrido[2,3]pyrazolo[2,4-d][1,2,5]oxadiazepine-10-carboxylate (1.20 g, 2.70 mmol, 1.00 eq), NaN₃ (877.53 mg, 13.50 mmol, 5.00 eq) in DMF (20.00 mL) was degassed and purged with N₂ for 3 times, and then the mixture was stirred at 70° C. for 16 hr under N₂ atmosphere. LCMS showed ~10% starting material, ~85% desired product. NaN₃ (351.01 mg, 5.40 mmol, 2.00 eq) was added to the mixture, the mixture was stirred at 70° C. for another 5 hr. LCMS showed the starting material was consumed completely, desired product was major. The mixture was diluted with ethyl acetate (60 mL) and washed with brine (100 mL, *3). The organic phase was dried over Na₂SO₄, filtered and concentrated in vacuo to give the title compound (1.24 g, crude) as a yellow solid. LCMS: 392 [M+1]

Intermediate 30. tert-butyl(9R)-4-(aminomethyl)-2,9-dimethyl-1-oxo-1,4,5,8,9,11-hexahydropyrido[4',3':3,4]pyrazolo[5,1-d][1,2,5]oxadiazepine-10(2H)-carboxylate

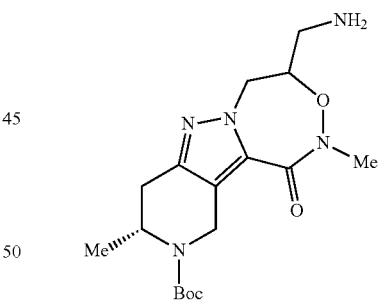

A mixture of tert-butyl (9R)-4-(azidomethyl)-2,9-dimethyl-1-oxo-1,4,5,8,9,11-hexahydropyrido[4',3':3,4]pyrazolo[5,1-d][1,2,5]oxadiazepine-10(2H)-carboxylate (Intermediate 29, 1.06 g, 2.71 mmol, 1.00 eq), PPh₃ (1.42 g, 5.42 mmol, 2.00 eq) in THF (12.00 mL) and H₂O (2.00 mL) was degassed and purged with N₂ for 3 times, and then the mixture was stirred at 30° C. for 16 hour under N₂ atmosphere. LCMS showed the starting material was consumed completely, desired product was major. The mixture was concentrated in vacuum. The residue was purified by column chromatography (SiO₂, Petroleum ether/Ethyl acetate= 100/1 to 0:1) to give the title compound (827.00 mg, 2.20 mmol, 81.00% yield, 97% purity) as a white solid. LCMS: 366 [M+1]

Compound 001: N-(3-bromophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide Step 1. 4-(hydroxymethyl)-2-methyl-4,5,8,9,10,11-hexahydropyrido[2,3]pyrazolo[2,4-d][1,2,5]oxadiazepin-1-one. A mixture of tert-butyl 3-[methyl(oxetan-3-yloxy)carbamoyl]-1,4,6,7-tetrahydropyrazolo[4,3-c]pyridine-5-carboxylate (Intermediate 1, 244.00 mg, 692.41 µmol, 1.00 eq) in DCM (3.00 mL) was added TFA (2.31 g, 20.26 mmol, 1.50 mL, 29.26 eq), and then the mixture was stirred at 30° C. for 1 hour. LCMS showed the reaction was completed. The mixture was concentrated in vacuum to afford the title compound (253.00 mg, 690.71 µmol, 99.75% yield, TFA) as yellow oil which was used directly for next step. LCMS: 253 [M+1].

Step 2. N-(3-bromophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide. A mixture of N-methyl-N-(oxetan-3-yloxy)-4,5,6,7-tetrahydro-1H-pyrazolo[4,3-c] pyridine-3-carboxamide (50.00 mg, 136.50 µmol, 1.00 eq, TFA), phenyl N-(3-bromophenyl) carbamate (39.88 mg, 136.50 µmol, 1.00 eq), TEA (20.72 mg, 204.75 µmol, 28.38 µL1.50 eq) in DCM (2.00 mL) was degassed and purged with $N_2$ for 3 times, and then the mixture was stirred at 30° C. for 16 hour under $N_2$ atmosphere. LCMS showed desired mass was detected. The mixture was poured into water (5 mL) and stirred for 5 min. The aqueous phase was extracted with DCM (3 mL×3). The combined organic phase was washed with brine (5 mL), dried with anhydrous $Na_2SO_4$, filtered and concentrated in vacuum. The residue was purified by Prep-HPLC (FA) to afford the title compound (25.00 mg, 54.96 µmol, 40.27% yield, 99% purity) as a white solid. LCMS: 450/452 [M+1]. $^1$H NMR (400 MHz, MeOD) 7.68 (s, 1H), 7.33-7.35 (m, 1H), 7.15-7.17 (m, 2H), 4.86 (s, 2H), 4.53-4.73 (m, 2H), 4.35-4.37 (m, 1H), 3.82-3.84 (m, 2H), 3.71-3.73 (m, 1H), 3.66-3.67 (m, 1H), 3.32 (s, 3H), 2.81-2.84 (m, 2H).

Compounds 002, 003, 004, 005, 006, 007, 008, 009, 010, 011, 012, 013, 014, 015, 016, 017, 018, 020, 021, 022, 023, 024, 025, 026, 027, 028, 029, 030, 031, 032, 033, 034, and 035 were prepared in a manner analogous to Compound 001.

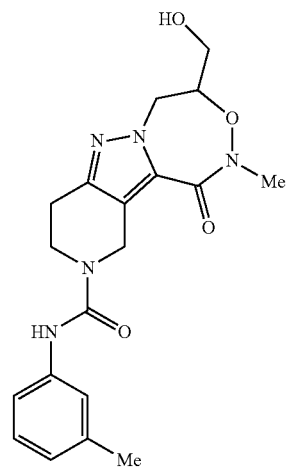

002

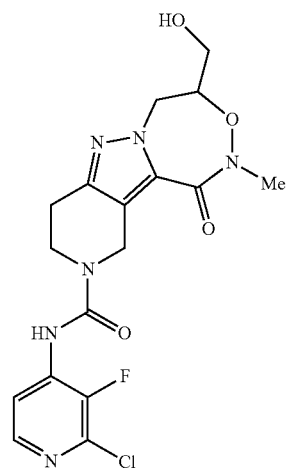

003

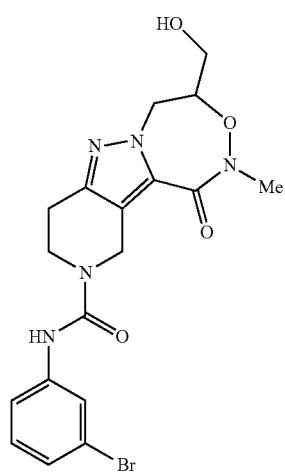

001

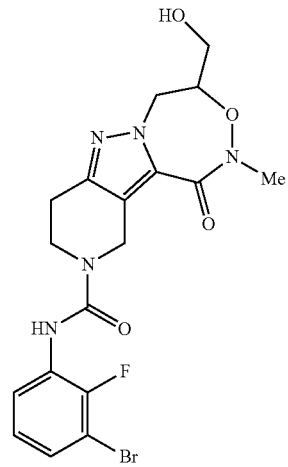

004

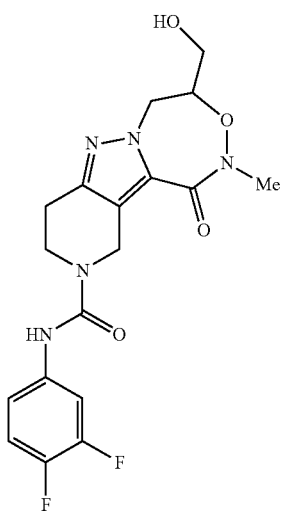
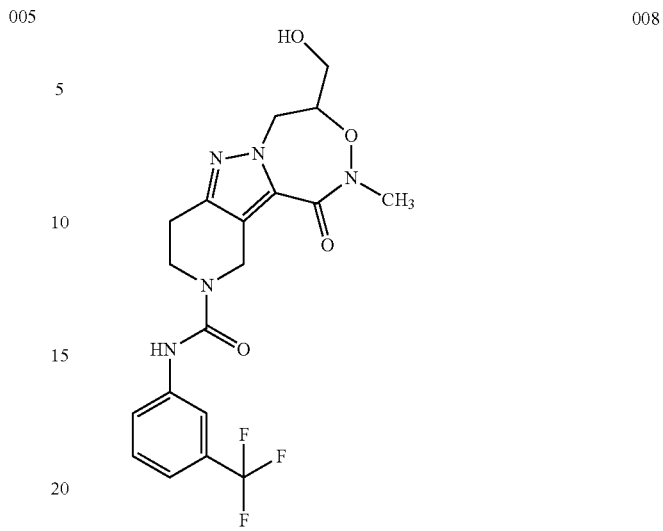
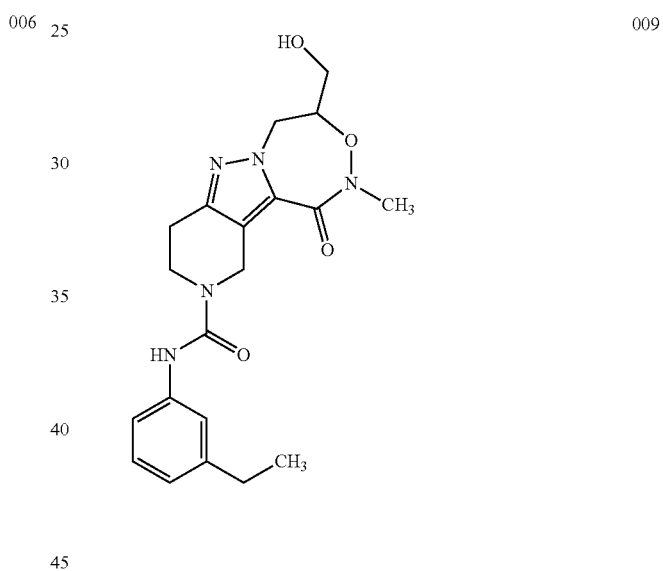
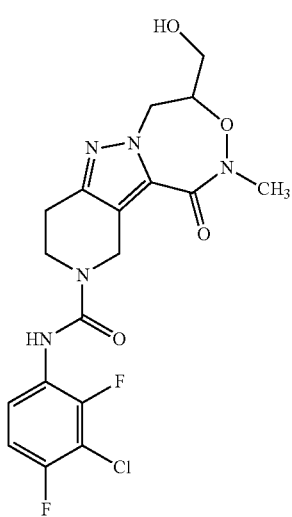
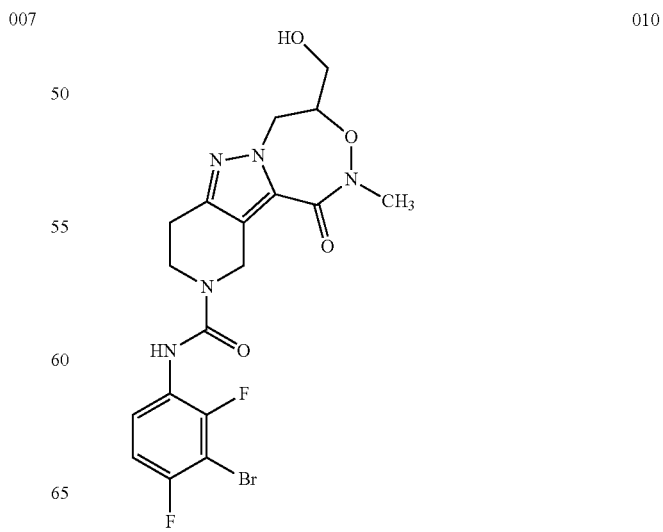

011
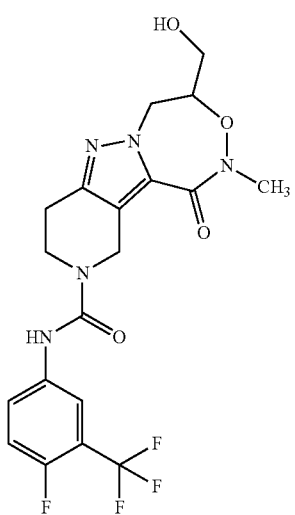
012
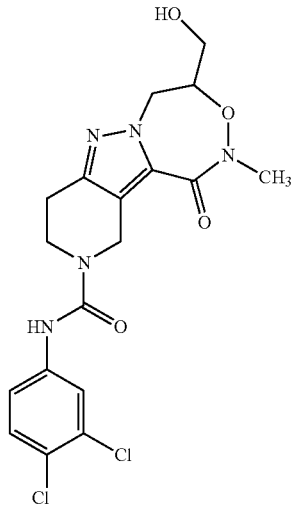
011 E1
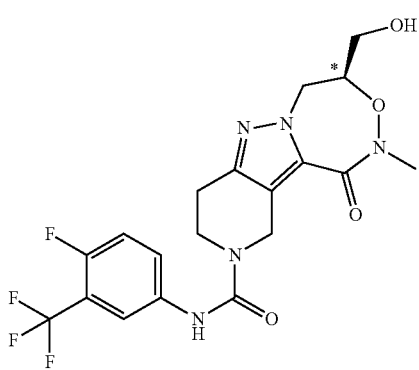
013
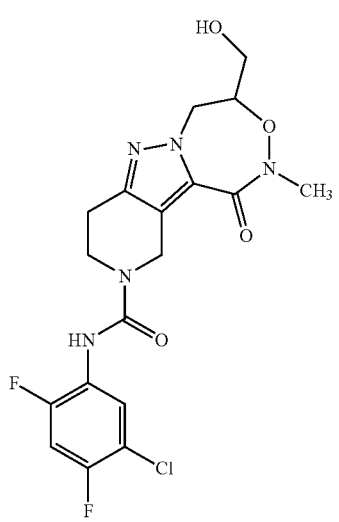
011 E2
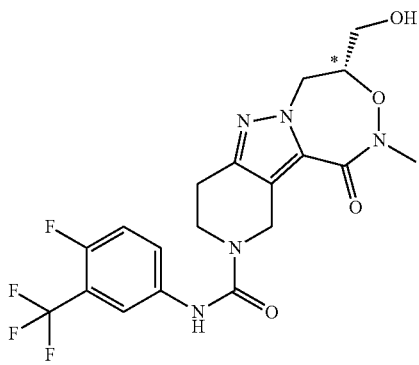
014
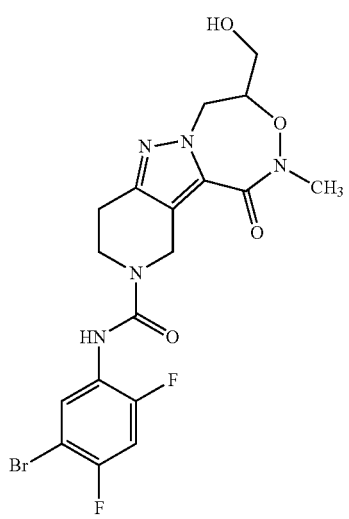

| 015 | 018 |
|---|---|
| 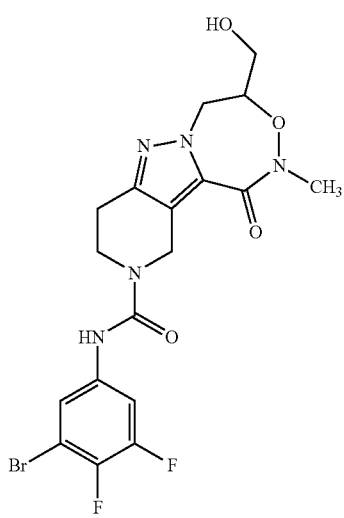 | 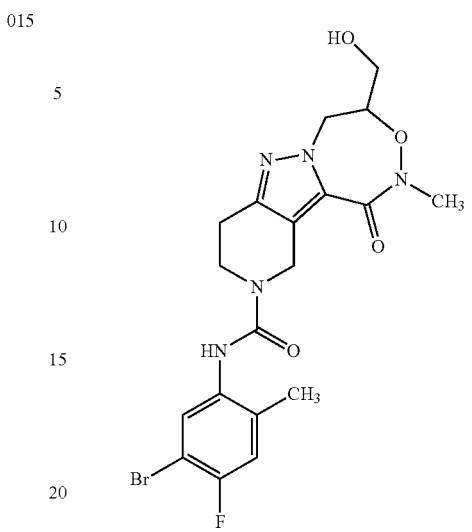 |
| 016 | 020 |
| 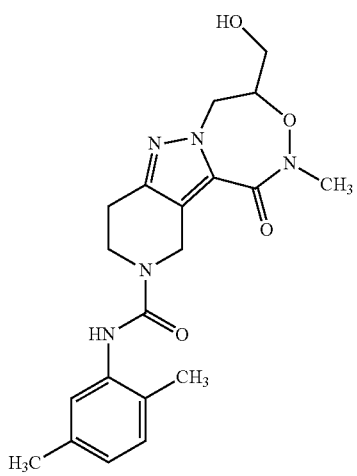 | 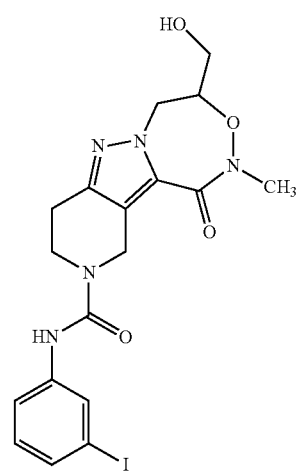 |
| 017 | 021 |
| 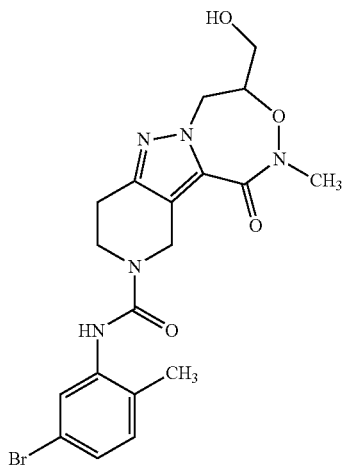 | 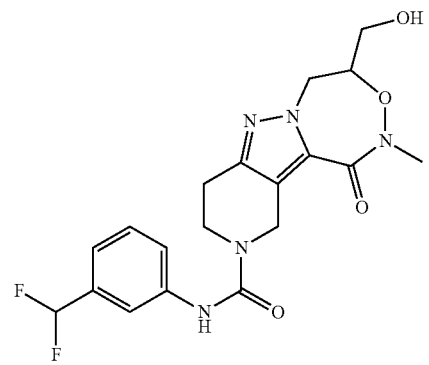 |

| 022 | 026 |
|---|---|
| 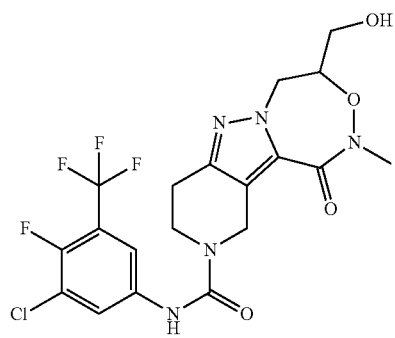 | 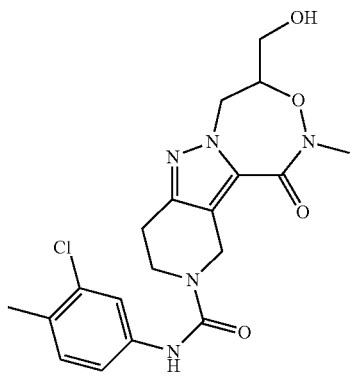 |
| 023 | 027 |
|---|---|
| 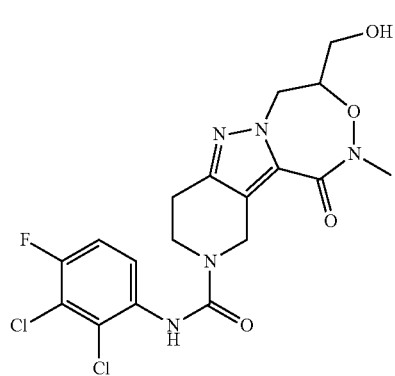 | 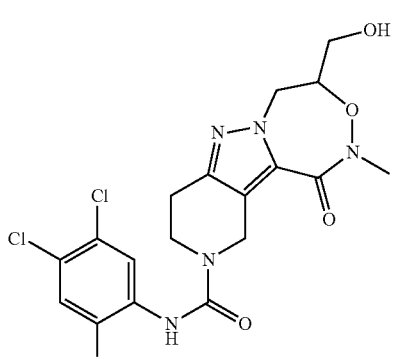 |
| 024 | 028 |
|---|---|
| 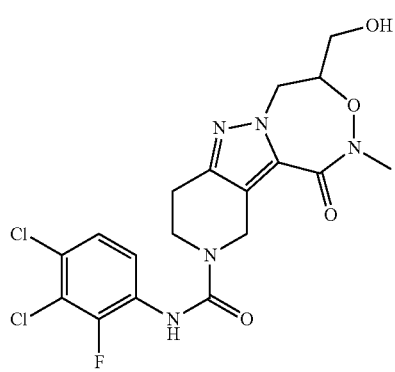 | 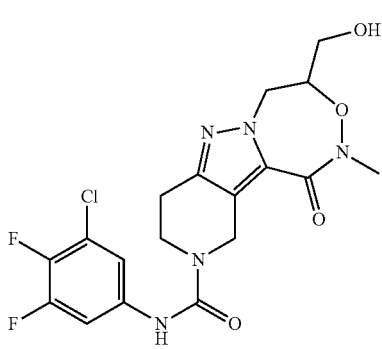 |
| 025 | 028 E1 |
|---|---|
| 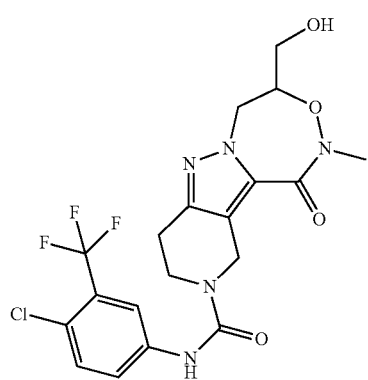 | 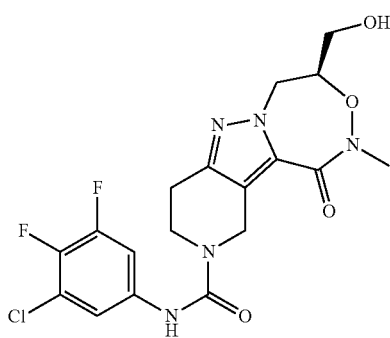 |

029
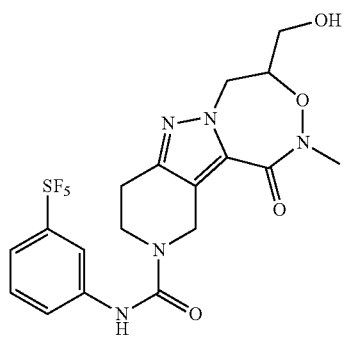
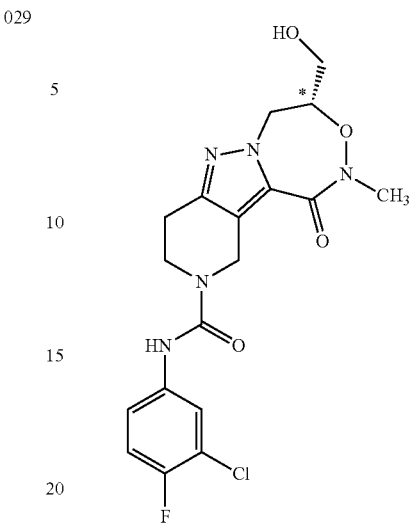
031 E2
030
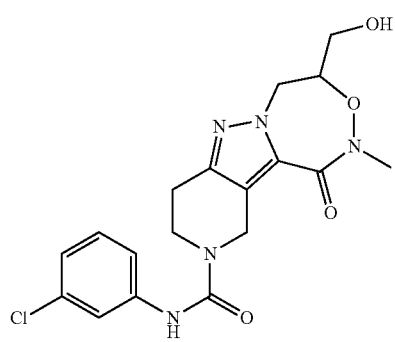
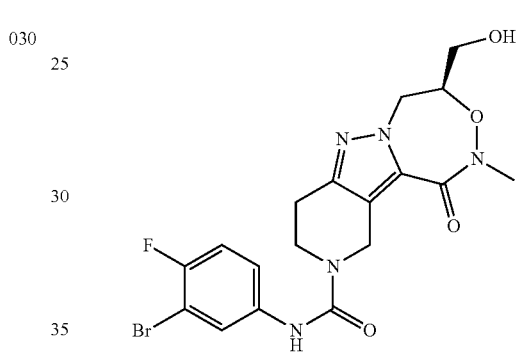
032 E1
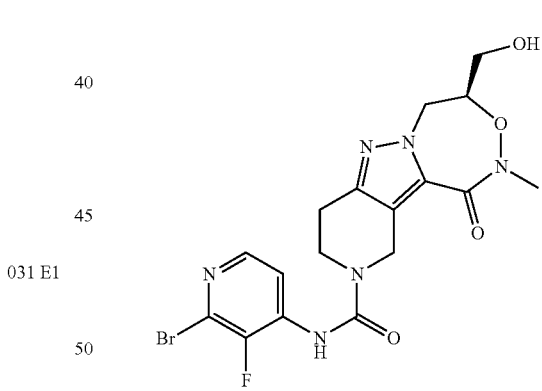
033 E1
031 E1
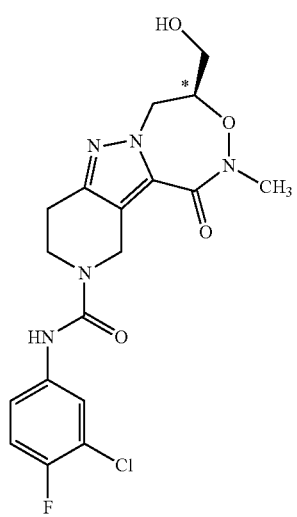
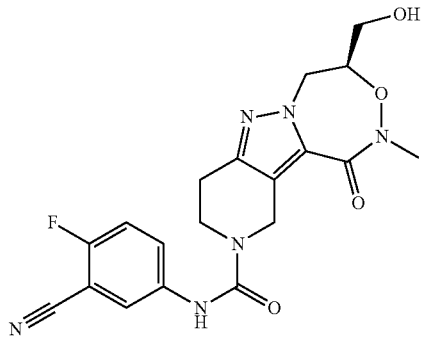
034 E1

-continued

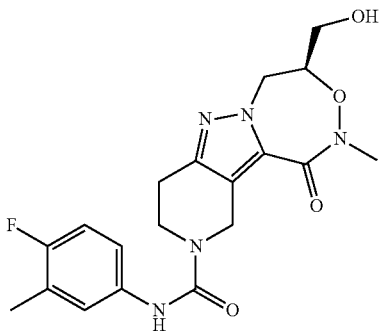

035 E1

Compound 002: 4-(hydroxymethyl)-2-methyl-1-oxo-N-(m-tolyl)-1,4,5,8,9,11-hexahydropyrido[4',3':3,4]pyrazolo[5,1-d][1,2,5]oxadiazepine-10(2H)-carboxamide

LCMS (M+1): 386.2

Compound 003: N-(2-chloro-3-fluoropyridin-4-yl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide

LCMS (M+1): 424.1,

Compound 004: N-(3-bromo-2-fluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide

LCMS (M+1): 468.1.

Compound 005: N-(3,4-difluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide

LCMS (M+1): 408.1.

Compound 006: 4-(hydroxymethyl)-2-methyl-1-oxo-N-(3,4,5-trifluorophenyl)-1,4,5,8,9,11-hexahydropyrido[4',3':3,4]pyrazolo[5,1-d][1,2,5]oxadiazepine-10(2H)-carboxamide LCMS (M+1): 426.1. 1H NMR (400 MHz, METHANOL-d$_4$) δ=7.24 (dd, J=10.29, 6.53 Hz, 2H) 4.71 (s, 2H) 4.48-4.62 (m, 2H) 4.32-4.41 (m, 1H) 3.82 (t, J=4.89 Hz, 2H) 3.70-3.77 (m, 1H) 3.62-3.68 (m, 1H) 3.31-3.33 (m, 3H) 2.82 (t, J=5.77 Hz, 2H).

Compound 007: N-(3-chloro-2,4-difluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide

LCMS (M+1): 442.1.

Compound 008: 4-(hydroxymethyl)-2-methyl-1-oxo-N-(3-(trifluoromethyl)phenyl)-1,4,5,8,9,11-hexahydropyrido[4',3':3,4]pyrazolo[5,1-d][1,2,5]oxadiazepine-10(2H)-carboxamide LCMS (M+1): 440.1. 1H NMR (400 MHz, METHANOL-d$_4$) δ=7.82 (s, 1H) 7.66 (d, J=8.03 Hz, 1H) 7.46 (t, J=8.03 Hz, 1H) 7.31 (d, J=7.53 Hz, 1H) 4.77 (s, 2H) 4.51-4.64 (m, 2H) 4.33-4.43 (m, 1H) 3.82-3.93 (m, 2H) 3.63-3.81 (m, 2H) 3.33-3.36 (m, 3H) 2.86 (t, J=5.77 Hz, 2H).

Compound 009: N-(3-ethylphenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide LCMS (M+1): 400.2. 1H NMR (400 MHz, METHANOL-d$_4$) δ=7.22 (s, 1H) 7.17 (m, 2H) 6.88 (m, 1H) 4.73 (s, 2H) 4.50-4.63 (m, 2H) 4.31-4.41 (m, 1H) 3.80-3.89 (m, 2H) 3.70-3.77 (m, 1H) 3.62-3.69 (m, 1H) 3.31-3.34 (m, 3H) 2.83 (t, J=5.65 Hz, 2H) 2.61 (q, J=7.53 Hz, 2H) 1.22 (t, J=7.65 Hz, 3H)

Compound 010: N-(3-bromo-2,4-difluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide

LCMS (M+1): 486.0.

Compound 011: N-(4-fluoro-3-(trifluoromethyl)phenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide

LCMS (M+1): 458.1.

Compound 011_E1: (S*)—N-(4-fluoro-3-(trifluoromethyl)phenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide LCMS (M+1): 458. 1H NMR (400 MHz, CHLOROFORM-d) δ=7.68 (dd, J=2.8, 6.0 Hz, 1H), 7.56-7.64 (m, 1H), 7.15 (t, J=9.3 Hz, 1H), 6.63 (s, 1H), 4.74 (d, J=3.4 Hz, 2H), 4.54-4.65 (m, 2H), 4.39-4.48 (m, 1H), 3.84-3.96 (m, 3H), 3.72-3.83 (m, 1H), 3.35 (s, 3H), 2.89 (t, J=5.8 Hz, 2H), 1.92 (brs, 1H).

*Pure but unknown enantiomer.

Compound 011_E2: (R*)—N-(4-fluoro-3-(trifluoromethyl)phenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide LCMS (M+1): 458. 1H NMR (400 MHz, CHLOROFORM-d) δ=7.66 (dd, J=6.09, 2.70 Hz, 1H) 7.55-7.61 (m, 1H) 7.13 (t, J=9.41 Hz, 1H) 6.64 (s, 1H) 4.72 (s, 2H) 4.51-4.62 (m, 2H) 4.37-4.46 (m, 1H) 3.75-3.93 (m, 4H) 3.33 (s, 3H) 2.86 (t, J=5.71 Hz, 2H) 2.02 (br. s., 1H).

*Pure but unknown enantiomer.

Compound 012: N-(3,4-dichlorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide

LCMS (M+1): 440.0.

Compound 013: N-(5-chloro-2,4-difluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide LCMS (M+1): 442.1 1H NMR (400 MHz, METHANOL-d$_4$) δ=7.60 (t, J=7.91 Hz, 1H) 7.19 (t, J=9.66 Hz, 1H) 4.73

(s, 2H) 4.49-4.63 (m, 2H) 4.30-4.44 (m, 1H) 3.84 (s, 2H) 3.61-3.78 (m, 2H) 3.33-3.39 (m, 3H) 2.83 (t, J=5.65 Hz, 2H).

Compound 014: N-(5-bromo-2,4-difluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide

LCMS (M+1): 486.0.

Compound 015: N-(3-bromo-4,5-difluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide

LCMS (M+1): 486.0.

Compound 016: N-(2,5-dimethylphenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide

LCMS (M+1): 400.2.

Compound 017: N-(5-bromo-2-methylphenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide

LCMS (M+1): 464.1.

Compound 018: N-(5-bromo-4-fluoro-2-methylphenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide LCMS (M+1): 482.0. $^1$H NMR (400 MHz, METHANOL-d$_4$) δ=7.42 (d, J=6.78 Hz, 1H) 7.09 (d, J=9.54 Hz, 1H) 4.74 (s, 2H) 4.50-4.64 (m, 2H) 4.34-4.44 (m, 1H) 3.84 (t, J=5.14 Hz, 2H) 3.71-3.78 (m, 1H) 3.63-3.69 (m, 1H) 3.32 (m, 3H) 2.83 (t, J=5.52 Hz, 2H) 2.19 (s, 3H).

Compound 019: 4-(hydroxymethyl)-2-methyl-N-(3-methylcyclohexyl)-1-oxo-1,4,5,8,9,11-hexahydropyrido[4',3':3,4]pyrazolo[5,1-d][1,2,5]oxadiazepine-10(2H)-carboxamide

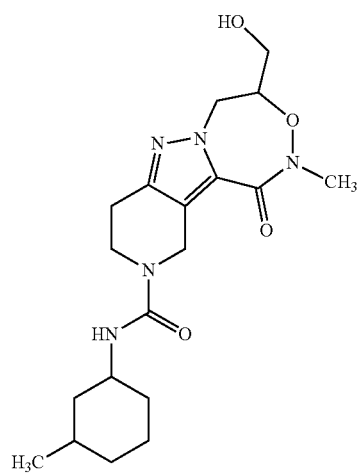

Step 1. 4-(hydroxymethyl)-2-methyl-4,5,8,9,10,11-hexahydropyrido[2,3]pyrazolo[2,4-d][1,2,5]oxadiazepin-1-one. A mixture of tert-butyl 4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxylate (Intermediate 1, 200.00 mg, 567.55 μmol, 1.00 eq) in DCM (2.00 mL) was added TFA (1.54 g, 13.51 mmol, 1.00 mL, 23.80 eq) and then the mixture was stirred at 15° C. for 30 min. TLC showed the starting material was consumed completely, and major desired product. The mixture was concentrated in vacuum to give the title compound (207.00 mg, 565.13 μmol, 99.57% yield, TFA) as a yellow oil, which was used directly for next step.

Step 2: 4-(hydroxymethyl)-2-methyl-N-(3-methylcyclohexyl)-1-oxo-1,4,5,8,9,11-hexahydropyrido[4',3':3,4]pyrazolo[5,1-d][1,2,5]oxadiazepine-10(2H)-carboxamide. A mixture of 3-methylcyclohexanamine (30.00 mg, 235.79 μmol, 1.00 eq, HCl) and TEA (146.00 mg, 1.44 mmol, 200.00 μL 9.25 eq) in DCM (2.0 mL) was added triphosgene (46.27 mg, 155.92 μmol, 1.00 eq) at 0° C. The mixture was stirred at 25° C. for 12 min. Then 4-(hydroxymethyl)-2-methyl-4,5,8,9,10,11-hexahydropyrido[2,3]pyrazolo[2,4-d][1,2,5]oxadiazepin-1-one (50.00 mg, 136.50 μmol, 0.5 eq, TFA) and TEA (100.00 μL 3.06 eq) was added to the reaction. The resulting mixture was stirred at 25° C. for 12 min. LCMS showed the reaction was completed. The solvent was evaporated in vacuo. The residue was adjusted to pH=6 and purified by prep-HPLC (FA) to afford the title compound. LCMS (M+1): 392.2.

Compound 020: 4-(hydroxymethyl)-N-(3-iodophenyl)-2-methyl-1-oxo-1,4,5,8,9,11-hexahydropyrido[4',3':3,4]pyrazolo[5,1-d][1,2,5]oxadiazepine-10(2H)-carboxamide

LCMS (M+1): 498.0.

Compound 021: N-(3-(difluoromethyl)phenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide LCMS (M+1): 422. $^1$H NMR (400 MHz, CHLOROFORM-d) δ=ppm 7.58-7.63 (m, 1H) 7.48 (s, 1H) 7.37 (t, J=7.84 Hz, 1H) 7.15-7.22 (m, 1H) 6.79 (s, 1H) 6.61 (s, 1H) 6.47 (s, 1H) 4.73 (s, 2H) 4.49-4.60 (m, 2H) 4.42 (s, 1H) 3.70-3.95 (m, 4H) 3.31 (s, 3H) 2.86 (s, 2H) 2.24-2.52 (m, 1H).

Compound 022: N-(3-chloro-4-fluoro-5-(trifluoromethyl)phenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide LCMS [M+1]: 492. $^1$H NMR (400 MHz, CHLOROFORM-d) δ=7.84 (dd, J=6.02, 2.64 Hz, 1H) 7.52 (dd, J=5.21, 2.57 Hz, 1H) 6.76 (s, 1H) 4.71 (d, J=3.89 Hz, 2H) 4.56 (d, J=13.30 Hz, 2H) 4.43 (s, 1H) 3.86 (dd, J=7.15, 5.52 Hz, 4H) 3.33 (s, 3H) 2.87 (t, J=5.71 Hz, 2H) 1.89-2.11 (m, 1H).

Compound 023: N-(2,3-dichloro-4-fluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide LCMS[M+1]: 458/460. $^1$H NMR (400 MHz, CHLOROFORM-d) δ=8.05 (dd, J=9.35, 5.21 Hz, 1H) 7.09 (t, J=8.78

Hz, 1H) 6.97 (s, 1H) 4.73-4.82 (m, 2H) 4.51-4.62 (m, 2H) 4.36-4.46 (m, 1H) 3.75-3.93 (m, 4H) 3.33 (s, 3H) 2.89 (t, J=5.71 Hz, 2H) 1.94 (brs, 1H).

Compound 024: N-(3,4-dichloro-2-fluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide LCMS[M+1]: 458. $^1$H NMR (400 MHz, CHLOROFORM-d) δ=7.88-8.01 (m, 1H), 7.23 (dd, J=1.9, 9.1 Hz, 1H), 6.70 (d, J=3.1 Hz, 1H), 4.76 (s, 2H), 4.51-4.65 (m, 2H), 4.34-4.48 (m, 1H), 3.72-3.96 (m, 4H), 3.34 (s, 3H), 2.89 (t, J=5.7 Hz, 2H).

Compound 025: N-(4-chloro-3-(trifluoromethyl)phenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide LCMS[M+1]: 474/476 $^1$H NMR (400 MHz, CHLOROFORM-d) δ=7.75 (d, J=2.38 Hz, 1H) 7.60 (dd, J=8.72, 2.45 Hz, 1H) 7.41 (d, J=8.66 Hz, 1H) 6.74 (s, 1H) 4.72 (s, 2H) 4.51-4.61 (m, 2H) 4.37-4.47 (m, 1H) 3.77-3.93 (m, 4H) 3.32 (s, 3H) 2.86 (t, J=5.71 Hz, 2H) 2.04 (d, J=15.06 Hz, 1H).

Compound 026: N-(3-chloro-4-methylphenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide LCMS[M+1]: 420. $^1$H NMR (400 MHz, CHLOROFORM-d) δ=7.51 (d, J=1.8 Hz, 1H), 7.12-7.20 (m, 2H), 6.48 (s, 1H), 4.72 (s, 2H), 4.51-4.64 (m, 2H), 4.35-4.47 (m, 1H), 3.74-3.97 (m, 4H), 3.34 (s, 3H), 2.87 (t, J=5.7 Hz, 2H), 2.33 (s, 3H), 1.98 (brs, 1H).

Compound 027: N-(4,5-dichloro-2-fluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide LCMS (M+1): 458/460. $^1$H NMR (400 MHz, CHLOROFORM-d) δ=8.25-8.38 (m, 1H), 7.21 (d, J=10.54 Hz, 1H), 6.61-6.69 (m, 1H), 4.74 (s, 2H), 4.51-4.63 (m, 2H), 4.35-4.47 (m, 1H), 3.86 (d, J=16.06 Hz, 4H), 3.33 (s, 3H), 2.88 (t, J=5.77 Hz, 2H), 1.81-1.92 (m, 1H).

Compound 028: N-(3-chloro-4,5-difluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide LCMS [M+1]: 442. $^1$H NMR (400 MHz, CHLOROFORM-d) δ=7.30-7.40 (m, 1H) 7.19-7.24 (m, 1H) 6.39-6.74 (m, 1H) 4.69 (d, J=2.38 Hz, 2H) 4.50-4.62 (m, 2H) 4.36-4.48 (m, 1H) 3.72-3.95 (m, 4H) 3.33 (s, 3H) 2.86 (t, J=5.58 Hz, 2H) 1.81-1.99 (m, 1H).

Compound 028_E1: (S*)—N-(3-chloro-4,5-difluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide LCMS (M+1):442. $^1$H NMR (400 MHz, CHLOROFORM-d) δ=7.33 (ddd, J=2.8, 6.4, 12.0 Hz, 1H), 7.21 (td, J=2.4, 5.2 Hz, 1H), 6.74 (brs, 1H), 4.69 (s, 2H), 4.49-4.62 (m, 2H), 4.37-4.47 (m, 1H), 3.71-3.92 (m, 4H), 3.31 (s, 3H), 2.84 (t, J=5.6 Hz, 2H), 2.28 (s, 1H).
*Pure but unknown enantiomer.

Compound 029: 4-(hydroxymethyl)-2-methyl-1-oxo-N-(3-(pentafluoro-16-sulfanyl)phenyl)-1,4,5,8,9,11-hexahydropyrido[4',3':3,4]pyrazolo[5,1-d][1,2,5]oxadiazepine-10(2H)-carboxamide LCMS [M+1]: 498. $^1$H NMR (400 MHz, CHLOROFORM-d) δ=7.86 (t, J=1.94 Hz, 1H) 7.60 (d, J=8.03 Hz, 1H) 7.34-7.45 (m, 2H) 6.80 (brs, 1H) 4.74 (s, 2H) 4.51-4.61 (m, 2H) 4.38-4.47 (m, 1H) 3.74-3.94 (m, 4H) 3.32 (s, 3H) 2.87 (t, J=5.77 Hz, 2H) 2.13 (brs, 1H).

Compound 030: N-(3-chlorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide LCMS (M+1): 406. $^1$H NMR (400 MHz, CHLOROFORM-d) δ=7.51 (s, 1H), 7.16-7.25 (m, 2H), 7.01 (m, 1H), 6.69 (s, 1H), 4.70 (s, 2H), 4.49-4.60 (m, 2H), 4.36-4.45 (m, 1H), 3.70-3.93 (m, 4H), 3.31 (s, 3H), 2.85 (t, J=8.0 Hz, 2H), 2.40 (s, 1H).

Compound 031_E1: (S*)—N-(3-chloro-4-fluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide LCMS (M+1): 424. $^1$H NMR (400 MHz, CHLOROFORM-d) δ=7.55 (dd, J=4.0, 8.0 Hz, 1H), 7.15-7.23 (m, 1H), 6.99-7.08 (m, 1H), 6.69 (s, 1H), 4.69 (s, 2H), 4.60-4.49 (m, 2H), 4.36-4.46 (m, 1H), 3.71-3.92 (m, 4H), 3.29-3.34 (m, 3H), 2.84 (t, J=8.0 Hz, 2H), 2.42 (s, 1H).
*Pure but unknown enantiomer.

Compound 031_E2: (R*)—N-(3-chloro-4-fluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide LCMS (M+1): 424. $^1$H NMR (400 MHz, CHLOROFORM-d) δ=7.56-7.58 (dd, J=6.53, 2.64 Hz, 1H) 7.17-7.20 (dt, J=8.88, 3.40 Hz, 1H) 7.03-7.08 (m, 1H) 6.49 (s, 1H) 4.57-4.70 (s, 2H) 4.52-4.54 (m, 2H) 4.40-4.42 (m, 1H) 3.79-3.89 (m, 4H) 3.32 (s, 3H) 2.84-2.87 (t, J=5.77 Hz, 2H) 1.89-1.94 (m, 1H).
*Pure but unknown enantiomer.

Compound 032_E1: (S*)—N-(3-bromo-4-fluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide LCMS (M+1): 468/470. $^1$H NMR (400 MHz, CHLOROFORM-d) δ=7.68 (dd, J=4.0, 8.0 Hz, 1H), 7.22-7.26 (m, 1H), 7.03 (t, J=8.0 Hz, 1H), 6.69 (s, 1H), 4.69 (s, 2H), 4.49-4.61 (m, 2H), 4.36-4.45 (m, 1H), 3.71-3.92 (m, 4H), 3.31 (s, 3H), 2.84 (t, J=8.0 Hz, 2H), 2.42 (s, 1H).
*Pure but unknown enantiomer.

Compound 033_E1: (S*)—N-(2-bromo-3-fluoropyridin-4-yl)-4-(hydroxymethyl)-2-methyl-1,4,5,8,9,11-hexahydropyrido[4',3':3,4]pyrazolo[5,1-d][1,2,5]oxadiazepine-10(2H)-carboxamide LCMS (M+1): 469/471. $^1$H NMR (400 MHz, CHLOROFORM-d) δ=8.10-8.18 (m, 1H), 8.06 (d, J=5.52 Hz, 1H), 6.99-7.10 (m, 1H), 4.76 (s, 2H), 4.50-4.62 (m, 2H), 4.37-4.46 (m, 1H), 3.71-3.95 (m, 4H), 3.32 (s, 3H), 2.89 (t, J=5.71 Hz, 2H), 2.20 (d, J=19.58 Hz, 1H).
*Pure but unknown enantiomer.

Compound 034_E1: (S*)—N-(3-cyano-4-fluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide LCMS (M+1): 415. $^1$H NMR (400 MHz, CHLOROFORM-d) δ=7.75 (dd, J=4.0, 8.0 Hz, 1H), 7.55-7.62 (m, 1H), 7.14 (t, J=8.0 Hz, 1H), 6.73 (s, 1H), 4.71 (d, J=4.0 Hz, 2H), 4.51-4.62 (m, 2H), 4.37-4.47 (m, 1H), 3.74-3.94 (m, 4H), 3.33 (s, 3H), 2.86 (t, J=8.0 Hz, 2H), 2.02 (s, 1H).
*Pure but unknown enantiomer.

Compound 035_E1: (S*)—N-(4-fluoro-3-methylphenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide LCMS (M+1): 404. $^1$H NMR (400 MHz, CHLOROFORM-d) δ=7.22 (dd, J=4.0, 8.0 Hz, 1H), 7.05-7.12 (m, 1H), 6.91 (t, J=8.0 Hz, 1H), 6.57 (s, 1H), 4.69 (s, 2H), 4.48-4.59 (m, 2H), 4.35-4.43 (m, 1H), 3.68-3.92 (m, 4H), 3.29 (s, 3H), 2.83 (t, J=5.6 Hz, 2H), 2.66 (brs, 1H), 2.23 (d, J=1.6 Hz, 3H).
*Pure but unknown enantiomer.

Compound 038_E1: (S*)—N-(3-chloro-4-fluorophenyl)-4-(fluoromethyl)-2-methyl-1-oxo-1,4,5,8,9,11-hexahydropyrido[4',3':3,4]pyrazolo[5,1-d][1,2,5]oxadiazepine-10(2H)-carboxamide

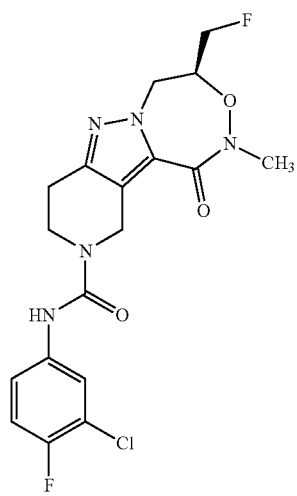

To a solution of N-(3-chloro-4-fluoro-phenyl)-4-(hydroxymethyl)-2-methyl-1-oxo-5,8,9,11-tetrahydro-4Hpyrido[2,3]pyrazolo[2,4-d][1,2,5]oxadiazepine-10-carboxamide (Compound 031_E1, 20.00 mg, 47.19 μmol, 1.00 eq) in DCM (1.00 mL) was added DAST (45.64 mg, 283.14 μmol, 37.41 μL 6.00 eq) at −30° C. under N$_2$, the reaction mixture was stirred at 10° C. for 2 hours. TLC indicated the starting material was consumed completely and one major new spot with lower polarity was detected. The reaction mixture was quenched with water (10 mL) and then extracted with DCM (20 mL*3), the combined organic phase was dried over anhydrous Na$_2$SO$_4$, filtered and concentrated in vacuum. The residue was purified via prep-TLC, followed by prep-HPLC (FA) to afford the title compound as white solid.

LCMS (M+1): 426/428. $^1$H NMR (400 MHz, CHLOROFORM-d) δ=7.58 (dd, J=6.53, 2.63 Hz, 1H) 7.15-7.22 (m, 1H) 7.03-7.10 (m, 1H) 6.45 (s, 1H) 4.53-4.73 (m, 6H) 4.42 (dd, J=14.43, 6.78 Hz, 1H) 3.81-3.91 (m, 2H) 3.33 (s, 3H) 2.87 (t, J=5.71 Hz, 2H).
*Pure but unknown enantiomer.

Compounds 036, 037, 039, 040, 041, 042, 043, and 044 were prepared in a manner analogous to Compound 038.

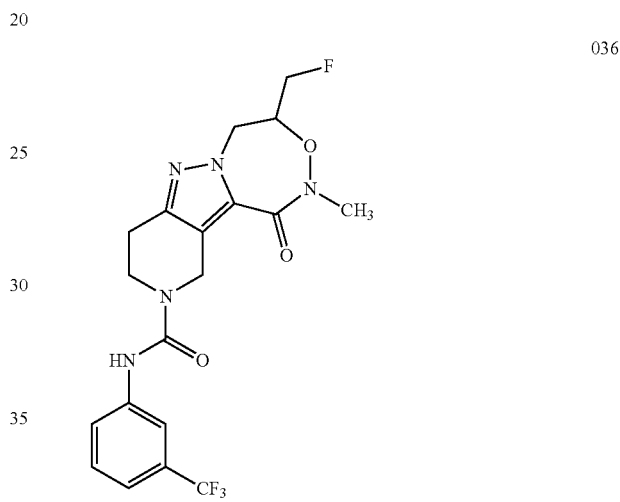

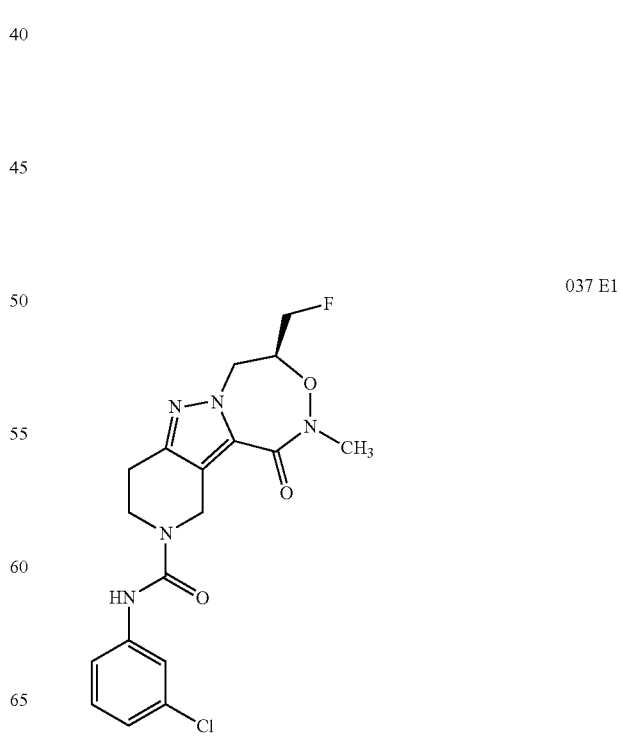

213
-continued
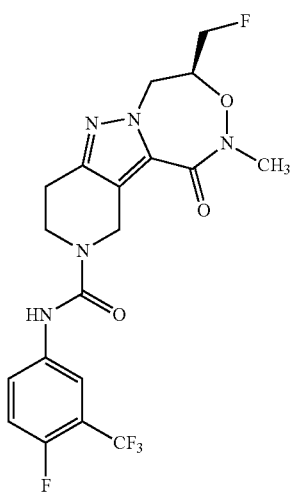
039 E1
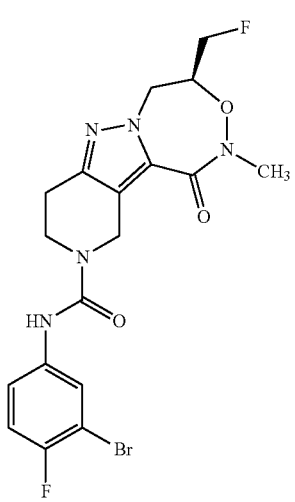
040 E1
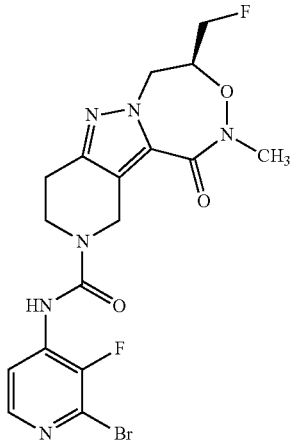
041 E1
214
-continued
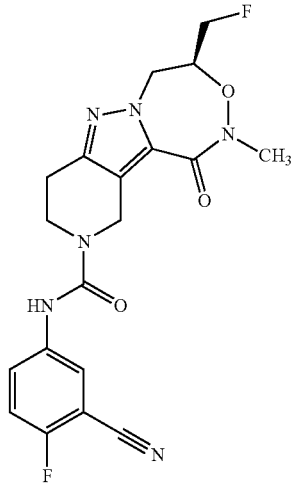
042 E1
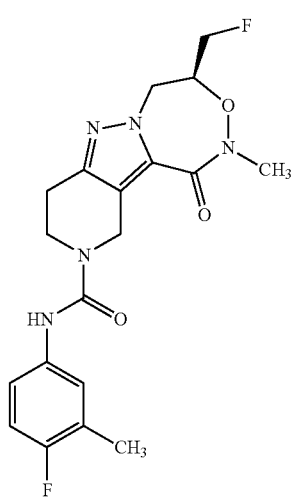 [SMILES: CN1O[C@H](CF)Cn2nc3c(c2C1=O)CN(C(=O)Nc1ccc(F)c(Cl)c1)CC3]
043 E1
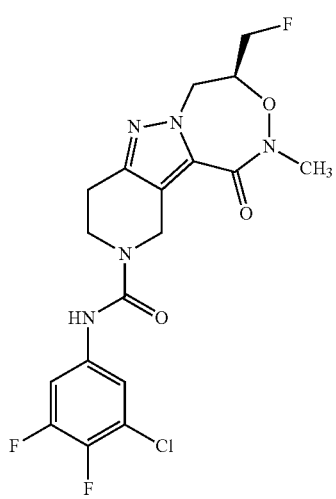
044 E1
Compound 036: 4-(fluoromethyl)-2-methyl-1-oxo-N-(3-(trifluoromethyl)phenyl)-1,4,5,8,9,11-hexahydropyrido[4',3':3,4]pyrazolo[5,1-d][1,2,5]oxadiazepine-10(2H)-carboxamide
LCMS: 442 [M+1]. $^1$H NMR (400 MHz, CHLOROFORM-d) δ=7.72 (s, 1H) 7.59 (d, J=7.53 Hz, 1H) 7.41 (t, J=7.91 Hz, 1H) 7.30 (d, J=7.78 Hz, 1H) 6.71 (s, 1H) 4.54-4.76 (m, 6H) 4.42 (dd, J=14.43, 6.90 Hz, 1H) 3.81-3.94 (m, 2H) 3.33 (s, 3H) 2.88 (t, J=5.77 Hz, 2H).

Compound 037_E1: (S*)—N-(3-chlorophenyl)-4-(fluoromethyl)-2-methyl-1-oxo-1,4,5,8,9,11-hexahydropyrido[4',3':3,4]pyrazolo[5,1-d][1,2,5]oxadiazepine-10(2H)-carboxamide LCMS (M+1): 408/410. $^1$H NMR (400 MHz, CHLOROFORM-d) δ=7.52-7.55 (m, 1H) 7.18-7.25 (m, 2H) 7.00-7.05 (m, 1H) 6.49 (s, 1H) 4.54-4.73 (m, 6H) 4.42 (dd, J=14.49, 6.84 Hz, 1H) 3.82-3.91 (m, 2H) 3.33 (s, 3H) 2.87 (t, J=5.77 Hz, 2H).

*Pure but unknown enantiomer.

Compound 039_E1: (S*)—N-(4-fluoro-3-(trifluoromethyl)phenyl)-4-(fluoromethyl)-2-methyl-1-oxo-1,4,5,8,9,11-hexahydropyrido[4',3':3,4]pyrazolo[5,1-d][1,2,5]oxadiazepine-10(2H)-carboxamide LCMS (M+1): 460. $^1$H NMR (400 MHz, CHLOROFORM-d) δ=7.57-7.61 (m, 1H), 7.47-7.54 (m, 1H), 7.06 (t, J=9.4 Hz, 1H), 6.46 (s, 1H), 4.57-4.67 (m, 4H), 4.45-4.56 (m, 2H), 4.34 (dd, J=6.9, 14.5 Hz, 1H), 3.80 (q, J=5.7 Hz, 2H), 3.25 (s, 3H), 2.80 (t, J=5.7 Hz, 2H).

*Pure but unknown enantiomer.

Compound 040_E1: (S*)—N-(3-bromo-4-fluorophenyl)-4-(fluoromethyl)-2-methyl-1-oxo-1,4,5,8,9,11-hexahydropyrido[4',3':3,4]pyrazolo[5,1-d][1,2,5]oxadiazepine-10(2H)-carboxamide LCMS (M+1): 470/472. $^1$H NMR (400 MHz, CHLOROFORM-d) δ=7.70 (dd, J=2.57, 5.96 Hz, 1H), 7.22-7.27 (m, 1H), 7.04 (t, J=8.53 Hz, 1H), 6.53 (s, 1H), 4.50-4.82 (m, 6H), 4.41 (dd, J=6.90, 14.43 Hz, 1H), 3.86 (q, J=5.56 Hz, 2H), 3.32 (s, 3H), 2.86 (t, J=5.71 Hz, 2H).

*Pure but unknown enantiomer.

Compound 041_E1: (S*)—N-(2-bromo-3-fluoropyridin-4-yl)-4-(fluoromethyl)-2-methyl-1-oxo-1,4,5,8,9,11-hexahydropyrido[4',3':3,4]pyrazolo[5,1-d][1,2,5]oxadiazepine-10(2H)-carboxamide LCMS (M+1): 471/473. $^1$H NMR (400 MHz, CHLOROFORM-d) δ=8.14-8.18 (m, 1H), 8.07 (d, J=5.5 Hz, 1H), 6.96 (d, J=3.4 Hz, 1H), 4.77 (s, 2H), 4.53-4.72 (m, 4H), 4.42 (dd, J=6.7, 14.5 Hz, 1H), 3.88 (t, J=5.9 Hz, 2H), 3.33 (s, 3H), 2.90 (t, J=5.7 Hz, 2H).

*Pure but unknown enantiomer.

Compound 042_E1: (S*)—N-(3-cyano-4-fluorophenyl)-4-(fluoromethyl)-2-methyl-1-oxo-1,4,5,8,9,11-hexahydropyrido[4',3':3,4]pyrazolo[5,1-d][1,2,5]oxadiazepine-10(2H)-carboxamide LCMS (M+1): 417. $^1$H NMR (400 MHz, CHLOROFORM-d) δ=7.71-7.81 (m, 1H), 7.53-7.64 (m, 1H), 7.15 (s, 1H), 6.58 (s, H), 4.72 (d, J=2.08 Hz, 4H), 4.56 (d, J=5.14 Hz, 2H), 4.37-4.48 (m, 1H), 3.80-3.93 (m, 2H), 3.33 (s, 3H), 2.88 (t, J=5.81 Hz, 2H).

*Pure but unknown enantiomer.

Compound 043_E1: (S*)—N-(4-fluoro-3-methylphenyl)-4-(fluoromethyl)-2-methyl-1-oxo-1,4,5,8,9,11-hexahydropyrido[4',3':3,4]pyrazolo[5,1-d][1,2,5]oxadiazepine-10(2H)-carboxamide LCMS (M+1):406, $^1$H NMR (CHLOROFORM-d, 400 MHz): δ=7.16 (d, J=2.9 Hz, 1H), 6.99-7.06 (m, 1H), 6.85 (t, J=8.9 Hz, 1H), 6.28 (s, 1H), 4.46-4.65 (m, 7H), 4.34 (dd, J=14.4, 6.8 Hz, 1H), 3.79 (q, J=5.4 Hz, 2H), 3.25 (s, 3H), 2.79 (t, J=5.7 Hz, 2H), 2.18 ppm (d, J=1.3 Hz, 3H).

*Pure but unknown enantiomer.

Compound 044_E1: (S*)—N-(3-chloro-4,5-difluorophenyl)-4-(fluoromethyl)-2-methyl-1-oxo-1,4,5,8,9,11-hexahydropyrido[4',3':3,4]pyrazolo[5,1-d][1,2,5]oxadiazepine-10(2H)-carboxamide LCMS (M+1): 444. $^1$H NMR (400 MHz, CHLOROFORM-d) δ=7.34 (ddd, J=11.76, 6.43, 2.64 Hz, 1H) 7.21 (dt, J=5.30, 2.43 Hz, 1H) 6.49 (s, 1H) 4.54-4.73 (m, 6H) 4.42 (dd, J=14.49, 6.96 Hz, 1H) 3.81-3.91 (m, 2H) 3.33 (s, 3H) 2.87 (t, J=5.71 Hz, 2H).

*Pure but unknown enantiomer.

Compound 045: N-(3-chloro-4-fluorophenyl)-4-(hydroxymethyl)-N,2-dimethyl-1-oxo-1,4,5,8,9,11-hexahydropyrido[4',3':3,4]pyrazolo[5,1-d][1,2,5]oxadiazepine-10(2H)-carboxamide

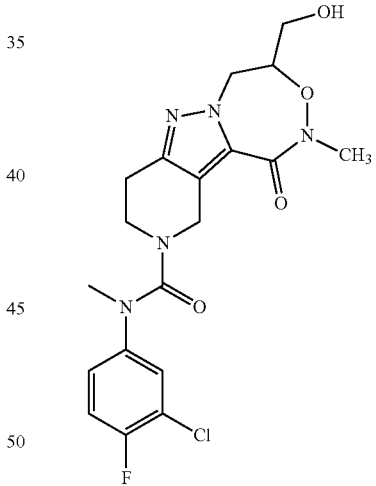

To a solution of 3-chloro-4-fluoro-N-methyl-aniline (Intermediate 2, 45.00 mg, 229.53 μmol, 1.00 eq, HCl) and triphosgene (34.06 mg, 114.77 μmol, 0.50 eq) in DCM (3.00 mL) was added TEA (116.13 mg, 1.15 mmol, 159.08 μL 5.00 eq) dropwise. The resulting mixture was stirred for 0.5 h at 0° C. and then stirred at 20° C. for 0.5 hr. 4-(hydroxymethyl)-2-methyl-4,5,8,9,10,11-hexahydropyrido[2,3]pyrazolo[2,4-d][1,2,5]oxadiazepin-1-one (Intermediate 1, 66.27 mg, 229.53 μmol, 1.00 eq, HCl) was added portionwise at 0° C., then warmed back to 20° C. and stirred for 1 hr. LCMS showed starting material consumed and 77.5% product was formed. Two batches of reaction mixture were poured into H$_2$O (5 mL), and extracted with DCM (3*5 ml). The combined organic phase was dried over anhydrous Na$_2$SO$_4$, and concentrated under reduced pressure. The residue was purified by prep-HPLC to obtain the title compound (70 mg, 84.92 µmol, 99.77% purity) as a white solid. $^1$H NMR (400 MHz, METHANOL-d$_4$) δ 7.33 (dd, J=2.70, 6.46 Hz, 1H), 7.19-7.26 (m, 1H), 7.12-7.18 (m, 1H), 4.43-4.55 (m, 2H), 4.23-4.36 (m, 3H), 3.66-3.75 (m, 1H), 3.55-3.66 (m, 3H), 3.31 (s, 6H), 3.26 (s, 3H), 3.18 (s, 3H). LCMS [M+1]: 438.

Compound 046: N-(3-chlorophenyl)-4-(hydroxymethyl)-2,8,8-trimethyl-1-oxo-1,4,5,8,9,11-hexahydropyrido[4',3':3,4]pyrazolo[5,1-d][1,2,5]oxadiazepine-10(2H)-carboxamide

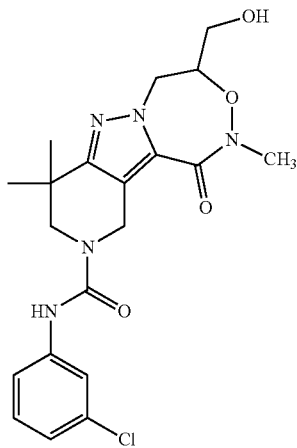

Step 1. 4-(hydroxymethyl)-2,8,8-trimethyl-4,5,8,9,10,11-hexahydropyrido[4',3':3,4] pyrazolo[5,1-d][1,2,5]oxadiazepin-1(2H)-one. To a solution of tert-butyl 4-(hydroxymethyl)-2,8,8-trimethyl-1-oxo-1,4,5,8,9,11-hexahydropyrido[4',3':3,4]pyrazolo[5,1-d][1,2,5]oxadiazepine-10(2H)-carboxylate (Intermediate 3, 43.00 mg, 113.03 µmol, 1.00 eq) in DCM (300.00 µL was added a solution of TFA (462.00 mg, 4.05 mmol, 300.00 µL35.85 eq) in DCM (300.00 µL at 0° C., the reaction mixture was stirred at 10° C. for one hour. TLC indicated starting material was consumed completely. The solvent was removed on a rotary evaporator to afford the title compound (40.00 mg, crude, TFA) as yellow oil. The product was used in the next step directly without further purification.

Step 2. N-(3-chlorophenyl)-4-(hydroxymethyl)-2,8,8-trimethyl-1-oxo-1,4,5,8,9,11-hexahydropyrido[4',3':3,4] pyrazolo[5,1-d][1,2,5]oxadiazepine-10(2H)-carboxamide. To a mixture of 4-(hydroxymethyl)-2,8,8-trimethyl-4,5,8,9,10,11-hexahydropyrido [4',3':3,4]pyrazolo[5,1-d][1,2,5] oxadiazepin-1(2H)-one (40.00 mg, 101.43 µmol, 1.00 eq, TFA) in DCM (2.00 mL) was added TEA (41.06 mg, 405.73 µmol, 56.24 µL4.00 eq), followed by phenyl N-(3-chlorophenyl)carbamate (25.12 mg, 101.43 µmol, 1.00 eq), the reaction mixture was stirred at 10° C. for 16 hours. LCMS showed the starting material was consumed completely and about 50% of desired compound was detected. The mixture was extracted with DCM (50 mL*3) and water (30 mL), the organic phase was dried with anhydrous Na$_2$SO$_4$, filtered and concentrated in vacuum. The residue was purified by prep-HPLC(FA) to afford the title compound (28.00 mg, 63.24 µmol, 62.35% yield, 98% purity) as white solid. $^1$H NMR (400 MHz, CHLOROFORM-d) δ=7.56 (s, 1H) 7.18-7.24 (m, 2H) 7.00-7.02 (d, J=7.78 Hz, 1H) 6.64 (s, 1H) 4.71 (s, 2H) 4.52-4.56 (m, 2H) 4.38-4.41 (m, 1H) 3.85-3.86 (m, 1H) 3.76-3.77 (m, 1H) 3.52-3.62 (m, 2H) 3.30 (s, 3H) 2.18 (brs, 1H) 1.34-1.36 (d, J=4.64 Hz, 6H). LCMS: 434/436 [M+1].

Compound 047: N-(3-chlorophenyl)-4-(hydroxymethyl)-2,8-dimethyl-1-oxo-1,4,5,8,9,11-hexahydropyrido[4',3':3,4]pyrazolo[5,1-d][1,2,5]oxadiazepine-10(2H)-carboxamide

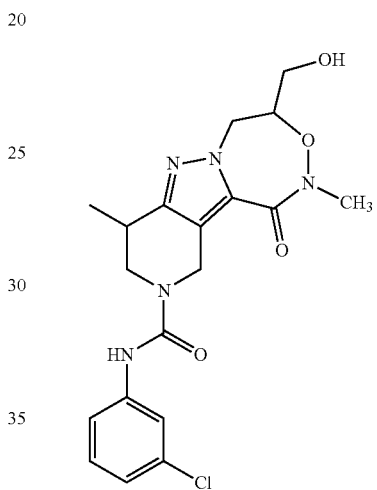

To a solution of tert-butyl 4-(hydroxymethyl)-2,8-dimethyl-1-oxo-1,2,4,5,8,9-hexahydropyrido[4',3':3,4]pyrazolo [5,1-d][1,2,5]oxadiazepine-10(11H)-carboxylate (Intermediate 4, 60.00 mg, 163.75 µmol, 1.00 eq) in DCM (3.00 mL) was added TFA (1.32 g, 11.58 mmol, 857.16 µL70.70 eq). The mixture was stirred at 15° C. for 1 hr. TLC (PE:EA=0:1) showed the starting material consumed. The mixture was concentrated in vacuum to afford 4-(hydroxymethyl)-2,8-dimethyl-4,5,8,9,10,11-hexahydropyrido [4',3':3,4]pyrazolo [5,1-d][1,2,5]oxadiazepin-1(2H)-one (64.00 mg, 168.28 µmol, 102.77% yield, TFA) as yellow oil. The resulting solid was dissolved with DCM (5.00 mL), and added TEA (82.48 mg, 815.10 µmol, 112.99 µL5.00 eq) followed by phenyl N-(3-chlorophenyl)carbamate (40.38 mg, 163.02 µmol, 1.00 eq). The mixture was stirred at 15° C. for 16 hr. LCMS showed major product. The mixture was concentrated in vacuum. The residue was purified by prep-HPLC (FA) to afford the title compound (25.00 mg, 59.25 µmol, 36.34% yield, 99.5% purity) as white solid. $^1$H NMR (400 MHz, CHLOROFORM-d) δ=7.56 (s, 1H), 7.19-7.27 (m, 2H), 7.03 (d, J=7.5 Hz, 1H), 6.60 (brs, 1H), 4.72-4.86 (m, 1H), 4.51-4.69 (m, 3H), 4.33-4.48 (m, 1H), 4.07-4.19 (m, 1H), 3.67-3.93 (m, 2H), 3.33 (s, 3H), 3.24 (ddd, J=8.3, 13.2, 17.4 Hz, 1H), 3.10 (d, J=6.7 Hz, 1H), 2.07 (brs, 1H), 1.36 (dd, J=2.3, 6.8 Hz, 1H). LCMS: 420/422 [M+1].

Compound 048: N-(3-chloro-4-fluoro-phenyl)-2-methyl-4-(methylsulfanylmethyl)-1-oxo-5,8,9,11-tetrahydro-4H-pyrido[2,3]pyrazolo[2,4-d][1,2,5]oxadiazepine-10-carboxamide

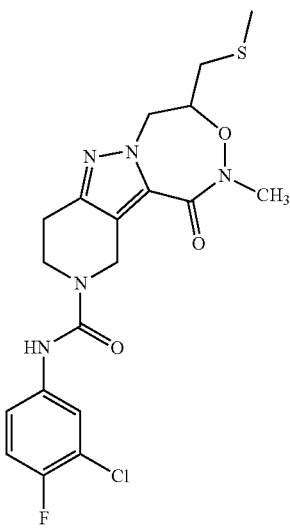 [SMILES: CSCC1Cn2nc3c(c2C(=O)N(C)O1)CN(C(=O)Nc1ccc(F)c(Cl)c1)CC3]

Step 1. [10-[(3-chloro-4-fluoro-phenyl)carbamoyl]-2-methyl-1-oxo-5,8,9,11-tetrahydro-4H-pyrido[2,3]pyrazolo[2,4-d][1,2,5]oxadiazepin-4-yl]methylmethanesulfonate. To a solution of N-(3-chloro-4-fluoro-phenyl)-4-(hydroxymethyl)-2-methyl-1-oxo-5,8,9,11-tetrahydro-4H-pyrido[2,3]pyrazolo[2,4-d][1,2,5]oxadiazepine-10-carboxamide (Compound 031, 500.00 mg, 1.18 mmol, 1.00 eq) in DCM (4.00 mL) was added Et3N (716.43 mg, 7.08 mmol, 981.40 µL 6.00 eq) followed by MsCl (540.68 mg, 4.72 mmol, 365.32 µL 4.00 eq) at 15° C. The resulting mixture was stirred for 20 hours at 25° C. TLC (Dichloromethane/Methanol=10/1) showed the starting material consumed nearly and major desired product was generated. The reaction mixture was diluted with dichloromethane (30 mL), and washed with 1N HCl (30 mL*2) and brine (30 mL). The organic layer was dried with $Na_2SO_4$, and concentrated to give the title compound (590.00 mg, 1.02 mmol, 86.67% yield, 87% purity) as a yellow solid.

Step 2. N-(3-chloro-4-fluoro-phenyl)-2-methyl-4-(methylsulfanylmethyl)-1-oxo-5,8,9,11-tetrahydro-4H-pyrido[2,3]pyrazolo[2,4-d][1,2,5]oxadiazepine-10-carboxamide To a solution of [10-[(3-chloro-4-fluoro-phenyl)carbamoyl]-2-methyl-1-oxo-5,8,9,11-tetrahydro-4H-pyrido[2,3]pyrazolo[2,4-d][1,2,5]oxadiazepin-4-yl]methylmethanesulfonate (150.00 mg, 298.85 µmol, 1.00 eq) in DMF (8.00 mL) was added NaSMe (125.68 mg, 1.79 mmol, 114.25 µL 6.00 eq). The resulting mixture was stirred for 16 hours at 15° C. TLC (Dichloromethane/Methanol=10/1) showed the starting material consumed nearly and desired product was generated mainly. The reaction mixture was diluted with EtOAc (30 mL) and washed with water (30 mL*2) and brine (30 mL). The organic layer was dried with $Na_2SO_4$, and concentrated tin vacuo. The residue was purified by column chromatography (Dichloromethane:Methanol=20:1~10:1) to give 145.00 mg of the desired product with 70.5% purity as a yellow liquid, 30 mg of which was further purified via Prep-HPLC (TFA) to give 14.81 mg of the title compound with 98% purity. $^1$H NMR: (CDCl$_3$, 400 MHz) δ=7.57-7.59 (m, 1H), 7.28-7.30 (m, 1H), 7.13 (t, J=9.20 Hz, 1H), 4.84 (s, 2H), 4.59-4.71 (m, 2H), 4.42-4.45 (m, 1H), 3.80-3.84 (t, J=6.00 Hz, 2H), 3.31 (s, 3H), 2.81-2.84 (m, 3H), 2.67-2.70 (m, 1H), 2.19 (s, 3H). LCMS [M+1]: 454.1

Compound 049_E1: (S*)—N-(3-chloro-4-fluoro-phenyl)-2-methyl-4-(((S*)-methylsulfinyl)methyl)-1-oxo-1,4,5,8,9,11-hexahydropyrido[4',3':3,4]pyrazolo[5,1-d][1,2,5]oxadiazepine-10(2H)-carboxamide

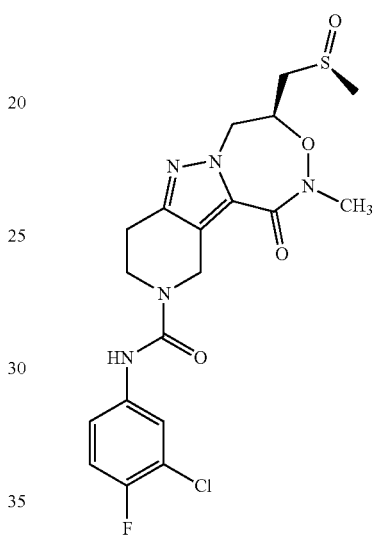

To a solution of N-(3-chloro-4-fluoro-phenyl)-2-methyl-4-(methylsulfanylmethyl)-1-oxo-5,8,9,11-tetrahydro-4H-pyrido[2,3]pyrazolo[2,4-d][1,2,5]oxadiazepine-10-carboxamide (Compound 048, 80.00 mg, 123.37 µmol, 1.00 eq) in DCM (5.00 mL) was added m-CPBA (29.27 mg, 135.71 µmol, 80% purity, 1.10 eq) at 15° C. The resulting mixture was stirred for 16 hours at 30° C. TLC (Dichloromethane/Methanol=10/1) and LCMS showed the starting material was consumed completely and sulfone and sulfoxide were generated. The reaction mixture was diluted with dichloromethane (20 mL), then washed with water (10 mL), brine (10 mL), dried with $Na_2SO_4$, filtered, concentrated in vacuo. The residue was purified by Prep-TLC (Dichloromethane/Methanol=15/1), followed by prep-HPLC to 9.77 mg of Compound 050 and 29.09 mg of racemic Compound 049. 29.09 mg of racemic Compound 049 was separated by two rounds of SFC, and further purified by prep-HPLC (TFA condition) to give 4 enantiomers: Compound 049_E1 (6.86 mg), Compound 049_E2 (5.78 mg); Compound 049_E3 (7.15 mg) and Compound 049_E4 (6.79 mg). $^1$H NMR: (CDCl$_3$, 400 MHz) δ=7.56-7.59 (m, 1H), 7.15-7.22 (m, 1H), 7.07 (t, J=9.20 Hz, 1H), 6.46 (s, 1H), 5.03-5.12 (m, 1H), 4.65-4.78 (m, 3H), 4.45 (dd, J=7.60 Hz, J=7.60 Hz, 1H), 3.75-3.96 (m, 2H), 3.34 (s, 3H), 2.85-3.05 (m, 4H), 2.69 (s, 3H).

* pure but unknown stereochemistry

Compound 049_E2: (S*)—N-(3-chloro-4-fluorophenyl)-2-methyl-4-(((R*)-methylsulfinyl)methyl)-1-oxo-1,4,5,8,9,11-hexahydropyrido[4',3':3,4]pyrazolo[5,1-d][1,2,5]oxadiazepine-10(2H)-carboxamide

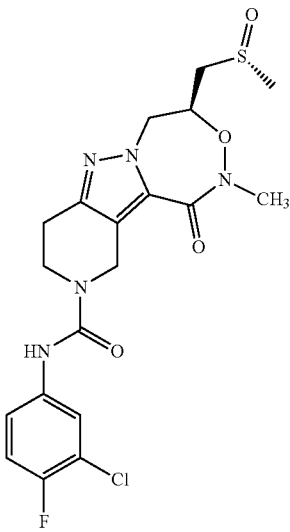 [SMILES: CN1O[C@H](C[S@@](C)=O)Cn2nc3c(c2C1=O)CN(C(=O)Nc1ccc(F)c(Cl)c1)CC3]

Compound 049_E2 was separated from the mixture described above.

¹H NMR: (CDCl₃, 400 MHz) δ=7.56-7.59 (m, 1H), 7.15-7.22 (m, 1H), 7.07 (t, J=9.20 Hz, 1H), 6.46 (s, 1H), 5.03-5.12 (m, 1H), 4.65-4.78 (m, 3H), 4.45 (dd, J=7.60 Hz, J=7.60 Hz, 1H), 3.75-3.96 (m, 2H), 3.34 (s, 3H), 2.85-3.05 (m, 4H), 2.69 (s, 3H).

* pure but unknown stereochemistry

Compound 049_E3: (R*)—N-(3-chloro-4-fluorophenyl)-2-methyl-4-(((R*)-methylsulfinyl)methyl)-1-oxo-1,4,5,8,9,11-hexahydropyrido[4',3':3,4]pyrazolo[5,1-d][1,2,5]oxadiazepine-10(2H)-carboxamide

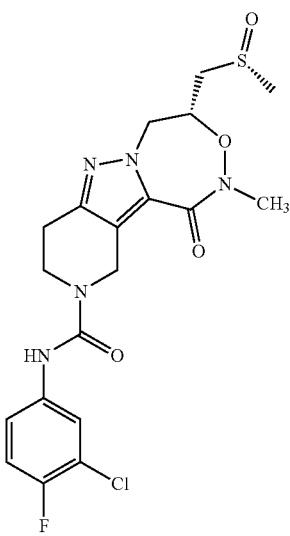 [SMILES: CN1O[C@@H](C[S@@](C)=O)Cn2nc3c(c2C1=O)CN(C(=O)Nc1ccc(F)c(Cl)c1)CC3]

Compound 049_E3 was separated from the mixture described above.

¹H NMR: (CDCl₃, 400 MHz) δ=7.56-7.59 (m, 1H), 7.15-7.22 (m, 1H), 7.07 (t, J=9.20 Hz, 1H), 6.46 (s, 1H), 5.03-5.12 (m, 1H), 4.65-4.78 (m, 3H), 4.45 (dd, J=7.60 Hz, J=7.60 Hz, 1H), 3.75-3.96 (m, 2H), 3.34 (s, 3H), 2.85-3.05 (m, 4H), 2.69 (s, 3H).

* pure but unknown stereochemistry

Compound 049_E4: (R*)—N-(3-chloro-4-fluorophenyl)-2-methyl-4-(((S*)-methylsulfinyl)methyl)-1-oxo-1,4,5,8,9,11-hexahydropyrido[4',3':3,4]pyrazolo[5,1-d][1,2,5]oxadiazepine-10(2H)-carboxamide

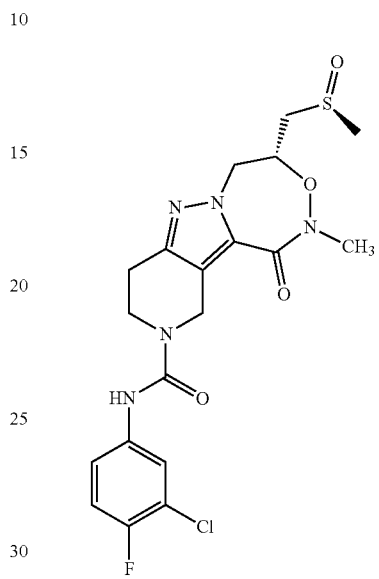

Compound 049_E4 was separated from the mixture described above.

¹H NMR: (CDCl₃, 400 MHz) δ=7.56-7.59 (m, 1H), 7.15-7.22 (m, 1H), 7.07 (t, J=9.20 Hz, 1H), 6.46 (s, 1H), 5.03-5.12 (m, 1H), 4.65-4.78 (m, 3H), 4.45 (dd, J=7.60 Hz, J=7.60 Hz, 1H), 3.75-3.96 (m, 2H), 3.34 (s, 3H), 2.85-3.05 (m, 4H), 2.69 (s, 3H).

* pure but unknown stereochemistry

Compound 050: N-(3-chloro-4-fluorophenyl)-2-methyl-4-((methylsulfonyl)methyl)-1-oxo-1,4,5,8,9,11-hexahydropyrido[4',3':3,4]pyrazolo[5,1-d][1,2,5]oxadiazepine-10(2H)-carboxamide

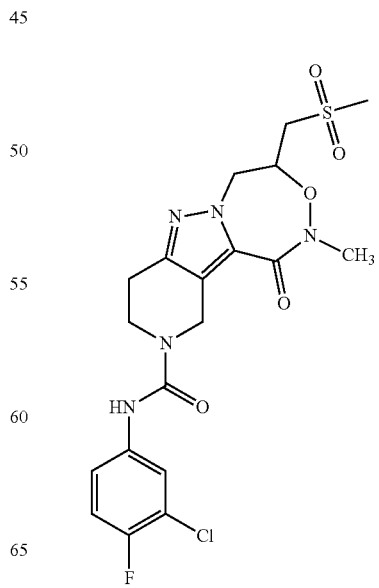

Compound 050 was separated from the mixture described above.

¹H NMR: (CDCl₃, 400 MHz) δ=7.53-7.57 (m, 1H), 7.15-7.20 (m, 1H), 7.07 (t, J=8.80 Hz, 1H), 6.45 (s, 1H), 5.12 (s, 1H), 4.65-4.78 (m, 3H), 4.53 (d, J=7.60 Hz, 1H), 3.75-3.90 (m, 3H), 3.32-3.45 (m, 3H), 3.27 (d, J=4.80 Hz, 1H), 3.03 (s, 3H), 2.88 (t, J=6.00 Hz, 2H). LCMS [M+1]: 486.3

Compound 051: (10-((3-chloro-4-fluorophenyl)carbamoyl)-2-methyl-1-oxo-1,2,4,5,8,9,10,11-octahydropyrido[4',3':3,4]pyrazolo[5,1-d][1,2,5]oxadiazepin-4-yl)methyl methyl carbonate

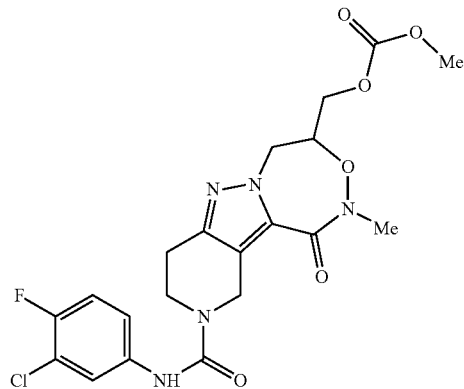 [SMILES: COC(=O)OCC1Cn2nc3c(c2C(=O)N(C)O1)CN(C(=O)Nc1ccc(F)c(Cl)c1)CC3]

To a solution of N-(3-chloro-4-fluoro-phenyl)-4-(hydroxymethyl)-2-methyl-1-oxo-5,8,9,11-tetrahydro-4H-pyrido[2,3]pyrazolo[2,4-d][1,2,5]oxadiazepine-10-carboxamide (Compound 031, 50.00 mg, 117.97 μmol, 1.00 eq) in DCM (10.00 mL) was added Et₃N (119.37 mg, 1.18 mmol, 163.53 μL 410.00 eq) followed by methyl carbonochloridate (111.48 mg, 1.18 mmol, 91.38 μL 10.00 eq) under ice-water bath (maintaining the inner temperature between 5~10° C.). The resulting mixture was stirred for 2 hours at 30° C. TLC and LCMS showed the starting material was consumed, and the desired product was generated. The reaction mixture was concentrated in vacuo. The residue was purified by Prep-HPLC to give the purified product (50.00 mg, 102.73 μmol, 87.08% yield, 99% purity) as a white solid. LCMS: 482.1 [M+1]. ¹H NMR: (CDCl₃, 400 MHz) δ=7.56-7.59 (m, 1H), 7.15-7.23 (m, 1H), 7.05 (t, J=8.80 Hz, 1H), 6.43 (s, 1H), 4.65-4.75 (m, 3H), 4.55-4.63 (m, 1H), 4.35-4.45 (m, 2H), 4.21-4.31 (m, 1H), 3.75-3.89 (m, 5H), 3.31 (s, 3H), 2.86 (t, J=6.00 Hz, 2H).

Compounds 052, 053, 054, 055 and 056 were prepared in a manner analogous to Compound 051.

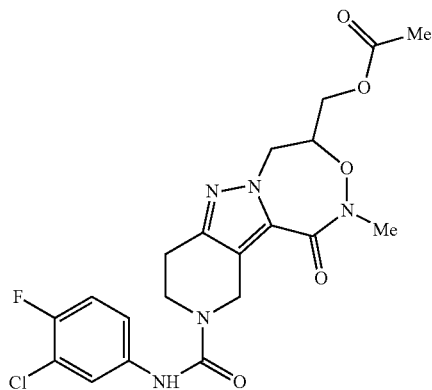

052

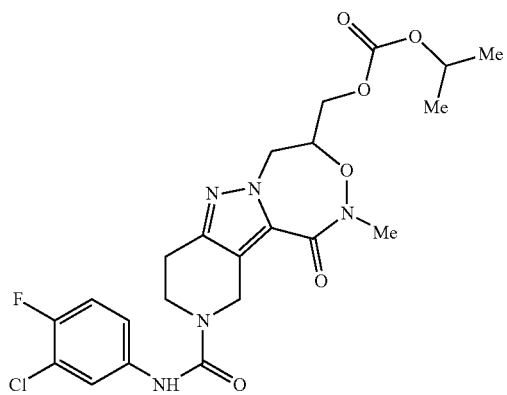

053

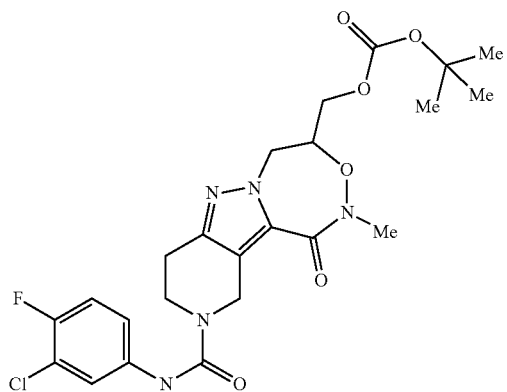

054

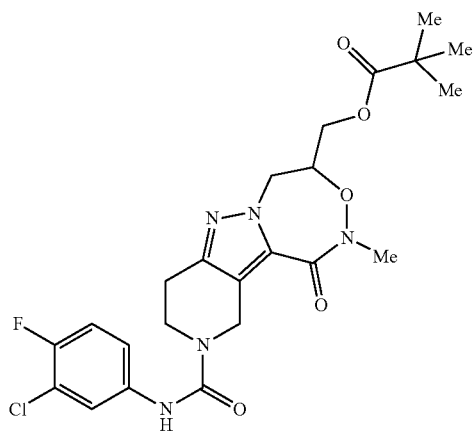

055

-continued

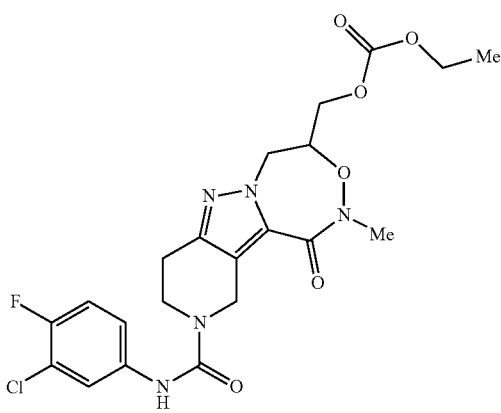

Compound 052: (10-((3-chloro-4-fluorophenyl)carbamoyl)-2-methyl-1-oxo-1,2,4,5,8,9,10,11-octahydropyrido[4',3':3,4]pyrazolo[5,1-d][1,2,5]oxadiazepin-4-yl)methyl acetate LCMS: 466.1 [M+1]. $^1$H NMR: (CDCl$_3$, 400 MHz) δ=7.56-7.59 (m, 1H), 7.15-7.21 (m, 1H), 7.06 (t, J=8.80 Hz, 1H), 6.45 (s, 1H), 4.55-4.75 (m, 4H), 4.31-4.42 (m, 2H), 4.14-4.22 (m, 1H), 4.21-4.31 (m, 1H), 3.79-3.91 (m, 2H), 3.30 (s, 3H), 2.86 (t, J=6.40 Hz, 2H), 2.12 (s, 3H).

Compound 053: (10-((3-chloro-4-fluorophenyl)carbamoyl)-2-methyl-1-oxo-1,2,4,5,8,9,10,11-octahydropyrido[4',3':3,4]pyrazolo[5,1-d][1,2,5]oxadiazepin-4-yl)methyl isopropyl carbonate LCMS: 510 [M+1]. $^1$H NMR (400 MHz, CHLOROFORM-d) δ=7.58 (dd, J=2.69, 6.48 Hz, 1H), 7.17-7.23 (m, 1H), 7.02-7.10 (m, 1H), 6.53 (s, 1H), 4.92 (m, J=6.24 Hz, 1H), 4.65-4.75 (m, 3H), 4.56-4.65 (m, 1H), 4.32-4.41 (m, 2H), 4.24 (dd, J=4.58, 11.92 Hz, 1H), 3.80-3.92 (m, 2H), 3.30 (s, 3H), 2.86 (t, J=5.75 Hz, 2H), 1.29-1.38 (m, 6H).

Compound 054: tert-butyl ((10-((3-chloro-4-fluorophenyl)carbamoyl)-2-methyl-1-oxo-1,2,4,5,8,9,10,11-octahydropyrido[4',3':3,4]pyrazolo[5,1-d][1,2,5]oxadiazepin-4-yl)methyl) carbonate LCMS: 546 [M+23]. $^1$H NMR (400 MHz, CHLOROFORM-d) δ=7.58 (dd, J=2.63, 6.54 Hz, 1H), 7.16-7.23 (m, 1H), 7.02-7.10 (m, 1H), 6.55 (s, 1H), 4.65-4.77 (m, 3H), 4.56-4.64 (m, 1H), 4.27-4.41 (m, 2H), 4.18 (dd, J=4.65, 11.98 Hz, 1H), 3.77-3.93 (m, 2H), 3.30 (s, 3H), 2.86 (t, J=5.75 Hz, 2H), 1.51 (s, 9H).

Compound 055; (10-((3-chloro-4-fluorophenyl)carbamoyl)-2-methyl-1-oxo-1,2,4,5,8,9,10,11-octahydropyrido[4',3':3,4]pyrazolo[5,1-d][1,2,5]oxadiazepin-4-yl)methyl pivalate LCMS: 508 [M+1]. $^1$H NMR (400 MHz, CHLOROFORM-d) δ=7.57 (dd, J=2.57, 6.48 Hz, 1H), 7.16-7.24 (m, 1H), 7.02-7.10 (m, 1H), 6.53 (s, 1H), 4.57-4.73 (m, 4H), 4.29-4.39 (m, 2H), 4.18-4.27 (m, 1H), 3.86 (t, J=5.81 Hz, 2H), 2.86 (t, J=5.75 Hz, 2H), 1.24 (s, 9H).

Compound 056: (10-((3-chloro-4-fluorophenyl)carbamoyl)-2-methyl-1-oxo-1,2,4,5,8,9,10,11-octahydropyrido[4',3':3,4]pyrazolo[5,1-d][1,2,5]oxadiazepin-4-yl)methyl ethyl carbonate LCMS: 496 [M+1]. $^1$H NMR (400 MHz, CHLOROFORM-d) δ=7.57 (dd, J=2.69, 6.48 Hz, 1H), 7.16-7.23 (m, 1H), 7.02-7.10 (m, 1H), 6.52 (s, 1H), 4.65-4.76 (m, 3H), 4.56-4.65 (m, 1H), 4.32-4.43 (m, 2H), 4.21-4.30 (m, 3H), 3.77-3.95 (m, 2H), 3.31 (s, 3H), 2.86 (t, J=5.75 Hz, 2H), 1.35 (t, J=7.09 Hz, 3H).

Compound 057: (10-((3-chloro-4-fluorophenyl)carbamoyl)-2-methyl-1-oxo-1,2,4,5,8,9,10,11-octahydropyrido[4',3':3,4]pyrazolo[5,1-d][1,2,5]oxadiazepin-4-yl)methyl carbamate

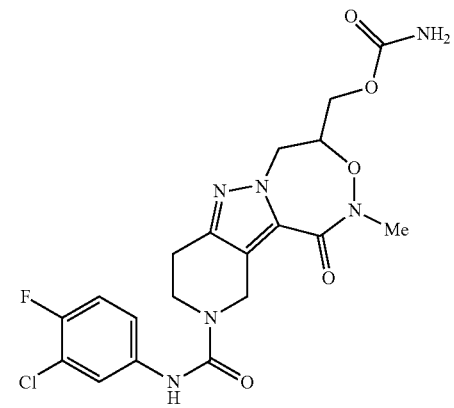 [SMILES: CN1OC(COC(N)=O)Cn2nc3c(c2C1=O)CN(C(=O)Nc1ccc(F)c(Cl)c1)CC3]

To a solution of N-(3-chloro-4-fluoro-phenyl)-4-(hydroxymethyl)-2-methyl-1-oxo-5,8,9,11-tetrahydro-4H-pyrido[2,3]pyrazolo[2,4-d][1,2,5]oxadiazepine-10-carboxamide (Compound 031, 50.00 mg, 117.97 μmol, 1.00 eq) in DCM (8.00 mL) was added sodium cyanate (230.08 mg, 3.54 mmol, 30.00 eq) followed by CF$_3$COOH (403.53 mg, 3.54 mmol, 262.03 μL30.00 eq) at 10° C. The resulting mixture was stirred for 48 hours at 30° C. LCMS and HPLC showed starting material/desired product=1/2. The reaction mixture was concentrated in vacuo. The residue was purified by Prep-HPLC (TFA condition) to give the desired product (16.74 mg, 35.86 μmol, 30.40% yield) as a white solid. $^1$H NMR: (MeOD, 400 MHz) δ=7.57-7.59 (m, 1H), 7.23-7.39 (m, 1H), 7.13 (t, J=9.20 Hz, 1H), 4.65-4.75 (m, 3H), 4.59-4.64 (m, 1H), 4.33-4.41 (m, 1H), 4.25-4.32 (m, 1H), 4.13-4.20 (m, 1H), 3.82 (t, J=6.00 Hz, 2H), 3.31 (s, 3H), 2.82 (t, J=6.40 Hz, 2H). LCMS: 467 [M+1].

Compound 058: N-(3-chloro-4-fluoro-phenyl)-4-[(dimethylamino)methyl]-2-methyl-1-oxo-5,8,9,11-tetrahydro-4H-pyrido[2,3]pyrazolo[2,4-d][1,2,5]oxadiazepine-10-carboxamide

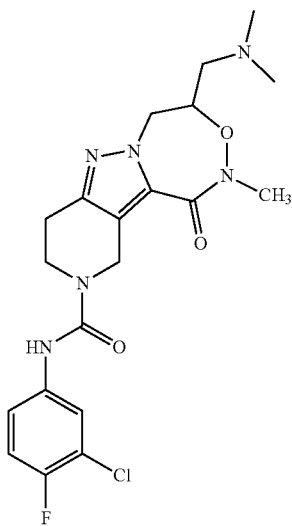 [SMILES: CN(C)CC1Cn2nc3c(c2C(=O)N(C)O1)CN(C(=O)Nc1ccc(F)c(Cl)c1)CC3]

Step 1. tert-butyl 2-methyl-4-(methylsulfonyloxymethyl)-1-oxo-5,8,9,11-tetrahydro-4H-pyrido[2,3]pyrazolo[2,4-d][1,2,5]oxadiazepine-10-carboxylate. To a solution of tert-butyl 4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxylate (Intermediate 1, 500.00 mg, 1.42 mmol, 1.00 eq) in DCM (2.00 mL) was added TEA (358.95 mg, 3.55 mmol, 491.72 µL 2.50 eq) and MsCl (211.30 mg, 1.84 mmol, 142.77 µL 1.30 eq). Then the mixture was stirred 20° C. for 2 hr. TLC (Ethyl acetate) showed the reaction was complete. The reaction mixture was diluted with DCM (20 mL) and washed with brine (10 mL), dried over anhydrous $Na_2SO_4$ and concentrated in vacuum to give tert-butyl 2-methyl-4-(methylsulfonyloxymethyl)-1-oxo-5,8,9,11-tetrahydro-4H-pyrido[2,3]pyrazolo[2,4-d][1,2,5]oxadiazepine-10-carboxylate (600.00 mg, 1.39 mmol, 98.16% yield) was obtained as yellow solid, which was used in the next step without further purification.

Step 2. tert-butyl 4-[(dimethylamino) methyl]-2-methyl-1-oxo-5,8,9,11-tetrahydro-4H-pyrido[2,3]pyrazolo[2,4-d][1,2,5]oxadiazepine-10-carboxylate and tert-butyl 4-(dimethylcarbamoyloxymethyl)-2-methyl-1-oxo-5,8,9,11-tetrahydro-4H-pyrido[2,3]pyrazolo[2,4-d][1,2,5]oxadiazepine-10-carboxylate. To a solution of tert-butyl 2-methyl-4-(methylsulfonyloxymethyl)-1-oxo-5,8,9,11-tetrahydro-4H-pyrido[2,3]pyrazolo[2,4-d][1,2,5]oxadiazepine-10-carboxylate (50.00 mg, 116.15 µmol, 1.00 eq) and $Me_2NH$ (94.71 mg, 1.16 mmol, 106.42 µL 10.00 eq, HCl) in DMF (3.00 mL) was added $K_2CO_3$ (160.53 mg, 1.16 mmol, 161.00 µL 10.00 eq). The mixture was stirred at 80° C. for 12 hr. LCMS showed the starting material was consumed and 19% 3 and 65% 3a were generated. The mixture was filtered and the filtrate was concentrated in vacuum. The crude was purified by prep-TLC (Dichloromethane:Methanol=10:1) to give the first titled compound (9.00 mg, 22.53 µmol, 19.40% yield, 95% purity) as the colorless oil, and the second titled compound (15.00 mg, 35.42 µmol, 30.50% yield) was obtained as colorless oil.

tert-butyl 4-[(dimethylamino)methyl]-2-methyl-1-oxo-5,8,9,11-tetrahydro-4H-pyrido[2,3]pyrazolo[2,4-d][1,2,5]oxadiazepine-10-carboxylate: $^1$H NMR (400 MHz, CHLOROFORM-d) δ 4.62-4.70 (m, 2H), 4.47-4.59 (m, 2H), 4.23-4.35 (m, 1H), 3.58-3.86 (m, 2H), 3.19-3.36 (m, 3H), 2.77 (t, J=5.44 Hz, 2H), 2.41-2.67 (m, 2H), 2.34 (s, 6H), 1.49 (s, 9H).

tert-butyl 4-(dimethylcarbamoyloxymethyl)-2-methyl-1-oxo-5,8,9,11-tetrahydro-4H-pyrido[2,3]pyrazolo[2,4-d][1,2,5]oxadiazepine-10-carboxylate: $^1$H NMR (400 MHz, CHLOROFORM-d) δ 4.51-4.72 (m, 4H), 4.27-4.39 (m, 2H), 4.15-4.25 (m, 1H), 3.71 (s, 2H), 3.28 (s, 3H), 2.92 (d, J=17.73 Hz, 5H), 2.70-2.80 (m, 2H), 1.48 (s, 9H).

Step 3. 4-[(dimethylamino)methyl]-2-methyl-4,5,8,9,10,11-hexahydropyrido[2,3] pyrazolo[2,4-d][1,2,5]oxadiazepin-1-one. To a solution of tert-butyl 4-[(dimethylamino)methyl]-2-methyl-1-oxo-5,8,9,11-tetrahydro-4H-pyrido[2,3]pyrazolo[2,4-d][1,2,5]oxadiazepine-10-carboxylate (67.00 mg, 176.57 µmol, 1.00 eq) in DCM (2.00 mL) was added TFA (3.08 g, 27.01 mmol, 2.00 mL, 152.99 eq). The mixture was stirred at 15° C. for 30 min. TLC (ethyl acetate) showed the reaction was complete. The mixture was evaporated to give the crude title compound (80.00 mg, crude, TFA) as colorless oil, which was used in the next step without further purification.

Step 4. N-(3-chloro-4-fluoro-phenyl)-4-[(dimethylamino)methyl]-2-methyl-1-oxo-5,8,9,11-tetrahydro-4H-pyrido[2,3]pyrazolo[2,4-d][1,2,5]oxadiazepine-10-carboxamide. To a solution of 4-[(dimethylamino)methyl]-2-methyl-4,5,8,9,10,11-hexahydropyrido [2,3]pyrazolo[2,4-d][1,2,5]oxadiazepin-1-one (49.00 mg, 175.41 µmol, 1.00 eq) and phenyl N-(3-chloro-4-fluoro-phenyl)carbamate (46.60 mg, 175.41 µmol, 1.00 eq) in DCM (2.00 mL) was added TEA (53.25 mg, 526.23 µmol, 72.95 µL 3.00 eq). The mixture was stirred at 15° C. for 16 hr. LCMS showed the reaction was completed. The mixture was evaporated in vacuo. The residue was purified by prep-HPLC (column: Boston Green ODS 150*30 5 u; mobile phase: [water (0.225% FA)-ACN]; B %: 11%-41%, 10 min) The title compound (48.00 mg, 106.24 µmol, 60.57% yield, 99.8% purity) was obtained as white solid. $^1$H NMR (400 MHz, CHLOROFORM-d) δ 7.57 (dd, J=2.63, 6.54 Hz, 1H), 7.17-7.22 (m, 1H), 7.03-7.09 (m, 1H), 6.53 (s, 1H), 4.77 (quin, J=5.81 Hz, 1H), 4.70 (s, 2H), 4.59 (dd, J=5.93, 14.61 Hz, 1H), 4.34 (dd, J=4.89, 14.67 Hz, 1H), 3.77-3.96 (m, 2H), 3.32 (s, 3H), 2.86 (t, J=5.75 Hz, 2H), 2.73 (d, J=6.72 Hz, 2H), 2.48 (s, 6H). LCMS: 451[M+1].

Compound 059: [10-[(3-chloro-4-fluoro-phenyl)carbamoyl]-2-methyl-1-oxo-5,8,9,11-tetrahydro-4H-pyrido[2,3]pyrazolo[2,4-d][1,2,5]oxadiazepin-4-yl]methyl N,N-dimethylcarbamate

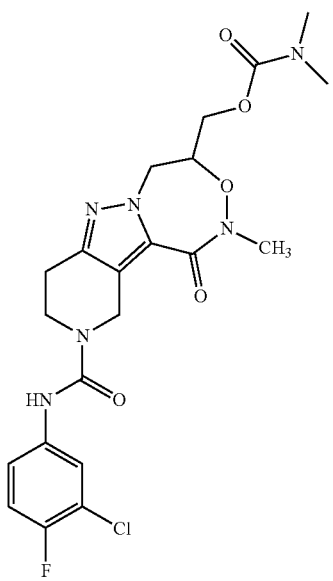 [SMILES: CN(C)C(=O)OCC1Cn2nc3c(c2C(=O)N(C)O1)CN(C(=O)Nc1ccc(F)c(Cl)c1)CC3]

Step 1. (2-methyl-1-oxo-4,5,8,9,10,11-hexahydropyrido[2,3]pyrazolo[2,4-d][1,2,5]oxadiazepin-4-yl)methyl N,N-dimethylcarbamate To a solution of tert-butyl 4-(dimethylcarbamoyloxymethyl)-2-methyl-1-oxo-5,8,9,11-tetrahydro-4H-pyrido[2,3]pyrazolo[2,4-d][1,2,5]oxadiazepine-10-carboxylate (As described above, 55.00 mg, 129.88 μmol, 1.00 eq) in DCM (2.00 mL) was added TFA (14.81 mg, 129.88 μmol, 9.62 μL1.00 eq). Then the mixture was stirred at 10° C. for 30 min. TLC (ethyl acetate) showed the reaction was complete. The mixture was evaporated to give the title compound (70.00 mg, crude, TFA) was obtained as colorless oil.

Step 2. [10-[(3-chloro-4-fluoro-phenyl)carbamoyl]-2-methyl-1-oxo-5,8,9,11-tetrahydro-4H-pyrido[2,3]pyrazolo[2,4-d][1,2,5]oxadiazepin-4-yl]methyl N,N-dimethylcarbamate To a solution of (2-methyl-1-oxo-4,5,8,9,10,11-hexahydropyrido[2,3]pyrazolo[2,4-d] [1,2,5]oxadiazepin-4-yl)methyl N,N-dimethylcarbamate (42.00 mg, 96.03 μmol, 1.00 eq, TFA) and phenyl N-(3-chloro-4-fluoro-phenyl)carbamate (25.51 mg, 96.03 μmol, 1.00 eq) in DCM (2.00 mL) was added TEA (29.15 mg, 288.09 μmol, 39.93 μL3.00 eq). Then the mixture was stirred at 15° C. for 12 hr. LCMS showed the reaction was complete. The mixture was concentrated in vacuo. The residue was purified by prep-HPLC (column: Phenomenex Synergi C18 150*25*10 um; mobile phase: [water (0.225% FA)-ACN]; B %: 35%-65%, 10 min) to give the title compound (35.00 mg, 69.17 μmol, 72.02% yield, 97.8% purity) as a white solid. $^1$H NMR (400 MHz, CHLOROFORM-d) δ 7.57 (dd, J=2.69, 6.48 Hz, 1H), 7.17-7.24 (m, 1H), 7.02-7.08 (m, 1H), 6.56 (s, 1H), 4.64-4.73 (m, 1H), 4.55-4.63 (m, 1H), 4.32-4.40 (m, 2H), 4.21-4.27 (m, 1H), 3.86 (t, J=5.87 Hz, 2H), 3.30 (s, 3H), 2.93 (d, J=16.99 Hz, 6H), 2.86 (t, J=5.69 Hz, 2H). LCMS: 495[M+1].

Compound 060_E1: (S*)—N-(3-chloro-4-fluoro-phenyl)-2-ethyl-4-(hydroxymethyl)-1-oxo-1,4,5,8,9,11-hexahydropyrido[4',3':3,4]pyrazolo[5,1-d][1,2,5]oxadiazepine-10(2H)-carboxamide

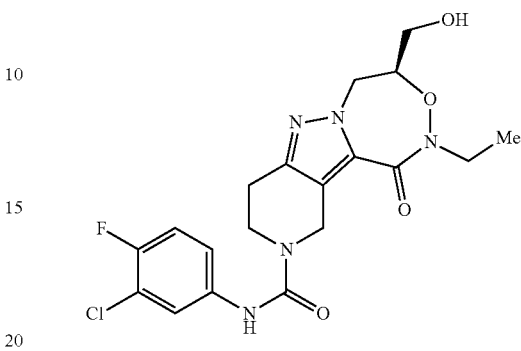

Step 1. 2-ethyl-4-(hydroxymethyl)-4,5,8,9,10,11 hexahydropyrido[2,3]pyrazolo[2,4-d][1,2,5]oxadiazepin-1-one. A solution of tert-butyl 2-ethyl-4-(hydroxymethyl)-1-oxo-1,4,5,8,9,11-hexahydropyrido[4',3':3,4]pyrazolo[5,1-d][1,2,5]oxadiazepine-10(2H)-carboxylate (Intermediate 5, 51.00 mg, 139.19 μmol, 1.00 eq) in DCM (2.00 mL) was added TFA (770.00 mg, 6.75 mmol, 500.00 μL48.52 eq). Then the mixture was stirred at 10° C. for 1 hr. LCMS showed the reaction was completed. The mixture was evaporated to give the title compound (60.00 mg, crude) as the colorless oil which was used in the next step directly without further purification.

Step 2. (S*)—N-(3-chloro-4-fluorophenyl)-2-ethyl-4-(hydroxymethyl)-1-oxo-1,4,5,8,9,11-hexahydropyrido[4',3':3,4]pyrazolo[5,1-d][1,2,5]oxadiazepine-10(2H)-carboxamide. To a solution of 2-ethyl-4-(hydroxymethyl)-4,5,8,9,10,11-hexahydropyrido[2,3] pyrazolo[2,4-d][1,2,5]oxadiazepin-1-one (60.00 mg, 135.19 μmol, 1.00 eq) and phenyl N-(3-chloro-4-fluoro-phenyl)carbamate (22.27 mg, 83.82 μmol, 0.62 eq) in DCM (3.00 mL) was added TEA (27.36 mg, 270.38 μmol, 37.48 μL2.00 eq). Then the mixture was stirred at 10° C. for 16 hr. LCMS showed the reaction was completed. The mixture was concentrated in vacuo. The residue was purified by Prep-HPLC (column: Phenomenex Synergi C18 150*25*10 um; mobile phase: [water (0.225% FA)-ACN]; B %: 30%-60%, 10 min). N-(3-chloro-4-fluoro-phenyl)-2-ethyl-4-(hydroxymethyl)-1-oxo-5,8,9,11-tetrahydro-4H-pyrido[2,3]pyrazolo[2,4-d][1,2,5]oxadiazepine-10-carboxamide (34.00 mg, 76.88 μmol, 56.87% yield, 99% purity) was obtained as white solid. 30 mg of the racemate was separated by SFC (column: Phenomenex Synergi Max-RP 250*80 10 u; mobile phase: [Base-MeOH]; B %: 40%-40%, 3 MIN; 90 min), followed by prep-HPLC to give both enantiomers (each 12.00 mg, 27.41 μmol, 40.00% yield) as white solid.

$^1$H NMR (400 MHz, CHLOROFORM-d) δ 7.54-7.62 (m, 1H), 7.16-7.24 (m, 1H), 7.02-7.12 (m, 1H), 6.53 (s, 1H), 4.63-4.79 (m, 2H), 4.43-4.60 (m, 3H), 3.78-3.96 (m, 4H), 3.74 (dd, J=4.52, 11.54 Hz, 1H), 3.64 (qd, J=6.84, 13.85 Hz, 1H), 2.85 (t, J=5.40 Hz, 2H), 2.03 (s, 1H), 1.34 (t, J=7.03 Hz, 3H). LCMS: 438/440[M+1].

*Pure but unknown enantiomer.

Compound 060_E2: (R*)—N-(3-chloro-4-fluoro-phenyl)-2-ethyl-4-(hydroxymethyl)-1-oxo-1,4,5,8,9,11-hexahydropyrido[4',3':3,4]pyrazolo[5,1-d][1,2,5]oxadiazepine-10(2H)-carboxamide

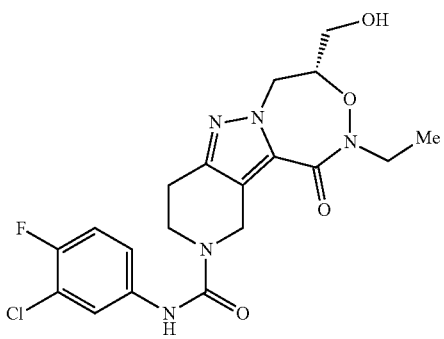 [SMILES: CCN1O[C@@H](CO)Cn2nc3c(c2C1=O)CN(C(=O)Nc1ccc(F)c(Cl)c1)CC3]

Compound 060_E2 was isolated from the above-described mixture.
$^1$H NMR (400 MHz, CHLOROFORM-d) δ 7.55 (dd, J=2.51, 6.40 Hz, 1H), 7.15-7.23 (m, 1H), 6.99-7.09 (m, 1H), 6.63 (s, 1H), 4.62-4.77 (m, 2H), 4.44-4.60 (m, 3H), 3.76-3.94 (m, 4H), 3.69-3.76 (m, 1H), 3.63 (qd, J=7.00, 14.13 Hz, 1H), 2.84 (t, J=5.58 Hz, 2H), 2.29 (s, 1H), 1.33 (t, J=7.09 Hz, 3H). LCMS: 438/440[M+1].
*Pure but unknown enantiomer.

Compound 061: N-(3-chloro-4-fluoro-phenyl)-2,5-dimethyl-1-oxo-5,8,9,11-tetrahydro-4H-pyrido[2,3]pyrazolo[2,4-d][1,2,5]oxadiazepine-10-carboxamide

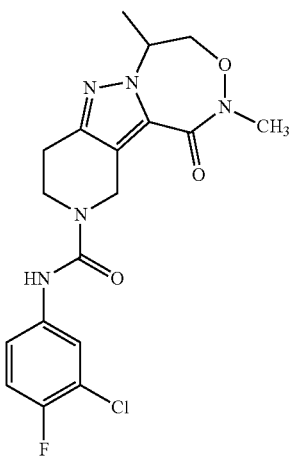 [SMILES: CC1CON(C)C(=O)c2c3c(nn21)CCN(C(=O)Nc1ccc(F)c(Cl)c1)C3]

Step 1. 2,5-dimethyl-4,5,8,9,10,11-hexahydropyrido[2,3]pyrazolo[2,4-d][1,2,5]oxadiazepin-1-one. To a solution of tert-butyl 2,5-dimethyl-1-oxo-1,4,5,8,9,11-hexahydropyrido[4',3':3,4]pyrazolo[5,1-d][1,2,5]oxadiazepine-10(2H)-carboxylate (Intermediate 7, 30.00 mg, 89.18 μmol, 1.00 eq) in DCM (2.00 mL) was added TFA (3.08 g, 27.01 mmol, 2.00 mL, 302.90 eq). The reaction 192mixture was stirred at 15° C. for 12 hr. LCMS showed the starting material was consumed completely and ~84% desired product was detected. The reaction mixture was concentrated in vacuo to give the title compound (35.00 mg, crude, TFA) as a off-white solid. LCMS: 237 [M+1].

Step 2. N-(3-chloro-4-fluoro-phenyl)-2,5-dimethyl-1-oxo-5,8,9,11-tetrahydro-4H-pyrido[2,3]pyrazolo[2,4-d][1,2,5]oxadiazepine-10-carboxamide. To a solution of 2,5-dimethyl-4,5,8,9,10,11-hexahydropyrido[2,3]pyrazolo [2,4-d][1,2,5]oxadiazepin-1-one (35.00 mg, 99.92 μmol, 1.00 eq, TFA) and phenyl N-(3-chloro-4-fluoro-phenyl)carbamate (26.00 mg, 97.92 μmol, 0.98 eq) in DCM (3.00 mL) was added TEA (73.00 mg, 721.42 μmol, 100.00 μL7.22 eq). The reaction mixture was stirred at 30° C. for 12 hr. LCMS showed compound 4 was consumed completely and ~75% desired product was detected. The reaction mixture was concentrated in vacuo. The residue was purified by prep-HPLC (HCl) to give the title compound (15.00 mg, 34.21 μmol, 34.23% yield, 93% purity) as a white solid. $^1$H NMR (400 MHz, CHLOROFORM-d) 7.49-7.65 (m, 1H), 7.19 (s, 1H), 7.00-7.09 (m, 1H), 6.61 (s, 1H), 4.62-4.81 (m, 4H), 4.53 (dd, J=5.01, 11.62 Hz, 1H), 4.04 (dd, J=8.25, 11.43 Hz, 1H), 3.86 (s, 2H), 3.33 (s, 3H), 2.88 (s, 2H), 1.64 (d, J=6.36 Hz, 3H). LCMS: 408 [M+1].

Compound 062: N-(3-chloro-4-fluorophenyl)-2,4-dimethyl-1-oxo-1,4,5,8,9,11-hexahydropyrido[4',3':3,4]pyrazolo[5,1-d][1,2,5]oxadiazepine-10(2H)-carboxamide

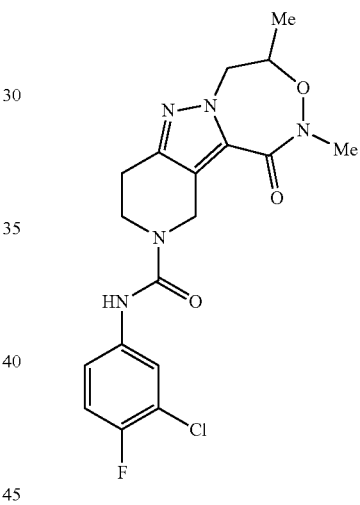

Step 1. 2,4-dimethyl-4,5,8,9,10,11-hexahydropyrido[2,3]pyrazolo[2,4-d][1,2,5]oxadiazepin-1-one. Tert-butyl 2,4-dimethyl-1-oxo-1,4,5,8,9,11-hexahydropyrido[4',3':3,4]pyrazolo[5,1-d][1,2,5]oxadiazepine-10(2H)-carboxylate (Intermediate 8, 50.00 mg, 148.64 μmol, 1.00 eq) was dissolved in TFA (5.13 g, 45.02 mmol, 3.33 mL, 302.90 eq). The mixture was stirred at 10° C. for 1 hr. TLC (PE:EA=0:1) showed the starting material consumed. The mixture was concentrated in vacuum to obtain the title compound (53.00 mg, crude, TFA) as colorless oil.

Step 2. N-(3-chloro-4-fluorophenyl)-2,4-dimethyl-1-oxo-1,4,5,8,9,11-hexahydropyrido[4',3':3,4]pyrazolo[5,1-d][1,2,5]oxadiazepine-10(2H)-carboxamide. To a solution of 2,4-dimethyl-4,5,8,9,10,11-hexahydropyrido[2,3]pyrazolo[2,4-d][1,2,5]oxadiazepin-1-one (45.00 mg, 128.46 μmol, 1.00 eq, TFA) in DCM (5.00 mL) was added TEA (65.00 mg, 642.32 μmol, 89.04 μL5.00 eq) followed by phenyl N-(3-chloro-4-fluoro-phenyl)carbamate (34.13 mg, 128.46 μmol, 1.00 eq). The mixture was stirred at 30° C. for 16 hr. LCMS showed one main peak with desired Ms detected. The mixture was concentrated in vacuum. The residue was purified by prep-HPLC (HCl) to get N-(3-chloro-4-fluoro-phenyl)-2,4-dimethyl-1-oxo-5,8,9,11-tetrahydro-4H-pyrido

[2,3]pyrazolo[2,4-d][1,2,5]oxadiazepine-10-carboxamide 062 (43.00 mg, 105.23 μmol, 81.91% yield, 99.8% purity) as white solid.
¹H NMR (400 MHz, METHANOL-d₄) δ=7.60 (dd, J=2.5, 6.7 Hz, 1H), 7.28-7.36 (m, 1H), 7.15 (t, J=8.9 Hz, 1H), 4.74 (s, 2H), 4.65-4.69 (m, 1H), 4.59 (dd, J=5.3, 14.4 Hz, 1H), 4.24 (dd, J=5.3, 14.5 Hz, 1H), 3.85 (t, J=5.6 Hz, 2H), 3.30 (s, 3H), 2.85 (t, J=5.6 Hz, 2H), 1.29-1.37 (m, 3H). LCMS: 408[M+1].

Compound 063 was prepared in a manner analogous to Compound 062.

Compound 063: N-(3-chlorophenyl)-2,4-dimethyl-1-oxo-1,4,5,8,9,11-hexahydropyrido[4',3':3,4]pyrazole [5,1-d][1,2,5]oxadiazepine-10(2H)-carboxamide

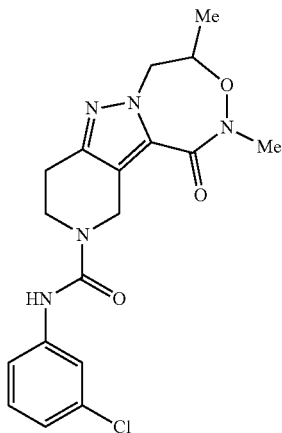 [SMILES: CC1Cn2nc3c(c2C(=O)N(C)O1)CN(C(=O)Nc1cccc(Cl)c1)CC3]

¹H NMR (400 MHz, METHANOL-d₄) δ=7.54 (t, J=2.0 Hz, 1H), 7.29-7.35 (m, 1H), 7.21-7.27 (m, 1H), 7.02 (d, J=7.8 Hz, 1H), 4.74 (s, 2H), 4.64-4.71 (m, 1H), 4.59 (dd, J=5.7, 14.4 Hz, 1H), 4.24 (dd, J=5.5, 14.3 Hz, 1H), 3.85 (t, J=5.9 Hz, 2H), 3.30 (s, 3H), 2.85 (t, J=5.8 Hz, 2H), 1.34 (d, J=6.2 Hz, 3H). LCMS: 390[M+1].

Compound 064: N-(3-chloro-4-fluoro-phenyl)-2,4,4-trimethyl-1-oxo-5,8,9,11-tetrahydro pyrido[2,3]pyrazolo[2,4-d][1,2,5]oxadiazepine-10-carboxamide

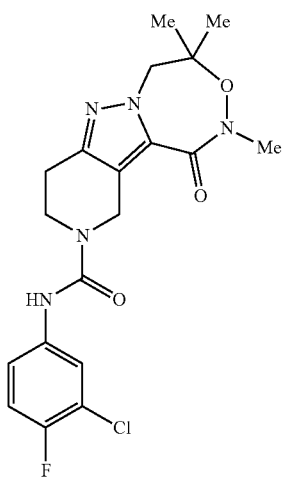 [SMILES: CN1OC(C)(C)Cn2nc3c(c2C1=O)CN(C(=O)Nc1ccc(F)c(Cl)c1)CC3]

Step 1. 2,4,4-trimethyl-8,9,10,11-tetrahydro-5H-pyrido[2,3]pyrazolo[2,4-d][1,2,5]oxadiazepin-1-one. To a solution of tert-butyl 2,4,4-trimethyl-1-oxo-1,4,5,8,9,11-hexahydro-pyrido[4',3':3,4]pyrazolo[5,1-d][1,2,5]oxadiazepine-10(2H)-carboxylate (Intermediate 9, 70.00 mg, 199.77 μmol, 1.00 eq) in DCM (3.00 mL) was added TFA (1.54 g, 13.51 mmol, 1.00 mL, 67.61 eq). The mixture was stirred at 10° C. for 1 hr. TLC (PE:EA=0:1) showed Compound 8 consumed. The mixture was concentrated in vacuum to get the title compound (73.00 mg, crude, TFA) as yellow oil.

Step 2. N-(3-chloro-4-fluoro-phenyl)-2,4,4-trimethyl-1-oxo-5,8,9,11-tetrahydro pyrido[2,3]pyrazolo[2,4-d][1,2,5]oxadiazepine-10-carboxamide. To a solution of 2,4,4-trimethyl-8,9,10,11-tetrahydro-5H-pyrido[2,3]pyrazolo[2,4-d][1,2,5]oxadiazepin-1-one (73.00 mg, 200.37 μmol, 1.00 eq, TFA) and phenyl N-(3-chloro-4-fluoro-phenyl)carbamate (53.23 mg, 200.37 μmol, 1.00 eq) in DCM (10.00 mL) was added TEA (101.38 mg, 1.00 mmol, 138.88 μL 5.00 eq). The mixture was stirred at 10° C. for 16 hr. LCMS showed 50% desired product detected. The mixture was concentrated in vacuum. The residue was purified by prep-HPLC (FA) to get the title compound (50.20 mg, 118.29 μmol, 59.03% yield, 99.4% purity) as white solid. ¹H NMR (400 MHz, CHLOROFORM-d) δ=7.60 (dd, J=2.64, 6.53 Hz, 1H), 7.21 (ddd, J=2.76, 4.02, 8.91 Hz, 1H), 7.04-7.11 (m, 1H), 6.48 (s, 1H), 4.71 (s, 2H), 4.25 (s, 2H), 3.88 (t, J=5.77 Hz, 2H), 3.29 (s, 3H), 2.88 (t, J=5.77 Hz, 2H), 1.39 (s, 6H). LCMS (M+1): 422.

Compound 065: N-(3-chloro-4-fluoro-phenyl)-4-(methoxymethyl)-2-methyl-1-oxo-5,8,9,11-tetrahydro-4H-pyrido[2,3]pyrazolo[2,4-d][1,2,5]oxadiazepine-10-carboxamide

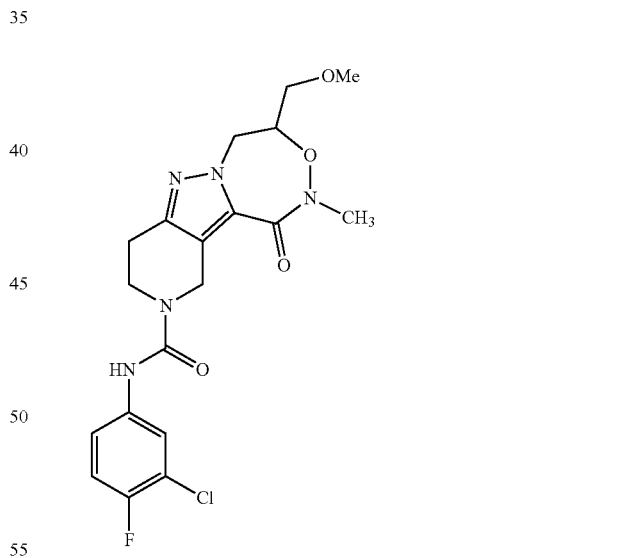

Step 1. Preparation of tert-butyl 4-(methoxymethyl)-2-methyl-1-oxo-5,8,9,11-tetrahydro-4H-pyrido[2,3]pyrazolo[2,4-d][1,2,5]oxadiazepine-10-carboxylate. To a mixture of tert-butyl 4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxylate (Intermediate 1, 50.00 mg, 141.89 μmol, 1.00 eq) in DMF (4.00 mL) was added NaH (8.51 mg, 212.83 μmol, 60% purity, 1.50 eq) in one portion at −40° C. under N₂. The mixture was stirred at −40~−10° C. for 30 min, then MeI (40.28 mg, 283.78 μmol, 17.67 μL 2.00 eq) was added to the mixture. The mixture was stirred at 0°

C. for 1 hour. TLC (ethyl acetate: petroleum ether=2:1) showed the reaction was completed. The residue was poured into water (10 mL) and stirred for 2 min. The aqueous phase was extracted with ethyl acetate (10 mL*2). The combined organic phase was washed with brine (5 mL*2), dried with anhydrous Na$_2$SO$_4$, filtered and concentrated in vacuum. The residue was purified by prep-TLC (ethyl acetate: petroleum ether=2:1) to afford the title compound (30.00 mg, 72.05 μmol, 50.78% yield, 88% purity) as a yellow solid. LCMS: 367 [M+1].

Step 2. Preparation of 4-(methoxymethyl)-2-methyl-4,5,8,9,10,11-hexahydropyrido[2,3]pyrazolo[2,4-d][1,2,5]oxadiazepin-1-one. To a mixture of tert-butyl 4-(methoxymethyl)-2-methyl-1-oxo-5,8,9,11-tetrahydro-4H-pyrido[2,3]pyrazolo[2,4-d][1,2,5]oxadiazepine-10-carboxylate (30.00 mg, 81.88 μmol, 1.00 eq) in DCM (2.00 mL) was added TFA (616.00 mg, 5.40 mmol, 400.00 μL65.98 eq) in one portion at 0° C. under N$_2$. The mixture was stirred at 0° C. for 2 hr. LCMS showed the reaction was completed. The residue was concentrated in vacuum to afford (31.34 mg, crude, TFA) as yellow solid. LCMS: 267 [M+1].

Step 3. Preparation of N-(3-chloro-4-fluoro-phenyl)-4-(methoxymethyl)-2-methyl-1-oxo-5,8,9,11-tetrahydro-4H-pyrido[2,3]pyrazolo[2,4-d][1,2,5]oxadiazepine-10-carboxamide. To a mixture of 4-(methoxymethyl)-2-methyl-4,5,8,9,10,11-hexahydropyrido[2,3] pyrazolo[2,4-d][1,2,5] oxadiazepin-1-one (31.14 mg, 81.88 μmol, 1.00 eq, TFA) and phenyl N-(3-chloro-4-fluoro-phenyl)carbamate (21.75 mg, 81.88 μmol, 1.00 eq) in DCM (4.00 mL) was added TEA (82.85 mg, 818.78 μmol, 113.50 μL10.00 eq) under N$_2$. The mixture was stirred at 25° C. for 10 hours. LCMS showed the reaction was completed. The residue was poured into water (10 mL) and stirred for 2 min. The aqueous phase was extracted with ethyl acetate (10 mL*2). The combined organic phase was washed with brine (10 mL*2), dried with anhydrous Na$_2$SO$_4$, filtered and concentrated in vacuum. The residue was purified by prep-HPLC(FA) to afford the title compound (24.00 mg, 54.16 μmol, 66.14% yield, 98.8% purity) as white solid. $^1$H NMR (400 MHz, CHLOROFORM-d) 7.53-7.63 (m, 1H), 7.14-7.23 (m, 1H), 7.06 (s, 1H), 6.46 (s, 1H), 4.70 (s, 2H), 4.48-4.65 (m, 2H), 4.41 (s, 1H), 3.86 (d, J=12.67 Hz, 2H), 3.57-3.67 (m, 1H), 3.49-3.56 (m, 1H), 3.44 (s, 3H), 3.31 (s, 3H), 2.82-2.93 (m, 2H). LCMS: 438 [M+1].

Compound 066: N-(3-chloro-4-fluoro-phenyl)-2-methyl-1-oxo-5,8,9,11-tetrahydro-4H-pyrido[2,3]pyrazolo[2,4-c][1,2,5]oxadiazepine-10-carboxamide

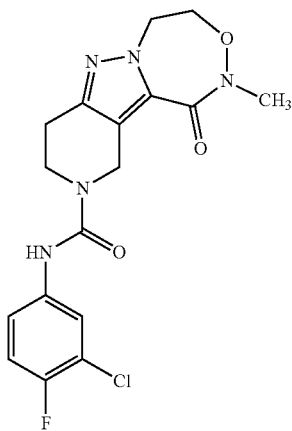 [SMILES: CN1OCCn2nc3c(c2C1=O)CN(C(=O)Nc1ccc(F)c(Cl)c1)CC3]

Step 1. 2-methyl-4,5,8,9,10,11-hexahydropyrido[2,3]pyrazolo[2,4-c][1,2,5]oxadiazepin-1-one. To a mixture of tert-butyl 2-methyl-1-oxo-1,4,5,8,9,11-hexahydropyrido[4',3':3,4]pyrazolo[5,1-d][1,2,5]oxadiazepine-10(2H)-carboxylate (Intermediate 10, 55.00 mg, 170.62 μmol, 1.00 eq) in DCM (2.00 mL) was added TFA (616.00 mg, 5.40 mmol, 400.00 μL31.66 eq) in one portion at 0° C. under N$_2$. The mixture was stirred at 0° C. for 2 hr. TLC (dichloromethane:methanol=10:1) showed the reaction was completed. The residue was concentrated to afford (57.37 mg, 170.61 μmol, 100.00% yield, TFA) as a yellow oil.

Step 2. N-(3-chloro-4-fluoro-phenyl)-2-methyl-1-oxo-5,8,9,11-tetrahydro-4H-pyrido[2,3]pyrazolo[2,4-c][1,2,5]oxadiazepine-10-carboxamide. To a mixture of 2-methyl-4,5,8,9,10,11-hexahydropyrido[2,3]pyrazolo[2,4-c][1,2,5] oxadiazepin-1-one (57.37 mg, 170.61 μmol, 1.00 eq, TFA) and phenyl N-(3-chloro-4-fluoro-phenyl)carbamate (45.33 mg, 170.61 μmol, 1.00 eq) in DCM (4.00 mL) was added TEA (172.64 mg, 1.71 mmol, 236.49 μL10.00 eq) under N$_2$. The mixture was stirred at 25° C. for 10 hours. LCMS showed the reaction was completed. The residue was poured into water (10 mL) and stirred for 2 min. The aqueous phase was extracted with ethyl acetate (10 mL*2). The combined organic phase was washed with brine (10 mL*2), dried with anhydrous Na$_2$SO$_4$, filtered and concentrated in vacuum. The residue was purified by prep-HPLC (FA) to afford the title compound (42.00 mg, 105.05 μmol, 61.58% yield, 98.5% purity) as white solid. $^1$H NMR (400 MHz, CHLOROFORM-d) 7.55-7.62 (m, 1H), 7.16-7.24 (m, 1H), 7.02-7.11 (m, 1H), 6.48-6.56 (m, 1H), 4.71 (s, 2H), 4.52-4.60 (m, 2H), 4.36-4.45 (m, 2H), 3.82-3.93 (m, 2H), 3.31 (s, 3H), 2.87 (s, 2H). LCMS:394 [M+1].

Compound 067: 2-allyl-N-(3-chloro-4-fluoro-phenyl)-1-oxo-5,8,9,11-tetrahydro-4H-pyrido[2,3]pyrazolo[2,4-c][1,2,5]oxadiazepine-10-carboxamide

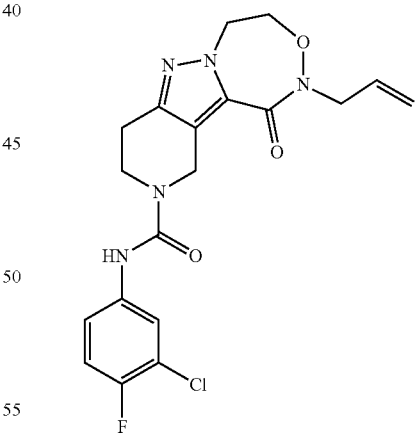

Step 1. 2-allyl-4,5,8,9,10,11-hexahydropyrido[2,3]pyrazolo[2,4-c][1,2,5]oxadiazepin-1-one. To a solution of tert-butyl 2-allyl-1-oxo-1,4,5,8,9,11-hexahydropyrido[4',3':3,4]pyrazolo[5,1-d][1,2,5]oxadiazepine-10(2H)-carboxylate (Intermediate 12, 30.00 mg, 86.11 μmol, 1.00 eq) in DCM (2.00 mL) was added TFA (770.00 mg, 6.75 mmol, 500.00 μL78.43 eq), the reaction mixture was stirred at 10° C. for one hour. TLC indicated Compound 7 was consumed completely, and one major new spot with larger polarity was detected. The solvent was removed on a rotary evaporator to give the title compound (30.00 mg, crude, TFA) as a yellow oil. The crude product was used in next step directly without purification.

Step 2. 2-allyl-N-(3-chloro-4-fluoro-phenyl)-1-oxo-5,8,9,11-tetrahydro-4H-pyrido[2,3]pyrazolo[2,4-c][1,2,5]oxadiazepine-10-carboxamide. To a solution of 2-allyl-4,5,8,9,10,11-hexahydropyrido[2,3]pyrazolo[2,4-c][1,2,5]oxadiazepin-1-one (30.00 mg, 82.80 μmol, 1.00 eq, TFA) in DCM (2.00 mL) was added TEA (33.52 mg, 331.22 μmol, 45.91 μL 4.00 eq), followed by phenyl N-(3-chloro-4-fluoro-phenyl)carbamate (22.00 mg, 82.80 μmol, 1.00 eq). The reaction mixture was stirred at 10° C. for 16 hours. LCMS showed Compound 8 was consumed completely and one main peak with desired MS was detected. The mixture was extracted with DCM (30 mL*2) and water (20 mL), the organic phase was dried with anhydrous $Na_2SO_4$, filtered and concentrated in vacuum. Further purification by prep-HPLC(FA) to give the title compound (32.60 mg, 75.68 μmol, 91.41% yield, 97.47% purity) as a white solid. $^1$H NMR (400 MHz, CHLOROFORM-d) δ=7.56-7.58 (dd, J=6.54, 2.63 Hz, 1H) 7.18-7.21 (m, 1H) 7.03-7.07 (m, 1H) 6.55 (s, 1H) 5.92-5.97 (ddt, J=16.93, 10.30, 6.31, 6.31 Hz, 1H) 5.32-5.34 (m, 2H) 4.71 (s, 2H) 4.54-4.57 (m, 2H) 4.36-4.39 (m, 2H) 4.28-4.30 (d, J=6.36 Hz, 2H) 3.85-3.87 (t, J=5.81 Hz, 2H) 2.85-2.87 (t, J=5.75 Hz, 2H). LCMS: 420/422 [M+1].

Compound 068: N-(3-chloro-4-fluoro-phenyl)-1-oxo-2-propyl-5,8,9,11-tetrahydro-4H-pyrido[2,3]pyrazolo[2,4-c][1,2,5]oxadiazepine-10-carboxamide

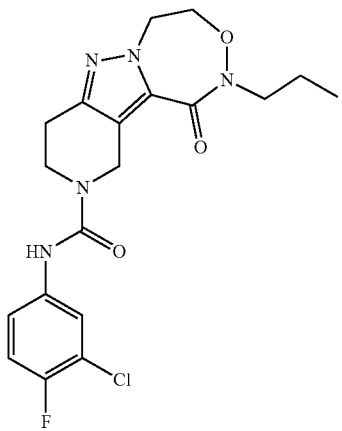 [SMILES: CCCN1OCCn2nc3c(c2C1=O)CN(C(=O)Nc1ccc(F)c(Cl)c1)CC3]

Step 1. tert-butyl 1-oxo-2-propyl-5,8,9,11-tetrahydro-4H-pyrido[2,3] pyrazolo[2,4-c][1,2,5]oxadiazepine-10-carboxylate. A mixture of tert-butyl 2-allyl-1-oxo-5,8,9,11-tetrahydro-4H-pyrido[2,3]pyrazolo [2,4-c][1,2,5]oxadiazepine-10-carboxylate (Compound 067, 40.00 mg, 114.81 μmol, 1.00 eq) and Pd/C (20.00 mg, 10% purity) in MeOH (20.00 mL) was stirred under $H_2$ (15 psi) at 10° C. for 16 hours. LCMS showed Compound 7 was consumed completely and one main peak with desired MS was detected. The reaction mixture was filtered and the filter was concentrated to give the title compound (38.00 mg, 108.44 μmol, 94.46% yield) as a yellow oil. LCMS: 373 [M+23].

Step 2. 2-propyl-4,5,8,9,10,11-hexahydropyrido[2,3]pyrazolo[2,4-c][1,2,5]oxadiazepin-1-one. To a solution of tert-butyl 1-oxo-2-propyl-5,8,9,11-tetrahydro-4H-pyrido[2,3] pyrazolo[2,4-c][1,2,5]oxadiazepine-10-carboxylate (38.00 mg, 108.44 μmol, 1.00 eq) in DCM (2.00 mL) was added TFA (1.54 g, 13.51 mmol, 1.00 mL, 124.55 eq). The reaction mixture was stirred at 10° C. for one hour. TLC indicated Compound 9 was consumed completely, and one major new spot with larger polarity was detected. The solvent was removed on a rotary evaporator to give (38.00 mg, crude, TFA) as a yellow oil, which was used in next step directly without further purification.

Step 3. N-(3-chloro-4-fluoro-phenyl)-1-oxo-2-propyl-5,8,9,11-tetrahydro-4H-pyrido[2,3]pyrazolo[2,4-c][1,2,5]oxadiazepine-10-carboxamide. To a solution of 2-propyl-4,5,8,9,10,11-hexahydropyrido[2,3]pyrazolo[2,4-c][1,2,5]oxadiazepin-1-one (38.00 mg, 104.30 μmol, 1.00 eq, TFA) in DCM (2.00 mL) was added TEA (42.22 mg, 417.20 μmol, 57.84 μL 4.00 eq), followed by phenyl N-(3-chloro-4-fluoro-phenyl)carbamate (27.71 mg, 104.30 μmol, 1.00 eq). The reaction mixture was stirred at 10° C. for 16 hours. LCMS showed Compound 10 was consumed completely and one main peak with desired MS was detected. The mixture was extracted with DCM (30 mL*2) and water (20 mL), the organic phase was dried with anhydrous $Na_2SO_4$, filtered and concentrated in vacuum. The residue was purification by prep-HPLC(FA) to give the title compound (35.39 mg, 82.06 μmol, 78.67% yield, 97.81% purity) was obtained as a white solid. $^1$H NMR (400 MHz, CHLOROFORM-d) δ=7.56-7.58 (dd, J=6.53, 2.63 Hz, 1H) 7.17-7.19 (m, 1H) 7.03-7.08 (m, 1H) 6.52 (s, 1H) 4.70 (s, 2H) 4.54-4.57 (m, 2H) 4.38-4.41 (m, 2H) 3.85-3.88 (t, J=5.77 Hz, 2H) 3.64-3.68 (m, 2H) 2.85-2.87 (t, J=5.77 Hz, 2H) 1.74-1.83 (m, J=7.38 Hz, 2H) 1.00-1.04 (t, J=7.40 Hz, 3H). LCMS: 422/424 [M+1].

Compound 069_E1: (4S*,9S*)—N-(3-chloro-4-fluorophenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide

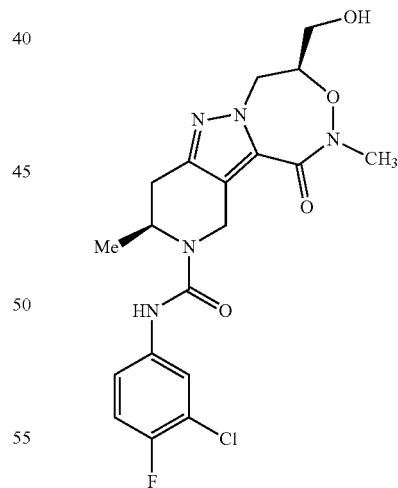

Step 1. 4-(hydroxymethyl)-2,9-dimethyl-4,5,8,9,10,11-hexahydropyrido[2,3]pyrazolo[2,4-d][1,2,5]oxadiazepin-1-one. To a mixture of tert-butyl 4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxylate (Intermediate 14, 100.00 mg, 272.92 μmol, 1.00 eq) in DCM (2.00 mL) was added TFA (616.00 mg, 5.40 mmol, 400.00 μL 19.80 eq) in one portion at 0° C. under $N_2$. The mixture was stirred at 0° C. for 2 hr. TLC and LCMS showed the reaction was completed. The mixture was concentrated in vacuum to afford the title compound (103.80 g, crude, TFA) as a yellow oil. LCMS: 267 [M+1].

Step 2. (4S*,9S*)—N-(3-chloro-4-fluorophenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide. To a mixture of 4-(hydroxymethyl)-2,9-dimethyl-4,5,8,9,10,11-hexahydropyrido[2,3]pyrazolo[2,4-d][1,2,5]oxadiazepin-1-one (103.80 mg, 272.93 µmol, 1.00 eq, TFA) and phenyl N-(3-chloro-4-fluoro-phenyl)carbamate (72.51 mg, 272.93 µmol, 1.00 eq) in DCM (6.00 mL) was added TEA (276.18 mg, 2.73 mmol, 378.32 µL 10.00 eq) under $N_2$. The mixture was stirred at 25° C. for 10 hours. LCMS and TLC (dichloromethane:methanol=10:1) showed the reaction was completed. The residue was poured into water (10 mL) and stirred for 2 min. The aqueous phase was extracted with ethyl acetate (10 mL*2). The combined organic phase was washed with brine (10 mL*2), dried with anhydrous $Na_2SO_4$, filtered and concentrated in vacuum. The residue was purified by silica gel chromatography (dichloromethane:methanol=100/1, 50/1) to afford the title compound (98.00 mg, 218.90 µmol, 80.20% yield, 97.8% purity) as a yellow solid, which was resolved by SFC (Instrument: SFC Waters 80_Q Column: OD-10 um. Mobile phase: A for $CO_2$ and B for Methanol (0.1% $NH_3$ $H_2O$) Isocratic: B 25%. Flow rate: 55 mL/min. Back pressure: 100 bar. Column temperature: 35° C.; Wavelength: 220 nm) to give two fractions. The first fraction was separated by SFC (Instrument: SFC Thar_80_Q. Column: OJ-5 um. Mobile phase: A for $CO_2$ and B for Isopropanol (0.1% $NH_3H_2O$). Isocratic: B 25%. Flow rate: 55 mL/min. Back pressure: 100 bar. Column temperature: 35° C. Wavelength: 220 nm) to give Compound 070_E1(8.68 mg, 95.8% purity) and Compound 069_E2 (20.43 mg, 98.0% purity) as a white solid. LCMS: 438 [M+1]. $^1$H NMR (400 MHz, CHLOROFORM-d) 7.55-7.63 (m, 1H), 7.16-7.24 (m, 1H), 7.02-7.10 (m, 1H), 6.43-6.52 (m, 1H), 5.09-5.21 (m, 1H), 4.80-4.93 (m, 1H), 4.52-4.65 (m, 2H), 4.33-4.50 (m, 2H), 3.74-3.96 (m, 2H), 3.34 (s, 3H), 2.98-3.10 (m, 1H), 2.63-2.74 (m, 1H), 1.82-1.99 (m, 1H), 1.18 (d, J=6.90 Hz, 3H).

* pure but unknown stereochemistry

Compound 069_E2: (4R*,9S*)—N-(3-chloro-4-fluorophenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS: 438 [M+1]. $^1$H NMR (400 MHz, CHLOROFORM-d) 7.53-7.64 (m, 1H), 7.16-7.23 (m, 1H), 7.02-7.12 (m, 1H), 6.42-6.50 (m, 1H), 5.07-5.18 (m, 1H), 4.77-4.86 (m, 1H), 4.38-4.66 (m, 4H), 3.71-3.93 (m, 2H), 3.33 (s, 3H), 2.97-3.10 (m, 1H), 2.68 (d, J=15.94 Hz, 1H), 1.85-1.98 (m, 1H), 1.19 (d, J=6.90 Hz, 3H).

* pure but unknown stereochemistry

The second fraction was separated by SFC (Instrument: SFC Thar_80_Q. Column: OJ-5 um. Mobile phase: A for $CO_2$ and B for Methanol (0.1% $NH_3H_2O$). Isocratic: B 25%. Flow rate: 55 mL/min. Back pressure: 100 bar. Column temperature: 35° C. Wavelength: 220 nm) to give Compound 069_E3(15.37 mg, 97.3% purity) and Compound 069_E4 (21.86 mg, 99.26% purity) as white solid.

Compound 069_E3: (4R*,9R*)—N-(3-chloro-4-fluorophenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS: 438 [M+1]. $^1$H NMR (400 MHz, CHLOROFORM-d) 7.55-7.65 (m, 1H), 7.16-7.23 (m, 1H), 7.01-7.13 (m, 1H), 6.40-6.52 (m, 1H), 5.07-5.23 (m, 1H), 4.80-4.92 (m, 1H), 4.52-4.63 (m, 2H), 4.34-4.50 (m, 2H), 3.74-3.96 (m, 2H), 3.02 (d, J=5.77 Hz, 1H), 2.71 (s, 1H), 1.80-1.96 (m, 1H), 1.18 (d, J=6.90 Hz, 3H).

* pure but unknown stereochemistry

Compound 069_E4: (4S*,9R*)—N-(3-chloro-4-fluorophenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS: 438 [M+1]. $^1$H NMR (400 MHz, CHLOROFORM-d) 7.54-7.65 (m, 1H), 7.15-7.23 (m, 1H), 7.01-7.11 (m, 1H), 6.40-6.52 (m, 1H), 5.06-5.19 (m, 1H), 4.75-4.86 (m, 1H), 4.36-4.65 (m, 4H), 3.71-3.91 (m, 2H), 2.98-3.10 (m, 1H), 2.68 (d, J=15.69 Hz, 1H), 1.84-2.01 (m, 1H), 1.19 (d, J=6.90 Hz, 3H).

* pure but unknown stereochemistry

Compound 070 N-(3-chlorophenyl)-4-(hydroxymethyl)-2,9-dimethyl-1-oxo-5,8,9,11-tetrahydro-4H-pyrido[2,3]pyrazolo[2,4-d][1,2,5]oxadiazepine-10-carboxamide

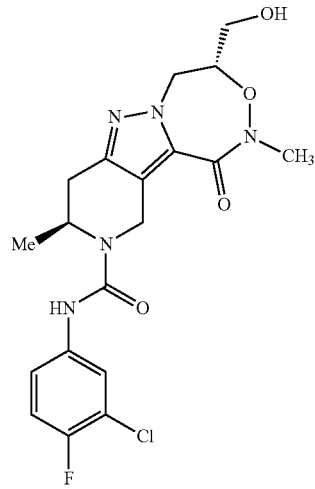 [SMILES: C[C@H]1Cc2nn3c(c2CN1C(=O)Nc1ccc(F)c(Cl)c1)C(=O)N(C)O[C@@H](CO)C3]

Obtained from the above-described mixture.

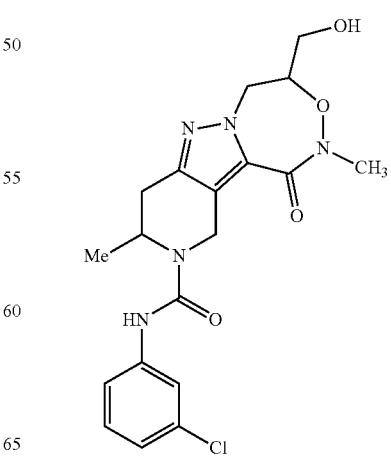

To a mixture of tert-butyl 6-methyl-3-(methyl(oxetan-3-yloxy)carbamoyl)-1,4,6,7-tetrahydro-5H-pyrazolo[4,3-c]pyridine-5-carboxylate (Intermediate 15, 40.00 mg, 109.17 µmol, 1.00 eq) in DCM (1.00 mL) was added TFA (770.00 mg, 6.75 mmol, 500.00 µL61.86 eq) in one portion at 0° C. under N₂. The mixture was stirred at 0° C. for 2 hours. LCMS and TLC (dichloromethane:methanol=5:1) showed the reaction was completed. The reaction mixture was treated with TEA (1 mL) at −78° C. To the resulting mixture, was added phenyl N-(3-chlorophenyl)carbamate (27.04 mg, 109.16 µmol, 1.00 eq) in DCM (4.00 mL), followed by TEA (110.46 mg, 1.09 mmol, 151.32 µL10.00 eq) under N₂. The mixture was stirred at 25° C. for 10 hours. LCMS showed the reaction was completed. The residue was poured into water (10 mL) and stirred for 5 min. The aqueous phase was extracted with ethyl acetate (10 mL*2). The combined organic phase was washed with brine (10 mL*2), dried with anhydrous Na₂SO₄, filtered and concentrated in vacuum. The residue was purified by prep-HPLC (FA) to afford the title compound (17.00 mg, 40.17 µmol, 36.80% yield, 99.2% purity) as a white solid. ¹H NMR (400 MHz, DMSO-d₆) δ 8.79-8.94 (m, 1H), 7.62 (s, 1H), 7.35-7.42 (m, 1H), 7.22-7.29 (m, 1H), 6.93-7.02 (m, 1H), 5.13-5.22 (m, 1H), 4.96-5.07 (m, 1H), 4.80-4.91 (m, 1H), 4.38-4.60 (m, 2H), 4.09-4.34 (m, 2H), 3.44-3.69 (m, 2H), 3.23 (d, J=3.14 Hz, 3H), 2.84-2.95 (m, 1H), 2.58 (dd, J=4.20, 15.75 Hz, 1H), 1.09 (d, J=6.78 Hz, 3H). LCMS: 420 [M+1].

Compound 071: methyl 10-[(3-chloro-4-fluoro-phenyl)carbamoyl]-2-methyl-1-oxo-5,8,9,11-tetrahydro-4H-pyrido[2,3]pyrazolo[2,4-d][1,2,5]oxadiazepine-4-carboxylate

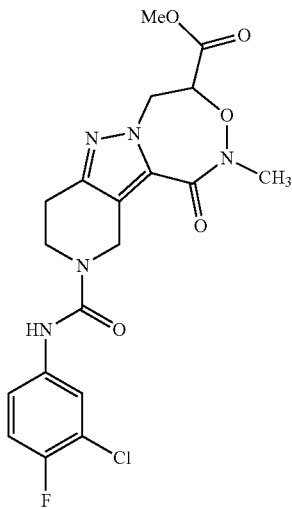 [SMILES: CN1OC(C(N)=O)Cn2nc3c(c2C1=O)CN(C(=O)Nc1ccc(F)c(Cl)c1)CC3]

To a mixture of 10-(tert-butyl) 4-methyl 2-methyl-1-oxo-1,4,5,8,9,11-hexahydropyrido[4',3':3,4]pyrazolo[5,1-d][1,2,5]oxadiazepine-4,10(2H)-dicarboxylate (Intermediate 16, 110.00 mg, 289.18 µmol, 1.00 eq) in DCM (2.00 mL) was added TFA (770.00 mg, 6.75 mmol, 500.00 µL23.35 eq) in one portion at 0° C. under N₂. The mixture was stirred at 0° C. for 2 hr. TLC (Dichloromethane:Methanol=10:1) showed the reaction was completed. The residue was concentrated in vacuum to give 2-methyl-1-oxo-4,5,8,9,10,11-hexahydropyrido[2,3]pyrazolo[2,4-d][1,2,5]oxadiazepine-4-carboxylate (114.02 mg, 289.17 µmol, 1.00 eq, TFA) as yellow oil.

The resulting oil and phenyl N-(3-chloro-4-fluoro-phenyl)carbamate (76.82 mg, 289.17 µmol, 1.00 eq) was dissolved in DCM (4.00 mL) and added TEA (292.61 mg, 2.89 mmol, 400.84 µL10.00 eq) under N₂. The mixture was stirred at 25° C. for 10 hours. LCMS showed the reaction was completed. The residue was poured into water (10 mL) and stirred for 2 min. The aqueous phase was extracted with ethyl acetate (10 mL*2). The combined organic phase was washed with brine (10 mL*2), dried with anhydrous Na₂SO₄, filtered and concentrated in vacuum. The residue was purified by prep-HPLC(FA) to afford the title compound (60.00 mg, 131.99 µmol, 45.65% yield, 99.4% purity) as white solid. LCMS: 452[M+1]. ¹H NMR (400 MHz, CHLOROFORM-d) 7.57 (dd, J=2.64, 6.53 Hz, 1H), 7.15-7.24 (m, 1H), 7.01-7.11 (m, 1H), 6.48 (s, 1H), 4.92 (s, 2H), 4.74 (s, 1H), 4.50-4.68 (m, 2H), 3.90 (s, 3H), 3.86 (s, 2H), 3.40 (s, 3H), 2.77-2.98 (m, 2H).

Compound 072: N10-(3-chloro-4-fluoro-phenyl)-2-methyl-1-oxo-5,8,9,11-tetrahydro-4H-pyrido[2,3]pyrazolo[2,4-d][1,2,5]oxadiazepine-4,10-dicarboxamide

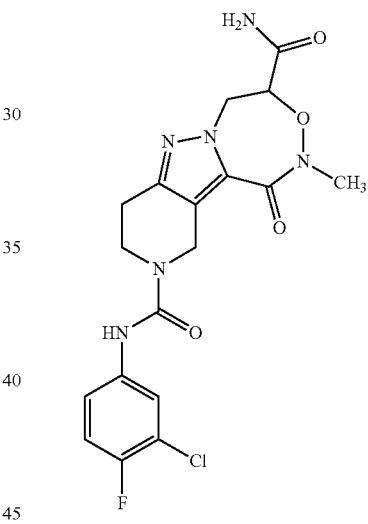

Step 1. 10-[(3-chloro-4-fluoro-phenyl)carbamoyl]-2-methyl-1-oxo-5,8,9,11-tetrahydro-4H-pyrido[2,3]pyrazolo[2,4-d][1,2,5]oxadiazepine-4-carboxylic acid. To a mixture of methyl 10-[(3-chloro-4-fluoro-phenyl)carbamoyl]-2-methyl-1-oxo-5,8,9,11-tetrahydro-4H-pyrido[2,3]pyrazolo[2,4-d][1,2,5]oxadiazepine-4-carboxylate (Compound 071, 40.00 mg, 88.53 µmol, 1.00 eq) in DCE (4.00 mL) was added hydroxyl (trimethyl) stannane (80.04 mg, 442.65 µmol, 5.00 eq) in one portion under N₂. The mixture was stirred at 30° C. for 12 hours. LCMS showed the reaction was completed. The residue was concentrated in vacuum. The residue was purified by prep-HPLC(FA) to afford the title compound (30.00 mg, 65.13 µmol, 73.57% yield, 95.05% purity) as a yellow solid. ¹H NMR (400 MHz, CHLOROFORM-d) δ 7.52-7.58 (m, 1H), 7.16-7.23 (m, 1H), 7.02-7.11 (m, 1H), 6.47-6.56 (m, 1H), 4.84-5.03 (m, 1H), 4.59-4.78 (m, 1H), 3.85 (s, 1H), 3.40 (s, 3H), 2.87 (br d, J=5.50 Hz, 1H). LCMS: 438[M+1].

Step 2. N10-(3-chloro-4-fluoro-phenyl)-2-methyl-1-oxo-5,8,9,11-tetrahydro-4H-pyrido[2,3]pyrazolo[2,4-d][1,2,5]oxadiazepine-4,10-dicarboxamide. To a mixture of 10-[(3- chloro-4-fluoro-phenyl)carbamoyl]-2-methyl-1-oxo-5,8,9,11-tetrahydro-4H-pyrido[2,3]pyrazolo[2,4-d][1,2,5]oxadiazepine-4-carboxylic acid (20.00 mg, 45.68 μmol, 1.00 eq) and NH₄Cl (24.44 mg, 456.82 μmol, 15.97 μL10.00 eq) in DMF (3.00 mL) was added HOBt (9.26 mg, 68.52 μmol, 1.50 eq), PyBOP (35.66 mg, 68.52 μmol, 1.50 eq) and DIPEA (88.56 mg, 685.23 μmol, 119.67 μL15.00 eq) in one portion under $N_2$. The mixture was stirred at 30° C. for 12 hours. LCMS showed the reaction was completed, and desired product was detected. The residue was poured into water (10 mL). The aqueous phase was extracted with ethyl acetate (10 mL*2). The combined organic phase was washed with brine (10 mL*2), dried with anhydrous $Na_2SO_4$, filtered and concentrated in vacuum. The residue was purified by prep-HPLC (FA) to afford the title compound (14.00 mg, 31.92 μmol, 69.88% yield, 99.6% purity) as a white solid. ¹H NMR (400 MHz, CHLOROFORM-d) 7.54-7.61 (m, 1H), 7.15-7.23 (m, 1H), 7.01-7.11 (m, 1H), 6.44-6.55 (m, 1H), 6.01-6.12 (m, 1H), 5.55-5.67 (m, 1H), 4.86-5.01 (m, 2H), 4.64-4.79 (m, 3H), 3.71-3.98 (m, 2H), 3.37 (s, 3H), 2.87 (s, 2H). LCMS: 437 [M+1].

Compound 073: N10-(3-chloro-4-fluoro-phenyl)-N4,2-dimethyl-1-oxo-5,8,9,11-tetrahydro-4H-pyrido[2,3]pyrazolo[2,4-d][1,2,5]oxadiazepine-4,10-dicarboxamide

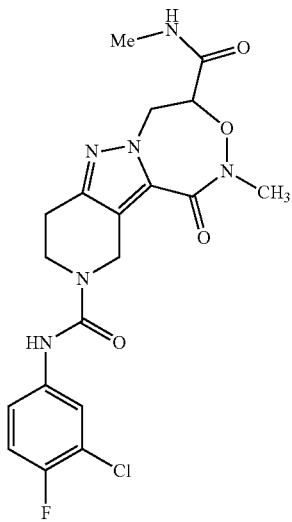 [SMILES: CNC(=O)C1Cn2nc3c(c2C(=O)N(C)O1)CN(C(=O)Nc1ccc(F)c(Cl)c1)CC3]

Step 1. 10-[(3-chloro-4-fluoro-phenyl)carbamoyl]-2-methyl-1-oxo-5,8,9,11-tetrahydro-4H-pyrido[2,3]pyrazolo[2,4-d][1,2,5]oxadiazepine-4-carboxylic acid. To a mixture of methyl 10-[(3-chloro-4-fluoro-phenyl)carbamoyl]-2-methyl-1-oxo-5,8,9,11-tetrahydro-4H-pyrido[2,3]pyrazolo[2,4-d][1,2,5]oxadiazepine-4-carboxylate (Compound 071, 40.00 mg, 88.53 μmol, 1.00 eq) in DCE (4.00 mL) was added hydroxyl (trimethyl) stannane (80.04 mg, 442.65 μmol, 5.00 eq) in one portion under $N_2$. The mixture was stirred at 30° C. for 12 hours. LCMS showed the reaction was completed. The residue was concentrated in vacuum. The residue was purified by prep-HPLC(FA) to afford the title compound (30.00 mg, 65.13 μmol, 73.57% yield, 95.05% purity) as a yellow solid. ¹H NMR (400 MHz, CHLOROFORM-d) δ=7.52-7.58 (m, 1H), 7.16-7.23 (m, 1H), 7.02-7.11 (m, 1H), 6.47-6.56 (m, 1H), 4.84-5.03 (m, 1H), 4.59-4.78 (m, 1H), 3.85 (s, 1H), 3.40 (s, 3H), 2.87 (br d, J=5.50 Hz, 1H). LCMS: 438[M+1].

Step 2. N10-(3-chloro-4-fluoro-phenyl)-N4,2-dimethyl-1-oxo-5,8,9,11-tetrahydro-4H-pyrido[2,3]pyrazolo[2,4-d][1,2,5]oxadiazepine-4,10-dicarboxamide. To a mixture of 10-[(3-chloro-4-fluoro-phenyl)carbamoyl]-2-methyl-1-oxo-5,8,9,11-tetrahydro-4H-pyrido[2,3]pyrazolo[2,4-d][1,2,5]oxadiazepine-4-carboxylic acid (25.00 mg, 57.10 μmol, 1.00 eq) and methanamine ($MeNH_2$) (38.55 mg, 571.00 μmol, 10.00 eq, HCl) in DMF (2.00 mL) was added HATU (32.57 mg, 85.65 μmol, 1.50 eq) and DIPEA (110.69 mg, 856.50 μmol, 149.58 μL15.00 eq) in one portion under $N_2$. The mixture was stirred at 30° C. for 12 hours. LCMS showed the reaction was not reacted. The mixture was stirred at 30° C. for another 12 hours, LCMS showed the reaction was completed. The residue was poured into water (10 mL) and stirred for 2 min. The aqueous phase was extracted with ethyl acetate (10 mL*2). The combined organic phase was washed with brine (10 mL*2), dried with anhydrous $Na_2SO_4$, filtered and concentrated in vacuum. The residue was purified by prep-HPLC (FA) to afford the title compound (20.00 mg, 44.01 μmol, 77.07% yield, 99.2% purity) as white solid. ¹H NMR (400 MHz, METHANOL-d₄) 7.56-7.64 (m, 1H), 7.26-7.36 (m, 1H), 7.08-7.21 (m, 1H), 4.98-5.05 (m, 1H), 4.74 (s, 4H), 3.72-3.96 (m, 2H), 3.34 (br. s., 4H), 2.80-2.90 (m, 2H), 2.76 (s, 3H). LCMS: 451 [M+1].

Compound 074: N10-(3-chloro-4-fluoro-phenyl)-N4,N4,2-trimethyl-1-oxo-5,8,9,11-tetrahydro-4H-pyrido[2,3]pyrazolo[2,4-d][1,2,5]oxadiazepine-4,10-dicarboxamide

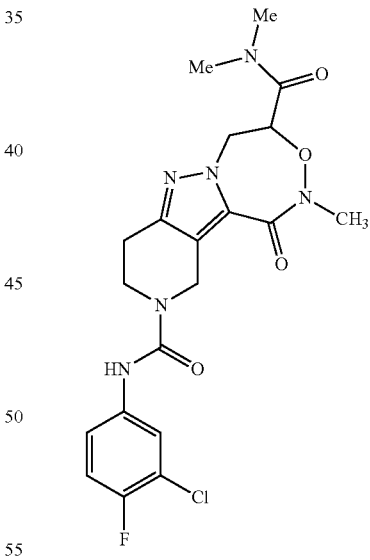

Step 1. 10-[(3-chloro-4-fluoro-phenyl)carbamoyl]-2-methyl-1-oxo-5,8,9,11-tetrahydro-4H-pyrido[2,3]pyrazolo[2,4-d][1,2,5]oxadiazepine-4-carboxylic acid. To a mixture of methyl 10-[(3-chloro-4-fluoro-phenyl)carbamoyl]-2-methyl-1-oxo-5,8,9,11-tetrahydro-4H-pyrido[2,3]pyrazolo[2,4-d][1,2,5]oxadiazepine-4-carboxylate (Compound 071, 40.00 mg, 88.53 μmol, 1.00 eq) in DCE (4.00 mL) was added hydroxyl (trimethyl) stannane (80.04 mg, 442.65 μmol, 5.00 eq) in one portion under $N_2$. The mixture was stirred at 30° C. for 12 hours. LCMS showed the reaction was completed. The residue was concentrated in vacuum.

The residue was purified by prep-HPLC(FA) to afford the title compound (30.00 mg, 65.13 μmol, 73.57% yield, 95.05% purity) as a yellow solid. $^1$H NMR (400 MHz, CHLOROFORM-d) δ=7.52-7.58 (m, 1H), 7.16-7.23 (m, 1H), 7.02-7.11 (m, 1H), 6.47-6.56 (m, 1H), 4.84-5.03 (m, 1H), 4.59-4.78 (m, 1H), 3.85 (s, 1H), 3.40 (s, 3H), 2.87 (br d, J=5.50 Hz, 1H). LCMS: 438[M+1].

Step 2. N10-(3-chloro-4-fluoro-phenyl)-N4,N4,2-trimethyl-1-oxo-5,8,9,11-tetrahydro-4H-pyrido[2,3]pyrazolo[2,4-d][1,2,5]oxadiazepine-4,10-dicarboxamide. To a mixture of 10-[(3-chloro-4-fluoro-phenyl)carbamoyl]-2-methyl-1-oxo-5,8,9,11-tetrahydro-4H-pyrido[2,3]pyrazolo[2,4-d][1,2,5]oxadiazepine-4-carboxylic acid (20.00 mg, 45.68 μmol, 1.00 eq) and N-methylmethanamine (18.62 mg, 228.40 μmol, 20.92 μL 5.00 eq, HCl) in DMF (5.00 mL) was added HATU (26.05 mg, 68.52 μmol, 1.50 eq) and DIPEA (88.56 mg, 685.20 μmol, 119.68 μL 15.00 eq) in one portion under N$_2$. The mixture was stirred at 30° C. for 12 hours. LCMS showed the reaction was completed, and the desired product was detected. The residue was poured into water (10 mL). The aqueous phase was extracted with ethyl acetate (10 mL*2). The combined organic phase was washed with brine (10 mL*2), dried with anhydrous Na$_2$SO$_4$, filtered and concentrated in vacuum. The residue was purified by prep-HPLC(FA) to afford the title compound (16.00 mg, 33.94 μmol, 74.29% yield, 98.6% purity) as a white solid. $^1$H NMR (400 MHz, METHANOL-d$_4$) 7.53-7.66 (m, 1H), 7.22-7.39 (m, 1H), 7.06-7.19 (m, 1H), 5.28-5.40 (m, 1H), 4.89-4.95 (m, 1H), 4.72 (s, 2H), 4.54-4.66 (m, 1H), 3.70-3.97 (m, 2H), 3.21 (d, J=9.41 Hz, 6H), 3.02 (s, 3H), 2.77-2.89 (m, 2H). LCMS: 465 [M+1].

Compound 075: (9R)—N-(3-chloro-4-fluoro-phenyl)-2,9-dimethyl-1-oxo-5,8,9,11-tetrahydro-4H-pyrido[2,3]pyrazolo[2,4-c][1,2,5]oxadiazepine-10-carboxamide

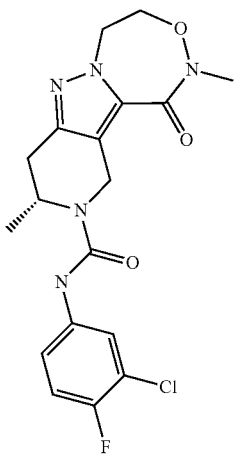

Step 1. (9R)-2,9-dimethyl-4,5,8,9,10,11-hexahydropyrido[2,3]pyrazolo[2,4-c][1,2,5]oxadiazepin-1-one. To a solution of tert-butyl (9R)-2,9-dimethyl-1-oxo-5,8,9,11-tetrahydro-4H-pyrido [2,3]pyrazolo[2,4-c][1,2,5]oxadiazepine-10-carboxylate (600.00 mg, 1.78 mmol, 1.00 eq) in DCM (5.00 mL) was added TFA (67.53 mmol, 5.00 mL, 37.94 eq). The mixture was stirred at 10° C. for 1 hr. TLC (petroleum ether:ethyl acetate=0:1) showed the starting material was consumed. The mixture was concentrated in vacuum to get the title compound (640.00 mg, crude, TFA) as yellow oil.

Step 2. (9R)—N-(3-chloro-4-fluoro-phenyl)-2,9-dimethyl-1-oxo-5,8,9,11-tetrahydro-4H-pyrido[2,3]pyrazolo[2,4-c][1,2,5]oxadiazepine-10-carboxamide. To a solution of (9R)-2,9-dimethyl-4,5,8,9,10,11-hexahydropyrido[2,3]pyrazolo [2,4-c][1,2,5]oxadiazepin-1-one (90.00 mg, 256.93 μmol, 1.00 eq, TFA) and phenyl N-(3-chloro-4-fluoro-phenyl)carbamate (71.67 mg, 269.78 μmol, 1.05 eq) in DCM (2.00 mL) was added TEA (78.00 mg, 770.79 μmol, 106.85 μL 3.00 eq). The mixture was stirred at 30° C. for 1 h under N$_2$ atmosphere. TLC (DCM:MeOH=10:1) showed that (9R)-2,9-dimethyl-4,5,8,9,10,11-hexahydropyrido[2,3]pyrazolo[2,4-c][1,2,5]oxadiazepin-1-one was consumed completely and one major spot formed. LCMS indicated that MS of desired product was detected. The mixture was diluted with DCM (10 mL) and washed with HCl (1%, 10 mL*2) and brine (10 mL*1). The organic phase was dried over anhydrous Na$_2$SO$_4$, filtered and concentrated to get the residue. The residue was purified by prep-HPLC (FA) to obtain the title compound (53.00 mg, 129.44 μmol, 50.38% yield, 99.6% purity) as a white solid. LCMS: 408 (M+1). $^1$H NMR (400 MHz, CHLOROFORM-d) δ=7.52-7.62 (m, 1H), 7.16-7.24 (m, 1H), 6.98-7.10 (m, 1H), 6.63 (s, 1H), 5.14 (quin, J=6.45 Hz, 1H), 4.85 (d, J=15.65 Hz, 1H), 4.53-4.59 (m, 2H), 4.35-4.50 (m, 3H), 3.23-3.35 (m, 3H), 3.03 (dd, J=5.81, 15.83 Hz, 1H), 2.67 (d, J=15.77 Hz, 1H), 1.17 (d, J=6.97 Hz, 3H).

Compounds 076, 077, 078, 079, 080, and 081 were prepared in a manner analogous to Compound 075.

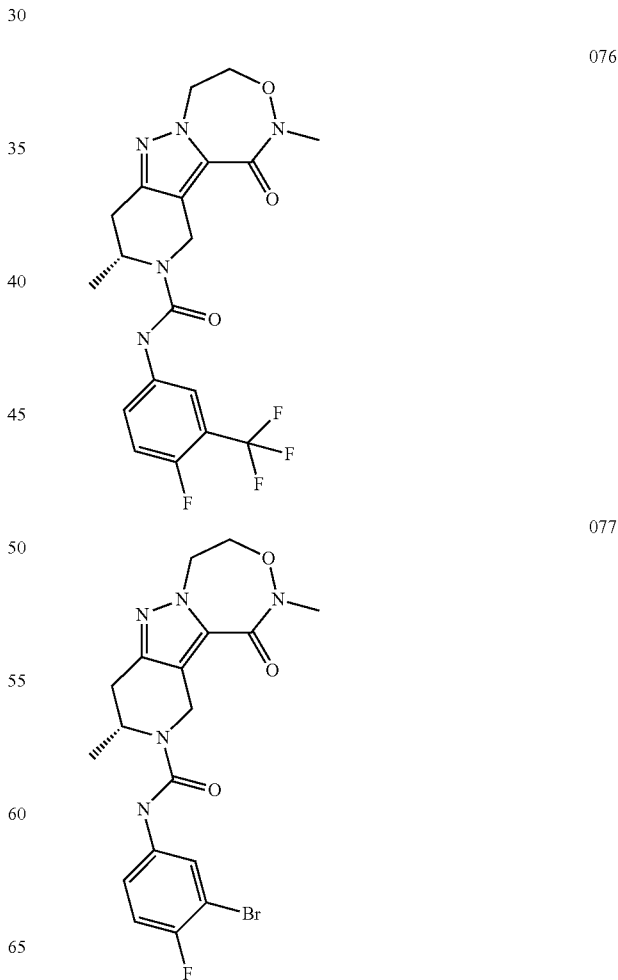

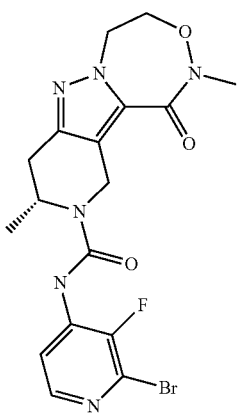

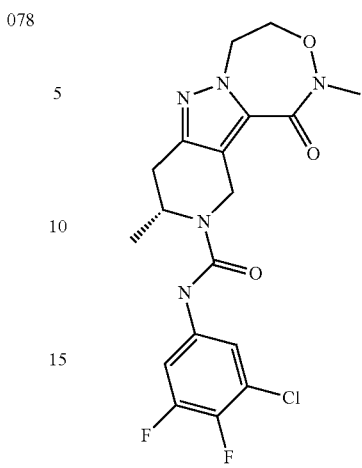

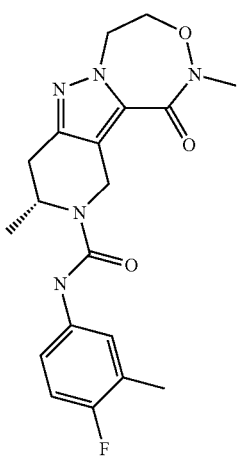

Compound 076: (R)—N-(4-fluoro-3-(trifluoromethyl)phenyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS: 442 (M+1). $^1$H NMR (400 MHz, CHLOROFORM-d) δ=7.68 (dd, J=2.69, 6.11 Hz, 1H), 7.53-7.62 (m, 1H), 7.12 (t, J=9.41 Hz, 1H), 6.72 (s, 1H), 5.15 (quin, J=6.42 Hz, 1H), 4.87 (d, J=15.65 Hz, 1H), 4.52-4.60 (m, 2H), 4.45-4.52 (m, 1H), 4.36-4.45 (m, 2H), 3.25-3.37 (m, 3H), 3.04 (dd, J=5.87, 15.89 Hz, 1H), 2.69 (d, J=15.89 Hz, 1H), 1.18 (d, J=6.97 Hz, 3H).

Compound 077: (R)—N-(3-bromo-4-fluorophenyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS: 452/454. $^1$H NMR (400 MHz, CHLOROFORM-d) δ=7.64-7.77 (m, 1H), 7.24-7.29 (m, 2H), 7.04 (t, J=8.50 Hz, 1H), 6.52-6.62 (m, 1H), 5.14 (quin, J=6.45 Hz, 1H), 4.79-4.92 (m, 1H), 4.53-4.62 (m, 2H), 4.37-4.51 (m, 3H), 3.31 (s, 3H), 3.04 (dd, J=5.81, 15.83 Hz, 1H), 2.68 (d, J=15.77 Hz, 1H), 1.17 (d, J=6.97 Hz, 3H).

Compound 078: (R)—N-(2-bromo-3-fluoropyridin-4-yl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS: 453/455. $^1$H NMR (400 MHz, CHLOROFORM-d) δ=8.10-8.19 (m, 1H), 7.97-8.08 (m, 1H), 6.95-7.11 (m, 1H), 5.00-5.15 (m, 1H), 4.92 (d, J=15.77 Hz, 1H), 4.48-4.61 (m, 3H), 4.31-4.47 (m, 2H), 3.25-3.38 (m, 3H), 2.94-3.13 (m, 1H), 2.63-2.79 (m, 1H), 1.12-1.30 (m, 3H).

Compound 079: (R)—N-(3-cyano-4-fluorophenyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS: 399 (M+1). $^1$H NMR (400 MHz, CHLOROFORM-d) δ=7.75 (dd, J=2.75, 5.44 Hz, 1H), 7.60 (ddd, J=2.81, 4.58, 9.11 Hz, 1H), 7.11 (t, J=8.68 Hz, 1H), 6.94 (s, 1H), 5.11 (quin, J=6.45 Hz, 1H), 4.88 (d, J=15.77 Hz, 1H), 4.52-4.62 (m, 2H), 4.32-4.50 (m, 3H), 3.29 (s, 3H), 2.94-3.08 (m, 1H), 2.61-2.73 (m, 1H), 1.17 (d, J=6.85 Hz, 3H).

Compound 080: (R)—N-(4-fluoro-3-methylphenyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS: 388 (M+1). ¹H NMR (400 MHz, CHLOROFORM-d) δ=7.22-7.28 (m, 1H), 7.05-7.16 (m, 1H), 6.91 (t, J=8.99 Hz, 1H), 6.45 (br s, 1H), 5.15 (quin, J=6.45 Hz, 1H), 4.85 (d, J=15.65 Hz, 1H), 4.51-4.60 (m, 2H), 4.29-4.50 (m, 3H), 3.22-3.38 (m, 3H), 2.96-3.10 (m, 1H), 2.67 (d, J=15.77 Hz, 1H), 2.24 (d, J=1.34 Hz, 3H), 1.17 (d, J=6.85 Hz, 3H).

Compound 081: (R)—N-(3-chloro-4,5-difluorophenyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS: 426. ¹H NMR (400 MHz, CHLOROFORM-d) δ=7.35 (ddd, J=63, 6.45, 11.95 Hz, 1H, 7.22 (td, J=2.43, 5.29 Hz, 1H), 6.70 (s, 1H), 5.12 (quin, J=6.45 Hz, 1H), 4.85 (d, J=15.65 Hz, 1H), 4.52-4.61 (m, 2H), 4.34-4.49 (m, 3H), 3.24-3.35 (m, 3H), 2.95-3.10 (m, 1H), 2.59-2.77 (m, 1H), 1.09-1.22 (m, 3H).

Compound 083: (9R)—N-(4-fluoro-3-methyl-phenyl)-4-(hydroxymethyl)-2,9-dimethyl-1-oxo-5,8,9,11-tetrahydro-4H-pyrido[2,3]pyrazolo[2,4-d][1,2,5]oxadiazepine-10-carboxamide

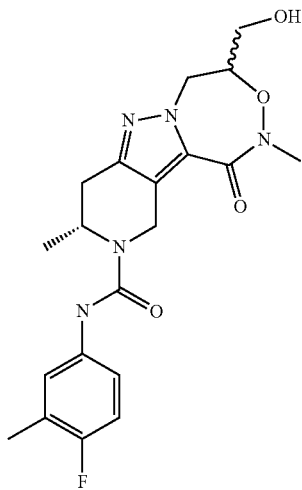

Step 1. (9R)-4-(hydroxymethyl)-2,9-dimethyl-4,5,8,9,10,11-hexahydropyrido[2,3]pyrazolo[2,4-d][1,2,5]oxadiazepin-1-one. To a solution of tert-butyl (9R)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxylate (Intermediate 18, 300.00 mg, (470.00 mg, 1.28 mmol, 1.00 eq) in DCM (5.00 mL) was added TFA (5.55 g, 48.67 mmol, 3.60 mL, 37.94 eq). The mixture was stirred at 10° C. for 1 hr. TLC (Ethyl acetate:MeOH=20:1) showed the starting material was consumed. The mixture was concentrated in vacuum to get the title compound (520.00 mg, crude, TFA) as yellow oil.

Step 2. (9R)—N-(4-fluoro-3-methyl-phenyl)-4-(hydroxymethyl)-2,9-dimethyl-1-oxo-5,8,9,11-tetrahydro-4H-pyrido[2,3]pyrazolo[2,4-d][1,2,5]oxadiazepine-10-carboxamide. To a mixture of (9R)-4-(hydroxymethyl)-2,9-dimethyl-4,5,8,9,10,11-hexahydropyrido [2,3]pyrazolo[2,4-d][1,2,5]oxadiazepin-1-one (138.00 mg, 362.85 μmol, 1.00 eq, TFA) in DCM (2.00 mL) was added TEA (146.87 mg, 1.45 mmol, 201.19 μL4.00 eq), followed by phenyl N-(4-fluoro-3-methyl-phenyl)carbamate (88.99 mg, 362.85 μmol, 1.00 eq), the reaction mixture was stirred at 10° C. for 16 hours. LCMS showed the starting material was consumed completely and one main peak with desired MS was detected. The mixture was extracted with DCM (50 mL*2) and water (30 mL), the organic phase was dried with anhydrous Na₂SO₄, filtered and concentrated in vacuum. 1/3 of the residue was purified by prep-HPLC (FA) to afford the title compound (32.00 mg, 99.24% purity) as white solid. ¹H NMR (400 MHz, CHLOROFORM-d) d ppm δ=7.25 (d, J=2.45 Hz, 1H) 7.11 (dt, J=7.98, 3.90 Hz, 1H) 6.93 (t, J=8.99 Hz, 1H) 6.37 (s, 1H) 5.15 (quin, J=6.30 Hz, 1H) 4.86 (d, J=15.53 Hz, 1H) 4.52-4.62 (m, 2H) 4.34-4.49 (m, 2H) 3.75-3.93 (m, 2H) 3.33 (s, 3H) 3.04 (dd, J=15.77, 5.87 Hz, 1H) 2.68 (d, J=15.65 Hz, 1H) 2.26 (d, J=1.59 Hz, 3H) 1.82-2.04 (m, 1H) 1.17 (d, J=6.97 Hz, 3H). LCMS: 418 [M+].

Compounds 069, 082, 084, 089, 090, and 091 were prepared in an analogous manner to Compound 083.

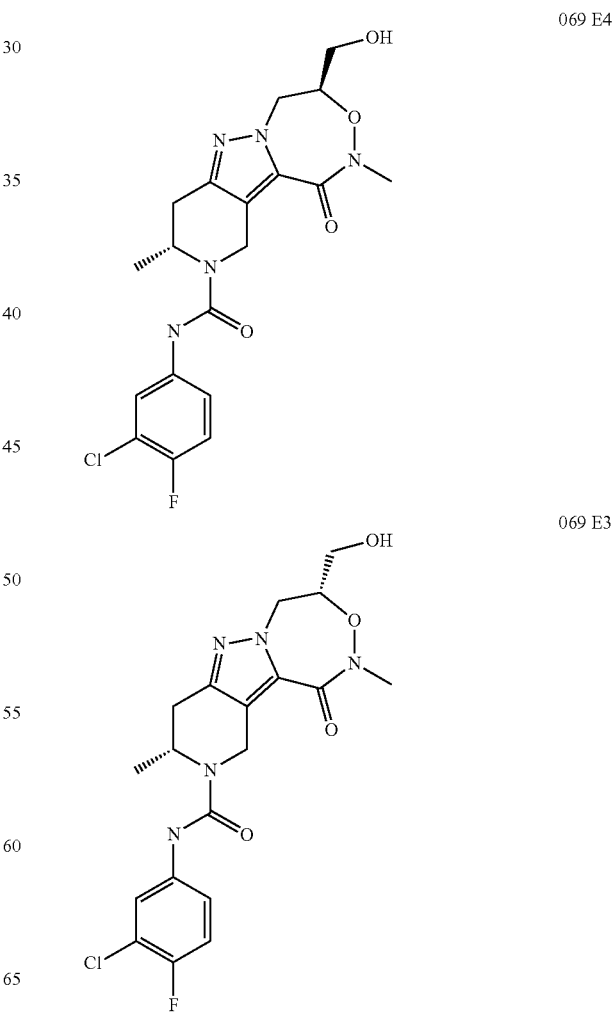

-continued
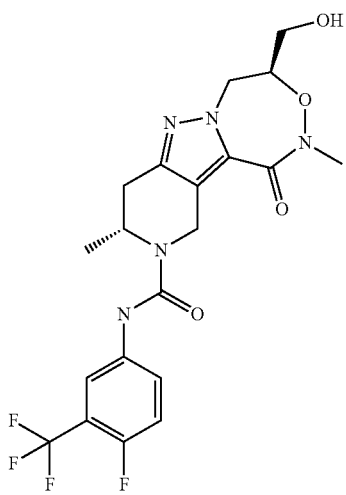
082 E1
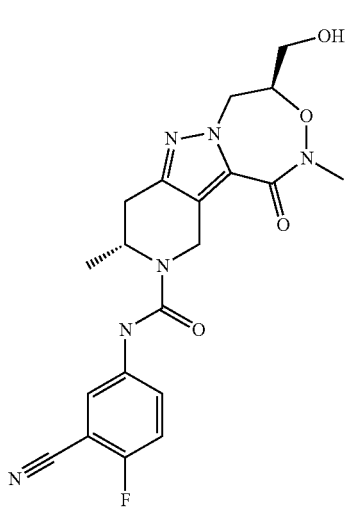
082 E2
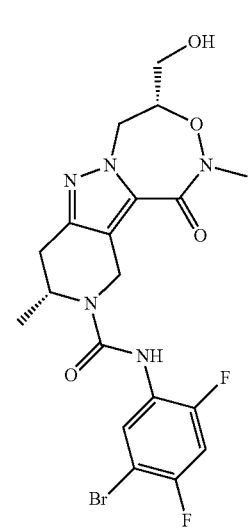
084 E1
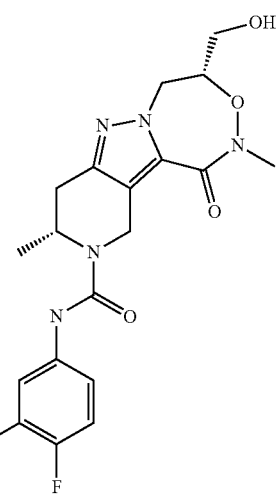
084 E2
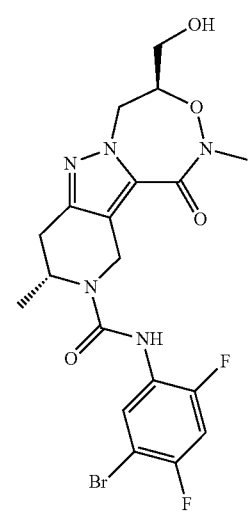
089 E1
089 E2

-continued

090 E1
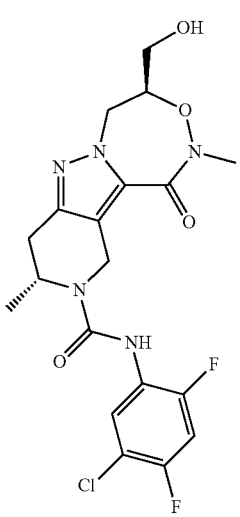

090 E2
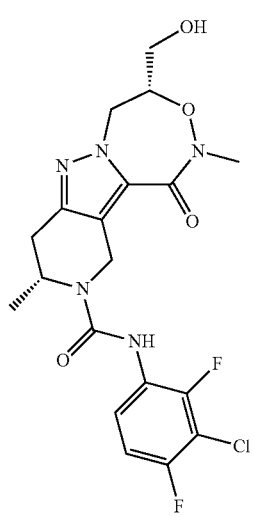

091 E1

091 E2
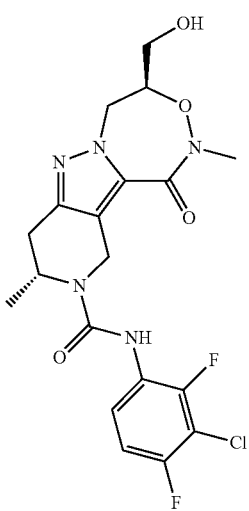

Compound 088: (9R)—N-(3-chloro-4-fluoro-phenyl)-4-(fluoromethyl)-2,9-dimethyl-1-oxo-5,8,9,11-tetrahydro-4H-pyrido[2,3]pyrazolo[2,4-d][1,2,5]oxadiazepine-10-carboxamide

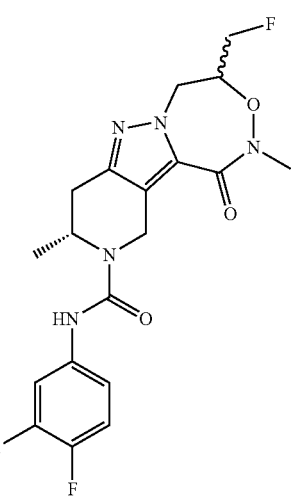

To a solution of (9R)—N-(3-chloro-4-fluoro-phenyl)-4-(hydroxymethyl)-2,9-dimethyl-1-oxo-5,8,9,11-tetrahydro-4H-pyrido[2,3]pyrazolo[2,4-d][1,2,5]oxadiazepine-10-carboxamide, (Compound 069, 75.00 mg, 171.29 µmol, 1.00 eq) in DCM (5.00 mL) was added DAST (165.66 mg, 1.03 mmol, 135.79 µL 6.00 eq) at −30° C. under $N_2$, the reaction mixture was stirred at 15° C. for 2 hours. LCMS indicated that reactant was consumed completely and desired MS was detected. The mixture was washed with saturated $NaHCO_3$ (10 mL*1) and brine (10 mL*1). Then the organic phase was dried over anhydrous $Na_2SO_4$, filtered and concentrated to get the residue. The residue was purified by prep-HPLC (FA) to obtain the title compound (39.70 mg, 87.28 µmol, 50.96% yield, 96.7% purity) as a white solid.

Compounds 085, 086, and 087 were prepared in an analogous manner to Compound 088.

255
085 E1
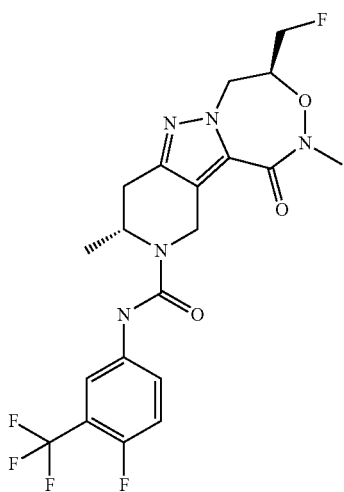
085 E2
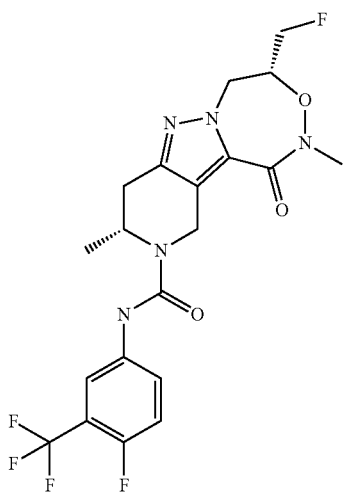
086 E1
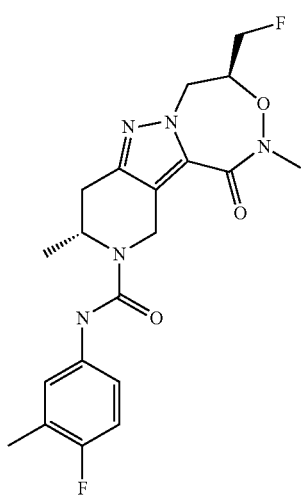
256
-continued
086 E2
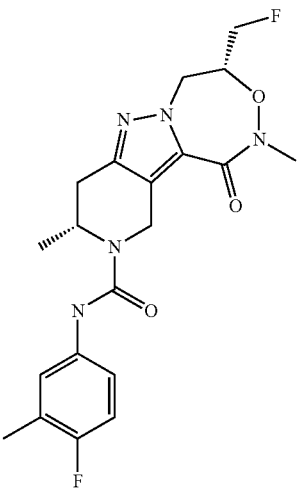
087 E1
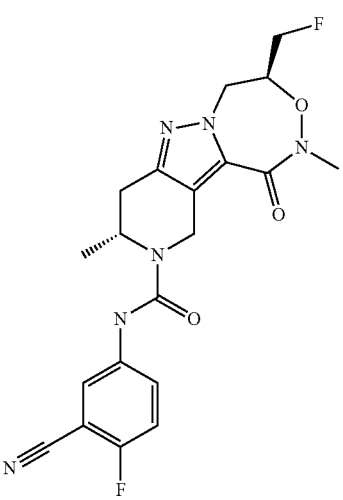
087 E2
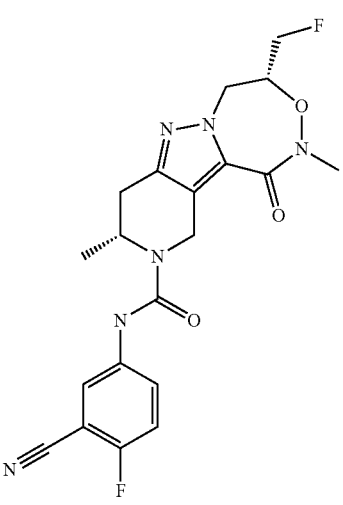

Compound 082_E1: (4S*,9R)—N-(4-fluoro-3-(trifluoromethyl)phenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS (M+1): 472. $^1$H NMR (400 MHz, CHLOROFORM-d) δ=7.68 (dd, J=6.05, 2.75 Hz, 1H) 7.55-7.62 (m, 1H) 7.14 (t, J=9.41 Hz, 1H) 6.56 (s, 1H) 5.15 (m, J=6.45 Hz, 1H) 4.88 (d, J=15.53 Hz, 1H) 4.54-4.62 (m, 2H) 4.36-4.51 (m, 2H) 3.77-3.93 (m, 2H) 3.34 (s, 3H) 3.05 (dd, J=15.96, 5.81 Hz, 1H) 2.70 (d, J=15.65 Hz, 1H) 1.89 (br. s., 1H) 1.19 (d, J=6.97 Hz, 3H).

*Pure but unknown enantiomer.

Compound 082_E2: (4R*,9R)—N-(4-fluoro-3-(trifluoromethyl)phenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS (M+1): 472. $^1$H NMR (400 MHz, CHLOROFORM-d) δ=7.66-7.73 (m, 1H), 7.56-7.65 (m, 1H), 7.15 (s, 1H), 6.59 (s, 1H), 5.09-5.22 (m, 1H), 4.76-4.92 (m, 1H), 4.55 (s, 4H), 3.87 (s, 2H), 3.35 (s, 3H), 3.00-3.12 (m, 1H), 2.71 (d, J=15.65 Hz, 1H), 1.88-2.01 (m, 1H), 1.21 (d, J=6.97 Hz, 3H).

*Pure but unknown enantiomer.

Compound 083_E1: (4S*,9R)—N-(4-fluoro-3-methylphenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide

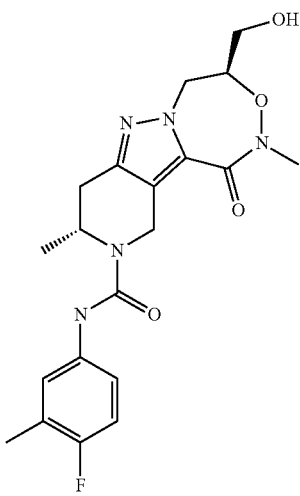

LCMS (M+1): 418. $^1$H NMR (400 MHz, CHLOROFORM-d) δ=7.25 (d, J=2.45 Hz, 1H) 7.11 (dt, J=7.98, 3.90 Hz, 1H) 6.93 (t, J=8.99 Hz, 1H) 6.37 (s, 1H) 5.15 (m, J=6.30 Hz, 1H) 4.86 (d, J=15.53 Hz, 1H) 4.52-4.62 (m, 2H) 4.34-4.49 (m, 2H) 3.75-3.93 (m, 2H) 3.33 (s, 3H) 3.04 (dd, J=15.77, 5.87 Hz, 1H) 2.68 (d, J=15.65 Hz, 1H) 2.26 (d, J=1.59 Hz, 3H) 1.82-2.04 (m, 1H) 1.17 (d, J=6.97 Hz, 3H).

*Pure but unknown enantiomer.

Compound 083_E2: (4R*,9R)—N-(4-fluoro-3-methylphenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide

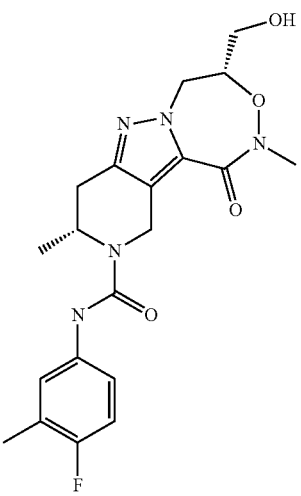

LCMS (M+1): 472. $^1$H NMR (400 MHz, CHLOROFORM-d) δ=7.24-7.27 (m, 1H), 7.08-7.15 (m, 1H), 6.89-6.97 (m, 1H), 6.37 (s, 1H), 5.04-5.25 (m, 1H), 4.82 (d, J=15.65 Hz, 1H), 4.29-4.65 (m, 4H), 3.68-3.93 (m, 2H), 3.33 (s, 3H), 2.94-3.13 (m, 1H), 2.56-2.74 (m, 1H), 2.26 (d, J=1.71 Hz, 3H), 1.89-2.01 (m, 1H), 1.18 (d, J=6.97 Hz, 3H).

*Pure but unknown enantiomer.

Compound 084_E1: (4S*,9R)—N-(3-cyano-4-fluorophenyl)-4-(hydroxymethyl)-2,9-dimethyl-1-oxo-1,4,5,8,9,11-hexahydropyrido[4',3':3,4]pyrazolo [5,1-d][1,2,5]oxadiazepine-10(2H)-carboxamide LCMS (M+1): 429. $^1$H NMR (400 MHz, CHLOROFORM-d) δ=7.79 (dd, J=5.44, 2.75 Hz, 1H) 7.54-7.61 (m, 1H) 7.15 (t, J=8.68 Hz, 1H) 6.50-6.58 (m, 1H) 5.08-5.19 (m, 1H) 4.78-4.91 (m, 1H) 4.53-4.61 (m, 2H) 4.37-4.51 (m, 2H) 3.78-3.93 (m, 2H) 3.35 (s, 3H) 3.04 (dd, J=15.83, 5.93 Hz, 1H) 2.70 (d, J=15.53 Hz, 1H) 1.78 (br. s., 1H) 1.17-1.22 (m, 3H).

*Pure but unknown enantiomer.

Compound 084_E2: (4R*,9R)—N-(3-cyano-4-fluorophenyl)-4-(hydroxymethyl)-2,9-dimethyl-1-oxo-1,4,5,8,9,11-hexahydropyrido[4',3':3,4]pyrazolo [5,1-d][1,2,5]oxadiazepine-10(2H)-carboxamide LCMS [M+1]: 429. $^1$H NMR (400 MHz, CHLOROFORM-d) δ=7.78 (br d, J=2.57 Hz, 1H), 7.59 (br d, J=4.40 Hz, 1H), 7.14 (br t, J=8.80 Hz, 1H), 6.62 (br d, J=16.14 Hz, 1H), 5.13 (br t, J=6.54 Hz, 1H), 4.82 (br d, J=15.77 Hz, 1H), 4.39-4.63 (m, 4H), 3.70-3.96 (m, 2H), 3.34 (s, 3H), 3.04 (br dd, J=5.99, 15.65 Hz, 1H), 2.70 (br d, J=16.02 Hz, 1H), 1.88 (br s, 1H), 1.20 (br d, J=6.97 Hz, 3H).

*Pure but unknown enantiomer.

Compound 085_E1: (4S*,9R)—N-(4-fluoro-3-(trifluoromethyl)phenyl)-4-(fluoromethyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS (M+1): 474. $^1$H NMR (400 MHz, CHLOROFORM-d) δ=7.68 (dd, J=6.11, 2.69 Hz, 1H) 7.56-7.62 (m, 1H) 7.14 (t, J=9.35 Hz, 1H) 6.54 (s, 1H) 5.15 (m, J=6.45 Hz, 1H) 4.85 (d, J=15.65 Hz, 1H) 4.57-4.73 (m, 4H) 4.39-4.54 (m, 2H) 3.33 (s, 3H) 3.05 (dd, J=15.83, 5.81 Hz, 1H) 2.71 (d, J=16.02 Hz, 1H) 1.20 (d, J=6.97 Hz, 3H).

Compound 085_E2: (4R*,9R)—N-(4-fluoro-3-(trifluoromethyl)phenyl)-4-(fluoromethyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS (M+1): 474. $^1$H NMR (400 MHz, CHLOROFORM-d) δ=7.65-7.73 (m, 1H), 7.56-7.63 (m, 1H), 7.14 (s, 1H), 6.54 (s, 1H), 5.08-5.22 (m, 1H), 4.82-4.92 (m, 1H), 4.37-4.79 (m, 6H), 3.34 (s, 3H), 2.99-3.13 (m, 1H), 2.62-2.79 (m, 1H), 1.19 (d, J=6.85 Hz, 3H).

*Pure but unknown enantiomer.

Compound 086_E1: (4S*,9R)—N-(4-fluoro-3-methylphenyl)-4-(fluoromethyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS (M+1): 420. $^1$H NMR (400 MHz, CHLOROFORM-d) δ=7.25 (d, J=2.57 Hz, 1H) 7.11 (dt, J=7.89, 3.88 Hz, 1H) 6.93 (t, J=8.99 Hz, 1H) 6.34 (s, 1H) 5.09-5.19 (m, 1H) 4.79-4.89 (m, 1H) 4.56-4.73 (m, 4H) 4.37-4.52 (m, 2H) 3.33 (s, 3H) 3.04 (dd, J=15.71, 5.81 Hz, 1H) 2.69 (d, J=15.77 Hz, 1H) 2.26 (d, J=1.59 Hz, 3H) 1.18 (d, J=6.85 Hz, 3H).

Compound 086_E2: (4R*,9R)—N-(4-fluoro-3-methylphenyl)-4-(fluoromethyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS (M+1): 420. $^1$H NMR (400 MHz, CHLOROFORM-d) δ=7.24-7.27 (m, 1H), 7.09-7.15 (m, 1H), 6.87-6.98 (m, 1H), 6.28-6.40 (m, 1H), 5.07-5.23 (m, 1H), 4.82-4.91 (m, 1H), 4.37-4.79 (m, 6H), 3.33 (s, 3H), 2.99-3.11 (m, 1H), 2.62-2.74 (m, 1H), 2.26 (d, J=1.71 Hz, 3H), 1.18 (d, J=6.85 Hz, 3H).

*Pure but unknown enantiomer.

Compound 087_E1: (4S*,9R)—N-(3-cyano-4-fluorophenyl)-4-(fluoromethyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS (M+1): 431. $^1$H NMR (400 MHz, CHLOROFORM-d) δ=7.78 (dd, J=5.46, 2.82 Hz, 1H) 7.58 (ddd, J=9.13, 4.55, 2.89 Hz, 1H) 7.09-7.18 (m, 1H) 6.62 (s, 1H) 5.08-5.19 (m, 1H) 4.84 (d, J=15.69 Hz, 1H) 4.57-4.73 (m, 4H) 4.38-4.54 (m, 2H) 3.33 (s, 3H) 3.04 (dd, J=15.94, 5.90 Hz, 1H) 2.71 (d, J=16.19 Hz, 1H) 1.19 (d, J=6.90 Hz, 3H).

Compound 087_E2: (4R*,9R)—N-(3-cyano-4-fluorophenyl)-4-(fluoromethyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS [M+1]: 431. $^1$H NMR (400 MHz, CHLOROFORM-d) δ=7.74-7.81 (m, 1H), 7.59 (ddd, J=2.82, 4.49, 9.13 Hz, 1H), 7.14 (t, J=8.66 Hz, 1H), 6.67 (s, 1H), 5.13 (quin, J=6.40 Hz, 1H), 4.87 (d, J=15.69 Hz, 1H), 4.58-4.78 (m, 3H), 4.39-4.57 (m, 3H), 3.33 (s, 3H), 3.04 (dd, J=5.77, 15.94 Hz, 1H), 2.69 (d, J=15.94 Hz, 1H), 1.19 (d, J=7.03 Hz, 3H).

Compound 088_E1: (4S*,9R)—N-(3-chloro-4-fluorophenyl)-4-(fluoromethyl)-2,9-dimethyl-1-oxo-1,4,5,8,9,11-hexahydropyrido[4',3':3,4]pyrazolo[5,1-d][1,2,5]oxadiazepine-10(2H)-carboxamide

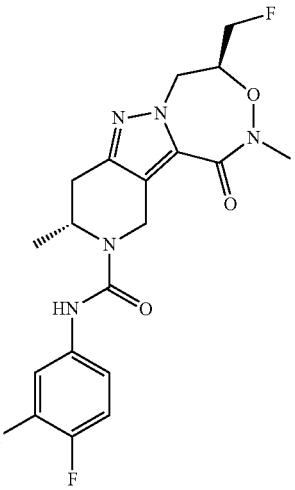

LCMS: 426. $^1$H NMR (400 MHz, CHLOROFORM-d) δ=7.37 (ddd, J=2.8, 6.4, 12.0 Hz, 1H), 7.24 (td, J=2.4, 5.2 Hz, 1H), 6.64 (s, 1H), 5.14 (m, 1H), 4.84 (d, J=16.0 Hz, 1H), 4.54-4.59 (m, 2H), 4.39-4.50 (m, 3H), 3.32 (s, 3H), 3.04 (dd, J=8.0, 16.0 Hz, 1H), 2.69 (d, J=16.0 Hz, 1H), 1.18 (d, J=8.0 Hz, 3H).

Compound 088_E2: (4R*,9R)—N-(3-chloro-4-fluorophenyl)-4-(fluoromethyl)-2,9-dimethyl-1-oxo-1,4,5,8,9,11-hexahydropyrido[4',3':3,4]pyrazolo[5,1-d][1,2,5]oxadiazepine-10(2H)-carboxamide

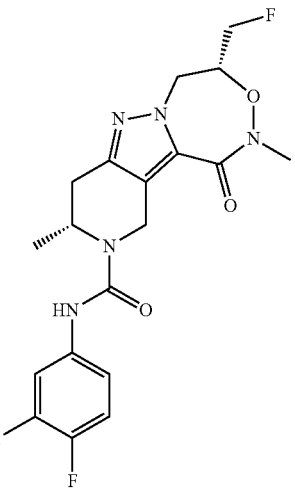

LCMS: 426. ¹H NMR (400 MHz, CHLOROFORM-d) δ=7.54-7.61 (m, 1H), 7.17-7.24 (m, 1H), 7.01-7.09 (m, 1H), 6.60 (s, 1H), 5.13 (quin, J=6.40 Hz, 1H), 4.86 (d, J=15.69 Hz, 1H), 4.57-4.75 (m, 3H), 4.52-4.56 (m, 1H), 4.37-4.48 (m, 2H), 3.25-3.38 (m, 3H), 2.96-3.10 (m, 1H), 2.67 (d, J=15.94 Hz, 1H), 1.17 (d, J=6.90 Hz, 3H).
*Pure but unknown enantiomer.

Compound 089_E1: (4S*,9R)—N-(5-bromo-2,4-difluorophenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS: 502/500 [M+1]. ¹H NMR (400 MHz, CHLOROFORM-d) δ=8.29 (t, J=7.89 Hz, 1H), 6.90 (dd, J=7.95, 10.64 Hz, 1H), 6.52 (br d, J=2.81 Hz, 1H), 4.97-5.18 (m, 1H), 4.82 (d, J=15.77 Hz, 1H), 4.35-4.65 (m, 4H), 3.66-3.86 (m, 2H), 3.30 (s, 3H), 3.02 (dd, J=5.75, 15.89 Hz, 1H), 2.66 (d, J=15.89 Hz, 1H), 1.18 (d, J=6.85 Hz, 3H).
*Pure but unknown enantiomer.

Compound 089_E2: (4R*,9R)—N-(5-bromo-2,4-difluorophenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS: 502/500[M+1]. ¹H NMR (400 MHz, CHLOROFORM-d) δ=8.32 (t, J=7.89 Hz, 1H), 6.94 (dd, J=7.95, 10.64 Hz, 1H), 6.57 (br d, J=2.69 Hz, 1H), 5.10 (br t, J=6.42 Hz, 1H), 4.91 (d, J=15.65 Hz, 1H), 4.33-4.61 (m, 4H), 3.70-3.97 (m, 2H), 3.33 (s, 3H), 3.05 (dd, J=5.81, 15.83 Hz, 1H), 2.70 (d, J=15.77 Hz, 1H), 1.20 (d, J=6.97 Hz, 3H).

Compound 090_E1: (4S*,9R)—N-(5-chloro-2,4-difluorophenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS: 456 [M+1]. ¹H NMR (400 MHz, CHLOROFORM-d) δ=8.19 (t, J=8.07 Hz, 1H), 6.95 (dd, J=8.50, 10.58 Hz, 1H), 6.54 (br s, 1H), 5.08 (br t, J=6.79 Hz, 1H), 4.85 (d, J=15.65 Hz, 1H), 4.41-4.67 (m, 4H), 3.68-3.94 (m, 2H), 3.34 (s, 2H), 2.97-3.12 (m, 1H), 2.70 (d, J=15.77 Hz, 1H), 1.21 (d, J=6.97 Hz, 3H).

Compound 090_E2: (4R*,9R)—N-(5-chloro-2,4-difluorophenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS: 456[M+1]. ¹H NMR (400 MHz, CHLOROFORM-d) δ=8.09-8.35 (m, 1H), 7.27 (s, 1H), 6.88-7.07 (m, 1H), 6.56 (br s, 1H), 5.11 (br d, J=6.27 Hz, 1H), 4.90 (br d, J=15.69 Hz, 1H), 4.32-4.73 (m, 4H), 3.69-4.00 (m, 2H), 3.33 (s, 3H), 3.05 (br dd, J=5.14, 16.06 Hz, 1H), 2.70 (br d, J=16.06 Hz, 1H), 1.20 (br d, J=6.78 Hz, 3H).

Compound 091_E1: (4S*,9R)—N-(3-chloro-2,4-difluorophenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS: 456[M+1]. ¹H NMR (400 MHz, CHLOROFORM-d) δ=7.89 (dt, J=5.62, 8.93 Hz, 1H), 6.90-7.02 (m, 1H), 6.55 (br s, 1H), 5.09 (br t, J=6.60 Hz, 1H), 4.89 (d, J=15.89 Hz, 1H), 4.42-4.64 (m, 4H), 3.69-3.93 (m, 2H), 3.35 (s, 3H), 3.07 (dd, J=6.05, 15.71 Hz, 1H), 2.71 (d, J=15.77 Hz, 1H), 1.23 (d, J=6.97 Hz, 3H).

Compound 091_E2: (4R*,9R)—N-(3-chloro-2,4-difluorophenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS: 456[M+1]. ¹H NMR (400 MHz, CHLOROFORM-d) δ=7.89 (dt, J=5.56, 8.89 Hz, 1H), 6.90-7.03 (m, 1H), 6.57 (br s, 1H), 5.10 (quin, J=6.27 Hz, 1H), 4.94 (d, J=15.77 Hz, 1H), 4.37-4.63 (m, 4H), 3.75-3.97 (m, 2H), 3.35 (s, 3H), 3.07 (dd, J=5.87, 15.77 Hz, 1H), 2.71 (d, J=15.77 Hz, 1H), 1.22 (d, J=6.85 Hz, 3H).

Compound 092_E1: (4S*,9R)—N-(3-bromo-2,4-difluorophenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide

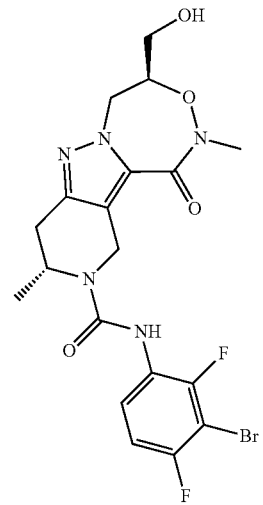 [SMILES: C[C@@H]1Cc2nn3c(c2CN1C(=O)Nc1ccc(F)c(Br)c1F)C(=O)N(C)O[C@H](CO)C3]

LCMS: 502/500[M+1] ¹H NMR (400 MHz, CHLOROFORM-d) δ=7.95 (dt, J=5.58, 8.94 Hz, 1H), 6.88-7.05 (m, 1H), 6.54 (br d, J=2.64 Hz, 1H), 5.09 (br t, J=6.53 Hz, 1H), 4.89 (d, J=15.94 Hz, 1H), 4.39-4.67 (m, 4H), 3.72-3.94 (m, 2H), 3.35 (s, 3H), 3.06 (dd, J=6.02, 15.81 Hz, 1H), 2.71 (d, J=15.81 Hz, 1H), 1.23 (d, J=6.90 Hz, 3H).

Compound 092_E2: (4R*,9R)—N-(3-bromo-2,4-difluorophenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide

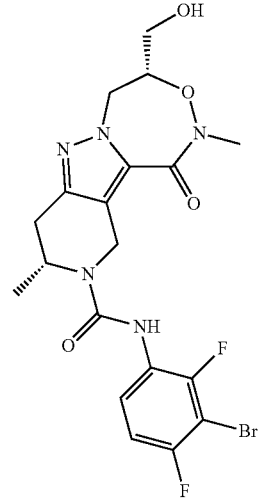 [SMILES: C[C@@H]1Cc2nn3c(c2CN1C(=O)Nc1ccc(F)c(Br)c1F)C(=O)N(C)O[C@@H](CO)C3]

LCMS: 502/500[M+1]. $^1$H NMR (400 MHz, CHLOROFORM-d) δ=7.95 (dt, J=5.69, 8.96 Hz, 1H), 6.88-7.03 (m, 1H), 6.60 (br s, 1H), 5.02-5.24 (m, 1H), 4.95 (d, J=15.65 Hz, 1H), 4.34-4.63 (m, 4H), 3.73-3.95 (m, 2H), 3.07 (dd, J=5.81, 15.96 Hz, 1H), 2.71 (d, J=16.02 Hz, 1H), 1.21 (d, J=6.85 Hz, 3H).

Compound 093_D1: (4S*,9R)—N-(3-chloro-4-fluorophenyl)-4-((dimethylamino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide

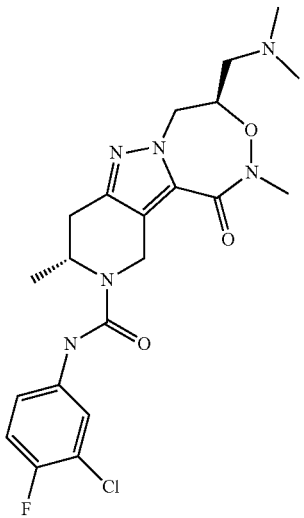

Step 1. tert-butyl (9R)-2,9-dimethyl-4-(methylsulfonyloxymethyl)-1-oxo-5,8,9,11-tetrahydro-4H-pyrido[2,3]pyrazolo[2,4-d][1,2,5]oxadiazepine-10-carboxylate. To a solution of tert-butyl (9R)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxylate (Intermediate 18, 1.50 g, 4.09 mmol, 1.00 eq) in DCM (4.00 mL) was added TEA (2.07 g, 20.47 mmol, 2.84 mL, 5.00 eq), and DMAP (50.01 mg, 409.38 µmol, 0.10 eq), followed by MsCl (1.41 g, 12.27 mmol, 949.68 µL3.00 eq) at 0° C. The mixture was stirred at 20° C. for 1 hr. TLC (petroleum ether:ethyl acetate=0:1) showed the starting material consumed and one main spot was generated. The mixture combined with another batch (1.3 g scale) was extracted with DCM (30 mL*2) and H$_2$O (20 mL). The combined organic layer was dried over Na$_2$SO$_4$, filtrated. The filtrate was concentrated in vacuum. The residue was purified by column chromatography (petroleum ether:ethyl acetate: 30%~50%) to get the title compound (1.50 g, 2.70 mmol, 66.01% yield) as a white solid.

Step 2. tert-butyl (9R)-4-[(dimethylamino)methyl]-2,9-dimethyl-1-oxo-5,8,9,11-tetrahydro-4H-pyrido[2,3]pyrazolo[2,4-d][1,2,5]oxadiazepine-10-carboxylate. To a solution of tert-butyl (9R)-2,9-dimethyl-4-(methylsulfonyloxymethyl)-1-oxo-5,8,9,11-tetrahydro-4H-pyrido[2,3]pyrazolo[2,4-d][1,2,5]oxadiazepine-10-carboxylate (1.10 g, 2.47 mmol, 1.00 eq) and Me$_2$NH (2.01 g, 24.70 mmol, 2.26 mL, 10.00 eq, HCl) in MeCN (60.00 mL) was added K$_2$CO$_3$ (4.44 g, 32.11 mmol, 13.00 eq). The mixture was heated to 80° C. for 16 hr. TLC (petroleum ether:ethyl acetate=0:1) showed the starting material consumed and one main spot was detected. The mixture was extracted with ethyl acetate (100 mL*2) and H$_2$O (50 mL). The combined organic layer was dried over Na$_2$SO$_4$, filtrated. The filtrate was concentrated in vacuum. The residue was purified by column chromatography (Petroleum ether:Ethyl acetate:80%~100%) to get the title compound (800.00 mg, 1.97 mmol, 79.76% yield, 96.7% purity) as yellow solid and (200.00 mg, 72% purity) as yellow oil.

The diastereomeric mixture (1.0 g) was separated via SFC to get both diasteremers (360 mg) and (360 mg). SFC separation method: Instrument: SFC Thar_80; Column: IC-10 um; Mobile phase: A for CO$_2$ and B for MeOH (0.1% Ammonia); Isocratic: B 25%; Flow rate: 55 mL/min; Back pressure: 100 bar; Column temperature: 35° C.; Wavelength: 220 nm.

Step 3. (9R)-4-[(dimethylamino)methyl]-2,9-dimethyl-4,5,8,9,10,11-hexahydropyrido[2,3]pyrazolo[2,4-d][1,2,5]oxadiazepin-1-one. To a solution of tert-butyl (9R)-4-[(dimethylamino)methyl]-2,9-dimethyl-1-oxo-5,8,9,11-tetrahydro-4H-pyrido[2,3]pyrazolo[2,4-d][1,2,5]oxadiazepine-10-carboxylate (360.00 mg, 914.91 µmol, 1.00 eq) in DCM (4.00 mL) was added TFA (6.16 g, 54.03 mmol, 4.00 mL, 59.05 eq). The mixture was stirred at 20° C. for 1 hr. TLC (DCM:MeOH=10:1) showed the starting material was consumed. The mixture was concentrated in vacuum to get the title compound (380.00 mg, crude, TFA) as yellow oil.

Step 4. (9R)—N-(3-chloro-4-fluoro-phenyl)-4-[(dimethylamino)methyl]-2,9-dimethyl-1-oxo-5,8,9,11-tetrahydro-4H-pyrido[2,3]pyrazolo[2,4-d][1,2,5]oxadiazepine-10-carboxamide. To a solution of (9R)-4-[(dimethylamino)methyl]-2,9-dimethyl-4,5,8,9,10,11-hexahydropyrido[2,3]pyrazolo[2,4-d][1,2,5]oxadiazepin-1-one (44.00 mg, 108.00 µmol, 1.00 eq, TFA) and phenyl N-(3-chloro-4-fluoro-phenyl)carbamate (28.69 mg, 108.00 µmol, 1.00 eq) in DCM (3.00 mL) was added TEA (54.64 mg, 540.00 µmol, 74.85 µL5.00 eq). The mixture was heated to 20° C. for 16 hr. LCMS showed one main peak with desired Ms. The mixture was concentrated in vacuum. The residue was purified by prep-HPLC (FA) to get the title compound (38.00 mg, 81.65 µmol, 75.60% yield, 99.9% purity) as a white solid. LCMS (M+1): 465. $^1$H NMR (400 MHz, CHLOROFORM-d) δ=8.21 (s, 1H), 7.61 (dd, J=2.64, 6.53 Hz, 1H), 7.19-7.26 (m, 1H), 7.03-7.12 (m, 1H), 6.61 (s, 1H), 5.08-5.19 (m, 1H), 4.75-4.89 (m, 2H), 4.62 (dd, J=5.90, 14.68 Hz, 1H), 4.50 (d, J=15.69 Hz, 1H), 4.37 (dd, J=4.77, 14.56 Hz, 1H), 3.34 (s, 3H), 3.05 (br dd, J=5.96, 15.87 Hz, 2H), 2.66-2.77 (m, 3H), 2.48 (s, 6H).

* pure but unknown stereochemistry

Compounds 094, 095, 096, 097, 098, 099, and 100 were prepared in an analogous method to Compound 093_D1.

093 D2

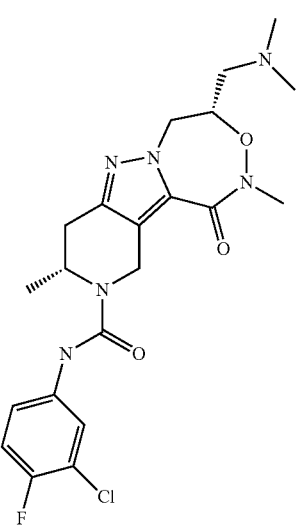

265
-continued
094 D1
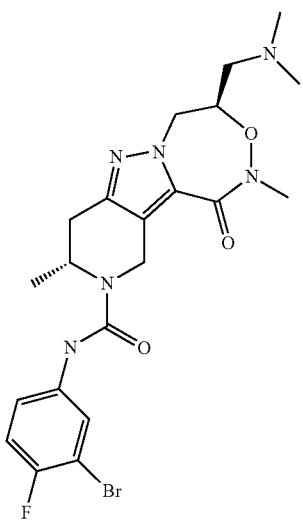 [SMILES: C[C@@H]1Cc2nn3c(c2CN1C(=O)Nc1ccc(F)c(Cl)c1)C(=O)N(C)O[C@H](CN(C)C)C3]
094 D2
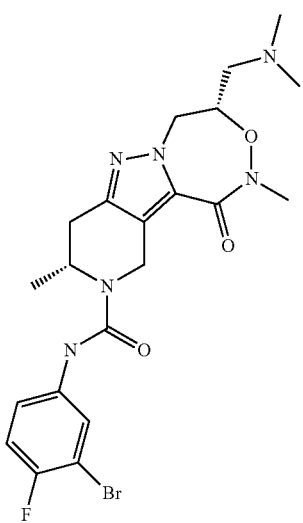
096 D1
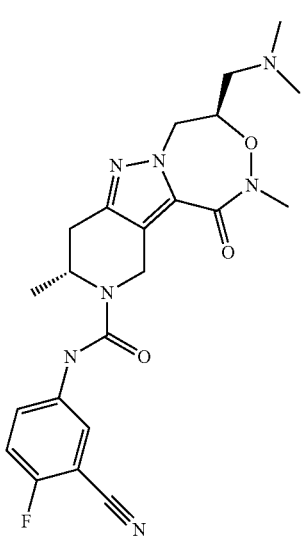
266
-continued
096 D2
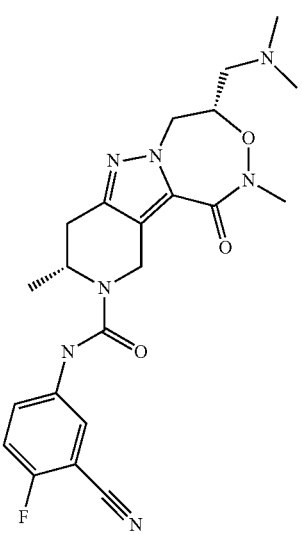
095 D1
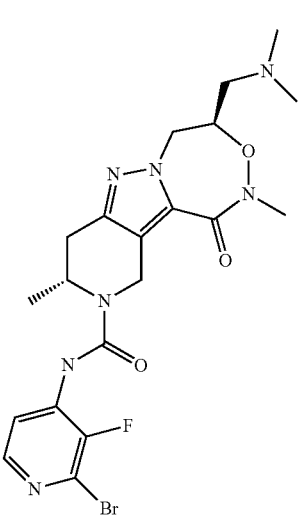
095 D2
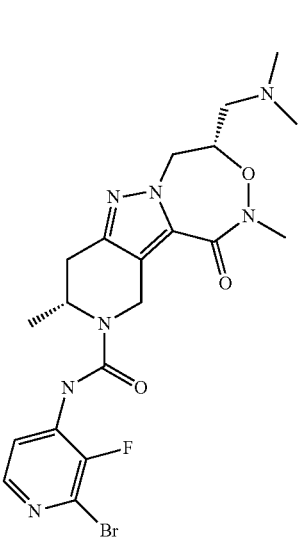

267
-continued
097 D1
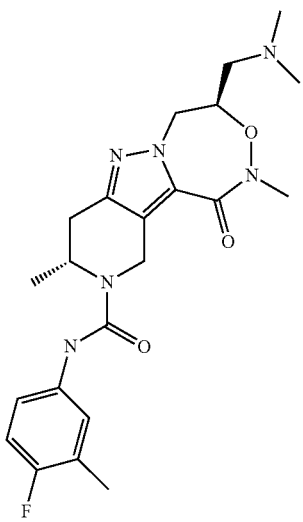
097 D2
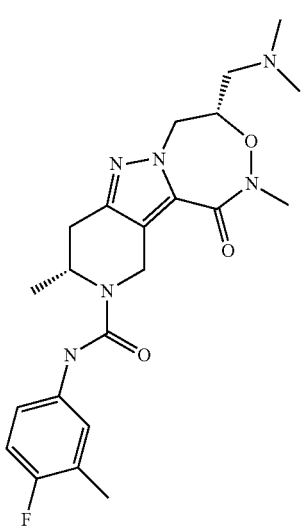
098 D1
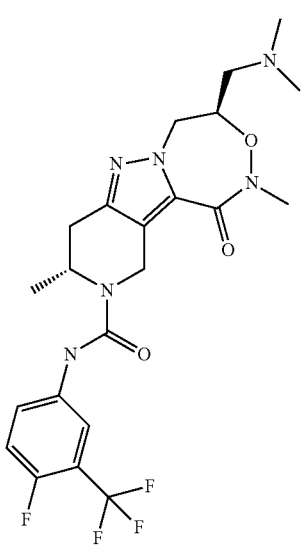
268
-continued
098 D2
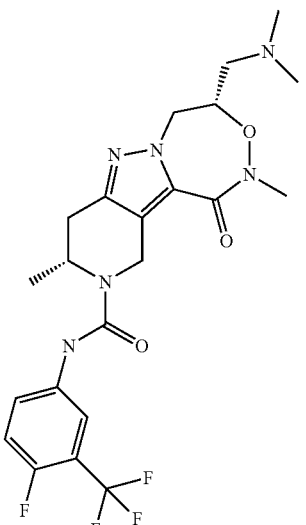
099 D1
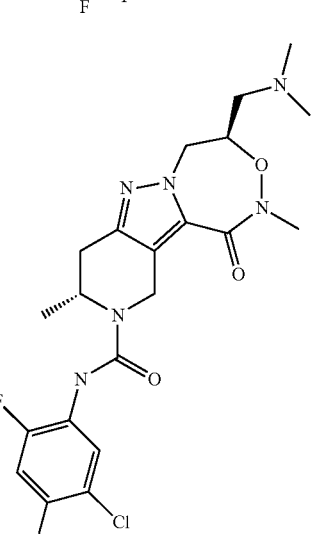
099 D2
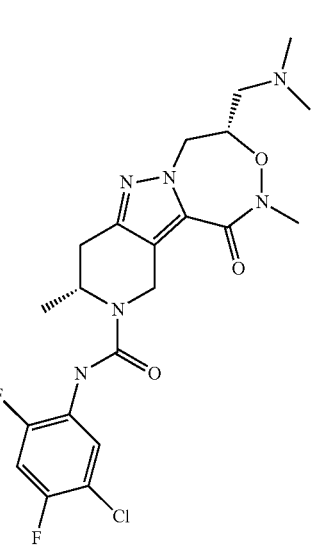

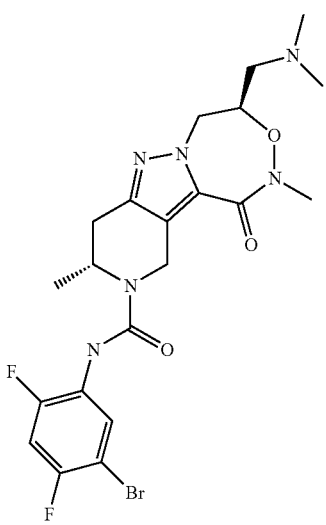

Compound 093_D2: (4R*,9R)—N-(3-chloro-4-fluorophenyl)-4-((dimethylamino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS (M+1): 465. ¹H NMR (400 MHz, CHLOROFORM-d) δ=8.13 (s, 1H), 7.61 (dd, J=2.64, 6.53 Hz, 1H), 7.17-7.25 (m, 1H), 7.03-7.12 (m, 1H), 6.56 (s, 1H), 5.16 (quin, J=6.68 Hz, 1H), 4.87 (d, J=15.56 Hz, 1H), 4.56-4.75 (m, 2H), 4.47 (d, J=15.56 Hz, 1H), 4.33 (dd, J=5.90, 14.43 Hz, 1H), 3.34 (s, 3H), 3.05 (dd, J=5.90, 15.81 Hz, 1H), 2.58-2.81 (m, 4H), 2.43 (s, 6H), 1.20 (d, J=6.90 Hz, 3H).
* pure but unknown stereochemistry Compound 094_D1: (4S*,9R)—N-(3-bromo-4-fluorophenyl)-4-((dimethylamino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS (M+1): 509/511. ¹H NMR (400 MHz, CHLOROFORM-d) δ=8.22 (brs, 1H), 7.73 (dd, J=2.64, 6.02 Hz, 1H), 7.30 (dd, J=2.70, 4.20 Hz, 1H), 7.27 (d, J=2.64 Hz, 1H), 7.06 (t, J=8.53 Hz, 1H), 6.59 (br s, 1H), 5.14 (quin, J=6.49 Hz, 1H), 4.71-4.90 (m, 2H), 4.61 (dd, J=5.90, 14.56 Hz, 1H), 4.50 (d, J=15.56 Hz, 1H), 4.37 (dd, J=4.83, 14.62 Hz, 1H), 3.34 (s, 3H), 3.05 (dd, J=5.77, 15.81 Hz, 1H), 2.65-2.77 (m, 3H), 2.47 (s, 6H), 1.20 (d, J=6.90 Hz, 3H).
* pure but unknown stereochemistry Compound 094_D2: (4R*,9R)—N-(3-bromo-4-fluorophenyl)-4-((dimethylamino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS (M+1): 509/511. ¹H NMR (400 MHz, CHLOROFORM-d) δ=8.12 (s, 1H), 7.75 (dd, J=2.64, 6.02 Hz, 1H), 7.30 (dd, J=2.76, 4.14 Hz, 1H), 7.02-7.10 (m, 1H), 6.60 (s, 1H), 5.16 (quin, J=6.27 Hz, 1H), 4.75-4.93 (m, 2H), 4.62 (dd, J=5.90, 14.56 Hz, 1H), 4.45 (d, J=15.56 Hz, 1H), 4.35 (dd, J=5.33, 14.62 Hz, 1H), 3.35 (s, 3H), 3.05 (dd, J=5.71, 15.87 Hz, 1H), 2.67-2.83 (m, 3H), 2.53 (s, 5H), 1.20 (d, J=6.90 Hz, 3H).
* pure but unknown stereochemistry Compound 096_D1: (4S*,9R)—N-(3-cyano-4-fluorophenyl)-4-((dimethylamino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS (M+1): 456. ¹H NMR (400 MHz, CHLOROFORM-d) δ=8.18 (s, 1H), 7.80 (dd, J=2.76, 5.40 Hz, 1H), 7.62 (ddd, J=2.76, 4.58, 9.10 Hz, 1H), 7.09-7.20 (m, 1H), 6.76 (s, 1H), 5.14 (quin, J=6.40 Hz, 1H), 4.79-4.90 (m, 2H), 4.63 (dd, J=5.90, 14.68 Hz, 1H), 4.51 (d, J=15.69 Hz, 1H), 4.38 (dd, J=4.71, 14.62 Hz, 1H), 3.35 (s, 3H), 3.05 (dd, J=5.90, 15.94 Hz, 1H), 2.66-2.82 (m, 3H), 2.52 (s, 6H), 1.21 (d, J=6.90 Hz, 3H).
* pure but unknown stereochemistry Compound 096_D2: (4R*,9R)—N-(3-cyano-4-fluorophenyl)-4-((dimethylamino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS (M+1): 456. ¹H NMR (400 MHz, CHLOROFORM-d) δ=8.10 (s, 1H), 7.81 (dd, J=2.82, 5.46 Hz, 1H), 7.62 (ddd, J=2.76, 4.58, 9.10 Hz, 1H), 7.15 (t, J=8.72 Hz, 1H), 6.81 (s, 1H), 5.16 (quin, J=6.40 Hz, 1H), 4.78-4.96 (m, 2H), 4.62 (dd, J=6.02, 14.68 Hz, 1H), 4.31-4.48 (m, 2H), 3.35 (s, 3H), 3.05 (dd, J=5.77, 16.06 Hz, 1H), 2.87 (br d, J=6.15 Hz, 2H), 2.70 (d, J=16.06 Hz, 1H), 2.58 (s, 6H), 1.21 (d, J=6.90 Hz, 3H).
* pure but unknown stereochemistry Compound 095_D1: (4S*,9R)—N-(2-bromo-3-fluoropyridin-4-yl)-4-((dimethylamino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS (M+1): 510/512. ¹H NMR (400 MHz, CHLOROFORM-d) δ=8.14-8.18 (m, 1H) 8.07 (d, J=5.62 Hz, 1H) 6.97 (br s, 1H) 5.05 (br t, J=6.54 Hz, 1H) 4.89 (br d, J=16.02 Hz, 1H) 4.81 (br d, J=6.36 Hz, 1H) 4.51-4.64 (m, 2H) 4.38 (dd, J=14.61, 4.34 Hz, 1H) 3.33 (s, 3H) 3.06 (dd, J=15.89, 5.75 Hz, 1H) 2.69-2.78 (m, 3H) 2.49 (s, 6H) 1.24 (d, J=6.97 Hz, 3H).
* pure but unknown stereochemistry Compound 095_D2: (4R*,9R)—N-(2-bromo-3-fluoropyridin-4-yl)-4-((dimethylamino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS (M+1): 510/512. ¹H NMR (400 MHz, CHLOROFORM-d) δ=8.13-8.17 (m, 1H) 8.06 (d, J=5.52 Hz, 1H) 7.02 (br d, J=3.89 Hz, 1H) 5.07 (br t, J=6.40 Hz, 1H) 4.93 (d, J=15.81 Hz, 1H) 4.48-4.68 (m, 3H) 4.29 (dd, J=14.24, 6.09 Hz, 1H) 3.32 (s, 3H) 3.05 (dd, J=15.94, 5.90 Hz, 1H) 2.68-2.76 (m, 2H) 2.60 (dd, J=13.24, 5.08 Hz, 1H) 2.40 (s, 6H) 1.23 (d, J=6.90 Hz, 3H).
* pure but unknown stereochemistry Compound 097_D1: (4S*,9R)-4-((dimethylamino)methyl)-N-(4-fluoro-3-methylphenyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS (M+1): 445. ¹H NMR (400 MHz, CHLOROFORM-d) δ=7.23-7.27 (m, 1H) 7.08-7.14 (m, 1H) 6.92 (t, J=8.97 Hz, 1H) 6.48 (s, 1H) 5.12 (m, J=6.49 Hz, 1H) 4.79-4.92 (m, 2H) 4.61 (dd, J=14.68, 6.02 Hz, 1H) 4.48 (d, J=15.69 Hz, 1H) 4.37 (dd, J=14.68, 4.27 Hz, 1H) 3.33 (s, 3H) 3.03 (dd, J=15.87, 5.96 Hz, 1H) 2.83-2.91 (m, 1H) 2.73-2.81 (m, 1H) 2.67 (d, J=15.81 Hz, 1H) 2.51-2.56 (m, 6H) 2.25 (d, J=1.76 Hz, 3H) 1.18 (d, J=6.90 Hz, 3H).
* pure but unknown stereochemistry Compound 097_D2: (4R*,9R)-4-((dimethylamino)methyl)-N-(4-fluoro-3-methylphenyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS (M+1): 445. ¹H NMR (400 MHz, CHLOROFORM-d) δ=7.23-7.27 (m, 1H) 7.11 (dt, J=7.87, 3.91 Hz, 1H) 6.92 (t, J=8.97 Hz, 1H) 6.56 (s, 1H) 5.13 (m, J=6.37 Hz, 1H) 4.86-4.98 (m, 2H) 4.62 (dd, J=14.81, 6.02 Hz, 1H) 4.32-4.43 (m, 2H) 3.33 (s, 3H) 2.98-3.09 (m, 2H) 2.92 (dd, J=13.55, 8.41 Hz, 1H) 2.62-2.70 (m, 7H) 2.24 (d, J=1.76 Hz, 3H) 1.17 (d, J=6.78 Hz, 3H).
* pure but unknown stereochemistry Compound 098_D1: (4S*,9R)-4-((dimethylamino)methyl)-N-(4-fluoro-3-(trifluoromethyl)phenyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS (M+1): 499. ¹H NMR (400 MHz, CHLOROFORM-d) δ=7.69 (dd, J=6.15, 2.76 Hz, 1H) 7.60 (dt, J=8.56, 3.62 Hz, 1H) 7.12 (t, J=9.41 Hz, 1H) 6.82 (s, 1H) 5.14 (m, J=6.46 Hz, 1H) 4.86 (d, J=15.69 Hz, 1H) 4.76 (m, J=5.65 Hz, 1H) 4.60 (dd, J=14.68, 5.90 Hz, 1H) 4.49 (d, J=15.56 Hz, 1H) 4.34 (dd, J=14.62, 5.08 Hz, 1H) 3.32 (s, 3H) 3.04 (dd, J=15.94, 5.77 Hz, 1H) 2.65-2.71 (m, 3H) 2.44 (s, 6H) 1.18 (d, J=6.90 Hz, 3H)
* pure but unknown stereochemistry Compound 098_D2: (4R*,9R)-4-((dimethylamino)methyl)-N-(4-fluoro-3-(trifluoromethyl)phenyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS (M+1): 499. ¹H NMR (400 MHz, CHLOROFORM-d) δ=7.69 (dd, J=6.05, 2.63 Hz, 1H) 7.57-7.64 (m, 1H) 7.12 (t, J=9.41 Hz, 1H) 6.85 (s, 1H) 5.15 (m, J=6.39 Hz, 1H) 4.85-4.96 (m, 2H) 4.61 (dd, J=14.67, 5.99 Hz, 1H) 4.32-4.46 (m, 2H) 3.33 (s, 3H) 3.03 (dd, J=15.96, 5.81 Hz, 1H) 2.83-2.96 (m, 2H) 2.67 (d, J=15.89 Hz, 1H) 2.60 (s, 6H) 1.18 (d, J=6.85 Hz, 3H).
* pure but unknown stereochemistry Compound 099_D1: (4S*,9R)—N-(5-chloro-2,4-difluorophenyl)-4-((dimethylamino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS (M+1): 483/485. 1H NMR (400 MHz, CHLOROFORM-d) δ=8.16-8.22 (m, 1H), 8.19 (t, J=7.72 Hz, 1H), 8.16 (s, 1H), 8.15-8.16 (m, 1H), 6.95 (dd, J=8.41, 10.54 Hz, 1H), 6.54 (d, J=3.26 Hz, 1H), 5.08 (s, 1H), 4.85 (d, J=15.69 Hz, 1H), 4.77 (dd, J=4.96, 5.96 Hz, 1H), 4.49-4.62 (m, 2H), 4.36 (dd, J=4.64, 14.56 Hz, 1H), 3.33 (s, 3H), 3.05 (dd, J=5.90, 15.81 Hz, 1H), 2.65-2.75 (m, 3H), 2.45 (s, 6H), 1.21 (d, J=6.90 Hz, 3H).
* pure but unknown stereochemistry Compound 099_D2: (4R*,9R)—N-(5-chloro-2,4-difluorophenyl)-4-((dimethylamino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS (M+1): 483/485. ¹H NMR (400 MHz, CHLOROFORM-d) δ=8.20 (t, J=7.98 Hz, 1H), 8.17-8.23 (m, 1H), 8.16 (s, 1H), 8.15-8.17 (m, 1H), 6.97 (dd, J=8.41, 10.54 Hz, 1H), 6.57 (br d, J=3.14 Hz, 1H), 5.11 (s, 1H), 4.91 (d, J=15.69 Hz, 1H), 4.78 (s, 1H), 4.62 (dd, J=5.96, 14.62 Hz, 1H), 4.49 (d, J=15.56 Hz, 1H), 4.33 (dd, J=5.71, 14.62 Hz, 1H), 3.34 (s, 3H), 3.05 (d, J=5.77 Hz, 1H), 2.63-2.86 (m, 3H), 2.51 (s, 6H), 1.22 (d, J=6.90 Hz, 3H).
* pure but unknown stereochemistry Compound 100_D1: (4S*,9R)—N-(5-bromo-2,4-difluorophenyl)-4-((dimethylamino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS (M+1): 527/529. ¹H NMR (400 MHz, CHLOROFORM-d) δ=8.33 (dd, J=7.59, 8.22 Hz, 1H), 8.22 (s, 1H), 7.29 (s, 1H), 6.95 (dd, J=7.91, 10.67 Hz, 1H), 6.57 (br d, J=3.01 Hz, 1H), 5.09 (br t, J=6.46 Hz, 1H), 4.79-4.91 (m, 2H), 4.49-4.65 (m, 2H), 4.38 (dd, J=4.45, 14.62 Hz, 1H), 3.34 (s, 3H), 3.02-3.10 (m, 1H), 2.68-2.83 (m, 3H), 2.50 (s, 6H), 1.22 (d, J=6.90 Hz, 3H).
* pure but unknown stereochemistry Compound 100_D2: (4R*,9R)—N-(5-bromo-2,4-difluorophenyl)-4-((dimethylamino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS (M+1): 527/529. ¹H NMR (400 MHz, CHLOROFORM-d) δ=8.34 (dd, J=7.53, 8.28 Hz, 1H), 8.17 (s, 1H), 6.95 (dd, J=7.91, 10.67 Hz, 1H), 6.57 (d, J=3.01 Hz, 1H), 5.11 (s, 1H), 4.91 (d, J=15.69 Hz, 1H), 4.74 (s, 1H), 4.62 (dd, J=5.90, 14.56 Hz, 1H), 4.49 (d, J=15.69 Hz, 1H), 4.33 (dd, J=5.96, 14.49 Hz, 1H), 3.34 (s, 3H), 3.02-3.10 (m, 1H), 2.62-2.83 (m, 3H), 2.55 (br s, 7H), 2.47 (s, 6H), 1.22 (d, J=6.90 Hz, 3H).

* pure but unknown stereochemistry

Compound 101: N-(3-chloro-4-fluoro-phenyl)-4-(ethoxymethyl)-2-methyl-1-oxo-5,8,9,11-tetrahydro-4H-pyrido[2,3]pyrazolo[2,4-d][1,2,5]oxadiazepine-10-carboxamide

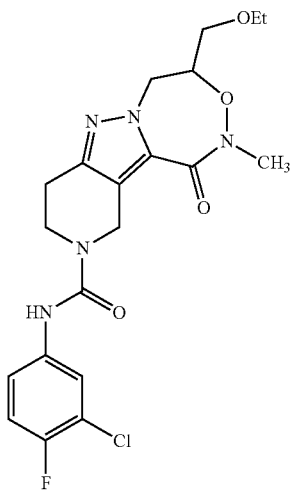 [SMILES: CCOCC1Cn2nc3c(c2C(=O)N(C)O1)CN(C(=O)Nc1ccc(F)c(Cl)c1)CC3]

Step 1. tert-butyl 4-(ethoxymethyl)-2-methyl-1-oxo-5,8,9,11-tetrahydro-4H-pyrido[2,3]pyrazolo [2,4-d][1,2,5]oxadiazepine-10-carboxylate. To a solution of tert-butyl 4-(hydroxymethyl)-2-methyl-1-oxo-1,4,5,8,9,11-hexahydropyrido[4',3':3,4]pyrazolo[5,1-d][1,2,5] oxadiazepine-10(2H)-carboxylate (Intermediate 1, 100.00 mg, 283.78 µmol, 1.00 eq) in DMF (2.00 mL) was added NaH (22.70 mg, 567.56 µmol, 22.70 µL60% purity, 2.00 eq) with stirring at −10° C. for 0.5 h under N$_2$. And then a solution of iodoethane (66.39 mg, 425.67 µmol, 34.04 µL1.50 eq) in DMF (1.00 mL) was added into the mixture. The mixture was stirred at 15° C. for 1 h. TLC (Petroleum ether:Ethyl acetate=1:5) showed that the starting material was consumed completely and one main new spot formed. LCMS indicated that MS of desired product was detected. The mixture was quenched with 1 mL of water and extracted with EtOAc (10 mL*3). The organic layers was combined and dried over anhydrous Na$_2$SO$_4$, filtered and concentrated to give the residue. The residue was purified by prep-TLC (Petroleum ether:Ethyl acetate=1:5) to obtain the title compound (105.00 mg, crude) as off-white oil. LCMS [M+1]: 381.

Step 2. Preparation of 4-(ethoxymethyl)-2-methyl-4,5,8,9,10,11-hexahydropyrido[2,3]pyrazolo [2,4-d][1,2,5] oxadiazepin-1-one. To a solution of tert-butyl 4-(ethoxymethyl)-2-methyl-1-oxo-5,8,9,11-tetrahydro-4H-pyrido[2,3]pyrazolo[2,4-d][1,2,5]oxadiazepine-10-carboxylate (50.00 mg, 131.43 µmol, 1.00 eq) in DCM (1.00 mL) was added TFA (1.54 g, 13.51 mmol, 1.00 mL, 102.76 eq) with stirring at 15° C. for 1 h. TLC (petroleum ether:ethyl acetate=1:5) showed that Reactant 2 was consumed completely and one main new spot formed. The mixture was directly evaporated to give the residue. The residue was not purified and directly used in the next step. The title compound (60.00 mg, crude, TFA) was obtained as a yellow oil.

Step 3. N-(3-chloro-4-fluoro-phenyl)-4-(ethoxymethyl)-2-methyl-1-oxo-5,8,9,11-tetrahydro-4H-pyrido[2,3]pyrazolo[2,4-d][1,2,5]oxadiazepine-10-carboxamide. To a solution of 4-(ethoxymethyl)-2-methyl-4,5,8,9,10,11-hexahydropyrido [2,3]pyrazolo [2,4-d][1,2,5]oxadiazepin-1-one (60.00 mg, 152.15 µmol, 1.00 eq, TFA) in DCM (2.00 mL) was TEA (46.19 mg, 456.45 µmol, 63.27 µL3.00 eq) with stirring at 15° C., and then the resulting mixture was stirred at 30° C. for 1 h. TLC showed the starting material was consumed completely and LCMS indicated that MS of desired product was detected. The mixture was evaporated to get the residue. The residue was purified by prep-HPLC (FA) to obtain the title compound (28.00 mg, 61.78 µmol, 40.60% yield, 99.7% purity) as a white solid. $^1$H NMR (400 MHz, CHLOROFORM-d) δ=7.58 (dd, J=2.8, 6.4 Hz, 1H), 7.20 (m, 1H), 7.03-7.10 (m, 1H), 6.55 (s, 1H), 4.70 (s, 2H), 4.51-4.64 (m, 2H), 4.35-4.46 (m, 1H), 3.79-3.94 (m, 2H), 3.51-3.67 (m, 4H), 3.31 (s, 3H), 2.86 (t, J=5.6 Hz, 2H), 1.24 (t, J=6.8 Hz, 3H). LCMS[M+1]: 452.

Compound 102: 4-(allyloxymethyl)-N-(3-chloro-4-fluoro-phenyl)-2-methyl-1-oxo-5,8,9,11-tetrahydro-4H-pyrido[2,3]pyrazolo[2,4-d][1,2,5]oxadiazepine-10-carboxamide

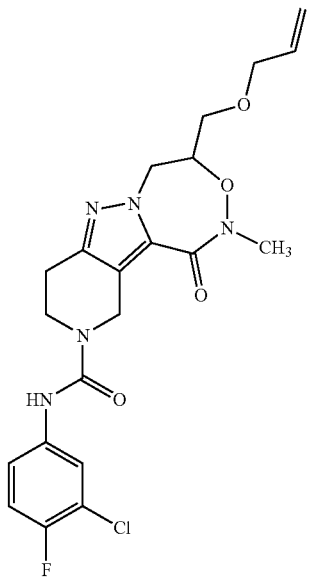 [SMILES: C=CCOCC1Cn2nc3c(c2C(=O)N(C)O1)CN(C(=O)Nc1ccc(F)c(Cl)c1)CC3]

Step 1. tert-butyl 4-(allyloxymethyl)-2-methyl-1-oxo-5,8,9,11-tetrahydro-4H-pyrido[2,3]pyrazolo[2,4-d][1,2,5]oxadiazepine-10-carboxylate. To a solution of tert-butyl 4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxylate (Intermediate 1, 200.00 mg, 567.57 µmol, 1.00 eq) in DMF (2.00 mL) was NaH (45.41 mg, 1.14 mmol, 22.70 µL60% purity, 2.00 eq) with stirring at −10° C. for 0.5 h under N$_2$. And then 3-bromoprop-1-ene (103.00 mg, 851.35 µmol, 1.50 eq) was added into the mixture. The mixture was stirred at 15° C. for 1 h. TLC (petroleum ether:ethyl acetate=1:5) showed that the starting material was consumed completely and one main new spot formed. LCMS indicated that MS of desired product was detected. The mixture was quenched with 1 mL of water and extracted with ethyl acetate (10 mL*3). The organic layers was combined and dried over anhydrous Na₂SO₄, filtered and concentrated to obtain the title compound (160.00 mg, 407.70 μmol, 71.83% yield) as off-white oil. ¹H NMR (400 MHz, CHLOROFORM-d) δ=5.96-5.84 (m, 1H), 5.33-5.20 (m, 2H), 4.63 (brs, 2H), 4.60-4.48 (m, 2H), 4.40-4.31 (m, 1H), 4.04 (d, J=5.6 Hz, 2H), 3.70 (d, J=5.2 Hz, 2H), 3.64 (dd, J=6.0, 12.0 Hz, 1H), 3.57-3.50 (m, 1H), 3.27 (s, 3H), 2.81-2.72 (m, 2H), 1.47 (s, 9H). LCMS [M+1]: 393.

Step 2. Preparation of 4-(allyloxymethyl)-2-methyl-4,5,8,9,10,11-hexahydropyrido[2,3] pyrazolo[2,4-d][1,2,5]oxadiazepin-1-one. To a solution of tert-butyl 4-(allyloxymethyl)-2-methyl-1-oxo-5,8,9,11-tetrahydro-4H-pyrido[2,3]pyrazolo[2,4-d][1,2,5]oxadiazepine-10-carboxylate (30.00 mg, 76.44 μmol, 1.00 eq) in DCM (1.00 mL) was added TFA (770.00 mg, 6.75 mmol, 500.00 μL 88.35 eq) with stirring at 15° C. for 1 h. TLC indicated that the starting material was consumed completely and one main spot formed. The mixture was directly evaporated to obtain the title compound (50.00 mg, crude, TFA) as a yellow oil and directly used in the next step.

Step 3. 4-(allyloxymethyl)-N-(3-chloro-4-fluoro-phenyl)-2-methyl-1-oxo-5,8,9,11-tetrahydro-4H-pyrido[2,3]pyrazolo[2,4-d][1,2,5]oxadiazepine-10-carboxamide. To a solution of 4-(allyloxymethyl)-2-methyl-4,5,8,9,10,11-hexahydropyrido [2,3]pyrazolo[2,4-d][1,2,5]oxadiazepin-1-one (31.00 mg, 76.29 μmol, 1.00 eq, TFA) and phenyl N-(3-chloro-4-fluoro-phenyl)carbamate (22.29 mg, 83.92 μmol, 1.10 eq) in DCM (2.00 mL) was added TEA (73.00 mg, 721.70 μmol, 100.00 μL 9.46 eq) with stirring at 30° C. for 1 h. LCMS indicated that the starting material was consumed completely and MS of desired product was detected. The mixture was evaporated to get the residue. The residue was purified by prep-HPLC (FA) to obtain the title compound (25.70 mg, 55.01 μmol, 72.11% yield, 99.3% purity) as a yellow solid. ¹H NMR (400 MHz, CHLOROFORM-d) δ=7.51-7.63 (m, 1H), 7.16-7.25 (m, 1H), 6.98-7.08 (m, 1H), 6.61-6.79 (m, 1H), 5.83-5.98 (m, 1H), 5.19-5.34 (m, 2H), 4.69 (s, 2H), 4.48-4.64 (m, 2H), 4.31-4.44 (m, 1H), 4.00-4.11 (m, 2H), 3.76-3.94 (m, 2H), 3.52-3.69 (m, 2H), 3.29 (s, 3H), 2.85 (t, J=5.60 Hz, 2H). LCMS[M+1]: 464.

Compound 103: N-(3-chloro-4-fluoro-phenyl)-2-methyl-1-oxo-4-(propoxymethyl)-5,8,9,11-tetrahydro-4H-pyrido[2,3]pyrazolo[2,4-d][1,2,5]oxadiazepine-10-carboxamide

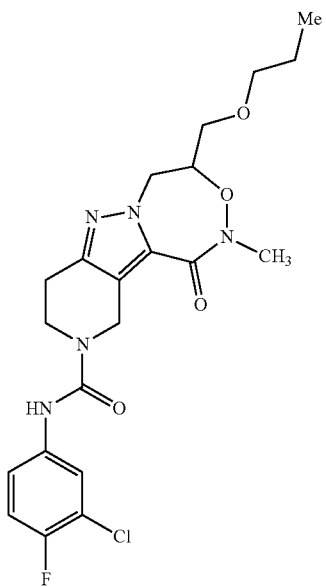 [SMILES: CCCOCC1Cn2nc3c(c2C(=O)N(C)O1)CN(C(=O)Nc1ccc(F)c(Cl)c1)CC3]

Step 1. tert-butyl 2-methyl-1-oxo-4-(propoxymethyl)-5,8,9,11-tetrahydro-4H-pyrido[2,3]pyrazolo[2,4-d][1,2,5]oxadiazepine-10-carboxylate. To a solution of tert-butyl 4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxylate (Intermediate 1, 100.00 mg, 283.78 μmol, 1.00 eq) in DMF (2.00 mL) was added NaH (45.41 mg, 1.14 mmol, 22.70 μL 60% purity, 2.00 eq) with stirring at –10° C. for 0.5 h under N₂. And then 1-bromopropane (52.35 mg, 425.68 μmol, 38.78 μL 1.50 eq) was added into the mixture. The mixture was stirred at 15° C. for 1 h. TLC (petroleum ether:ethyl acetate=1:5) showed that the starting material, was consumed completely and one main new spot formed. LCMS indicated that MS of desired product was detected. The mixture was quenched with 1 mL of water and extracted with ethyl acetate (10 mL*3). The organic layers was combined and dried over anhydrous Na₂SO₄, filtered and concentrated to obtain the title compound (60.00 mg, 152.11 μmol, 53.60% yield) as off-white oil. ¹H NMR (400 MHz, CHLOROFORM-d) δ=4.62 (brs, 2H), 4.46-4.58 (m, 2H), 4.29-4.39 (m, 1H), 3.69 (d, J=4.77 Hz, 2H), 3.58-3.64 (m, 1H), 3.47-3.55 (m, 1H), 3.39-3.47 (m, 2H), 3.26 (s, 3H), 2.74 (t, J=5.14 Hz, 2H), 1.55-1.64 (m, 2H), 1.46 (s, 9H), 0.86-0.97 (m, 3H). LCMS[M+1]: 395.

Step 2. 2-methyl-4-(propoxymethyl)-4,5,8,9,10,11-hexahydropyrido [2,3]pyrazolo[2,4-d][1,2,5]oxadiazepin-1-one. To a solution of tert-butyl 2-methyl-1-oxo-4-(propoxymethyl)-5,8,9,11-tetrahydro-4H-pyrido[2,3]pyrazolo[2,4-d][1,2,5]oxadiazepine-10-carboxylate (60.00 mg, 152.11 μmol, 1.00 eq) in DCM (1.00 mL) was added TFA (1.54 g, 13.51 mmol, 1.00 mL, 88.79 eq) with stirring at 15° C. for 1 h. TLC indicated that the starting material was consumed completely and one main spot formed. The mixture was directly evaporated to obtain the title compound (70.00 mg, crude, TFA) as yellow oil and directly used in the next step. ¹H NMR (400 MHz, CHLOROFORM-d) δ=4.47-4.71 (m, 5H), 3.57-3.73 (m, 4H), 3.42-3.54 (m, 2H), 3.33 (s, 3H), 3.17 (t, J=6.0 Hz, 2H), 1.59-1.69 (m, 2H), 0.89-0.98 (m, 3H).

Step 3. N-(3-chloro-4-fluoro-phenyl)-2-methyl-1-oxo-4-(propoxymethyl)-5,8,9,11-tetrahydro-4H-pyrido[2,3]pyrazolo[2,4-d][1,2,5]oxadiazepine-10-carboxamide. To a solution of 2-methyl-4-(propoxymethyl)-4,5,8,9,10,11-hexahydropyrido [2,3]pyrazolo[2,4-d][1,2,5]oxadiazepin-1-one (70.00 mg, 171.41 μmol, 1.00 eq, TFA) and phenyl N-(3-chloro-4-fluoro-phenyl)carbamate (45.54 mg, 171.41 μmol, 1.00 eq) in DCM (2.00 mL) was added TEA (164.09 mg, 1.62 mmol, 224.78 μL 9.46 eq) with stirring at 30° C. for 1 h. LCMS indicated that the starting material was consumed completely and MS of desired product was detected. The mixture was evaporated to get the residue. The residue was purified by prep-HPLC (FA) to obtain the title compound (19.00 mg, 40.46 μmol, 23.60% yield, 99.2% purity) as a yellow solid. ¹H NMR (400 MHz, CHLOROFORM-d) δ=7.58 (dd, J=2.63, 6.54 Hz, 1H), 7.16-7.22 (m, 1H), 7.03-7.09 (m, 1H), 6.48 (s, 1H), 4.70 (s, 2H), 4.51-4.63 (m, 2H), 4.37-4.43 (m, 1H), 3.80-3.93 (m, 2H), 3.62-3.68 (m, 1H), 3.52-3.59 (m, 1H), 3.44-3.51 (m, 2H), 3.31 (s, 3H), 2.86 (t, J=5.81 Hz, 2H), 1.61-1.68 (m, 2H), 0.95 (t, J=7.40 Hz, 3H). LCMS[M+1]: 466.

Compound 104: N-(3-chloro-4-fluoro-phenyl)-4-(cyclopropylmethoxymethyl)-2-methyl-1-oxo-5,8,9,11-tetrahydro-4H-pyrido[2,3]pyrazolo[2,4-d][1,2,5]oxadiazepine-10-carboxamide

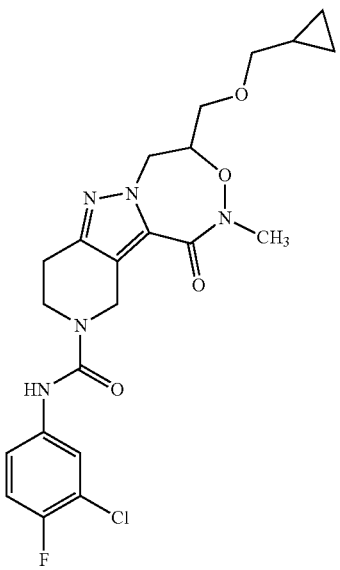 [SMILES: CN1OC(COCC2CC2)Cn2nc3c(c2C1=O)CN(C(=O)Nc1ccc(F)c(Cl)c1)CC3]

Step 1. Preparation of tert-butyl4-(cyclopropylmethoxymethyl)-2-methyl-1-oxo-5,8,9,11-tetrahy-dro-4H-pyrido[2,3]pyrazolo[2,4-d][1,2,5]oxadiazepine-10-carboxylate. To a solution of tert-butyl 4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxylate (Intermediate 1, 500.00 mg, 1.42 mmol, 1.00 eq) in DMF (5.00 mL) was added NaH (113.51 mg, 2.84 mmol, 22.70 µL 60% purity, 2.00 eq) with stirring at −10° C. for 0.5 h under $N_2$. Then bromomethylcyclopropane (287.33 mg, 2.13 mmol, 203.78 µL 1.50 eq) was added into the mixture. The mixture was stirred at 0° C. for 1 h. TLC showed that the starting material was consumed completely and one main new spot formed. The mixture was quenched with 1 mL of water and extracted with EtOAc (10 mL*3). The organic layers was combined and dried over anhydrous $Na_2SO_4$, filtered and concentrated to give a residue. The residue was purified by prep-TLC to obtain the title compound (290.00 mg, 713.46 µmol, 50.24% yield) as yellow oil. $^1$H NMR (400 MHz, CHLOROFORM-d) δ=4.62 (brs, 2H), 4.46-4.59 (m, 2H), 4.28-4.38 (m, 1H), 3.66 (dt, J=5.50, 11.07 Hz, 3H), 3.53 (dd, J=5.26, 10.15 Hz, 1H), 3.33 (dd, J=2.32, 6.85 Hz, 2H), 3.27 (s, 3H), 2.74 (br s, 2H), 1.39-1.53 (m, 9H), 0.99-1.10 (m, 1H), 0.49-0.59 (m, 2H), 0.15-0.24 (m, 2H).

Step 2. Preparation of 4-(cyclopropylmethoxymethyl)-2-methyl-4,5,8,9,10,11-hexahydropyrido[2,3]pyrazolo[2,4-d][1,2,5]oxadiazepin-1-one. To a solution of tert-butyl 4-(cyclopropylmethoxymethyl)-2-methyl-1-oxo-5,8,9,11-tetrahydro-4H-pyrido[2,3]pyrazolo[2,4-d][1,2,5]oxadiazepine-10-carboxylate (80.00 mg, 196.82 µmol, 1.00 eq) in DCM (2.00 mL) was added TFA (3.99 g, 34.95 mmol, 2.59 mL, 177.60 eq) with stirring at 15° C. for 1 h. TLC showed that the starting material was consumed completely. The mixture was directly evaporated to get the title compound (85.00 mg, crude, TFA) as a yellow oil and directly used in the next step.

Step 3. N-(3-chloro-4-fluoro-phenyl)-4-(cyclopropylmethoxymethyl)-2-methyl-1-oxo-5,8,9,11-tetrahydro-4H-pyrido[2,3]pyrazolo[2,4-d][1,2,5]oxadiazepine-10-carboxamide. To a solution of 4-(cyclopropylmethoxymethyl)-2-methyl-4,5,8,9,10,11-hexahydropyrido[2,3]pyrazolo[2,4-d][1,2,5]oxadiazepin-1-one (83.00 mg, 197.44 µmol, 1.00 eq, TFA) and phenyl N-(3-chloro-4-fluoro-phenyl)carbamate (57.70 mg, 217.18 µmol, 1.10 eq) in DCM (2.00 mL) was added TEA (201.99 mg, 2.00 mmol, 276.70 µL 10.11 eq) with stirring at 30° C. for 1 h. LCMS indicated that reactant was consumed completely and MS of desired product was detected. The mixture was evaporated to get the residue. The residue was purified by prep-HPLC (FA) to obtain the title compound (48.60 mg, 100.67 µmol, 50.99% yield, 99% purity) as white solid. $^1$H NMR (400 MHz, CHLOROFORM-d) δ=7.54 (dd, J=2.63, 6.54 Hz, 1H), 7.14-7.23 (m, 1H), 7.03 (t, J=8.80 Hz, 1H), 6.71 (s, 1H), 4.69 (s, 2H), 4.51-4.63 (m, 2H), 4.34-4.44 (m, 1H), 3.75-3.91 (m, 2H), 3.52-3.72 (m, 2H), 3.33-3.39 (m, 2H), 3.29 (s, 3H), 2.84 (t, J=5.75 Hz, 2H), 1.01-1.12 (m, 1H), 0.52-0.61 (m, 2H), 0.19-0.26 (m, 2H). LCMS (M+1): 478.

Compound 105: N-(3-chloro-4-fluoro-phenyl)-4-(2,2-difluoroethoxymethyl)-2-methyl-1-oxo-5,8,9,11-tetrahydro-4H-pyrido[2,3]pyrazolo[2,4-d][1,2,5]oxadiazepine-10-carboxamide

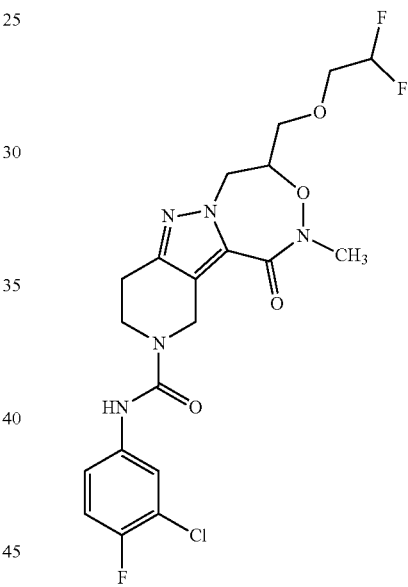

Step 1. tert-butyl 4-(2,2-difluoroethoxymethyl)-2-methyl-1-oxo-5,8,9,11-tetrahydro-4H-pyrido[2,3]pyrazolo[2,4-d][1,2,5]oxadiazepine-10-carboxylate. To a solution of tert-butyl 4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxylate (Intermediate 1, 200.00 mg, 567.57 µmol, 1.00 eq) in DMF (2.00 mL) was added NaH (68.11 mg, 1.70 mmol, 22.70 µL 60% purity, 3.00 eq) with stirring at −10° C. for 0.5 h under $N_2$. Then the resulting DMF solution of 2, 2-difluoroethyl trifluoromethanesulfonate (Intermediate 19, 5.68 mmol, 1.00 mL, 10.00 eq) was added into the mixture. The mixture was stirred at 0° C. for 2 h. TLC (PE:EtOAc=1:5) showed that the first reactant was consumed completely and some new spots formed. LCMS indicated that the desired product was detected. The mixture was poured into 10 mL of ice water and extracted with Ethyl acetate (10 mL*3). The organic layers was combined and dried over anhydrous $Na_2SO_4$, filtered and concentrated to give the residue. The residue was purified by prep-TLC to obtain the title compound (100.00 mg, 240.14 µmol, 42.31% yield) as yellow oil. $^1$H NMR (400 MHz, CHLOROFORM-d) δ=5.69-6.04 (m, 1H), 4.45-4.63 (m, 4H), 4.27-4.40 (m, 1H), 3.59-3.79 (m, 6H), 3.24 (s, 3H), 2.64-2.78 (m, 2H), 1.45 (s, 9H).

Step 3. Preparation of 4-(2,2-difluoroethoxymethyl)-2-methyl-4,5,8,9,10,11-hexahydropyrido[2,3]pyrazolo[2,4-d][1,2,5]oxadiazepin-1-one. To a solution of tert-butyl 4-(2,2-difluoroethoxymethyl)-2-methyl-1-oxo-5,8,9,11-tetrahydro-4H-pyrido[2,3]pyrazolo[2,4-d][1,2,5]oxadiazepine-10-carboxylate (100.00 mg, 240.14 μmol, 1.00 eq) in DCM (2.00 mL) was added TFA (1.54 g, 13.51 mmol, 1.00 mL, 56.24 eq) with stirring at 15° C. for 1 h. TLC showed that reactant was consumed completely and one new spot formed. The mixture was directly evaporated to get the title compound (110.00 mg, crude, TFA) as yellow oil and directly used in the next step.

Step 4. N-(3-chloro-4-fluoro-phenyl)-4-(2,2-difluoroethoxymethyl)-2-methyl-1-oxo-5,8,9,11-tetrahydro-4H-pyrido[2,3]pyrazolo[2,4-d][1,2,5]oxadiazepine-10-carboxamide. To a solution of 4-(2,2-difluoroethoxymethyl)-2-methyl-4,5,8,9,10,11-hexahydropyrido[2,3]pyrazolo[2,4-d][1,2,5]oxadiazepin-1-one (103.00 mg, 239.35 μmol, 1.00 eq, TFA) in DCM (2.00 mL) was added TEA (193.76 mg, 1.91 mmol, 265.42 μL 8.00 eq) with stirring at 30° C. for 1 h. LCMS indicated that reactant was consumed completely and the desired product was detected. The mixture was evaporated to get the residue. The residue was purified by prep-HPLC (FA) to obtain the title compound (61.00 mg, 124.29 μmol, 51.93% yield, 99.4% purity) as a white solid. $^1$H NMR (400 MHz, CHLOROFORM-d) δ=7.54 (dd, J=2.70, 6.59 Hz, 1H), 7.19 (ddd, J=2.70, 4.05, 8.94 Hz, 1H), 6.99-7.08 (m, 1H), 6.73 (s, 1H), 5.72-6.06 (m, 1H), 4.69 (s, 2H), 4.51-4.64 (m, 2H), 4.33-4.43 (m, 1H), 3.81-3.90 (m, 2H), 3.66-3.80 (m, 4H), 3.24-3.35 (m, 3H), 2.77-2.91 (m, 2H). LCMS (M+1): 488.

Compound 106: N-(3-chloro-4-fluoro-phenyl)-2-methyl-1-oxo-4-(2,2,2-trifluoroethoxymethyl)-5,8,9,11-tetrahydro-4H-pyrido[2,3]pyrazolo[2,4-d][1,2,5]oxadiazepine-10-carboxamide

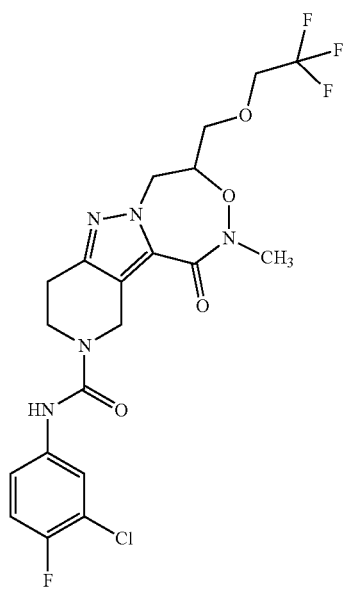 [SMILES: CN1OC(COCC(F)(F)F)Cn2nc3c(c2C1=O)CN(C(=O)Nc1ccc(F)c(Cl)c1)CC3]

Step 1. tert-butyl 2-methyl-1-oxo-4-(2,2,2-trifluoroethoxymethyl)-5,8,9,11-tetrahydro-4H-pyrido[2,3]pyrazolo[2,4-d][1,2,5]oxadiazepine-10-carboxylate. To a solution of tert-butyl 4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxylate (Intermediate 1, 500.00 mg, 1.42 mmol, 1.00 eq) in DMF (2.00 mL) was added NaH (170.27 mg, 4.26 mmol, 22.70 μL 60% purity, 3.00 eq) at −10° C. The mixture was stirred for 0.5 h under N$_2$. Then a DMF solution of 2,2,2-trifluoroethyl trifluoromethanesulfonate (Intermediate 20, 14.19 mmol, 1 mL, 10.00 eq) was added to the mixture. The mixture was stirred at 0° C. for 5 h. LCMS indicated that the MS of desired product was detected. The mixture was poured into 10 mL of ice water and extracted with Ethyl acetate (10 mL*3). The organic layers were combined and dried over anhydrous Na$_2$SO$_4$, filtered and concentrated to give the residue. The residue was purified by prep-TLC to obtain the title compound (160.00 mg, crude) as yellow oil. LCMS: 435 (M+1).

Step 3. Preparation of 2-methyl-4-(2,2,2-trifluoroethoxymethyl)-4,5,8,9,10,11-hexahydropyrido[2,3]pyrazolo[2,4-d][1,2,5]oxadiazepin-1-one. To a solution of tert-butyl 2-methyl-1-oxo-4-(2,2,2-trifluoroethoxymethyl)-5,8,9,11-tetrahydro-4H-pyrido[2,3]pyrazolo[2,4-d][1,2,5]oxadiazepine-10-carboxylate (80.00 mg, 184.16 μmol, 1.00 eq) in DCM (2.00 mL) was added TFA (1.54 g, 13.51 mmol, 1.00 mL, 73.34 eq) with stirring at 15° C. for 1 h. TLC showed that reactant was consumed completely and one new spot formed. The mixture was directly evaporated to get the title compound (85.00 mg, crude, TFA) as yellow oil.

Step 4. Preparation of Compound 106: N-(3-chloro-4-fluoro-phenyl)-2-methyl-1-oxo-4-(2,2,2-trifluoroethoxymethyl)-5,8,9,11-tetrahydro-4H-pyrido[2,3]pyrazolo[2,4-d][1,2,5]oxadiazepine-10-carboxamide. To a solution of 2-methyl-4-(2,2,2-trifluoroethoxymethyl)-4,5,8,9,10,11-hexahydropyrido[2,3]pyrazolo[2,4-d][1,2,5]oxadiazepin-1-one (30.00 mg, 66.92 μmol, 1.00 eq, TFA) and phenyl N-(3-chloro-4-fluoro-phenyl)carbamate (17.78 mg, 66.92 μmol, 1.00 eq) in DCM (2.00 mL) was added TEA (54.17 mg, 535.33 μmol, 74.21 μL 8.00 eq) with stirring at 30° C. for 1 h. LCMS indicated that reactant was consumed completely and the desired product was detected. The mixture was evaporated in vacuo. The residue was purified by prep-HPLC (FA) to obtain the title compound (23.00 mg, 44.33 μmol, 33.12% yield, 97.5% purity) as a white solid. $^1$H NMR (400 MHz, METHANOL-d$_4$) δ=7.58 (dd, J=2.51, 6.65 Hz, 1H), 7.23-7.36 (m, 1H), 7.06-7.19 (m, 1H), 4.65-4.75 (m, 1H), 4.59 (br dd, J=5.71, 14.49 Hz, 1H), 4.37 (dd, J=6.90, 14.56 Hz, 1H), 4.02 (q, J=8.87 Hz, 1H), 3.75-3.91 (m, 1H), 3.28 (s, 1H), 2.82 (br t, J=5.58 Hz, 1H). LCMS: 506 (M+1).

Compound 107: N-(3-chloro-4-fluoro-phenyl)-4-(hydroxymethyl)-1-oxo-2-(trideuteriomethyl)-5,8,9,11-tetrahydro-4H-pyrido[2,3]pyrazolo[2,4-d][1,2,5]oxadiazepine-10-carboxamide

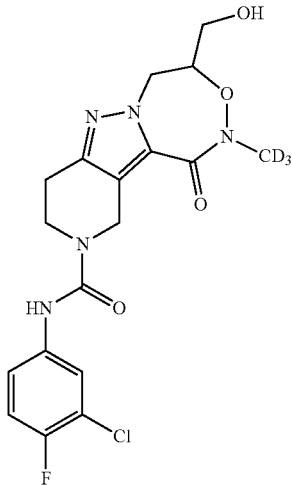

Step 1. Preparation of 4-(hydroxymethyl)-2-(trideuteriomethyl)-4,5,8,9,10,11-hexahydropyrido[2,3]pyrazolo[2,4-d][1,2,5]oxadiazepin-1-one. A mixture of tert-butyl 4-(hydroxymethyl)-2-(methyl-d3)-1-oxo-1,4,5,8,9,11-hexahydropyrido[4',3':3,4]pyrazolo[5,1-d][1,2,5]oxadiazepine-10(2H)-carboxylate (Intermediate 21, 40.00 mg, 112.55 µmol, 1.00 eq) in DCM (2.00 mL) was added TFA (1.54 g, 13.51 mmol, 1.00 mL, 120.00 eq), and then the mixture was stirred at 10° C. for 1 hour. TLC showed the starting material was consumed completely and a new spot appeared. The mixture was concentrated in vacuum to give the title compound (41.57 mg, 112.56 µmol, 100.00% yield, TFA) as a yellow oil.

Step 2. N-(3-chloro-4-fluoro-phenyl)-4-(hydroxymethyl)-1-oxo-2-(trideuteriomethyl)-5,8,9,11-tetrahydro-4H-pyrido[2,3]pyrazolo[2,4-d][1,2,5]oxadiazepine-10-carboxamide. A mixture of 4-(hydroxymethyl)-2-(trideuteriomethyl)-4,5,8,9,10,11-hexahydropyrido [2,3]pyrazolo[2,4-d][1,2,5]oxadiazepin-1-one (41.57 mg, 112.56 µmol, 1.00 eq, TFA), phenyl N-(3-chloro-4-fluoro-phenyl)carbamate (32.89 mg, 123.82 µmol, 1.10 eq), TEA (22.78 mg, 225.12 µmol, 31.21 µL 2.00 eq) in DCM (3.00 mL) was degassed and purged with $N_2$ for 3 times, and then the mixture was stirred at 10° C. for 16 hour under $N_2$ atmosphere. LCMS showed the starting material was consumed completely and desired product was major. The mixture was poured into water (5 mL) and stirred at 5 min. The aqueous phase was extracted with DCM (3 mL*3). The combined organic phase was washed with brine (5 mL), dried with anhydrous $Na_2SO_4$, filtered and concentrated in vacuum. The residue was purified by prep-HPLC(FA) to give the title compound (21.00 mg, 48.21 µmol, 42.83% yield, 98% purity) as a white solid. $^1$H NMR (400 MHz, CHLOROFORM-d) δ 7.54-7.59 (m, 1H) 7.16-7.22 (m, 1H) 7.06 (t, J=8.78 Hz, 1H) 6.51 (s, 1H) 4.70 (s, 2H) 4.51-4.62 (m, 2H) 4.34-4.47 (m, 1H) 3.74-3.93 (m, 4H) 2.86 (s, 2H) 1.87-2.07 (m, 1H). LCMS: 427 [M+1].

Compound 108_D1: (4S*,9R)—N-(5-bromo-2,4-difluorophenyl)-4-((2,2-difluoroethoxy)methyl)-2,9-dimethyl-1-oxo-1,4,5,8,9,11-hexahydropyrido[4',3':3,4]pyrazolo[5,1-d][1,2,5]oxadiazepine-10(2H)-carboxamide

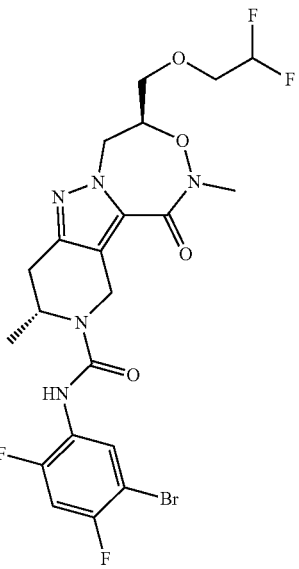

Compound 108_D1 was prepared in an analogous manner to Compound 121.
LC-MS: 564/566 [M+1]. $^1$H NMR (400 MHz, CHLOROFORM-d) δ=8.34 (t, J=7.89 Hz, 1H), 6.94 (dd, J=7.95, 10.64 Hz, 1H), 6.53 (br s, 1H), 5.68-6.13 (m, 1H), 5.09 (br t, J=6.17 Hz, 1H), 4.86 (d, J=15.77 Hz, 1H), 4.35-4.71 (m, 4H), 3.61-3.84 (m, 4H), 3.31 (s, 3H), 3.05 (dd, J=5.69, 15.71 Hz, 1H), 2.70 (d, J=15.89 Hz, 1H), 1.21 (d, J=6.85 Hz, 3H).
* pure but unknown stereochemistry Compound 108_D2: (4R*,9R)—N-(5-bromo-2,4-difluorophenyl)-4-((2,2-difluoroethoxy)methyl)-2,9-dimethyl-1-oxo-1,4,5,8,9,11-hexahydropyrido[4',3':3,4]pyrazolo[5,1-d][1,2,5]oxadiazepine-10(2H)-carboxamide

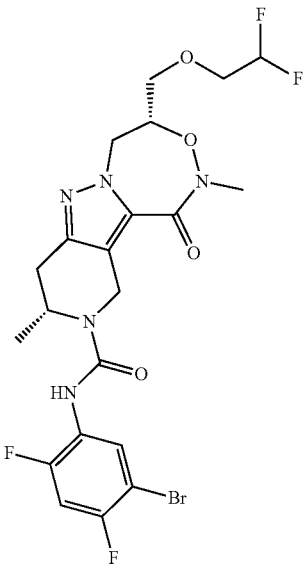 [SMILES: C[C@@H]1Cc2nn3c(c2CN1C(=O)Nc1cc(Br)c(F)cc1F)C(=O)N(C)O[C@@H](COCC(F)F)C3]

Compound 108_D1 was prepared in an analogous manner to Compound 121.

LCMS (M+1): 564/566. $^1$H NMR (400 MHz, CHLOROFORM-d) δ=8.31-8.37 (m, 1H), 6.94 (dd, J=7.91, 10.67 Hz, 1H), 6.53 (br s, 1H), 5.75-6.06 (m, 1H), 5.10 (br t, J=6.09 Hz, 1H), 4.88 (d, J=15.69 Hz, 1H), 4.37-4.64 (m, 4H), 3.71-3.85 (m, 4H), 3.31 (s, 3H), 3.05 (dd, J=5.46, 16.00 Hz, 1H), 2.71 (d, J=15.81 Hz, 1H), 1.20 (d, J=6.90 Hz, 3H).

* pure but unknown stereochemistry

Compound 109: (4S*,9S*)—N-(3-chloro-4-fluorophenyl)-9-ethyl-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide

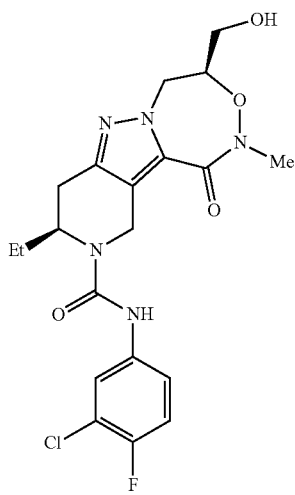 [SMILES: CC[C@H]1Cc2nn3c(c2CN1C(=O)Nc1ccc(F)c(Cl)c1)C(=O)N(C)O[C@H](CO)C3]

Step 11. 9-ethyl-4-(hydroxymethyl)-2-methyl-4,5,8,9,10,11-hexahydropyrido[2,3]pyrazolo[2,4-d][1,2,5]oxadiazepin-1-one. To a solution of tert-butyl 9-ethyl-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxylate (Intermediate 23, 50.00 mg, 131.43 μmol, 1.00 eq) in DCM (2.00 mL) was added TFA (1.54 g, 13.51 mmol, 1.00 mL, 102.76 eq). The reaction mixture was stirred at 25° C. for 30 minutes. TLC indicated the starting material consumed completely, and one major new spot with larger polarity was detected. The reaction mixture was concentrated on a rotary evaporator to give the title compound (50.00 mg, crude, TFA) as yellow oil, used in next step directly.

Step 2. (4S*,9S*)—N-(3-chloro-4-fluorophenyl)-9-ethyl-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide. To a mixture of 9-ethyl-4-(hydroxymethyl)-2-methyl-4,5,8,9,10,11-hexahydro pyrido[2,3]pyrazolo[2,4-d][1,2,5]oxadiazepin-1-one (50.00 mg, 126.79 μmol, 1.00 eq, TFA) in DCM (3.00 mL) was added TEA (51.32 mg, 507.16 μmol, 70.30 μL4.00 eq), followed by phenyl N-(3-chloro-4-fluoro-phenyl)carbamate (33.68 mg, 126.79 μmol, 1.00 eq), and the reaction mixture was stirred at 25° C. for 16 hours. LCMS showed one main peak with desired MS was detected. The mixture was extracted with DCM (50 mL) and water (30 mL*2), the organic phase was dried with anhydrous $Na_2SO_4$, filtered and concentrated in vacuum. The residue was purified by prep-HPLC(FA) to give the title compound (46.00 mg, 99.76 μmol, 78.68% yield, 98% purity) as white solid, which was separated by SFC, followed by prep-HPLC to get both diastereomers (109_D1: 20 mg and 109_D2: 20 mg).

SFC separation condition: Instrument: SFC 80; Column: AD-5 um; Mobile phase: A for $CO_2$ and B for IPA (0.1% $NH_3H_2O$); Gradient: B 30%; Flow rate: 60 mL/min; Back pressure: 100 bar; Column temperature: 35° C.; Wavelength: 220 nm. 1H NMR (400 MHz, CHLOROFORM-d) δ=7.59 (dd, J=2.70, 6.46 Hz, 1H), 7.16-7.23 (m, 1H), 7.03-7.10 (m, 1H), 6.50 (s, 1H), 4.81-4.89 (m, 2H), 4.51-4.63 (m, 2H), 4.40-4.48 (m, 2H), 3.72-3.89 (m, 2H), 3.33 (s, 3H), 3.00 (dd, J=5.77, 15.94 Hz, 1H), 2.77 (d, J=16.19 Hz, 1H), 1.95 (br s, 1H), 1.40-1.54 (m, 2H), 0.94 (t, J=7.40 Hz, 3H). LCMS: 452/454 [M+1]

* pure but unknown stereochemistry

Compound 109_D2: (4S*,9R*)—N-(3-chloro-4-fluorophenyl)-9-ethyl-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide

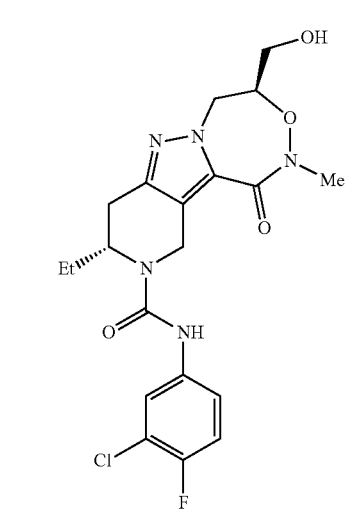 [SMILES: CC[C@@H]1Cc2nn3c(c2CN1C(=O)Nc1ccc(F)c(Cl)c1)C(=O)N(C)O[C@H](CO)C3]

1H NMR (400 MHz, CHLOROFORM-d) δ=7.60 (dd, J=2.64, 6.53 Hz, 1H), 7.18-7.23 (m, 1H), 7.03-7.09 (m, 1H), 6.58 (s, 1H), 4.84-4.93 (m, 2H), 4.52-4.60 (m, 2H), 4.35-4.43 (m, 2H), 3.75-3.92 (m, 2H), 3.33 (s, 3H), 3.00 (dd, J=6.02, 16.06 Hz, 1H), 2.77 (d, J=15.81 Hz, 1H), 1.92-2.08 (m, 1H), 1.42-1.55 (m, 2H), 0.94 (t, J=7.34 Hz, 3H). LCMS: 452/454 [M+1]

* pure but unknown stereochemistry

Compounds 109_D3/D4 were prepared through the similar procedure of 109_D1/D2. SFC separation condition: Instrument: SFC 80; Column: OJ-5 um; Mobile phase: A for $CO_2$ and B for EtOH (0.1% $NH_3H_2O$); Gradient: B 20%; Flow rate: 50 mL/min; Back pressure: 100 bar; Column temperature: 35° C.; Wavelength: 220 nm.

109_D3: (4R*,9R*)—N-(3-chloro-4-fluorophenyl)-9-ethyl-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide

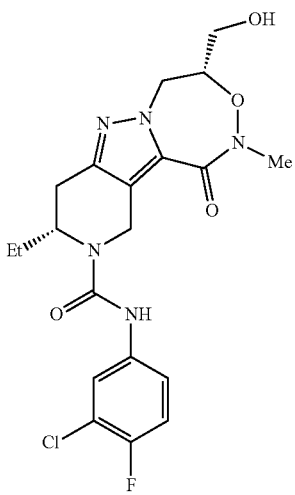 [SMILES: CC[C@@H]1Cc2nn3c(c2CN1C(=O)Nc1ccc(F)c(Cl)c1)C(=O)N(C)O[C@@H](CO)C3]

1H NMR (400 MHz, CHLOROFORM-d) δ=7.60 (dd, J=2.64, 6.53 Hz, 1H), 7.18-7.23 (m, 1H), 7.03-7.09 (m, 1H), 6.52 (s, 1H), 4.84-4.92 (m, 2H), 4.52-4.59 (m, 2H), 4.36-4.43 (m, 2H), 3.86-3.92 (m, 1H), 3.76-3.82 (m, 1H), 3.33 (s, 3H), 3.00 (dd, J=5.83, 16.00 Hz, 1H), 2.77 (d, J=15.94 Hz, 1H), 1.83-2.04 (m, 1H), 1.41-1.55 (m, 2H), 0.94 (t, J=7.40 Hz, 3H)

LCMS: 452 [M+1].

* pure but unknown stereochemistry

109_D4: (4R*,9S*)—N-(3-chloro-4-fluorophenyl)-9-ethyl-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide

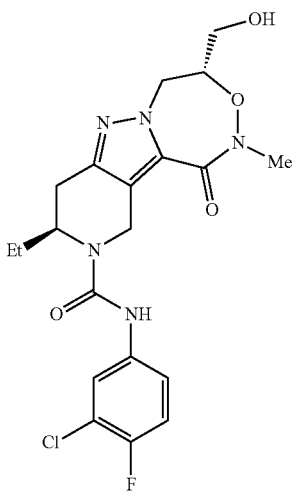 [SMILES: CC[C@H]1Cc2nn3c(c2CN1C(=O)Nc1ccc(F)c(Cl)c1)C(=O)N(C)O[C@@H](CO)C3]

1H NMR (400 MHz, CHLOROFORM-d) δ=7.59 (dd, J=2.64, 6.53 Hz, 1H), 7.20 (ddd, J=2.70, 4.05, 8.94 Hz, 1H), 7.03-7.09 (m, 1H), 6.55 (br s, 1H), 4.84 (br d, J=15.69 Hz, 2H), 4.51-4.62 (m, 2H), 4.39-4.46 (m, 2H), 3.81-3.88 (m, 1H), 3.72-3.78 (m, 1H), 3.33 (s, 3H), 2.99 (dd, J=5.83, 16.00 Hz, 1H), 2.77 (d, J=15.94 Hz, 1H), 1.87-2.19 (m, 1H), 1.42-1.56 (m, 2H), 0.94 (t, J=7.40 Hz, 3H)

LCMS: 452 [M+1].

* pure but unknown stereochemistry

Compound 110_D1: (4S*,9R)—N10-(3-chloro-2,4-difluorophenyl)-N4,2,9-trimethyl-1-oxo-1,4,5,8,9,11-hexahydropyrido[4',3':3,4]pyrazolo[5,1-d][1,2,5]oxadiazepine-4,10(2H)-dicarboxamide

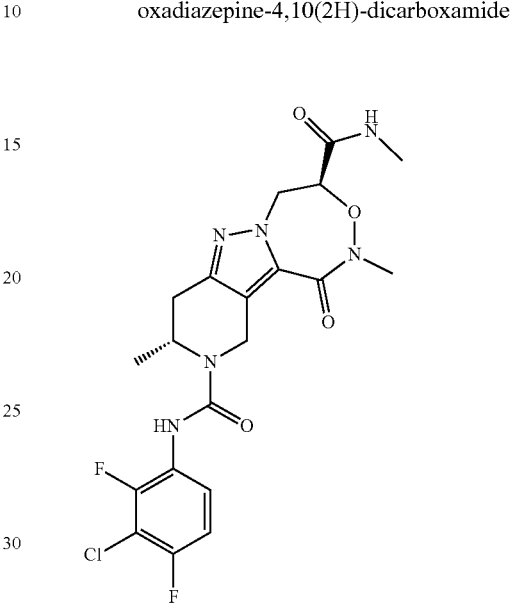

Step 1. (9R)—N,2,9-trimethyl-1-oxo-4,5,8,9,10,11-hexahydropyrido[2,3]pyrazolo[2,4-d][1,2,5]oxadiazepine-4-carboxamide. A solution of tert-butyl (9R)-2,9-dimethyl-4-(methylcarbamoyl)-1-oxo-1,4,5,8,9,11-hexahydropyrido[4',3':3,4]pyrazolo[5,1-d][1,2,5]oxadiazepine-10(2H)-carboxylate (Intermediate 25, 165.00 mg, 419.38 μmol, 1.00 eq) in DCM (2.00 mL) was added TFA (1.54 g, 13.51 mmol, 1.00 mL, 32.21 eq), and then the mixture was stirred at 30° C. for 0.5 hour. TLC showed the starting material was consumed completely, desired product was major. The mixture was concentrated in vacuum to give the title compound (170.00 mg, 417.34 μmol, 99.51% yield, TFA) as a yellow oil, which was used directly for next step.

Step 2. (9R)—N10-(3-chloro-2,4-difluoro-phenyl)-N4,2,9-trimethyl-1-oxo-5,8,9,11-tetrahydro-4H-pyrido[2,3]pyrazolo[2,4-d][1,2,5]oxadiazepine-4,10-dicarboxamide. A mixture of (9R)—N,2,9-trimethyl-1-oxo-4,5,8,9,10,11-hexahydropyrido[2,3]pyrazolo[2,4-d][1,2,5]oxadiazepine-4-carboxamide (56.00 mg, 137.48 μmol, 1.00 eq, TFA), phenyl N-(3-chloro-2,4-difluoro-phenyl)carbamate (46.80 mg, 164.97 μmol, 1.20 eq), TEA (27.82 mg, 274.95 μmol, 38.11 μL 2.00 eq) in DCM (3.00 mL) was degassed and purged with N₂ for 3 times, and then the mixture was stirred at 30° C. for 16 hour under N₂ atmosphere. LCMS showed the starting material was consumed completely and desired product was major. The mixture was poured into water (10 mL) and extracted with DCM (5 mL*3). The combined organic phase was washed with brine (10 mL), dried with anhydrous Na₂SO₄, filtered and concentrated in vacuum. The residue was purified by Prep-HPLC (FA) to give the title compound (40.00 mg, 80.35 μmol, 58.45% yield, 97% purity) as a white solid. LCMS: 483/484[M+1]. ¹H NMR (400 MHz, CHLOROFORM-d) δ 7.84-7.93 (m, 1H), 6.92-7.00 (m, 1H), 6.49-6.57 (m, 1H), 6.01-6.10 (m, 1H), 4.95-5.05 (m, 2H), 4.87-4.94 (m, 2H), 4.64-4.71 (m, 1H), 4.55 (s, 1H), 3.35 (s, 3H), 3.00-3.07 (m, 1H), 2.85 (d, J=4.89 Hz, 3H), 2.68-2.75 (m, 1H), 1.22 (d, J=6.90 Hz, 2H), 1.18-1.26 (m, 1H).

* pure but unknown stereochemistry

Compound 110_D2: (4R*,9R)—N10-(3-chloro-2,4-difluorophenyl)-N4,2,9-trimethyl-1-oxo-1,4,5,8,9,11-hexahydropyrido[4',3':3,4]pyrazolo[5,1-d][1,2,5]oxadiazepine-4,10(2H)-dicarboxamide

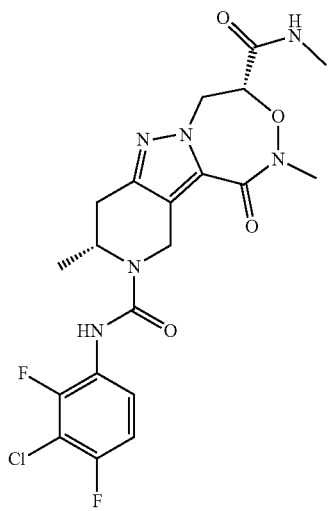

Compound 110_D2 was prepared in an analogous manner to 110_D1 using the opposite enantiomer of Intermediate 25.

LCMS: 483/484[M+1]. ¹H NMR (400 MHz, CHLOROFORM-d) δ=7.81-7.96 (m, 1H), 6.96 (br d, J=1.10 Hz, 1H), 6.49-6.61 (m, 1H), 6.07-6.22 (m, 1H), 5.02-5.11 (m, 1H), 4.84-5.00 (m, 3H), 4.75 (s, 1H), 4.48 (s, 1H), 3.35 (s, 3H), 3.00-3.10 (m, 1H), 2.89 (d, J=4.89 Hz, 3H), 2.72 (d, J=15.89 Hz, 1H), 1.19 (d, J=6.85 Hz, 3H).

* pure but unknown stereochemistry

Compounds 156, 111, and 112 were prepared in an analogous manner to Compound 110.

111 D1

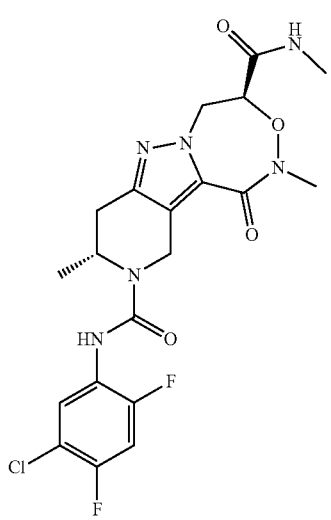 [SMILES: CNC(=O)[C@@H]1Cn2nc3c(c2C(=O)N(C)O1)CN(C(=O)Nc1ccc(F)c(Cl)c1F)[C@H](C)C3]

111 D2

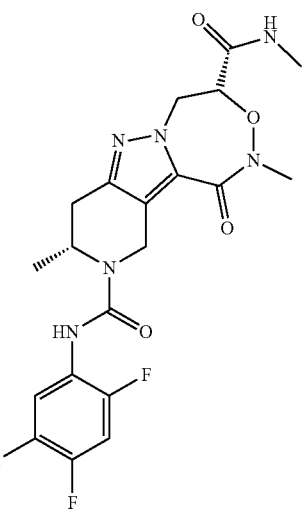

112 D1

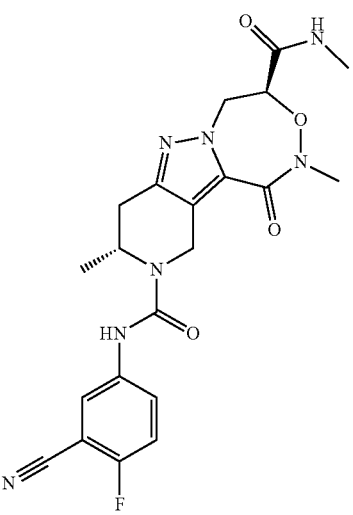

112 D2

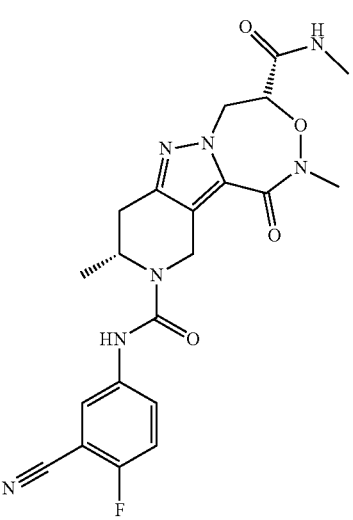

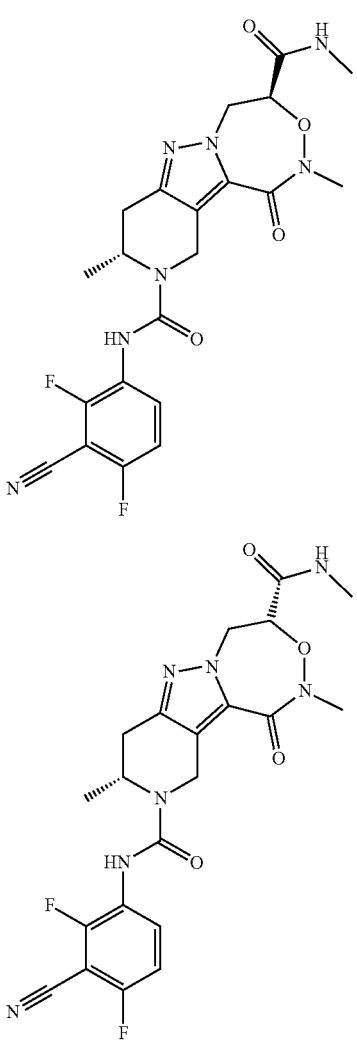

156 D1

156 D2

Compound 111_D1: (4S*,9R)—N10-(5-chloro-2,4-difluorophenyl)-N4,2,9-trimethyl-1-oxo-1,4,5,8,9,11-hexahydropyrido[4',3':3,4]pyrazolo[5,1-d][1,2,5]oxadiazepine-4,10(2H)-dicarboxamide LCMS: 483/484[M+1]. $^1$H NMR (400 MHz, CHLOROFORM-d) δ 8.15-8.24 (m, 1H), 6.91-7.01 (m, 1H), 6.51-6.57 (m, 1H), 6.00-6.08 (m, 1H), 4.95-5.05 (m, 2H), 4.85-4.94 (m, 2H), 4.64-4.71 (m, 1H), 4.48-4.55 (m, 1H), 3.35 (s, 3H), 2.99-3.08 (m, 1H), 2.85 (d, J=4.89 Hz, 3H), 2.68-2.76 (m, 1H), 1.19-1.25 (m, 3H).
* pure but unknown stereochemistry Compound 111_D2: (4R*,9R)—N10-(5-chloro-2,4-difluorophenyl)-N4,2,9-trimethyl-1-oxo-1,4,5,8,9,11-hexahydropyrido[4',3':3,4]pyrazolo[5,1-d][1,2,5]oxadiazepine-4,10(2H)-dicarboxamide LCMS: 483/484[M+1]. $^1$H NMR (400 MHz, CHLOROFORM-d) δ=8.16-8.22 (m, 1H), 6.91-7.00 (m, 1H), 6.53-6.59 (m, 1H), 6.11-6.20 (m, 1H), 5.02-5.12 (m, 1H), 4.85-4.98 (m, 3H), 4.69-4.76 (m, 1H), 4.47 (s, 1H), 3.35 (s, 3H), 3.00-3.08 (m, 1H), 2.89 (d, J=4.89 Hz, 3H), 2.69-2.76 (m, 1H), 1.19 (d, J=6.90 Hz, 3H).
* pure but unknown stereochemistry Compound 112_D1: (4S*,9R)—N10-(3-cyano-4-fluorophenyl)-N4,2,9-trimethyl-1-oxo-1,4,5,8,9,11-hexahydropyrido[4',3':3,4]pyrazolo[5,1-d][1,2,5]oxadiazepine-4,10(2H)-dicarboxamide LCMS: 456[M+1]. $^1$H NMR (400 MHz, CHLOROFORM-d) δ=7.73-7.79 (m, 1H), 7.57-7.64 (m, 1H), 7.10-7.19 (m, 1H), 6.67 (s, 1H), 6.01-6.10 (m, 1H), 4.81-5.12 (m, 4H), 4.64-4.74 (m, 1H), 4.51 (d, J=15.77 Hz, 1H), 3.35 (s, 3H), 2.98-3.08 (m, 1H), 2.86 (d, J=4.89 Hz, 3H), 2.66-2.75 (m, 1H), 1.20 (d, J=6.97 Hz, 3H).
* pure but unknown stereochemistry Compound 112_D2: (4R*,9R)—N10-(3-cyano-4-fluorophenyl)-N4,2,9-trimethyl-1-oxo-1,4,5,8,9,11-hexahydropyrido[4',3':3,4]pyrazolo[5,1-d][1,2,5]oxadiazepine-4,10(2H)-dicarboxamide LCMS: 456[M+1]. $^1$H NMR (400 MHz, CHLOROFORM-d) δ=7.75-7.80 (m, 1H), 7.59-7.66 (m, 1H), 7.11-7.18 (m, 1H), 6.80 (s, 1H), 6.12-6.19 (m, 1H), 5.08-5.16 (m, 1H), 4.87-4.99 (m, 3H), 4.68-4.75 (m, 1H), 4.42 (d, J=15.69 Hz, 1H), 3.35 (s, 3H), 2.98-3.06 (m, 1H), 2.89 (d, J=4.89 Hz, 3H), 2.68-2.76 (m, 1H), 1.15-1.20 (m, 3H).
* pure but unknown stereochemistry Compound 113: 4-(aminomethyl)-N-(3-chloro-4-fluoro-phenyl)-2-methyl-1-oxo-5,8,9,11-tetrahydro-4H-pyrido[2,3]pyrazolo[2,4-d][1,2,5]oxadiazepine-10-carboxamide

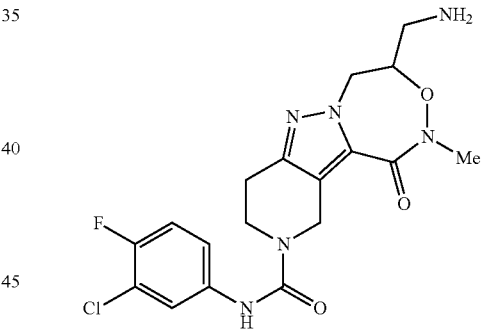

Step 1. Preparation of [10-[(3-chloro-4-fluoro-phenyl)carbamoyl]-2-methyl-1-oxo-5,8,9,11-tetrahydro-4H-pyrido[2,3]pyrazolo[2,4-d][1,2,5]oxadiazepin-4-yl]methyl methanesulfonate. A mixture of N-(3-chloro-4-fluoro-phenyl)-4-(hydroxymethyl)-2-methyl-1-oxo-5,8,9,11-tetrahydro-4H-pyrido[2,3]pyrazolo[2,4-d][1,2,5] oxadiazepine-10-carboxamide (Compound 031, 1.00 g, 2.36 mmol, 1.00 eq) and TEA (1.19 g, 11.80 mmol, 1.64 mL, 5.00 eq) in DCM (10.00 mL) was added MsCl (1.08 g, 9.44 mmol, 730.64 μL4.00 eq) at 0° C. under $N_2$, and then the mixture was stirred at 30° C. for 2 hour under $N_2$ atmosphere. TLC showed the starting material was consumed completely and a new spot formed. The mixture was poured into ice-water (20 mL) and stirred at 5 min. The aqueous phase was extracted with DCM (10 mL*2). The combined organic phase was washed with brine (20 mL), dried with anhydrous $Na_2SO_4$, filtered and concentrated in vacuum to give the title compound (1.40 g, crude) as a yellow solid. LCMS: 502/504 [M+1].

Step 2. 4-(azidomethyl)-N-(3-chloro-4-fluoro-phenyl)-2-methyl-1-oxo-5,8,9,11-tetrahydro-4H-pyrido[2,3]pyrazolo[1,2,5]oxadiazepine-10-carboxamide. A solution of [10-[(3-chloro-4-fluoro-phenyl)carbamoyl]-2-methyl-1-oxo-5,8,9,11-tetrahydro-4H-pyrido[2,3]pyrazolo[2,4-d][1,2,5]oxadiazepin-4-yl]methylmethanesulfonate (1.18 g, 2.35 mmol, 1.00 eq) in DMF (15.00 mL) was added NaN$_3$ (458.51 mg, 7.05 mmol, 247.84 µL3.00 eq) at 0° C. under N$_2$, and then the mixture was stirred at 50° C. for 16 hr under N$_2$ atmosphere. LCMS showed starting material/desired product=1/1. Then NaN$_3$ (458.32 mg, 7.05 mmol, 3.00 eq) was added to the mixture at 0° C. under N$_2$, and the mixture was stirred at 70° C. for another 16 hr. LCMS showed the starting material was consumed completely, desired product was major. The mixture was diluted with ethyl acetate (20 mL) and washed with brine (20 mL, *3). The organic phase was dried over Na$_2$SO$_4$, filtered and concentrated in vacuo to give the title compound (1.40 g, crude) as a yellow oil. LCMS: 449/451 [M+1]

Step 3. 4-(aminomethyl)-N-(3-chloro-4-fluoro-phenyl)-2-methyl-1-oxo-5,8,9,11-tetrahydro-4H-pyrido[2,3]pyrazolo[2,4-d][1,2,5]oxadiazepine-10-carboxamide. A solution of 4-(azidomethyl)-N-(3-chloro-4-fluoro-phenyl)-2-methyl-1-oxo-5,8,9,11-tetrahydro-4H-pyrido[2,3]pyrazolo[2,4-d][1,2,5]oxadiazepine-10-carboxamide (1.06 g, 2.36 mmol, 1.00 eq) in THF (12.00 mL) and H$_2$O (2.00 mL) was added PPh$_3$ (1.24 g, 4.72 mmol, 2.00 eq), and then the mixture was stirred at 30° C. for 16 hour under N$_2$ atmosphere. LCMS showed the starting material was consumed completely, desired product was major. The mixture was poured into water (30 mL) and stirred at 5 min. The aqueous phase was extracted with ethyl acetate (15 mL*2). The combined organic phase was washed with brine (30 mL), dried with anhydrous Na$_2$SO$_4$, filtered and concentrated in vacuum. The residue was purified by column chromatography (DCM/MeOH=100/1 to 20:1) to give the title compound (702.00 mg, 1.49 mmol, 63.31% yield, 90% purity) as a yellow solid, 75 mg of which was further purified by Prep-HPLC to give 25 mg pure desired product. LCMS: 423/425 [M+1]; $^1$H NMR (400 MHz, METHANOL-d$_4$) δ 7.55-7.63 (m, 1H), 7.26-7.34 (m, 1H), 7.14 (s, 1H), 4.72 (br d, J=2.13 Hz, 4H), 4.38-4.47 (m, 1H), 3.73-3.92 (m, 2H), 3.33 (s, 3H), 2.96-3.18 (m, 2H), 2.80-2.87 (m, 2H).

Compound 114_E1: (S*)-4-(aminomethyl)-N-(3-cyano-4-fluoro-phenyl)-2-methyl-1-oxo-5,8,9,11-tetrahydro-4H-pyrido[2,3]pyrazolo[2,4-d][1,2,5]oxadiazepine-10-carboxamide

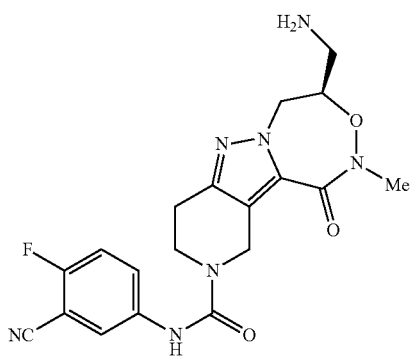 [SMILES: CN1O[C@H](CN)Cn2nc3c(c2C1=O)CN(C(=O)Nc1ccc(F)c(C#N)c1)CC3]

Step 1. 4-(azidomethyl)-2-methyl-4,5,8,9,10,11-hexahydropyrido[2,3]pyrazolo[2,4-d][1,2,5]oxadiazepin-1-one. A mixture of tert-butyl 4-(azidomethyl)-2-methyl-1-oxo-1,4,5,8,9,11-hexahydropyrido[4',3':3,4]pyrazolo[5,1-d][1,2,5]oxadiazepine-10(2H)-carboxylate (Intermediate 28, 120.00 mg, 317.97 µmol, 1.00 eq) in DCM (2.00 mL) was added TFA (1.54 g, 13.51 mmol, 1.00 mL, 42.48 eq), and then the mixture was stirred at 25° C. for 1 hour. TLC showed the starting material was consumed completely, a new spot appeared. The mixture was concentrated in vacuum to give the title compound (124.00 mg, 316.89 µmol, 99.66% yield, TFA) as a yellow oil, which was used directly for next step.

Step 2. Preparation of 4-(azidomethyl)-N-(3-cyano-4-fluoro-phenyl)-2-methyl-1-oxo-5,8,9,11-tetrahydro-4H-pyrido[2,3]pyrazolo[2,4-d][1,2,5]oxadiazepine-10-carboxamide. A mixture of 4-(azidomethyl)-2-methyl-4,5,8,9,10,11-hexahydropyrido[2,3] pyrazolo[2,4-d][1,2,5]oxadiazepin-1-one (124.00 mg, 316.89 µmol, 1.00 eq, TFA), phenyl N-(3-cyano-4-fluoro-phenyl)carbamate (81.20 mg, 316.89 µmol, 1.00 eq), TEA (96.20 mg, 950.67 µmol, 131.78 µL3.00 eq) in DCM (5.00 mL) was degassed and purged with N$_2$ for 3 times, and then the mixture was stirred at 25° C. for 16 hour under N$_2$ atmosphere. TLC showed the starting material was consumed completely, desired product was major. The mixture was poured into water (10 mL). The aqueous phase was extracted with DCM (5 mL*3). The combined organic phase was washed with brine (10 mL), dried with anhydrous Na$_2$SO$_4$, filtered and concentrated in vacuum. The residue was purified by column chromatography (SiO$_2$, Petroleum ether/Ethyl acetate=100/1 to 1:2) to give the title compound (115.00 mg, 235.55 µmol, 74.33% yield, 90% purity) as a yellow solid. LCMS: 440[M+1].

Step 3. (S*)-4-(aminomethyl)-N-(3-cyano-4-fluoro-phenyl)-2-methyl-1-oxo-5,8,9,11-tetrahydro-4H-pyrido[2,3]pyrazolo[2,4-d][1,2,5]oxadiazepine-10-carboxamide. A solution of 4-(azidomethyl)-N-(3-cyano-4-fluoro-phenyl)-2-methyl-1-oxo-5,8,9,11-tetrahydro-4H-pyrido[2,3]pyrazolo[2,4-d][1,2,5]oxadiazepine-10-carboxamide (120.00 mg, 273.10 µmol, 1.00 eq) in THF (6.00 mL) and H$_2$O (1.00 mL) was added PPh$_3$ (143.26 mg, 546.20 µmol, 2.00 eq), and then the mixture was stirred at 30° C. for 16 hour under N$_2$ atmosphere. LCMS showed the starting material was consumed completely and the desired product was major. The mixture was poured into water (30 mL) and stirred at 5 min. The aqueous phase was extracted with ethyl acetate (15 mL*2). The combined organic phase was washed with brine (30 mL), dried with anhydrous Na$_2$SO$_4$, filtered and concentrated in vacuum. The residue was purified by column chromatography (DCM/MeOH=100/1 to 20:1), following by Prep-HPLC (HCl) to give the title compound (42.70 mg, 101.53 µmol, 37.18% yield, 98.3% purity) as a yellow solid. LCMS: 414[M+1]. $^1$H NMR (400 MHz, METHANOL-d$_4$) δ 7.76-7.83 (m, 1H), 7.66-7.72 (m, 1H), 7.27 (s, 1H), 4.67-4.82 (m, 4H), 4.38-4.47 (m, 1H), 3.75-3.93 (m, 2H), 3.40-3.67 (m, 1H), 3.33 (s, 3H), 3.05-3.19 (m, 1H), 2.79-2.89 (m, 2H)

* pure but unknown stereochemistry

Compound 115_D1: (4S*,9R)-4-(aminomethyl)-N-(3-cyano-4-fluorophenyl)-2,9-dimethyl-1-oxo-1,4,5,8,9,11-hexahydropyrido[4',3':3,4]pyrazolo[5,1-d][1,2,5]oxadiazepine-10(2H)-carboxamide

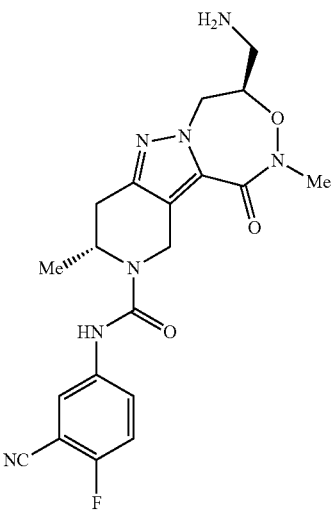 [SMILES: C[C@@H]1Cc2nn3c(c2CN1C(=O)Nc1ccc(F)c(C#N)c1)C(=O)N(C)O[C@H](CN)C3]

Step 1. (9R)-4-(azidomethyl)-2,9-dimethyl-4,5,8,9,10,11-hexahydropyrido[2,3]pyrazolo[2,4-d][1,2,5]oxadiazepin-1-one. A mixture of tert-butyl (9R)-4-(azidomethyl)-2,9-dimethyl-1-oxo-1,4,5,8,9,11-hexahydropyrido[4',3':3,4]pyrazolo[5,1-d][1,2,5]oxadiazepine-10(2H)-carboxylate (Intermediate 29, 120.00 mg, 306.57 μmol, 1.00 eq) in DCM (2.00 mL) was added TFA (1.54 g, 13.51 mmol, 1.00 mL, 44.06 eq), and then the mixture was stirred at 16° C. for 1 hour. TLC showed the starting material was consumed completely, a new spot appeared. The mixture was concentrated in vacuum to give the title compound (124.00 mg, 305.92 μmol, 99.79% yield, TFA) as a yellow oil, which was used directly for next step.

Step 2. (9R)-4-(azidomethyl)-N-(3-cyano-4-fluoro-phenyl)-2,9-dimethyl-1-oxo-5,8,9,11-tetrahydro-4H-pyrido[2,3]pyrazolo[2,4-d][1,2,5]oxadiazepine-10-carboxamide. A mixture of (9R)-4-(azidomethyl)-2,9-dimethyl-4,5,8,9,10,11-hexahydropyrido[2,3] pyrazolo[2,4-d][1,2,5]oxadiazepin-1-one (124.00 mg, 305.92 μmol, 1.00 eq, TFA), phenyl N-(3-cyano-4-fluoro-phenyl)carbamate (78.39 mg, 305.92 μmol, 1.00 eq), TEA (92.87 mg, 917.77 μmol, 127.22 μL 3.00 eq) in DCM (5.00 mL) was degassed and purged with $N_2$ for 3 times, and then the mixture was stirred at 25° C. for 16 hour under $N_2$ atmosphere. TLC showed the starting material was consumed completely, desired product was major. The mixture was poured into water (10 mL). The aqueous phase was extracted with DCM (5 mL*3). The combined organic phase was washed with brine (10 mL), dried with anhydrous $Na_2SO_4$, filtered and concentrated in vacuum. The residue was purified by column chromatography ($SiO_2$, Petroleum ether/Ethyl acetate=100/1 to 1:2) to give the title compound (114.00 mg, 236.33 μmol, 77.25% yield, 94% purity) as a white solid. LCMS: 454[M+1]

Step 3. (4S*,9R)-4-(aminomethyl)-N-(3-cyano-4-fluoro-phenyl)-2,9-dimethyl-1-oxo-1,4,5,8,9,11-hexahydropyrido[4',3':3,4]pyrazolo[5,1-d][1,2,5]oxadiazepine-10(2H)-carboxamide. A solution of (9R)-4-(azidomethyl)-N-(3-cyano-4-fluoro-phenyl)-2,9-dimethyl-1-oxo-5,8,9,11-tetrahydro-4H-pyrido[2,3]pyrazolo[2,4-d][1,2,5]oxadiazepine-10-carboxamide (114.00 mg, 251.42 μmol, 1.00 eq) in THF (6.00 mL) and $H_2O$ (1.00 mL) was added $PPh_3$ (131.89 mg, 502.83 μmol, 2.00 eq), and then the mixture was stirred at 15° C. for 16 hour under $N_2$ atmosphere. TLC showed the starting material was consumed completely, desired product was major. The mixture was poured into water (30 mL) and stirred at 5 min. The aqueous phase was extracted with ethyl acetate (15 mL*2). The combined organic phase was washed with brine (30 mL), dried with anhydrous $Na_2SO_4$, filtered and concentrated in vacuum. The residue was purified by column chromatography (DCM/MeOH=100/1 to 20:1), following by Prep-HPLC (HCl) to give the title compound (13.00 mg, 27.52 μmol, 10.94% yield, 90.47% purity) as a yellow solid. LCMS: 428[M+1]. $^1$H NMR (400 MHz, DMSO-$d_6$) δ 9.06 (br s, 1H), 8.23 (br s, 2H), 7.91-7.98 (m, 1H), 7.75-7.84 (m, 1H), 7.42 (t, J=9.10 Hz, 1H), 4.98-5.11 (m, 1H), 4.72 (br s, 3H), 4.31-4.43 (m, 1H), 4.11-4.21 (m, 1H), 3.28 (s, 3H), 3.03-3.19 (m, 2H), 2.88-2.95 (m, 1H), 2.61 (br d, J=15.81 Hz, 1H), 1.10 (d, J=6.78 Hz, 3H).
* pure but unknown stereochemistry Compound 115_D2: (4R*,9R)-4-(aminomethyl)-N-(3-cyano-4-fluorophenyl)-2,9-dimethyl-1-oxo-1,4,5,8,9,11-hexahydropyrido[4',3':3,4]pyrazolo[5,1-d][1,2,5]oxadiazepine-10(2H)-carboxamide

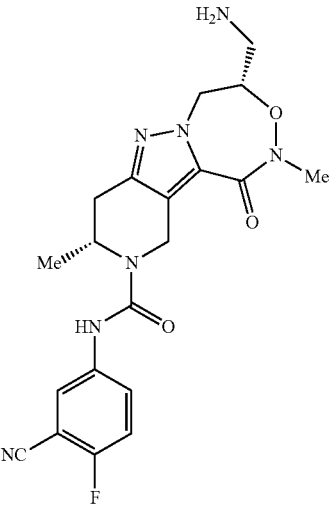 [SMILES: C[C@@H]1Cc2nn3c(c2CN1C(=O)Nc1ccc(F)c(C#N)c1)C(=O)N(C)O[C@@H](CN)C3]

Compound 115_D2 was prepared using the other enantiomer of Intermediate 29.

LCMS: 428[M+1]. $^1$H NMR (400 MHz, DMSO-$d_6$) δ 9.06 (br s, 1H), 8.23 (br s, 2H), 7.91-7.98 (m, 1H), 7.75-7.84 (m, 1H), 7.42 (t, J=9.10 Hz, 1H), 4.98-5.11 (m, 1H), 4.72 (br s, 3H), 4.31-4.43 (m, 1H), 4.11-4.21 (m, 1H), 3.28 (s, 3H), 3.03-3.19 (m, 2H), 2.88-2.95 (m, 1H), 2.61 (br d, J=15.81 Hz, 1H), 1.10 (d, J=6.78 Hz, 3H)
* pure but unknown stereochemistry Compounds 116 and 117 were prepared in an analogous manner to Compound 115.

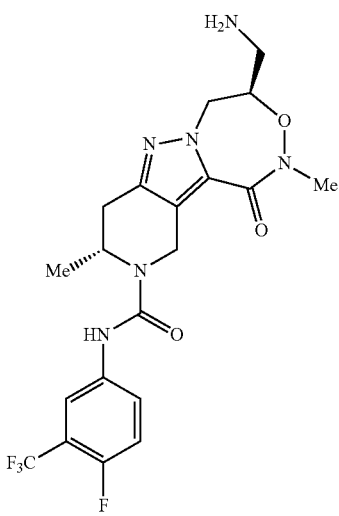

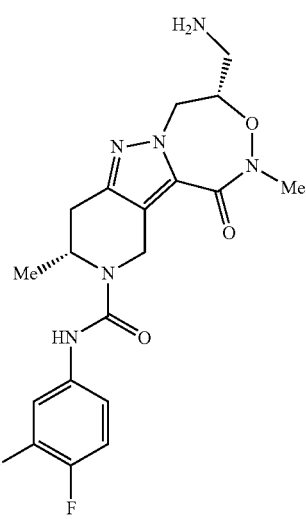

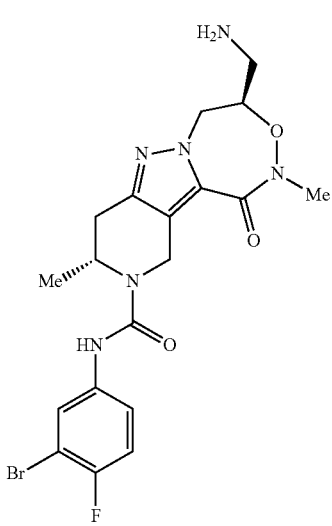

Compound 116_D1: (4S*,9R)-4-(aminomethyl)-N-(4-fluoro-3-(trifluoromethyl)phenyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS: 471[M+1]. $^1$H NMR (400 MHz, METHANOL-$d_4$) δ 7.77 (dd, J=2.45, 6.21 Hz, 1H), 7.54-7.67 (m, 1H), 7.54-7.69 (m, 1H), 7.24 (t, J=9.66 Hz, 1H), 5.03 (d, J=17.07 Hz, 1H), 4.93 (br d, J=5.77 Hz, 1H), 4.77-4.81 (m, 1H), 4.72 (br dd, J=6.09, 14.87 Hz, 1H), 4.31-4.50 (m, 2H), 3.32-3.37 (m, 4H), 2.97-3.16 (m, 2H), 2.69 (br d, J=15.69 Hz, 1H), 1.23 (d, J=6.90 Hz, 3H).
* pure but unknown stereochemistry Compound 116_D2: (4R*,9R)-4-(aminomethyl)-N-(4-fluoro-3-(trifluoromethyl)phenyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS: 471[M+1]. $^1$H NMR (400 MHz, METHANOL-$d_4$) δ 7.78 (dd, J=2.75, 6.17 Hz, 1H), 7.61-7.68 (m, 1H), 7.20-7.28 (m, 1H), 5.09 (s, 1H), 4.92-4.96 (m, 1H), 4.75-4.81 (m, 1H), 4.66-4.74 (m, 1H), 4.39-4.47 (m, 1H), 4.29-4.37 (m, 1H), 3.34 (s, 4H), 3.13-3.21 (m, 1H), 2.99-3.08 (m, 1H), 2.63-2.72 (m, 1H), 1.20 (d, J=6.85 Hz, 3H).
* pure but unknown stereochemistry Compound 117_D1: (4S*,9R)-4-(aminomethyl)-N-(3-bromo-4-fluorophenyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS: 481/483[M+1]. $^1$H NMR (400 MHz, METHANOL-$d_4$) δ 7.72 (dd, J=2.64, 6.27 Hz, 1H), 7.33 (td, J=3.40, 8.88 Hz, 1H), 7.12 (t, J=8.72 Hz, 1H), 5.01 (br d, J=16.81 Hz, 1H), 4.90-4.92 (m, 1H), 4.63-4.77 (m, 1H), 4.29-4.50 (m, 2H), 3.32-3.39 (m, 1H), 3.32-3.38 (m, 3H), 2.95-3.13 (m, 2H), 2.68 (d, J=16.06 Hz, 1H), 1.22 (d, J=6.90 Hz, 3H).
* pure but unknown stereochemistry Compound 117_D2: (4R*,9R)-4-(aminomethyl)-N-(3-bromo-4-fluorophenyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS: 481/483[M+1]. $^1$H NMR (400 MHz, METHANOL-$d_4$) δ 7.68-7.76 (m, 1H), 7.30-7.38 (m, 1H), 7.12 (t, J=8.68 Hz, 1H), 5.09 (d, J=16.87 Hz, 1H), 4.90-4.95 (m, 1H), 4.75-4.82 (m, 1H), 4.66-4.75 (m, 1H), 4.43 (dd, J=4.89, 14.79 Hz, 1H), 4.31 (d, J=16.87 Hz, 1H), 3.34 (s, 4H), 3.12-3.23 (m, 1H), 2.98-3.08 (m, 1H), 2.67 (br d, J=15.89 Hz, 1H), 1.19 (d, J=6.85 Hz, 3H).

* pure but unknown stereochemistry

Compound 118: N10-(3-chloro-2,4-difluorophenyl)-N4,2-dimethyl-1-oxo-1,4,5,8,9,11-hexahydropyrido[4',3':3,4]pyrazolo[5,1-d][1,2,5]oxadiazepine-4,10(2H)-dicarboxamide

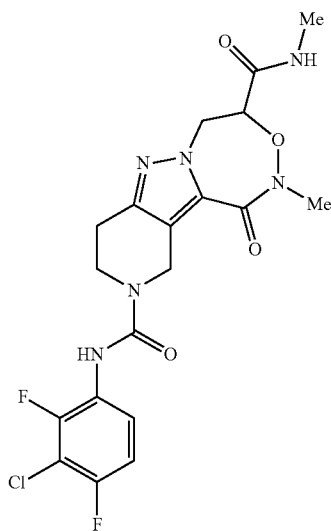 [SMILES: CNC(=O)C1Cn2nc3c(c2C(=O)N(C)O1)CN(C(=O)Nc1ccc(F)c(Cl)c1F)CC3]

Step 1. Preparation of tert-butyl 2-methyl-4-(methylcarbamoyl)-1-oxo-5,7,7a,8,9,11,11a,11b-octahydro-4H-pyrido[1,2]pyrazolo[3,5-c][1,2,5]oxadiazepine-10-carboxylate. A mixture of 10-(tert-butoxycarbonyl)-2-methyl-1-oxo-1,2,4,5,8,9,10,11-octahydropyrido[4',3':3,4]pyrazolo[5,1-d][1,2,5]oxadiazepine-4-carboxylic acid (Intermediate 26, 500.00 mg, 1.35 mmol, 1.00 eq), T₃P (1.72 g, 2.70 mmol, 1.61 mL, 50% purity, 2.00 eq) and Et3N (1.37 g, 13.50 mmol, 1.87 mL, 10.00 eq) in THF (8.00 mL) was added to methanamine; hydrochloride (455.72 mg, 6.75 mmol, 5.00 eq). The mixture was stirred at 70° C. for 16 h under N₂ in a sealed tube. The mixture was adjusted with HCl (1 M) to pH=6, then diluted with H₂O (20 mL) and extracted Ethyl acetate (20 mL*2). The combined organic layers were dried over Na₂SO₄, filtered and concentrated under reduced pressure. The residue was purified by column chromatography (Petroleum ether:Ethyl acetate=1:3) to afford the title compound (235.00 mg, 612.87 μmol, 45.40% yield) as yellow solid. LCMS: 380 [M+1]

Step 2. Preparation of N,2-dimethyl-1-oxo-4,5,8,9,10,11-hexahydropyrido[2,3]pyrazolo[2,4-d][1,2,5]oxadiazepine-4-carboxamide. To a solution of tert-butyl 2-methyl-4-(methylcarbamoyl)-1-oxo-5,8,9,11-tetrahydro-4H-pyrido[2,3]pyrazolo[2,4-d][1,2,5]oxadiazepine-10-carboxylate (259.00 mg, 682.64 μmol, 1.00 eq) in DCM (3.00 mL) was added TFA (4.43 g, 38.87 mmol, 2.88 mL, 56.94 eq) at 0° C. The mixture was stirred at 25° C. for 1 h. The mixture was concentrated under reduced pressure to afford the title compound (268.00 mg, 681.38 μmol, 99.82% yield, TFA) as yellow oil, the crude product was used directly for the next step. LCMS: 280 [M+1].

Step 3. N10-(3-chloro-2,4-difluoro-phenyl)-N4,2-dimethyl-1-oxo-5,8,9,11-tetrahydro-4H-pyrido[2,3]pyrazolo[2,4-d][1,2,5]oxadiazepine-4,10-dicarboxamide. To a solution of N,2-dimethyl-1-oxo-4,5,8,9,10,11-hexahydropyrido[2,3]pyrazolo[2,4-d][1,2,5]oxadiazepine-4-carboxamide (60.00 mg, 152.55 μmol, 1.00 eq, TFA) in DCM (3.00 mL) was added phenyl N-(3-chloro-2,4-difluoro-phenyl) carbamate (64.91 mg, 228.82 μmol, 1.50 eq) and Et3N (77.18 mg, 762.74 μmol, 105.73 μL5.00 eq). The mixture was stirred at 25° C. for 16 h. The mixture was adjusted to pH=6 with FA, filtered and concentrated under reduced pressure. The residue was purified by prep-HPLC (FA), following by prep-TLC (DCM/MeOH=10/1) and prep-HPLC (FA) to afford (20.00 mg, 42.23 μmol, 27.68% yield, 99% purity) as white solid. LCMS [M+1]: 469/471. ¹H NMR (400 MHz, CHLOROFORM-d) δ 7.88 (dt, J=5.52, 8.97 Hz, 1H), 6.96 (ddd, J=2.13, 8.41, 9.29 Hz, 1H), 6.57 (br d, J=2.76 Hz, 1H), 6.08 (br d, J=5.02 Hz, 1H), 4.86-5.00 (m, 2H), 4.61-4.82 (m, 3H), 3.93 (td, J=5.49, 13.74 Hz, 1H), 3.72-3.82 (m, 1H), 3.34 (s, 3H), 2.80-2.94 (m, 5H).

Compounds 195, 119, and 120 were prepared in an analogous manner to Compound 118.

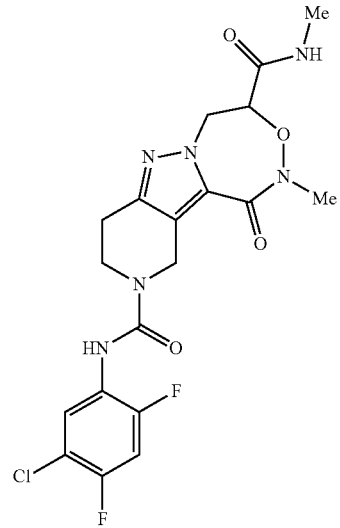

119

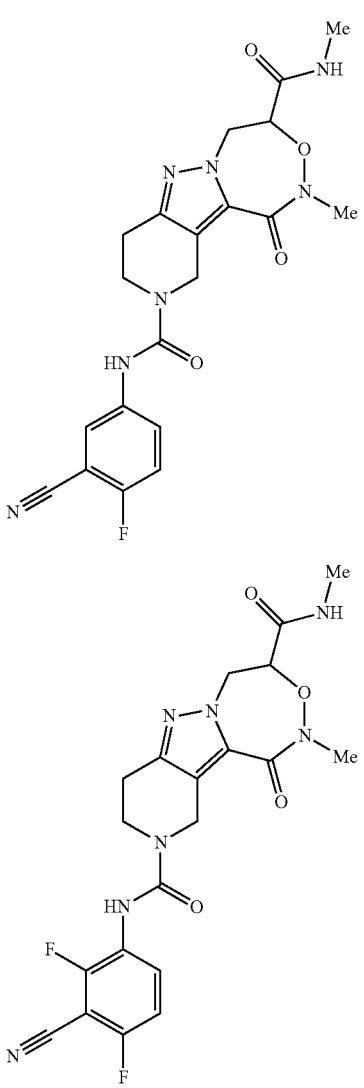

Compound 119: N10-(5-chloro-2,4-difluorophenyl)-N4,2-dimethyl-1-oxo-1,4,5,8,9,11-hexahydropyrido[4',3':3,4]pyrazolo[5,1-d][1,2,5]oxadiazepine-4,10(2H)-dicarboxamide LCMS [M+1]: 469/471. $^1$H NMR (400 MHz, CHLOROFORM-d) δ 8.18 (t, J=8.03 Hz, 1H), 6.95 (dd, J=8.41, 10.54 Hz, 1H), 6.57 (br d, J=3.14 Hz, 1H), 6.07 (br d, J=4.39 Hz, 1H), 4.87-4.99 (m, 2H), 4.64-4.77 (m, 3H), 3.92 (td, J=5.52, 13.68 Hz, 1H), 3.70-3.81 (m, 1H), 3.34 (s, 3H), 2.81-2.93 (m, 5H).

Compound 120: N10-(3-cyano-4-fluorophenyl)-N4,2-dimethyl-1-oxo-1,4,5,8,9,11-hexahydropyrido[4',3':3,4]pyrazolo[5,1-d][1,2,5]oxadiazepine-4,10(2H)-dicarboxamide LCMS [M+1]: 442. $^1$H NMR (400 MHz, CHLOROFORM-d) δ 7.75 (dd, J=2.76, 5.40 Hz, 1H), 7.61 (ddd, J=2.82, 4.58, 9.16 Hz, 1H), 7.14 (t, J=8.72 Hz, 1H), 6.77 (s, 1H), 6.10 (br d, J=4.89 Hz, 1H), 4.85-5.00 (m, 2H), 4.62-4.76 (m, 3H), 3.77-3.93 (m, 2H), 3.34 (s, 3H), 2.81-2.93 (m, 5H).

Compound 121_D1: (4S*,9R)—N-(3-chloro-4-fluorophenyl)-4-((2,2-difluoroethoxy)methyl)-2,9-dimethyl-1-oxo-1,4,5,8,9,11-hexahydropyrido[4',3':3,4]pyrazolo[5,1-d][1,2,5]oxadiazepine-10(2H)-carboxamide

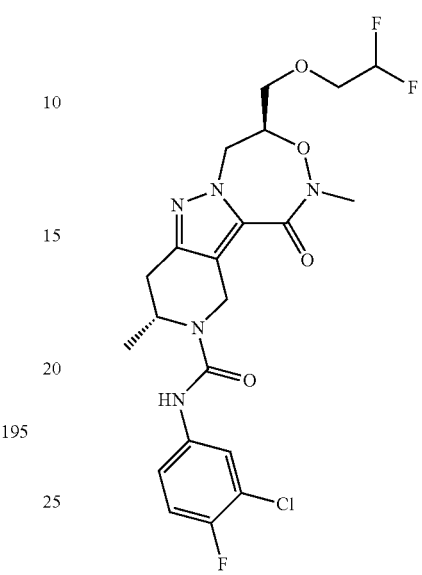

Step 1. tert-butyl (9R)-4-((2,2-difluoroethoxy)methyl)-2,9-dimethyl-1-oxo-1,4,5,8,9,11-hexahydropyrido[4',3':3,4]pyrazolo[5,1-d][1,2,5]oxadiazepine-10(2H)-carboxylate. To a solution of tert-butyl (9R)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxylate (Intermediate 18, 700 mg, 1.91 mmol, 1.00 eq, single diastereomer separated by SFC) in DMF (5.00 mL) was added NaH (152.80 mg, 3.82 mmol, 60% purity, 2.00 eq) at −40° C. The mixture was stirred at −40° C. for 30 min. A solution of 2,2-difluoroethyl trifluoromethanesulfonate (1.23 g, 5.73 mmol, 3.00 eq) in was added dropwise at −40° C. The mixture was stirred at −20° C. for 0.5 hr. TLC (PE:ethyl acetate=1:1) showed the starting material consumed nearly and a new spot formed. The mixture was added into ice-water (50 mL) and extracted with ethyl acetate (50 mL*3). The combined organic layer was washed with H$_2$O (50 mL*3), dried over Na$_2$SO$_4$, filtrated. The filtrate vs concentrated in vacuum. The residue was purified through column chromatography (PE:ethyl acetate: 30%~50%) to get the title compound (580.00 mg, 1.35 mmol, 70.55% yield) as colorless oil.

Step 2. Preparation of (9R)-2-(2,2-difluoroethyl)-4-(hydroxymethyl)-9-methyl-4,5,8,9,10,11-hexahydropyrido[2,3]pyrazolo[2,4-d][1,2,5]oxadiazepin-1-one. To a solution of tert-butyl (9R)-2-(2,2-difluoroethyl)-4-(hydroxymethyl)-9-methyl-1-oxo-5,8,9,11-tetrahydro-4H-pyrido[2,3]pyrazolo[2,4-d][1,2,5]oxadiazepine-10-carboxylate (440.00 mg, 1.06 mmol, 1.00 eq) in DCM (5.00 mL) was added TFA (8.06 g, 70.65 mmol, 5.23 mL, 66.86 eq). The mixture was stirred at 20° C. for 1 hr. TLC (PE:ethyl acetate=1:1) showed the starting material consumed. The mixture was concentrated in vacuum to get the title compound (460.00 mg, crude, TFA) as brown oil.

Step 3. (4S*,9R)—N-(3-chloro-4-fluorophenyl)-4-((2,2-difluoroethoxy)methyl)-2,9-dimethyl-1-oxo-1,4,5,8,9,11-hexahydropyrido[4',3':3,4]pyrazolo[5,1-d][1,2,5]oxadiazepine-10(2H)-carboxamide. To a solution of (9R)-4-(2,2-difluoroethoxymethyl)-2,9-dimethyl-4,5,8,9,10,11- hexahydropyrido[2,3]pyrazolo[2,4-d][1,2,5]oxadiazepin-1-one (55.00 mg, 123.78 μmol, 1.00 eq, TFA) and phenyl N-(3-chloro-4-fluoro-phenyl)carbamate (34.53 mg, 129.97 μmol, 1.05 eq) in DCM (3.00 mL) was added TEA (75.15 mg, 742.68 μmol, 102.95 μL 6.00 eq) at 20° C. The mixture was stirred at 20° C. for 16 h. LCMS indicated desired product was detected. The mixture was directly concentrated in vacuo. The residue was purified by prep-HPLC (FA) to afford the title compound (42.30 mg, 82.17 μmol, 66.39% yield, 97.5% purity) as white solid. LCMS: 502 [M+1]. $^1$H NMR (400 MHz, CHLOROFORM-d) δ=7.59 (dd, J=2.64, 6.53 Hz, 1H), 7.16-7.23 (m, 1H), 7.02-7.10 (m, 1H), 6.49 (s, 1H), 6.45-6.46 (m, 1H), 5.73-6.07 (m, 1H), 5.08-5.18 (m, 1H), 5.08-5.18 (m, 1H), 4.82-4.83 (m, 1H), 4.35-4.70 (m, 4H), 3.65-3.81 (m, 4H), 3.31 (s, 3H), 3.01-3.04 (m, 1H), 2.66-2.70 (m, 1H), 1.18 (d, J=6.90 Hz, 3H).

\* pure but unknown stereochemistry

Compounds 108, 122, 123, 124, 125, 126, and 127 were prepared in an analogous method to Compound 121.

122 D2

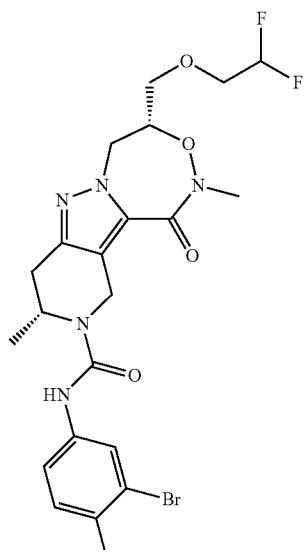

121 D2

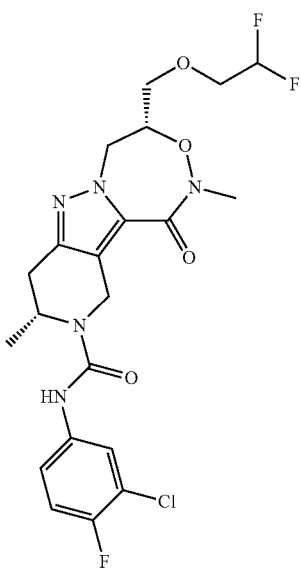

123 D1

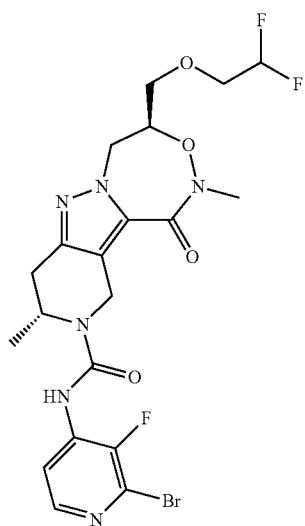

122 D1

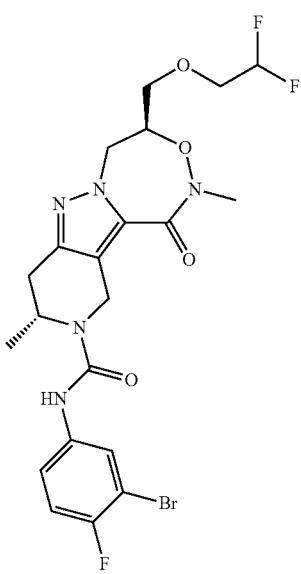

123 D2

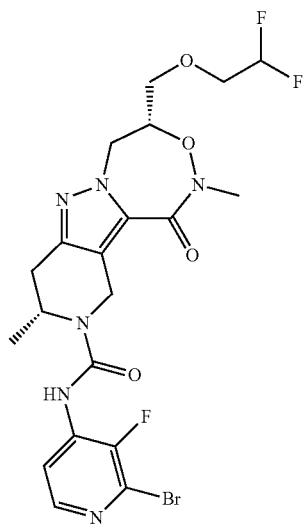

303
-continued
124 D1
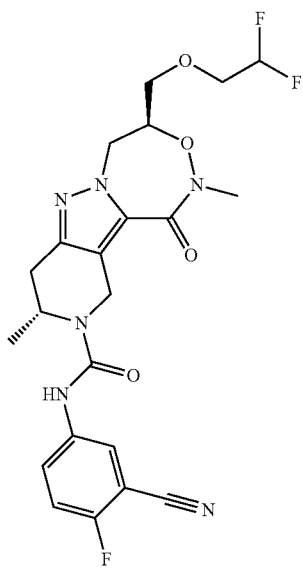
124 D2
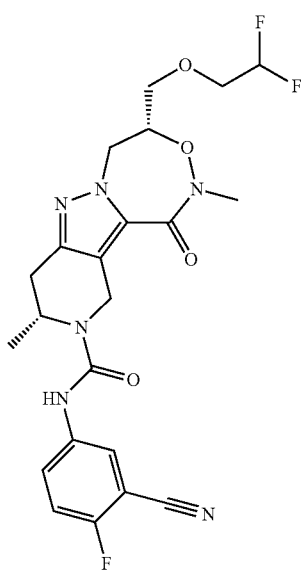
304
-continued
125 D1
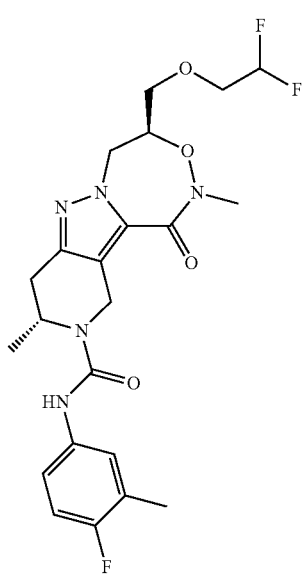 [SMILES: C[C@@H]1Cc2nn3c(c2CN1C(=O)Nc1ccc(F)c(Cl)c1)C(=O)N(C)O[C@H](COCC(F)F)C3]
125 D2
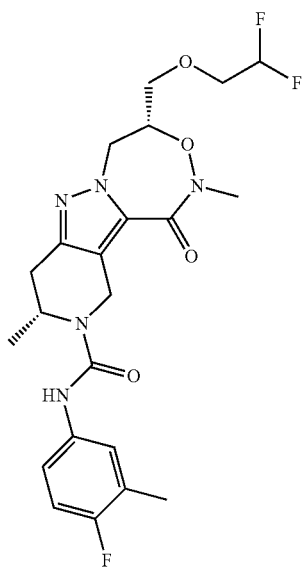

305
-continued
126 D1
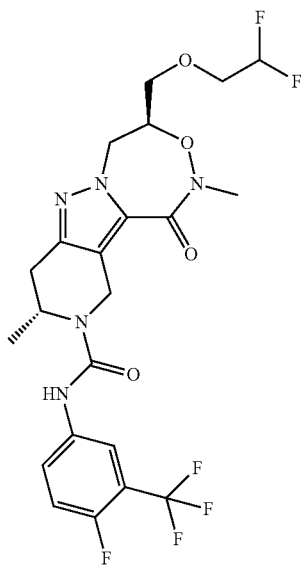
126 D2
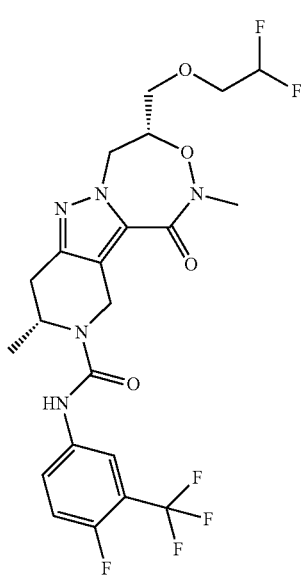
306
-continued
127 D1
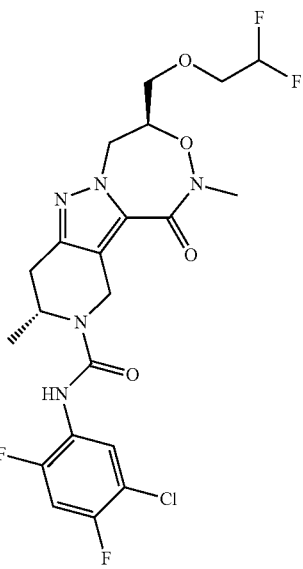
127 D2
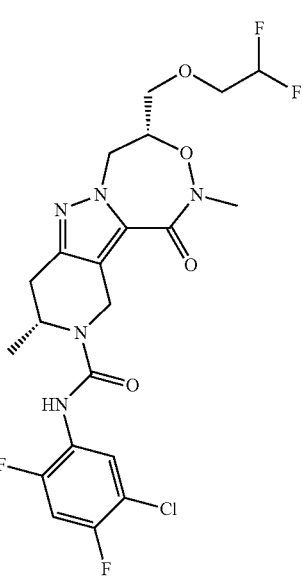

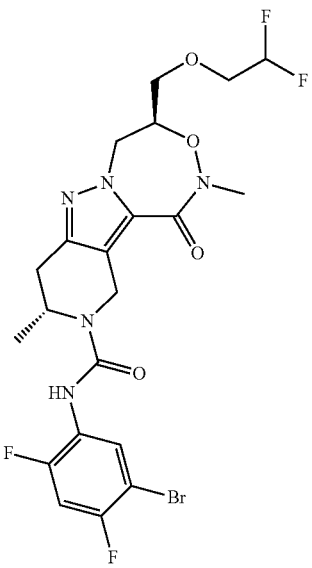

Compound 121_D2: (4R*,9R)—N-(3-chloro-4-fluorophenyl)-4-((2,2-difluoroethoxy)methyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS (M+1): 502. ¹H NMR (400 MHz, CHLOROFORM-d) δ=7.60 (dd, J=2.70, 6.59 Hz, 1H), 7.20 (ddd, J=2.76, 4.05, 8.88 Hz, 1H), 7.03-7.09 (m, 1H), 6.47 (s, 1H), 5.75-6.06 (m, 1H), 5.10-5.19 (m, 1H), 4.84 (d, J=15.43 Hz, 1H), 4.54-4.66 (m, 2H), 4.37-4.50 (m, 2H), 3.71-3.85 (m, 4H), 3.31 (s, 3H), 3.04 (dd, J=5.96, 15.87 Hz, 1H), 2.69 (d, J=15.94 Hz, 1H), 1.18 (d, J=6.90 Hz, 3H).
* pure but unknown stereochemistry Compound 122_D1: (4S*,9R)—N-(3-bromo-4-fluorophenyl)-4-((2,2-difluoroethoxy)methyl)-2,9-dimethyl-1-oxo-1,4,5,8,9,11-hexahydropyrido[4',3':3,4]pyrazolo[5,1-d][1,2,5]oxadiazepine-10(2H)-carboxamide LC-MS: 546/548 [M+1]. ¹H NMR (400 MHz, CHLOROFORM-d) δ=7.72 (dd, J=2.57, 6.09 Hz, 1H), 7.24-7.29 (m, 2H), 7.04 (t, J=8.47 Hz, 1H), 6.51 (br s, 1H), 5.73-6.06 (m, 1H), 5.13 (m, 1H), 4.83 (m, 1H), 4.35-4.68 (m, 4H), 3.64-3.81 (m, 4H), 3.50 (s, 1H), 3.31 (s, 3H), 3.04 (m, 1H), 2.68 (m, 1H), 1.18 (d, J=6.90 Hz, 3H).
* pure but unknown stereochemistry Compound 122_D2: (4R*,9R)—N-(3-bromo-4-fluorophenyl)-4-((2,2-difluoroethoxy)methyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS (M+1): 546/548. ¹H NMR (400 MHz, CHLOROFORM-d) δ=7.73 (dd, J=2.64, 6.02 Hz, 1H), 7.23-7.27 (m, 1H), 7.05 (t, J=8.47 Hz, 1H), 6.45 (s, 1H), 5.74-6.06 (m, 1H), 5.14 (br t, J=6.59 Hz, 1H), 4.84 (d, J=15.56 Hz, 1H), 4.54-4.65 (m, 2H), 4.37-4.50 (m, 2H), 3.71-3.85 (m, 4H), 3.31 (s, 3H), 3.04 (dd, J=6.09, 16.12 Hz, 1H), 2.69 (d, J=16.31 Hz, 1H), 1.18 (d, J=6.90 Hz, 3H).
* pure but unknown stereochemistry Compound 123_D1: (4S*,9R)—N-(2-bromo-3-fluoropyridin-4-yl)-4-((2,2-difluoroethoxy)methyl)-2,9-dimethyl-1-oxo-1,4,5,8,9,11-hexahydropyrido[4',3':3,4]pyrazolo[5,1-d][1,2,5]oxadiazepine-10(2H)-carboxamide LC-MS: 547/549 [M+1]. ¹H NMR (400 MHz, CHLOROFORM-d) δ=8.02-8.21 (m, 2H), 6.99 (br s, 1H), 5.73-6.07 (m, 1H), 4.85-5.10 (m, 2H), 4.39-4.66 (m, 4H), 3.64-3.81 (m, 4H), 3.31 (s, 3H), 3.00-3.13 (m, 1H), 2.72 (br d, J=15.94 Hz, 1H), 1.23 (d, J=6.78 Hz, 3H).
* pure but unknown stereochemistry Compound 123_D2: (4R*,9R)—N-(2-bromo-3-fluoropyridin-4-yl)-4-((2,2-difluoroethoxy)methyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS (M+1): 547/549. ¹H NMR (400 MHz, CHLOROFORM-d) δ=8.14-8.18 (m, 1H), 8.07 (d, J=5.52 Hz, 1H), 6.95 (br d, J=3.89 Hz, 1H), 5.74-6.07 (m, 1H), 5.07 (m, 1H), 4.92 (m, 1H), 4.35-4.66 (m, 4H), 3.69-3.87 (m, 4H), 3.31 (s, 3H), 3.06 (m, 1H), 2.73 (d, J=15.94 Hz, 1H), 1.23 (d, J=6.90 Hz, 3H.
* pure but unknown stereochemistry Compound 124_D1: (4S*,9R)—N-(3-cyano-4-fluorophenyl)-4-((2,2-difluoroethoxy)methyl)-2,9-dimethyl-1-oxo-1,4,5,8,9,11-hexahydropyrido[4',3':3,4]pyrazolo[5,1-d][1,2,5]oxadiazepine-10(2H)-carboxamide LC-MS: 493 [M+1]. ¹H NMR (400 MHz, CHLOROFORM-d) δ=7.77 (dd, J=2.76, 5.52 Hz, 1H), 7.59 (ddd, J=2.82, 4.55, 9.07 Hz, 1H), 7.14 (t, J=8.72 Hz, 1H), 6.71 (s, 1H), 5.71-6.08 (m, 1H), 5.06-5.19 (m, 1H), 4.85 (d, J=15.69

Hz, 1H), 4.36-4.69 (m, 4H), 3.62-3.85 (m, 4H), 3.31 (s, 3H), 3.04 (dd, J=5.77, 15.94 Hz, 1H), 2.69 (d, J=15.81 Hz, 1H), 1.19 (d, J=6.90 Hz, 3H).

* pure but unknown stereochemistry

Compound 124_D2: (4R*,9R)—N-(3-cyano-4-fluorophenyl)-4-((2,2-difluoroethoxy)methyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS (M+1): 493. $^{1}$H NMR (400 MHz, CHLOROFORM-d) δ=7.79 (dd, J=2.76, 5.40 Hz, 1H), 7.59 (m, 1H), 7.11-7.18 (m, 1H), 6.64 (s, 1H), 5.74-6.06 (m, 1H), 5.15 (br t, J=6.21 Hz, 1H), 4.86 (d, J=15.43 Hz, 1H), 4.37-4.66 (m, 4H), 3.70-3.86 (m, 4H), 3.31 (s, 3H), 3.04 (dd, J=5.83, 15.75 Hz, 1H), 2.70 (d, J=16.31 Hz, 1H), 1.19 (d, J=6.90 Hz, 3H).

* pure but unknown stereochemistry

Compound 125_D1: (4S*,9R)-4-((2,2-difluoroethoxy)methyl)-N-(4-fluoro-3-methylphenyl)-2,9-dimethyl-1-oxo-1,4,5,8,9,11-hexahydropyrido[4',3':3,4]pyrazolo[5,1-d][1,2,5]oxadiazepine-10(2H)-carboxamide LC-MS: 482 [M+1]. $^{1}$H NMR (400 MHz, CHLOROFORM-d) δ=7.25 (br d, J=2.51 Hz, 1H), 7.08-7.14 (m, 1H), 6.93 (t, J=8.97 Hz, 1H), 6.38 (s, 1H), 5.74-6.07 (m, 1H), 5.14 (quin, J=6.40 Hz, 1H), 4.83 (d, J=15.69 Hz, 1H), 4.38-4.68 (m, 4H), 3.63-3.84 (m, 4H), 3.50 (s, 1H), 3.31 (s, 3H), 3.04 (dd, J=5.83, 15.87 Hz, 1H), 2.67 (d, J=15.81 Hz, 1H), 2.26 (d, J=1.63 Hz, 3H), 1.18 (d, J=6.90 Hz, 3H).

* pure but unknown stereochemistry

Compound 125_D2: (4R*,9R)-4-((2,2-difluoroethoxy)methyl)-N-(4-fluoro-3-methylphenyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS (M+1): 482. $^{1}$H NMR (400 MHz, CHLOROFORM-d) δ=7.26 (d, J=2.89 Hz, 1H), 7.11 (td, J=3.87, 8.19 Hz, 1H), 6.89-6.96 (m, 1H), 6.37 (s, 1H), 5.74-6.06 (m, 1H), 5.15 (m, J=6.34 Hz, 1H), 4.85 (d, J=15.56 Hz, 1H), 4.54-4.66 (m, 2H), 4.36-4.50 (m, 2H), 3.71-3.85 (m, 4H), 3.31 (s, 3H), 3.04 (dd, J=5.84, 16.00 Hz, 1H), 2.68 (d, J=16.06 Hz, 1H), 2.26 (d, J=1.76 Hz, 3H), 1.17 (d, J=6.90 Hz, 3H).

* pure but unknown stereochemistry

Compound 126_D1: (4S*,9R)-4-((2,2-difluoroethoxy)methyl)-N-(4-fluoro-3-(trifluoromethyl)phenyl)-2,9-dimethyl-1-oxo-1,4,5,8,9,11-hexahydropyrido[4',3':3,4]pyrazolo[5,1-d][1,2,5]oxadiazepine-10(2H)-carboxamide LC-MS: 536 [M+1]. $^{1}$H NMR (400 MHz, CHLOROFORM-d) δ=7.68 (dd, J=2.70, 6.09 Hz, 1H), 7.56-7.62 (m, 1H), 7.13 (t, J=9.41 Hz, 1H), 6.61 (s, 1H), 5.72-6.11 (m, 1H), 5.15 (quin, J=6.43 Hz, 1H), 4.85 (d, J=15.56 Hz, 1H), 4.36-4.70 (m, 4H), 3.65-3.83 (m, 4H), 3.31 (s, 3H), 3.05 (dd, J=5.84, 15.87 Hz, 1H), 2.69 (d, J=15.81 Hz, 1H), 1.19 (d, J=6.90 Hz, 3H).

* pure but unknown stereochemistry

Compound 126_D2: (4R*,9R)-4-((2,2-difluoroethoxy)methyl)-N-(4-fluoro-3-(trifluoromethyl)phenyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS (M+1): 536. $^{1}$H NMR (400 MHz, CHLOROFORM-d) δ=7.69 (dd, J=2.82, 6.21 Hz, 1H), 7.56-7.62 (m, 1H), 7.14 (t, J=9.29 Hz, 1H), 6.59 (s, 1H), 5.75-6.06 (m, 1H), 5.16 (m, J=6.78 Hz, 1H), 4.87 (d, J=15.56 Hz, 1H), 4.54-4.66 (m, 2H), 4.38-4.52 (m, 2H), 3.71-3.85 (m, 4H), 3.31 (s, 3H), 3.04 (dd, J=5.65, 15.81 Hz, 1H), 2.70 (d, J=16.19 Hz, 1H), 1.19 (d, J=6.90 Hz, 3H).

* pure but unknown stereochemistry

Compound 127_D1: (4S*,9R)—N-(5-chloro-2,4-difluorophenyl)-4-((2,2-difluoroethoxy)methyl)-2,9-dimethyl-1-oxo-1,4,5,8,9,11-hexahydropyrido[4',3':3,4]pyrazolo[5,1-d][1,2,5]oxadiazepine-10(2H)-carboxamide LC-MS: 520 [M+1]. $^{1}$H NMR (400 MHz, CHLOROFORM-d) δ=8.19 (t, J=8.09 Hz, 1H), 6.95 (dd, J=8.47, 10.60 Hz, 1H), 6.55 (br d, J=2.76 Hz, 1H), 5.64-6.18 (m, 1H), 4.79-5.25 (m, 2H), 4.34-4.67 (m, 4H), 3.59-3.86 (m, 4H), 3.26-3.41 (m, 3H), 3.05 (dd, J=5.77, 15.81 Hz, 1H), 2.70 (d, J=15.81 Hz, 1H), 1.21 (d, J=6.90 Hz, 3H).

* pure but unknown stereochemistry

Compound 127_D2: (4R*,9R)—N-(5-chloro-2,4-difluorophenyl)-4-((2,2-difluoroethoxy)methyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS (M+1): 520/522. $^{1}$H NMR (400 MHz, CHLOROFORM-d) δ=8.20 (t, J=8.09 Hz, 1H), 6.95 (dd, J=8.41, 10.54 Hz, 1H), 6.53 (br d, J=2.76 Hz, 1H), 5.74-6.06 (m, 1H), 5.06-5.14 (m, 1H), 4.88 (d, J=15.69 Hz, 1H), 4.37-4.63 (m, 4H), 3.71-3.85 (m, 4H), 3.31 (s, 3H), 3.05 (dd, J=5.83, 16.12 Hz, 1H), 2.71 (d, J=15.94 Hz, 1H), 1.20 (d, J=6.90 Hz, 3H).

* pure but unknown stereochemistry

Compound 128: N-(3-chloro-4-fluorophenyl)-2-methyl-1-oxo-4-((trifluoromethoxy)methyl)-1,4,5,8,9,11-hexahydropyrido[4',3':3,4]pyrazolo[5,1-d][1,2,5]oxadiazepine-10(2H)-carboxamide

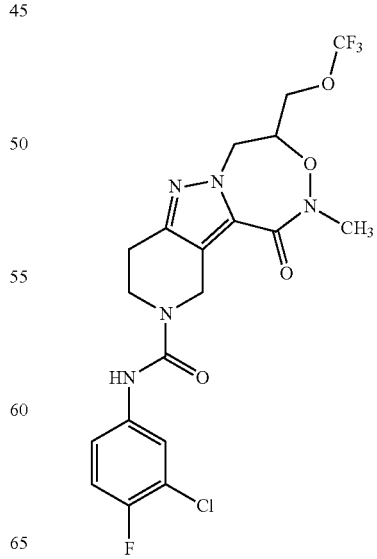

Step 1 tert-butyl 2-methyl-1-oxo-4-(trifluoromethoxymethyl)-5,8,9,11-tetrahydro-4H-pyrido[2,3]pyraz-olo[2,4-d][1,2,5]oxadiazepine-10-carboxylate. To a reaction bottle, AgOTf (192.50 mg, 749.19 μmol, 3.00 eq), Select Fluor® (301.60 mg, 851.36 μmol, 1.50 eq), KF (131.90 mg, 2.27 mmol, 53.19 μL4.00 eq), tert-butyl 4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxylate (Intermediate 1, 200.00 mg, 567.57 μmol, 1.00 eq) were added successively in a nitrogen-filled glovebox. Then EtOAc (6.00 mL), 2-fluoropyridine (165.32 mg, 1.70 mmol, 146.30 μL3.00 eq) and TMSCF$_3$ (242.12 mg, 1.70 mmol, 3.00 eq) were added successively under N$_2$ atmosphere. The reaction mixture was stirred at 20° C. for 16 h. Several peaks showed on LCMS and 23% starting material remained and 13% desired product detected. The mixture was extracted with EtOAc (20 mL*2) and H$_2$O (20 mL). The combined organic layer was dried over Na$_2$SO$_4$, filtrated. The filtrate was concentrated in vacuum. The residue was purified by prep-HPLC (FA) to get the title compound (30.00 mg, 71.36 μmol, 12.57% yield) as white solid.

Step 2. N-(3-chloro-4-fluoro-phenyl)-2-methyl-1-oxo-4-(trifluoromethoxymethyl)-5,8,9,11-tetrahydro-4H-pyrido[2,3]pyrazolo[2,4-d][1,2,5]oxadiazepine-10-carboxamide. To a solution of tert-butyl 2-methyl-1-oxo-4-(trifluoromethoxymethyl)-5,8,9,11-tetra hydro-4H-pyrido[2,3]pyrazolo[2,4-d][1,2,5]oxadiazepine-10-carboxylate (45.00 mg, 107.05 μmol, 1.00 eq) in DCM (5.00 mL) was added TFA (5.00 mL). The mixture was stirred at 20° C. for 5 hr. TLC (PE:EtOAc=0:1) showed the starting material consumed. The mixture was concentrated in vacuum to get 2-methyl-4-(trifluoromethoxymethyl)-4,5,8,9,10,11-hexahydropyrido[2,3]pyrazolo[2,4-d][1,2,5]oxadiazepin-1-one (48.00 mg, crude, TFA) as brown oil. To a solution of 2-methyl-4-(trifluoromethoxymethyl)-4,5,8,9,10,11-hexaHydropyrido[2,3]pyrazolo[2,4-d][1,2,5]oxadiazepin-1-one (48.00 mg, 110.53 μmol, 1.00 eq, TFA) in DCM (3.00 mL) was added TEA (55.92 mg, 552.63 μmol, 76.60 μL5.00 eq) followed by phenyl N-(3-chloro-4-fluoro-phenyl)carbamate (35.24 mg, 132.64 μmol, 1.20 eq). The mixture was stirred at 20° C. for 16 hr. LCMS showed one main peak with desired MS detected. The mixture was concentrated in vacuum. The residue was purified by prep-HPLC (FA), repurified by prep-TLC (PE:EtOAc=1:1), further purification by prep-HPLC (base) to get the title compound (28.00 mg, 56.31 μmol, 50.94% yield, 98.9% purity) as white solid. 1H NMR (400 MHz, CHLOROFORM-d) δ=7.59 (dd, J=2.69, 6.48 Hz, 1H), 7.18-7.25 (m, 1H), 7.03-7.11 (m, 1H), 6.61 (s, 1H), 4.68-4.78 (m, 3H), 4.59-4.67 (m, 1H), 4.39 (dd, J=6.60, 14.43 Hz, 1H), 4.14-4.22 (m, 1H), 4.05-4.13 (m, 1H), 3.80-3.94 (m, 2H), 3.32 (s, 3H), 2.88 (t, J=5.75 Hz, 2H)

LCMS: 492 [M+1].

Compound 129: N-(3-chloro-4-fluorophenyl)-4-(ethylsulfonamidomethyl)-2-methyl-1-oxo-1,4,5,8,9,11-hexahydropyrido[4',3':3,4]pyrazolo[5,1-d][1,2,5]oxadiazepine-10(2H)-carboxamide

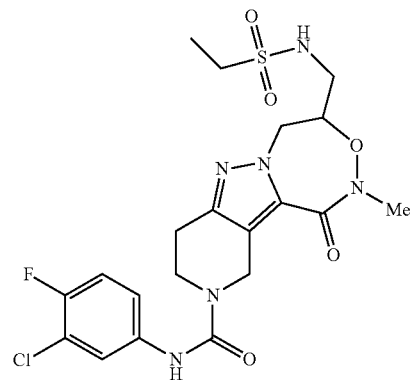 [SMILES: CCS(=O)(=O)NCC1Cn2nc3c(c2C(=O)N(C)O1)CN(C(=O)Nc1ccc(F)c(Cl)c1)CC3]

Compound 129 was prepared in an analogous manner to Compound 208.

LCMS: 527 [M+1]. $^1$H NMR (400 MHz, DMSO-d$_6$) δ=8.90 (s, 1H), 7.72 (dd, J=2.57, 6.85 Hz, 1H), 7.48 (br s, 1H), 7.41 (ddd, J=2.69, 4.28, 9.05 Hz, 1H), 7.24-7.33 (m, 1H), 4.58-4.68 (m, 3H), 4.51 (quin, J=6.39 Hz, 1H), 4.29 (dd, J=7.40, 14.37 Hz, 1H), 3.66-3.82 (m, 2H), 3.24 (s, 5H), 2.72 (br t, J=5.38 Hz, 2H), 2.60-2.66 (m, 1H), 0.88-1.00 (m, 4H).

Compound 130: N-(3-chloro-4-fluorophenyl)-2-methyl-1-oxo-4-(((2,2,2-trifluoroethyl)sulfonamido)methyl)-1,4,5,8,9,11-hexahydropyrido[4',3':3,4]pyrazolo[5,1-d][1,2,5]oxadiazepine-10(2H)-carboxamide

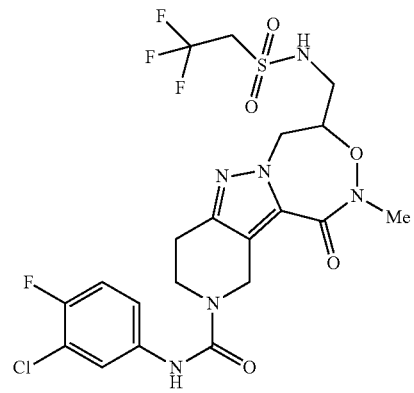 [SMILES: CN1OC(CNS(=O)(=O)CC(F)(F)F)Cn2nc3c(c2C1=O)CN(C(=O)Nc1ccc(F)c(Cl)c1)CC3]

Compound 130 was prepared in an analogous manner to Compound 208.

LCMS: 569 [M+1]. $^1$H NMR (400 MHz, DMSO-d$_6$) δ=8.90 (s, 1H), 7.72 (dd, J=2.51, 6.78 Hz, 1H), 7.41 (td, J=4.36, 7.22 Hz, 1H), 7.25-7.31 (m, 1H), 4.58-4.65 (m, 3H), 4.44-4.57 (m, 3H), 4.29 (dd, J=6.96, 14.24 Hz, 1H), 3.70-3.79 (m, 2H), 3.28-3.30 (m, 2H), 3.24 (s, 3H), 2.72 (br t, J=5.58 Hz, 2H), 2.70-2.76 (m, 1H)

313

Compound 131: N-(3-chloro-4-fluorophenyl)-4-(3,3-difluoroazetidine-1-carbonyl)-2-methyl-1-oxo-1,4,5,8,9,11-hexahydropyrido[4',3':3,4]pyrazolo[5,1-d][1,2,5]oxadiazepine-10(2H)-carboxamide

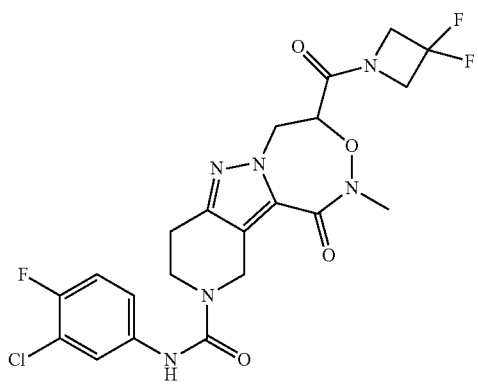 [SMILES: CN1OC(C(=O)N2CC(F)(F)C2)Cn2nc3c(c2C1=O)CN(C(=O)Nc1ccc(F)c(Cl)c1)CC3]

Step 1. methyl 2-methyl-1-oxo-4,5,8,9,10,11-hexahydropyrido[2,3]pyrazolo [2,4-d][1,2,5]oxadiazepine-4-carboxylate. To a solution of 10-(tert-butyl) 4-methyl 2-methyl-1-oxo-1,4,5,8,9,11-hexahydropyrido[4',3':3,4]pyrazolo[5,1-d][1,2,5]oxadiazepine-4,10(2H)-dicarboxylate (Intermediate 22, 1.00 g, 2.63 mmol, 1.00 eq) in DCM (40.00 mL) was added TFA (135.08 mmol, 10.00 mL, 51.36 eq). The mixture was stirred at 10° C. for 1 hr. TLC(PE:ethyl acetate=0:1) showed the starting material consumed. The mixture was concentrated in vacuum to get the title compound (1.10 g, crude, TFA) as brown oil.

Step 2. methyl 10-[(3-chloro-4-fluoro-phenyl)carbamoyl]-2-methyl-1-oxo-5,8,9,11-tetrahydro-4H-pyrido[2,3]pyrazolo[2,4-d][1,2,5]oxadiazepine-4-carboxylate. To a mixture of methyl 2-methyl-1-oxo-4,5,8,9,10,11-hexahydropyrido[2,3]pyrazolo [2,4-d][1,2,5]oxadiazepine-4-carboxylate (1.10 g, 2.79 mmol, 1.00 eq, TFA) and phenyl N-(3-chloro-4-fluoro-phenyl)carbamate (741.15 mg, 2.79 mmol, 1.00 eq) in DCM (20.00 mL) was added TEA (1.41 g, 13.95 mmol, 1.93 mL, 5.00 eq). The mixture was heated to 20° C. for 16 hr. LCMS showed one main peak with desired MS was detected and TLC (PE: ethyl acetate=0:1) showed two spots formed. The mixture was diluted with H$_2$O (30 mL). The organic phase was dried over Na$_2$SO$_4$, filtrated and concentrated in vacuum. The residue was purified by flash chromatography (PE:ethyl acetate: 50%~80%) to get the title compound (1.00 g, 2.21 mmol, 79.33% yield) as white solid.

Step 3. 10-[(3-chloro-4-fluoro-phenyl)carbamoyl]-2-methyl-1-oxo-5,8,9,11-tetrahydro-4H-pyrido[2,3]pyrazolo[2,4-d][1,2,5]oxadiazepine-4-carboxylic acid. To a solution of methyl 10-[(3-chloro-4-fluoro-phenyl)carbamoyl]-2-methyl-1-oxo-5,8,9,11-tetrahydro-4H-pyrido[2,3]pyrazolo[2,4-d][1,2,5]oxadiazepine-4-carboxylate (900.00 mg, 1.99 mmol, 1.00 eq) in DCE (10.00 mL) was added hydroxy(trimethyl)stannane (1.44 g, 7.96 mmol, 4.00 eq). The mixture was stirred at 50° C. for 16 hr. TLC (PE:ethyl acetate=0:1) showed the starting material consumed. The mixture was diluted with DCM (100 mL) and quenched by a aqueous solution of KF (500 mg, 5 mL). The mixture was dried over Na$_2$SO$_4$ and filtrated. The filtrate was concentrated in vacuum to get the title compound (700.00 mg, 1.60 mmol, 80.35% yield) as white solid.

314

Step 4. N-(3-chloro-4-fluoro-phenyl)-4-(3,3-difluoroazetidine-1-carbonyl)-2-methyl-1-oxo-5,8,9,11-tetrahydro-4H-pyrido[2,3]pyrazolo[2,4-d][1,2,5]oxadiazepine-10-carboxamide. To a solution of 10-[(3-chloro-4-fluoro-phenyl)carbamoyl]-2-methyl-1-oxo-5,8,9,11-tetrahydro-4H-pyrido[2,3]pyrazolo[2,4-d][1,2,5]oxadiazepine-4-carboxylic acid (80.00 mg, 182.73 µmol, 1.00 eq) in DMF (3.00 mL) was added 3,3-difluoroazetidine hydrochloride (94.68 mg, 730.92 µmol, 4.00 eq), followed by DIEA (296.00 mg, 2.29 mmol, 400.00 µL12.53 eq), PyBOP (142.64 mg, 274.09 µmol, 1.50 eq) and HOBt (24.69 mg, 182.73 µmol, 1.00 eq). The mixture was stirred at 20° C. for 16 h. The mixture was diluted with 0.5 M HCl (30 mL) and extracted with ethyl acetate (20 mL*2), then washed with NaHCO$_3$ (30 mL). The combined organic was dried over Na$_2$SO$_4$, filtered and concentrated under reduced pressure. The residue was purified by prep-TLC (DCM:MeOH=15:1), followed by prep-HPLC (FA) to get the title compound (15.50 mg, 30.04 µmol, 16.44% yield, 99.4% purity) as white solid. LCMS [M+1]: 513. $^1$H NMR (400 MHz, CHLOROFORM-d) δ=7.54-7.59 (m, 1H), 7.17-7.23 (m, 1H), 7.06 (s, 1H), 6.50-6.54 (m, 1H), 4.86-5.02 (m, 2H), 4.62-4.77 (m, 3H), 4.33-4.61 (m, 4H), 3.85 (s, 2H), 3.31 (s, 3H), 2.88 (br s, 2H).

Compounds 132, 134, 135, and 136 were prepared in an analogous manner to Compound 131.

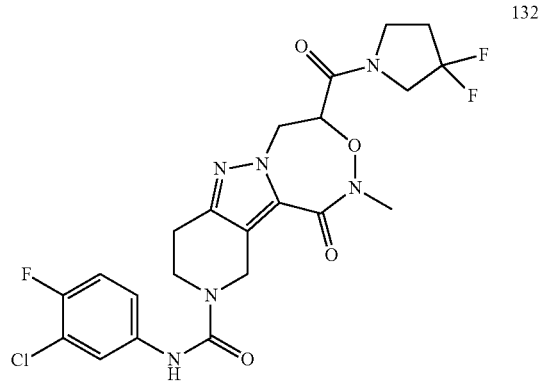

132

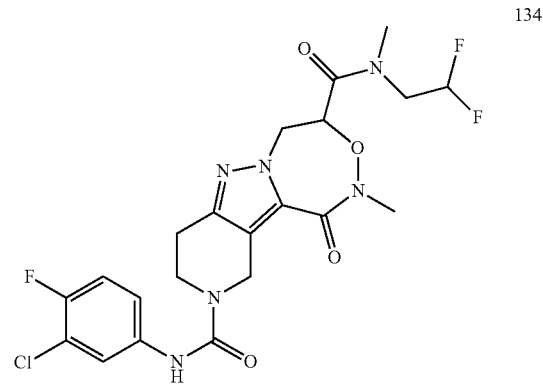

134

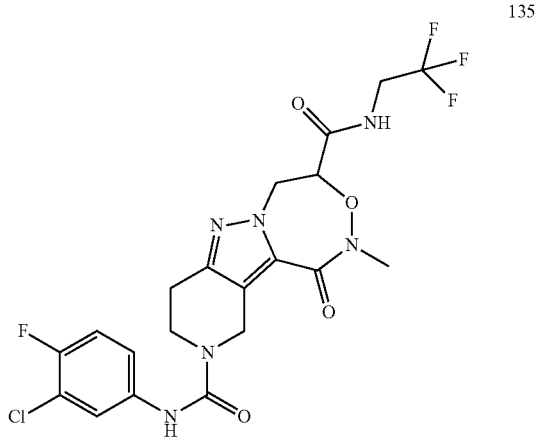

135

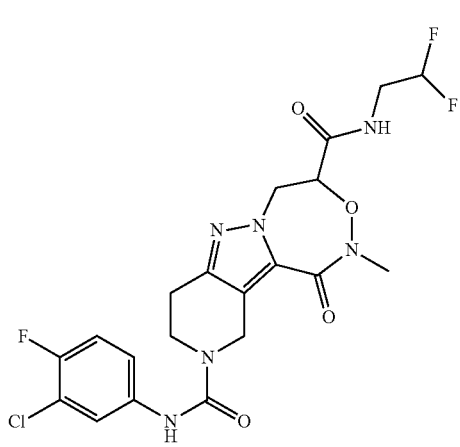

136

Compound 132: N-(3-chloro-4-fluorophenyl)-4-(3,3-difluoropyrrolidine-1-carbonyl)-2-methyl-1-oxo-1,4,5,8,9,11-hexahydropyrido[4',3':3,4]pyrazolo[5,1-d][1,2,5]oxadiazepine-10(2H)-carboxamide LCMS [M+1]: 527. ¹H NMR (400 MHz, CHLOROFORM-d) δ=7.55-7.59 (m, 1H), 7.19 (br s, 1H), 7.03-7.09 (m, 1H), 6.55 (s, 1H), 4.96-5.06 (m, 1H), 4.88-4.95 (m, 1H), 4.72-4.84 (m, 2H), 4.60-4.69 (m, 2H), 3.97-4.17 (m, 1H), 3.74-3.96 (m, 5H), 3.24 (s, 3H), 2.87 (br d, J=5.6 Hz, 2H), 2.36-2.61 (m, 2H).

Compound 133: N10-(3-chloro-4-fluorophenyl)-N4,2-dimethyl-1-oxo-N4-(2,2,2-trifluoroethyl)-1,4,5,8,9,11-hexahydropyrido[4',3':3,4]pyrazolo[5,1-d][1,2,5]oxadiazepine-4,10(2H)-dicarboxamide

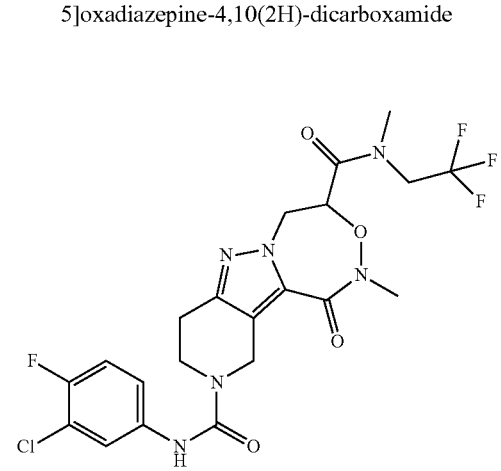

To a mixture of 10-[(3-chloro-4-fluoro-phenyl)carbamoyl]-2-methyl-1-oxo-5,8,9,11-tetrahydro-4H-pyrido[2,3]pyrazolo[2,4-d][1,2,5]oxadiazepine-4-carboxylic acid (80.00 mg, 182.73 μmol, 1.00 eq), 2,2,2-trifluoro-N-methylethanamine (27.33 mg, 182.73 μmol, 1.00 eq, HCl) and 3-picoline (51.05 mg, 548.18 μmol, 53.18 μL3.00 eq) in MeCN (5.00 mL) was added MsCl (29.30 mg, 255.82 μmol, 19.80 μL1.40 eq) dropwise at 0° C. under N₂, and then the mixture was stirred at 20° C. for 0.5 hour under N₂ atmosphere. LCMS showed the starting material was consumed completely and major desired product formed. The mixture was poured into water (10 mL) and extracted with ethyl acetate (5 mL). The organic layer was washed with brine (10 mL), dried with anhydrous Na₂SO₄, filtered and concentrated in vacuum. The residue was purified by prep-HPLC to give the title compound (42.00 mg, 78.03 μmol, 42.70% yield, 99% purity) as a white solid. LCMS [M+1]: 533. ¹H NMR (400 MHz, CHLOROFORM-d) δ=7.55-7.60 (m, 1H), 7.16-7.22 (m, 1H), 7.03-7.09 (m, 1H), 6.51 (s, 1H), 4.94-5.10 (m, 2H), 4.75 (s, 1H), 4.49-4.70 (m, 3H), 3.86 (s, 3H), 3.16-3.37 (m, 6H), 2.88 (d, J=6.02 Hz, 2H).

Compound 134: N10-(3-chloro-4-fluorophenyl)-N4-(2,2-difluoroethyl)-N4,2-dimethyl-1-oxo-1,4,5,8,9,11-hexahydropyrido[4',3':3,4]pyrazolo[5,1-d][1,2,5]oxadiazepine-4,10(2H)-dicarboxamide LCMS [M+1]: 515. ¹H NMR (400 MHz, CHLOROFORM-d) δ=7.54-7.61 (m, 1H), 7.16-7.23 (m, 1H), 7.06 (s, 1H), 6.55 (s, 1H), 6.04 (s, 1H), 5.03 (s, 2H), 4.74 (s, 1H), 4.65 (s, 2H), 3.93-4.15 (m, 1H), 3.86 (br t, J=5.7 Hz, 2H), 3.51-3.71 (m, 1H), 3.15-3.34 (m, 6H), 2.88 (br d, J=5.7 Hz, 2H).

Compound 135: N10-(3-chloro-4-fluorophenyl)-2-methyl-1-oxo-N4-(2,2,2-trifluoroethyl)-1,4,5,8,9,11-hexahydropyrido[4',3':3,4]pyrazolo[5,1-d][1,2,5]oxadiazepine-4,10(2H)-dicarboxamide LCMS [M+1]: 519. ¹H NMR (400 MHz, CHLOROFORM-d) δ=7.54-7.58 (m, 1H), 7.17-7.23 (m, 1H), 7.07 (s, 1H), 6.47-6.52 (m, 1H), 6.34-6.41 (m, 1H), 4.95 (s, 2H), 4.72 (d, J=2.3 Hz, 3H), 3.78-4.04 (m, 4H), 3.35 (s, 3H), 2.86 (t, J=5.7 Hz, 2H).

317

Compound 136: N10-(3-chloro-4-fluorophenyl)-N4-(2,2-difluoroethyl)-2-methyl-1-oxo-1,4,5,8,9,11-hexahydropyrido[4',3':3,4]pyrazolo[5,1-d][1,2,5]oxadiazepine-4,10(2H)-dicarboxamide LCMS [M+1]: 501. $^1$H NMR (400 MHz, CHLOROFORM-d) δ 7.57 (dd, J=2.63, 6.54 Hz, 1H), 7.18-7.25 (m, 1H), 7.04-7.11 (m, 1H), 6.57 (s, 1H), 6.37 (br t, J=6.17 Hz, 1H), 5.68-6.02 (m, 1H), 4.88-4.98 (m, 2H), 4.67-4.77 (m, 3H), 3.85 (t, J=5.81 Hz, 2H), 3.58-3.78 (m, 2H), 3.36 (s, 3H), 2.87 (t, J=5.75 Hz, 2H), 2.19 (s, 1H).

Compound 138_E1: (S*)—N-(3-chloro-2,6-difluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide

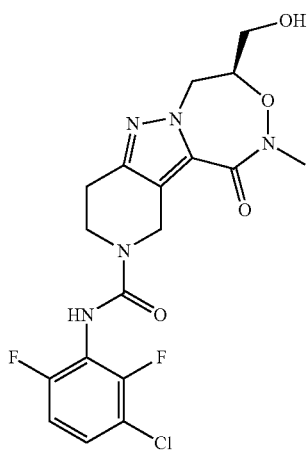

Step 1. 4-(hydroxymethyl)-2-methyl-4,5,8,9,10,11-hexahydropyrido[2,3]pyrazolo[2,4-d][1,2,5]oxadiazepin-1-one. A mixture of tert-butyl 4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxylate (Intermediate 1, 320.00 mg, 908.08 µmol, 1.00 eq, sing enantiomer separated by SFC) in DCM (10.00 mL) was added TFA (7.70 g, 67.53 mmol, 5.00 mL, 74.37 eq) dropwise at 0° C., and then the mixture was stirred at 30° C. for 1 hour. TLC and LCMS showed the starting material was consumed completely, desired product was major. The mixture was concentrated in vacuum to give the title compound (332.60 mg, 908.02 µmol, 99.99% yield, TFA) as a yellow oil, which was used directly for next step.

Step 2. N-(3-chloro-2,6-difluoro-phenyl)-4-(hydroxymethyl)-2-methyl-1-oxo-5,8,9,11-tetrahydro-4H-pyrido[2,3]pyrazolo[2,4-d][1,2,5]oxadiazepine-10-carboxamide. A mixture of 4-(hydroxymethyl)-2-methyl-4,5,8,9,10,11-hexahydropyrido[2,3]pyrazolo[2,4-d][1,2,5]oxadiazepin-1-one (40.00 mg, 109.20 µmol, 1.00 eq, TFA), phenyl N-(3-chloro-2,6-difluoro-phenyl)carbamate (34.07 mg, 120.12 µmol, 1.10 eq), TEA (22.10 mg, 218.40 µmol, 30.27 µL 2.00 eq) in DCM (3.00 mL) was degassed and purged with N$_2$ for 3 times, and then the mixture was stirred at 30° C. for 16 hour under N$_2$ atmosphere. LCMS showed the starting material was consumed completely, desired product was major. The

318 mixture was poured into water (10 mL) and extracted with DCM (5 mL*3). The combined organic phase was washed with brine (10 mL), dried with anhydrous Na$_2$SO$_4$, filtered and concentrated in vacuum. The residue was purified by Prep-HPLC (FA) to afford the title compound (25.00 mg, 56.58 µmol, 51.82% yield, 100% purity) as a white solid.

Compounds 137, 139, 140, 141, 142, 143, 144, 145, 146, 147, 148, 149, 150, and 151 were prepared in an analogous method to Compound 138.

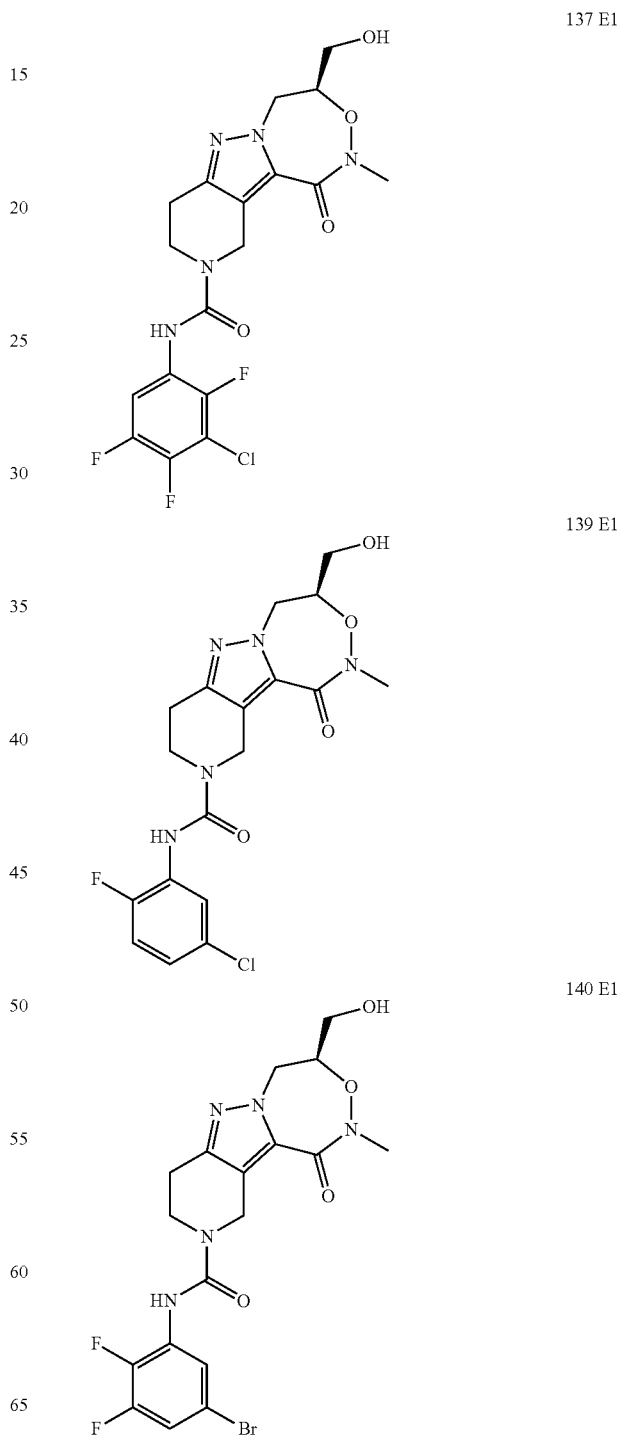

| 141 E1 | 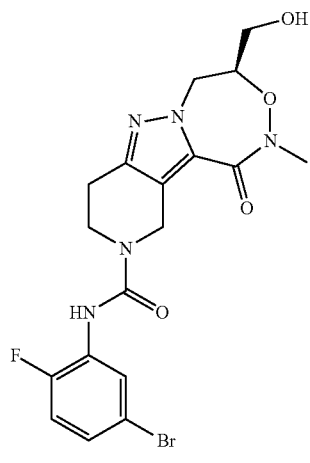 [SMILES: CN1O[C@H](CO)Cn2nc3c(c2C1=O)CN(C(=O)Nc1c(F)ccc(Cl)c1F)CC3] | 144 E1 | 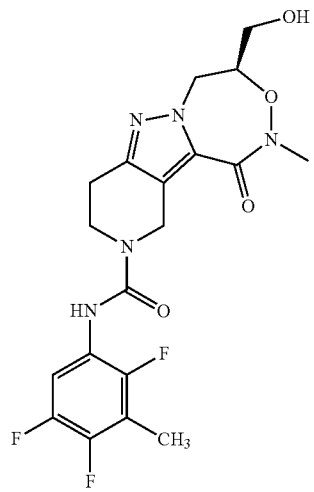 |
| 142 E1 | 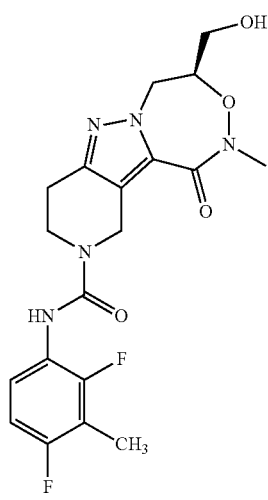 | 145 E1 | 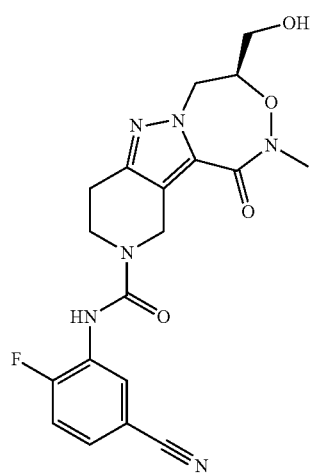 |
| 143 E1 | 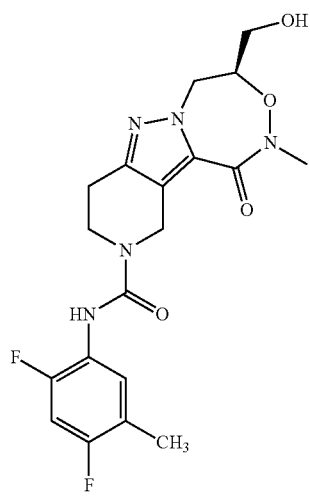 | 146 E1 | 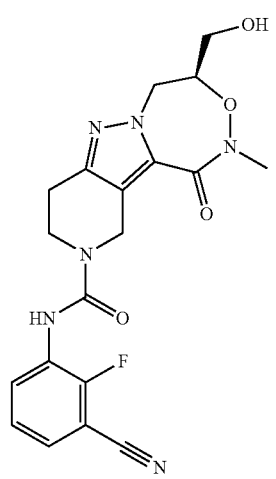 |

-continued

147 E1
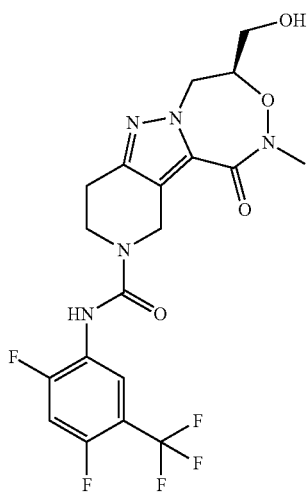

148 E1
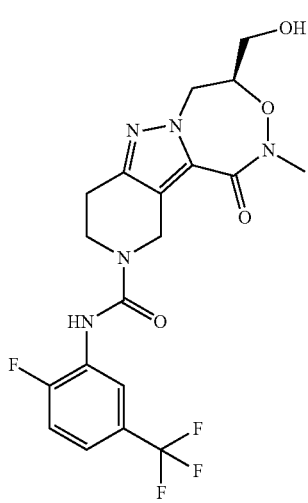

149 E1

-continued

150 E1
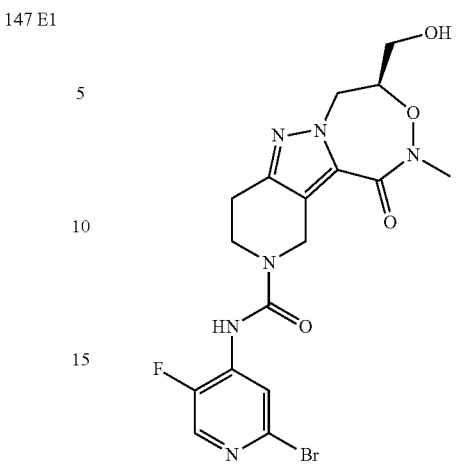

151 E1
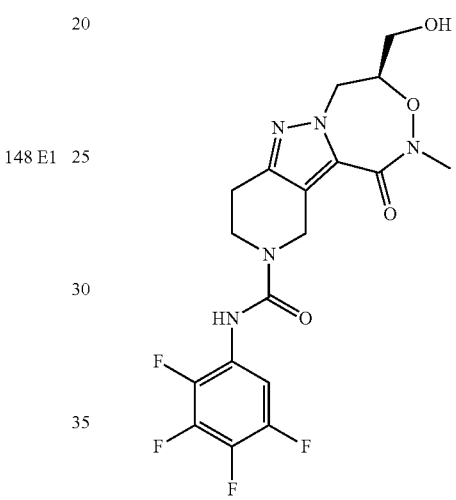

Compound 137_E1: (S*)—N-(3-chloro-2,4,5-trifluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide LCMS: 460/462 [M+1]. $^1$H NMR (400 MHz, CHLOROFORM-d) δ 7.95-8.05 (m, 1H), 6.64-6.70 (m, 1H), 4.74 (d, J=3.01 Hz, 2H), 4.50-4.63 (m, 2H), 4.37-4.48 (m, 1H), 3.72-3.94 (m, 4H), 3.33 (s, 3H), 2.88 (s, 2H).
* pure but unknown stereochemistry Compound 138_E1: (S*)—N-(3-chloro-2,6-difluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide LCMS: 442/444 [M+1]. $^1$H NMR (400 MHz, CHLOROFORM-d) δ 7.17-7.25 (m, 1H), 6.91 (br d, J=1.83 Hz, 1H), 6.08-6.16 (m, 1H), 4.79 (s, 2H), 4.56 (br d, J=12.59 Hz, 2H), 4.43 (s, 1H), 3.73-3.97 (m, 4H), 3.32 (s, 3H), 2.88 (t, J=5.69 Hz, 1H), 2.84-2.92 (m, 1H).
* pure but unknown stereochemistry Compound 139_E1: (S*)—N-(5-chloro-2-fluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide LCMS: 424/426 [M+1]. $^1$H NMR (400 MHz, CHLOROFORM-d) δ 8.14-8.19 (m, 1H), 6.90-7.04 (m, 2H), 6.68-6.73

(m, 1H), 4.74 (s, 2H), 4.55 (br d, J=13.18 Hz, 2H), 4.37-4.47 (m, 1H), 3.71-3.95 (m, 4H), 3.33 (s, 3H), 2.88 (t, J=5.77 Hz, 2H).

\* pure but unknown stereochemistry

Compound 140_E1: (S\*)—N-(5-bromo-2,3-difluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide LCMS: 486/488 [M+1]. $^1$H NMR (400 MHz, CHLOROFORM-d) δ 8.10 (br s, 1H), 6.97-7.05 (m, 1H), 6.69-6.76 (m, 1H), 4.75 (s, 2H), 4.55 (br d, J=13.45 Hz, 2H), 4.43 (s, 1H), 3.72-3.95 (m, 4H), 3.33 (s, 3H), 2.88 (t, J=5.75 Hz, 2H), 1.53-1.64 (m, 1H).

\* pure but unknown stereochemistry

Compound 141_E1: (S\*)—N-(5-bromo-2-fluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide LCMS: 468/470 [M+1]. $^1$H NMR (400 MHz, CHLOROFORM-d) δ 8.29-8.34 (m, 1H), 7.06-7.13 (m, 1H), 6.91-6.98 (m, 1H), 6.66-6.72 (m, 1H), 4.74 (s, 2H), 4.51-4.62 (m, 2H), 4.37-4.46 (m, 1H), 3.72-3.96 (m, 4H), 3.33 (s, 3H), 2.88 (s, 2H).

\* pure but unknown stereochemistry

Compound 142_E1: (S\*)—N-(2,4-difluoro-3-methylphenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide LCMS: 422 [M+1]. $^1$H NMR (400 MHz, CHLOROFORM-d) δ 7.69-7.79 (m, 1H), 6.77-6.86 (m, 1H), 6.48-6.55 (m, 1H), 4.74 (s, 2H), 4.51-4.61 (m, 2H), 4.36-4.46 (m, 1H), 3.73-3.93 (m, 4H), 3.33 (s, 3H), 2.83-2.90 (m, 2H), 2.21 (s, 3H).

\* pure but unknown stereochemistry

Compound 143_E1: (S\*)—N-(2,4-difluoro-5-methylphenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide LCMS: 422 [M+1]. $^1$H NMR (400 MHz, CHLOROFORM-d) δ 7.75-7.81 (m, 1H), 6.76-6.84 (m, 1H), 6.49 (br d, J=2.51 Hz, 1H), 4.73 (s, 2H), 4.50-4.62 (m, 2H), 4.37-4.47 (m, 1H), 3.86 (br d, J=14.81 Hz, 4H), 3.32 (s, 3H), 2.87 (t, J=5.71 Hz, 2H), 2.22 (s, 3H), 2.00-2.15 (m, 1H).

\* pure but unknown stereochemistry

Compound 144_E1: (S\*)-4-(hydroxymethyl)-2-methyl-1-oxo-N-(2,4,5-trifluoro-3-methylphenyl)-1,4,5,8,9,11-hexahydropyrido[4',3':3,4]pyrazolo[5,1-d][1,2,5]oxadiazepine-10(2H)-carboxamide LCMS: 440 [M+1]. $^1$H NMR (400 MHz, CHLOROFORM-d) δ 7.78-7.89 (m, 1H), 6.57-6.63 (m, 1H), 4.73 (s, 2H), 4.51-4.62 (m, 2H), 4.37-4.47 (m, 1H), 3.71-3.94 (m, 4H), 3.33 (s, 3H), 2.87 (t, J=1.90 Hz, 2H), 2.24 (t, J=1.90 Hz, 2H), 2.20-2.28 (m, 1H).

\* pure but unknown stereochemistry

Compound 145_E1: (S\*)—N-(5-cyano-2-fluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide LCMS: 415 [M+1]. $^1$H NMR (400 MHz, CHLOROFORM-d) δ 8.29-8.36 (m, 1H), 7.41-7.46 (m, 1H), 7.35-7.40 (m, 1H), 6.91-6.95 (m, 1H), 4.77 (s, 2H), 4.50-4.64 (m, 2H), 4.37-4.48 (m, 1H), 3.72-3.96 (m, 4H), 3.33 (s, 3H), 2.89 (t, J=5.75 Hz, 2H), 1.84-1.92 (m, 1H).

\* pure but unknown stereochemistry

Compound 146_E1: (S\*)—N-(3-cyano-2-fluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide LCMS: 415 [M+1]. $^1$H NMR (400 MHz, CHLOROFORM-d) δ 8.32-8.38 (m, 1H), 7.24-7.27 (m, 1H), 7.18-7.24 (m, 1H), 6.70-6.83 (m, 1H), 4.77 (s, 2H), 4.50-4.63 (m, 2H), 4.37-4.47 (m, 1H), 3.73-3.97 (m, 4H), 3.33 (s, 3H), 2.89 (t, J=5.75 Hz, 2H).

\* pure but unknown stereochemistry

Compound 147_E1: (S\*)—N-(2,4-difluoro-5-(trifluoromethyl)phenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide LCMS: 476 [M+1]. $^1$H NMR (400 MHz, CHLOROFORM-d) δ 8.35-8.42 (m, 1H), 6.95-7.05 (m, 1H), 6.59-6.67 (m, 1H), 4.75 (s, 2H), 4.56 (br d, J=12.23 Hz, 2H), 4.36-4.47 (m, 1H), 3.72-3.97 (m, 4H), 3.33 (s, 3H), 2.88 (t, J=5.75 Hz, 2H).

\* pure but unknown stereochemistry

Compound 148_E1: (S\*)—N-(2-fluoro-5-(trifluoromethyl)phenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide LCMS: 458 [M+1]. $^1$H NMR (400 MHz, CHLOROFORM-d) δ 8.47 (dd, J=2.01, 7.28 Hz, 1H), 7.24-7.27 (m, 1H), 7.14-7.21 (m, 1H), 6.80 (br d, J=3.76 Hz, 1H), 4.76 (s, 2H), 4.51-4.62 (m, 2H), 4.38-4.47 (m, 1H), 3.72-3.97 (m, 4H), 3.33 (s, 3H), 2.85-2.93 (m, 2H).

\* pure but unknown stereochemistry

Compound 149_E1: (S\*)—N-(2,4-difluoro-3-(trifluoromethyl)phenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide LCMS: 476 [M+1]. $^1$H NMR (400 MHz, CHLOROFORM-d) δ 8.17-8.26 (m, 1H), 6.95-7.03 (m, 1H), 6.62-6.68 (m, 1H), 4.75 (d, J=2.13 Hz, 2H), 4.56 (br d, J=12.93 Hz, 2H), 4.43 (s, 1H), 3.73-3.94 (m, 4H), 3.33 (s, 3H), 2.88 (s, 2H).

\* pure but unknown stereochemistry

Compound 150_E1: (S\*)—N-(2-bromo-5-fluoropyridin-4-yl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide LCMS: 469/471 [M+1]. $^1$H NMR (400 MHz, CHLOROFORM-d) δ 8.38-8.43 (m, 1H), 8.14 (d, J=2.13 Hz, 1H), 6.94-7.00 (m, 1H), 4.75 (d, J=3.26 Hz, 2H), 4.51-4.63 (m, 2H), 4.43 (br d, J=9.16 Hz, 1H), 3.72-3.96 (m, 4H), 3.33 (s, 3H), 2.89 (t, J=5.83 Hz, 2H).

* pure but unknown stereochemistry

Compound 151_E1: (S*)-4-(hydroxymethyl)-2-methyl-1-oxo-N-(2,3,4,5-tetrafluorophenyl)-1,4,5,8,9,11-hexahydropyrido[4',3':3,4]pyrazolo[5,1-d][1,2,5]oxadiazepine-10(2H)-carboxamide LCMS: 444 [M+1]. ¹H NMR (400 MHz, CHLOROFORM-d) δ 7.80-7.90 (m, 1H), 6.65 (br s, 1H), 4.74 (d, J=3.14 Hz, 2H), 4.51-4.62 (m, 2H), 4.38-4.48 (m, 1H), 3.85 (br d, J=5.65 Hz, 4H), 3.33 (s, 3H), 2.88 (t, J=5.83 Hz, 2H).

* pure but unknown stereochemistry

Compound 152_D1: (4S*,9R)—N10-(3-chloro-2,4-difluorophenyl)-N4-(2,2-difluoroethyl)-N4,2,9-trimethyl-1-oxo-1,4,5,8,9,11-hexahydropyrido[4',3':3,4]pyrazolo[5,1-d][1,2,5]oxadiazepine-4,10(2H)-dicarboxamide

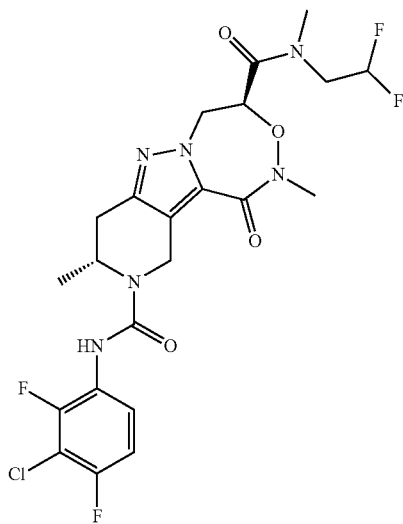 [SMILES: C[C@@H]1Cc2nn3c(c2CN1C(=O)Nc1ccc(F)c(Cl)c1F)C(=O)N(C)O[C@H](C(=O)N(C)CC(F)F)C3]

Step 1. (9R)-10-tert-butoxycarbonyl-2,9-dimethyl-1-oxo-5,8,9,11-tetrahydro-4H-pyrido[2,3]pyrazolo[2,4-d][1,2,5]oxadiazepine-4-carboxylic acid. To a solution of tert-butyl (9R)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxylate (Intermediate 18, 500.00 mg, 1.36 mmol, 1.00 eq, diastereomer separated by SFC) and NMO (1.19 g, 10.20 mmol, 1.08 mL, 7.50 eq) in MeCN (10.00 mL) was added TPAP (119.49 mg, 340.00 μmol, 0.25 eq). The mixture was stirred at 30° C. for 12 hr. LCMS showed the starting material was consumed completely, desired product was major. The mixture was poured into water (20 mL) and washed with tert-butyl methyl ether (10 mL), the aqueous layer was acidified by 0.5 N HCl to pH 3, extracted with DCM (20 mL*2), the organic layer was washed with brine (10 mL), dried over anhydrous Na₂SO₄ and concentrated in vacuum to give the title compound (520.00 mg, crude) as a black brown solid. LCMS: 381[M+1].

Step 2. tert-butyl (9R)-4-[2,2-di fluoroethyl(methyl)carbamoyl]-2,9-dimethyl-1-oxo-5,8,9,11-tetrahydro-4H-pyrido[2,3]pyrazolo[2,4-d][1,2,5]oxadiazepine-10-carboxylate. To a mixture of (9R)-10-tert-butoxycarbonyl-2,9-dimethyl-1-oxo-5,8,9,11-tetra hydro-4H-pyrido[2,3]pyrazolo[2,4-d][1,2,5]oxadiazepine-4-carboxylic acid (250.00 mg, 657.22 μmol, 1.00 eq), 2,2-difluoro-N-methyl-ethanamine (172.91 mg, 1.31 mmol, 2.00 eq, HCl), 3-picoline (183.62 mg, 1.97 mmol, 191.27 μL3.00 eq) in MeCN (5.00 mL) was added MsCl (112.93 mg, 985.83 μmol, 76.30 μL1.50 eq) dropwise at 0° C. under N₂, and then the mixture was stirred at 30° C. for 2 hour under N₂ atmosphere. LCMS showed the starting material was consumed completely, desired product was major. The mixture was poured into water (10 mL) and stirred at 5 min. The aqueous phase was extracted with DCM (5 mL*3). The combined organic phase was washed with brine (20 mL), dried with anhydrous Na₂SO₄, filtered and concentrated in vacuum. The residue was purified by column chromatography (SiO₂, Petroleum ether/Ethyl acetate=100/1 to 1/2) to give the title compound (244.00 mg, 517.37 μmol, 78.72% yield, 97% purity) as a white solid. LCMS: 458[M+1].

Step 3. (9R)—N-(2,2-difluoroethyl)-N,2,9-trimethyl-1-oxo-4,5,8,9,10,11-hexahydropyrido[2,3]pyrazolo[2,4-d][1,2,5]oxadiazepine-4-carboxamide. A solution of tert-butyl (9R)-4-[2,2-difluoroethyl(methyl)carbamoyl]-2,9-dimethyl-1-oxo-5,8,9,11-tetrahydro-4H-pyrido[2,3]pyrazolo[2,4-d][1,2,5]oxadiazepine-10-carboxylate (180.00 mg, 393.47 μmol, 1.00 eq) in DCM (2.00 mL) was added TFA (1.85 g, 16.21 mmol, 1.20 mL, 41.19 eq), and then the mixture was stirred at 30° C. for 1 hour. TLC showed the starting material was consumed completely, a new spot appeared. The mixture was concentrated in vacuum to give the title compound (185.47 mg, 393.46 μmol, 100.00% yield, TFA) as a yellow oil, which was used directly for next step.

Step 4. (9R)—N10-(3-chloro-2,4-difluoro-phenyl)-N4-(2,2-difluoro ethyl)-N4,2,9-trimethyl-1-oxo-5,8,9,11-tetrahydro-4H-pyrido[2,3]pyrazolo[2,4-d][1,2,5]oxadiazepine-4,10-dicarboxamide. To a mixture of (9R)—N-(2,2-difluoroethyl)-N,2,9-trimethyl-1-oxo-4,5,8,9,10,11-hexahydropyrido[2,3]pyrazolo[2,4-d][1,2,5]oxadiazepine-4-carboxamide (60.00 mg, 127.29 μmol, 1.00 eq, TFA), phenyl N-(3-chloro-2,4-difluoro-phenyl)carbamate (43.33 mg, 152.75 μmol, 1.20 eq), TEA (25.76 mg, 254.58 μmol, 35.29 μL2.00 eq) in DCM (3.00 mL) was degassed and purged with N₂ for 3 times, and then the mixture was stirred at 30° C. for 16 hour under N₂ atmosphere. LCMS showed the starting material was consumed completely, desired product was major. The mixture was poured into water (10 mL) and extracted with DCM (5 mL*3). The combined organic phase was washed with brine (10 mL), dried with anhydrous Na₂SO₄, filtered and concentrated in vacuum. The residue was purified by Prep-HPLC (FA) to give the title compound (51.00 mg, 86.73 μmol, 68.13% yield, 93% purity) as a white solid. LCMS: 547/548[M+1]. ¹H NMR (400 MHz, CHLOROFORM-d) δ 7.87 (br d, J=5.50 Hz, 1H), 6.92-7.00 (m, 1H), 6.56 (br s, 1H), 6.04 (s, 1H), 4.94-5.16 (m, 4H), 4.59-4.70 (m, 1H), 4.42 (d, J=15.53 Hz, 1H), 3.94-4.10 (m, 1H), 3.60 (br dd, J=4.34, 13.02 Hz, 1H), 3.15-3.35 (m, 6H), 3.05-3.13 (m, 1H), 2.62-2.74 (m, 1H), 1.19 (d, J=6.85 Hz, 3H).

* pure but unknown stereochemistry

327

Compound 152_D2: (4R*,9R)—N10-(3-chloro-2,4-difluorophenyl)-N4-(2,2-difluoroethyl)-N4,2,9-trimethyl-1-oxo-1,4,5,8,9,11-hexahydropyrido[4',3':3,4]pyrazolo[5,1-d][1,2,5]oxadiazepine-4,10(2H)-dicarboxamide

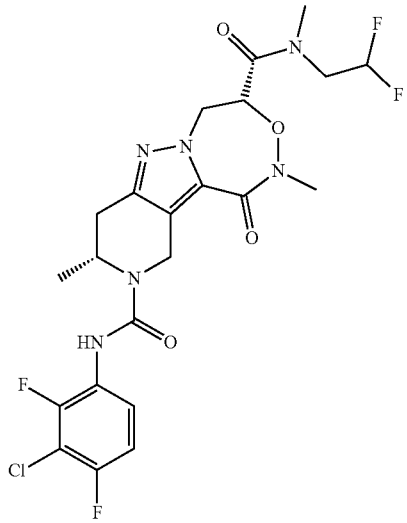

Compound 152_D2 was prepared in an analogous manner to Compound 152_D1 using the opposite enantiomer of Intermediate 18.

LCMS: 547/548[M+1]. $^1$H NMR (400 MHz, CHLOROFORM-d) δ 7.83-7.93 (m, 1H), 6.91-7.02 (m, 1H), 6.46-6.55 (m, 1H), 5.86-6.21 (m, 1H), 5.03 (s, 3H), 4.78-4.87 (m, 1H), 4.51-4.71 (m, 2H), 3.95-4.11 (m, 1H), 3.52-3.67 (m, 1H), 3.16-3.33 (m, 6H), 3.00-3.09 (m, 1H), 2.70-2.78 (m, 1H), 1.21-1.27 (m, 3H).

* pure but unknown stereochemistry

Compounds 153, 154, and 155 were prepared in an analogous manner to Compound 152.

153 D1

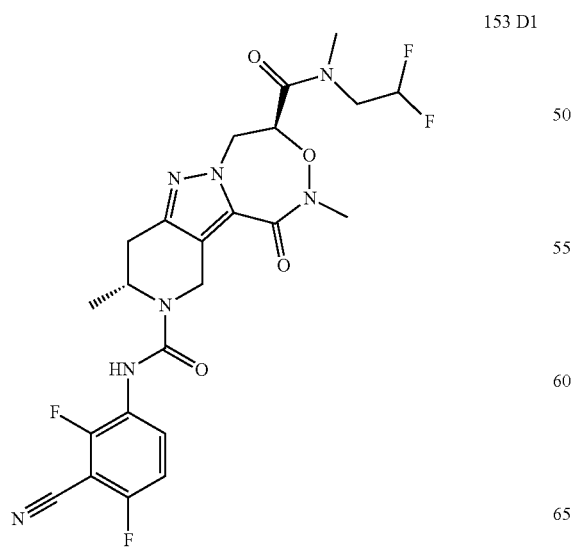

328

-continued

153 D2

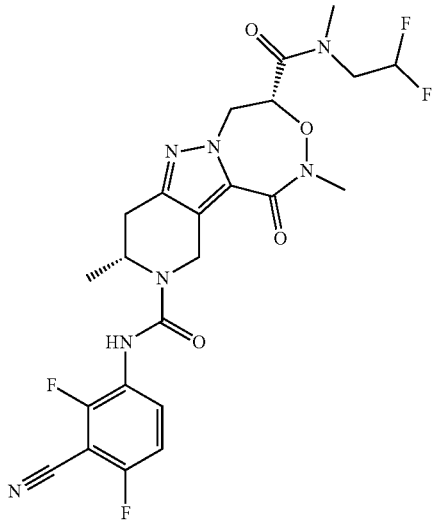

154 D1

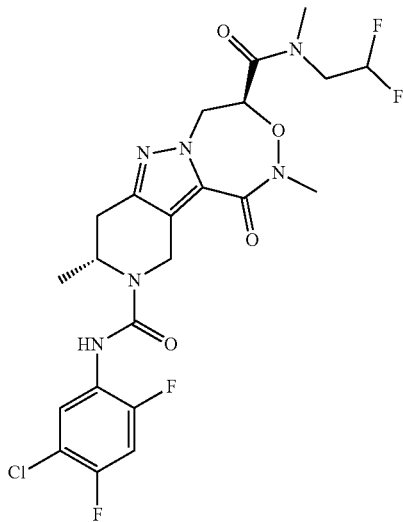

154 D2

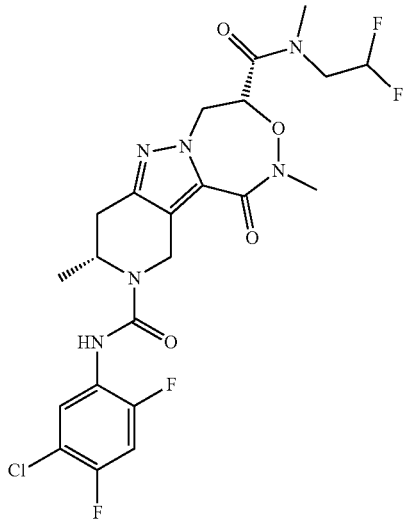

-continued

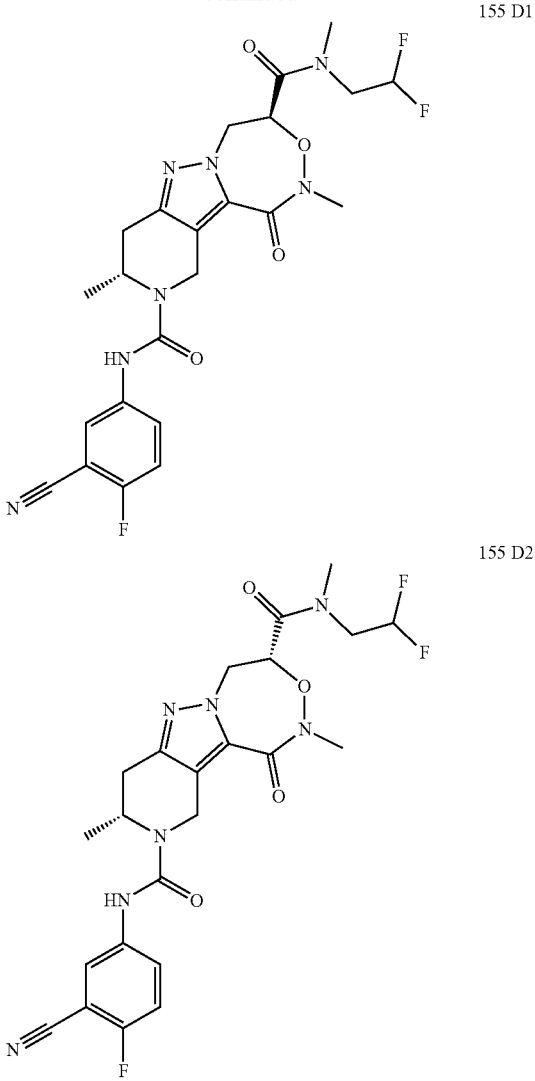

155 D1

155 D2

Compound 153_D1: (4S*,9R)—N10-(3-cyano-2,4-difluorophenyl)-N4-(2,2-difluoroethyl)-N4,2,9-trimethyl-1-oxo-1,4,5,8,9,11-hexahydropyrido[4',3':3,4]pyrazolo[5,1-d][1,2,5]oxadiazepine-4,10(2H)-dicarboxamide LCMS: 538[M+1]. $^1$H NMR (400 MHz, CHLOROFORM-d) δ 8.22-8.32 (m, 1H), 6.99-7.06 (m, 1H), 6.61-6.68 (m, 1H), 6.04 (s, 1H), 4.94-5.16 (m, 4H), 4.59-4.70 (m, 1H), 4.39-4.47 (m, 1H), 3.93-4.08 (m, 1H), 3.52-3.70 (m, 1H), 3.15-3.34 (m, 6H), 3.04-3.13 (m, 1H), 2.66-2.74 (m, 1H), 1.20 (d, J=6.85 Hz, 3H).
* pure but unknown stereochemistry Compound 153_D2: (4R*,9R)—N10-(3-cyano-2,4-difluorophenyl)-N4-(2,2-difluoroethyl)-N4,2,9-trimethyl-1-oxo-1,4,5,8,9,11-hexahydropyrido[4',3':3,4]pyrazolo[5,1-d][1,2,5]oxadiazepine-4,10(2H)-dicarboxamide LCMS: 538[M+1]. $^1$H NMR (400 MHz, CHLOROFORM-d) δ 8.24-8.37 (m, 1H), 6.97-7.09 (m, 1H), 6.50-6.62 (m, 1H), 6.04 (s, 1H), 5.03 (s, 3H), 4.53-4.87 (m, 3H), 3.95-4.12 (m, 1H), 3.53-3.69 (m, 1H), 3.16-3.33 (m, 6H), 2.99-3.09 (m, 1H), 2.70-2.79 (m, 1H), 1.24 (d, J=6.85 Hz, 3H).
* pure but unknown stereochemistry Compound 154_D1: (4S*,9R)—N10-(5-chloro-2,4-difluorophenyl)-N4-(2,2-difluoroethyl)-N4,2,9-trimethyl-1-oxo-1,4,5,8,9,11-hexahydropyrido[4',3':3,4]pyrazolo[5,1-d][1,2,5]oxadiazepine-4,10(2H)-dicarboxamide LCMS: 547/548[M+1]. $^1$H NMR (400 MHz, CHLOROFORM-d) δ 8.19 (s, 1H), 6.92-6.99 (m, 1H), 6.56-6.61 (m, 1H), 5.87-6.21 (m, 1H), 4.93-5.17 (m, 4H), 4.60-4.70 (m, 1H), 4.41 (d, J=15.65 Hz, 1H), 3.94-4.18 (m, 1H), 3.51-3.73 (m, 1H), 3.14-3.34 (m, 6H), 3.06 (br d, J=5.75 Hz, 1H), 2.72 (s, 1H), 1.19 (d, J=6.85 Hz, 3H).
* pure but unknown stereochemistry Compound 154_D2: (4R*,9R)—N10-(5-chloro-2,4-difluorophenyl)-N4-(2,2-difluoroethyl)-N4,2,9-trimethyl-1-oxo-1,4,5,8,9,11-hexahydropyrido[4',3':3,4]pyrazolo[5,1-d][1,2,5]oxadiazepine-4,10(2H)-dicarboxamide LCMS: 547/548[M+1]. $^1$H NMR (400 MHz, CHLOROFORM-d) δ 8.16-8.23 (m, 1H), 6.91-6.99 (m, 1H), 6.48-6.55 (m, 1H), 5.87-6.22 (m, 1H), 5.03 (s, 3H), 4.76-4.84 (m, 1H), 4.51-4.72 (m, 2H), 3.95-4.11 (m, 1H), 3.51-3.68 (m, 1H), 3.15-3.34 (m, 6H), 2.98-3.09 (m, 1H), 2.70-2.78 (m, 1H), 1.23 (d, J=6.90 Hz, 3H).
* pure but unknown stereochemistry Compound 155_D1: (4S*,9R)—N10-(3-cyano-4-fluorophenyl)-N4-(2,2-difluoroethyl)-N4,2,9-trimethyl-1-oxo-1,4,5,8,9,11-hexahydropyrido[4',3':3,4]pyrazolo[5,1-d][1,2,5]oxadiazepine-4,10(2H)-dicarboxamide LCMS: 520[M+1]. $^1$H NMR (400 MHz, CHLOROFORM-d) δ 7.78-7.83 (m, 1H), 7.58-7.65 (m, 1H), 7.14 (s, 1H), 6.84 (s, 1H), 5.85-6.26 (m, 1H), 4.89-5.23 (m, 4H), 4.60-4.72 (m, 1H), 4.39 (d, J=15.65 Hz, 1H), 3.95-4.14 (m, 1H), 3.52-3.75 (m, 1H), 3.15-3.35 (m, 6H), 3.02-3.11 (m, 1H), 2.71 (s, 1H), 1.13-1.22 (m, 3H).
* pure but unknown stereochemistry Compound 155_D2: (4R*,9R)—N10-(3-cyano-4-fluorophenyl)-N4-(2,2-difluoroethyl)-N4,2,9-trimethyl-1-oxo-1,4,5,8,9,11-hexahydropyrido[4',3':3,4]pyrazolo[5,1-d][1,2,5]oxadiazepine-4,10(2H)-dicarboxamide LCMS: 520[M+1]. $^1$H NMR (400 MHz, CHLOROFORM-d) δ 7.76 (s, 1H), 7.54-7.61 (m, 1H), 7.11-7.19 (m, 1H), 6.56-6.62 (m, 1H), 5.88-6.21 (m, 1H), 5.04 (s, 3H), 4.74-4.82 (m, 1H), 4.51-4.70 (m, 2H), 3.93-4.15 (m, 1H), 3.52-3.72 (m, 1H), 3.15-3.35 (m, 6H), 2.97-3.09 (m, 1H), 2.76 (s, 1H), 1.22 (d, J=6.90 Hz, 3H).
* pure but unknown stereochemistry Compound 156_D1: (4S*,9R)—N10-(3-cyano-2,4-difluorophenyl)-N4,2,9-trimethyl-1-oxo-1,4,5,8,9,11-hexahydropyrido[4',3':3,4]pyrazolo[5,1-d][1,2,5]oxadiazepine-4,10(2H)-dicarboxamide

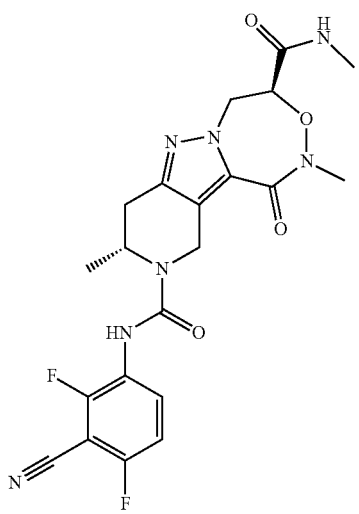 [SMILES: CNC(=O)[C@@H]1Cn2nc3c(c2C(=O)N(C)O1)CN(C(=O)Nc1ccc(F)c(C#N)c1F)[C@H](C)C3]

Compound 156 was prepared in an analogous manner to Compound 110.

LCMS: 474[M+1]. ¹H NMR (400 MHz, CHLOROFORM-d) δ 8.25-8.36 (m, 1H), 6.98-7.08 (m, 1H), 6.57-6.64 (m, 1H), 6.00-6.11 (m, 1H), 4.95-5.07 (m, 2H), 4.91 (s, 2H), 4.65-4.72 (m, 1H), 4.51-4.57 (m, 1H), 3.35 (s, 3H), 2.99-3.08 (m, 1H), 2.85 (d, J=4.89 Hz, 3H), 2.68-2.77 (m, 1H), 1.23 (d, J=6.85 Hz, 2H), 1.19-1.26 (m, 1H).

* pure but unknown stereochemistry

Compound 156_D2: (4R*,9R)—N10-(3-cyano-2,4-difluorophenyl)-N4,2,9-trimethyl-1-oxo-1,4,5,8,9,11-hexahydropyrido[4',3':3,4]pyrazolo[5,1-d][1,2,5]oxadiazepine-4,10(2H)-dicarboxamide

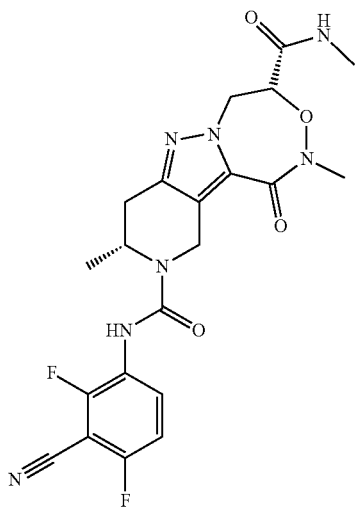

LCMS: 474[M+1]. ¹H NMR (400 MHz, CHLOROFORM-d) δ 8.24-8.34 (m, 1H), 6.99-7.06 (m, 1H), 6.62-6.68 (m, 1H), 6.09-6.20 (m, 1H), 5.02-5.11 (m, 1H), 4.86-4.99 (m, 3H), 4.68-4.77 (m, 1H), 4.46 (d, J=15.89 Hz, 1H), 3.35 (s, 3H), 2.99-3.09 (m, 1H), 2.89 (d, J=4.89 Hz, 3H), 2.69-2.78 (m, 1H), 1.20 (d, J=6.85 Hz, 3H).

* pure but unknown stereochemistry

Compound 157_D1: (4S*,9R)—N-[2-fluoro-5-(trifluoromethyl)phenyl]-4-(hydroxymethyl)-2,9-dimethyl-1-oxo-5,8,9,11-tetrahydro-4H-pyrido[2,3]pyrazolo[2,4-d][1,2,5]oxadiazepine-10-carboxamide

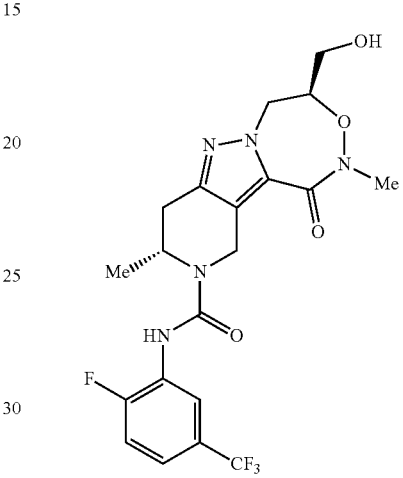

Step 1. (9R)-4-(hydroxymethyl)-2,9-dimethyl-4,5,8,9,10,11-hexahydropyrido[2,3]pyrazolo[2,4-d][1,2,5]oxadiazepin-1-one. A solution of tert-butyl (9R)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxylate (Intermediate 18, 40.00 mg, 109.17 μmol, 1.00 eq) in DCM (2.00 mL) was added TFA (1.54 g, 13.51 mmol, 1.00 mL, 123.72 eq), and then the mixture was stirred at 20° C. for 1 hour. TLC showed the starting material was consumed completely, a new spot appeared. The mixture was concentrated in vacuum to afford the title compound (41.52 mg, 109.17 μmol, 100.00% yield, TFA) as a yellow oil, which was used directly for next step.

Step 2. (4S*,9R)—N-[2-fluoro-5-(trifluoromethyl)phenyl]-4-(hydroxymethyl)-2,9-dimethyl-1-oxo-5,8,9,11-tetrahydro-4H-pyrido[2,3]pyrazolo[2,4-d][1,2,5]oxadiazepine-10-carboxamide. A mixture of (9R)-4-(hydroxymethyl)-2,9-dimethyl-4,5,8,9,10,11-hexahydropyrido[2,3]pyrazolo[2,4-d][1,2,5]oxadiazepin-1-one (41.00 mg, 107.80 μmol, 1.00 eq, TFA), phenylN-[2-fluoro-5-(trifluoromethyl)phenyl]carbamate (35.48 mg, 118.58 μmol, 1.10 eq), TEA (21.82 mg, 215.61 μmol, 29.89 μL2.00 eq) in DCM (5.00 mL) was degassed and purged with N₂ for 3 times, and then the mixture was stirred at 30° C. for 16 hour under N₂ atmosphere. LCMS showed the starting material was consumed completely, desired product was major. The mixture was poured into water (10 mL) and extracted with DCM (5 mL*3). The combined organic phase was washed with brine (10 mL), dried with anhydrous Na₂SO₄, filtered and concentrated in vacuum. The residue was purified by Prep-HPLC (FA) to afford the title compound (35.00 mg, 73.50 μmol, 68.19% yield, 99% purity) as a white solid. LCMS: 472 [M+1]. ¹H NMR (400 MHz, CHLOROFORM-d) δ 8.48

(dd, J=1.90, 7.27 Hz, 1H), 7.24-7.27 (m, 1H), 7.17 (s, 1H), 6.73-6.81 (m, 1H), 5.05-5.17 (m, 1H), 4.87 (s, 1H), 4.52-4.64 (m, 3H), 4.46 (s, 1H), 3.81-3.88 (m, 1H), 3.71-3.80 (m, 1H), 3.34 (s, 3H), 3.01-3.11 (m, 1H), 2.71 (d, J=15.89 Hz, 1H), 1.22 (d, J=6.85 Hz, 3H).

* pure but unknown stereochemistry

Compound 157_D2: (4R*,9R)—N-[2-fluoro-5-(trifluoromethyl)phenyl]-4-(hydroxymethyl)-2,9-dimethyl-1-oxo-5,8,9,11-tetrahydro-4H-pyrido[2,3]pyrazolo[2,4-d][1,2,5]oxadiazepine-10-carboxamide

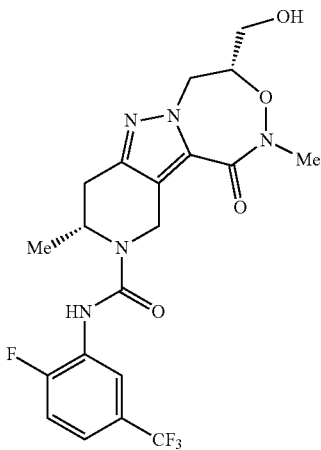 [SMILES: C[C@@H]1Cc2nn3c(c2CN1C(=O)Nc1cc(C(F)(F)F)ccc1F)C(=O)N(C)O[C@@H](CO)C3]

¹H NMR (400 MHz, CHLOROFORM-d) δ 8.46-8.52 (m, 1H), 8.46-8.52 (m, 1H), 7.24-7.27 (m, 1H), 7.14-7.22 (m, 1H), 6.75-6.82 (m, 1H), 5.06-5.19 (m, 1H), 4.92 (s, 1H), 4.48-4.62 (m, 3H), 4.35-4.44 (m, 1H), 3.86-3.94 (m, 1H), 3.75-3.82 (m, 1H), 3.34 (s, 3H), 3.02-3.11 (m, 1H), 3.02-3.11 (m, 1H), 2.65-2.78 (m, 1H), 1.21 (d, J=6.85 Hz, 2H), 1.19-1.24 (m, 1H).

* pure but unknown stereochemistry

Compound 158: N10-(3-chloro-2,4-difluorophenyl)-N4-(2,2-difluoroethyl)-N4,2-dimethyl-1-oxo-1,4,5,8,9,11-hexahydropyrido[4',3':3,4]pyrazolo[5,1-d][1,2,5]oxadiazepine-4,10(2H)-dicarboxamide Step 1. N-(2,2-difluoroethyl)-N,2-dimethyl-1-oxo-4,5,8,9,10,11-hexahydropyrido[2,3]pyrazolo[2,4-d][1,2,5]oxadiazepine-4-carboxamide To a solution of tert-butyl 4-[2,2-difluoroethyl(methyl)carbamoyl]-2-methyl-1-oxo-5,8,9,11-tetrahydro-4H-pyrido[2,3]pyrazolo[2,4-d][1,2,5]oxadiazepine-10-carboxylate (150.00 mg, 338.26 μmol, 1.00 eq) in DCM (4.00 mL) was added TFA (3.08 g, 27.01 mmol, 2.00 mL, 79.86 eq) at 0° C. The mixture was stirred at 25° C. for 1 h. The mixture was concentrated under reduced pressure to afford the title compound (154.70 mg, 338.25 μmol, 100.00% yield, TFA) as yellow oil, the crude product was used directly for the next step. LCMS: 344 [M+1]

Step 2. N10-(3-chloro-2,4-difluoro-phenyl)-N4-(2,2-difluoroethyl)-N4,2-dimethyl-1-oxo-5,8,9,11-tetrahydro-4H-pyrido[2,3]pyrazolo[2,4-d][1,2,5]oxadiazepine-4,10-dicarboxamide To a solution of N-(2,2-difluoroethyl)-N,2-dimethyl-1-oxo-4,5,8,9,10,11-hexahydropyrido[2,3]pyrazolo[2,4-d][1,2,5]oxadiazepine-4-carboxamide (50.00 mg, 109.33 μmol, 1.00 eq, TFA) in DCM (3.00 mL) was added phenyl N-(3-chloro-2,4-difluoro-phenyl)carbamate (46.52 mg, 164.00 μmol, 1.50 eq) and Et3N (55.32 mg, 546.65 μmol, 75.78 μL 5.00 eq). The mixture was stirred at 25° C. for 16 h. The mixture was adjusted to neutral condition (pH~6) with FA and concentrated in vacuo. The resulting residue was purified by prep-HPLC(FA) to afforded N10-(3-chloro-2,4-difluoro-phenyl)-N4-(2,2-difluoroethyl)-N4,2-dimethyl-1-oxo-5,8,9,11-tetrahydro-4H-pyrido[2,3]pyrazolo[2,4-d][1,2,5]oxadiazepine-4,10-dicarboxamide (40.00 mg, 74.31 μmol, 67.97% yield, 99% purity) as white solid. LCMS [M+1]: 533/535. ¹H NMR (400 MHz, CHLOROFORM-d) δ7.86-7.88 (m, 1H), 6.90-7.03 (m, 1H), 6.57 (br s, 1H), 5.85-6.22 (m, 1H), 4.94-5.12 (m, 2H), 4.58-4.84 (m, 3H), 3.76-4.13 (m, 3H), 3.50-3.69 (m, 1H), 3.13-3.37 (m, 6H), 2.80-2.98 (m, 2H).

Compounds 159, 160, and 161 were prepared in an analogous manner to 158.

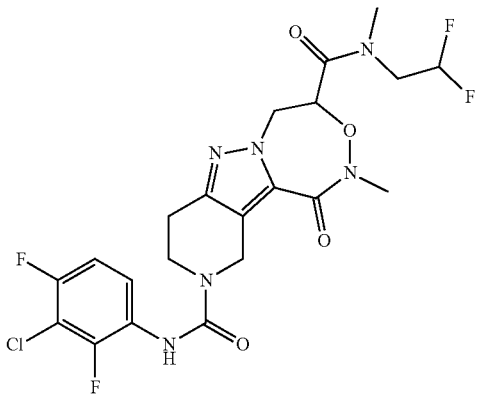 [SMILES: CN(CC(F)F)C(=O)C1Cn2nc3c(c2C(=O)N(C)O1)CN(C(=O)Nc1ccc(F)c(Cl)c1F)CC3]

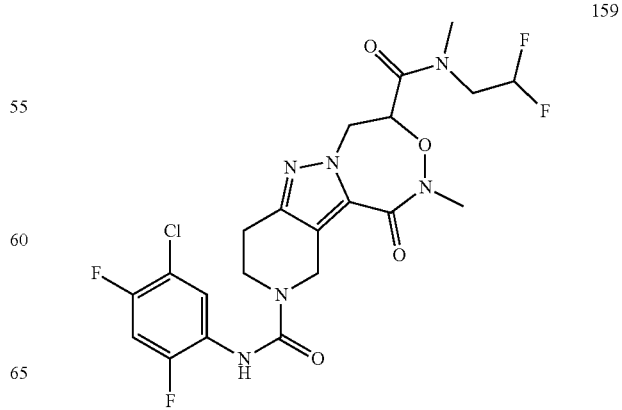

159

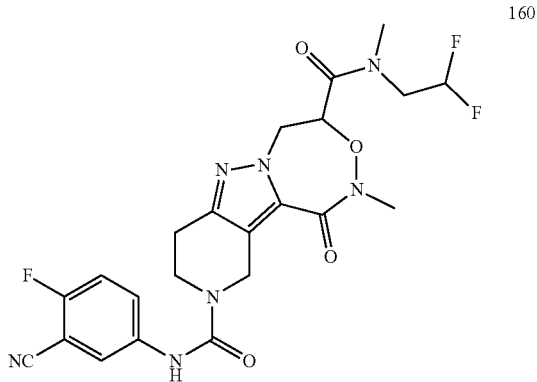

160

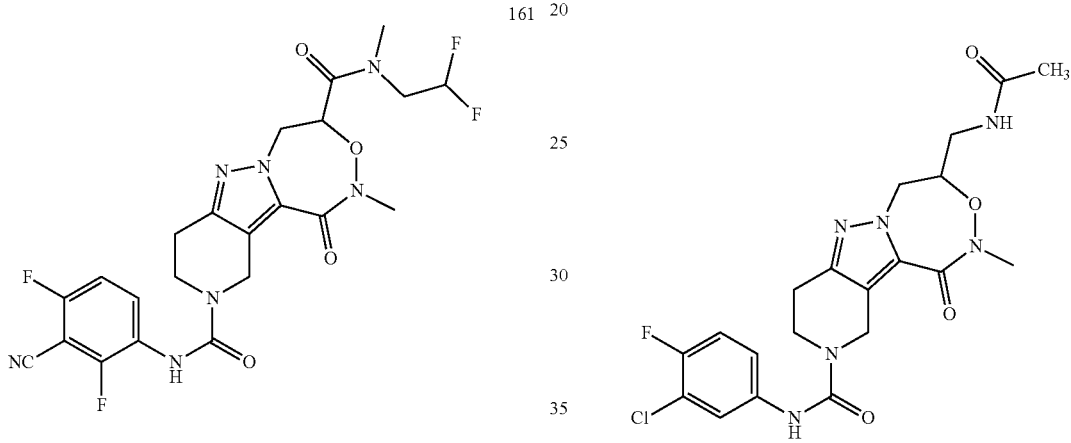

161

Compound 159: N10-(5-chloro-2,4-difluorophenyl)-N4-(2,2-difluoroethyl)-N4,2-dimethyl-1-oxo-1,4,5,8,9,11-hexahydropyrido[4',3':3,4]pyrazolo[5,1-d][1,2,5]oxadiazepine-4,10(2H)-dicarboxamide LCMS [M+1]:533/535. $^1$H NMR (400 MHz, CHLOROFORM-d) δ 8.17 (t, J=8.07 Hz, 1H), 6.95 (dd, J=8.44, 10.64 Hz, 1H), 6.59 (br d, J=2.81 Hz, 1H), 5.85-6.20 (m, 1H), 4.93-5.09 (m, 2H), 4.58-4.83 (m, 3H), 3.80-4.12 (m, 3H), 3.59 (br dd, J=4.28, 13.08 Hz, 1H), 3.12-3.34 (m, 6H), 2.82-2.96 (m, 2H).

Compound 160: N10-(3-cyano-4-fluorophenyl)-N4-(2,2-difluoroethyl)-N4,2-dimethyl-1-oxo-1,4,5,8,9,11-hexahydropyrido[4',3':3,4]pyrazolo[5,1-d][1,2,5]oxadiazepine-4,10(2H)-dicarboxamide LCMS [M+1]: 506. $^1$H NMR (400 MHz, CHLOROFORM-d) δ 7.77 (dd, J=2.76, 5.40 Hz, 1H), 7.54-7.63 (m, 1H), 7.14 (t, J=8.72 Hz, 1H), 6.71 (s, 1H), 5.86-6.22 (m, 1H), 4.95-5.10 (m, 2H), 4.73-4.84 (m, 1H), 4.57-4.69 (m, 2H), 3.78-4.09 (m, 3H), 3.47-3.68 (m, 1H), 3.14-3.36 (m, 6H), 2.81-2.95 (m, 2H).

Compound 161: N10-(3-cyano-2,4-difluorophenyl)-N4-(2,2-difluoroethyl)-N4,2-dimethyl-1-oxo-1,4,5,8,9,11-hexahydropyrido[4',3':3,4]pyrazolo[5,1-d][1,2,5]oxadiazepine-4,10(2H)-dicarboxamide LCMS [M+1]: 524. $^1$H NMR (400 MHz, CHLOROFORM-d) δ 8.28 (dt, J=5.90, 9.10 Hz, 1H), 7.02 (ddd, J=1.69, 8.00, 9.51 Hz, 1H), 6.63 (d, J=2.51 Hz, 1H), 5.83-6.20 (m, 1H), 4.95-5.10 (m, 2H), 4.58-4.85 (m, 3H), 3.79-4.09 (m, 3H), 3.52-3.69 (m, 1H), 3.13-3.34 (m, 6H), 2.79-2.97 (m, 2H).

Compound 162: -(acetamidomethyl)-N-(3-chloro-4-fluoro-phenyl)-2-methyl-1-oxo-5,8,9,11-tetrahydro-4H-pyrido[2,3]pyrazolo[2,4-d][1,2,5]oxadiazepine-10-carboxamide A mixture of 4-(aminomethyl)-N-(3-chloro-4-fluoro-phenyl)-2-methyl-1-oxo-5,8,9,11-tetrahydro-4H-pyrido[2,3]pyrazolo[2,4-d][1,2,5]oxadiazepine-10-carboxamide (Compound 113, 80.00 mg, 189.20 μmol, 1.00 eq), TEA (95.72 mg, 946.00 μmol, 131.12 μL5.00 eq) in DCM (3.00 mL) was added acetyl acetate (77.26 mg, 756.80 μmol, 70.88 μL4.00 eq) dropwise at 0° C. under N$_2$, and then the mixture was stirred at 30° C. for 2 hour under N$_2$ atmosphere. LCMS showed the starting material was consumed completely, desired product was major. The mixture was poured into ice-water (10 mL) and stirred at 5 min. The aqueous phase was extracted with DCM (5 mL*2). The combined organic phase was washed with brine (20 mL), dried with anhydrous Na$_2$SO$_4$, filtered and concentrated in vacuum. The residue was purified by Prep-HPLC (FA) to give 4the title compound (48.00 mg, 102.22 μmol, 54.03% yield, 99% purity) as a white solid. LCMS: 465/467 [M+1]. $^1$H NMR (400 MHz, Acetone) δ 8.33-8.39 (m, 1H), 7.82-7.88 (m, 1H), 7.43-7.49 (m, 1H), 7.32-7.41 (m, 1H), 7.16 (t, J=9.10 Hz, 1H), 4.55-4.69 (m, 4H), 4.36 (s, 1H), 3.83 (s, 2H), 3.52-3.62 (m, 1H), 3.35-3.44 (m, 1H), 3.24 (s, 3H), 2.74-2.78 (m, 2H), 1.90 (s, 3H).

Compounds 163, 164, 165, and 166 were prepared by an analogous method.

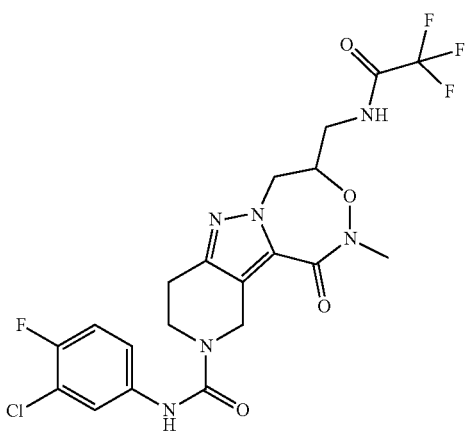

163

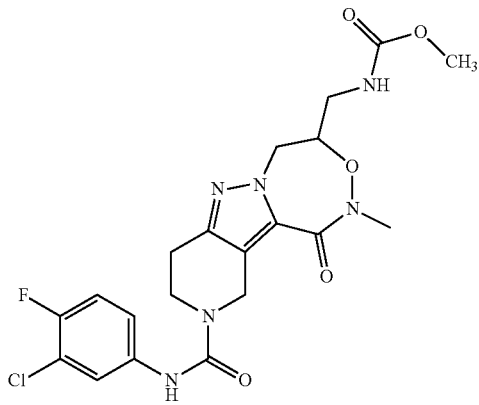

166

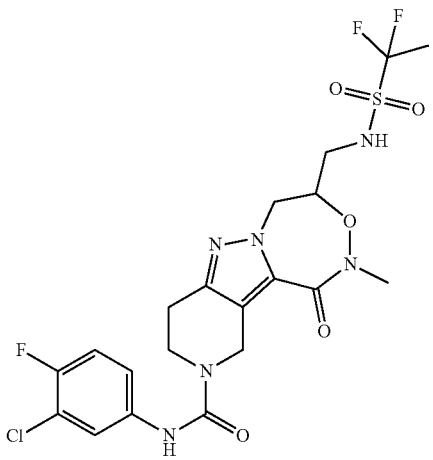

164

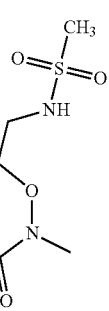

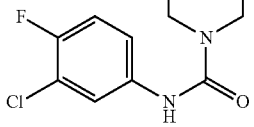

165

Compound 163: N-(3-chloro-4-fluorophenyl)-2-methyl-1-oxo-4-((2,2,2-trifluoroacetamido)methyl)-1,4,5,8,9,11-hexahydropyrido[4',3':3,4]pyrazolo[5,1-d][1,2,5]oxadiazepine-10(2H)-carboxamide LCMS: 519/520 [M+1]. $^1$H NMR (400 MHz, CHLOROFORM-d) δ 7.55-7.60 (m, 1H), 7.17-7.23 (m, 1H), 7.07 (s, 1H), 6.60-6.69 (m, 1H), 6.47-6.51 (m, 1H), 4.64-4.79 (m, 3H), 4.56-4.63 (m, 1H), 4.44-4.51 (m, 1H), 3.76-3.94 (m, 2H), 3.66 (s, 2H), 3.31 (s, 3H), 2.81-2.91 (m, 2H).

Compound 164: N-(3-chloro-4-fluorophenyl)-2-methyl-1-oxo-4-(((trifluoromethyl)sulfonamido)methyl)-1,4,5,8,9,11-hexahydropyrido[4',3':3,4]pyrazolo[5,1-d][1,2,5]oxadiazepine-10(2H)-carboxamide LCMS: 555/556 [M+1]. $^1$H NMR (400 MHz, CHLOROFORM-d) δ 7.54-7.60 (m, 1H), 7.17-7.24 (m, 1H), 7.06 (s, 1H), 6.58 (s, 1H), 4.67 (s, 4H), 4.43-4.49 (m, 1H), 3.76-3.95 (m, 2H), 3.39-3.51 (m, 2H), 3.31 (s, 3H), 2.81-2.89 (m, 2H), 2.81-2.89 (m, 2H).

Compound 165: N-(3-chloro-4-fluorophenyl)-2-methyl-4-(methylsulfonamidomethyl)-1-oxo-1,4,5,8,9,11-hexahydropyrido[4',3':3,4]pyrazolo[5,1-d][1,2,5]oxadiazepine-10(2H)-carboxamide LCMS: 501/502 [M+1]. $^1$H NMR (400 MHz, CHLOROFORM-d) δ 7.57-7.62 (m, 1H), 7.21-7.26 (m, 1H), 7.02-7.09 (m, 1H), 6.79-6.84 (m, 1H), 5.16-5.25 (m, 1H), 4.69 (s, 3H), 4.51-4.58 (m, 1H), 4.38-4.45 (m, 1H), 3.76-3.95 (m, 2H), 3.35-3.45 (m, 1H), 3.23-3.33 (m, 1H), 3.19 (s, 3H), 3.03 (s, 3H), 2.85 (br s, 2H).

Compound 166: methyl((10-((3-chloro-4-fluorophenyl)carbamoyl)-2-methyl-1-oxo-1,2,4,5,8,9,10,11-octahydropyrido[4',3':3,4]pyrazolo[5,1-d][1,2,5]oxadiazepin-4-yl)methyl)carbamate LCMS: 481/482 [M+1]. $^1$H NMR (400 MHz, CHLOROFORM-d) δ 7.55-7.61 (m, 1H), 7.17-7.23 (m, 1H), 7.03-7.09 (m, 1H), 6.53-6.59 (m, 1H), 4.95-5.06 (m, 1H), 4.50-4.76 (m, 4H), 4.38 (br dd, J=4.39, 14.05 Hz, 1H), 3.79-3.94 (m, 2H), 3.72 (s, 3H), 3.39-3.49 (m, 2H), 3.30 (s, 3H), 2.85 (s, 2H).

339

Compound 167_E1: (S*)-4-(acetamidomethyl)-N-(3-cyano-2,4-difluorophenyl)-2-methyl-1-oxo-1,4,5,8,9,11-hexahydropyrido[4',3':3,4]pyrazolo[5,1-d][1,2,5]oxadiazepine-10(2H)-carboxamide

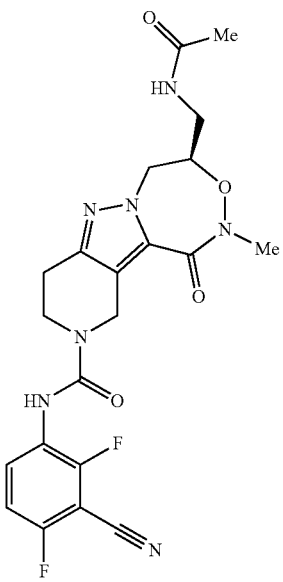 [SMILES: CC(=O)NC[C@@H]1Cn2nc3c(c2C(=O)N(C)O1)CN(C(=O)Nc1ccc(F)c(C#N)c1F)CC3]

Step 1. tert-butyl 4-(aminomethyl)-2-methyl-1-oxo-5,8,9,11-tetrahydro-4H-pyrido[2,3]pyrazolo[2,4-d][1,2,5]oxadiazepine-10-carboxylate. To a solution of tert-butyl 4-(azidomethyl)-2-methyl-1-oxo-1,4,5,8,9,11-hexahydropyrido[4',3':3,4]pyrazolo[5,1-d][1,2,5]oxadiazepine-10(2H)-carboxylate (Intermediate 28, 850.00 mg, 2.25 mmol, 1.00 eq) in THF (12.00 mL) and H$_2$O (2.00 mL) was added PPh$_3$ (1.18 g, 4.50 mmol, 2.00 eq). The mixture was stirred at 25° C. for 16 hr. LCMS showed the reactant consumed completely. The mixture was poured into water (20 mL) and extracted with ethyl acetate (20 mL*3), the organic layer was washed with brine (20 mL), dried over anhydrous Na$_2$SO$_4$, filtered and concentrated in vacuum. The crude was purified by column chromatography to afford the title compound (790.00 mg, 2.25 mmol, 99.92% yield) as white solid.

Step 2. tert-butyl 4-(acetamidomethyl)-2-methyl-1-oxo-5,8,9,11-tetrahydro-4H-pyrido[2,3]pyrazolo[2,4-d][1,2,5]oxadiazepine-10-carboxylate. To a solution of tert-butyl 4-(aminomethyl)-2-methyl-1-oxo-5,8,9,11-tetrahydro-4H-pyrido[2,3]pyrazolo[2,4-d][1,2,5]oxadiazepine-10-carboxylate (720.00 mg, 2.05 mmol, 1.00 eq) in DCM (10.00 mL) was added TEA (622.00 mg, 6.15 mmol, 852.05 µL 3.00 eq) and Ac$_2$O (251.01 mg, 2.46 mmol, 230.29 µL 1.20 eq). The mixture was stirred at 25° C. for 2 hr. TLC showed the reaction completed. The mixture was poured into water (20 mL), extracted with DCM (20 mL*3), the organic layer was washed with HCl (20 mL, 1N), brine (20 mL), dried over anhydrous Na$_2$SO$_4$ and concentrated in vacuum to afford the title compound (770.00 mg, 1.96 mmol, 95.66% yield) as white solid

340

Step 3. N-[(2-methyl-1-oxo-4,5,8,9,10,11-hexahydropyrido[2,3]pyrazolo[2,4-d][1,2,5]oxadiazepin-4-yl)methyl]acetamide. To a solution of tert-butyl 4-(acetamidomethyl)-2-methyl-1-oxo-5,8,9,11-tetrahydro-4H-pyrido[2,3]pyrazolo[2,4-d][1,2,5]oxadiazepine-10-carboxylate (450.00 mg, 1.14 mmol, 1.00 eq) in DCM (4.00 mL) was added TFA (3.08 g, 27.02 mmol, 2.00 mL, 23.70 eq) at 0° C. The mixture was stirred at 25° C. for 1 h. The mixture was concentrated under reduced pressure to afford the title compound (464.00 mg, 1.14 mmol, 99.92% yield, TFA) as yellow oil, which was used directly for the next step.

Step 4. (S*)-4-(acetamidomethyl)-N-(3-cyano-2,4-difluorophenyl)-2-methyl-1-oxo-1,4,5,8,9,11-hexahydropyrido[4',3':3,4]pyrazolo[5,1-d][1,2,5]oxadiazepine-10(2H)-carboxamide To a solution of (3R)-10-(2,2-difluoroethyl)-3-methyl-2,3,4,7,8,9-hexahydro-1H-pyrido[2,3]pyrazolo[2,4-b][1,4]diazepin-11-one (55.00 mg, 138.08 µmol, 1.00 eq, TFA) and Et3N (69.86 mg, 690.40 µmol, 95.70 µL 5.00 eq) in DCM (2.00 mL) was added phenyl N-(3-chloro-4-fluorophenyl)carbamate (36.68 mg, 138.08 µmol, 1.00 eq), the mixture was stirred at 25° C. for 16 h. The mixture was adjusted to neutral condition (pH~6) with FA and directly evaporated to give the residue. The residue was purified by prep-HPLC (FA) to afford the title compound (31.70 mg, 69.33 µmol, 50.21% yield, 99.7% purity) as white solid. LCMS: 474 [M+1]. LCMS: 474 [M+1]. $^1$H NMR (400 MHz, CHLOROFORM-d) δ 8.28 (dt, J=5.77, 9.10 Hz, 1H), 6.96-7.07 (m, 1H), 6.62 (d, J=2.64 Hz, 1H), 5.74 (br s, 1H), 4.68-4.82 (m, 2H), 4.59-4.66 (m, 1H), 4.50-4.56 (m, 1H), 4.36-4.57 (m, 1H), 3.76-3.96 (m, 2H), 3.42-3.59 (m, 2H), 3.31 (s, 3H), 2.81-2.92 (m, 2H), 2.02 (s, 3H).

* pure but unknown stereochemistry

Compounds 168, 169, 170, 171, 172, 173, 174, and 175 were prepared by an analogous manner to Compound 167.

168 E1

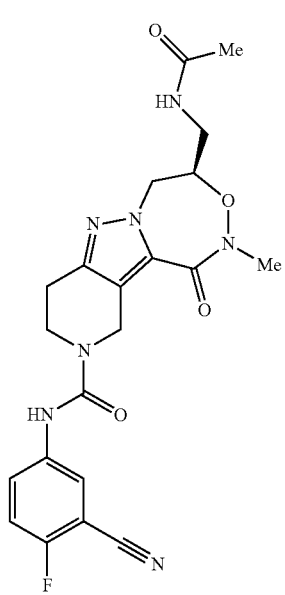

341
-continued
169 E1
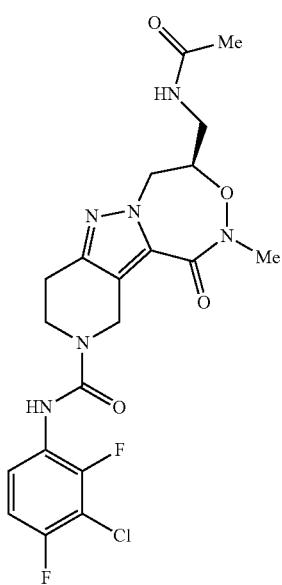
170 E1
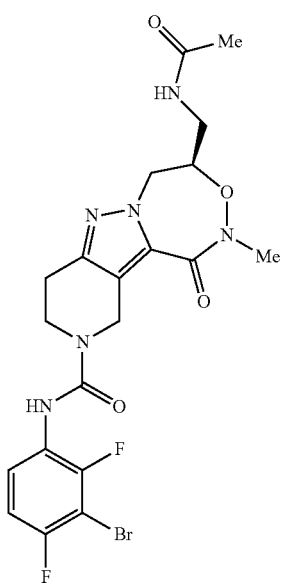
342
-continued
171 E1
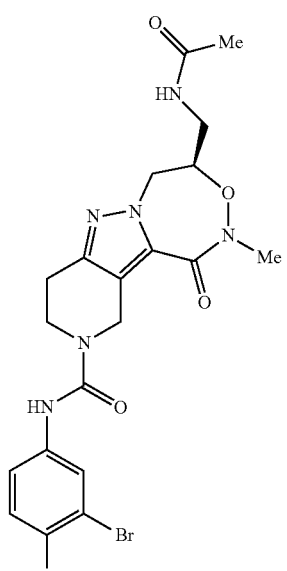
172 E1
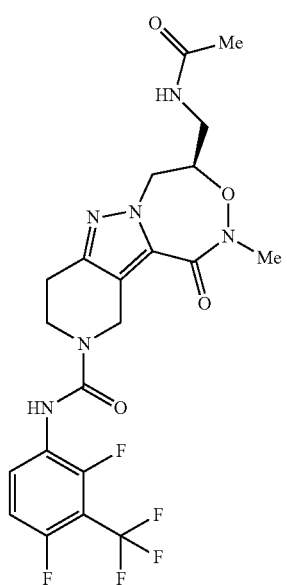

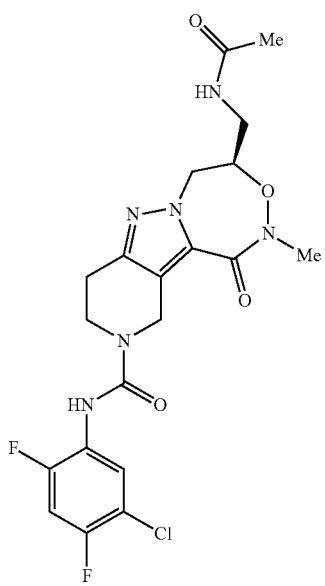

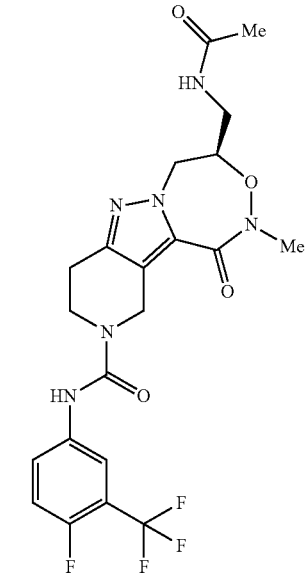

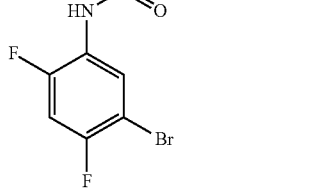

Compound 168_E1: (S*)-4-(acetamidomethyl)-N-(3-cyano-4-fluorophenyl)-2-methyl-1-oxo-1,4,5,8,9,11-hexahydropyrido[4',3':3,4]pyrazolo[5,1-d][1,2,5]oxadiazepine-10(2H)-carboxamide LCMS: 456 [M+1]. $^1$H NMR (400 MHz, CHLOROFORM-d) δ 7.77 (dd, J=2.76, 5.40 Hz, 1H), 7.59 (ddd, J=2.82, 4.49, 9.13 Hz, 1H), 7.10-7.19 (m, 1H), 6.69 (s, 1H), 5.75 (br s, 1H), 4.68-4.78 (m, 2H), 4.59-4.67 (m, 1H), 4.36-4.57 (m, 2H), 3.82-3.92 (m, 2H), 3.43-3.58 (m, 2H), 3.31 (s, 3H), 2.82-2.91 (m, 2H), 2.02 (s, 3H).

\* pure but unknown stereochemistry

Compound 169_E1: (S*)-4-(acetamidomethyl)-N-(3-chloro-2,4-difluorophenyl)-2-methyl-1-oxo-1,4,5,8,9,11-hexahydropyrido[4',3':3,4]pyrazolo[5,1-d][1,2,5]oxadiazepine-10(2H)-carboxamide LCMS: 483/485 [M+1]. $^1$H NMR (400 MHz, CHLOROFORM-d) δ 7.87 (dt, J=5.58, 8.94 Hz, 1H), 6.90-7.02 (m, 1H), 6.56 (d, J=2.76 Hz, 1H), 5.77 (br s, 1H), 4.68-4.81 (m, 2H), 4.62 (quin, J=5.46 Hz, 1H), 4.35-4.56 (m, 2H), 3.76-3.95 (m, 2H), 3.42-3.57 (m, 2H), 3.30 (s, 3H), 2.79-2.92 (m, 2H), 2.01 (s, 3H).

\* pure but unknown stereochemistry

Compound 170_E1: (S*)-4-(acetamidomethyl)-N-(3-bromo-2,4-difluorophenyl)-2-methyl-1-oxo-1,4,5,8,9,11-hexahydropyrido[4',3':3,4]pyrazolo[5,1-d][1,2,5]oxadiazepine-10(2H)-carboxamide LCMS: 527/529[M+1]. $^1$H NMR (400 MHz, CHLOROFORM-d) δ 7.94 (dt, J=5.65, 8.97 Hz, 1H), 6.94 (ddd, J=2.07, 7.72, 9.41 Hz, 1H), 6.56 (d, J=3.01 Hz, 1H), 5.73 (br s, 1H), 4.70-4.80 (m, 2H), 4.58-4.67 (m, 1H), 4.34-4.57 (m, 2H), 3.74-3.97 (m, 2H), 3.43-3.60 (m, 2H), 3.30 (s, 3H), 2.81-2.93 (m, 2H), 2.01 (s, 3H).

\* pure but unknown stereochemistry

Compound 171_E1: (S*)-4-(acetamidomethyl)-N-(3-bromo-4-fluorophenyl)-2-methyl-1-oxo-1,4,5,8,9,11-hexahydropyrido[4',3':3,4]pyrazolo[5,1-d][1,2,5]oxadiazepine-10(2H)-carboxamide LCMS: 509/511 [M+1]. $^1$H NMR (400 MHz, CHLOROFORM-d) δ 7.71 (dd, J=2.64, 6.02 Hz, 1H), 7.24-7.27 (m, 1H), 7.00-7.10 (m, 1H), 6.52 (s, 1H), 5.75 (br s, 1H), 4.67-4.78 (m, 2H), 4.59-4.66 (m, 1H), 4.35-4.57 (m, 2H), 3.76-3.94 (m, 2H), 3.44-3.61 (m, 2H), 3.30 (s, 3H), 2.80-2.91 (m, 2H), 2.01 (s, 3H).

* pure but unknown stereochemistry

Compound 172_E1: (S*)-4-(acetamidomethyl)-N-(2,4-difluoro-3-(trifluoromethyl)phenyl)-2-methyl-1-oxo-1,4,5,8,9,11-hexahydropyrido[4',3':3,4]pyrazolo[5,1-d][1,2,5]oxadiazepine-10(2H)-carboxamide LCMS: 517 [M+1]. $^1$H NMR (400 MHz, CHLOROFORM-d) δ 8.22 (dt, J=5.40, 8.91 Hz, 1H), 6.94-7.05 (m, 1H), 6.64 (br d, J=3.64 Hz, 1H), 5.75 (br s, 1H), 4.75 (d, J=1.51 Hz, 2H), 4.58-4.67 (m, 1H), 4.35-4.57 (m, 2H), 3.76-3.96 (m, 2H), 3.42-3.60 (m, 2H), 3.30 (s, 3H), 2.81-2.95 (m, 2H), 2.01 (s, 3H).

* pure but unknown stereochemistry

Compound 173_E1: (S*)-4-(acetamidomethyl)-N-(5-chloro-2,4-difluorophenyl)-2-methyl-1-oxo-1,4,5,8,9,11-hexahydropyrido[4',3':3,4]pyrazolo[5,1-d][1,2,5]oxadiazepine-10(2H)-carboxamide LCMS:483/485 [M+1]. $^1$H NMR (400 MHz, CHLOROFORM-d) δ 8.18 (t, J=8.03 Hz, 1H), 6.95 (dd, J=8.47, 10.60 Hz, 1H), 6.56 (d, J=3.14 Hz, 1H), 5.74 (br s, 1H), 4.69-4.77 (m, 2H), 4.59-4.66 (m, 1H), 4.35-4.56 (m, 2H), 3.74-3.96 (m, 2H), 3.43-3.58 (m, 2H), 3.30 (s, 3H), 2.82-2.92 (m, 2H), 2.01 (s, 3H).

* pure but unknown stereochemistry

Compound 174_E1: (S*)-4-(acetamidomethyl)-N-(5-bromo-2,4-difluorophenyl)-2-methyl-1-oxo-1,4,5,8,9,11-hexahydropyrido[4',3':3,4]pyrazolo[5,1-d][1,2,5]oxadiazepine-10(2H)-carboxamide LCMS: 527/529 [M+1]. $^1$H NMR (400 MHz, CHLOROFORM-d) δ 8.27-8.36 (m, 1H), 6.94 (dd, J=7.91, 10.79 Hz, 1H), 6.56 (br d, J=3.14 Hz, 1H), 5.76 (br s, 1H), 4.73 (s, 2H), 4.62 (quin, J=5.43 Hz, 1H), 4.35-4.56 (m, 2H), 3.74-3.97 (m, 2H), 3.42-3.57 (m, 2H), 3.30 (s, 3H), 2.80-2.93 (m, 2H), 2.01 (s, 3H).

* pure but unknown stereochemistry

Compound 175_E1: (S*)-4-(acetamidomethyl)-N-(4-fluoro-3-(trifluoromethyl)phenyl)-2-methyl-1-oxo-1,4,5,8,9,11-hexahydropyrido[4',3':3,4]pyrazolo[5,1-d][1,2,5]oxadiazepine-10(2H)-carboxamide LCMS: 499 [M+1]. $^1$H NMR (400 MHz, CHLOROFORM-d) δ 7.67 (dd, J=2.76, 6.02 Hz, 1H), 7.54-7.62 (m, 1H), 7.13 (t, J=9.41 Hz, 1H), 6.66 (s, 1H), 5.76 (br s, 1H), 4.70-4.78 (m, 2H), 4.58-4.68 (m, 1H), 4.36-4.57 (m, 2H), 3.79-3.94 (m, 2H), 3.45-3.57 (m, 2H), 3.30 (s, 3H), 2.80-2.92 (m, 2H), 2.01 (s, 3H).

* pure but unknown stereochemistry

Compound 176_D1: (4S*,9R)-4-(acetamidomethyl)-N-(3-cyano-4-fluorophenyl)-2,9-dimethyl-1-oxo-1,4,5,8,9,11-hexahydropyrido[4',3':3,4]pyrazolo[5,1-d][1,2,5]oxadiazepine-10(2H)-carboxamide

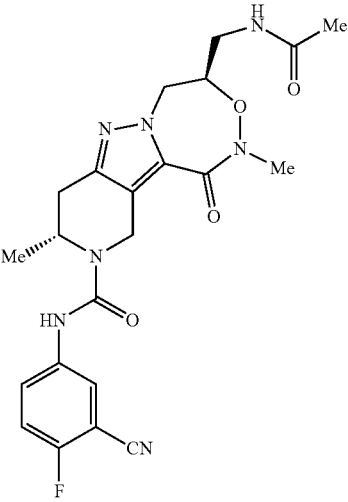 [SMILES: CC(=O)NC[C@@H]1Cn2nc3c(c2C(=O)N(C)O1)CN(C(=O)Nc1ccc(F)c(C#N)c1)[C@H](C)C3]

Step 1. tert-butyl(9R)-4-(aminomethyl)-2,9-dimethyl-1-oxo-5,8,9,11-tetrahydro-4H-pyrido[2,3]pyrazolo[2,4-d][1,2,5]oxadiazepine-10-carboxylate. A mixture of tert-butyl (9R)-4-(azidomethyl)-2,9-dimethyl-1-oxo-1,4,5,8,9,11-hexahydropyrido[4',3':3,4]pyrazolo[5,1-d][1,2,5]oxadiazepine-10(2H)-carboxylate (Intermediate 29, 1.06 g, 2.71 mmol, 1.00 eq), PPh$_3$ (1.42 g, 5.42 mmol, 2.00 eq) in THF (12.00 mL) and H$_2$O (2.00 mL) was degassed and purged with N$_2$ for 3 times, and then the mixture was stirred at 30° C. for 16 hour under N$_2$ atmosphere. LCMS showed the starting material was consumed completely, desired product was major. The mixture was concentrated in vacuum. The residue was purified by column chromatography (SiO$_2$, Petroleum ether/Ethyl acetate=100/1 to 0:1) to give the title compound (827.00 mg, 2.20 mmol, 81.00% yield, 97% purity) as a white solid. LCMS: 366 [M+1]

Step 2. Preparation of tert-butyl (9R)-4-(acetamidomethyl)-2,9-dimethyl-1-oxo-5,8,9,11-tetrahydro-4H-pyrido[2,3]pyrazolo[2,4-d][1,2,5]oxadiazepine-10-carboxylate. A mixture of tert-butyl(9R)-4-(aminomethyl)-2,9-dimethyl-1-oxo-5,8,9,11-tetrahydro-4H-pyrido[2,3]pyrazolo[2,4-d][1,2,5]oxadiazepine-10-carboxylate (250.00 mg, 684.13 μmol, 1.00 eq), TEA (346.13 mg, 3.42 mmol, 474.16 μL5.00 eq) in DCM (5.00 mL) was added Ac$_2$O (279.37 mg, 2.74 mmol, 256.30 μL4.00 eq) dropwise at 0° C. under N$_2$, and then the mixture was stirred at 30° C. for 2 hour under N$_2$ atmosphere. LCMS showed the starting material was consumed completely, desired product was major. The mixture was poured into water (10 mL) and stirred at 5 min. The aqueous phase was extracted with DCM (5 mL*3). The combined organic phase was washed with brine (10 mL), dried with anhydrous Na$_2$SO$_4$, filtered and concentrated in vacuum to give the title compound (270.00 mg, crude) as a white solid. LCMS: 408 [M+1].

Step 3. (4S*,9R)-4-(acetamidomethyl)-N-(3-cyano-4-fluorophenyl)-2,9-dimethyl-1-oxo-1,4,5,8,9,11-hexahydropyrido[4',3':3,4]pyrazolo[5,1-d][1,2,5]oxadiazepine-10(2H)-carboxamide A solution of tert-butyl(9R)-4-(acetamidomethyl)-2,9-dimethyl-1-oxo-5,8,9,11-tetrahydro-4H-pyrido[2,3]pyrazolo[2,4-d][1,2,5]oxadiazepine-10-carboxylate (140.00 mg, 343.59 μmol, 1.00 eq) in DCM (2.00 mL) was added TFA (1.54 g, 13.51 mmol, 1.00 mL, 39.31 eq), and then the mixture was stirred at 30° C. for 1 hour. TLC showed the starting material was consumed completely and a new spot formed. The mixture was concentrated in vacuum to give N-[[(9R)-2,9-dimethyl-1-oxo-4,5,8,9,10,11-hexahydropyrido[2,3]pyrazolo[2,4-d][1,2,5]oxadiazepin-4-yl]methyl]acetamide (144.78 mg, 343.59 μmol, 100.00% yield, TFA) as a yellow oil, which was used directly for next step.

Step 4. (4S*,9R)-4-(acetamidomethyl)-N-(3-cyano-4-fluorophenyl)-2,9-dimethyl-1-oxo-1,4,5,8,9,11-hexahydropyrido[4',3':3,4]pyrazolo[5,1-d][1,2,5]oxadiazepine-10(2H)-carboxamide. A mixture of N-[[(9R)-2,9-dimethyl-1-oxo-4,5,8,9,10,11-hexahydropyrido[2,3]pyrazolo[2,4-d][1,2,5]oxadiazepin-4-yl]methyl]acetamide (70.00 mg, 166.12 μmol, 1.00 eq, TFA), phenyl N-(3-cyano-4-fluoro-phenyl)carbamate (42.57 mg, 166.12 μmol, 1.00 eq), TEA (50.43 mg, 498.36 μmol, 69.08 μL3.00 eq) in DCM (3.00 mL) was degassed and purged with $N_2$ for 3 times, and then the mixture was stirred at 30° C. for 16 hour under $N_2$ atmosphere. LCMS showed the starting material was consumed completely, desired product was major. The mixture was poured into water (10 mL) and stirred at 5 min. The aqueous phase was extracted with DCM (5 mL*3). The combined organic phase was washed with brine (10 mL), dried with anhydrous $Na_2SO_4$, filtered and concentrated in vacuum. The residue was purified by Prep-HPLC (FA) to give the title compound (30.00 mg, 61.98 μmol, 37.31% yield, 97% purity) as a white solid. LCMS: 470 [M+1] $^1$H NMR (400 MHz, CHLOROFORM-d) δ 8.04 (s, 1H), 7.77 (dd, J=2.76, 5.40 Hz, 1H), 7.56-7.63 (m, 1H), 7.14 (s, 1H), 6.67 (s, 1H), 5.74-5.86 (m, 1H), 5.06-5.22 (m, 1H), 4.77-4.87 (m, 1H), 4.62-4.70 (m, 1H), 4.49-4.59 (m, 2H), 4.39-4.47 (m, 1H), 3.50 (s, 2H), 3.31 (s, 3H), 2.97-3.07 (m, 1H), 2.66-2.75 (m, 1H), 2.01 (s, 3H), 1.20 (d, J=7.03 Hz, 3H).

* pure but unknown stereochemistry

Compound 176_D2: (4R*,9R)-4-(acetamidomethyl)-N-(3-cyano-4-fluorophenyl)-2,9-dimethyl-1-oxo-1,4,5,8,9,11-hexahydropyrido[4',3':3,4]pyrazolo[5,1-d][1,2,5]oxadiazepine-10(2H)-carboxamide

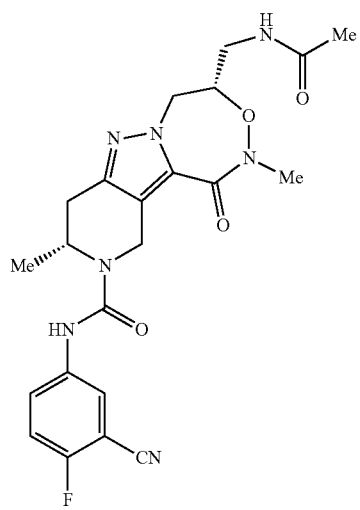

LCMS: 470 [M+1]. $^1$H NMR (400 MHz, CHLOROFORM-d) δ=7.78 (dd, J=2.69, 5.26 Hz, 1H), 7.56-7.66 (m, 1H), 7.14 (t, J=8.74 Hz, 1H), 6.78 (br s, 1H), 5.80 (br s, 1H), 5.14 (m, J=6.48 Hz, 1H), 4.90 (d, J=15.65 Hz, 1H), 4.63 (q, J=5.47 Hz, 1H), 4.51-4.58 (m, 1H), 4.37-4.46 (m, 2H), 3.50-3.57 (m, 2H), 3.31 (s, 3H), 3.04 (dd, J=5.87, 15.77 Hz, 1H), 2.68 (d, J=15.65 Hz, 1H), 2.02 (s, 3H), 1.18 (d, J=6.97 Hz, 3H).

* pure but unknown stereochemistry

Compound 177 was prepared in an analogous manner to 176.

Compound 177_D1: (4S*,9R)-4-(acetamidomethyl)-N-(4-fluoro-3-(trifluoromethyl)phenyl)-2,9-dimethyl-1-oxo-1,4,5,8,9,11-hexahydropyrido[4',3':3,4]pyrazolo[5,1-d][1,2,5]oxadiazepine-10(2H)-carboxamide

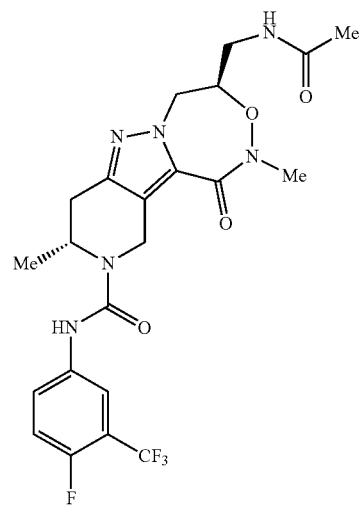

LCMS: 513 [M+1]. $^1$H NMR (400 MHz, CHLOROFORM-d) δ 7.64-7.73 (m, 1H), 7.56-7.62 (m, 1H), 7.10-7.17 (m, 1H), 6.55-6.65 (m, 1H), 5.69-5.83 (m, 1H), 5.05-5.22 (m, 1H), 4.78-4.88 (m, 1H), 4.62-4.69 (m, 1H), 4.55 (s, 2H), 4.39-4.46 (m, 1H), 3.51 (br d, J=4.77 Hz, 2H), 3.31 (s, 3H), 3.01 (s, 1H), 2.70 (d, J=15.69 Hz, 1H), 1.97-2.05 (m, 3H), 1.20 (d, J=6.90 Hz, 3H).

* pure but unknown stereochemistry

Compound 177_D2: (4R*,9R)-4-(acetamidomethyl)-N-(4-fluoro-3-(trifluoromethyl)phenyl)-2,9-dimethyl-1-oxo-1,4,5,8,9,11-hexahydropyrido[4',3':3,4]pyrazolo[5,1-d][1,2,5]oxadiazepine-10(2H)-carboxamide

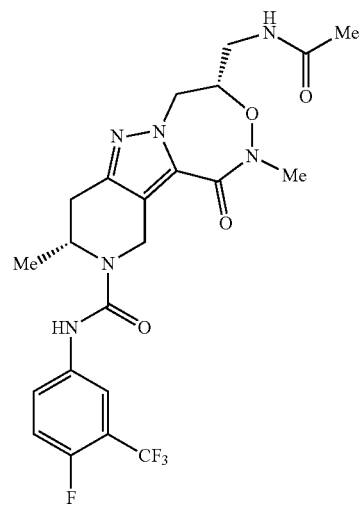 [SMILES: CC(=O)NC[C@H]1Cn2nc3c(c2C(=O)N(C)O1)CN(C(=O)Nc1ccc(F)c(C#N)c1)[C@H](C)C3]

LCMS: 513 [M+1]. ¹H NMR (400 MHz, CHLOROFORM-d) δ=7.69 (dd, J=2.69, 6.11 Hz, 1H), 7.57-7.63 (m, 1H), 7.13 (t, J=9.35 Hz, 1H), 6.68 (br s, 1H), 5.79 (br s, 1H), 5.15 (m, J=6.42 Hz, 1H), 4.91 (d, J=15.53 Hz, 1H), 4.59-4.67 (m, 1H), 4.51-4.58 (m, 1H), 4.36-4.48 (m, 2H), 3.47-3.60 (m, 2H), 3.31 (s, 3H), 3.04 (dd, J=5.87, 16.02 Hz, 1H), 2.67 (d, J=16.02 Hz, 1H), 2.02 (s, 3H), 1.18 (d, J=6.85 Hz, 3H).
* pure but unknown stereochemistry Compound 178_D1: (4S*,9R)—N-(3-cyano-4-fluorophenyl)-2,9-dimethyl-4-(methylsulfonamidomethyl)-1-oxo-1,4,5,8,9,11-hexahydropyrido[4',3':3,4]pyrazolo[5,1-d][1,2,5]oxadiazepine-10(2H)-carboxamide

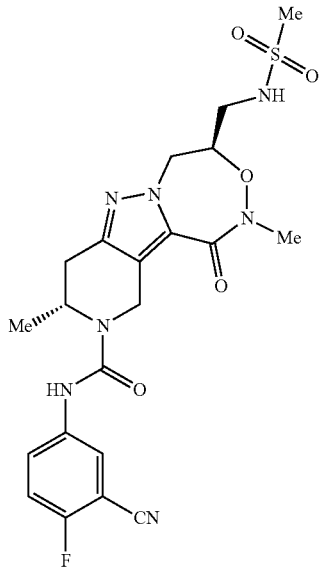

Step 1. Preparation of tert-butyl(9R)-4-(methanesulfonamidomethyl)-2,9-dimethyl-1-oxo-5,8,9,11-tetrahydro-4H-pyrido[2,3]pyrazolo[2,4-d][1,2,5]oxadiazepine-10-carboxylate. A mixture of tert-butyl (9R)-4-(aminomethyl)-2,9-dimethyl-1-oxo-1,4,5,8,9,11-hexahydropyrido[4',3':3,4]pyrazolo[5,1-d][1,2,5]oxadiazepine-10(2H)-carboxylate (Intermediate 30, 250.00 mg, 684.13 μmol, 1.00 eq), TEA (138.45 mg, 1.37 mmol, 189.66 μL 2.00 eq) in DCM (5.00 mL) was added MsCl (117.55 mg, 1.03 mmol, 79.43 μL 1.50 eq) dropwise at 0° C. under N₂, and then the mixture was stirred at 30° C. for 2 hour under N₂ atmosphere. LCMS showed the starting material was consumed completely, desired product was major. The mixture was poured into ice-water (10 mL) and stirred at 5 min. The aqueous phase was extracted with DCM (5 mL*2). The combined organic phase was washed with brine (20 mL), dried with anhydrous Na₂SO₄, filtered and concentrated in vacuum. The residue was purified by Prep-TLC (PE/EA=0/1) to give the title compound (218.00 mg, 471.86 μmol, 68.97% yield, 96% purity) as a white solid. LCMS: 444 [M+1]

Step 2. (4S*,9R)—N-(3-cyano-4-fluorophenyl)-2,9-dimethyl-4-(methylsulfonamidomethyl)-1-oxo-1,4,5,8,9,11-hexahydropyrido[4',3':3,4]pyrazolo[5,1-d][1,2,5]oxadiazepine-10(2H)-carboxamide. A mixture of tert-butyl(9R)-4-(methanesulfonamidomethyl)-2,9-dimethyl-1-oxo-5,8,9,11-tetrahydro-4H-pyrido[2,3]pyrazolo[2,4-d][1,2,5]oxadiazepine-10-carboxylate (109.00 mg, 245.76 μmol, 1.00 eq) in DCM (3.00 mL) was added TFA (2.31 g, 20.26 mmol, 1.50 mL, 82.44 eq), and then the mixture was stirred at 30° C. for 1 hour. TLC showed the starting material was consumed completely, a new spot appeared. The mixture was concentrated in vacuum to give N-[[(9R)-2,9-dimethyl-oxo-4,5,8,9,10,11-hexahydropyrido[2,3]pyrazolo[2,4-d][1,2,5]oxadiazepin-4-yl]methyl]methanesulfonamide (112.40 mg, 245.73 μmol, 99.99% yield, TFA) as a yellow oil, which was used directly for next step.

Step 3. 4S*,9R)—N-(3-cyano-4-fluorophenyl)-2,9-dimethyl-4-(methylsulfonamidomethyl)-1-oxo-1,4,5,8,9,11-hexahydropyrido[4',3':3,4]pyrazolo[5,1-d][1,2,5]oxadiazepine-10(2H)-carboxamide A mixture of N-[[(9R)-2,9-dimethyl-1-oxo-4,5,8,9,10,11-hexahydropyrido[2,3]pyrazolo[2,4-d][1,2,5]oxadiazepin-4-yl]methyl]methanesulfonamide (56.00 mg, 122.43 μmol, 1.00 eq, TFA), phenyl N-(3-cyano-4-fluoro-phenyl)carbamate (31.37 mg, 122.43 μmol, 1.00 eq), TEA (24.78 mg, 244.86 μmol, 33.95 μL 2.00 eq) in DCM (3.00 mL) was degassed and purged with N₂ for 3 times, and then the mixture was stirred at 30° C. for 16 hour under N₂ atmosphere. LCMS showed the starting material was consumed completely, desired product was major. The mixture was poured into water (10 mL) and stirred at 5 min. The aqueous phase was extracted with DCM (5 mL*3). The combined organic phase was washed with brine (10 mL), dried with anhydrous Na₂SO₄, filtered and concentrated in vacuum. The residue was purified by Prep-HPLC (FA) to give the title compound (33.30 mg, 65.87 μmol, 53.80% yield, 100% purity) as a white solid. LCMS: 506 [M+1] ¹H NMR (400 MHz, CHLOROFORM-d) δ 7.75-7.81 (m, 1H), 7.56-7.65 (m, 1H), 7.11-7.19 (m, 1H), 6.68-6.77 (m, 1H), 5.05-5.15 (m, 1H), 4.84-4.97 (m, 1H), 4.67-4.82 (m, 2H), 4.55 (br d, J=17.85 Hz, 3H), 3.31 (s, 5H), 3.01 (s, 4H), 2.64-2.73 (m, 1H), 1.19 (d, J=6.85 Hz, 3H).
* pure but unknown stereochemistry Compound 178_D2: (4R*,9R)—N-(3-cyano-4-fluorophenyl)-2,9-dimethyl-4-(methylsulfonamidomethyl)-1-oxo-1,4,5,8,9,11-hexahydropyrido[4',3':3,4]pyrazolo[5,1-d][1,2,5]oxadiazepine-10(2H)-carboxamide

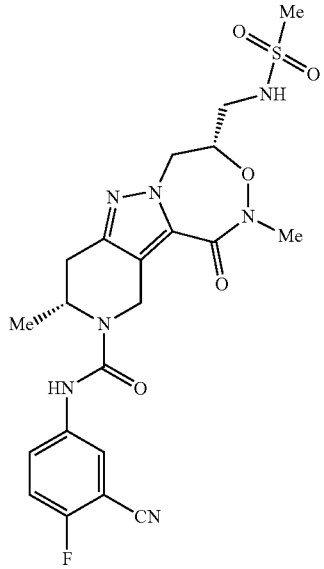

LCMS: 506 [M+1]. ¹H NMR (400 MHz, CHLOROFORM-d) δ 7.80 (dd, J=2.76, 5.52 Hz, 1H), 7.58-7.67 (m, 1H), 7.15 (t, J=8.72 Hz, 1H), 6.78 (s, 1H), 5.16 (br t, J=6.40 Hz, 1H), 4.91 (s, 2H), 4.55-4.74 (m, 2H), 4.36-4.50 (m, 2H), 3.36-3.43 (m, 2H), 3.33 (s, 3H), 2.97-3.11 (m, 4H), 2.69 (d, J=15.94 Hz, 1H), 1.20 (d, J=7.03 Hz, 3H).
* pure but unknown stereochemistry Compound 179 was prepared in an analogous manner to Compound 178.

Compound 179_D1: (4 S*,9R)—N-(4-fluoro-3-(trifluoromethyl)phenyl)-2,9-dimethyl-4-(methylsulfonamidomethyl)-1-oxo-1,4,5,8,9,11-hexahydropyrido[4',3':3,4]pyrazolo[5,1-d][1,2,5]oxadiazepine-10(2H)-carboxamide

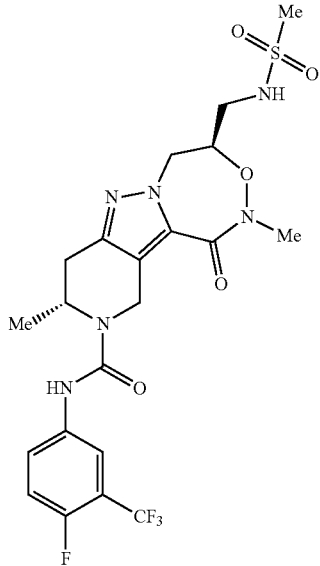 [SMILES: C[C@@H]1Cc2nn3c(c2CN1C(=O)Nc1ccc(F)c(C#N)c1)C(=O)N(C)O[C@H](CNS(C)(=O)=O)C3]

LCMS: 549 [M+1]. $^1$H NMR (400 MHz, CHLOROFORM-d) δ 7.65-7.71 (m, 1H), 7.56-7.62 (m, 1H), 7.14 (s, 1H), 6.60 (s, 1H), 5.06-5.18 (m, 1H), 4.76-4.87 (m, 2H), 4.66-4.75 (m, 1H), 4.49-4.63 (m, 2H), 4.44 (d, J=3.42 Hz, 1H), 3.28-3.42 (m, 5H), 3.00 (s, 4H), 2.65-2.74 (m, 1H), 1.20 (d, J=6.97 Hz, 3H).
* pure but unknown stereochemistry Compound 179_D2: (4R*,9R)—N-(4-fluoro-3-(trifluoromethyl)phenyl)-2,9-dimethyl-4-(methylsulfonamidomethyl)-1-oxo-1,4,5,8,9,11-hexahydropyrido[4',3':3,4]pyrazolo[5,1-d][1,2,5]oxadiazepine-10(2H)-carboxamide

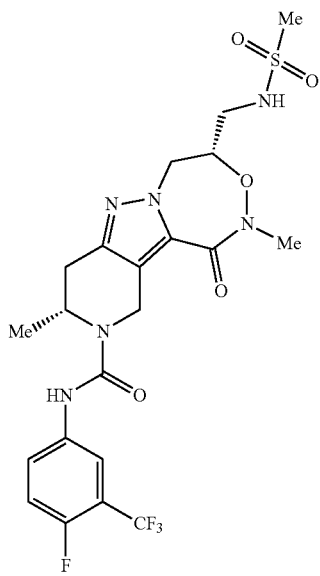 [SMILES: C[C@@H]1Cc2nn3c(c2CN1C(=O)Nc1ccc(F)c(C#N)c1)C(=O)N(C)O[C@@H](CNS(C)(=O)=O)C3]

LCMS: 549 [M+1]. $^1$H NMR (400 MHz, CHLOROFORM-d) δ 7.70 (dd, J=2.70, 6.21 Hz, 1H), 7.60 (br s, 1H), 7.15 (s, 1H), 6.69 (s, 1H), 5.17 (s, 1H), 4.93 (d, J=15.69 Hz, 1H), 4.86 (s, 1H), 4.56-4.74 (m, 2H), 4.34-4.50 (m, 2H), 3.36-3.44 (m, 2H), 3.33 (s, 3H), 3.01-3.10 (m, 4H), 2.69 (d, J=15.81 Hz, 1H), 1.19 (d, J=6.90 Hz, 3H).
* pure but unknown stereochemistry Compound 180_D1: methyl (((4S*,9R)-10-((3-cyano-4-fluorophenyl)carbamoyl)-2,9-dimethyl-1-oxo-1,2,4,5,8,9,10,11-octahydropyrido[4',3':3,4]pyrazolo[5,1-d][1,2,5]oxadiazepin-4-yl)methyl)carbamate

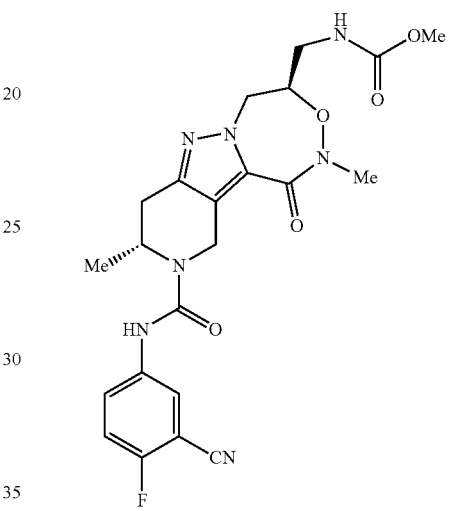

Step 1. tert-butyl(9R)-4-[(methoxycarbonylamino)methyl]-2,9-dimethyl-1-oxo-5,8,9,11-tetrahydro-4H-pyrido[2,3]pyrazolo[2,4-d][1,2,5]oxadiazepine-10-carboxylate. A mixture of tert-butyl (9R)-4-(aminomethyl)-2,9-dimethyl-1-oxo-1,4,5,8,9,11-hexahydropyrido[4',3':3,4]pyrazolo[5,1-d][1,2,5]oxadiazepine-10(2H)-carboxylate (Intermediate 30, 250.00 mg, 684.13 µmol, 1.00 eq), TEA (346.14 mg, 3.42 mmol, 474.16 µL 5.00 eq) in DCM (5.00 mL) was added methyl carbonochloridate (258.60 mg, 2.74 mmol, 211.97 µL 4.00 eq) dropwise at 0° C. under N$_2$, and then the mixture was stirred at 30° C. for 2 hour under N$_2$ atmosphere. LCMS showed the starting material was consumed completely, desired product was major. The mixture was poured into ice-water (10 mL) and stirred at 5 min. The aqueous phase was extracted with DCM (5 mL*2). The combined organic phase was washed with brine (20 mL), dried with anhydrous Na$_2$SO$_4$, filtered and concentrated in vacuum. The residue was purified by Prep-TLC to give the title compound (180.00 mg, 412.32 µmol, 60.27% yield, 97% purity) as a white solid. LCMS: 424 [M+1].

Step 2. methyl N-[[(9R)-10-[(3-cyano-4-fluoro-phenyl)carbamoyl]-2,9-dimethyl-1-oxo-5,8,9,11-tetrahydro-4H-pyrido[2,3]pyrazolo[2,4-d][1,2,5]oxadiazepin-4-yl]methyl]carbamate. A mixture of tert-butyl(9R)-4-[(methoxycarbonylamino)methyl]-2,9-dimethyl-1-oxo-5,8,9,11-tetrahydro-4H-pyrido[2,3]pyrazolo[2,4-d][1,2,5]oxadiazepine-10-carboxylate (90.00 mg, 212.53 µmol, 1.00 eq) in DCM (2.00 mL) was added TFA (1.54 g, 13.51 mmol, 1.00 mL, 63.55 eq), and then the mixture was stirred at 30° C. for 1 hour. TLC showed the starting material was consumed completely, a new spot appeared. The mixture was concentrated in vacuum to give methyl N-[[(9R)-2,9-dimethyl-1-oxo-4,5,8,9,10,11-hexahydropyrido[2,3]pyrazolo[2,4-d][1,2,5]oxadiazepin-4-yl]methyl]carbamate (92.95 mg, 212.52 µmol, 100.00% yield, TFA) as a yellow oil, which was used directly for next step.

Step 3. methyl (((4S*,9R)-10-((3-cyano-4-fluorophenyl)carbamoyl)-2,9-dimethyl-1-oxo-1,2,4,5,8,9,10,11-octahydropyrido[4',3':3,4]pyrazolo[5,1-d][1,2,5]oxadiazepin-4-yl)methyl)carbamate. A mixture of methyl N-[[(9R)-2,9-dimethyl-1-oxo-4,5,8,9,10,11-hexahydropyrido[2,3]pyrazolo[2,4-d][1,2,5]oxadiazepin-4-yl]methyl]carbamate (46.00 mg, 105.17 µmol, 1.00 eq, TFA), phenyl N-(3-cyano-4-fluoro-phenyl)carbamate (26.95 mg, 105.17 µmol, 1.00 eq), TEA (21.28 mg, 210.34 µmol, 29.15 µL 2.00 eq) in DCM (3.00 mL) was degassed and purged with N$_2$ for 3 times, and then the mixture was stirred at 30° C. for 16 hour under N$_2$ atmosphere. LCMS showed the starting material was consumed completely, desired product was major. The mixture was poured into water (10 mL) and stirred at 5 min. The aqueous phase was extracted with DCM (5 mL*3). The combined organic phase was washed with brine (10 mL), dried with anhydrous Na$_2$SO$_4$, filtered and concentrated in vacuum. The residue was purified by Prep-HPLC (FA) to give the title compound (36.40 mg, 74.23 µmol, 70.58% yield, 99% purity) as a white solid. LCMS: 486 [M+1]. $^1$H NMR (400 MHz, CHLOROFORM-d) δ 7.78 (dd, J=2.81, 5.38 Hz, 1H), 7.55-7.62 (m, 1H), 7.14 (s, 1H), 6.62 (s, 1H), 5.08-5.20 (m, 1H), 4.92-5.02 (m, 1H), 4.79 (s, 1H), 4.37-4.66 (m, 4H), 3.72 (s, 3H), 3.44 (br d, J=5.38 Hz, 2H), 3.31 (s, 3H), 2.98-3.07 (m, 1H), 2.66-2.74 (m, 1H), 1.19 (d, J=6.97 Hz, 3H).

* pure but unknown stereochemistry

Compound 180_D2: methyl (((4R*,9R)-10-((3-cyano-4-fluorophenyl)carbamoyl)-2,9-dimethyl-1-oxo-1,2,4,5,8,9,10,11-octahydropyrido[4',3':3,4]pyrazolo[5,1-d][1,2,5]oxadiazepin-4-yl)methyl)carbamate

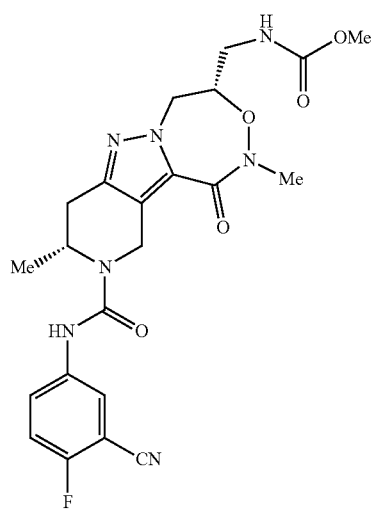 [SMILES: COC(=O)NC[C@H]1Cn2nc3c(c2C(=O)N(C)O1)CN(C(=O)Nc1ccc(F)c(C#N)c1)[C@H](C)C3]

LCMS: 486 [M+1]. $^1$H NMR (400 MHz, CHLOROFORM-d) δ 7.80 (dd, J=2.82, 5.46 Hz, 1H), 7.58-7.67 (m, 1H), 7.16 (t, J=8.66 Hz, 1H), 6.70 (s, 1H), 5.16 (br t, J=6.40 Hz, 1H), 5.00 (br s, 1H), 4.90 (d, J=15.56 Hz, 1H), 4.52-4.68 (m, 2H), 4.46 (br d, J=15.69 Hz, 2H), 3.73 (s, 3H), 3.42-3.57 (m, 2H), 3.33 (s, 3H), 3.00-3.10 (m, 1H), 2.70 (d, J=15.94 Hz, 1H), 1.20 (d, J=6.90 Hz, 3H).

* pure but unknown stereochemistry

Compound 181 was prepared in an analogous manner to Compound 180.

Compound 181_D 1: methyl(((4S*,9R)-10-((4-fluoro-3-(trifluoromethyl)phenyl)carbamoyl)-2,9-dimethyl-1-oxo-1,2,4,5,8,9,10,11-octahydropyrido[4',3':3,4]pyrazolo[5,1-d][1,2,5]oxadiazepin-4-yl)methyl)carbamate

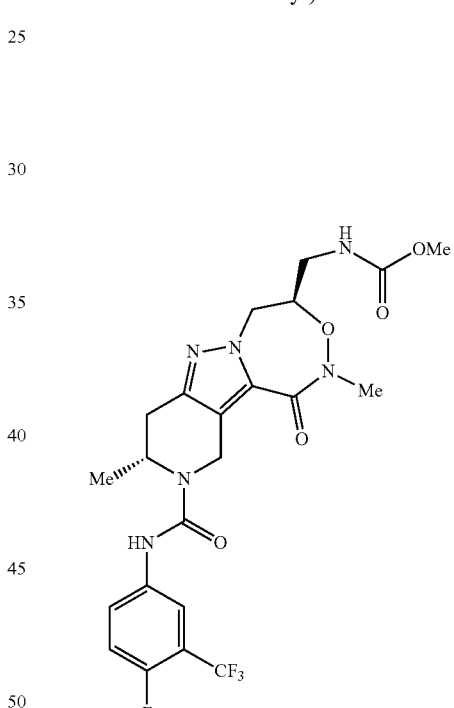

LCMS: 529 [M+1]. $^1$H NMR (400 MHz, CHLOROFORM-d) δ 7.68 (br s, 1H), 7.56-7.62 (m, 1H), 7.14 (s, 1H), 6.56 (s, 1H), 5.08-5.22 (m, 1H), 4.92-5.02 (m, 1H), 4.82 (d, J=15.65 Hz, 1H), 4.55 (s, 4H), 3.72 (s, 3H), 3.36-3.52 (m, 2H), 3.31 (s, 3H), 2.98-3.08 (m, 1H), 2.69 (d, J=15.89 Hz, 1H), 1.19 (d, J=6.97 Hz, 3H).

* pure but unknown stereochemistry

Compound 181_D2: methyl (((4R*,9R)-10-((4-fluoro-3-(trifluoromethyl)phenyl)carbamoyl)-2,9-dimethyl-1-oxo-1,2,4,5,8,9,10,11-octahydropyrido[4',3':3,4]pyrazolo[5,1-d][1,2,5]oxadiazepin-4-yl)methyl)carbamate

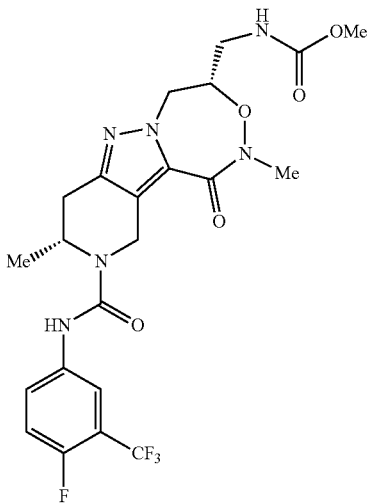 [SMILES: COC(=O)NC[C@H]1Cn2nc3c(c2C(=O)N(C)O1)CN(C(=O)Nc1ccc(F)c(C(F)(F)F)c1)[C@H](C)C3]

LCMS: 529 [M+1]. $^1$H NMR (400 MHz, CHLOROFORM-d) δ 7.70 (dd, J=2.70, 6.21 Hz, 1H), 7.58-7.65 (m, 1H), 7.15 (s, 1H), 6.63 (s, 1H), 5.11-5.23 (m, 1H), 4.95-5.04 (m, 1H), 4.91 (d, J=15.56 Hz, 1H), 4.58 (br d, J=13.68 Hz, 2H), 4.47 (br d, J=15.56 Hz, 2H), 3.73 (s, 3H), 3.48 (br d, J=5.27 Hz, 2H), 3.33 (s, 3H), 3.01-3.11 (m, 1H), 2.70 (d, J=15.69 Hz, 1H), 1.19 (d, J=6.90 Hz, 3H).

* pure but unknown stereochemistry

Compound 182_D1: (4S*,9R)-4-(((2,2-difluoroethyl)amino)methyl)-N-(4-fluoro-3-(trifluoromethyl)phenyl)-2,9-dimethyl-1-oxo-1,4,5,8,9,11-hexahydropyrido[4',3':3,4]pyrazolo[5,1-d][1,2,5]oxadiazepine-10(2H)-carboxamide

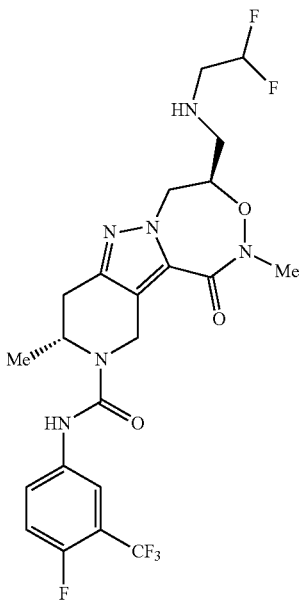 [SMILES: C[C@@H]1Cc2nn3c(c2CN1C(=O)Nc1ccc(F)c(C(F)(F)F)c1)C(=O)N(C)O[C@H](CNCC(F)F)C3]

Step 1. tert-butyl (9R)-2,9-dimethyl-4-(methylsulfonyloxymethyl)-1-oxo-5,8,9,11-tetrahydro-4H-pyrido[2,3]pyrazolo[2,4-d][1,2,5]oxadiazepine-10-carboxylate. A mixture of tert-butyl (9R)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxylate (Intermediate 18, 3.00 g, 8.19 mmol, 1.00 eq), TEA (4.14 g, 40.95 mmol, 5.67 mL, 5.00 eq) in DCM (40.00 mL) was added MsCl (3.75 g, 32.76 mmol, 2.53 mL, 4.00 eq) dropwise at 0° C. under N$_2$, and then the mixture was stirred at 30° C. for 3 hour under N$_2$ atmosphere. TLC showed the starting material was consumed completely, a new spot appeared. The mixture was poured into ice-water (50 mL) and stirred at 5 min. The aqueous phase was extracted with DCM (40 mL*2). The combined organic phase was washed with brine (50 mL), dried with anhydrous Na$_2$SO$_4$, filtered and concentrated in vacuum. The residue was purified by column chromatography (SiO$_2$, Petroleum ether/Ethyl acetate=100/1 to 1:2) to give the title compound (3.40 g, 7.34 mmol, 89.66% yield, 96% purity) as a white solid. LCMS: 445 [M+1].

Step 2. tert-butyl (9R)-4-[(2,2-difluoroethylamino)methyl]-2,9-dimethyl-1-oxo-5,8,9,11-tetrahydro-4H-pyrido[2,3]pyrazolo[2,4-d][1,2,5]oxadiazepine-10-carboxylate. To a solution of tert-butyl (9R)-2,9-dimethyl-4-(methylsulfonyloxymethyl)-1-oxo-5,8,9,11-tetrahydro-4H-pyrido[2,3]pyrazolo[2,4-d][1,2,5]oxadiazepine-10-carboxylate (1.10 g, 2.47 mmol, 1.00 eq) in DMSO (12.00 mL) was added 2,2-difluoroethanamine (12.01 g, 148.20 mmol, 60.00 eq), the mixture was stirred at 90° C. for 72 h. LCMS showed that the reactant was remained. the mixture was stirred at 90° C. for 24 h. The mixture was diluted with H$_2$O 30 mL and extracted with EtOAc (30 mL*2). The combined organic layers were washed with brine (30 mL*3), dried over Na$_2$SO$_4$, filtered and concentrated under reduced pressure. The residue was purification by column chromatography (PE:EtOAc=1:2) to afford the title compound (510.00 mg, 1.01 mmol, 40.87% yield, 85% purity) as yellow oil.

Step 3. (9R)-4-[(2,2-difluoroethylamino)methyl]-2,9-dimethyl-4,5,8,9,10,11-hexahydropyrido[2,3]pyrazolo[2,4-d][1,2,5]oxadiazepin-1-one. To a solution of tert-butyl (9R)-4-[(2,2-difluoroethylamino)methyl]-2,9-dimethyl-1-oxo-5,8,9,11-tetrahydro-4Hpyrido[2,3]pyrazolo[2,4-d][1,2,5]oxadiazepine-10-carboxylate (220.00 mg, 512.27 µmol, 1.00 eq) in DCM (8.00 mL) was added TFA (3.08 g, 27.01 mmol, 2.00 mL, 52.73 eq), the reaction mixture was stirred at 25° C. for one hour. TLC indicated starting material was consumed completely. Removed the solvent on a rotary evaporator to give the title compound (220.00 mg, crude, TFA) as yellow oil, used in the next step directly without purification.

Step 3. (4S*,9R)-4-(((2,2-difluoroethyl)amino)methyl)-N-(4-fluoro-3-(trifluoromethyl)phenyl)-2,9-dimethyl-1-oxo-1,4,5,8,9,11-hexahydropyrido[4',3':3,4]pyrazolo[5,1-d][1,2,5]oxadiazepine-10(2H)-carboxamide. To a mixture of (9R)-4-[(2,2-difluoroethylamino)methyl]-2,9-dimethyl-4,5,8,9,10,11-hexahydropyrido[2,3]pyrazolo[2,4-d][1,2,5]oxadiazepin-1-one (55.00 mg, 124.05 μmol, 1.00 eq, TFA) in DCM (2.00 mL) was added TEA (50.21 mg, 496.20 μmol, 68.78 μL 4.00 eq), followed by phenyl N-[4-fluoro-3-(trifluoromethyl)phenyl] carbamate (37.12 mg, 124.05 μmol, 1.00 eq), the reaction mixture was stirred at 25° C. for 4 hours. Several new peaks were shown on LCMS and 40% of desired compound was detected. Removed the solvent on a rotary evaporator. The residue was purified by prep-HPLC (HCl) to give the title compound (15.00 mg, 27.22 μmol, 21.95% yield, 97% purity) as white solid. LCMS: 571 [M+1]. $^1$H NMR (400 MHz, DMSO-$d_6$) δ 9.03-9.10 (m, 1H), 9.06 (s, 1H), 7.88-7.96 (m, 1H), 7.75-7.84 (m, 1H), 7.41 (d, J=9.91 Hz, 1H), 6.23-6.62 (m, 1H), 4.94-5.10 (m, 2H), 4.82-4.93 (m, 1H), 4.70 (dd, J=6.09, 14.87 Hz, 1H), 4.44 (dd, J=4.45, 14.87 Hz, 1H), 4.18 (d, J=17.19 Hz, 1H), 3.47-3.62 (m, 2H), 3.29 (s, 3H), 3.14-3.24 (m, 2H), 2.86-2.96 (m, 1H), 2.57-2.69 (m, 2H), 2.30-2.36 (m, 1H), 1.11 (d, J=6.90 Hz, 3H).

\* pure but unknown stereochemistry

Compound 182_D2: (4R\*,9R)-4-(((2,2-difluoroethyl)amino)methyl)-N-(4-fluoro-3-(trifluoromethyl)phenyl)-2,9-dimethyl-1-oxo-1,4,5,8,9,11-hexahydropyrido[4',3':3,4]pyrazolo[5,1-d][1,2,5]oxadiazepine-10(2H)-carboxamide

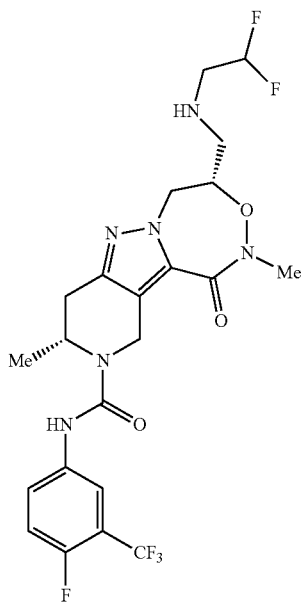 [SMILES: C[C@@H]1Cc2nn3c(c2CN1C(=O)Nc1ccc(F)c(C(F)(F)F)c1)C(=O)N(C)O[C@@H](CNCC(F)F)C3]

LCMS: 535 [M+1]. $^1$H NMR (400 MHz, METHANOL-$d_4$) δ=7.78 (dd, J=2.57, 6.34 Hz, 1H), 7.62-7.68 (m, 1H), 7.24 (t, J=9.66 Hz, 1H), 6.19-6.50 (m, 1H), 5.13 (d, J=16.81 Hz, 1H), 4.95 (br d, J=6.78 Hz, 2H), 4.74 (dd, J=6.02, 14.93 Hz, 1H), 4.46 (dd, J=3.83, 15.00 Hz, 1H), 4.31 (d, J=16.81 Hz, 1H), 3.67 (dt, J=2.89, 15.50 Hz, 2H), 3.55 (dd, J=2.64, 13.68 Hz, 1H), 3.38-3.44 (m, 1H), 3.36 (s, 3H), 3.05 (dd, J=5.90, 16.06 Hz, 1H), 2.68 (d, J=15.94 Hz, 1H), 1.19 (d, J=6.90 Hz, 3H).

\* pure but unknown stereochemistry

Compounds 183, 184, and 185 were prepared in an analogous manner to Compound 182.

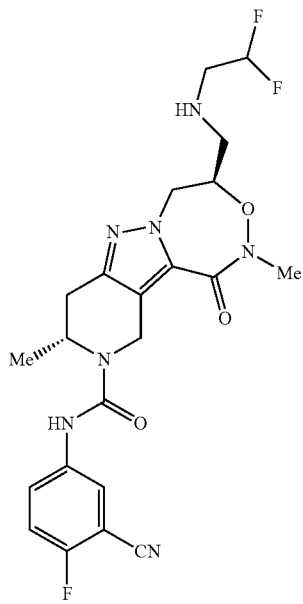

183 D1

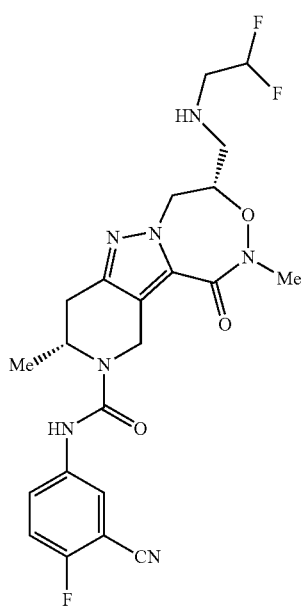

183 D2

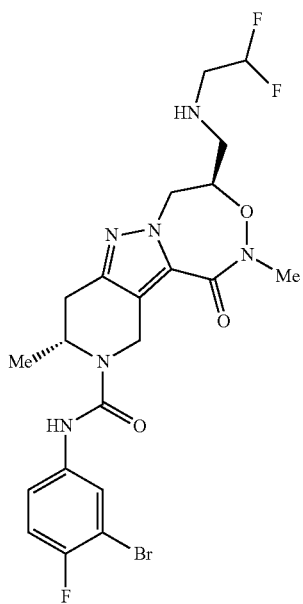
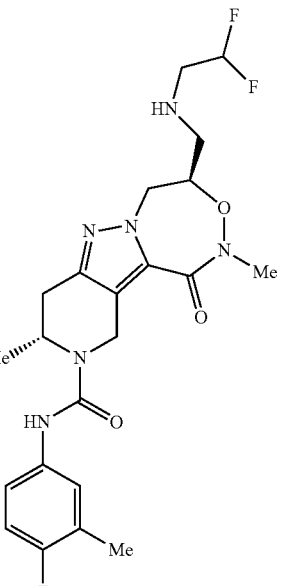
184 D1
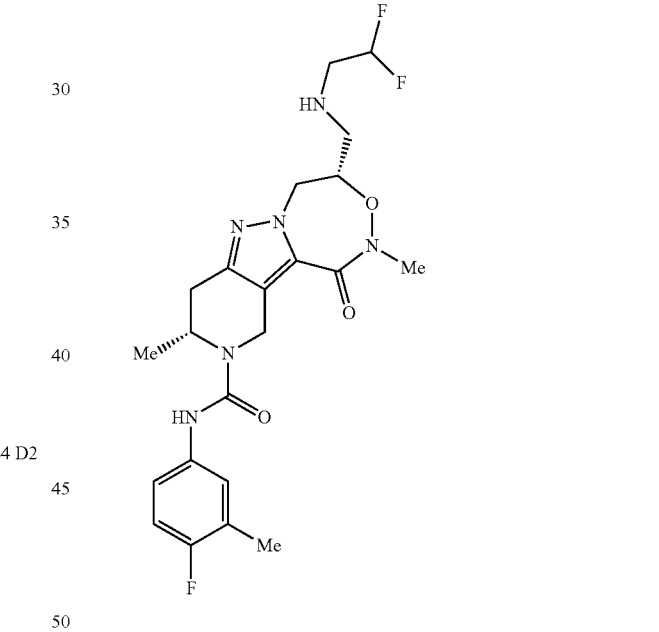
185 D1
185 D2
184 D2
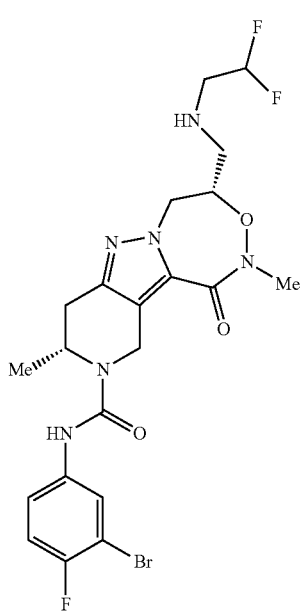
Compound 183_D1: (4S*,9R)—N-(3-cyano-4-fluorophenyl)-4-(((2,2-difluoroethyl)amino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide
LCMS: 528 [M+1]. $^1$H NMR (400 MHz, DMSO-d$_6$) δ 9.08 (s, 1H), 7.91-7.98 (m, 1H), 7.76-7.84 (m, 1H), 7.43 (t, J=9.10 Hz, 1H), 6.24-6.62 (m, 1H), 5.02 (br d, J=17.19 Hz, 2H), 4.82-4.92 (m, 1H), 4.68 (br d, J=5.90 Hz, 1H), 4.40-4.49 (m, 1H), 4.18 (br d, J=17.32 Hz, 1H), 3.50-3.64 (m, 1H), 3.29 (s, 3H), 3.13-3.24 (m, 2H), 2.85-2.95 (m, 1H), 2.58-2.69 (m, 2H), 2.31-2.34 (m, 1H), 1.07-1.15 (m, 3H).
* pure but unknown stereochemistry Compound 183_D2: (4R*,9R)—N-(3-cyano-4-fluorophenyl)-4-(((2,2-difluoroethyl)amino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS: 492 [M+1]. ¹H NMR (400 MHz, CHLOROFORM-d) δ=7.79 (dd, J=2.76, 5.40 Hz, 1H), 7.60 (ddd, J=2.82, 4.52, 9.10 Hz, 1H), 7.14 (t, J=8.72 Hz, 1H), 6.74 (s, 1H), 5.69-6.02 (m, 1H), 5.10-5.20 (m, 1H), 4.89 (d, J=15.56 Hz, 1H), 4.51-4.60 (m, 2H), 4.35-4.48 (m, 2H), 3.32 (s, 3H), 2.98-3.11 (m, 4H), 2.87 (dd, J=4.45, 12.99 Hz, 1H), 2.69 (d, J=16.19 Hz, 1H), 1.19 (d, J=6.90 Hz, 3H)
* pure but unknown stereochemistry Compound 184_D1: (4S*,9R)—N-(3-bromo-4-fluorophenyl)-4-(((2,2-difluoroethyl)amino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS: 581 [M+1]. ¹H NMR (400 MHz, DMSO-d₆) δ 8.89 (s, 1H), 7.85 (dd, J=2.64, 6.40 Hz, 1H), 7.42-7.50 (m, 1H), 7.26 (t, J=8.85 Hz, 1H), 6.23-6.61 (m, 1H), 5.01 (br d, J=17.07 Hz, 2H), 4.81-4.90 (m, 1H), 4.68 (br d, J=6.15 Hz, 1H), 4.46 (br d, J=4.27 Hz, 1H), 4.16 (d, J=17.19 Hz, 1H), 3.56 (br s, 2H), 3.29 (s, 3H), 3.17-3.23 (m, 2H), 2.85-2.95 (m, 1H), 2.65-2.70 (m, 1H), 2.56-2.63 (m, 1H), 2.28-2.36 (m, 1H), 1.10 (d, J=6.78 Hz, 3H)
* pure but unknown stereochemistry Compound 184_D2: (4R*,9R)—N-(3-bromo-4-fluorophenyl)-4-(((2,2-difluoroethyl)amino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS: 545/547 [M+1]. ¹H NMR (400 MHz, CHLOROFORM-d) δ=7.73 (dd, J=2.57, 6.09 Hz, 1H), 7.29 (br d, J=3.01 Hz, 1H), 7.05 (t, J=8.53 Hz, 1H), 6.57 (br s, 1H), 5.69-6.02 (m, 1H), 5.09-5.20 (m, 1H), 4.87 (d, J=15.56 Hz, 1H), 4.31-4.62 (m, 4H), 3.32 (s, 3H), 2.96-3.13 (m, 4H), 2.86 (dd, J=4.33, 12.99 Hz, 1H), 2.68 (d, J=15.81 Hz, 1H), 1.18 (d, J=6.90 Hz, 3H)
* pure but unknown stereochemistry Compound 185_D1: (4S*,9R)-4-(((2,2-difluoroethyl)amino)methyl)-N-(4-fluoro-3-methylphenyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS: 517 [M+1]. ¹H NMR (400 MHz, METHANOL-d₄) δ 7.18-7.24 (m, 1H), 7.13 (br d, J=4.40 Hz, 1H), 6.93 (t, J=9.11 Hz, 1H), 6.32 (s, 1H), 4.95-5.05 (m, 2H), 4.90-4.93 (m, 2H), 4.70-4.80 (m, 1H), 4.31-4.52 (m, 2H), 3.50-3.70 (m, 3H), 3.35 (s, 3H), 2.94-3.06 (m, 1H), 2.59-2.76 (m, 1H), 2.23 (d, J=1.83 Hz, 3H), 1.22 (d, J=6.85 Hz, 3H)
* pure but unknown stereochemistry Compound 185_D2: (4R*,9R)-4-(((2,2-difluoroethyl)amino)methyl)-N-(4-fluoro-3-methylphenyl)-2,9-dimethyl-1-oxo-1,4,5,8,9,11-hexahydropyrido[4',3':3,4]pyrazolo[5,1-d][1,2,5]oxadiazepine-10(2H)-carboxamide LCMS: 481 [M+1]. ¹H NMR (400 MHz, CHLOROFORM-d) δ=7.26 (br s, 1H), 7.09-7.15 (m, 1H), 6.93 (t, J=9.03 Hz, 1H), 6.41 (s, 1H), 5.68-6.02 (m, 1H), 5.15 (quin, J=6.37 Hz, 1H), 4.87 (d, J=15.69 Hz, 1H), 4.50-4.61 (m, 2H), 4.31-4.48 (m, 2H), 3.31 (s, 3H), 2.96-3.12 (m, 4H), 2.86 (dd, J=4.33, 12.99 Hz, 1H), 2.67 (d, J=15.94 Hz, 1H), 2.26 (d, J=1.51 Hz, 3H), 1.17 (d, J=6.90 Hz, 3H)
* pure but unknown stereochemistry Compound 186_E1: (S*)—N-(3-cyano-2,4-difluorophenyl)-4-(((2,2-difluoroethyl)amino)methyl)-2-methyl-1-oxo-1,4,5,8,9,11-hexahydropyrido[4',3':3,4]pyrazolo[5,1-d][1,2,5]oxadiazepine-10(2H)-carboxamide

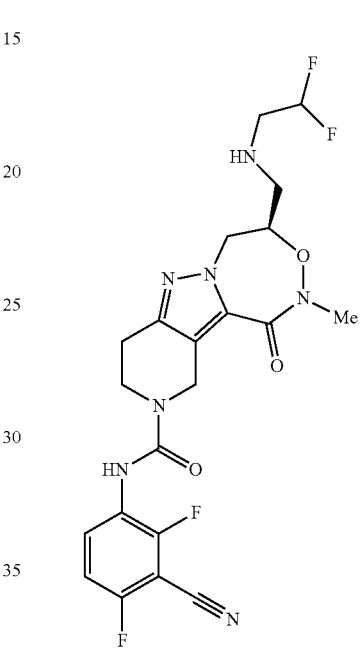

Step 1. tert-butyl 2-methyl-4-(methylsulfonyloxymethyl)-1-oxo-5,8,9,11-tetrahydro-4H-pyrido[2,3]pyrazolo[2,4-d][1,2,5]oxadiazepine-10-carboxylate. To a solution of tert-butyl 4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxylate (Intermediate 1, 500.00 mg, 1.42 mmol, 1.00 eq) in DCM (2.00 mL) was added TEA (358.95 mg, 3.55 mmol, 491.72 µL 2.50 eq) and MsCl (211.30 mg, 1.84 mmol, 142.77 µL 1.30 eq). Then the mixture was stirred 20° C. for 2 hr. TLC (Ethyl acetate) showed the reaction was complete. The reaction mixture was diluted with DCM (20 mL) and washed with brine (10 mL), dried over anhydrous Na₂SO₄ and concentrated in vacuum to give tert-butyl 2-methyl-4-(methylsulfonyloxymethyl)-1-oxo-5,8,9,11-tetrahydro-4H-pyrido[2,3]pyrazolo[2,4-d][1,2,5]oxadiazepine-10-carboxylate (600.00 mg, 1.39 mmol, 98.16% yield) was obtained as yellow solid, which was used in the next step without further purification.

Step 2. tert-butyl 4-[(2,2-difluoroethylamino)methyl]-2-methyl-1-oxo-5,8,9,11-tetrahydro-4H-pyrido[2,3]pyrazolo[2,4-d][1,2,5]oxadiazepine-10-carboxylate. To a solution of tert-butyl 2-methyl-4-(methylsulfonyloxymethyl)-1-oxo-5,8,9,11-tetrahydro-4H-pyrido[2,3]pyrazolo[2,4-d][1,2,5]oxadiazepine-10-carboxylate (640.00 mg, 1.49 mmol, 1.00 eq) in DMSO (15.00 mL) was added 2,2-difluoroethanamine (7.25 g, 89.40 mmol, 60.00 eq). The mixture was stirred in a sealed tube at 90° C. for 72 hr. LCMS showed 82% desired product, 2% reactant and 4% by-product detected. The mixture was poured into water (50 mL), extracted with ethyl acetate (20 mL*3), the organic layer was washed with brine (20 mL), dried over anhydrous Na₂SO₄, filtered and concentrated in vacuum. The crude was purified by column chromatography to afford the title compound (540.00 mg, 1.30 mmol, 87.24% yield) as yellow solid. LCMS: 416 [M+1].

Step 3. 4-[(2,2-difluoroethylamino)methyl]-2-methyl-4,5,8,9,10,11-hexahydropyrido[2,3]pyrazolo[2,4-d][1,2,5]oxadiazepin-1-one. To a solution of tert-butyl 4-[(2,2-difluoroethylamino)methyl]-2-methyl-1-oxo-5,8,9,11-tetrahydro-4-H-pyrido[2,3]pyrazolo[2,4-d][1,2,5]oxadiazepine-10-carboxylate (70.00 mg, 168.50 μmol, 1.00 eq) in DCM (2.00 mL) was added TFA (1.54 g, 13.51 mmol, 1.00 mL, 80.16 eq) at 0° C. The mixture was stirred at 25° C. for 1 h. The mixture was concentrated under reduced pressure to afford the title compound (80.00 mg, 147.23 μmol, 87.38% yield, 2TFA) as yellow oil, the crude product was used directly for the next step.

Step 4. (S*)—N-(3-cyano-2,4-difluorophenyl)-4-(((2,2-difluoroethyl)amino)methyl)-2-methyl-1-oxo-1,4,5,8,9,11-hexahydropyrido[4',3':3,4]pyrazolo[5,1-d][1,2,5]oxadiazepine-10(2H)-carboxamide. To a solution of 4-[(2,2-difluoroethylamino)methyl]-2-methyl-4,5,8,9,10,11-hexahydropyrido[2,3]pyrazolo[2,4-d][1,2,5]oxadiazepin-1-one (80.00 mg, 147.23 μmol, 1.00 eq, 2TFA) in DCM (3.00 mL) was added phenyl N-[2,4-difluoro-3-(trifluoromethyl)phenyl]carbamate (56.04 mg, 176.68 μmol, 1.20 eq) and Et3N (74.49 mg, 736.16 μmol, 102.04 μL 5.00 eq). The mixture was stirred at 25° C. for 16 h. The mixture was concentrated under reduced pressure. The residue was purified by prep-HPLC(FA) to afford the title compound (29.00 mg, 50.63 μmol, 34.39% yield, 94% purity) as white solid. LCMS: 496 [M+1]. ¹H NMR (400 MHz, CHLOROFORM-d) δ 8.29 (dt, J=5.90, 8.97 Hz, 1H), 7.02 (t, J=8.72 Hz, 1H), 6.60 (br s, 1H), 5.67-6.02 (m, 1H), 4.68-4.81 (m, 2H), 4.48-4.59 (m, 2H), 4.32-4.43 (m, 1H), 3.76-3.95 (m, 2H), 3.31 (s, 3H), 2.95-3.09 (m, 3H), 2.78-2.93 (m, 3H).

* pure but unknown stereochemistry

Compounds 187, 188, 189, 190, 191, 192, 193, and 194 were prepared in an analogous manner to Compound 186.

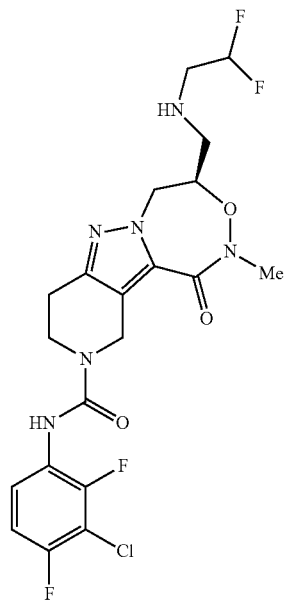

188 E1

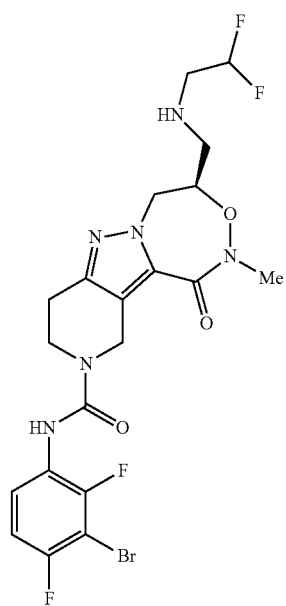 [SMILES: CN1O[C@H](CNCC(F)F)Cn2nc3c(c2C1=O)CN(C(=O)Nc1ccc(F)c(C#N)c1F)CC3]

187 E1

189 E1

365
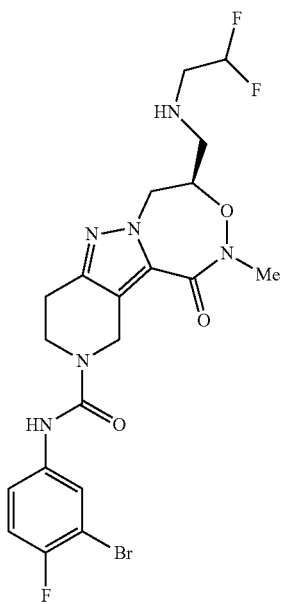
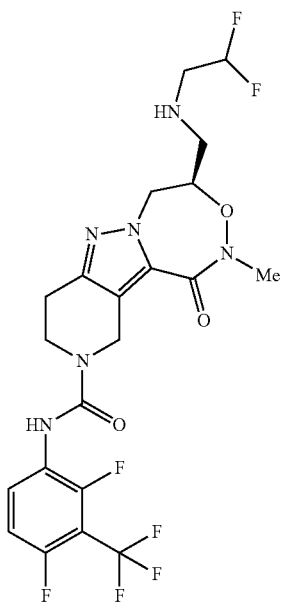
366
190 E1
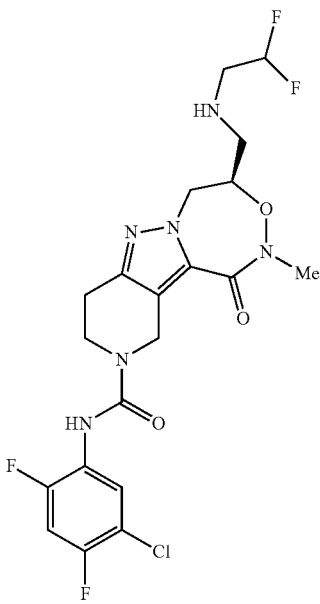
191 E1
192 E1
193 E1
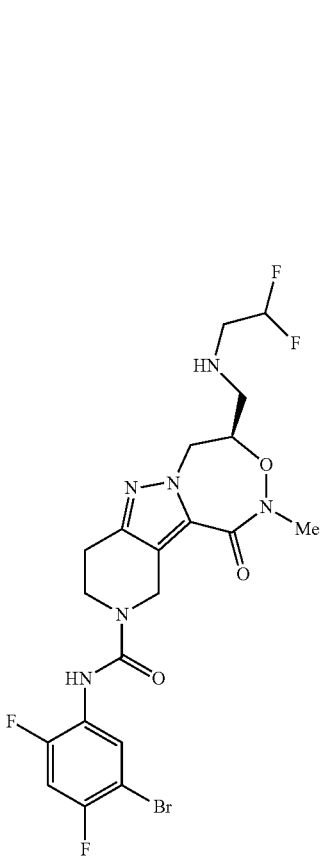 [SMILES: CN1O[C@H](CNCC(F)F)Cn2nc3c(c2C1=O)CN(C(=O)Nc1cc(Br)c(F)cc1F)CC3]

-continued

194 E1

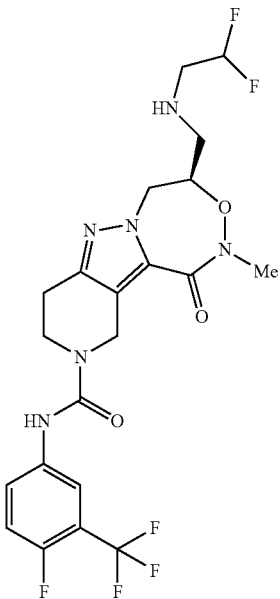

Compound 187_E1: (S*)—N-(3-cyano-4-fluorophenyl)-4-(((2,2-difluoroethyl)amino)methyl)-2-methyl-1-oxo-1,4,5,8,9,11-hexahydropyrido[4',3':3,4]pyrazolo[5,1-d][1,2,5]oxadiazepine-10(2H)-carboxamide LCMS:478 [M+1]. ¹H NMR (400 MHz, CHLOROFORM-d) δ 7.77 (dd, J=2.76, 5.27 Hz, 1H), 7.53-7.62 (m, 1H), 7.14 (t, J=8.72 Hz, 1H), 6.64 (s, 1H), 5.67-6.03 (m, 1H), 4.63-4.79 (m, 2H), 4.48-4.59 (m, 2H), 4.31-4.42 (m, 1H), 3.80-3.93 (m, 2H), 3.31 (s, 3H), 2.96-3.11 (m, 3H), 2.77-2.92 (m, 3H).
* pure but unknown stereochemistry Compound 188_E1: (S*)—N-(3-chloro-2,4-difluorophenyl)-4-(((2,2-difluoroethyl)amino)methyl)-2-methyl-1-oxo-1,4,5,8,9,11-hexahydropyrido[4',3':3,4]pyrazolo[5,1-d][1,2,5]oxadiazepine-10(2H)-carboxamide LCMS: 505/507 [M+1]. ¹H NMR (400 MHz, CHLOROFORM-d) δ 7.88 (dt, J=5.52, 8.85 Hz, 1H), 6.89-7.01 (m, 1H), 6.54 (br s, 1H), 5.67-6.04 (m, 1H), 4.68-4.80 (m, 2H), 4.48-4.60 (m, 2H), 4.29-4.40 (m, 1H), 3.76-3.98 (m, 2H), 3.31 (s, 3H), 2.95-3.10 (m, 3H), 2.77-2.93 (m, 3H).
* pure but unknown stereochemistry Compound 189_E1: (S*)—N-(3-bromo-2,4-difluorophenyl)-4-(((2,2-difluoroethyl)amino)methyl)-2-methyl-1-oxo-1,4,5,8,9,11-hexahydropyrido[4',3':3,4]pyrazolo[5,1-d][1,2,5]oxadiazepine-10(2H)-carboxamide LCMS: 549/551 [M+1]. ¹H NMR (400 MHz, CHLOROFORM-d) δ 7.95 (dt, J=5.83, 8.88 Hz, 1H), 6.94 (br t, J=8.47 Hz, 1H), 6.54 (br s, 1H), 5.68-6.02 (m, 1H), 4.67-4.81 (m, 2H), 4.47-4.61 (m, 2H), 4.30-4.42 (m, 1H), 3.75-3.95 (m, 2H), 3.31 (s, 3H), 2.94-3.09 (m, 3H), 2.77-2.92 (m, 3H).
* pure but unknown stereochemistry Compound 190_E1: (S*)—N-(3-bromo-4-fluorophenyl)-4-(((2,2-difluoroethyl)amino)methyl)-2-methyl-1-oxo-1,4,5,8,9,11-hexahydropyrido[4',3':3,4]pyrazolo[5,1-d][1,2,5]oxadiazepine-10(2H)-carboxamide LCMS: 531/533 [M+1]. ¹H NMR (400 MHz, CHLOROFORM-d) δ 7.71 (dd, J=2.57, 5.96 Hz, 1H), 7.24 (br d, J=2.89 Hz, 1H), 7.05 (t, J=8.53 Hz, 1H), 6.48 (s, 1H), 5.68-6.03 (m, 1H), 4.63-4.76 (m, 2H), 4.49-4.59 (m, 2H), 4.32-4.41 (m, 1H), 3.78-3.93 (m, 2H), 3.31 (s, 3H), 2.95-3.09 (m, 3H), 2.78-2.90 (m, 3H).
* pure but unknown stereochemistry Compound 191_E1: (S*)—N-(2,4-difluoro-3-(trifluoromethyl)phenyl)-4-(((2,2-difluoroethyl)amino)methyl)-2-methyl-1-oxo-1,4,5,8,9,11-hexahydropyrido[4',3':3,4]pyrazolo[5,1-d][1,2,5]oxadiazepine-10(2H)-carboxamide LCMS: 539 [M+1]. ¹H NMR (400 MHz, CHLOROFORM-d) δ 8.22 (dt, J=5.58, 8.88 Hz, 1H), 6.99 (t, J=9.60 Hz, 1H), 6.63 (br d, J=3.51 Hz, 1H), 5.67-6.02 (m, 1H), 4.75 (d, J=2.64 Hz, 2H), 4.48-4.59 (m, 2H), 4.29-4.42 (m, 1H), 3.78-3.96 (m, 2H), 3.27-3.34 (m, 3H), 2.96-3.09 (m, 3H), 2.77-2.91 (m, 3H).
* pure but unknown stereochemistry Compound 192_E1: (S*)—N-(5-chloro-2,4-difluorophenyl)-4-(((2,2-difluoroethyl)amino)methyl)-2-methyl-1-oxo-1,4,5,8,9,11-hexahydropyrido[4',3':3,4]pyrazolo[5,1-d][1,2,5]oxadiazepine-10(2H)-carboxamide LCMS: 505/507 [M+1]. ¹H NMR (400 MHz, CHLOROFORM-d) δ 8.19 (t, J=8.09 Hz, 1H), 6.95 (dd, J=8.60, 10.48 Hz, 1H), 6.55 (br d, J=2.51 Hz, 1H), 5.68-6.02 (m, 1H), 4.73 (d, J=1.88 Hz, 2H), 4.49-4.60 (m, 2H), 4.30-4.42 (m, 1H), 3.77-3.94 (m, 2H), 3.31 (s, 3H), 2.96-3.09 (m, 3H), 2.78-2.92 (m, 3H).
* pure but unknown stereochemistry Compound 193_E1: (S*)—N-(5-bromo-2,4-difluorophenyl)-4-(((2,2-difluoroethyl)amino)methyl)-2-methyl-1-oxo-1,4,5,8,9,11-hexahydropyrido[4',3':3,4]pyrazolo[5,1-d][1,2,5]oxadiazepine-10(2H)-carboxamide

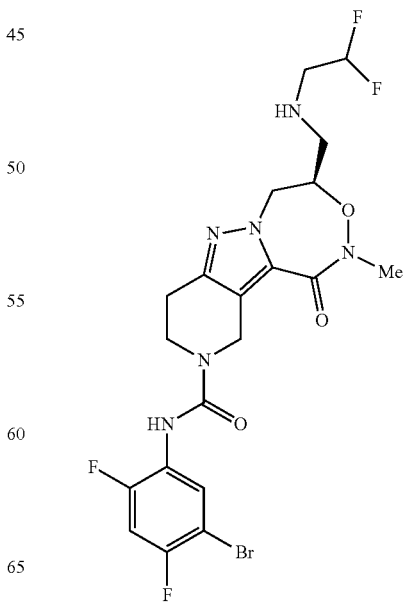

LCMS: 549/551 [M+1]. ¹H NMR (400 MHz, CHLOROFORM-d) δ 8.33 (t, J=7.91 Hz, 1H), 6.94 (dd, J=7.91, 10.67 Hz, 1H), 6.54 (br d, J=2.51 Hz, 1H), 5.67-6.04 (m, 1H), 4.66-4.80 (m, 2H), 4.49-4.59 (m, 2H), 4.30-4.42 (m, 1H), 3.77-3.97 (m, 2H), 3.31 (s, 3H), 2.96-3.10 (m, 3H), 2.79-2.92 (m, 3H).

* pure but unknown stereochemistry

Compound 194_E1: (S*)-4-4(2,2-difluoroethyl)amino)methyl)-N-(4-fluoro-3-(trifluoromethyl)phenyl)-2-methyl-1-oxo-1,4,5,8,9,11-hexahydropyrido[4',3':3,4]pyrazolo[5,1-d][1,2,5]oxadiazepine-10(2H)-carboxamide

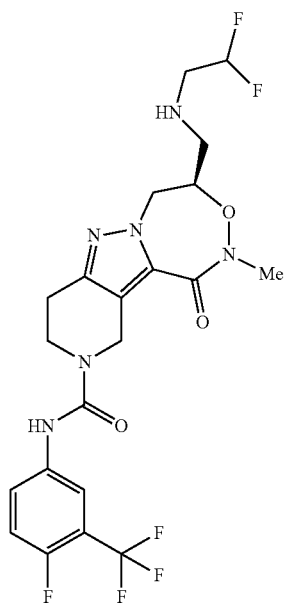 [SMILES: CN1O[C@H](CNCC(F)F)Cn2nc3c(c2C1=O)CN(C(=O)Nc1ccc(F)c(C(F)(F)F)c1)CC3]

LCMS: 521 [M+1]. ¹H NMR (400 MHz, CHLOROFORM-d) δ 7.64-7.71 (m, 1H), 7.59 (br dd, J=3.70, 8.47 Hz, 1H), 7.13 (t, J=9.35 Hz, 1H), 6.62 (s, 1H), 5.68-6.03 (m, 1H), 4.65-4.78 (m, 2H), 4.49-4.60 (m, 2H), 4.31-4.43 (m, 1H), 3.79-3.93 (m, 2H), 3.31 (s, 3H), 2.96-3.10 (m, 3H), 2.80-2.91 (m, 3H).

* pure but unknown stereochemistry

Compound 195: N10-(3-cyano-2,4-difluorophenyl)-N4,2-dimethyl-1-oxo-1,4,5,8,9,11-hexahydropyrido[4',3':3,4]pyrazolo[5,1-d][1,2,5]oxadiazepine-4,10(2H)-dicarboxamide

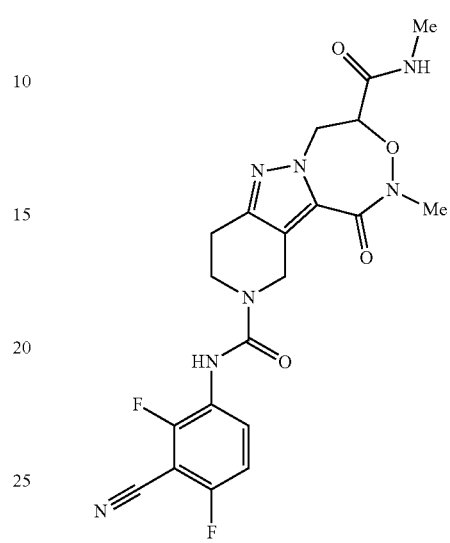

Compound 195 was prepared in an analogous manner to 118.

LCMS [M+1]:460. ¹H NMR (400 MHz, CHLOROFORM-d) δ 8.29 (dt, J=5.77, 9.10 Hz, 1H), 6.95-7.09 (m, 1H), 6.64 (br s, 1H), 6.09 (br d, J=3.76 Hz, 1H), 4.85-5.01 (m, 2H), 4.63-4.80 (m, 3H), 3.73-3.97 (m, 2H), 3.35 (s, 3H), 2.82-2.96 (m, 5H).

Compound 196: N-(3-chloro-4-fluoro-phenyl)-2-methyl-1-oxo-4-[(2-oxopyrrolidin-1-yl)methyl]-5,8,9,11-tetrahydro-4H-pyrido[2,3]pyrazolo[2,4-d][1,2,5]oxadiazepine-10-carboxamide

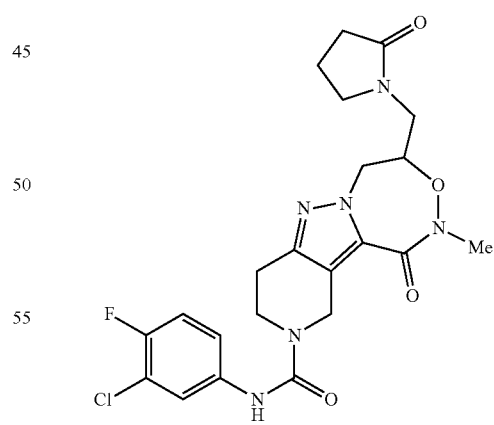

Step 1. 4-[(4-chlorobutanoylamino)methyl]-N-(3-chloro-4-fluoro-phenyl)-2-methyl-1-oxo-5,8,9,11-tetrahydro-4H-pyrido[2,3]pyrazolo[2,4-d][1,2,5]oxadiazepine-10-carboxamide. To a mixture of 4-(aminomethyl)-N-(3-chloro-4-fluoro-phenyl)-2-methyl-1-oxo-5,8,9,11-tetrahydro-4H-pyrido[2,3]pyrazolo[2,4-d][1,2,5]oxadiazepine-10-carboxamide (Compound 113, 80.00 mg, 189.20 μmol, 1.00 eq) and TEA (38.29 mg, 378.40 μmol, 52.45 μL 2.00 eq) in DCM (5.00 mL) was added 4-chlorobutanoyl chloride (26.68 mg, 189.20 μmol, 21.17 μL 1.00 eq), the mixture was stirred at 15° C. for 4 h. The residue was diluted with H₂O (10 mL) and extracted with DCM (10 mL*2). The combined organic layers were washed with brine (20 mL*2), dried over Na₂SO₄, filtered and concentrated under reduced pressure. The residue was purified by prep-TLC (Dichloromethane:Methanol=10:1 Plate 1) to afford the title compound (60.00 mg, 113.77 μmol, 60.13% yield) as white solid. LCMS: 528 [M+1].

Step 2. N-(3-chloro-4-fluoro-phenyl)-2-methyl-1-oxo-4-[(2-oxopyrrolidin-1-yl) methyl]-5,8,9,11-tetrahydro-4H-pyrido [2,3]pyrazolo [2,4-d][1,2,5]oxadiazepine-10-carboxamide. To a solution of 4-[(4-chlorobutanoylamino)methyl]-N-(3-chloro-4-fluoro-phenyl)-2-methyl-1-oxo-5,8,9,11-tetrahydro-4H-pyrido[2,3]pyrazolo[2,4-d][1,2,5] oxadiazepine-10-carboxamide (40.00 mg, 75.85 μmol, 1.00 eq) in THF (4.00 mL) was added NaH (6.07 mg, 151.69 μmol, 60% purity, 2.00 eq) at 0° C. for 0.5 h, then the mixture was stirred at 15° C. for 1 h. The mixture was diluted with H₂O (10 mL) and extracted with EtOAc (10 mL*2). The combined organic layers were washed with brine (10 mL*2), dried over Na₂SO₄, filtered and concentrated under reduced pressure. The residue combined with the reaction mixture of was purified by prep-HPLC(FA) to afford the title compound (13.00 mg, 25.16 μmol, 95% purity) as yellow solid, LCMS: 491 [M+1]. ¹H NMR (400 MHz, CHLOROFORM-d) δ 7.58 (dd, J=2.64, 6.40 Hz, 1H), 7.16-7.24 (m, 1H), 7.02-7.10 (m, 1H), 6.56 (s, 1H), 4.70 (s, 3H), 4.40-4.55 (m, 2H), 3.79-3.94 (m, 2H), 3.74 (dd, J=7.40, 14.68 Hz, 1H), 3.35-3.46 (m, 2H), 3.31 (s, 3H), 3.23 (dt, J=5.65, 8.91 Hz, 1H), 2.80-2.91 (m, 2H), 2.36-2.48 (m, 2H), 1.89-2.07 (m, 2H).

Compound 204: N-(3-chloro-4-fluorophenyl)-4-((3,3-dimethylureido)methyl)-2-methyl-1-oxo-1,4,5,8,9,11-hexahydropyrido[4',3':3,4]pyrazolo[5,1-d][1,2,5]oxadiazepine-10(2H)-carboxamide

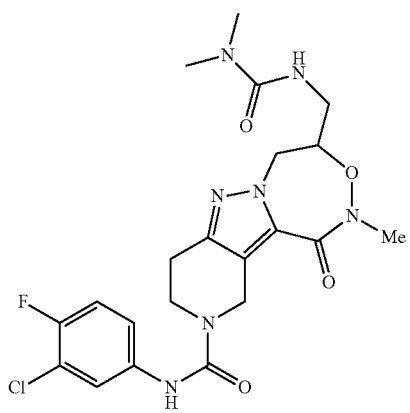

To a solution of 4-(aminomethyl)-N-(3-chloro-4-fluorophenyl)-2-methyl-1-oxo-5,8,9,11-tetrahydro-4H-pyrido[2,3]pyrazolo[2,4-d][1,2,5]oxadiazepine-10-carboxamide (Compound 113, 40.00 mg, 94.60 μmol, 1.00 eq) and TEA (19.14 mg, 189.20 μmol, 26.23 μL 2.00 eq) in DCM (2.00 mL) was added N,N-dimethylcarbamoyl chloride (15.26 mg, 141.90 μmol, 13.04 μL 1.50 eq), then the mixture was stirred at 25° C. for 16 h. LCMS indicated that the starting material was consumed completely and desired product was detected. The mixture was concentrated in vacuum. The residue was purified by prep-HPLC (FA) to obtain the title compound (27.00 mg, 54.50 μmol, 57.61% yield, 99.7% purity) as white solid. LCMS: 494 [M+1]. ¹H NMR (400 MHz, DMSO-d₆) δ=8.90 (s, 1H), 7.72 (dd, J=2.57, 6.85 Hz, 1H), 7.39-7.44 (m, 1H), 7.29 (t, J=9.11 Hz, 1H), 6.54 (t, J=5.14 Hz, 1H), 4.61 (s, 2H), 4.49-4.56 (m, 2H), 4.27-4.35 (m, 1H), 3.74 (br s, 2H), 3.22 (s, 3H), 3.11-3.18 (m, 1H), 3.11-3.18 (m, 1H), 3.11-3.18 (m, 1H), 2.79 (s, 6H), 2.72 (br t, J=5.38 Hz, 2H).

Compounds 197, 198, 200, 201, and 202 were prepared in an analogous manner to Compound 204.

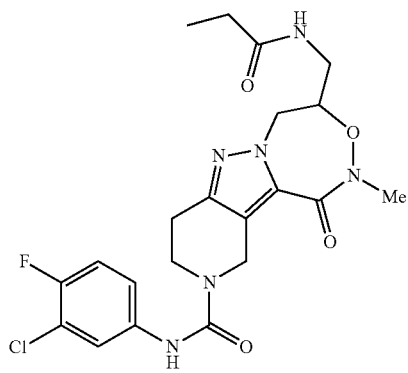

197

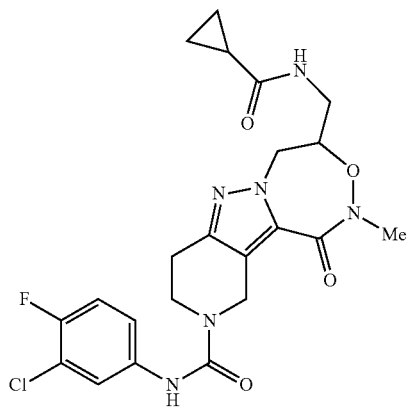

198

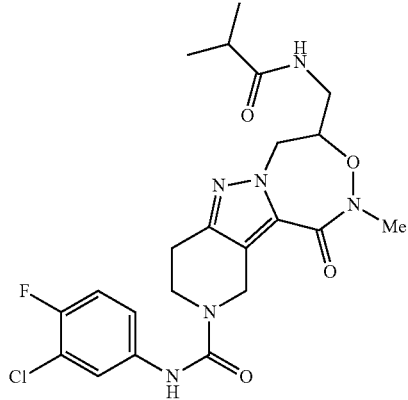 [SMILES: CN(C)C(=O)NCC1Cn2nc3c(c2C(=O)N(C)O1)CN(C(=O)Nc1ccc(F)c(Cl)c1)CC3]

200

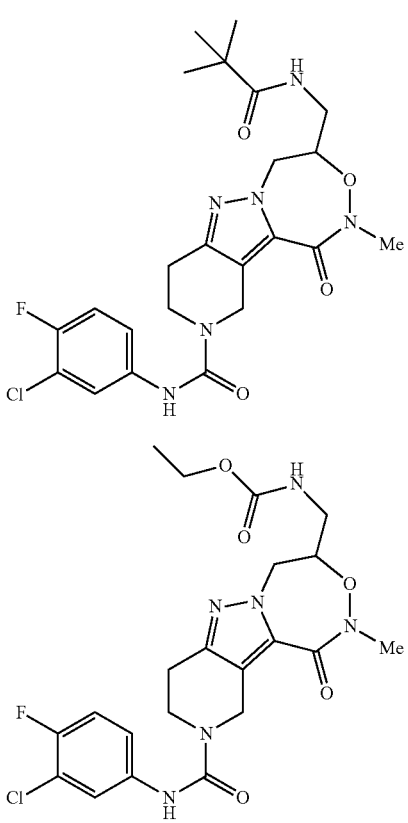

Compound 197: N-(3-chloro-4-fluorophenyl)-2-methyl-1-oxo-4-(propionamidomethyl)-1,4,5,8,9,11-hexahydropyrido[4',3':3,4]pyrazolo[5,1-d][1,2,5]oxadiazepine-10(2H)-carboxamide LCMS: 479 [M+1]. ¹H NMR (400 MHz, DMSO-d₆) δ=8.90 (s, 1H), 8.05 (t, J=5.75 Hz, 1H), 7.72 (dd, J=2.63, 6.91 Hz, 1H), 7.41 (ddd, J=2.75, 4.34, 9.05 Hz, 1H), 7.25-7.32 (m, 1H), 4.61 (s, 2H), 4.54-4.60 (m, 1H), 4.44-4.52 (m, 1H), 4.28 (dd, J=7.03, 14.24 Hz, 1H), 3.69-3.78 (m, 2H), 3.44 (br d, J=7.70 Hz, 1H), 3.16-3.23 (m, 4H), 2.72 (br t, J=5.69 Hz, 2H), 2.07-2.15 (m, 2H), 1.00 (t, J=7.58 Hz, 3H).

Compound 198: N-(3-chloro-4-fluorophenyl)-4-(cyclopropanecarboxamidomethyl)-2-methyl-1-oxo-1,4,5,8,9,11-hexahydropyrido[4',3':3,4]pyrazolo[5,1-d][1,2,5]oxadiazepine-10(2H)-carboxamide LCMS: 491 [M+1]. ¹H NMR (400 MHz, DMSO-d₆) δ=8.90 (s, 1H), 8.36 (br t, J=5.33 Hz, 1H), 7.73 (dd, J=2.57, 6.84 Hz, 1H), 7.42 (ddd, J=2.64, 4.27, 9.03 Hz, 1H), 7.26-7.32 (m, 1H), 4.62 (s, 2H), 4.54-4.61 (m, 1H), 4.45-4.53 (m, 1H), 4.28 (dd, J=7.22, 14.24 Hz, 1H), 3.68-3.81 (m, 2H), 3.44 (td, J=7.17, 14.40 Hz, 1H), 3.25 (br t, J=4.58 Hz, 1H), 3.21 (s, 3H), 2.72 (br t, J=5.58 Hz, 2H), 1.54-1.67 (m, 1H), 0.64-0.72 (m, 4H).

Compound 200: N-(3-chloro-4-fluorophenyl)-4-(isobutyramidomethyl)-2-methyl-1-oxo-1,4,5,8,9,11-hexahydropyrido[4',3':3,4]pyrazolo[5,1-d][1,2,5]oxadiazepine-10(2H)-carboxamide LCMS: 493 [M+1]. ¹H NMR (400 MHz, DMSO-d₆) δ=8.90 (s, 1H), 8.02 (br t, J=5.50 Hz, 1H), 7.72 (dd, J=2.57, 6.85 Hz, 1H), 7.41 (ddd, J=2.63, 4.28, 8.99 Hz, 1H), 7.25-7.32 (m, 1H), 4.61 (s, 2H), 4.57 (dd, J=5.69, 14.12 Hz, 1H), 4.45-4.53 (m, 1H), 4.28 (dd, J=6.91, 14.12 Hz, 1H), 3.70-3.79 (m, 2H), 3.39-3.47 (m, 2H), 3.15-3.23 (m, 4H), 2.72 (br t, J=5.50 Hz, 2H), 2.39 (td, J=6.80, 13.66 Hz, 1H), 1.01 (dd, J=3.91, 6.85 Hz, 6H)

Compound 201: N-(3-chloro-4-fluorophenyl)-2-methyl-1-oxo-4-(pivalamidomethyl)-1,4,5,8,9,11-hexahydropyrido[4',3':3,4]pyrazolo[5,1-d][1,2,5]oxadiazepine-10(2H)-carboxamide LCMS: 507 [M+1]. ¹H NMR (400 MHz, METHANOL-d₄) δ=7.58 (dd, J=2.57, 6.71 Hz, 1H), 7.29 (ddd, J=2.64, 4.17, 9.00 Hz, 1H), 7.10-7.16 (m, 1H), 4.71 (s, 2H), 4.52-4.65 (m, 2H), 4.36 (dd, J=5.71, 14.49 Hz, 1H), 3.74-3.90 (m, 2H), 3.54 (dd, J=7.22, 14.24 Hz, 1H), 3.33-3.37 (m, 1H), 3.28 (s, 3H), 2.83 (t, J=5.77 Hz, 2H), 1.18 (s, 9H).

Compound 202: ethyl ((10-((3-chloro-4-fluorophenyl)carbamoyl)-2-methyl-1-oxo-1,2,4,5,8,9,10,11-octahydropyrido[4',3':3,4]pyrazolo[5,1-d][1,2,5]oxadiazepin-4-yl)methyl)carbamate LCMS: 495 [M+1]. ¹H NMR (400 MHz, METHANOL-d₄) δ=7.56-7.61 (m, 1H), 7.56-7.61 (m, 1H), 7.58 (dd, J=2.64, 6.65 Hz, 1H), 7.56-7.61 (m, 1H), 7.29 (ddd, J=2.64, 4.05, 9.00 Hz, 1H), 7.10-7.16 (m, 1H), 4.72 (s, 2H), 4.53-4.61 (m, 2H), 4.31-4.39 (m, 1H), 4.10 (q, J=7.19 Hz, 2H), 3.75-3.88 (m, 1H), 3.75-3.88 (m, 1H), 3.37-3.44 (m, 1H), 3.29 (s, 4H), 2.82 (t, J=5.77 Hz, 2H), 1.20-1.29 (m, 3H)

Compound 203: cyclopropyl ((10-((3-chloro-4-fluorophenyl)carbamoyl)-2-methyl-1-oxo-1,2,4,5,8,9,10,11-octahydropyrido[4',3':3,4]pyrazolo[5,1-d][1,2,5]oxadiazepin-4-yl)methyl)carbamate

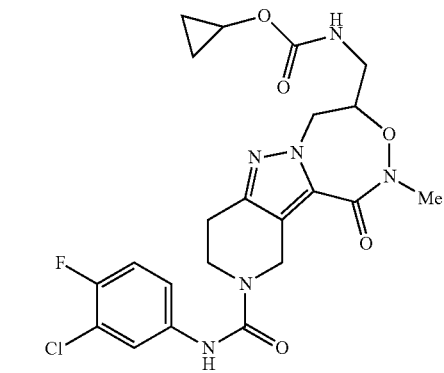 [SMILES: CN1OC(CNC(=O)OC2CC2)Cn2nc3c(c2C1=O)CN(C(=O)Nc1ccc(F)c(Cl)c1)CC3]

To a solution of cyclopropanol (100.00 mg, 1.72 mmol, 1.00 eq) and pyridine (408.16 mg, 5.16 mmol, 416.49 μL 3.00 eq) in DCM (5.00 mL) was added (4-nitrophenyl)carbonochloridate (346.68 mg, 1.72 mmol, 1.00 eq). The mixture was stirred at 20° C. for 1 h. TLC (PE:EtOAc=3:1) showed that reactant (4-nitrophenyl)carbonochloridate was consumed completely and one main new spot formed. The mixture was diluted with 10 mL of DCM and washed with HCl (1N, 30 mL*1), saturated NaHCO₃ solution (30 mL) and brine (20 mL*1). The organic phase was dried over anhydrous Na₂SO₄, filtered and concentrated in vacuum to give cyclopropyl (4-nitrophenyl)carbonate (400.00 mg, crude) as white solid and directly used in the next step.

Step 2. cyclopropyl ((10-((3-chloro-4-fluorophenyl)carbamoyl)-2-methyl-1-oxo-1,2,4,5,8,9,10,11-octahydropyrido[4',3':3,4]pyrazolo[5,1-d][1,2,5]oxadiazepin-4-yl)methyl) carbamate. To a solution of 4-(aminomethyl)-N-(3-chloro-4-fluoro-phenyl)-2-methyl-1-oxo-5,8,9,11-tetrahydro-4H-pyrido[2,3]pyrazolo[2,4-d][1,2,5]oxadiazepine-10-carboxamide (Compound 113, 35.00 mg, 82.77 µmol, 1.00 eq) and TEA (25.13 µmol, 248.32 µmol, 34.42 µL3.00 eq) in THF (1.00 mL) was added cyclopropyl (4-nitrophenyl) carbonate (36.95 mg, 165.54 µmol, 2.00 eq), then the mixture was stirred at 45° C. for 16 h. TLC (PE:EtOAc=0:1) showed that reactant cyclopropyl (4-nitrophenyl) carbonate was consumed completely and two new spots formed. The mixture combined with a pilot reaction (5 mg) was diluted with 15 mL of DCM and washed with water (10 mL*1) and brine (10 mL*1). Then the combined organic phases were dried over anhydrous $Na_2SO_4$, filtered and concentrated in vacuum. The residue was purified by prep-TLC (PE:EtOAc=0:1), following by prep-HPLC (FA) to obtain the title compound (17.2 mg, 33.93 µmol, 37.59% yield, 95% purity) as white solid. LCMS: 507 [M+1]. $^1$H NMR (400 MHz, CHLOROFORM-d) δ=7.58 (dd, J=2.64, 6.53 Hz, 1H), 7.17-7.22 (m, 1H), 7.03-7.09 (m, 1H), 6.51 (s, 1H), 4.92 (br s, 1H), 4.64-4.76 (m, 2H), 4.50-4.63 (m, 2H), 4.38 (br dd, J=4.20, 14.49 Hz, 1H), 4.09 (br d, J=3.89 Hz, 1H), 3.79-3.92 (m, 2H), 3.39-3.49 (m, 2H), 3.30 (s, 3H), 2.85 (t, J=5.77 Hz, 2H), 0.71 (br d, J=6.02 Hz, 4H).

Compound 199: N-(3-chloro-4-fluorophenyl)-2-methyl-1-oxo-4-((3,3,3-trifluoropropanamido)methyl)-1,4,5,8,9,11-hexahydropyrido[4',3':3,4]pyrazolo[5,1-d][1,2,5]oxadiazepine-10(2H)-carboxamide

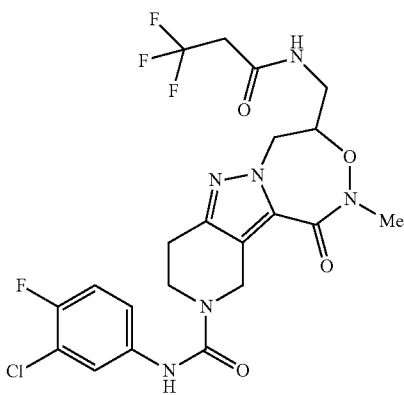 [SMILES: CN1OC(CNC(=O)CC(F)(F)F)Cn2nc3c(c2C1=O)CN(C(=O)Nc1ccc(F)c(Cl)c1)CC3]

To a solution of 4-(aminomethyl)-N-(3-chloro-4-fluorophenyl)-2-methyl-1-oxo-5,8,9,11-tetrahydro-4H-pyrido[2,3]pyrazolo[2,4-d][1,2,5]oxadiazepine-10-carboxamide (Compound 113, 40.00 mg, 94.60 µmol, 1.00 eq) and 3,3,3-trifluoropropanoic acid (14.54 mg, 113.52 µmol, 10.03 µL1.20 eq) in DMF (2.00 mL) was added HATU (43.16 mg, 113.52 µmol, 1.20 eq) and DIPEA (73.36 mg, 567.60 µmol, 99.14 µL6.00 eq), then the mixture was stirred at 25° C. for 2 h. LCMS indicated that the starting material was consumed completely and desired product was detected. The mixture was diluted with 15 mL of DCM and washed with water (10 mL*1) and brine (10 mL*1). Then the combined organic phases were dried over anhydrous $Na_2SO_4$, filtered and concentrated in vacuum. The residue was purified by prep-HPLC (FA) to get Compound 199(33.00 mg, 61.25 µmol, 64.74% yield, 98.9% purity) as white solid. LCMS: 533 [M+1]. $^1$H NMR (400 MHz, DMSO-$d_6$) δ=8.90 (s, 1H), 8.55 (br t, J=5.44 Hz, 1H), 7.72 (dd, J=2.57, 6.85 Hz, 1H), 7.38-7.45 (m, 1H), 7.25-7.32 (m, 1H), 4.57-4.66 (m, 3H), 4.47-4.55 (m, 1H), 4.28 (dd, J=7.15, 14.37 Hz, 1H), 3.68-3.81 (m, 2H), 3.48 (td, J=7.11, 14.52 Hz, 1H), 3.25-3.31 (m, 3H), 3.20 (s, 3H), 2.72 (br t, J=5.50 Hz, 2H).

Compounds 205 and 206 were prepared in an analogous method to Compound 199.

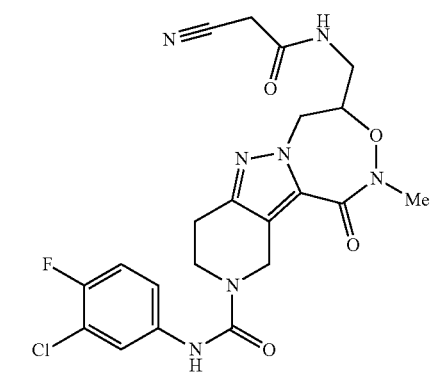

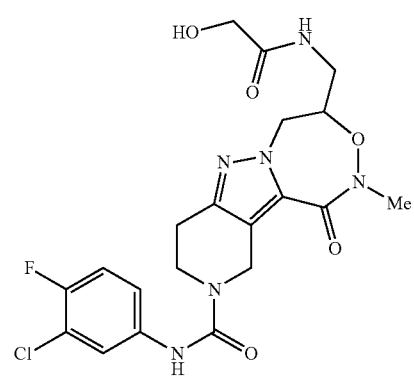

Compound 205: N-(3-chloro-4-fluorophenyl)-4-((2-cyanoacetamido)methyl)-2-methyl-1-oxo-1,4,5,8,9,11-hexahydropyrido[4',3':3,4]pyrazolo[5,1-d][1,2,5]oxadiazepine-10(2H)-carboxamide LCMS: 490 [M+1]. $^1$H NMR (400 MHz, METHANOL-$d_4$) δ=7.58 (dd, J=2.64, 6.65 Hz, 1H), 7.29 (ddd, J=2.76, 4.11, 8.94 Hz, 1H), 7.08-7.18 (m, 1H), 4.72 (s, 2H), 4.50-4.67 (m, 3H), 4.33-4.44 (m, 1H), 3.74-3.91 (m, 2H), 3.63 (dd, J=7.09, 14.62 Hz, 1H), 3.36-3.56 (m, 2H), 3.29-3.30 (m, 1H), 3.29 (br s, 2H), 2.84 (t, J=5.71 Hz, 2H).

Compound 206: N-(3-chloro-4-fluorophenyl)-4-((2-hydroxyacetamido)methyl)-2-methyl-1-oxo-1,4,5,8,9,11-hexahydropyrido[4',3':3,4]pyrazolo[5,1-d][1,2,5]oxadiazepine-10(2H)-carboxamide LCMS: 481 [M+1]. $^1$H NMR (400 MHz, METHANOL-$d_4$) δ=7.58 (dd, J=2.64, 6.65 Hz, 1H), 7.29 (ddd, J=2.64, 4.17, 9.00 Hz, 1H), 7.13 (t, J=8.97 Hz, 1H), 4.72 (s, 2H), 4.70-4.71 (m, 1H), 4.55-4.68 (m, 2H), 4.55-4.68 (m, 1H), 4.38 (dd, J=5.71, 14.24 Hz, 1H), 3.97-4.02 (m, 1H), 4.00 (s, 1H), 3.79-3.85 (m, 2H), 3.65 (dd, J=7.15, 14.18 Hz, 1H), 3.42 (dd, J=4.33, 14.24 Hz, 1H), 3.29 (br s, 2H), 3.29-3.30 (m, 1H), 2.83 (t, J=5.65 Hz, 2H).

377

Compound 207: 2,2,2-trifluoroethyl ((10-((3-chloro-4-fluorophenyl)carbamoyl)-2-methyl-1-oxo-1,2,4,5,8,9,10,11-octahydropyrido[4',3':3,4]pyrazolo[5,1-d][1,2,5]oxadiazepin-4-yl)methyl)carbamate

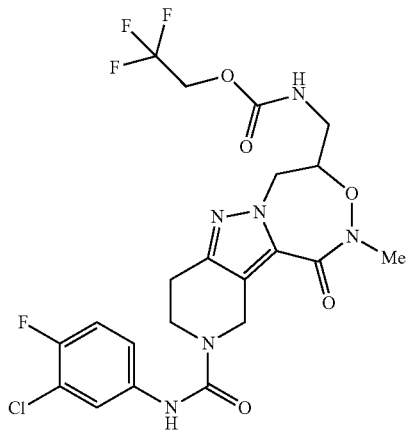 [SMILES: CN1OC(CNC(=O)OCC(F)(F)F)Cn2nc3c(c2C1=O)CN(C(=O)Nc1ccc(F)c(Cl)c1)CC3]

Step 1. 4-(aminomethyl)-N-(3-chloro-4-fluoro-phenyl)-2-methyl-1-oxo-5,8,9,11-tetrahydro-4H-pyrido[2,3]pyrazolo[2,4-d][1,2,5]oxadiazepine-10-carboxamide (Compound 113). To a solution of 2,2,2-trifluoroethanol (100.00 mg, 999.60 μmol, 71.94 μL1.00 eq) and pyridine (237.21 mg, 3.00 mmol, 242.05 μL3.00 eq) in DCM (20.00 mL) was added phenyl carbonochloridate (156.51 mg, 999.60 μmol, 125.21 μL1.00 eq). The mixture was stirred at 20° C. for 1 h. TLC (PE:EtOAc=3:1) showed that reactant phenyl carbonochloridate was consumed completely and one main new spot formed. The mixture was diluted with 10 mL of DCM and washed with HCl (1N, 30 mL*1) and brine (20 mL*1). The organic phase was dried over anhydrous $Na_2SO_4$, filtered and concentrated in vacuo to give phenyl 2,2,2-trifluoroethyl carbonate (250.00 mg, crude) as colorless oil.

Step 2. 2,2,2-trifluoroethyl ((10-((3-chloro-4-fluorophenyl)carbamoyl)-2-methyl-1-oxo-1,2,4,5,8,9,10,11-octahydropyrido[4',3':3,4]pyrazolo[5,1-d][1,2,5]oxadiazepin-4-yl)methyl)carbamate. To a solution of 4-(aminomethyl)-N-(3-chloro-4-fluoro-phenyl)-2-methyl-1-oxo-5,8,9,11-tetrahydro-4H-pyrido[2,3]pyrazolo[2,4-d][1,2,5]oxadiazepine-10-carboxamide (Compound 113, 35.00 mg, 82.77 μmol, 1.00 eq) and TEA (25.13 mg, 248.31 μmol, 34.42 μL3.00 eq) in THF (2.00 mL) was added phenyl 2,2,2-trifluoroethyl carbonate (54.67 mg, 248.31 μmol, 3.00 eq), then the mixture was stirred at 45° C. for 16 h. LCMS indicated that reactant phenyl 2,2,2-trifluoroethyl carbonate was consumed completely and desired product was detected. The mixture combined with a pilot reaction (5 mg) was concentrated in vacuum. The residue was purified by prep-HPLC (TFA), following by prep-TLC (PE:EtOAc=0:1) and prep-HPLC (FA) to obtain the title compound (6.5 mg, 11.84 μmol, 12.30% yield, 98% purity) white solid. LCMS: 549 [M+1]. $^1$H NMR (400 MHz, CHLOROFORM-d) δ=7.57 (dd, J=2.70, 6.46 Hz, 1H), 7.17-7.23 (m, 1H), 7.03-7.10 (m, 1H), 6.50 (s, 1H), 5.22 (br s, 1H), 4.64-4.76 (m, 2H), 4.36-4.63 (m, 5H), 3.80-3.92 (m, 2H), 3.42-3.55 (m, 2H), 3.30 (s, 3H), 2.85 (t, J=5.58 Hz, 2H).

378

Compound 208: N-(3-chloro-4-fluorophenyl)-4-(ethylsulfonamidomethyl)-2-methyl-1-oxo-1,4,5,8,9,11-hexahydropyrido[4',3':3,4]pyrazolo[5,1-d][1,2,5]oxadiazepine-10(2H)-carboxamide

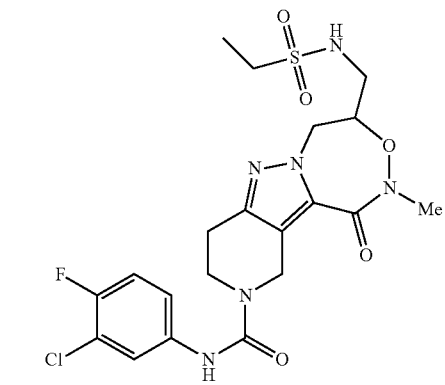 [SMILES: CCS(=O)(=O)NCC1Cn2nc3c(c2C(=O)N(C)O1)CN(C(=O)Nc1ccc(F)c(Cl)c1)CC3]

To a solution of 4-(aminomethyl)-N-(3-chloro-4-fluorophenyl)-2-methyl-1-oxo-5,8,9,11-tetrahydro-4H-pyrido[2,3]pyrazolo[2,4-d][1,2,5]oxadiazepine-10-carboxamide (Compound 113, 40.00 mg, 94.60 μmol, 1.00 eq) and TEA (19.14 mg, 189.20 μmol, 26.23 μL2.00 eq) in DCM (2.00 mL) was added ethanesulfonyl chloride (18.25 mg, 141.90 μmol, 13.42 μL1.50 eq), then the mixture was stirred at 25° C. for 16 h. LCMS indicated that the starting material was consumed completely and desired product was detected. The mixture was concentrated in vacuum. The residue was purified by prep-HPLC to obtain the title compound (25.00 mg, 46.61 μmol, 49.27% yield, 96% purity) as white solid. LCMS: 515 [M+1]. $^1$H NMR (400 MHz, DMSO-$d_6$) δ=8.91 (s, 1H), 7.72 (dd, J=2.57, 6.84 Hz, 1H), 7.38-7.49 (m, 2H), 7.25-7.32 (m, 1H), 4.57-4.65 (m, 3H), 4.50 (quin, J=6.31 Hz, 1H), 4.28 (dd, J=7.22, 14.37 Hz, 1H), 3.67-3.80 (m, 2H), 3.24 (s, 3H), 3.20 (br s, 2H), 3.07 (q, J=7.28 Hz, 2H), 2.72 (br t, J=5.58 Hz, 2H), 1.20 (t, J=7.34 Hz, 3H), 1.16-1.24 (m, 1H).

Compounds 129 and 130 were prepared in an analogous method to Compound 208.

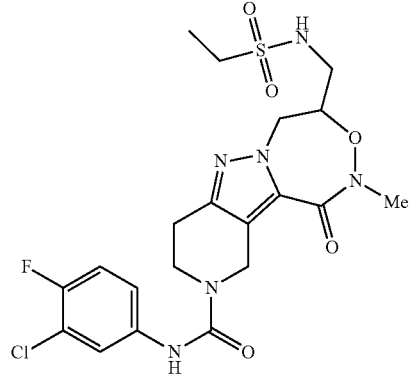

129

130

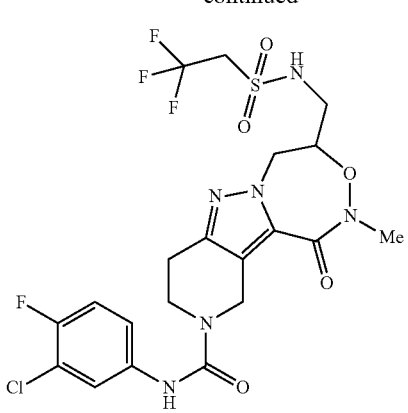

Compound 209: N-(3-chloro-4-fluoro-phenyl)-4-(hydroxymethyl)-2-methyl-1-oxo-4,5,8,9,10,11-hexahydro-[1,2,5]oxadiazepino[5,4-b]indazole-10-carboxamide

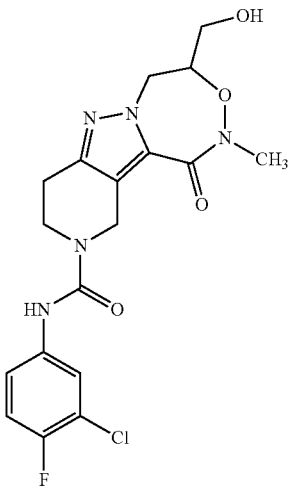 [SMILES: CN1OC(CO)Cn2nc3c(c2C1=O)CN(C(=O)Nc1ccc(F)c(Cl)c1)CC3]

Step 1. ethyl 3-(2-tert-butoxy-2-oxo-acetyl)-4-oxo-cyclohexane carboxylate. To a solution of LiHMDS (1 M, 35.26 mL, 1.20 eq) in THF (30.00 mL) was added ethyl 4-oxo-cyclohexanecarboxylate (5.00 g, 29.38 mmol, 4.67 mL, 1.00 eq) drop-wise at −65° C., after stirring for 30 min, ditert-butyl oxalate (6.54 g, 32.32 mmol, 1.10 eq) in THF (10.00 mL) was added at −65° C., the mixture was slowly warmed to 20° C. and stirred at 20° C. for 1 hr. TLC showed the reaction was completed. The mixture was poured into HCl (0.5 N, 200 mL), extracted with ethyl acetate (80 mL*3). The combined organic layer was washed with saturate NaHCO₃ aqueous (100 mL), brine (100 mL), dried over anhydrous Na₂SO₄ and concentrated in vacuum to afford the title compound (6.90 g, 23.13 mmol, 78.73% yield) which was used for the next step without further purification.

Step 2. 3-tert-butyl 5-ethyl 4,5,6,7-tetrahydro-2H-indazole-3,5-dicarboxylate. To a solution of ethyl 3-(2-tert-butoxy-2-oxo-acetyl)-4-oxo-cyclohexanecarboxylate (6.70 g, 22.46 mmol, 1.00 eq) in EtOH (70.00 mL) was added N₂H₄.H₂O (1.32 g, 22.46 mmol, 1.28 mL, 1.00 eq). The mixture was stirred at 20° C. for 2 hr. TLC showed the reaction was completed. The mixture concentrated in vacuum, the residue was poured into aqueous HCl (0.5 N, 50 mL), extracted with ethyl acetate (100 mL*2). The organic layer was washed with brine (50 mL), and dried over anhydrous Na₂SO₄ and concentrated in vacuum. The crude was purified by column chromatography to afford the title compound (4.70 g, 15.17 mmol, 67.54% yield, 95% purity) as colorless oil.

Step 3. 3-tert-butoxycarbonyl-4,5,6,7-tetrahydro-2H-indazole-5-carboxylic acid. To a solution of 3-tert-butyl 5-ethyl 4,5,6,7-tetrahydro-2H-indazole-3,5-dicarboxylate (2.40 g, 8.15 mmol, 1.00 eq) in MeOH (20.00 mL), THF (20.00 mL) and H₂O (10.00 mL) was added LiOH.H₂O (1.50 g, 35.75 mmol, 4.39 eq) at 10° C. with ice-water bath. The mixture was stirred at 20° C. for 3 hr. TLC showed the reactant was consumed and a major spot detected. The mixture was concentrated in vacuum, the residue was acidified by 1 N HCl to pH=5, and filtered to give the title compound (1.60 g, 5.41 mmol, 66.35% yield, 90% purity) as white solid Step 4. tert-butyl 5-[(3-chloro-4-fluoro-phenyl)carbamoyl]-4,5,6,7-tetrahydro-2H-indazole-3-carboxylate. To a solution of 3-tert-butoxycarbonyl-4,5,6,7-tetrahydro-2H-indazole-5-carboxylic acid (1.50 g, 5.63 mmol, 1.00 eq) and 3-chloro-4-fluoro-aniline (983.92 mg, 6.76 mmol, 1.20 eq) in DMF (5.00 mL) was added DIPEA (2.18 g, 16.90 mmol, 2.95 mL, 3.00 eq) and HATU (2.36 g, 6.20 mmol, 1.10 eq). The mixture was stirred at 20° C. for 16 hr. LCMS showed the reactant consumed, and 45% desired product and multiple peaks detected. The mixture was poured into water (200 mL), extracted with ethyl acetate (100 mL*3). The combined organic layer was washed with brine (50 mL*2), dried over anhydrous Na₂SO₄ and concentrated in vacuum. The crude was purified by reversed-phase flash separation to afford the title compound (650.00 mg, 1.65 mmol, 29.26% yield, 99.8% purity) as white solid.

Step 5. 5-[(3-chloro-4-fluoro-phenyl)carbamoyl]-4,5,6,7-tetrahydro-2H-indazole-3-carboxylic acid. To a solution of tert-butyl 5-[(3-chloro-4-fluoro-phenyl)carbamoyl]-4,5,6,7-tetrahydro-2H-indazole-3-carboxylate (300.00 mg, 761.73 μmol, 1.00 eq) in DCM (6.00 mL) was added TFA (4.27 g, 37.41 mmol, 2.77 mL, 49.11 eq) at 10° C. with ice-water bath. The mixture was stirred at 20° C. for 3 hr. TLC and LCMS showed the reactant was consumed and a major spot detected. The mixture was concentrated in vacuum to afford the title compound (250.00 mg, 740.24 μmol, 97.18% yield) as white solid. $^1$H NMR (400 MHz, DMSO-d₆) δ 10.22 (s, 1H), 7.96 (dd, J=2.64, 6.90 Hz, 1H), 7.49 (ddd, J=2.57, 4.30, 9.07 Hz, 1H), 7.31-7.41 (m, 1H), 3.02 (d, J=11.54 Hz, 1H), 2.57-2.83 (m, 5H), 2.09 (d, J=10.16 Hz, 1H), 1.65-1.86 (m, 1H).

Step 6. N5-(3-chloro-4-fluoro-phenyl)-N3-hydroxy-N3-methyl-4,5,6,7-tetrahydro-2H-indazole-3,5-dicarboxamide. To a solution of 5-[(3-chloro-4-fluoro-phenyl)carbamoyl]-4,5,6,7-tetrahydro-2H-indazole-3-carboxylic acid (100.00 mg, 296.09 μmol, 1.00 eq) and N-methylhydroxylamine (74.19 mg, 888.28 μmol, 3.00 eq, HCl) in DMF (2.00 mL) was added HATU (135.10 mg, 355.31 μmol, 1.20 eq) and DIPEA (191.34 mg, 1.48 mmol, 258.56 μL5.00 eq). The mixture was stirred at 20° C. for 16 hr. LCMS showed the reaction was completed. The reaction mixture was quenched by water (20 mL) and extracted with ethyl acetate (20 mL*3). The combined organic layers were washed with brine (20 mL), dried over anhydrous Na₂SO₄ and concentrated under reduced pressure to afford the title compound (90.00 mg, 223.30 μmol, 75.42% yield, 91% purity) as yellow solid. LCMS: 367/369 [M+1].

Step 7. N-(3-chloro-4-fluoro-phenyl)-4-(hydroxymethyl)-2-methyl-1-oxo-4,5,8,9,10,11-hexahydro-[1,2,5]oxadiazepino[5,4-b]indazole-10-carboxamide. To a solution of N5-(3-chloro-4-fluoro-phenyl)-N3-hydroxy-N3-methyl-4,5,6,7-tetrahydro-2H-indazole-3,5-dicarboxamide (50.00 mg, 136.33 μmol, 1.00 eq) and 3-bromooxetane (37.35 mg, 272.65 μmol, 2.00 eq) in DMF (2.00 mL) was added Cs$_2$CO$_3$ (66.63 mg, 204.49 μmol, 1.50 eq) and TBAI (5.04 mg, 13.63 μmol, 0.10 eq). The mixture was stirred at 80° C. for 7.5 hr. LCMS showed the reactant consumed and the major desired product detected. The mixture was poured into water (20 mL), extracted with ethyl acetate (10 mL*3), the organic layer was washed with brine (20 mL), dried over anhydrous Na$_2$SO$_4$ and concentrated in vacuum. The crude was purified by prep-HPLC to afford N-(3-chloro-4-fluoro-phenyl)-4-(hydroxymethyl)-2-methyl-1-oxo-4,5,8,9,10,11-hexahydro-[1,2,5]oxadiazepino[5,4-b]indazole-10-carboxamide (45.00 mg, 101.10 μmol, 74.16% yield, 95% purity) as white solid. LCMS: 423/425 [M+1]. 1H NMR (400 MHz, CHLOROFORM-d) δ 7.74 (dd, J=2.26, 6.53 Hz, 1H), 7.56 (br d, J=10.04 Hz, 1H), 7.34 (td, J=2.13, 4.77 Hz, 1H), 7.08 (dt, J=1.19, 8.75 Hz, 1H), 4.45-4.63 (m, 2H), 4.34-4.43 (m, 1H), 3.63-3.88 (m, 2H), 3.31 (d, J=1.25 Hz, 3H), 3.10-3.25 (m, 1H), 2.82-3.04 (m, 2H), 2.40-2.71 (m, 3H), 2.26 (br d, J=13.05 Hz, 1H), 1.94-2.09.

Compound 210: (4S,9R)—N-(3-cyano-4-fluorophenyl)-2,9-dimethyl-1-oxo-4-((2,2,2-trifluoroethoxy)methyl)-1,4,5,8,9,11-hexahydropyrido[4',3':3,4]pyrazolo[5,1-d][1,2,5]oxadiazepine-10(2H)-carboxamide

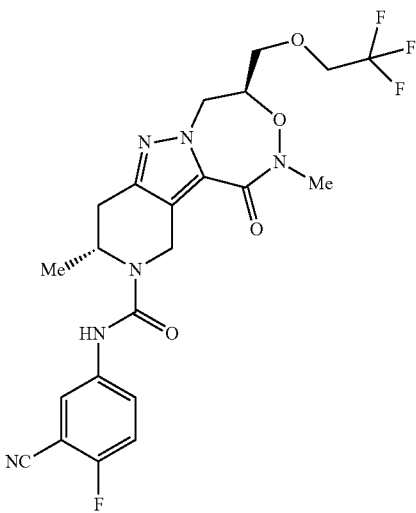 [SMILES: C[C@@H]1Cc2nn3c(c2CN1C(=O)Nc1ccc(F)c(C#N)c1)C(=O)N(C)O[C@H](COCC(F)(F)F)C3]

Step 1. tert-Butyl (5R)-5,13-dimethyl-14-oxo-11-(2,2,2-trifluoroethoxymethyl)-12-oxa-4,8,9,13-tetrazatricyclo[7.5.0.0$^{2.7}$]tetradeca-1,7-diene-4-carboxylate. NaH (10.04 mg, 251.08 μmol, 22.70 μL, 60% purity, 1.0 eq) was added to a solution of tert-butyl (5R)-11-(hydroxymethyl)-5,13-dimethyl-14-oxo-12-oxa-4,8,9,13-tetrazatricyclo[7.5.0.0$^{2.7}$]tetradeca-1,7-diene-4-carboxylate (100.00 mg, 251.08 μmol, 1.00 eq) in THF (1.00 mL) with stirring at −10° C. for 0.5 h under N$_2$ Then a solution of 2,2,2-trifluoroethyl trifluoromethanesulfonate (233.11 mg, 1.00 mmol, 35.39 μL, 4 eq) in THF (0.5 mL) was added into the mixture. The mixture was stirred at 0° C. for 2 h. The mixture was cooled to −10° C., and NaH (10.04 mg, 251.08 μmol, 60% purity, 1.0 eq) was added, and the mixture was stirred for 30 min, followed by 2,2,2-trifluoroethyl trifluoromethanesulfonate (233.11 mg, 1.00 mmol, 4 eq) was added. The mixture was stirred at 0° C. for 1 h. The mixture was poured into 10 mL of ice aqueous 1N HCl solution and extracted with EtOAc (15 mL*3). The organic layers were combined and dried over anhydrous Na$_2$SO$_4$, filtered and concentrated to give the residue. The residue was purified by prep-TLC (Ethyl acetate: Petroleum ether=1:3) to give the title compound (30 mg, 26.64% yield) as colorless oil and by-product tert-butyl (5R)-5,13-dimethyl-11-methylene-14-oxo-12-oxa-4,8,9,13-tetrazatricyclo[7.5.0.0$^{2.7}$]tetradeca-1,7-diene-4-carboxylate (45 mg, 51.44% yield) as colorless oil.

Step 2. (5R)-5,13-Dimethyl-11-(2,2,2-trifluoroethoxymethyl)-12-oxa-4,8,9,13-tetrazatricyclo[7.5.0.0$^{2.7}$]tetradeca-1,7-dien-14-one. To a solution of tert-butyl (5R)-5,13-dimethyl-14-oxo-11-(2,2,2-trifluoroethoxymethyl)-12-oxa-4,8,9,13-tetrazatricyclo[7.5.0.0$^{2.7}$]tetradeca-1,7-diene-4-carboxylate (58 mg, 129.34 μmol, 1 eq) in DCM (3 mL) was added TFA (462.00 mg, 4.05 mmol, 0.3 mL, 31.33 eq), then the mixture was stirred at 15° C. for 1 h. The mixture was directly concentrated in vacuo to afford the title compound (60 mg, crude, TFA) as yellow oil, which was directly used in the next step.

Step 3. (4S,9R)—N-(3-cyano-4-fluorophenyl)-2,9-dimethyl-1-oxo-4-((2,2,2-trifluoroethoxy)methyl)-1,4,5,8,9,11-hexahydropyrido[4',3':3,4]pyrazolo[5,1-d][1,2,5]oxadiazepine-10(2H)-carboxamide. To a solution of (5R)-5,13-dimethyl-11-(2,2,2-trifluoroethoxymethyl)-12-oxa-4,8,9,13-tetrazatricyclo[7.5.0.0$^{2.7}$]tetradeca-1,7-dien-14-one (60 mg, 129.77 μmol, 1 eq, TFA) in DCM (7 mL) was added TEA (78.79 mg, 778.64 μmol, 108.38 μL, 6 eq) and (5R)-5,13-dimethyl-11-(2,2,2-trifluoroethoxymethyl)-12-oxa-4,8,9,13-tetrazatricyclo[7.5.0.0$^{2.7}$]tetradeca-1,7-dien-14-one (60 mg, 129.77 μmol, 1 eq, TFA), then the mixture was stirred at 15° C. for 16 h. The mixture was concentrated in vacuo. The residue was purified by prep-HPLC (FA) to obtain the title compound (43 mg, 84.24 μmol, 64.91% yield, 100% purity) as white solid. LCMS: 511[M+1]; $^1$H NMR (400 MHz, CDCl$_3$) δ=7.78 (dd, J=2.82, 5.46 Hz, 1H), 7.58 (m, 1H), 7.11-7.18 (m, 1H), 6.54 (s, 1H), 5.13 (m, 1H), 4.84 (d, J=15.69 Hz, 1H), 4.63-4.69 (m, 1H), 4.55-4.62 (m, 1H), 4.50 (d, J=15.56 Hz, 1H), 4.39-4.46 (m, 1H), 3.88-3.97 (m, 2H), 3.73-3.87 (m, 2H), 3.31 (s, 3H), 3.05 (dd, J=5.83, 16.00 Hz, 1H), 2.70 (d, J=15.94 Hz, 1H), 1.20 (d, J=6.90 Hz, 3H).

Compound 211: (S*)—N-(3-cyano-4-fluorophenyl)-2-methyl-1-oxo-4-((2,2,2-trifluoroethoxy)methyl)-1,4,5,8,9,11-hexahydropyrido[4',3':3,4]pyrazolo[5,1-d][1,2,5]oxadiazepine-10(2H)-carboxamide

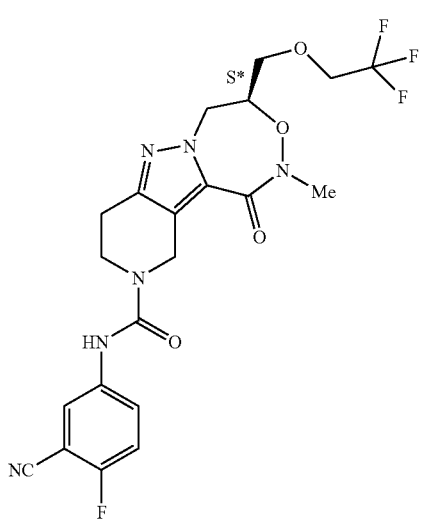 [SMILES: CN1O[C@H](COCC(F)(F)F)Cn2nc3c(c2C1=O)CN(C(=O)Nc1ccc(F)c(C#N)c1)CC3]

Step 1. tert-Butyl 4-(2,2-difluoroethoxymethyl)-2-methyl-1-oxo-5,8,9,11-tetrahydro-4H-pyrido[2,3]pyrazolo[2,4-d][1,2,5]oxadiazepine-10-carboxylate. To a suspension of NaH (85.13 mg, 2.13 mmol, 60% purity, 2.5 eq) in DMF (3 mL) was added a solution of tert-butyl 4-(hydroxymethyl)-2-methyl-1-oxo-5,8,9,11-tetrahydro-4H-pyrido[2,3]pyrazolo[2,4-d][1,2,5]oxadiazepine-10-carboxylate (single enantiomer, 300 mg, 851.34 μmol, 1 eq) in DMF (0.5 mL) at −40° C. dropwise under $N_2$. The mixture was stirred at −40° C. for 0.5 hr. 2,2-difluoroethyl trifluoromethanesulfonate (546.85 mg, 2.55 mmol, 3 eq) was added at −40° C. The reaction mixture was stirred at −20° C. for 1 hr. The reaction mixture was quenched with 1N HCl (30 mL) at 0° C. and extracted with EA (30 mL*3). The combined organic layers were dried over $Na_2SO_4$, filtered and concentrated in vacuo. The residue was combined with another batch to purify by column chromatography ($SiO_2$, PE:EA:3:1-1:1) to give 400 mg of the title compound as a white solid.

Step 2. 4-(2,2-difluoroethoxymethyl)-2-methyl-4,5,8,9,10,11-hexahydropyrido[2,3]pyrazolo[2,4-d][1,2,5]oxadiazepin-1-one. To a solution of tert-butyl 4-(2,2-difluoroethoxymethyl)-2-methyl-1-oxo-5,8,9,11-tetrahydro-4H-pyrido[2,3]pyrazolo[2,4-d][1,2,5] oxadiazepine-10-carboxylate (160 mg, 384.23 μmol, 1 eq) in DCM (4 mL) was added TFA (6.16 g, 54.02 mmol, 4.00 mL, 140.60 eq). The mixture was stirred at 20° C. for 30 min. TLC (DCM:MeOH=10:1) showed starting material was consumed. The mixture was concentrated in vacuo to give the title compound (180 mg, crude, TFA) as brown oil.

Step 3. (S*) N-(3-cyano-4-fluoro-phenyl)-4-(2,2-difluoroethoxymethyl)-2-methyl-1-oxo-5,8,9,11-tetrahydro-4H-pyrido[2,3]pyrazolo[2,4-d][1,2,5]oxadiazepine-10-carboxamide. To a mixture of 4-(2,2-difluoroethoxymethyl)-2-methyl-4,5,8,9,10,11-hexahydropyrido[2,3]pyrazolo[2,4-d][1,2,5]oxadiazepin-1-one (84 mg, 195.20 μmol, 1 eq, TFA) and phenyl N-(3-cyano-4-fluoro-phenyl)carbamate (50.02 mg, 195.20 μmol, 1 eq) in DCM (5 mL) was added TEA (98.76 mg, 976.00 μmol, 135.85 μL, 5 eq). The mixture was stirred at 20° C. for 2 h. LCMS showed one main peak with desired MS was detected. The mixture was concentrated in vacuo. The residue was purified by prep-HPLC(FA) to give the title compound (45.93 mg, 94.72 μmol, 48.52% yield, 98.66% purity) as white solid. LCMS: 479 [M+1]. 1H NMR (400 MHz, CDCl$_3$) δ=7.69 (dd, J=2.75, 5.44 Hz, 1H), 7.52 (ddd, J=2.81, 4.58, 9.11 Hz, 1H), 7.06 (t, J=8.68 Hz, 1H), 6.67 (s, 1H), 5.68-5.98 (m, 1H), 4.56 (quin, J=5.72 Hz, 1H), 4.45-4.52 (m, 1H), 4.30-4.37 (m, 1H), 3.75-3.84 (m, 2H), 3.60-3.74 (m, 4H), 3.23 (s, 3H), 2.79 (t, J=5.81 Hz, 2H).

Compound 212: (S*)-4-((2,2-difluoroethoxy)methyl)-N-(4-fluoro-3-(trifluoromethyl)phenyl)-2-methyl-1-oxo-1,4,5,8,9,11-hexahydropyrido[4',3':3,4]pyrazolo[5,1-d][1,2,5]oxadiazepine-10(2H)-carboxamide

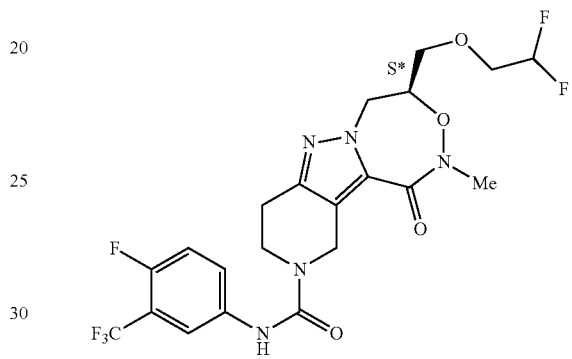

The title compound was prepared in a manner analogous to Compound 211 using 4-(2,2-difluoroethoxymethyl)-2-methyl-4,5,8,9,10,11-hexahydropyrido[2,3]pyrazolo[2,4-d][1,2,5]oxadiazepin-1-one and phenyl (4-fluoro-3-(trifluoromethyl)phenyl)carbamate in step 3. LCMS: 522 [M+1]; $^1$H NMR (400 MHz, CDCl$_3$) δ=7.68 (dd, J=2.75, 6.17 Hz, 1H), 7.57-7.63 (m, 1H), 7.15 (t, J=9.35 Hz, 1H), 6.68 (s, 1H), 5.75-6.09 (m, 1H), 4.73 (s, 2H), 4.54-4.68 (m, 2H), 4.38-4.46 (m, 1H), 3.84-3.96 (m, 2H), 3.69-3.83 (m, 4H), 3.32 (s, 3H), 2.88 (t, J=5.75 Hz, 2H).

*Pure but unknown enantiomer.

Compound 213: (R)—N-(3-cyano-4-fluorophenyl)-2,4,4,9-tetramethyl-1-oxo-1,4,5,8,9,11-hexahydropyrido[4',3':3,4]pyrazolo[5,1-d][1,2,5]oxadiazepine-10(2H)-carboxamide

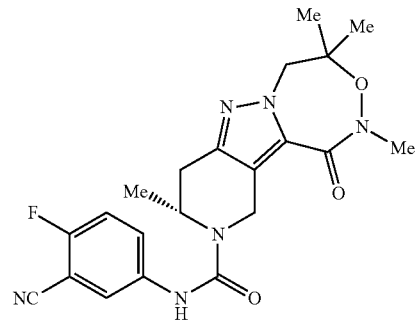 [SMILES: C[C@@H]1Cc2nn3c(c2CN1C(=O)Nc1ccc(F)c(C#N)c1)C(=O)N(C)OC(C)(C)C3]

Step 1. tert-Butyl N-hydroxy-N-methyl-carbamate. To a solution of N-methylhydroxylamine (20 g, 425.02 mmol, 1 eq, HCl) and NaHCO$_3$ (53.56 g, 637.53 mmol, 24.80 mL, 1.5 eq) in THF (400 mL) and H$_2$O (200 mL) was added a solution Boc$_2$O (92.76 g, 425.02 mmol, 97.64 mL, 1 eq) in THF (100 mL) at 0° C. slowly. Then the mixture was stirred at 16° C. for 16 hr. The mixture was diluted with H$_2$O (200 mL) and extracted with EtOAc (200 mL*3). Then the organic layer was extracted with 1N HCl (200 mL). The combined organic layered were dried over MgSO$_4$, filtered and concentrated under reduced pressure to give the title compound (29.6 g, crude) as red liquid.

Step 2. Methyl 2-[tert-butoxycarbonyl(methyl)amino] oxy-2-methyl-propanoate. To a solution of tert-butyl N-hydroxy-N-methyl-carbamate (5 g, 33.97 mmol, 1 eq) in MeOH (50 mL) was added CH$_3$ONa (1.84 g, 33.97 mmol, 1 eq) and methyl 2-bromo-2-methyl-propanoate (6.15 g, 33.97 mmol, 4.39 mL, 1 eq) at 0° C. Then the mixture was heated to 60° C. with stirring for 16 h. Then to the mixture was added another batch of CH$_3$ONa (0.92 g, 17 mmol, 0.5 eq) and methyl 2-bromo-2-methylpropanoate (3.08 g, 17 mmol, 2.2 mL, 0.5 eq). The mixture was stirred at 60° C. for 5 hr. The mixture was concentrated under reduced pressure. The residue was dissolved with H$_2$O (80 mL) and extracted with EA (80 mL*3). The combined organic layers were dried over Na$_2$SO$_4$, filtered and concentrated under reduced pressure. The residue was purified by column chromatography (SiO$_2$, Petroleum ether/Ethyl acetate=100/1 to 20/1) to afford the title compound (8.05 g, crude) as white liquid.

Step 3. tert-Butyl N-(2-hydroxy-1,1-dimethyl-ethoxy)-N-methyl-carbamate. To a suspension of LiBH$_4$ (1.42 g, 65.11 mmol, 2 eq) in THF (80 mL) was added a solution of methyl 2-[tert-butoxycarbonyl(methyl)amino]oxy-2-methyl-propanoate (8.05 g, 32.55 mmol, 1 eq) in THF (20 mL) at −40° C. under N$_2$. Then the mixture was stirred at 0° C. for 4 hr. The reaction was poured into sat. aq. NH$_4$Cl (200 mL) and extracted with EtOAc (150 mL*3). The combined organic layers were dried over anhydrous Na$_2$SO$_4$, filtered and concentrated under reduced pressure. The residue was purified via column chromatography (SiO$_2$, Petroleum ether/Ethyl acetate=100/1 to 20/1) to give the title compound (3.8 g, 17.33 mmol, 53.24% yield) as white liquid and impure product with 80% purity (2.4 g, 8.76 mmol) as white liquid.

Step 4. 2-Methyl-2-(methylaminooxy)propan-1-ol. To a solution of tert-butyl N-(2-hydroxy-1,1-dimethyl-ethoxy)-N-methyl-carbamate (3.8 g, 17.33 mmol, 1 eq) in dioxane (10 mL) was added HCl/dioxane (4 M, 6 mL, 1.38 eq). The mixture was stirred at 16° C. for 2 hr. The mixture was concentrated under reduced pressure to give the title compound (3.04 g, crude, HCl) as light yellow oil, used in the next step directly.

Step 5. tert-Butyl (6R)-3-[(2-hydroxy-1,1-dimethyl-ethoxy)-methyl-carbamoyl]-6-methyl-2,4,6,7-tetrahydropyrazolo[4,3-c]pyridine-5-carboxylate. To a solution of (6R)-5-tert-butoxycarbonyl-6-methyl-2,4,6,7-tetrahydropyrazolo[4,3-c]pyridine-3-carboxylic acid (800 mg, 2.84 mmol, 1 eq) and 2-methyl-2-(methylaminooxy)propan-1-ol (575.34 mg, 3.70 mmol, 1.3 eq, HCl) in pyridine (5 mL) was added EDCI (708.73 mg, 3.70 mmol, 1.3 eq). The mixture was stirred at 30° C. for 16 hr. The mixture was combined with another batch and was diluted with H$_2$O (50 mL) and extracted with EtOAc (50 mL*3). The combined organic layers were washed with 1N HCl (100 mL*2), dried over anhydrous Na$_2$SO$_4$ and filtered. The filtrate was concentrated under reduced pressure. The residue was purified by column chromatography (SiO$_2$, Petroleum ether/Ethyl acetate=20/1 to 1/5) to give the title compound (918 mg) as light yellow solid.

Step 6. tert-Butyl (R)-6-methyl-3-(methyl((2-methyl-1-((methylsulfonyl)oxy)propan-2-yl)oxy)carbamoyl)-2,4,6,7-tetrahydro-5H-pyrazolo[4,3-c]pyridine-5-carboxylate and tert-butyl (R)-6-methyl-3-(methyl((2-methyl-1-((methylsulfonyl)oxy)propan-2-yl)oxy)carbamoyl)-2-(methylsulfonyl)-2,4,6,7-tetrahydro-5H-pyrazolo[4,3-c]pyridine-5-carboxylate. To a solution of tert-butyl (6R)-3-[(2-hydroxy-1,1-dimethyl-ethoxy)-methyl-carbamoyl]-6-methyl-2,4,6,7-tetrahydropyrazolo[4,3-c]pyridine-5-carboxylate (600 mg, 1.57 mmol, 1 eq) in DCM (10 mL) was added DIEA (608.27 mg, 4.71 mmol, 819.78 µL, 3 eq) and MsCl (215.65 mg, 1.88 mmol, 145.71 µL, 1.2 eq) at 0° C. The mixture was stirred at 0° C. for 2 h. Additional MsCl (215.65 mg, 1.88 mmol, 145.71 µL, 1.2 eq) was added and the mixture was stirred at 0° C. for 0.5 hr. The mixture was diluted with H$_2$O (20 mL) and extracted with DCM (20 mL). The organic layer was washed with 0.5N HCl (10 mL), dried over Na$_2$SO$_4$, filtered and concentrated in vacuum to give a mixture (900 mg crude) of tert-butyl (R)-6-methyl-3-(methyl((2-methyl-1-((methylsulfonyl)oxy)propan-2-yl)oxy)carbamoyl)-2,4,6,7-tetrahydro-5H-pyrazolo[4,3-c]pyridine-5-carboxylate and tert-butyl (R)-6-methyl-3-(methyl((2-methyl-1-((methylsulfonyl)oxy)propan-2-yl)oxy)carbamoyl)-2-(methylsulfonyl)-2,4,6,7-tetrahydro-5H-pyrazolo[4,3-c]pyridine-5-carboxylate as white solid, used in the next step directly.

Step 7. tert-Butyl (5R)-5,11,11,13-tetramethyl-14-oxo-12-oxa-4,8,9,13-tetrazatricyclo[7.5.0.0$^{2.7}$]tetradeca-1,7-diene-4-carboxylate. To a mixture of tert-butyl (R)-6-methyl-3-(methyl((2-methyl-1-((methylsulfonyl)oxy)propan-2-yl)oxy)carbamoyl)-2,4,6,7-tetrahydro-5H-pyrazolo[4,3-c]pyridine-5-carboxylate and tert-butyl (R)-6-methyl-3-(methyl((2-methyl-1-((methyl sulfonyl)oxy)propan-2-yl)oxy)carbamoyl)-2-(methyl sulfonyl)-2,4,6,7-tetrahydro-5H-pyrazolo[4,3-c]pyridine-5-carboxylate (820 mg crude) in THF (15 mL) was added NaH (164.00 mg, 4.10 mmol, 60% purity, 2.5 eq) at 0° C. The mixture was heated to 45° C. with stirring for 14 hr. The mixture was poured into aqueous 1N HCl (40 mL) solution and extracted with EtOAc (20 mL*3). The combined organic layers were washed with aqueous saturated NaHCO$_3$ solution (40 mL), dried over Na$_2$SO$_4$, filtered and concentrated under reduced pressure. The residue was purified by column chromatography (SiO$_2$, Petroleum ether/Ethyl acetate=30/1 to 1:1) to give the title compound (440 mg, 1.15 mmol, 70.16% yield, 95.3% purity) as white solid.

Step 8. (5R)-5,11,11,13-Tetramethyl-12-oxa-4,8,9,13-tetrazatricyclo[7.5.0.0$^{2.7}$]tetradeca-1,7-dien-14-one. To a solution of tert-butyl (5R)-5,11,11,13-tetramethyl-14-oxo-12-oxa-4,8,9,13-tetrazatricyclo[7.5.0.0$^{2.7}$]tetradeca-1,7-diene-4-carboxylate (150 mg, 411.59 µmol, 1 eq) in DCM (5 mL) was added TFA (770.00 mg, 6.75 mmol, 0.5 mL, 16.41 eq). The mixture was stirred at 16° C. for 2 hr. The mixture was concentrated under reduced pressure to give the title compound (164 mg, crude, TFA) yellow oil. The crude title compound was not purified and used in the next step directly.

Step 9. (R)—N-(3-Cyano-4-fluorophenyl)-2,4,4,9-tetramethyl-1-oxo-1,4,5,8,9,11-hexahydropyrido[4',3':3,4]pyrazolo[5,1-d][1,2,5]oxadiazepine-10(2H)-carboxamide. To a solution of (5R)-5,11,11,13-tetramethyl-12-oxa-4,8,9,13-tetrazatricyclo[7.5.0.0$^{2.7}$]tetradeca-1,7-dien-14-one (82 mg, 216.73 µmol, 1 eq, TFA) in DCM (2 mL) was added TEA (109.66 mg, 1.08 mmol, 150.83 µL, 5 eq) and phenyl N-(3-cyano-4-fluoro-phenyl)carbamate (55.53 mg, 216.73 µmol, 1 eq). The mixture was stirred at 16° C. for 16 hr. The mixture was concentrated under reduced pressure. The residue was purified by prep-HPLC (FA) to give the title compound (54.35 mg, 127.32 μmol, 58.75% yield, 99.9% purity) as white solid. LCMS: 427 [M+1]. ¹H NMR (400 MHz, CDCl₃) δ=7.79 (dd, J=2.8, 5.2 Hz, 1H), 7.57-7.58 (m, 1H), 7.15 (t, J=8.4 Hz, 1H), 6.53 (s, 1H), 5.11-5.17 (m, 1H), 4.83 (d, J=15.2 Hz, 1H), 4.51 (d, J=15.2 Hz, 1H), 4.25 (s, 2H), 3.29 (s, 3H), 3.05 (dd, J=2.0, 15.6 Hz, 1H), 2.70 (d, J=15.6 Hz, 1H), 1.38 (d, J=17.6 Hz, 6H), 1.19 (d, J=6.8 Hz, 3H).

Compound 214: (5R)—N-[4-Fluoro-3-(trifluoromethyl)phenyl]-5,11,11,13-tetramethyl-14-oxo-12-oxa-4,8,9,13-tetrazatricyclo[7.5.0.0²·⁷]tetradeca-1,7-diene-4-carboxamide

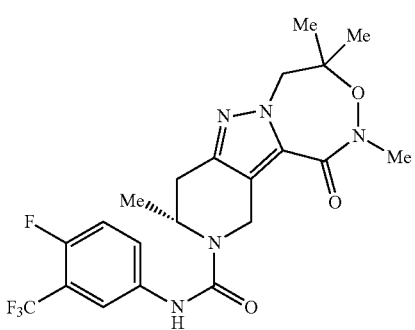 [SMILES: C[C@@H]1Cc2nn3c(c2CN1C(=O)Nc1ccc(F)c(C(F)(F)F)c1)C(=O)N(C)OC(C)(C)C3]

To a solution of (5R)-5,11,11,13-tetramethyl-12-oxa-4,8,9,13-tetrazatricyclo[7.5.0.0²·⁷]tetradeca-1,7-dien-14-one (82 mg, 216.73 μmol, 1 eq, TFA) in DCM (2 mL) was added TEA (131.59 mg, 1.30 mmol, 181.00 μL, 6 eq) and phenyl N-[4-fluoro-3-(trifluoromethyl)phenyl]carbamate (64.85 mg, 216.73 μmol, 1 eq). The mixture was stirred at 16° C. for 16 hr. The mixture was concentrated under reduced pressure. The residue was purified by prep-HPLC (FA) to give the title compound (46.1 mg, 98.01 μmol, 45.22% yield, 99.8% purity) as white solid. LCMS: 470 [M+1]. ¹H NMR (400 MHz, CDCl₃) δ=7.68 (dd, J=2.8, 6.0 Hz, 1H), 7.57-7.60 (m, 1H), 7.14 (t, J=9.2 Hz, 1H), 6.53 (s, 1H), 5.12-5.18 (m, 1H), 4.83 (d, J=15.2 Hz, 1H), 4.51 (d, J=15.2 Hz, 1H), 4.25 (s, 2H), 3.28 (s, 3H), 3.05 (dd, J=5.6, 16.0 Hz, 1H), 2.70 (d, J=16.0 Hz, 1H), 1.38 (d, J=17.6 Hz, 6H), 1.19 (d, J=6.8 Hz, 3H).

Compound 215: (4S,9R)-4-(Hydroxymethyl)-10-(4-iodobenzoyl)-2,9-dimethyl-4,5,8,9,10,11-hexahydropyrido[4',3':3,4]pyrazolo[5,1-d][1,2,5]oxadiazepin-1(2H)-one

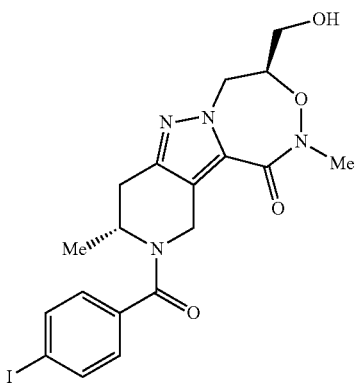 [SMILES: C[C@@H]1Cc2nn3c(c2CN1C(=O)c1ccc(I)cc1)C(=O)N(C)O[C@H](CO)C3]

Step 1. (4S,9R)-4-(Hydroxymethyl)-2,9-dimethyl-4,5,8,9,10,11-hexahydropyrido[2,3]pyrazolo[2,4-d][1,2,5]oxadiazepin-1-one. A mixture of tert-butyl (4S,9R)-4-(hydroxymethyl)-2,9-dimethyl-1-oxo-5,8,9,11-tetrahydro-4H-pyrido[2,3]pyrazolo[2,4-d][1,2,5]oxadiazepine-10-carboxylate (120 mg, 327.50 μmol, 1 eq), and TFA (3.08 g, 27.01 mmol, 2.00 mL, 82.48 eq) in DCM (4 mL) was stirred at 15° C. for 1 hr under N₂ atmosphere. The mixture was concentrated in vacuum to give the title compound (124 mg, 326.04 μmol, 99.55% yield, TFA) as a yellow oil, which was used directly in next step.

Step 2. (4S,9R)-4-(Hydroxymethyl)-10-(4-iodobenzoyl)-2,9-dimethyl-4,5,8,9,10,11-hexahydropyrido[4',3':3,4]pyrazolo[5,1-d][1,2,5]oxadiazepin-1(2H)-one. A mixture of (4S,9R)-4-(hydroxymethyl)-2,9-dimethyl-4,5,8,9,10,11-hexahydropyrido[2,3]pyrazolo[2,4-d][1,2,5]oxadiazepin-1-one (124 mg, 326.04 μmol, 1 eq, TFA), 4-iodobenzoyl chloride (104.25 mg, 391.25 μmol, 1.2 eq), TEA (98.98 mg, 978.13 μmol, 136.14 μL, 3 eq), and DMAP (3.98 mg, 32.60 μmol, 0.1 eq) in DCM (5 mL) was degassed and purged with N₂ for 3 times. The mixture was stirred at 15° C. for 16 hr under N₂ atmosphere. The mixture was concentrated in vacuum. The residue was purified by Prep-HPLC to give the title compound (150.08 mg, 281.23 μmol, 86.26% yield, 93% purity) as a white solid. LCMS: 497 [M+1]. ¹H NMR (400 MHz, CDCl₃) δ 7.78 (br d, J=7.53 Hz, 2H), 7.17 (d, J=7.91 Hz, 2H), 5.36-5.71 (m, 1H), 4.18-4.81 (m, 5H), 3.63-3.92 (m, 2H), 3.29 (br s, 4H), 2.50-2.77 (m, 1H), 1.84-2.28 (m, 1H), 1.25 (br s, 2H), 1.09-1.37 (m, 1H).

Compound 216: N-(3-Chloro-4-fluoro-phenyl)-2-methyl-1-oxo-3,4,5,8,9,11-hexahydropyrido[2,3]pyrazolo[2,4-c][1,2,5]triazepine-10-carboxamide

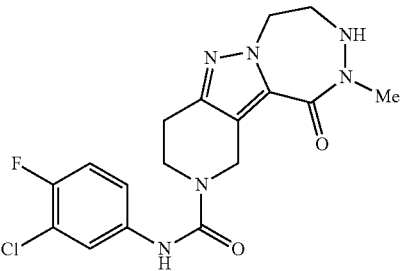 [SMILES: CN1NCCn2nc3c(c2C1=O)CN(C(=O)Nc1ccc(F)c(Cl)c1)CC3]

Step 1. tert-Butyl N-(benzyloxy carbonylamino)-N-methyl-carbamate. To a solution of tert-butyl N-amino-N-methyl-carbamate (3.00 g, 20.52 mmol, 1.00 eq) in dioxane (20.00 mL) was added a solution of NaOH (820.80 mg, 20.52 mmol, 1.00 eq) in H₂O (5.00 mL), followed by CbzCl (4.55 g, 26.68 mmol, 3.79 mL, 1.30 eq), the reaction mixture was stirred at 25° C. for one hour. The reaction mixture was diluted with EA (200 mL) and washed with water (80 mL×3), the organic phase was dried with anhydrous Na₂SO₄, filtered and concentrated in vacuo. The residue was purified by silica gel chromatography to afford the title compound (4.00 g, 14.27 mmol, 69.54% yield) was obtained as yellow oil. LCMS: 303 [M+23].

Step 2. Methyl 2-[benzyloxycarbonyl-[tert-butoxycarbonyl(methyl)amino]amino]acetate. To a mixture of tert-butyl N-(benzyloxycarbonylamino)-N-methyl-carbamate (4.00 g, 14.27 mmol, 1.00 eq) and methyl 2-bromoacetate (3.27 g, 21.41 mmol, 2.02 mL, 1.50 eq) in DMF (10.00 mL) was added K₂CO₃ (2.96 g, 21.41 mmol, 1.50 eq) under N₂, the reaction mixture was stirred at 50° C. for 16 hours. The reaction mixture was diluted with EA (150 mL) and washed with water (50 mL×3), the organic phase was dried with anhydrous Na$_2$SO$_4$, filtered and concentrated in vacuo. The residue was purified by silica gel chromatography to afford the title compound (3.50 g, 9.93 mmol, 69.60% yield) as yellow oil. LCMS: 375 [M+23].

Step 3. tert-Butyl N-[benzyloxycarbonyl(2-hydroxyethyl) amino]-N-methyl-carbamate. To a solution of methyl 2-[benzyloxycarbonyl-[tert-butoxycarbonyl(methyl)amino] amino]acetate (3.50 g, 9.93 mmol, 1.00 eq) in THF (30.00 mL) was added LiBH$_4$ (432.55 mg, 19.86 mmol, 2.00 eq) under N$_2$ at 0° C., the reaction mixture was stirred at 20° C. for 2 hours The reaction was quenched with water (150 mL) and then extracted with EA (200 mL×3), the combined organic phase was dried over anhydrous Na$_2$SO$_4$, filtered and concentrated in vacuo. The residue was purified by silica gel chromatography to afford the title compound (2.40 g, 7.40 mmol, 74.51% yield) was obtained as yellow oil. LCMS: 347 [M+23].

Step 4. Benzyl N-(2-hydroxyethyl)-N-(methylamino) carbamate. To a solution of tert-butyl N-[benzyloxycarbonyl (2-hydroxyethyl)amino]-N-methyl-carbamate (2.40 g, 7.40 mmol, 1.00 eq) in dioxane (20.00 mL) was added HCl/ dioxane (4 M, 20.00 mL, 10.81 eq), the reaction mixture was stirred at 25° C. for one hour. Organics were removed under reduced pressure to afford the title compound (1.80 g, crude, HCl) as yellow oil. The crude product was used in next step directly without purification.

Step 5. tert-Butyl 3-[[benzyloxycarbonyl(2-hydroxyethyl)amino]-methyl-carbamoyl]-2,4,6,7-tetrahydropyrazolo[4,3-c]pyridine-5-carboxylate. To a mixture of 5-tert-butoxycarbonyl-2,4,6,7-tetrahydropyrazolo[4,3-c]pyridine-3-carboxylic acid (1.50 g, 5.61 mmol, 1.00 eq) and benzyl N-(2-hydroxyethyl)-N-(methylamino)carbamate (1.76 g, 6.73 mmol, 1.20 eq, HCl) in DMF (20.00 mL) were added PYBOP (3.50 g, 6.73 mmol, 1.20 eq), HOBt (909.97 mg, 6.73 mmol, 1.20 eq) and DIPEA (2.90 g, 22.45 mmol, 3.92 mL, 4.00 eq), the reaction mixture was stirred at 40° C. for 2 hours. The reaction mixture was diluted with EA (200 mL) and washed with water (100 mL×3), the organic layer was dried with anhydrous Na$_2$SO$_4$, filtered and concentrated in vacuo. The residue was purified by silica gel chromatography. Further purification by prep-HPLC (FA) afforded the title compound (1.50 g, 2.53 mmol, 45.17% yield, 80% purity) as yellow solid. LCMS: 474 [M+1].

Step 6. tert-Butyl 3-[[benzyloxycarbonyl (2-methylsulfonyloxyethyl)amino]-methyl-carbamoyl]-2,4,6,7-tetrahydropyrazolo[4,3-c]pyridine-5-carboxylate. To a mixture of tert-butyl 3-[[benzyloxycarbonyl(2-hydroxyethyl)amino]-methyl-carbamoyl]-2,4,6,7-tetrahydropyrazolo[4,3-c] pyridine-5-carboxylate (500.00 mg, 1.06 mmol, 1.00 eq) and TEA (214.52 mg, 2.12 mmol, 293.86 μL, 2.00 eq) in DCM (10.00 mL) was added MsCl (242.85 mg, 2.12 mmol, 164.09 μL, 2.00 eq) under N$_2$ at 0° C., the reaction mixture was stirred at 20° C. for 30 minutes. The reaction was quenched with water (30 mL) and then extracted with DCM (80 mL×2), the combined organic layers were dried over anhydrous Na$_2$SO$_4$, filtered and concentrated in vacuum. The residue was purified by silica gel chromatography to give the title compound (380.00 mg, 661.34 μmol, 62.39% yield, 96% purity) as white solid. LCMS: 552 [M+1].

Step 7. O$_3$-benzyl O$_{10}$-tert-butyl 2-methyl-1-oxo-5,8,9,11-tetrahydro-4H-pyrido[2,3]pyrazolo[2,4-c][1,2,5]triazepine-3,10-dicarboxylate. To a solution of tert-butyl 3-[[benzyloxycarbonyl(2-methylsulfonyloxyethyl)amino]-methyl-carbamoyl]-2,4,6,7-tetrahydropyrazolo[4,3-c]pyridine-5-carboxylate (380.00 mg, 688.89 μmol, 1.00 eq) in THF (15.00 mL) was added NaH (55.11 mg, 1.38 mmol, 60% purity, 2.00 eq) under N$_2$ at −10° C., the reaction mixture was stirred at 25° C. for 16 hours. The reaction was quenched with water (20 mL) and then extracted with EA (50 mL×3), the combined organic layers were dried over anhydrous Na$_2$SO$_4$, filtered and concentrated in vacuo. The residue was purified by silica gel chromatography to afford the title compound (130.00 mg, 285.39 μmol, 41.43% yield) as white solid. LCMS: 456 [M+1].

Step 8. tert-Butyl 2-methyl-1-oxo-3,4,5,8,9,11-hexahydropyrido[2,3]pyrazolo[2,4-c][1,2,5]triazepine-10-carboxylate. To a solution of O$_3$-benzyl O$_{10}$-tert-butyl 2-methyl-1-oxo-5,8,9,11-tetrahydro-4H-pyrido[2,3]pyrazolo[2,4-c][1,2,5]triazepine-3,10-dicarboxylate (250.00 mg, 548.84 μmol, 1.00 eq) in MeOH (15.00 mL) was added Pd/C (50.00 mg, 10% purity) under N$_2$, the suspension was degassed under vacuum and purged with H$_2$ three times, the mixture was stirred under H$_2$ (15 psi) at 25° C. for 2 hours. The reaction mixture was filtered and the filtrate was concentrated under reduced pressure to give the title compound (145.00 mg, crude) as yellow oil. The crude product was used in the next step directly without purification. LCMS: 322 [M+1].

Step 9. 2-Methyl-4,5,8,9,10,11-hexahydro-3H-pyrido[2,3]pyrazolo[2,4-c][1,2,5]triazepin-1-one. To a solution of tert-butyl 2-methyl-1-oxo-3,4,5,8,9,11-hexahydropyrido[2,3]pyrazolo[2,4-c][1,2,5]triazepine-10-carboxylate (15.00 mg, 46.67 μmol, 1.00 eq) in DCM (2.00 mL) was added TFA (384.97 mg, 3.38 mmol, 249.98 μL, 72.34 eq), the reaction mixture was stirred at 25° C. for one hour. Solvent was removed under reduced pressure. The title compound (15.00 mg, crude, TFA) was obtained as yellow oil. The crude product was used in next step directly without purification.

Step 10. N-(3-Chloro-4-fluoro-phenyl)-2-methyl-1-oxo-3,4,5,8,9,11-hexahydropyrido[2,3]pyrazolo[2,4-c][1,2,5]triazepine-10-carboxamide. To a mixture of 2-methyl-4,5,8,9,10,11-hexahydro-3H-pyrido[2,3]pyrazolo[2,4-c][1,2,5]triazepin-1-one (15.00 mg, 44.74 μmol, 1.00 eq, TFA) in DCM (2.00 mL) was added TEA (18.11 mg, 178.95 μmol, 24.81 μL, 4.00 eq), followed by phenyl N-(3-chloro-4-fluoro-phenyl)carbamate (11.89 mg, 44.74 μmol, 1.00 eq), the reaction mixture was stirred at 25° C. for 2 hours. The mixture was diluted with water (20 mL) and extracted with DCM (30 mL×2), the organic layers were combined, dried with anhydrous Na$_2$SO$_4$, filtered and concentrated in vacuo. The residue was purified by prep-HPLC (FA) to afford the title compound (11.00 mg, 26.60 μmol, 59.46% yield, 95% purity) was obtained as white solid. LCMS: 393/395 [M+1]; $^1$H NMR (400 MHz, CDCl$_3$) δ=7.59 (dd, J=2.63, 6.54 Hz, 1H), 7.17-7.24 (m, 1H), 7.02-7.09 (m, 1H), 6.75 (s, 1H), 4.69 (s, 2H), 4.55 (t, J=7.76 Hz, 1H), 4.40 (t, J=6.42 Hz, 2H), 3.86 (t, J=5.81 Hz, 2H), 3.47 (q, J=6.72 Hz, 2H), 3.23 (s, 3H), 2.85 (t, J=5.75 Hz, 2H).

Compound 217: N-(3-Chloro-4-fluorophenyl)-2,3-dimethyl-1-oxo-1,2,3,4,5,8,9,11-octahydro-10H-pyrido[4',3':3,4]pyrazolo[5,1-d][1,2,5]triazepine-10-carboxamide

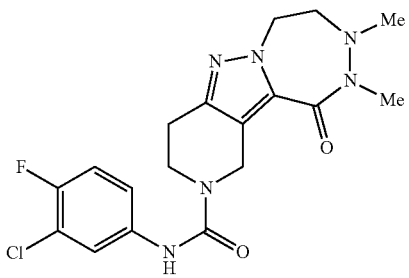 [SMILES: CN1CCn2nc3c(c2C(=O)N1C)CN(C(=O)Nc1ccc(F)c(Cl)c1)CC3]

Step 1. O5-tert-butyl O3-ethyl 2-allyl-6,7-dihydro-4H-pyrazolo[4,3-c]pyridine-3,5-dicarboxylate. To a solution of O5-tert-butyl O3-ethyl 2,4,6,7-tetrahydropyrazolo[4,3-c]pyridine-3,5-dicarboxylate (20.00 g, 67.72 mmol, 1.00 eq) and 3-bromoprop-1-ene (12.29 g, 101.58 mmol, 1.50 eq) in DMF (200.00 mL) was added Cs₂CO₃ (55.16 g, 169.30 mmol, 2.50 eq). Then the mixture was stirred at 25° C. for 16 h. TLC (petroleum ether:EtOAc=3:1) showed that O5-tert-butyl O3-ethyl 2,4,6,7-tetrahydropyrazolo[4,3-c]pyridine-3,5-dicarboxylate was consumed completely and two new spots formed. The mixture was diluted with 100 mL of water and extracted with EtOAc (100 mL*3). The combined organic phase was washed with brine (100 mL) and dried over anhydrous Na₂SO₄, filtered and concentrated in vacuo. The residue was purified via column chromatography (SiO₂, Petroleum ether/Ethyl acetate=50/1 to 3/1) to give the title compound (13.50 g, 40.25 mmol, 59.44% yield) as white solid and its regioisomer (9.50 g, 28.32 mmol, 41.83% yield) as white solid.

Step 2. tert-Butyl ethyl 2-(2-oxoethyl)-6,7-dihydro-4H-pyrazolo[4,3-c]pyridine-3,5-dicarboxylate. To a solution of O5-tert-butyl O3-ethyl 2-allyl-6,7-dihydro-4H-pyrazolo[4,3-c]pyridine-3,5-dicarboxylate (1.00 g, 2.98 mmol, 1.00 eq) in THF (1.00 mL) and H₂O (500.00 µL) was added OsO₄ (75.80 mg, 298.15 µmol, 15.47 µL, 0.10 eq), followed by NaIO₄ (1.91 g, 8.94 mmol, 495.63 µL, 3.00 eq) at 0° C. The mixture was stirred at 25° C. for 5 hr. The mixture was quenched by saturated Na₂S₂O₃ (50 mL) and extracted with EA (80 mL×2). The combined organic layers were dried over Na₂SO₄, filtered and concentrated in vacuo. The residue was used in the next step directly. The title compound (700.00 mg, crude) was obtained as colorless oil.

Step 3. O5-tert-butyl O3-ethyl2-[2-[[tert-butoxycarbonyl(methyl)amino]-methyl-amino]ethyl]-6,7-dihydro-4H-pyrazolo[4,3-c]pyridine-3,5-dicarboxylate. To a solution of tert-butyl N-methyl-N-(methylamino)carbamate (432.14 mg, 2.70 mmol, 1.30 eq) and O5-tert-butyl O3-ethyl 2-(2-oxoethyl)-6,7-dihydro-4H-pyrazolo [4,3-c]pyridine-3,5-dicarboxylate (700.00 mg, 2.07 mmol, 1.00 eq) in EtOH (15.00 mL) was added HOAc (1.25 mg, 20.75 µmol, 1.19 µL, 0.01 eq). The mixture was stirred at 20° C. for 5 hr. NaBH₃CN (391.16 mg, 6.22 mmol, 3.00 eq) was added and the mixture was stirred at 20° C. for 16 hr. The mixture was diluted with H₂O (50 mL) and extracted with EA (60 mL×2). The combined organic layers were dried over Na₂SO₄, filtered and concentrated in vacuo. The residue was purified by column chromatography (PE:EA=15%~25%) and then prep-HPLC (FA) to give the title compound (100.00 mg, 186.88 µmol, 9.03% yield, 90% purity) as colorless oil. ¹H NMR (400 MHz, CDCl₃) δ=4.38-4.60 (m, 4H), 4.17-4.31 (m, 2H), 3.51-3.67 (m, 2H), 2.77 (s, 3H), 2.67 (s, 2H), 2.55 (s, 3H), 1.40 (d, J=10.9 Hz, 18H), 1.31 (t, J=7.2 Hz, 3H).

Step 4. Ethyl2-[2-[methyl(methylamino)amino]ethyl]-4,5,6,7-tetrahydropyrazolo[4,3-c]pyridine-3-carboxylate. O5-tert-butyl O3-ethyl 2-[2-[[tert-butoxycarbonyl(methyl)amino]-methyl-amino]ethyl]-6,7-dihydro-4H-pyrazolo[4,3-c]pyridine-3,5-dicarboxylate (50.00 mg, 103.82 µmol, 1.00 eq) was dissolved in HCl/dioxane (103.82 µmol, 2.00 mL, 4M, 1.00 eq) and the mixture was stirred at 25° C. for 1 hr. The reaction mixture was concentrated under reduced pressure to give the title compound (40.00 mg, crude, 2HCl) as colorless oil.

Step 5. tert-Butyl2,3-dimethyl-1-oxo-5,8,9,11-tetrahydro-4H-pyrido[2,3]pyrazolo[2,4-c][1,2,5]triazepine-10-carboxylate. To a solution of ethyl 2-[2-[methyl(methylamino)amino]ethyl]-4,5,6,7-tetrahydropyrazolo[4,3-c]pyridine-3-carboxylate (60.00 mg, 169.36 µmol, 1.00 eq, 2HCl) in MeOH (500.00 µL) was added CH₃ONa (45.74 mg, 846.80 µmol, 5.00 eq). The mixture was stirred at 25° C. for 2 hr. The mixture was stirred at 25° C. for another 16 hr. Additional CH₃ONa (20 mg) was added and the mixture was stirred at 25° C. for another 16 hr. The mixture was concentrated in vacuo to give a residue. The residue was dissolved in H₂O (500.00 µL) and THF (3.00 mL). To the solution were added Boc₂O (44.35 mg, 203.23 µmol, 46.68 µL, 1.20 eq) and NaHCO₃ (28.46 mg, 338.72 µmol, 13.18 µL, 2.00 eq). The mixture was stirred at 25° C. for 3 hr. The mixture was diluted with H₂O (10 mL) and extracted with EA (20 mL×2). The combined organic layer was dried over Na₂SO₄, filtered and concentrated in vacuo to give the title compound (60.00 mg, crude) as brown oil.

Step 6. 2,3-dimethyl-4,5,8,9,10,11-hexahydropyrido[2,3]pyrazolo[2,4-c][1,2,5]triazepin-1-one To a solution of tert-butyl 2,3-dimethyl-1-oxo-5,8,9,11-tetrahydro-4H-pyrido[2,3] pyrazolo[2,4-c][1,2,5]triazepine-10-carboxylate (70.00 mg, 208.71 µmol, 1.00 eq) in DCM (1.00 mL) was added TFA (1.54 g, 13.51 mmol, 1.00 mL, 64.71 eq), the mixture was stirred at 25° C. for 16 hr. The mixture was concentrated in vacuo to give the title compound (77.00 mg, crude, TFA) as brown oil.

Step 7. N-(3-chloro-4-fluorophenyl)-2,3-dimethyl-1-oxo-1,2,3,4,5,8,9,11-octahydro-10H-pyrido[4',3':3,4]pyrazolo[5,1-d][1,2,5]triazepine-10-carboxamide. To a solution of 2,3-dimethyl-4,5,8,9,10,11-hexahydropyrido[2,3]pyrazolo[2,4-c][1,2,5]triazepin-1-one (75.00 mg, 214.71 µmol, 1.00 eq, TFA) and phenyl N-(3-chloro-4-fluoro-phenyl)carbamate (57.04 mg, 214.71 µmol, 1.00 eq) in DCM (3.00 mL) was added TEA (108.63 mg, 1.07 mmol, 148.81 µL, 5.00 eq). The mixture was stirred at 25° C. for 16 hr. The mixture was concentrated in vacuo. The residue was purified by prep-HPLC (FA) to afford the title compound (20.00 mg, 48.82 µmol, 22.74% yield, 99.3% purity) as white solid. LCMS: 407 [M+1]. ¹H NMR (400 MHz, CDCl₃) δ=7.61 (dd, J=2.6, 6.5 Hz, 1H), 7.19-7.25 (m, 1H), 7.02-7.09 (t, 1H), 6.70 (s, 1H), 4.73 (s, 2H), 4.53 (t, J=6.1 Hz, 2H), 3.88 (t, J=5.8 Hz, 2H), 3.61 (t, J=6.1 Hz, 2H), 3.25 (s, 3H), 2.86 (t, J=5.8 Hz, 2H), 2.69 (s, 3H).

Compound 218: (R)-3-allyl-N-(3-cyano-4-fluoro-phenyl)-2,9-dimethyl-1-oxo-1,2,3,4,5,8,9,11-octa-hydro-10H-pyrido[4',3':3,4]pyrazolo[5,1-d][1,2,5]triazepine-10-carboxamide

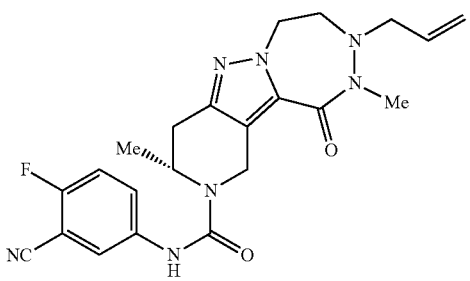 [SMILES: C=CCN1CCn2nc3c(c2C(=O)N1C)CN(C(=O)Nc1ccc(F)c(C#N)c1)[C@H](C)C3]

Step 1. tert-butyl N-[2-[tert-butyl(dimethyl)silyl]oxyethylamino]-N-methyl-carbamate. To a solution of tert-butyl N-amino-N-methyl-carbamate (2.00 g, 13.68 mmol, 1.00 eq) in DMF (20.00 mL) were added 2-bromoethoxy-tert-butyl-dimethyl-silane (3.60 g, 15.05 mmol, 1.10 eq) and DIEA (2.30 g, 17.78 mmol, 3.11 mL, 1.30 eq). The mixture was stirred at 90° C. for 32 hr. The mixture was diluted with H₂O (100 mL) and extracted with EA (100 mL×2). The combined organic layer was washed with H₂O (50 mL×2), dried over Na₂SO₄, filtered and concentrated in vacuo. The residue was purified by column chromatography (PE/EA: 0%~10%) to get tert-butyl N-[2-[tert-butyl(dimethyl)silyl]oxyethylamino]-N-methyl-carbamate (4.00 g, 10.51 mmol, 76.82% yield, 80% purity) as colorless oil.

Step 2. tert-butyl N-[allyl-[2-[tert-butyl(dimethyl)silyl]oxyethyl]amino]-N-methyl-carbamate To a solution of tert-butyl N-[2-[tert-butyl(dimethyl)silyl]oxyethylamino]-N-methyl-carbamate (4.00 g, 10.51 mmol, 1.00 eq) and 3-bromoprop-1-ene (1.91 g, 15.76 mmol, 1.50 eq) in DMF (40.00 mL) was added DIEA (1.77 g, 13.66 mmol, 2.39 mL, 1.30 eq). Then the mixture was heated to 65° C. for 16 hr. The mixture was diluted with H₂O (100 mL) and extracted with ethyl acetate (200 mL×2). The combined organic layer was washed with H₂O (50 mL×2), dried over Na₂SO₄, filtered and concentrated in vacuo. The residue was purified by column chromatography (PE:EA: 0%~5%) to give tert-butylN-[allyl-[2-[tert-butyl(dimethyl)silyl]oxyethyl]amino]-N-methyl-carbamate (2.80 g, 6.50 mmol, 61.85% yield, 80% purity) as colorless oil.

Step 3. 2-[allyl(methylamino)amino]ethanol. To a solution of tert-butyl N-[allyl-[2-[tert-butyl(dimethyl)silyl]oxyethyl]amino]-N-methyl-carbamate (2.00 g, 4.64 mmol, 1.00 eq) in EtOAc (20.00 mL) was added HCl/EtOAc (4 M, 10.00 mL, 8.62 eq). The mixture was stirred at 10° C. for 3 hr. The mixture was concentrated in vacuo to get 2-[allyl(methylamino)amino]ethanol (1.30 g, crude, HCl) as brown oil.

Step 4. tert-butyl(6R)-3-[[allyl(2-hydroxyethyl)amino]-methyl-carbamoyl]-6-methyl-2,4,6,7-tetrahydropyrazolo[4,3-c]pyridine-5-carboxylate. To a solution of (6R)-5-tert-butoxycarbonyl-6-methyl-2,4,6,7-tetrahydropyrazolo [4,3-c]pyridine-3-carboxylic acid (1.00 g, 3.35 mmol, 1.00 eq) and 2-[allyl(methylamino)amino]ethanol (888.61 mg, 5.33 mmol, 1.50 eq, HCl) in DMF (20.00 mL) were added PYBOP (2.03 g, 3.91 mmol, 1.10 eq), HOBt (528.36 mg, 3.91 mmol, 1.10 eq) and DIEA (2.30 g, 17.77 mmol, 3.10 mL, 5.00 eq). The mixture was stirred at 40° C. for 16 hr. The mixture was diluted with H₂O (100 mL) and extracted with ethyl acetate (200 mL×2). The combined organic layer was washed with H₂O (100 mL×2), 1N HCl (50 mL), saturated NaHCO₃ (50 mL), dried over Na₂SO₄, filtered and concentrated in vacuo. The residue was purified by flash chromatography (Petroleum ether:Ethyl acetate: 60%~100%) to get tert-butyl(6R)-3-[[allyl(2-hydroxyethyl)amino]-methyl-carbamoyl]-6-methyl-2,4,6,7-tetrahydropyrazolo[4,3-c]pyridine-5-carboxylate (860.00 mg, 1.92 mmol, 58.08% yield, 88% purity) as white solid. LCMS: 394 [M+1].

Step 5. tert-butyl(6R)-3-[[allyl(2-methylsulfonyloxyethyl)amino]-methyl-carbamoyl]-6-methyl-2,4,6,7-tetrahydropyrazolo[4,3-c]pyridine-5-carboxylate. To a solution of tert-butyl (6R)-3-[[allyl(2-hydroxyethyl)amino]-methyl-carbamoyl]-6-methyl-2,4,6,7-tetrahydropyrazolo[4,3-c]pyridine-5-carboxylate (800.00 mg, 1.79 mmol, 1.00 eq) and DIEA (462.46 mg, 3.58 mmol, 624.95 µL, 2.00 eq) in DCM (8.00 mL) was added a solution of MsCl (246.05 mg, 2.15 mmol, 166.25 µL, 1.20 eq) in DCM (500.00 µL) dropwise at 0° C. The mixture was stirred at 0° C. for 0.5 hr. MsCl (205.05 mg, 1.79 mmol, 138.55 µL, 1.00 eq) was added and the mixture was stirred at 10° C. for 0.5 hr. The mixture was diluted with H₂O (50 mL) and extracted with DCM (100 mL). The organic layer was washed with 0.5 N HCl (20 mL), saturated NaHCO₃ (20 mL), dried over Na₂SO₄, filtered and concentrated in vacuo to give the title compound (800.00 mg, crude) as colorless oil. LCMS: 472 [M+1].

Step 6. tert-Butyl (R)-3-allyl-2,9-dimethyl-1-oxo-1,2,3,4,5,8,9,11-octahydro-10H-pyrido[4',3':3,4]pyrazolo[1,2,5]triazepine-10-carboxylate. To a solution of tert-butyl (6R)-3-[[allyl(2-methylsulfonyloxyethyl)amino]-methyl-carbamoyl]-6-methyl-2,4,6,7-tetrahydropyrazolo[4,3-c]pyridine-5-carboxylate (800.00 mg, 1.70 mmol, 1.00 eq) in THF (10.00 mL) was added NaH (203.58 mg, 5.09 mmol, 60% purity, 3.00 eq) at 0° C. The mixture was stirred at 25° C. for 16 hr. Additional NaH (203.58 mg) added and the mixture was heated to 40° C. for 16 h. The mixture was quenched by 0.5 N HCl (20 mL) and extracted with ethyl acetate (80 mL×2). The combined organic layers were dried over Na₂SO₄, filtered and concentrated in vacuo. The residue was purified by column chromatography (PE:EA: 30%~50%) to afford the title compound (450.00 mg, 970.81 µmol, 57.11% yield, 81% purity) as white solid. LCMS: 376 [M+1].

Step 7. (R)-3-Allyl-2,9-dimethyl-2,3,4,5,8,9,10,11-octahydro-1H-pyrido[4',3':3,4]pyrazolo[5,1-d][1,2,5]triazepin-1-one. To a solution of tert-butyl (R)-3-allyl-2,9-dimethyl-1-oxo-1,2,3,4,5,8,9,11-octahydro-10H-pyrido[4',3':3,4]pyrazolo[5,1-d][1,2,5]triazepine-10-carboxylate (250.00 mg, 539.34 µmol, 1.00 eq) in DCM (3.00 mL) was added TFA (3.12 g, 27.35 mmol, 2.02 mL, 50.71 eq). The mixture was stirred at 10° C. for 2 hr. The mixture was concentrated in vacuo to get the title compound (212.00 mg, crude, TFA) as brown oil.

Step 8. (R)-3-Allyl-N-(3-cyano-4-fluorophenyl)-2,9-dimethyl-1-oxo-1,2,3,4,5,8,9,11-octahydro-10H-pyrido[4',3':3,4]pyrazolo[5,1-d][1,2,5]triazepine-10-carboxamide. To a solution of (R)-3-allyl-2,9-dimethyl-2,3,4,5,8,9,10,11-octahydro-1H-pyrido[4',3':3,4]pyrazolo[5,1-d][1,2,5]triazepin-1-one (212.00 mg, 544.47 µmol, 1.00 eq, TFA) in DCM (5.00 mL) were added phenyl N-(3-cyano-4-fluoro-phenyl) carbamate (139.51 mg, 544.47 µmol, 1.00 eq) and TEA (330.57 mg, 3.27 mmol, 452.83 µL, 6.00 eq). The mixture was stirred at 30° C. for 16 hr. The mixture was concentrated in vacuo. The residue was purified by prep-HPLC (FA) to afford the title compound (150.00 mg, 335.68 µmol, 61.65% yield, 97.9% purity) as white solid. 58.48 mg desired product was produced. LCMS: 438 [M+1]; ¹H NMR (400 MHz, CD₃OD) δ 7.82-7.84 (m, 1H), 7.70-7.72 (m, 1H), 7.29 (t, J=9.05 Hz, 1H), 5.83 (m, 1H), 5.14-5.23 (m, 2H), 4.96-5.09 (m, 2H), 4.31-4.50 (m, 3H), 3.61 (t, J=6.36 Hz, 2H), 3.45-3.47 (m, 2H), 3.21 (s, 3H), 3.04 (dd, 1H), 2.66-2.70 (d, 1H), 1.22 (d, J=6.85 Hz, 3H).

Compound 219: (R)—N-(3-cyano-4-fluorophenyl)-2,9-dimethyl-1-oxo-3-propyl-1,2,3,4,5,8,9,11-octahydro-10H-pyrido[4',3':3,4]pyrazolo[5,1-d][1,2,5]triazepine-10-carboxamide

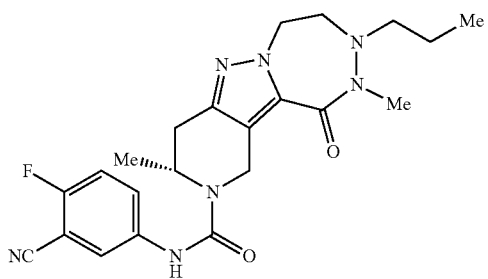 [SMILES: CCCN1CCn2nc3c(c2C(=O)N1C)CN(C(=O)Nc1ccc(F)c(C#N)c1)[C@H](C)C3]

To a solution of (R)-3-allyl-N-(3-cyano-4-fluorophenyl)-2,9-dimethyl-1-oxo-1,2,3,4,5,8,9,11-octahydro-10H-pyrido[4',3':3,4]pyrazolo[5,1-d][1,2,5]triazepine-10-carboxamide (Compound 218, 25 mg, 57.15 μmol, 1 eq) in MeOH (10 mL) was added Pd/C (2 mg, 10% purity, 1.00 eq) under N₂. The suspension was degassed under vacuum and purged with Hz several times. The mixture was stirred under Hz (20 psi) at 15° C. for 20 min. The mixture was combined with (1753, 5 mg) to diluted with MeOH (20 mL), filtered and concentrated in vacuo. The residue was purified by prep-HPLC (FA) to afford 13 mg of the title compound as a white solid. LCMS: 440 [M+1]; ¹H NMR (400 MHz, CD₃OD) δ=7.81-7.83 (m, 1H), 7.70-7.72 (m, 1H), 7.28 (t, J=8.97 Hz, 1H), 4.92-5.08 (m, 2H), 4.33-4.49 (m, 3H), 3.56 (t, J=6.40 Hz, 2H), 3.21 (s, 3H), 3.03-3.05 (dd, 1H), 2.79-2.81 (m, 2H), 2.67 (d, J=15.81 Hz, 1H), 1.42-1.48 (m, 2H), 1.21 (d, J=6.90 Hz, 3H), 0.86 (t, J=7.40 Hz, 3H).

Compound 220: (R)—N-(3-Cyano-4-fluorophenyl)-3-(2-hydroxyethyl)-2,9-dimethyl-1-oxo-1,2,3,4,5,8,9,11-octahydro-10H-pyrido[4',3':3,4]pyrazolo[5,1-d][1,2,5]triazepine-10-carboxamide

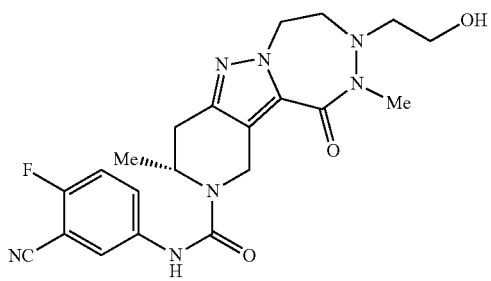

Step 1. (R)—N-(3-Cyano-4-fluorophenyl)-2,9-dimethyl-1-oxo-3-(2-oxoethyl)-1,2,3,4,5,8,9,11-octahydro-10H-pyrido[4',3':3,4]pyrazolo[5,1-d][1,2,5]triazepine-10-carboxamide. To a solution of (R)-3-allyl-N-(3-cyano-4-fluorophenyl)-2,9-dimethyl-1-oxo-1,2,3,4,5,8,9,11-octahydro-10H-pyrido[4',3':3,4]pyrazolo[5,1-d][1,2,5]triazepine-10-carboxamide (Compound 218, 70 mg, 156.65 μmol, 1.00 eq) in THF (4.00 mL) and H₂O (2.00 mL) were added OsO₄ (7.97 mg, 31.33 μmol, 1.63 μL, 0.20 eq) and NaIO₄ (100.52 mg, 469.95 μmol, 26.04 μL, 3.00 eq). The mixture was stirred at 15° C. for 6 hr. The mixture was diluted with H₂O (10 mL) and extracted with EA (20 mL×2). The combined organic layers were washed sat.Na₂S₂O₃ (10 mL×2), dried over Na₂SO₄, filtered and concentrated in vacuo. The residue was purified by silica gel column chromatography (Petroleum ether/Ethyl acetate=1:1-0:1) to afford the title compound (40 mg, 91.02 μmol, 58.11% yield) as brown oil.

Step 2. (R)—N-(3-Cyano-4-fluorophenyl)-3-(2-hydroxyethyl)-2,9-dimethyl-1-oxo-1,2,3,4,5,8,9,11-octahydro-10H-pyrido[4',3':3,4]pyrazolo[5,1-d][1,2,5]triazepine-10-carboxamide. To a solution of (R)—N-(3-cyano-4-fluorophenyl)-2,9-dimethyl-1-oxo-3-(2-oxoethyl)-1,2,3,4,5,8,9,11-octahydro-10H-pyrido[4',3':3,4]pyrazolo[5,1-d][1,2,5]triazepine-10-carboxamide (20.00 mg, 45.51 μmol, 1.00 eq) in THF (1.00 mL) and EtOH (100.00 μL) was added NaBH₄ (5.16 mg, 136.53 μmol, 3.00 eq) at 0° C. The mixture was stirred at 15° C. for 30 min. The mixture was quenched with sat.NH₄Cl (10 mL) and extracted with EA (10 mL×2). The combined organic layers were dried over Na₂SO₄, filtered and concentrated in vacuo. The residue was purified by prep-HPLC (FA). The title compound (3.77 mg, 8.10 μmol, 17.79% yield, 94.8% purity) was obtained as white solid. LCMS: 442 [M+1]; ¹H NMR (400 MHz, CD₃OD) δ=7.83 (dd, J=2.75, 5.56 Hz, 1H), 7.71 (m, 1H), 7.28 (t, J=9.05 Hz, 1H), 4.98-5.08 (m, 1H), 4.97 (s, 1H), 4.31-4.54 (m, 3H), 3.68 (t, J=6.30 Hz, 2H), 3.59 (t, J=5.56 Hz, 2H), 3.27 (s, 3H), 3.02 (dd, J=5.75, 15.65 Hz, 1H), 2.93 (d, J=3.42 Hz, 2H), 2.67 (d, J=16.14 Hz, 1H), 1.22 (d, J=6.85 Hz, 3H).

Compound 221: (R)—N-(3-Cyano-4-fluorophenyl)-3-(2,2-difluoroethyl)-2,9-dimethyl-1-oxo-1,2,3,4,5,8,9,11-octahydro-10H-pyrido[4',3':3,4]pyrazolo[5,1-d][1,2,5]triazepine-10-carboxamide

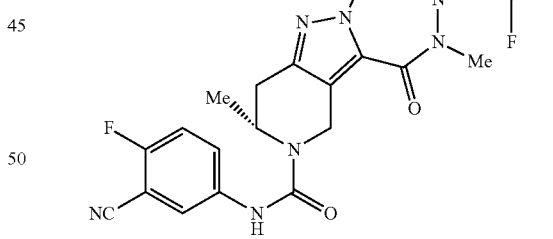

To a solution of (R)—N-(3-cyano-4-fluorophenyl)-2,9-dimethyl-1-oxo-3-(2-oxoethyl)-1,2,3,4,5,8,9,11-octahydro-10H-pyrido[4',3':3,4]pyrazolo[5,1-d][1,2,5]triazepine-10-carboxamide (20.00 mg, 45.51 μmol, 1.00 eq) in DCM (2.00 mL) was added DAST (44.01 mg, 273.06 μmol, 36.08 μL, 6.00 eq) at −40° C. The mixture was stirred at 0° C. for 30 min. The mixture was diluted with H₂O (10 mL) and extracted with DCM (10 mL×2). The combined organic layers were dried over Na₂SO₄, filtered and concentrated in vacuo. The residue was purified by prep-HPLC (FA) to give the title compound (3.67 mg, 7.65 μmol, 16.81% yield, 96.2% purity) as white solid. LCMS: 462 [M+1]; ¹H NMR (400 MHz, CD₃OD) δ=7.83 (dd, J=2.7, 5.5 Hz, 1H), 7.71

(m, 1H), 7.28 (t, J=9.0 Hz, 1H), 5.72-6.05 (m, 1H), 4.92-5.07 (m, 2H), 4.33-4.56 (m, 3H), 3.70 (s, 2H), 3.25 (s, 3H), 3.12-3.22 (m, 2H), 3.04 (dd, J=5.7, 15.8 Hz, 1H), 2.69 (d, J=15.8 Hz, 1H), 1.22 (d, J=6.8 Hz, 3H).

Compound 222: (R)—N-(3-Cyano-4-fluorophenyl)-3-(3-hydroxypropyl)-2,9-dimethyl-1-oxo-1,2,3,4,5,8,9,11-octahydro-10H-pyrido[4',3':3,4]pyrazolo[5,1-d][1,2,5]triazepine-10-carboxamide

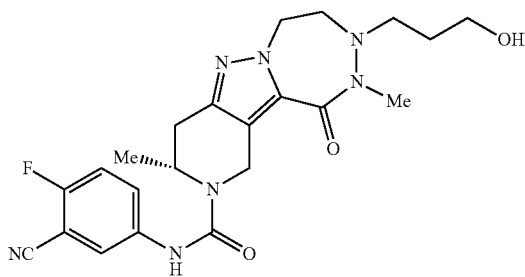

Step 1. tert-Butyl (R)-3-(3-hydroxypropyl)-2,9-dimethyl-1-oxo-1,2,3,4,5,8,9,11-octahydro-10H-pyrido[4',3':3,4]pyrazolo[5,1-d][1,2,5]triazepine-10-carboxylate and tert-butyl (9R)-3-(2-hydroxypropyl)-2,9-dimethyl-1-oxo-1,2,3,4,5,8,9,11-octahydro-10H-pyrido[4',3':3,4]pyrazolo[5,1-d][1,2,5]triazepine-10-carboxylate. To a solution of tert-butyl (R)-3-allyl-2,9-dimethyl-1-oxo-1,2,3,4,5,8,9,11-octahydro-10H-pyrido[4',3':3,4]pyrazolo[5,1-d][1,2,5]triazepine-10-carboxylate (30.00 mg, 64.72 µmol, 1.00 eq) and Rh(PPh₃)₃Cl (11.98 mg, 12.94 µmol, 0.20 eq) in THF (1.00 mL) was added 1,3,2-benzodioxaborole (1 M, 40.42 µL, 5.00 eq). The mixture was stirred at 0° C. for 1 hr. Then a solution of NaOH (18.12 mg, 453.04 µmol, 7.00 eq) in H₂O (500.00 µL) was added at −30° C., H₂O₂ (205.07 mg, 1.81 mmol, 173.79 µL, 30% purity, 27.95 eq) was added and the mixture was stirred at 10° C. for 1 hr. The mixture was diluted with H₂O (20 mL) and extracted with DCM (20 mL×2). The combined organic layers were washed with aqueous NaOH (0.25 N, 30 mL), dried over Na₂SO₄, filtered and concentrated in vacuo. The residue was purified by prep-HPLC (FA) to afford tert-butyl (R)-3-(3-hydroxypropyl)-2,9-dimethyl-1-oxo-1,2,3,4,5,8,9,11-octahydro-10H-pyrido[4',3':3,4]pyrazolo[5,1-d][1,2,5]triazepine-10-carboxylate (10 mg, 25.41 µmol, 39.27% yield) as colorless oil and tert-butyl (9R)-3-(2-hydroxypropyl)-2,9-dimethyl-1-oxo-1,2,3,4,5,8,9,11-octahydro-10H-pyrido[4',3':3,4]pyrazolo[5,1-d][1,2,5]triazepine-10-carboxylate (2 mg, 5.08 µmol, 7.85% yield) as colorless oil.

Step 2. (R)-3-(3-Hydroxypropyl)-2,9-dimethyl-2,3,4,5,8,9,10,11-octahydro-1H-pyrido[4',3':3,4]pyrazolo[5,1-d][1,2,5]triazepin-1-one. To a mixture of tert-butyl (R)-3-(3-hydroxypropyl)-2,9-dimethyl-1-oxo-1,2,3,4,5,8,9,11-octahydro-10H-pyrido[4',3':3,4]pyrazolo[5,1-d][1,2,5]triazepine-10-carboxylate (98 mg, 249.06 µmol, 1 eq) in DCM (3 mL) was added TFA (4.62 g, 40.52 mmol, 3 mL, 162.68 eq). The mixture was stirred at 20° C. for 0.5 hr. The mixture was concentrated under reduced pressure to give a residue. The title compound (103 mg, crude, TFA) was obtained as yellow oil.

Step 3. (R)—N-(3-Cyano-4-fluorophenyl)-3-(3-hydroxypropyl)-2,9-dimethyl-1-oxo-1,2,3,4,5,8,9,11-octahydro-10H-pyrido[4',3':3,4]pyrazolo[5,1-d][1,2,5]triazepine-10-carboxamide. To a solution of (R)-3-(3-hydroxypropyl)-2,9-dimethyl-2,3,4,5,8,9,10,11-octahydro-1H-pyrido[4',3':3,4]pyrazolo[5,1-d][1,2,5]triazepin-1-one (103 mg, 252.83 µmol, 1 eq, TFA) and phenyl 3-cyano-4-fluoro-benzoate (60.99 mg, 252.83 µmol, 1 eq) in DCM (5 mL) was added TEA (153.50 mg, 1.52 mmol, 211.15 µL, 6 eq). The mixture was stirred at 20° C. for 16 hr. The mixture was concentrated under reduced pressure to give a residue. The residue was purified by prep-HPLC (FA) to give the title compound (60.2 mg, 130.85 µmol, 51.75% yield, 99.0% purity) as white solid. LCMS: 456 [M+1]; ¹H NMR (400 MHz, CDCl₃) δ 7.77 (dd, J=2.64, 5.40 Hz, 1H), 7.56-7.62 (m, 1H), 7.13 (t, J=8.66 Hz, 1H), 6.74 (s, 1H), 5.15 (t, J=6.71 Hz, 1H), 4.83 (d, J=16.31 Hz, 1H), 4.47-4.48 (m, 1H), 4.45-4.53 (m, 3H), 3.69-3.72 (m, 2H), 3.59-3.62 (m, 2H), 3.25 (s, 3H), 2.91-3.08 (m, 3H), 2.67 (d, J=16.06 Hz, 1H), 1.71-1.77 (m, 2H), 1.19 (d, J=6.90 Hz, 3H).

Compound 223: (9R)—N-(3-Cyano-4-fluorophenyl)-3-(2-hydroxypropyl)-2,9-dimethyl-1-oxo-1,2,3,4,5,8,9,11-octahydro-10H-pyrido[4',3':3,4]pyrazolo[5,1-d][1,2,5]triazepine-10-carboxamide

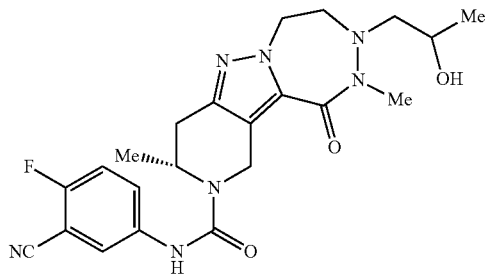 [SMILES: CC(O)CN1CCn2nc3c(c2C(=O)N1C)CN(C(=O)Nc1ccc(F)c(C#N)c1)[C@H](C)C3]

Step 1. (9R)-3-(2-Hydroxypropyl)-2,9-dimethyl-2,3,4,5,8,9,10,11-octahydro-1H-pyrido[4',3':3,4]pyrazolo[5,1-d][1,2,5]triazepin-1-one. To a mixture of tert-butyl (9R)-3-(2-hydroxypropyl)-2,9-dimethyl-1-oxo-1,2,3,4,5,8,9,11-octahydro-10H-pyrido[4',3':3,4]pyrazolo[5,1-d][1,2,5]triazepine-10-carboxylate (52.26 mg, 132.82 µmol, 1 eq) in DCM (3 mL) was added TFA (4.62 g, 40.52 mmol, 3.00 mL, 305.07 eq). The mixture was stirred at 20° C. for 0.5 hr. The mixture was concentrated under reduced pressure to afford the title compound (40.5 mg, crude, TFA) as yellow oil.

Step 2. (9R)—N-(3-Cyano-4-fluorophenyl)-3-(2-hydroxypropyl)-2,9-dimethyl-1-oxo-1,2,3,4,5,8,9,11-octahydro-10H-pyrido[4',3':3,4]pyrazolo[5,1-d][1,2,5]triazepine-10-carboxamide. To a solution of (9R)-3-(2-hydroxypropyl)-2,9-dimethyl-2,3,4,5,8,9,10,11-octahydro-1H-pyrido[4',3':3,4]pyrazolo[5,1-d][1,2,5]triazepin-1-one (40.5 mg, 99.41 µmol, 1 eq, TFA) and phenyl N-(3-cyano-4-fluorophenyl)carbamate (25.47 mg, 99.41 µmol, 1 eq) in DCM (3 mL) was added TEA (60.36 mg, 596.46 µmol, 83.02 µL, 6 eq). The mixture was stirred at 20° C. for 16 hr. The mixture was concentrated under reduced pressure to give a residue. The residue was purified by prep-HPLC (FA). The title compound (30.22 mg, 64.95 µmol, 65.34% yield, 97.9% purity) was obtained as white solid. LCMS: 456 [M+1]; ¹H NMR (400 MHz, CDCl₃) δ 7.79 (dd, J=2.76, 5.40 Hz, 1H), 7.52-7.56 (m, 1H), 7.14 (t, J=8.66 Hz, 1H), 6.67 (s, 1H), 5.06-5.25 (m, 1H), 4.84 (m, J=10.29 Hz, 1H), 4.39-4.63 (m, 3H), 3.56-3.91 (m, 3H), 3.28 (d, J=4.27 Hz, 3H), 2.84-3.10 (m, 2H), 2.58-2.74 (m, 2H), 1.08-1.22 (m, 6H).

Compound 224: (R)—N-(3-Cyano-4-fluorophenyl)-2,3,9-trimethyl-1-oxo-1,2,3,4,5,8,9,11-octahydro-10H-pyrido[4',3':3,4]pyrazolo[5,1-d][1,2,5]triazepine-10-carboxamide

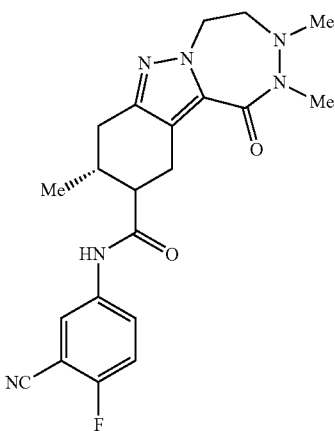 [SMILES: C[C@@H]1Cc2nn3c(c2CC1C(=O)Nc1ccc(F)c(C#N)c1)C(=O)N(C)N(C)CC3]

Step 1. tert-Butyl N-[2-[tert-butyl(dimethyl)silyl]oxyethylamino]-N-methyl-carbamate. To a solution of tert-butyl N-amino-N-methyl-carbamate (10 g, 68.41 mmol, 1 eq) and 2-bromoethoxy-tert-butyl-dimethyl-silane (18.00 g, 75.25 mmol, 1.1 eq) in DMF (85 mL) was added DIEA (11.49 g, 88.93 mmol, 15.49 mL, 1.3 eq). The mixture was stirred at 90° C. for 48 hr. The mixture was diluted with 50 mL of water and extracted with EtOAc (50 mL×3), and then the combined organic layers were washed with 0.5N HCl (50 mL×1), water (50 mL×2) and brine (50 mL×1), dried over anhydrous Na$_2$SO$_4$, filtered and concentrated in vacuo. The residue was purified by column chromatography (SiO$_2$, Petroleum ether/Ethyl acetate=100/1 to 30/1 (9.7 g, 27.40 mmol, 40.05% yield, 86% purity) to afford the title compound as colorless liquid.

Step 2. tert-Butyl N-[2-[tert-butyl(dimethyl)silyl]oxyethyl-methyl-amino]-N-methyl-carbamate
To a solution of tert-butyl N-[2-[tert-butyl(dimethyl)silyl]oxyethylamino]-N-methyl-carbamate (5 g, 14.12 mmol, 1 eq) in DMF (5 mL) was added MeI (12.03 g, 84.73 mmol, 5.27 mL, 6 eq) at 15° C., and then the mixture was heated to 70° C. with stirring for 3 h. The mixture was quenched with 0.5 N HCl (30 mL) and extracted with EtOAc (30 mL×4), and the organic layers were washed with water (30 mL×2) and brine (30 mL×1), dried over anhydrous Na$_2$SO$_4$, filtered and concentrated in vacuo. The residue was purified by column chromatography (SiO$_2$, Petroleum ether/Ethyl acetate=100/1 to 30/1). The title compound (2.7 g, 8.48 mmol, 60.03% yield) was obtained as yellow liquid.

Step 3. 2-[Methyl(methylamino)amino]ethanol. To a solution of tert-butyl N-[2-[tert-butyl(dimethyl)silyl]oxyethyl-methyl-amino]-N-methyl-carbamate (2.94 g, 9.23 mmol, 1 eq) in dioxane (6 mL) was added HCl/dioxane (4 M, 6.92 mL, 3 eq), and then the mixture was stirred at 15° C. for 3 h. The mixture was concentrated in vacuo. The residue was not purified. The title compound (1.35 g, crude, HCl) was obtained as colorless oil.

Step 4. tert-Butyl (6R)-3-[[2-hydroxyethyl(methyl)amino]-methyl-carbamoyl]-6-methyl-2,4,6,7-tetrahydropyrazolo[4,3-c]pyridine-5-carboxylate. To a solution of (6R)-5-tert-butoxycarbonyl-6-methyl-2,4,6,7-tetrahydropyrazolo[4,3-c]pyridine-3-carboxylic acid (1.0 g, 3.55 mmol, 1 eq) in pyridine (10 mL) was added EDCI (817.76 mg, 4.27 mmol, 1.2 eq), and the mixture was heated to 15° C. with stirring for 16 h. The mixture was diluted with 20 mL of water and extracted with EtOAc (20 mL×3), and the combined organic layers were washed with aqueous solution of HCl (1N, 30 mL×3), saturated aqueous solution of NaHCO$_3$ (20 mL) and brine (20 mL), dried over anhydrous Na$_2$SO$_4$, filtered and concentrated in vacuo. The residue was purified by column chromatography (SiO$_2$, Petroleum ether/Ethyl acetate=10/1 to 1/3). The title compound (970 mg, 2.64 mmol, 74.26% yield) was obtained as red solid.

Step 5. tert-Butyl (6R)-6-methyl-3-[methyl-[methyl(2-methylsulfonyl oxyethyl)amino]carbamoyl]-2,4,6,7-tetrahydropyrazolo[4,3-c]pyridine-5-carboxylate
To a solution of tert-butyl (6R)-3-[[2-hydroxyethyl(methyl)amino]-methyl-carbamoyl]-6-methyl-2,4,6,7-tetrahydropyrazolo[4,3-c]pyridine-5-carboxylate (970 mg, 2.64 mmol, 1 eq) and DIEA (1.36 g, 10.56 mmol, 1.84 mL, 4 eq) in DCM (25 mL) was added MsCl (362.88 mg, 3.17 mmol, 245.19 μL, 1.2 eq) at 0° C. with stirring for 1 h. The mixture was diluted with 20 mL of water and extracted with DCM (20 mL×3), and the combined organic layers were washed with aqueous solution of HCl (1N, 30 mL×3), saturated aqueous solution of NaHCO$_3$ (20 mL) and brine (20 mL), dried over anhydrous Na$_2$SO$_4$, filtered and concentrated in vacuo. The residue was not purified. The title compound (1.2 g, crude) was obtained as yellow solid and used directly in the next step.

Step 6. tert-Butyl (R)-2,3,9-trimethyl-1-oxo-1,2,3,4,5,8,9,11-octahydro-10H-pyrido[4',3':3,4]pyrazolo[5,1-d][1,2,5]triazepine-10-carboxylate. To a solution of tert-butyl (6R)-6-methyl-3-[methyl-[methyl(2-methylsulfonyl oxyethyl)amino]carbamoyl]-2,4,6,7-tetrahydropyrazolo[4,3-c]pyridine-5-carboxylate (1.2 g, crude, 2.69 mmol, 1 eq) in THF (25 mL) was added NaH (269.31 mg, 6.73 mmol, 60% purity, 2.5 eq) at 0° C., and then the mixture was heated to 40° C. with stirring for 16 h. The mixture was quenched with aqueous solution of HCl (1 N, 10 mL) and extracted with EtOAc (20 mL×3), and the combined organic layers were washed with saturated aqueous solution of NaHCO$_3$ (30 mL) and brine (30 mL), dried over anhydrous Na$_2$SO$_4$, filtered and concentrated in vacuo. The residue was not purified and used in the next step. 850 mg of the title compound was obtained as yellow oil.

Step 7. (R)-2,3,9-Trimethyl-2,3,4,5,8,9,10,11-octahydro-1H-pyrido[4',3':3,4]pyrazolo[5,1-d][1,2,5]triazepin-1-one.
To a solution of tert-butyl (R)-2,3,9-trimethyl-1-oxo-1,2,3,4,5,8,9,11-octahydro-10H-pyrido[4',3':3,4]pyrazolo[5,1-d][1,2,5]triazepine-10-carboxylate (200 mg, 89% purity, 509.41 μmol, 1 eq) in DCM (3 mL) was added TFA (462.00 mg, 4.05 mmol, 0.3 mL, 7.95 eq), and the mixture was stirred at 15° C. for 1 h. The mixture was concentrated in vacuo. The residue was not purified and used directly in the next step. The title compound (190 mg, crude, TFA) was obtained as yellow oil.

Step 8. (R)—N-(3-Cyano-4-fluorophenyl)-2,3,9-trimethyl-1-oxo-1,2,3,4,5,8,9,11-octahydro-10H-pyrido[4',3':3,4]pyrazolo[5,1-d][1,2,5]triazepine-10-carboxamide. To a solution of (R)-2,3,9-trimethyl-2,3,4,5,8,9,10,11-octahydro-1H-pyrido[4',3':3,4]pyrazolo[5,1-d][1,2,5]triazepin-1-one (95 mg, 261.47 μmol, 1 eq, TFA) in DCM (3 mL) was added TEA (158.75 mg, 1.57 mmol, 218.36 μL, 6 eq) and phenyl N-(3-cyano-4-fluoro-phenyl)carbamate (70.35 mg, 274.54 μmol, 1.05 eq), and the mixture was stirred at 15° C. for 16 h. The mixture was concentrated in vacuo. The residue was purified by prep-HPLC(FA) to obtain the title compound (57 mg, 138.26 μmol, 52.88% yield, 99.8% purity) as white solid. LCMS: 412[M+1]; ¹H NMR (400 MHz, CDCl₃) δ=7.81 (dd, J=2.76, 5.52 Hz, 1H), 7.60 (m, J=2.76, 4.58, 9.10 Hz, 1H), 7.15 (t, J=8.72 Hz, 1H), 6.71 (s, 1H), 5.14-5.23 (m, 1H), 4.88 (d, J=15.81 Hz, 1H), 4.50-4.60 (m, 3H), 3.64 (t, J=6.09 Hz, 2H), 3.27 (s, 3H), 3.05 (dd, J=5.96, 15.87 Hz, 1H), 2.66-2.73 (m, 4H), 1.19 (d, J=6.90 Hz, 3H).

Compound 225: (R)—N-(4-Fluoro-3-(trifluoromethyl)phenyl)-2,3,9-trimethyl-1-oxo-1,2,3,4,5,8,9,11-octahydro-10H-pyrido[4',3':3,4]pyrazolo[5,1-d][1,2,5]triazepine-10-carboxamide

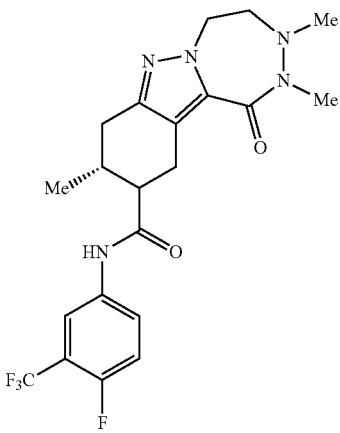

To a solution of (R)-2,3,9-trimethyl-2,3,4,5,8,9,10,11-octahydro-1H-pyrido[4',3':3,4]pyrazolo[5,1-d][1,2,5]triazepin-1-one (95 mg, 261.47 µmol, 1 eq, TFA) in DCM (3 mL) was added TEA (158.75 mg, 1.57 mmol, 218.36 µL, 6 eq) and phenyl N-[4-fluoro-3-(trifluoromethyl)phenyl]carbamate (82.15 mg, 274.54 µmol, 1.05 eq). The mixture was stirred at 15° C. for 16 h. The mixture was concentrated in vacuo. The residue was purified by prep-HPLC (FA) to obtain the title compound (57 mg, 125.43 µmol, 47.97% yield, 100% purity) as white solid. LCMS: 455[M+1]; ¹H NMR (400 MHz, CDCl₃) δ=7.69 (dd, J=2.70, 6.09 Hz, 1H), 7.57-7.63 (m, 1H), 7.13 (t, J=9.41 Hz, 1H), 6.65 (s, 1H), 5.14-5.24 (m, 1H), 4.87 (d, J=15.69 Hz, 1H), 4.49-4.59 (m, 3H), 3.60-3.65 (m, 2H), 3.25 (s, 3H), 3.04 (dd, J=5.90, 15.81 Hz, 1H), 2.65-2.71 (m, 4H), 1.17 (d, J=6.90 Hz, 3H).

Compound 226: N-(3-Chloro-4-fluorophenyl)-4-hydroxy-2-methyl-1-oxo-4-(trifluoromethyl)-1,2,3,4,5,8,9,11-octahydro-10H-pyrido[4',3':3,4]pyrazolo[5,1-d][1,2,5]triazepine-10-carboxamide

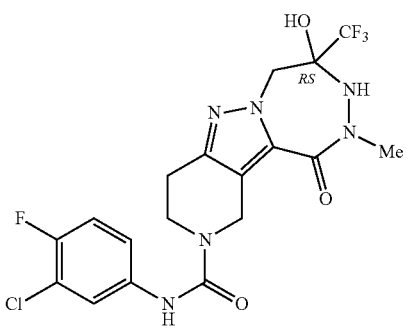 [SMILES: CN1NC(O)(C(F)(F)F)Cn2nc3c(c2C1=O)CN(C(=O)Nc1ccc(F)c(Cl)c1)CC3]

Step 1. tert-Butyl 3-[benzyloxycarbonylamino(methyl)carbamoyl]-2,4,6,7-tetrahydropyrazolo[4,3-c]pyridine-5-carboxylate. To a solution of 5-tert-butoxycarbonyl-2,4,6,7-tetrahydropyrazolo[4,3-c]pyridine-3-carboxylic acid (6.00 g, 22.45 mmol, 1.00 eq) and benzyl N-(methylamino)carbamate (6.32 g, 29.19 mmol, 1.30 eq, HCl) in DMF (50.00 mL) were added PYBOP (1.29 g, 2.47 mmol, 0.11 eq), HOBt (3.34 g, 24.69 mmol, 1.10 eq) and DIPEA (17.41 g, 134.69 mmol, 23.52 mL, 6.00 eq) at 25° C. The mixture was stirred at 25° C. for 3 h. LCMS indicated that most of 5-tert-butoxycarbonyl-2,4,6,7-tetrahydropyrazolo[4,3-c]pyridine-3-carboxylic acid remained and a little desired product was detected. The mixture was diluted with 50 mL of water and extracted with ethyl acetate (30 mL×3). The combined organic layers were washed with brine (50 mL), dried over anhydrous Na₂SO₄, filtered and concentrated to give the residue which was purified by column chromatography (SiO₂, Petroleum ether/Ethyl acetate=1/0 to 1/1) to recover 5-tert-butoxycarbonyl-2,4,6,7-tetrahydropyrazolo[4,3-c]pyridine-3-carboxylic acid.

The recovered 5-tert-butoxycarbonyl-2,4,6,7-tetrahydropyrazolo[4,3-c]pyridine-3-carboxylic acid was dissolved in the 50 mL of DMF. To the solution were added PYBOP (12.85 g, 24.69 mmol, 1.10 eq), HOBt (3.34 g, 24.69 mmol, 1.10 eq), DIPEA (17.41 g, 134.69 mmol, 23.52 mL, 6.00 eq) and benzyl N-(methylamino)carbamate (6.32 g, 29.19 mmol, 1.30 eq, HCl). The mixture was stirred at 25° C. for 16 h. The mixture was diluted with 50 mL of water and extracted with ethyl acetate (30 mL×3). The combined organic layers were washed with saturated NaHCO₃ (30 mL), HCl (1N, 30 mL) and brine (50 mL), dried over anhydrous Na₂SO₄, filtered and concentrated to give the residue. The residue was purified by column chromatography (SiO₂, Petroleum ether/Ethyl acetate=1/0 to 1/1,) to give the title compound (2.60 g, 5.31 mmol, 23.65% yield, 87.7% purity) as white solid.

Step 2. tert-Butyl 3-[amino(methyl)carbamoyl]-2,4,6,7-tetrahydropyrazolo[4,3-c]pyridine-5-carboxylate. To a solution of tert-butyl 3-[benzyloxycarbonylamino(methyl)carbamoyl]-2,4,6,7-tetrahydropyrazolo[4,3-c]pyridine-5-carboxylate (2.60 g, 6.05 mmol, 1.00 eq) in MeOH (50.00 mL) was added Pd/C (500.00 mg, 10% purity) under N₂. The suspension was degassed under vacuum and purged with H₂ several times. The mixture was stirred under H₂ (15 psi) at 25° C. for 16 hours. The mixture was diluted with 30 mL of MeOH, filtered and concentrated in vacuo. The residue was purified by column chromatography (SiO₂, Petroleum ether/Ethyl acetate=30/1 to 1/4) to give the title compound (1.30 g, 4.18 mmol, 69.12% yield, 95% purity) as white solid.

Step 3. tert-Butyl3-[[(Z)-[1-(bromomethyl)-2,2,2-trifluoro-ethylidene]amino]-methyl-carbamoyl]-2,4,6,7-tetrahydropyrazolo[4,3-c]pyridine-5-carboxylate. To a mixture of tert-butyl 3-[amino(methyl)carbamoyl]-2,4,6,7-tetrahydropyrazolo [4,3-c]pyridine-5-carboxylate (150.00 mg, 507.89 µmol, 1.00 eq) and 3-bromo-1,1,1-trifluoro-propan-2-one (145.47 mg, 761.84 µmol, 79.06 µL, 1.50 eq) in DCM (15.00 mL) was added TsOH.H₂O (19.32 mg, 101.58 µmol, 0.20 eq) in one portion at 25° C. The mixture was stirred at 25° C. for 2 hours. 3-Bromo-1,1,1-trifluoro-propan-2-one (77.59 mg, 406.31 µmol, 42.17 µL, 0.80 eq) was added into the mixture and the mixture was stirred at 25° C. for another 12 hours. The reaction mixture was quenched by H₂O (5 mL), and then extracted with DCM (10×2 mL). The combined organic layers were washed with brine (10 mL), dried over Na₂SO₄, filtered and concentrated under reduced pressure. The residue was purified by prep-TLC (PE/EA=1/1).

The title compound (210.00 mg, 448.46 µmol, 88.30% yield) was obtained as white solid. LCMS: 411 [M−56].

Step 4. tert-Butyl 2-methyl-1-oxo-4-(trifluoromethyl)-1,2,5,8,9,11-hexahydro-10H-pyrido[4',3':3,4]pyrazolo[5,1-d][1,2,5]triazepine-10-carboxylate. To a solution of tert-butyl 3-[[(Z)-[1-(bromomethyl)-2,2,2-trifluoro-ethylidene]amino]-methyl-carbamoyl]-2,4,6,7-tetrahydropyrazolo[4,3-c]pyridine-5-carboxylate (100.00 mg, 213.55 µmol, 1.00 eq) in DMF (5.00 mL) was added $Cs_2CO_3$ (139.16 mg, 427.10 µmol, 2.00 eq) in one portion at 25° C. under $N_2$. The mixture was stirred at 25° C. for 2 h. The reaction mixture was diluted with $H_2O$ (40 mL) and then extracted with EtOAc (10×2 mL). The combined organic layers were washed with brine (15 mL), dried over $Na_2SO_4$, filtered and concentrated under reduced pressure. The residue was purified by prep-TLC (Petroleum ether: Ethyl acetate=3:1). The title compound (45.00 mg, 116.17 µmol, 54.40% yield) was obtained as yellow oil.

Step 5. 2-Methyl-4-(trifluoromethyl)-2,5,8,9,10,11-hexahydro-1H-pyrido[4',3':3,4]pyrazolo[5,1-d][1,2,5]triazepin-1-one. To a solution of tert-butyl 2-methyl-1-oxo-4-(trifluoromethyl)-1,2,5,8,9,11-hexahydro-10H-pyrido[4',3':3,4]pyrazolo[5,1-d][1,2,5]triazepine-10-carboxylate (100.00 mg, 258.16 µmol, 1.00 eq) in DCM (5.00 mL) was added TFA (29.44 mg, 258.16 µmol, 19.12 µL, 1.00 eq) with stirring at 30° C. for 1 h. The mixture was concentrated under reduced pressure to give the title compound (40.00 mg, 99.69 µmol, 38.61% yield, TFA) as yellow oil, which was used directly for next step.

Step 6. N-(3-Chloro-4-fluorophenyl)-4-hydroxy-2-methyl-1-oxo-4-(trifluoromethyl)-1,2,3,4,5,8,9,11-octahydro-10H-pyrido[4',3':3,4]pyrazolo[5,1-d][1,2,5]triazepine-10-carboxamide. To a solution of 2-methyl-4-(trifluoromethyl)-2,5,8,9,10,11-hexahydro-1H-pyrido[4',3':3,4]pyrazolo[5,1-d][1,2,5]triazepin-1-one (35.00 mg, 87.23 µmol, 1.00 eq, TFA) and TEA (52.96 mg, 523.38 µmol, 72.55 µL, 6.00 eq) in DCM (8.00 mL) was added phenyl N-(3-chloro-4-fluorophenyl)carbamate (23.17 mg, 87.23 µmol, 1.00 eq) with stirring at 30° C. for 1 h. The mixture was directly evaporated in vacuo and purified by prep-HPLC (FA) to afford the title compound as white solid (12 mg, 29.46%). LCMS: 459[M+1]; $^1$H NMR (400 MHz, $CDCl_3$) δ 7.58 (dd, J=2.63, 6.54 Hz, 1H), 7.16-7.24 (m, 1H), 7.02-7.10 (m, 1H), 6.65 (s, 1H), 4.76 (s, 2H), 3.82-3.92 (t, 2H), 3.45 (s, 3H), 3.06 (d, J=1.71 Hz, 1H), 2.96 (m, J=6.19 Hz, 2H), 2.22 (s, 1H).

Compound 227: N-(3-Chloro-4-fluorophenyl)-4-(hydroxymethyl)-2-methyl-1-oxo-1,2,5,8,9,11-hexahydro-10H-pyrido[4',3':3,4]pyrazolo[5,1-d][1,2,5]triazepine-10-carboxamide

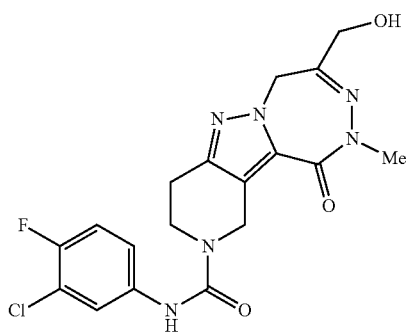 [SMILES: CN1N=C(CO)Cn2nc3c(c2C1=O)CN(C(=O)Nc1ccc(F)c(Cl)c1)CC3]

Step 1. tert-Butyl 3-[[(Z)[1-(acetoxymethyl)-2-chloro-ethylidene]amino]-methyl-carbamoyl]-2,4,6,7-tetrahydropyrazolo[4,3-c]pyridine-5-carboxylate. To a solution of tert-butyl 3-[amino(methyl)carbamoyl]-2,4,6,7-tetrahydropyrazolo[4,3-c]pyridine-5-carboxylate (200.00 mg, 677.19 µmol, 1.00 eq) and p-TsOH (11.66 mg, 67.72 µmol, 0.10 eq) in DCM (15.00 mL) was added (3-chloro-2-oxo-propyl)acetate (132.54 mg, 880.35 µmol, 1.30 eq) with stirring at 25° C. under $N_2$ for 4 h. The mixture was diluted with 30 mL of DCM and washed with brine (50 mL×1). The organic phase was dried over anhydrous $Na_2SO_4$, filtered and concentrated in vacuo. The residue was purified by prep-TLC (PE:EtOAc=1:1) to give the title compound (250.00 mg, 584.28 µmol, 86.28% yield) as white solid.

Step 2. tert-Butyl 4-(acetoxymethyl)-2-methyl-1-oxo-1,2,5,8,9,11-hexahydro-10H-pyrido[4',3':3,4]pyrazolo[5,1-d][1,2,5]triazepine-10-carboxylate. To a solution of tert-butyl 3-[[(Z)-[1-(acetoxymethyl)-2-chloro-ethylidene]amino]-methyl-carbamoyl]-2,4,6,7-tetrahydropyrazolo[4,3-c]pyridine-5-carboxylate (250.00 mg, 584.28 µmol, 1.00 eq) in DMF (10.00 mL) were added $Cs_2CO_3$ (380.74 mg, 1.17 mmol, 2.00 eq) and TBAI (21.58 mg, 58.43 µmol, 0.10 eq) with stirring at 25° C. for 2 h. The mixture was diluted with 20 mL of water and extracted with EtOAc (20 mL×3). The combined organic layers were washed with brine (20 mL×1), dried over anhydrous $Na_2SO_4$, filtered and concentrated in vacuo. The title compound (270.00 mg, crude) was obtained as yellow oil.

Step 3. tert-Butyl 4-(hydroxymethyl)-2-methyl-1-oxo-1,2,5,8,9,11-hexahydro-10H-pyrido[4',3':3,4]pyrazolo[5,1-d][1,2,5]triazepine-10-carboxylate. To a solution of tert-butyl 4-(acetoxymethyl)-2-methyl-1-oxo-1,2,5,8,9,11-hexahydro-10H-pyrido[4',3':3,4]pyrazolo[5,1-d][1,2,5]triazepine-10-carboxylate (250.00 mg, 638.70 µmol, 1.00 eq) in THF (10.00 mL) and $H_2O$ (1.00 mL) was added $LiOH.H_2O$ (53.60 mg, 1.28 mmol, 2.00 eq) with stirring at 25° C. for 2 h. The mixture was diluted with 20 mL of water and extracted with EtOAc (20 mL×3). The combined organic layers were washed with brine (20 mL), dried over anhydrous $Na_2SO_4$, filtered and concentrated in vacuo. The residue was purified by prep-TLC (PE:EtOAc=1:3) to the title compound (160.00 mg, crude) as off-white gum.

Step 4. 4-(Hydroxymethyl)-2-methyl-2,5,8,9,10,11-hexahydro-1H-pyrido[4',3':3,4]pyrazolo[5,1-d][1,2,5]triazepin-1-one. To a solution of tert-butyl 4-(hydroxymethyl)-2-methyl-1-oxo-1,2,5,8,9,11-hexahydro-10H-pyrido[4',3':3,4]pyrazolo[5,1-d][1,2,5]triazepine-10-carboxylate (40.00 mg, 114.49 µmol, 1.00 eq) in DCM (3.00 mL) was added TFA (308.07 mg, 2.70 mmol, 200.05 µL, 23.60 eq) with stirring at 30° C. for 0.5 h. The mixture was concentrated in vacuo at 30° C. The title compound (45.00 mg, crude, TFA) was obtained as yellow oil.

Step 5. N-(3-Chloro-4-fluorophenyl)-4-(hydroxymethyl)-2-methyl-1-oxo-1,2,5,8,9,11-hexahydro-10H-pyrido[4',3':3,4]pyrazolo[5,1-d][1,2,5]triazepine-10-carboxamide. To a solution of 4-(hydroxymethyl)-2-methyl-2,5,8,9,10,11-hexahydro-1H-pyrido[4',3':3,4]pyrazolo[5,1-d][1,2,5]triazepin-1-one (45.00 mg, 123.87 µmol, 1.00 eq, TFA) and phenyl N-(3-chloro-4-fluoro-phenyl)carbamate (34.55 mg, 130.06 µmol, 1.05 eq) in DCM (5.00 mL) was added TEA (75.21 mg, 743.21 µmol, 103.02 µL, 6.00 eq) with stirring at 25° C. for 16 h. The mixture was concentrated in vacuo. The residue was purified by prep-HPLC (FA) to give the title compound (18.00 mg, 42.35 µmol, 34.19% yield, 99% purity) as white solid. LCMS: 421[M+1]; $^1$H NMR (400 MHz, $CDCl_3$) δ=7.57 (dd, J=2.63, 6.54 Hz, 1H), 7.17-7.22

(m, 1H), 7.03-7.09 (m, 1H), 6.56 (s, 1H), 4.87 (s, 2H), 4.72 (s, 2H), 4.51 (s, 2H), 3.85 (t, J=5.75 Hz, 2H), 3.50 (s, 3H), 2.83 (t, J=5.75 Hz, 2H).

Compound 228: N-(3-Cyano-4-fluorophenyl)-4-(hydroxymethyl)-2-methyl-1-oxo-1,2,5,8,9,11-hexahydro-10H-pyrido[4',3':3,4]pyrazolo[5,1-d][1,2,5]triazepine-10-carboxamide

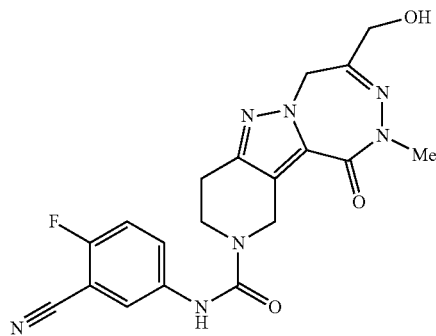 [SMILES: CN1N=C(CO)Cn2nc3c(c2C1=O)CN(C(=O)Nc1ccc(F)c(C#N)c1)CC3]

To a solution of 4-(hydroxymethyl)-2-methyl-2,5,8,9,10,11-hexahydro-1H-pyrido[4',3':3,4]pyrazolo[5,1-d][1,2,5]triazepin-1-one (85.00 mg, 233.97 μmol, 1.00 eq, TFA) and phenyl N-(3-cyano-4-fluoro-phenyl)carbamate (62.95 mg, 245.67 μmol, 1.05 eq) in DCM (5.00 mL) was added TEA (142.05 mg, 1.40 mmol, 194.59 μL, 6.00 eq) with stirring at 25° C. for 16 h. The mixture was concentrated in vacuo. The residue was purified by prep-HPLC (TFA) to give the title compound (12.05 mg, 28.71 μmol, 12.27% yield, 98% purity) as white solid. LCMS: 412[M+1; $^1$H NMR (400 MHz, CDCl$_3$) δ=7.77 (dd, J=2.81, 5.50 Hz, 1H), 7.57-7.64 (m, 1H), 7.14 (t, J=8.68 Hz, 1H), 6.86 (s, 1H), 4.88 (s, 2H), 4.73 (s, 2H), 4.51 (s, 2H), 3.86 (t, J=5.75 Hz, 2H), 3.51 (s, 3H), 2.84 (t, J=5.75 Hz, 2H).

Compound 229: N-(3-Chloro-4-fluorophenyl)-4-(1-hydroxypropyl)-2-methyl-1-oxo-1,2,5,8,9,11-hexahydro-10H-pyrido[4',3':3,4]pyrazolo[5,1-d][1,2,5]triazepine-10-carboxamide

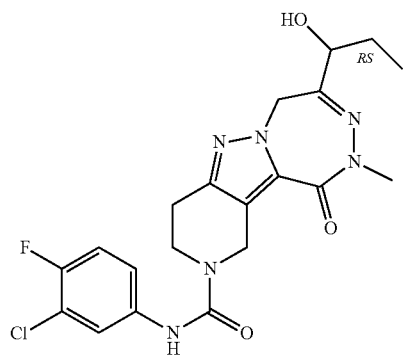 [SMILES: CCC(O)C1=NN(C)C(=O)c2c3c(nn2C1)CCN(C(=O)Nc1ccc(F)c(Cl)c1)C3]

Step 1. tert-Butyl 4-formyl-2-methyl-1-oxo-1,2,5,8,9,11-hexahydro-10H-pyrido[4',3':3,4]pyrazolo[5,1-d][1,2,5]triazepine-10-carboxylate. To a solution of tert-butyl 4-(hydroxymethyl)-2-methyl-1-oxo-5,8,9,11-tetrahydropyrido[2,3]pyrazolo[2,4-d][1,2,5]triazepine-10-carboxylate (600.00 mg, 1.72 mmol, 1.00 eq) in DCM (30.00 mL) was added DMP (1.46 g, 3.43 mmol, 1.06 mL, 2.00 eq) with stirring at 25° C. for 2 h. The mixture was filtered and the filtrate was concentrated in vacuo. The residue was purified by column chromatography (SiO$_2$, PE/EtOAc=10/1 to 3/1) to afford the title compound (450.00 mg, 1.30 mmol, 75.32% yield) as light yellow solid.

Step 2. tert-Butyl 4-(1-hydroxypropyl)-2-methyl-1-oxo-1,2,5,8,9,11-hexahydro-10H-pyrido[4',3':3,4]pyrazolo[5,1-d][1,2,5]triazepine-10-carboxylate. To a solution of tert-butyl 4-formyl-2-methyl-1-oxo-1,2,5,8,9,11-hexahydro-10H-pyrido[4',3':3,4]pyrazolo[5,1-d][1,2,5]triazepine-10-carboxylate (50.00 mg, 143.94 μmol, 1.00 eq) in THF (10.00 mL) was added EtMgBr (3 M, 57.58 μL, 1.20 eq) dropwise at −78° C. under N$_2$. Then the mixture was warmed to 25° C. with stirring for 1 h. Then EtMgBr (3 M, 719.70 μL, 15.00 eq) was added in three portions at −78° C. and the mixture was warmed to 25° C. with stirring for one hour each time. The mixture was quenched with 10 mL of water and extracted with EtOAc (20 mL×3). The organic phase was collected and washed with brine (20 mL). The organic phase was dried over anhydrous Na$_2$SO$_4$, filtered and concentrated in vacuo. The residue was purified by prep-TLC (PE:EtOAc=1:2) to give the title compound (14.00 mg, 37.09 μmol, 25.77% yield) as off-white oil.

Step 3. 4-(1-Hydroxypropyl)-2-methyl-2,5,8,9,10,11-hexahydro-1H-pyrido[4',3':3,4]pyrazolo[5,1-d][1,2,5]triazepin-1-one. To a solution of tert-butyl 4-(1-hydroxypropyl)-2-methyl-1-oxo-1,2,5,8,9,11-hexahydro-10H-pyrido[4',3':3,4]pyrazolo[5,1-d][1,2,5]triazepine-10-carboxylate (14.00 mg, 37.09 μmol, 1.00 eq) in DCM (3.00 mL) was added TFA (77.00 mg, 675.32 μmol, 50.00 μL, 18.21 eq). Then the mixture was stirring at 25° C. for 1 h. The mixture was concentrated in vacuo to give the title compound (15.00 mg, crude, TFA) as yellow oil and used in the next step directly.

Step 4. N-(3-Chloro-4-fluorophenyl)-4-(1-hydroxypropyl)-2-methyl-1-oxo-1,2,5,8,9,11-hexahydro-10H-pyrido[4',3':3,4]pyrazolo[5,1-d][1,2,5]triazepine-10-carboxamide. To a solution of 4-(1-hydroxypropyl)-2-methyl-2,5,8,9,10,11-hexahydro-1H-pyrido[4',3':3,4]pyrazolo[5,1-d][1,2,5]triazepin-1-one (15.00 mg, 38.33 μmol, 1.00 eq, TFA) and phenyl N-(3-chloro-4-fluoro-phenyl)carbamate (10.18 mg, 38.33 μmol, 1.00 eq) in DCM (3.00 mL) was added TEA (31.03 mg, 306.64 μmol, 42.51 μL, 8.00 eq), then the mixture was stirring at 25° C. for 16 h. The mixture was concentrated in vacuo. The residue was purified by prep-HPLC (FA) to obtain the title compound (6.01 mg, 13.12 μmol, 34.23% yield, 98% purity) as white solid. LCMS: 449[M+1]; $^1$H NMR (400 MHz, CDCl$_3$) δ=7.57 (dd, J=2.63, 6.54 Hz, 1H), 7.17-7.23 (m, 1H), 7.02-7.09 (m, 1H), 5.11-5.15 (d, 1H), 4.93-5.01 (m, 1H), 4.71 (s, 2H), 4.60 (s, 2H), 4.44 (t, J=5.20, 7.03 Hz, 1H), 3.80-3.87 (m, 2H), 3.48 (s, 3H), 2.83 (t, J=5.75 Hz, 2H), 1.71-1.59 (m, 2H), 0.83 (t, J=7.40 Hz, 3H).

Compound 230: N-(3-Chloro-4-fluorophenyl)-4-(1-hydroxyethyl)-2-methyl-1-oxo-1,2,5,8,9,11-hexahydro-10H-pyrido[4',3':3,4]pyrazolo[5,1-d][1,2,5]triazepine-10-carboxamide

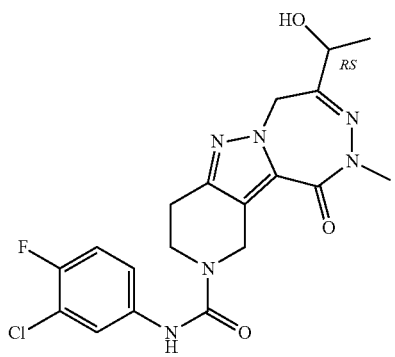 [SMILES: CC(O)C1=NN(C)C(=O)c2c3c(nn2C1)CCN(C(=O)Nc1ccc(F)c(Cl)c1)C3]

Step 1. tert-Butyl 4-(1-hydroxyethyl)-2-methyl-1-oxo-1,2,5,8,9,11-hexahydro-10H-pyrido[4',3':3,4]pyrazolo[5,1-d][1,2,5]triazepine-10-carboxylate. To a solution of tert-butyl 4-formyl-2-methyl-1-oxo-1,2,5,8,9,11-hexahydro-10H-pyrido[4',3':3,4]pyrazolo[5,1-d][1,2,5]triazepine-10-carboxylate (100.00 mg, 287.88 µmol, 1.00 eq) in THF (10.00 mL) was added dropwise MeMgBr (3 M, 576.67 µL, 6.00 eq) in three portions at −78° C. under $N_2$. Then the mixture was warmed to 25° C. with stirring for 4 h. The mixture was quenched with 10 mL of water and extracted with EtOAc (20 mL×3). The combined organic layers were collected and washed with brine (20 mL). The organic phase was dried over anhydrous $Na_2SO_4$, filtered and concentrated in vacuo. The residue was purified by prep-TLC (PE:EtOAc=0:1) to give the title compound (24.00 mg, 66.04 µmol, 22.94% yield) as colorless oil.

Step 2. 4-(1-Hydroxyethyl)-2-methyl-2,5,8,9,10,11-hexahydro-1H-pyrido[4',3':3,4]pyrazolo[5,1-d][1,2,5]triazepin-1-one. To a solution of tert-butyl 4-(1-hydroxyethyl)-2-methyl-1-oxo-1,2,5,8,9,11-hexahydro-10H-pyrido[4',3':3,4]pyrazolo[5,1-d][1,2,5]triazepine-10-carboxylate (24.00 mg, 66.04 µmol, 1.00 eq) in DCM (1.00 mL) was added TFA (77.00 mg, 675.59 µmol, 50.00 µL, 10.23 eq), then the mixture was stirring at 25° C. for 1 h. The mixture was concentrated in vacuo. The title compound (25.00 mg, crude, TFA) was obtained as yellow oil and used in the next step directly.

Step 3. N-(3-Chloro-4-fluorophenyl)-4-(1-hydroxyethyl)-2-methyl-1-oxo-1,2,5,8,9,11-hexahydro-10H-pyrido[4',3':3,4]pyrazolo[5,1-d][1,2,5]triazepine-10-carboxamide. To a solution of 4-(1-hydroxyethyl)-2-methyl-2,5,8,9,10,11-hexahydro-1H-pyrido[4',3':3,4]pyrazolo[5,1-d][1,2,5]triazepin-1-one (25.00 mg, 66.26 µmol, 1.00 eq, TFA) and phenyl N-(3-chloro-4-fluoro-phenyl)carbamate (17.60 mg, 66.26 µmol, 1.00 eq) in DCM (3.00 mL) was added TEA (53.64 mg, 530.05 µmol, 73.47 µL, 8.00 eq), then the mixture was stirring at 25° C. for 3 h. The mixture was concentrated in vacuo. The residue was purified by prep-HPLC (FA). The title compound (16.00 mg, 36.06 µmol, 54.42% yield, 98% purity) was obtained as white solid. LCMS: 435 [M+1]; $^1H$ NMR (400 MHz, $CDCl_3$) δ=7.58 (dd, J=2.76, 6.53 Hz, 1H), 7.27-7.19 (m, J=2.70, 4.05, 8.94 Hz, 1H), 7.02-7.09 (m, 1H), 6.53 (s, 1H), 4.86-5.02 (m, 2H), 4.71 (s, 2H), 4.64 (m, J=6.65 Hz, 1H), 3.85 (t, J=5.84 Hz, 2H), 3.49 (s, 3H), 2.84 (t, J=5.77 Hz, 2H), 1.42 (d, J=6.65 Hz, 3

Compound 231: N-(3-Chloro-4-fluorophenyl)-4-(cyclopropyl(hydroxy)methyl)-2-methyl-1-oxo-1,2,5,8,9,11-hexahydro-10H-pyrido[4',3':3,4]pyrazolo[5,1-d][1,2,5]triazepine-10-carboxamide

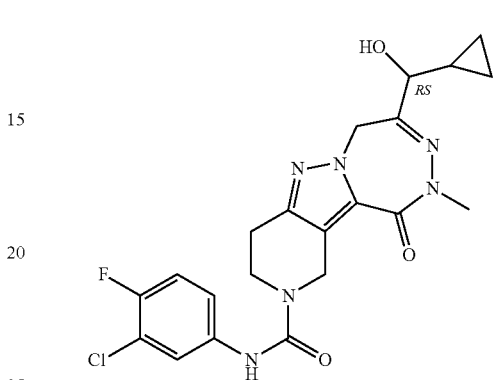

Step 1. tert-Butyl 4-(cyclopropyl(hydroxy)methyl)-2-methyl-1-oxo-1,2,5,8,9,11-hexahydro-10H-pyrido[4',3':3,4]pyrazolo[5,1-d][1,2,5]triazepine-10-carboxylate. To a solution of tert-butyl 4-formyl-2-methyl-1-oxo-1,2,5,8,9,11-hexahydro-10H-pyrido[4',3':3,4]pyrazolo[5,1-d][1,2,5]triazepine-10-carboxylate (200.00 mg, 575.75 µmol, 1.00 eq) in THF (10.00 mL) was added drop wise bromo(cyclopropyl)magnesium (0.458 M, 5.03 mL, 4.00 eq) under $N_2$ at −78° C. The mixture was warmed to 20° C. with stirring for 1 h. Then bromo(cyclopropyl)magnesium (0.458 M, 5.03 mL, 4.00 eq) was added dropwise at 0° C. and the mixture was warmed to 20° C. with stirring for 1 h. Bromo(cyclopropyl)magnesium (0.458 M, 12.57 mL, 10.00 eq) was added dropwise at 0° C. and the mixture was warmed to 20° C. with stirring for 2 h. The mixture was combined with an earlier batch (200 mg) and diluted with 10 mL of DCM, washed with HCl (1N, 30 mL) and brine (20 mL). The organic phase was dried over anhydrous $Na_2SO_4$, filtered and concentrated in vacuo. The residue was purified by prep-TLC (PE:EtOAc=1:1) and prep-HPLC(FA) to give 13 mg of the title compound as white solid.

Step 2. 4-(Cyclopropyl(hydroxy)methyl)-2-methyl-2,5,8,9,10,11-hexahydro-1H-pyrido[4',3':3,4]pyrazolo[5,1-d][1,2,5]triazepin-1-one. To a solution of tert-butyl 4-(cyclopropyl(hydroxy)methyl)-2-methyl-1-oxo-1,2,5,8,9,11-hexahydro-10H-pyrido[4',3':3,4]pyrazolo[5,1-d][1,2,5]triazepine-10-carboxylate (13.00 mg, 33.38 µmol, 1.00 eq) in DCM (1.00 mL) was added TFA (38.94 mg, 341.48 µmol, 25.28 µL, 10.23 eq), then the mixture was stirring at 25° C. for 1 h. The mixture was concentrated in vacuo. The residue was not purified. The title compound (14.00 mg, crude, TFA) was obtained as yellow oil and used in the next step directly.

Step 3. N-(3-Chloro-4-fluorophenyl)-4-(cyclopropyl(hydroxy)methyl)-2-methyl-1-oxo-1,2,5,8,9,11-hexahydro-10H-pyrido[4',3':3,4]pyrazolo[5,1-d][1,2,5]triazepine-10-carboxamide. To a solution of 4-(cyclopropyl(hydroxy)methyl)-2-methyl-2,5,8,9,10,11-hexahydro-1H-pyrido[4',3':3,4]pyrazolo[5,1-d][1,2,5]triazepin-1-one (14.00 mg, 34.71 µmol, 1.00 eq, TFA) and phenyl N-(3-chloro-4-fluoro-phenyl)carbamate (9.22 mg, 34.71 µmol, 1.00 eq) in DCM (3.00 mL) was added TEA (28.10 mg, 277.67 µmol, 38.49 µL, 8.00 eq), then the mixture was stirring at 25° C. for 3 h. The mixture was concentrated in vacuo. The residue was purified by prep-HPLC (FA) to give the title compound (8.50 mg, 18.20 μmol, 52.44% yield, 98.7% purity) as white solid. LCMS: 461[M+1]. $^1$H NMR (400 MHz, CDCl$_3$) δ=7.58 (dd, J=2.64, 6.53 Hz, 1H), 7.16-7.22 (m, 1H), 7.03-7.09 (m, 1H), 6.55 (s, 1H), 5.07-5.13 (m, 1H), 4.92-4.99 (m, 1H), 4.72 (d, J=2.89 Hz, 2H), 3.81-3.88 (m, 3H), 3.49 (s, 3H), 2.79-2.88 (m, 3H), 0.98-1.09 (m, 1H), 0.57-0.67 (m, 2H), 0.45-0.54 (m, 2H).

Compound 232: N-(3-Chloro-4-fluorophenyl)-2,4-dimethyl-1-oxo-1,2,5,8,9,11-hexahydro-10H-pyrido[4',3':3,4]pyrazolo[5,1-d][1,2,5]triazepine-10-carboxamide

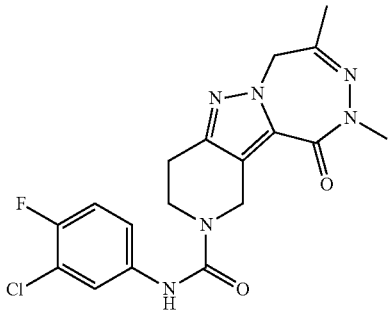 [SMILES: CC1=NN(C)C(=O)c2c3c(nn2C1)CCN(C(=O)Nc1ccc(F)c(Cl)c1)C3]

Step 1. tert-Butyl 3-[[(E)-(2-hydroxy-1-methyl-ethylidene)amino]-methyl-carbamoyl]-2,4,6,7-tetrahydropyrazolo[4,3-c]pyridine-5-carboxylate. To a solution of tert-butyl 3-[amino(methyl)carbamoyl]-2,4,6,7-tetrahydropyrazolo [4,3-c]pyridine-5-carboxylate (300.00 mg, 1.02 mmol, 1.00 eq) and p-TsOH (17.56 mg, 102.00 μmol, 0.10 eq) in DCM (20.00 mL) was added 1-hydroxypropan-2-one (377.81 mg, 5.10 mmol, 349.82 μL, 5.00 eq) with stirring at 20° C. under N$_2$ for 2 h. The mixture was directly evaporated. The residue was purified by prep-TLC (PE:EA=0:1) to give the title compound (240.00 mg, 682.98 μmol, 66.96% yield) as off-white oil.

Step 2. tert-Butyl 3-[methyl-[(E)-(1-methyl-2-methylsulfonyloxy-ethylidene)amino]carbamoyl]-2,4,6,7-tetrahydropyrazolo[4,3-c]pyridine-5-carboxylate. To a solution of tert-butyl 3-[[(E)-(2-hydroxy-1-methyl-ethylidene)amino]-methyl-carbamoyl]-2,4,6,7-tetrahydropyrazolo[4,3-c]pyridine-5-carboxylate (100.00 mg, 284.58 μmol, 1.00 eq) in DCM (3.00 mL) was added pyridine (45.02 mg, 569.15 μmol, 45.94 μL, 2.00 eq) followed by MsCl (65.20 mg, 569.15 μmol, 44.05 μL, 2.00 eq). The mixture was stirred at 20° C. for 20 hr. The mixture was diluted with H$_2$O (30 mL) and extracted with EA (50 mL×2). The combined organic layer was washed saturated Cu$_2$SO$_4$ (30 mL), dried over Na$_2$SO$_4$, filtered. The filtrate was concentrated in vacuo. The residue was purified by prep-TLC (PE:EA=1:1). The title compound (70.00 mg, 162.98 μmol, 57.27% yield) was obtained as colorless oil.

Step 3. tert-Butyl 2,4-dimethyl-1-oxo-1,2,5,8,9,11-hexahydro-10H-pyrido[4',3':3,4]pyrazolo[5,1-d][1,2,5]triazepine-10-carboxylate. To a suspension of NaH (9.31 mg, 232.84 μmol, 60% purity, 2.00 eq) in THF (5.00 mL) was added a solution of tert-butyl 3-[methyl-[(E)-(1-methyl-2-methylsulfonyloxy-ethylidene)amino]carbamoyl]-2,4,6,7-tetrahydropyrazolo[4,3-c]pyridine-5-carboxylate (50.00 mg, 116.42 μmol, 1.00 eq) in THF (500.00 μL) at −10° C. The mixture was stirred at 20° C. for 2 hr. The mixture was quenched by H$_2$O (10 mL) and extracted with EA (20 mL×2). The combined organic layers were dried over Na$_2$SO$_4$, filtered. The filtrate was concentrated in vacuo. The residue was purified by prep-TLC (PE:EA=1:1) to give the title compound (20.00 mg, 49.19 μmol, 42.25% yield, 82% purity) as colorless oil.

Step 4. 2,4-Dimethyl-2,5,8,9,10,11-hexahydro-1H-pyrido[4',3':3,4]pyrazolo[5,1-d][1,2,5]triazepin-1-one. To a solution of tert-butyl 2,4-dimethyl-1-oxo-1,2,5,8,9,11-hexahydro-10H-pyrido[4',3':3,4]pyrazolo[5,1-d][1,2,5]triazepine-10-carboxylate (20.00 mg, 59.99 μmol, 1.00 eq) in DCM (3.00 mL) was added TFA (3.08 g, 27.01 mmol, 2.00 mL, 450.31 eq). The mixture was stirred at 20° C. for 0.5 hr. The residue was concentrated in vacuo to afford the title compound (22.00 mg, crude, TFA) as brown oil.

Step 5. N-(3-Chloro-4-fluorophenyl)-2,4-dimethyl-1-oxo-1,2,5,8,9,11-hexahydro-10H-pyrido[4',3':3,4]pyrazolo[5,1-d][1,2,5]triazepine-10-carboxamide. To a solution of 2,4-dimethyl-2,5,8,9,10,11-hexahydro-1H-pyrido[4',3':3,4]pyrazolo[5,1-d][1,2,5]triazepin-1-one (22.00 mg, 63.35 μmol, 1.00 eq, TFA) in DCM (5.00 mL) was added TEA (32.05 mg, 316.75 μmol, 43.90 μL, 5.00 eq) followed by phenyl 3-chloro-4-fluoro-benzoate (15.88 mg, 63.35 μmol, 1.00 eq). The mixture was stirred at 20° C. for 16 hr. The mixture was concentrated in vacuo. The residue was purified by prep-HPLC (FA) to afford the title compound (16.00 mg, 35.25 μmol, 55.65% yield, 89.2% purity) as white solid. LCMS: 405 [M+1]; $^1$H NMR (400 MHz, DMSO-d$_6$) δ=8.98 (s, 1H), 7.79 (dd, J=2.57, 6.85 Hz, 1H), 7.48 (m, J=2.69, 4.28, 9.05 Hz, 1H), 7.29-7.37 (m, 1H), 4.99 (s, 2H), 4.69 (s, 2H), 3.79 (t, J=5.62 Hz, 2H), 3.36 (s, 3H), 2.77 (t, J=5.56 Hz, 2H), 2.24 (s, 3H).

Compound 233: (R)—N-(3-Cyano-4-fluorophenyl)-4-(hydroxymethyl)-2,9-dimethyl-1-oxo-1,2,5,8,9,11-hexahydro-10H-pyrido[4',3':3,4]pyrazolo[5,1-d][1,2,5]triazepine-10-carboxamide

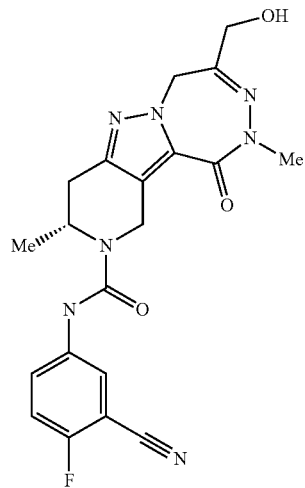

Step 1. tert-Butyl (R)-3-(2-((benzyloxy)carbonyl)-1-methylhydrazine-1-carbonyl)-6-methyl-2,4,6,7-tetrahydro-5H-pyrazolo[4,3-c]pyridine-5-carboxylate. To a solution of (R)-5-(tert-butoxycarbonyl)-6-methyl-4,5,6,7-tetrahydro-2H-pyrazolo[4,3-c]pyridine-3-carboxylic acid (4.80 g, 17.06 mmol, 1.00 eq) and benzyl N-(methylamino)carbamate (4.81 g, 22.18 mmol, 1.30 eq, HCl) in DMF (30.00 mL) were added PYBOP (9.77 g, 18.77 mmol, 1.10 eq), HOBT (2.54 g, 18.77 mmol, 1.10 eq) and DIPEA (13.23 g, 102.37 mmol, 17.88 mL, 6.00 eq). The mixture was stirred at 25° C. for 3 hr. The reaction mixture was diluted with $H_2O$ (100 mL) and extracted with EA (100 mL×3). The combined organic layers were separated, washed with $H_2O$ (100 mL×3), 1N HCl (80 mL) and $NaHCO_3$ (sat. aq. 80 mL). The combined organic layer was dried over $Na_2SO_4$, filtered. The filtrate was concentrated in vacuo. The residue was purified by column chromatography ($SiO_2$, PE/EA=10:1 to 1:3) to give the title compound (6.80 g, 15.33 mmol, 89.87% yield) as white solid.

Step 2. tert-Butyl (R)-6-methyl-3-(1-methylhydrazine-1-carbonyl)-2,4,6,7-tetrahydro-5H-pyrazolo[4,3-c]pyridine-5-carboxylate. To a solution of tert-butyl (R)-3-(2-((benzyloxy)carbonyl)-1-methylhydrazine-1-carbonyl)-6-methyl-2,4,6,7-tetrahydro-5H-pyrazolo[4,3-c]pyridine-5-carboxylate (2.00 g, 4.51 mmol, 1.00 eq) in MeOH (20.00 mL) was added Pd/C (400.00 mg, 10% purity) under $N_2$. The suspension was degassed under vacuum and purged with $H_2$ several times. The mixture was stirred under $H_2$ (15 psi) at 25° C. for 16 hours. The reaction solution was filtered directly. The filtrate was concentrated under vacuum. The residue was purified by column chromatography ($SiO_2$, PE/EA=1:2-0:1~EA/MeOH=50:1) to afford the title compound (1.20 g, 3.88 mmol, 86.01% yield) as white solid.

Step 3. tert-Butyl (R,Z)-3-(2-(1-acetoxy-3-chloropropan-2-ylidene)-1-methylhydrazine-1-carbonyl)-6-methyl-2,4,6,7-tetrahydro-5H-pyrazolo[4,3-c]pyridine-5-carboxylate. To a solution of tert-butyl (R)-6-methyl-3-(1-methylhydrazine-1-carbonyl)-2,4,6,7-tetrahydro-5H-pyrazolo[4,3-c]pyridine-5-carboxylate (1.80 g, 5.82 mmol, 1.00 eq) and (3-chloro-2-oxo-propyl) acetate (1.14 g, 7.56 mmol, 1.30 eq) in DCM (15.00 mL) was added p-TsOH (100.19 mg, 581.85 µmol, 0.10 eq). The mixture was stirred at 25° C. for 4 hr under $N_2$. The mixture was concentrated in vacuo. The residue was purified by column chromatography (PE:EA:30%~50%) to afford the title compound (2.32 g, 5.25 mmol, 90.21% yield) as white solid.

Step 4. tert-Butyl (R)-4-(hydroxymethyl)-2,9-dimethyl-1-oxo-1,2,5,8,9,11-hexahydro-10H-pyrido[4',3':3,4]pyrazolo[5,1-d][1,2,5]triazepine-10-carboxylate. To a solution of tert-butyl (R,Z)-3-(2-(1-acetoxy-3-chloropropan-2-ylidene)-1-methylhydrazine-1-carbonyl)-6-methyl-2,4,6,7-tetrahydro-5H-pyrazolo[4,3-c]pyridine-5-carboxylate (2.00 g, 4.53 mmol, 1.00 eq) in THF (30.00 mL) was added DBU (1.38 g, 9.06 mmol, 1.37 mL, 2.00 eq). The mixture was heated to 70° C. for 16 hr. The mixture was cooled to 25° C. and added $H_2O$ (10.00 mL). The reaction mixture was stirred at 25° C. for 5 hr. The mixture was diluted with $H_2O$ (100 mL) and extracted with EA (50 mL×2). The combined organic layer was dried over $Na_2SO_4$, filtered and concentrated in vacuo to give a residue. The residue was purified by column chromatography (PE:EA:50%~100%) to give 1 g of the title compound as yellow solid.

Step 5. (R)-4-(Hydroxymethyl)-2,9-dimethyl-2,5,8,9,10,11-hexahydro-1H-pyrido[4',3':3,4]pyrazolo[5,1-d][1,2,5]tri-azepin-1-one. To a solution of tert-butyl (R)-4-(hydroxymethyl)-2,9-dimethyl-1-oxo-1,2,5,8,9,11-hexahydro-10H-pyrido[4',3':3,4]pyrazolo[5,1-d][1,2,5]triazepine-10-carboxylate (100.00 mg, 214.63 µmol, 1.00 eq) in DCM (5.00 mL) was added TFA (7.21 g, 63.21 mmol, 4.68 mL, 294.49 eq) at 0° C. slowly. The mixture was stirred at 25° C. for 1 hr. The mixture was concentrated in vacuo. The title compound was obtained as brown oil.

Step 6. (R)—N-(3-Cyano-4-fluorophenyl)-4-(hydroxymethyl)-2,9-dimethyl-1-oxo-1,2,5,8,9,11-hexahydro-10H-pyrido[4',3':3,4]pyrazolo[5,1-d][1,2,5]triazepine-10-carboxamide. To a solution of (R)-4-(hydroxymethyl)-2,9-dimethyl-2,5,8,9,10,11-hexahydro-1H-pyrido[4',3':3,4]pyrazolo[5,1-d][1,2,5]triazepin-1-one (95.00 mg, 251.78 µmol, 1.00 eq, TFA) and phenyl N-(3-cyano-4-fluoro-phenyl)carbamate (64.51 mg, 251.78 µmol, 1.00 eq) in DCM (5.00 mL) was added TEA (127.39 mg, 1.26 mmol, 174.50 µL, 5.00 eq). The mixture was stirred at 25° C. for 3 hr. The mixture was diluted in $H_2O$ (10 mL) and extracted with DCM (20 mL×2). The combined organic layers were washed 1N HCl (10 mL), dried over $Na_2SO_4$, filtered and concentrated in vacuo. The residue was purified by prep-TLC (PE:EA=0:1) and prep-HPLC (base) to afford the title compound (25.00 mg, 57.18 µmol, 22.71% yield, 97.31% purity) as white solid. LCMS: 426[M+1]; $^1H$ NMR (400 MHz, Acetone) δ=8.55 (s, 1H), 8.06 (dd, J=2.7, 5.8 Hz, 1H), 7.91-7.81 (m, 1H), 7.31 (t, J=9.0 Hz, 1H), 5.19-4.95 (m, 4H), 4.70-4.58 (m, 1H), 4.40-4.33 (m, 2H), 3.40 (s, 3H), 2.95-3.25 (dd, J=6.1, 16.0 Hz, 1H), 2.88-2.85 (m, 1H), 2.61-2.65 (d, J=15.9 Hz, 1H), 1.16 (d, J=6.9 Hz, 3H).

Compound 234: (R)—N-(3-Bromo-4-fluorophenyl)-4-(hydroxymethyl)-2,9-dimethyl-1-oxo-1,2,5,8,9,11-hexahydro-10H-pyrido[4',3':3,4]pyrazolo[5,1-d][1,2,5]triazepine-10-carboxamide

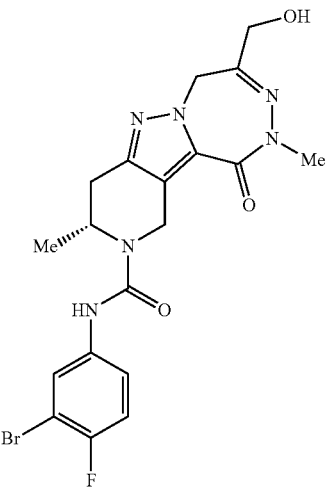

To a solution of (R)-4-(hydroxymethyl)-2,9-dimethyl-2,5,8,9,10,11-hexahydro-1H-pyrido[4',3':3,4]pyrazolo[5,1-d][1,2,5]triazepin-1-one (52.00 mg, 137.81 μmol, 1.00 eq, TFA) and phenyl N-(3-bromo-4-fluoro-phenyl)carbamate (42.74 mg, 137.81 μmol, 1.00 eq) in DCM (5.00 mL) was added TEA (69.72 mg, 689.05 μmol, 95.51 μL, 5.00 eq). The mixture was stirred at 25° C. for 3 hr. The mixture was concentrated in vacuo. The residue was purified by pre-HPLC (Base) twice to give the title compound (20.00 mg, 40.48 μmol, 29.37% yield, 97% purity) as white solid. LCMS: 479/481[M+1]; $^1$H NMR (400 MHz, CDCl$_3$) δ=7.74 (dd, J=2.6, 6.1 Hz, 1H), 7.31-7.29 (m, 1H), 7.06 (t, J=8.5 Hz, 1H), 6.57 (s, 1H), 5.20-5.11 (m, 1H), 4.90 (s, 2H), 4.86 (s, 1H), 4.87-4.84 (m, 1H), 4.57-4.46 (m, 3H), 3.53 (s, 3H), 3.33 (d, J=2.8 Hz, 1H), 3.03 (dd, J=5.5, 15.6 Hz, 1H), 2.80 (t, J=5.2 Hz, 1H), 2.67 (d, J=16.1 Hz, 1H), 1.18 (d, J=6.9 Hz, 3H).

Compound 235: (R)—N-(3-Chloro-4-fluorophenyl)-4-(hydroxymethyl)-2,9-dimethyl-1-oxo-1,2,5,8,9,11-hexahydro-10H-pyrido[4',3':3,4]pyrazolo[5,1-d][1,2,5]triazepine-10-carboxamide

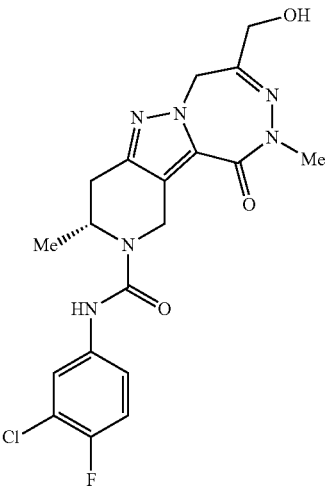 [SMILES: C[C@@H]1Cc2nn3c(c2CN1C(=O)Nc1ccc(F)c(Cl)c1)C(=O)N(C)N=C(CO)C3]

To a solution of (R)-4-(hydroxymethyl)-2,9-dimethyl-2,5,8,9,10,11-hexahydro-1H-pyrido[4',3':3,4]pyrazolo[5,1-d][1,2,5]triazepin-1-one (52.00 mg, 137.81 μmol, 1.00 eq, TFA) and phenyl N-(3-chloro-4-fluoro-phenyl)carbamate (36.61 mg, 137.81 μmol, 1.00 eq) in DCM (5.00 mL) was added TEA (69.72 mg, 689.05 μmol, 95.51 μL, 5.00 eq). The mixture was stirred at 25° C. for 3 hr. The mixture was concentrated in vacuo. The residue was purified by pre-HPLC(FA), and then purified by prep-TLC(PE:EA=0:1). Further purification by prep-HPLC (Base) to afford the title compound (8.00 mg, 17.86 μmol, 12.96% yield, 97.1% purity) as white solid. LCMS: 435[M+1]; $^1$H NMR (400 MHz, CDCl$_3$) δ=7.61 (dd, J=2.6, 6.5 Hz, 1H), 7.18-7.25 (m, 1H), 7.04-7.11 (m, 1H), 6.55 (s, 1H), 5.16 (m, J=6.5 Hz, 1H), 4.90 (s, 2H), 4.86 (s, 1H), 4.45-4.56 (m, 3H), 3.53 (s, 3H), 3.33 (d, J=2.3 Hz, 1H), 2.98-3.07 (m, 1H), 2.80 (s, 1H), 2.67 (m, J=15.8 Hz, 1H), 1.18 (d, J=6.9 Hz, 3H).

Compound 236: (R)—N-(3-Bromo-4-fluorophenyl)-4-((2,2-difluoroethoxy)methyl)-2,9-dimethyl-1-oxo-1,2,5,8,9,11-hexahydro-10H-pyrido[4',3':3,4]pyrazolo[5,1-d][1,2,5]triazepine-10-carboxamide

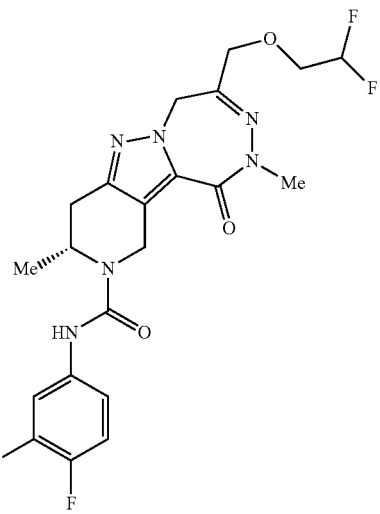

Step 1. tert-Butyl (R)-4-((2,2-difluoroethoxy)methyl)-2,9-dimethyl-1-oxo-1,2,5,8,9,11-hexahydro-10H-pyrido[4',3':3,4]pyrazolo[5,1-d][1,2,5]triazepine-10-carboxylate. To a solution of tert-butyl (R)-4-(hydroxymethyl)-2,9-dimethyl-1-oxo-1,2,5,8,9,11-hexahydro-10H-pyrido[4',3':3,4]pyrazolo[5,1-d][1,2,5]triazepine-10-carboxylate (50.00 mg, 107.32 μmol, 1.00 eq) in DMF (1.00 mL) was added NaH (8.59 mg, 214.63 μmol, 60% purity, 2.00 eq) at −40° C. The mixture was stirred at −20° C. for 0.5 hr. Then a solution of 2,2-difluoroethyl trifluoromethanesulfonate (68.93 mg, 321.95 μmol, 3.00 eq) in DMF (300.00 μL) was added at −20° C. The reaction mixture was stirred at −20° C. for 0.5 hr. The reaction mixture was quenched by saturated NH$_4$Cl (10 mL) and extracted with EA (20 mL×2). The combined organic layer were washed with H$_2$O (20 mL), dried over Na$_2$SO$_4$, filtered and concentrated in vacuo. The title compound (40.00 mg, crude) was obtained as colorless oil.

Step 2. (R)-4-((2,2-Difluoroethoxy)methyl)-2,9-dimethyl-2,5,8,9,10,11-hexahydro-1H-pyrido[4',3':3,4]pyrazolo[5,1-d][1,2,5]triazepin-1-one. To a solution of tert-butyl (R)-4-((2,2-difluoroethoxy)methyl)-2,9-dimethyl-1-oxo-1,2,5,8,9,11-hexahydro-10H-pyrido[4',3':3,4]pyrazolo[5,1-d][1,2,5]triazepine-10-carboxylate (40.00 mg, 93.58 μmol, 1.00 eq) in DCM (2.00 mL) was added TFA (27.01 mmol, 2.00 mL, 288.66 eq). The mixture was stirred at 25° C. for 1 hr. The mixture was concentrated in vacuo. The title compound (43.00 mg, crude, TFA) was obtained as brown oil.

Step 3. (R)—N-(3-Bromo-4-fluorophenyl)-4-((2,2-difluoroethoxy)methyl)-2,9-dimethyl-1-oxo-1,2,5,8,9,11-hexahydro-10H-pyrido[4',3':3,4]pyrazolo[5,1-d][1,2,5]triazepine-10-carboxamide. To a solution of (R)-4-((2,2-difluoroethoxy)methyl)-2,9-dimethyl-2,5,8,9,10,11-hexahydro-1H-pyrido[4',3':3,4]pyrazolo[5,1-d][1,2,5]triazepin-1-one (40.00 mg, 90.63 µmol, 1.00 eq, TFA) and phenyl N-(3-bromo-4-fluoro-phenyl)carbamate (28.11 mg, 90.63 µmol, 1.00 eq) in DCM (4.00 mL) was added TEA (45.85 mg, 453.15 µmol, 62.81 µL, 5.00 eq). The mixture was stirred at 25° C. for 5 hr. The mixture was diluted with H$_2$O (15 mL) and extracted with DCM (20 mL×2). The combined organic layers were dried over Na$_2$SO$_4$, filtered and concentrated in vacuo. The residue was purified by prep-HPLC (Base) to afford the title compound (18.00 mg, 32.63 µmol, 36.01% yield, 98.5% purity) as white solid. LCMS: 543/545[M+1]; $^1$H NMR (400 MHz, CDCl$_3$) δ=7.75 (dd, J=2.7, 6.1 Hz, 1H), 7.24-7.28 (m, 1H), 7.02-7.11 (m, 1H), 6.54 (s, 1H), 5.77-6.10 (m, 1H), 5.12-5.21 (m, 1H), 4.93-5.04 (m, 2H), 4.87 (d, J=15.9 Hz, 1H), 4.49 (d, J=15.9 Hz, 1H), 4.41 (s, 2H), 3.66-3.77 (m, 2H), 3.51 (s, 3H), 3.35 (d, J=4.0 Hz, 1H), 3.03 (dd, J=6.0, 16.1 Hz, 1H), 2.68 (d, J=16.1 Hz, 1H), 1.17 (d, J=6.9 Hz, 3H).

Compound 237: (R)—N-(3-Cyano-4-fluorophenyl)-4-((2,2-difluoroethoxy)methyl)-2,9-dimethyl-1-oxo-1,2,5,8,9,11-hexahydro-10H-pyrido[4',3':3,4]pyrazolo[5,1-d][1,2,5]triazepine-10-carboxamide

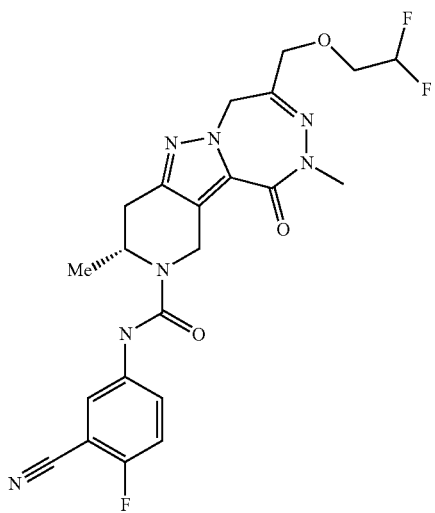 [SMILES: C[C@@H]1Cc2nn3c(c2CN1C(=O)Nc1ccc(F)c(C#N)c1)C(=O)N(C)N=C(COCC(F)F)C3]

To a mixture of (R)-4-((2,2-difluoroethoxy)methyl)-2,9-dimethyl-2,5,8,9,10,11-hexahydro-1H-pyrido[4',3':3,4]pyrazolo[5,1-d][1,2,5]triazepin-1-one (150.00 mg, 339.87 µmol, 1.00 eq, TFA) in DCM (3.00 mL) was added TEA (137.57 mg, 1.36 mmol, 188.45 µL, 4.00 eq), followed by phenyl N-(3-cyano-4-fluoro-phenyl)carbamate (87.08 mg, 339.87 µmol, 1.00 eq), the reaction mixture was stirred at 20° C. for 3 hours. The mixture was diluted in water (20 mL) and extracted with DCM (30 mL×3), the combined organic layers were dried with anhydrous Na$_2$SO$_4$, filtered and concentrated in vacuum. The residue was purified by prep-HPLC(Base) to afford the title compound (48.00 mg, 96.11 µmol, 28.28% yield, 98% purity) as white solid. LCMS: 490[M+1]; $^1$H NMR (400 MHz, CDCl$_3$) δ 7.79 (dd, J=2.82, 5.46 Hz, 1H), 7.58 (m, J=2.82, 4.55, 9.07 Hz, 1H), 7.14 (t, J=8.72 Hz, 1H), 6.52-6.72 (m, 1H), 5.75-6.09 (m, 1H), 5.15 (m, J=6.27 Hz, 1H), 4.91-5.03 (m, 2H), 4.87 (d, J=15.81 Hz, 1H), 4.50 (d, J=15.69 Hz, 1H), 4.33-4.44 (m, 2H), 3.66-3.77 (m, 2H), 3.50 (s, 3H), 3.34 (d, J=3.14 Hz, 1H), 2.98-3.06 (m, 1H), 2.68 (d, J=16.19 Hz, 1H), 1.14-1.19 (d, 3H).

Compound 238: (R)-4-((2,2-Difluoroethoxy)methyl)-N-(4-fluoro-3-(trifluoromethyl)phenyl)-2,9-dimethyl-1-oxo-1,2,5,8,9,11-hexahydro-10H-pyrido[4',3':3,4]pyrazolo[5,1-d][1,2,5]triazepine-10-carboxamide

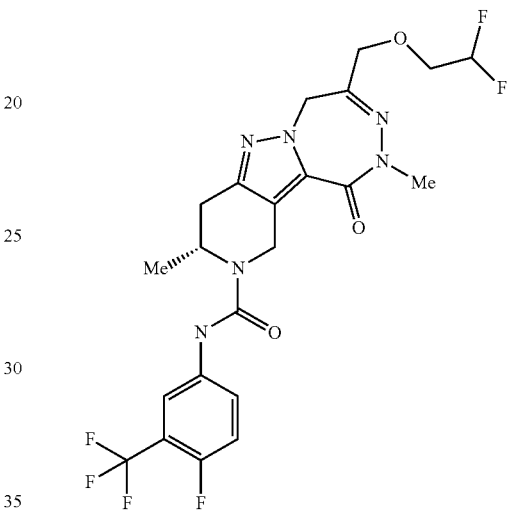

To a mixture of (R)-4-((2,2-difluoroethoxy)methyl)-2,9-dimethyl-2,5,8,9,10,11-hexahydro-1H-pyrido[4',3':3,4] pyrazolo[5,1-d][1,2,5]triazepin-1-one (150.00 mg, 339.87 µmol, 1.00 eq, TFA) in DCM (3.00 mL) was added TEA (137.57 mg, 1.36 mmol, 188.45 µL, 4.00 eq), followed by phenyl N-[4-fluoro-3-(trifluoromethyl)phenyl] carbamate (101.69 mg, 339.87 µmol, 1.00 eq), the reaction mixture was stirred at 20° C. for 3 hours. The mixture was diluted in water (20 mL) and extracted with DCM (30 mL×3), the combined organic layers were dried with anhydrous Na$_2$SO$_4$, filtered and concentrated in vacuo. The residue was purified by prep-HPLC (Base) to afford the title compound (30.00 mg, 53.53 µmol, 15.75% yield, 95% purity) as white solid. LCMS: 533[M+1]; $^1$H NMR (400 MHz, CDCl$_3$) δ 7.68 (dd, J=2.82, 6.09 Hz, 1H), 7.56-7.62 (m, 1H), 7.14 (t, J=9.47 Hz, 1H), 6.57 (s, 1H), 5.76-6.08 (m, 1H), 5.16 (m, J=6.02 Hz, 1H), 4.92-5.02 (m, 2H), 4.88 (d, J=15.69 Hz, 1H), 4.46-4.55 (m, 1H), 4.39 (s, 2H), 3.65-3.76 (m, 2H), 3.50 (s, 3H), 3.34 (d, J=4.27 Hz, 1H), 2.97-3.07 (m, 1H), 2.67 (d, J=16.44 Hz, 1H), 1.14-1.21 (d, 3H).

Example 1: HBV Assembly Assay

The interference of compounds from this invention with HBV capsid assembly could be measured using an in vitro assembly assay based on fluorescence quenching, which was developed according to a method described by Zlotnick and coworkers (Nature Biotechnology 2006, 24:358). In a typical assay, a mutant HBV C150 protein (amino acids 1-150, C49A, C61A, C107A, 150C) is cloned into a T7 RNA-polymerase based expression vector, expressed in *E. coli* and purified to homogeneity as a dimer. The purified HBV core protein is desalted and labeled with BODIPY-FL Dye.

In a non-limiting embodiment, the assembly assay is conducted in 96-well plate format. The assembly reactions are carried out in 50 mM Hepes buffer, pH 7.5 and 150 mM NaCl. The compounds are pre-incubated with the HBV CA protein for 15 min, and the assembly reactions are initiated by addition of NaCl. The reaction is allowed to continue for 1 hour at room temperature. The changes in fluorescence between DMSO treated and compound treated samples are recorded and analyzed for assembly modulation.

Example 2: HBV Replication Inhibition Assay

HBV replication inhibition by the disclosed compounds were determined in cells infected or transfected with HBV or cells with stably integrated HBV, such as HepG2.2.15 cells (Sells et al. 1987). In this example, HepG2.2.15 cells were maintained in cell culture medium containing 10% fetal bovine serum (FBS), Geneticin, L-glutamine, penicillin and streptomycin. HepG2.2.15 cells were seeded in 96-well plates at a density of 40,000 cells/well and were treated with serially diluted compounds at a final DMSO concentration of 0.5% either alone or in combination by adding drugs in a checker box format. Cells were incubated with compounds for three days, after which medium was removed and fresh medium containing compounds was added to cells and incubated for another three days. At day 6, supernatant was removed and treated with DNase at 37° C. for 60 minutes, followed by enzyme inactivation at 75° C. for 15 minutes. Encapsidated HBV DNA was released from the virions and covalently linked HBV polymerase by incubating in lysis buffer (Affymetrix QS0010) containing 2.5 µg proteinase K at 50° C. for 40 minutes. HBV DNA was denatured by addition of 0.2 M NaOH and detected using a branched DNA (BDNA) QuantiGene assay kit according to manufacturer recommendation (Affymetrix). HBV DNA levels were also quantified using qPCR, based on amplification of encapsidated HBV DNA extraction with QuickExtraction Solution (Epicentre Biotechnologies) and amplification of HBV DNA using HBV specific PCR probes that can hybridize to HBV DNA and a fluorescently labeled probe for quantitation. In addition, cell viability of HepG2.2.15 cells incubated with test compounds alone or in combination was determined by using CellTitre-Glo reagent according to the manufacturer protocol (Promega). The mean background signal from wells containing only culture medium was subtracted from all other samples, and percent inhibition at each compound concentration was calculated by normalizing to signals from HepG2.2.15 cells treated with 0.5% DMSO using equation E1.

$$\% \text{ inhibition} = (\text{DMSOave} - Xi)/\text{DMSOave} \times 100\% \quad \text{E1:}$$

where DMSOave is the mean signal calculated from the wells that were treated with DMSO control (0% inhibition control) and Xi is the signal measured from the individual wells. EC50 values, effective concentrations that achieved 50% inhibitory effect, were determined by non-linear fitting using Graphpad Prism software (San Diego, Calif.) and equation E2:

$$Y = Y\min + (Y\max - Y\min)/(1 + 10(\text{Log EC50} - X) \times \text{Hill-Slope}) \quad \text{E2:}$$

where Y represents percent inhibition values and X represents the logarithm of compound concentrations.

Selected disclosed compounds were assayed in the HBV replication assay (BDNA assay), as described above, and a representative group of these active compounds is shown in Table 7. Table 7 shows $EC_{50}$ values obtained by the BDNA assay for a group of select compounds. In Table 7, "A" represents $1 < EC_{50} \leq 100$; "B" represents $100 < EC_{50} \leq 500$; "C" represents $500 < EC_{50} \leq 1000$; and "D" represents $EC_{50} > 1000$.

TABLE 7

| Compound ID | Compound Name | DNA $EC_{50}$ (nM) |
|---|---|---|
| 001 | N-(3-bromophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide | A |
| 002 | 4-(hydroxymethyl)-2-methyl-1-oxo-N-(m-tolyl)-1,4,5,8,9,11-hexahydropyrido[4',3':3,4]pyrazolo[5,1-d][1,2,5]oxadiazepine-10(2H)-carboxamide | A |
| 003 | N-(2-chloro-3-fluoropyridin-4-yl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide | B |
| 004 | N-(3-bromo-2-fluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide | A |
| 005 | N-(3,4-difluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide | A |
| 006 | 4-(hydroxymethyl)-2-methyl-1-oxo-N-(3,4,5-trifluorophenyl)-1,4,5,8,9,11-hexahydropyrido[4',3':3,4]pyrazolo[5,1-d][1,2,5]oxadiazepine-10(2H)-carboxamide | A |
| 007 | N-(3-chloro-2,4-difluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide | A |

TABLE 7-continued

Activity in BDNA-assay (EC$_{50}$)

| Compound ID | Compound Name | DNA EC$_{50}$ (nM) |
|---|---|---|
| 008 | 4-(hydroxymethyl)-2-methyl-1-oxo-N-(3-(trifluoromethyl)phenyl)-1,4,5,8,9,11-hexahydropyrido[4',3':3,4]pyrazolo[5,1-d][1,2,5]oxadiazepine-10(2H)-carboxamide | A |
| 009 | N-(3-ethylphenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide | A |
| 010 | N-(3-bromo-2,4-difluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide | A |
| 011_E1 | (S*)-N-(4-fluoro-3-(trifluoromethyl)phenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide | A |
| 011_E2 | (R*)-N-(4-fluoro-3-(trifluoromethyl)phenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide | A |
| 012 | N-(3,4-dichlorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide | A |
| 013 | N-(5-chloro-2,4-difluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide | A |
| 014 | N-(5-bromo-2,4-difluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide | A |
| 015 | N-(3-bromo-4,5-difluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide | A |
| 016 | N-(2,5-dimethylphenyl)-4-(hydroxymethyl)-2-methyl-1-oxo-1,4,5,8,9,11-hexahydropyrido[4',3':3,4]pyrazolo[5,1d]-[1,2,5]oxadiazepine-10(2H)-carboxamide | A |
| 017 | N-(5-bromo-2-methylphenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide | A |
| 018 | N-(5-bromo-4-fluoro-2-methylphenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide | A |
| 019 | 4-(hydroxymethyl)-2-methyl-N-(3-methylcyclohexyl)-1-oxo-1,4,5,8,9,11-hexahydropyrido[4',3':3,4]pyrazolo[5,1-d][1,2,5]oxadiazepine-10(2H)-carboxamide | C |
| 020 | 4-(hydroxymethyl)-N-(3-iodophenyl)-2-methyl-1-oxo-1,4,5,8,9,11-hexahydropyrido[4',3':3,4]pyrazolo[5,1-d][1,2,5]oxadiazepine-10(2H)-carboxamide | A |
| 021 | N-(3-(difluoromethyl)phenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide | A |
| 022 | N-(3-chloro-4-fluoro-5-(trifluoromethyl)phenyl)-4-(hydroxymethyl)-2-methyl-1-oxo-1,4,5,8,9,11-hexahydropyrido[4',3':3,4]pyrazolo[5,1d]-[1,2,5]oxadiazepine-10(2H)-carboxamide | A |
| 023 | N-(2,3-dichloro-4-fluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide | A |
| 024 | N-(3,4-dichloro-2-fluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide | A |
| 025 | N-(4-chloro-3-(trifluoromethyl)phenyl)-4-(hydroxymethyl)-2-methyl-1-oxo-1,4,5,8,9,11-hexahydropyrido[4',3':3,4]pyrazolo[5,1d]-[1,2,5]oxadiazepine-10(2H)-carboxamide | A |
| 026 | N-(3-chloro-4-methylphenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide | A |

TABLE 7-continued

Activity in BDNA-assay (EC$_{50}$)

| Compound ID | Compound Name | DNA EC$_{50}$ (nM) |
|---|---|---|
| 027 | N-(4,5-dichloro-2-fluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide | A |
| 028_E1 | (S*)-N-(3-chloro-4,5-difluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide | A |
| 029 | 4-(hydroxymethyl)-2-methyl-1-oxo-N-(3-(pentafluoro-16-sulfanyl)phenyl)-1,4,5,8,9,11-hexahydropyrido[4',3':3,4]pyrazolo[5,1-d][1,2,5]oxadiazepine-10(2H)-carboxamide | A |
| 030 | N-(3-chlorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide | A |
| 031_E1 | (S*)-N-(3-chloro-4-fluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide | A |
| 031_E2 | (R*)-N-(3-chloro-4-fluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide | A |
| 032_E1 | (S*)-N-(3-bromo-4-fluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide | A |
| 033_E1 | (S*)-N-(2-bromo-3-fluoropyridin-4-yl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide | A |
| 034_E1 | (S*)-N-(3-cyano-4-fluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide | A |
| 035_E1 | (S*)-N-(4-fluoro-3-methylphenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide | A |
| 036 | 4-(fluoromethyl)-2-methyl-1-oxo-N-(3-(trifluoromethyl)phenyl)-1,4,5,8,9,11-hexahydropyrido[4',3':3,4]pyrazolo[5,1-d][1,2,5]oxadiazepine-10(2H)-carboxamide | A |
| 037_E1 | (S*)-N-(3-chlorophenyl)-4-(fluoromethyl)-2-methyl-1-oxo-1,4,5,8,9,11-hexahydropyrido[4',3':3,4]pyrazolo[5,1-d][1,2,5]oxadiazepine-10(2H)-carboxamide | A |
| 038_E1 | (S*)-N-(3-chloro-4-fluorophenyl)-4-(fluoromethyl)-2-methyl-1-oxo-1,4,5,8,9,11-hexahydropyrido[4',3':3,4]pyrazolo[5,1-d][1,2,5]oxadiazepine-10(2H)-carboxamide | A |
| 039_E1 | (S*)-N-(4-fluoro-3-(trifluoromethyl)phenyl)-4-(fluoromethyl)-2-methyl-1-oxo-1,4,5,8,9,11-hexahydropyrido[4',3':3,4]pyrazolo[5,1-d][1,2,5]oxadiazepine-10(2H)-carboxamide | A |
| 040_E1 | (S*)-N-(3-bromo-4-fluorophenyl)-4-(fluoromethyl)-2-methyl-1-oxo-1,4,5,8,9,11-hexahydropyrido[4',3':3,4]pyrazolo[5,1-d][1,2,5]oxadiazepine-10(2H)-carboxamide | A |
| 041_E1 | (S*)-N-(2-bromo-3-fluoropyridin-4-yl)-4-(fluoromethyl)-2-methyl-1-oxo-1,4,5,8,9,11-hexahydropyrido[4',3':3,4]pyrazolo[5,1-d][1,2,5]oxadiazepine-10(2H)-carboxamide | A |
| 042_E1 | (S*)-N-(3-cyano-4-fluorophenyl)-4-(fluoromethyl)-2-methyl-1-oxo-1,4,5,8,9,11-hexahydropyrido[4',3':3,4]pyrazolo[5,1-d][1,2,5]oxadiazepine-10(2H)-carboxamide | A |
| 043_E1 | (S*)-N-(4-fluoro-3-methylphenyl)-4-(fluoromethyl)-2-methyl-1-oxo-1,4,5,8,9,11-hexahydropyrido[4',3':3,4]pyrazolo[5,1-d][1,2,5]oxadiazepine-10(2H)-carboxamide | A |
| 044_E1 | (S*)-N-(3-chloro-4,5-difluorophenyl)-4-(fluoromethyl)-2-methyl-1-oxo-1,4,5,8,9,11-hexahydropyrido[4',3':3,4]pyrazolo[5,1-d][1,2,5]oxadiazepine-10(2H)-carboxamide | A |

TABLE 7-continued

Activity in BDNA-assay (EC$_{50}$)

| Compound ID | Compound Name | DNA EC$_{50}$ (nM) |
|---|---|---|
| 045 | N-(3-chloro-4-fluorophenyl)-4-(hydroxymethyl)-N,2-dimethyl-1-oxo-1,4,5,8,9,11-hexahydropyrido[4',3':3,4]pyrazolo[5,1-d][1,2,5]oxadiazepine-10(2H)-carboxamide | B |
| 046 | N-(3-chlorophenyl)-4-(hydroxymethyl)-2,8,8-trimethyl-1-oxo-1,4,5,8,9,11-hexahydropyrido[4',3':3,4]pyrazolo[5,1-d][1,2,5]oxadiazepine-10(2H)-carboxamide | B |
| 047 | N-(3-chlorophenyl)-4-(hydroxymethyl)-2,8-dimethyl-1-oxo-1,4,5,8,9,11-hexahydropyrido[4',3':3,4]pyrazolo[5,1-d][1,2,5]oxadiazepine-10(2H)-carboxamide | B |
| 048 | N-(3-chloro-4-fluoro-phenyl)-2-methyl-4-(methylsulfanylmethyl)-1-oxo-5,8,9,11-tetrahydro-4H-pyrido[2,3]pyrazolo[2,4-d][1,2,5]oxadiazepine-10-carboxamide | A |
| 049_E1 | (S*)-N-(3-chloro-4-fluorophenyl)-2-methyl-4-(((S*)-methylsulfinyl)methyl)-1-oxo-1,4,5,8,9,11-hexahydropyrido[4',3':3,4]pyrazolo[5,1-d][1,2,5]oxadiazepine-10(2H)-carboxamide | B |
| 049_E2 | (S*)-N-(3-chloro-4-fluorophenyl)-2-methyl-4-(((R*)-methylsulfinyl)methyl)-1-oxo-1,4,5,8,9,11-hexahydropyrido[4',3':3,4]pyrazolo[5,1-d][1,2,5]oxadiazepine-10(2H)-carboxamide | A |
| 049_E3 | (R*)-N-(3-chloro-4-fluorophenyl)-2-methyl-4-(((R*)-methylsulfinyl)methyl)-1-oxo-1,4,5,8,9,11-hexahydropyrido[4',3':3,4]pyrazolo[5,1-d][1,2,5]oxadiazepine-10(2H)-carboxamide | A |
| 049_E4 | (R*)-N-(3-chloro-4-fluorophenyl)-2-methyl-4-(((S*)-methylsulfinyl)methyl)-1-oxo-1,4,5,8,9,11-hexahydropyrido[4',3':3,4]pyrazolo[5,1-d][1,2,5]oxadiazepine-10(2H)-carboxamide | B |
| 050 | N-(3-chloro-4-fluorophenyl)-2-methyl-4-((methylsulfonyl)methyl)-1-oxo-1,4,5,8,9,11-hexahydropyrido[4',3':3,4]pyrazolo[5,1-d][1,2,5]oxadiazepine-10(2H)-carboxamide | A |
| 051 | (10-((3-chloro-4-fluorophenyl)carbamoyl)-2-methyl-1-oxo-1,2,4,5,8,9,10,11-octahydropyrido[4',3':3,4]pyrazolo[5,1-d][1,2,5]oxadiazepin-4-yl)methyl methyl carbonate | A |
| 052 | (10-((3-chloro-4-fluorophenyl)carbamoyl)-2-methyl-1-oxo-1,2,4,5,8,9,10,11-octahydropyrido[4',3':3,4]pyrazolo[5,1-d][1,2,5]oxadiazepin-4-yl)methyl acetate | A |
| 053 | (10-((3-chloro-4-fluorophenyl)carbamoyl)-2-methyl-1-oxo-1,2,4,5,8,9,10,11-octahydropyrido[4',3':3,4]pyrazolo[5,1-d][1,2,5]oxadiazepin-4-yl)methyl isopropyl carbonate | A |
| 054 | tert-butyl((10-((3-chloro-4-fluorophenyl)carbamoyl)-2-methyl-1-oxo-1,2,4,5,8,9,10,11-octahydropyrido[4',3':3,4]pyrazolo[5,1-d][1,2,5]oxadiazepin-4-yl)methyl) carbonate | A |
| 055 | (10-((3-chloro-4-fluorophenyl)carbamoyl)-2-methyl-1-oxo-1,2,4,5,8,9,10,11-octahydropyrido[4',3':3,4]pyrazolo[5,1-d][1,2,5]oxadiazepin-4-yl)methyl pivalate | A |
| 056 | (10-((3-chloro-4-fluorophenyl)carbamoyl)-2-methyl-1-oxo-1,2,4,5,8,9,10,11-octahydropyrido[4',3':3,4]pyrazolo[5,1-d][1,2,5]oxadiazepin-4-yl)methyl ethyl carbonate | A |
| 057 | (104-3-chloro-4-fluorophenyl)carbamoyl)-2-methyl-1-oxo-1,2,4,5,8,9,10,11-octahydropyrido[4',3':3,4]pyrazolo[5,1-d][1,2,5]oxadiazepin-4-yl)methyl carbamate | A |
| 058 | N-(3-chloro-4-fluoro-phenyl)-4-[(dimethylamino)methyl]-2-methyl-1-oxo-5,8,9,11-tetrahydro-4H-pyrido[2,3]pyrazolo[2,4-d][1,2,5]oxadiazepine-10-carboxamide | A |
| 059 | [10-[(3-chloro-4-fluoro-phenyl)carbamoyl]-2-methyl-1-oxo-5,8,9,11-tetrahydro-4H-pyrido[2,3]pyrazolo[2,4-d][1,2,5]oxadiazepin-4-yl]methyl N,N-dimethylcarbamate | A |
| 060_E1 | (S*)-N-(3-chloro-4-fluorophenyl)-2-ethyl-4-(hydroxymethyl)-1-oxo-1,4,5,8,9,11-hexahydropyrido[4',3':3,4]pyrazolo[5,1-d][1,2,5]oxadiazepine-10(2H)-carboxamide | A |

TABLE 7-continued

Activity in BDNA-assay (EC$_{50}$)

| Compound ID | Compound Name | DNA EC$_{50}$ (nM) |
|---|---|---|
| 060_E2 | (R*)-N-(3-chloro-4-fluorophenyl)-2-ethyl-4-(hydroxymethyl)-1-oxo-1,4,5,8,9,11-hexahydropyrido[4',3':3,4]pyrazolo[5,1-d][1,2,5]oxadiazepine-10(2H)-carboxamide | A |
| 061 | N-(3-chloro-4-fluoro-phenyl)-2,5-dimethyl-1-oxo-5,8,9,11-tetrahydro-4H-pyrido[2,3]pyrazolo[2,4-d][1,2,5]oxadiazepine-10-carboxamide | A |
| 062 | N-(3-chloro-4-fluorophenyl)-2,4-dimethyl-1-oxo-1,4,5,8,9,11-hexahydropyrido[4',3':3,4]pyrazolo[5,1-d][1,2,5]oxadiazepine-10(2H)-carboxamide | A |
| 063 | N-(3-chlorophenyl)-2,4-dimethyl-1-oxo-1,4,5,8,9,11-hexahydropyrido[4',3':3,4]pyrazole[5,1-d][1,2,5]oxadiazepine-10(2H)-carboxamide | A |
| 064 | N-(3-chloro-4-fluoro-phenyl)-2,4,4-trimethyl-1-oxo-5,8,9,11-tetrahydro pyrido[2,3]pyrazolo[2,4-d][1,2,5]oxadiazepine-10-carboxamide | A |
| 065 | N-(3-chloro-4-fluoro-phenyl)-4-(methoxymethyl)-2-methyl-1-oxo-5,8,9,11-tetrahydro-4H-pyrido[2,3]pyrazolo[2,4-d][1,2,5]oxadiazepine-10-carboxamide | A |
| 066 | N-(3-chloro-4-fluoro-phenyl)-2-methyl-1-oxo-5,8,9,11-tetrahydro-4H-pyrido[2,3]pyrazolo[2,4-c][1,2,5]oxadiazepine-10-carboxamide | A |
| 067 | 2-allyl-N-(3-chloro-4-fluoro-phenyl)-1-oxo-5,8,9,11-tetrahydro-4H-pyrido[2,3]pyrazolo[2,4-c][1,2,5]oxadiazepine-10-carboxamide | A |
| 068 | N-(3-chloro-4-fluoro-phenyl)-1-oxo-2-propyl-5,8,9,11-tetrahydro-4H-pyrido[2,3]pyrazolo[2,4-c][1,2,5]oxadiazepine-10-carboxamide | A |
| 069_E1 | (4S*,9S*)-N-(3-chloro-4-fluorophenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 069_E2 | (4R*,9S*)-N-(3-chloro-4-fluorophenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 069_E3 | (4R*,9R*)-N-(3-chloro-4-fluorophenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide | B |
| 069_E4 | (4S*,9R*)-N-(3-chloro-4-fluorophenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 070 | N-(3-chloro-4-fluoro-phenyl)-4-(hydroxymethyl)-2,9-dimethyl-1-oxo-5,8,9,11-tetrahydro-4H-pyrido[2,3]pyrazolo[2,4-d][1,2,5]oxadiazepine-10-carboxamide | A |
| 071 | methyl 10-[(3-chloro-4-fluoro-phenyl)carbamoyl]-2-methyl-1-oxo-5,8,9,11-tetrahydro-4H-pyrido[2,3]pyrazolo[2,4-d][1,2,5]oxadiazepine-10-carboxylate | D |
| 072 | N10-(3-chloro-4-fluoro-phenyl)-2-methyl-1-oxo-5,8,9,11-tetrahydro-4H-pyrido[2,3]pyrazolo[2,4-d][1,2,5]oxadiazepine-4,10-dicarboxamide | A |
| 073 | N10-(3-chloro-4-fluoro-phenyl)-N4,2-dimethyl-1-oxo-5,8,9,11-tetrahydro-4H-pyrido[2,3]pyrazolo[2,4-d][1,2,5]oxadiazepine-4,10-dicarboxamide | A |
| 074 | N10-(3-chloro-4-fluoro-phenyl)-N4,N4,2-trimethyl-1-oxo-5,8,9,11-tetrahydro-4H-pyrido[2,3]pyrazolo[2,4-d][1,2,5]oxadiazepine-4,10-dicarboxamide | A |
| 075 | (9R)-N-(3-chloro-4-fluoro-phenyl)-2,9-dimethyl-1-oxo-5,8,9,11-tetrahydro-4H-pyrido[2,3]pyrazolo[2,4-c][1,2,5]oxadiazepine-10-carboxamide | A |
| 076 | (R)-N-(4-fluoro-3-(trifluoromethyl)phenyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 077 | (R)-N-(3-bromo-4-fluorophenyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 078 | (R)-N-(2-bromo-3-fluoropyridin-4-yl)-2,9-dimethyl-1-oxo-1,4,5,8,9,11-hexahydropyrido[4',3':3,4]pyrazolo[5,1-d][1,2,5]oxadiazepine-10(2H)-carboxamide | A |

TABLE 7-continued

Activity in BDNA-assay ($EC_{50}$)

| Compound ID | Compound Name | DNA $EC_{50}$ (nM) |
|---|---|---|
| 079 | (R)-N-(3-cyano-4-fluorophenyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 080 | (R)-N-(4-fluoro-3-methylphenyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 081 | (R)-N-(3-chloro-4,5-difluorophenyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 082_E1 | (4S*,9R)-N-(4-fluoro-3-(trifluoromethyl)phenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 082_E2 | (4R*,9R)-N-(4-fluoro-3-(trifluoromethyl)phenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 083_E1 | (4S*,9R)-N-(4-fluoro-3-methylphenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 083_E2 | (4R*,9R)-N-(4-fluoro-3-methylphenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 084_E1 | (4S*,9R)-N-(3-cyano-4-fluorophenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 084_E2 | (4R*,9R)-N-(3-cyano-4-fluorophenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 085_E1 | (4S*,9R)-N-(4-fluoro-3-(trifluoromethyl)phenyl)-4-(fluoromethyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 085_E2 | (4R*,9R)-N-(4-fluoro-3-(trifluoromethyl)phenyl)-4-(fluoromethyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 086_E1 | (4S*,9R)-N-(4-fluoro-3-methylphenyl)-4-(fluoromethyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 086_E2 | (4R*,9R)-N-(4-fluoro-3-methylphenyl)-4-(fluoromethyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 087_E1 | (4S*,9R)-N-(3-cyano-4-fluorophenyl)-4-(fluoromethyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 087_E2 | (4R*,9R)-N-(3-cyano-4-fluorophenyl)-4-(fluoromethyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 088_E1 | (4S*,9R)-N-(3-chloro-4-fluorophenyl)-4-(fluoromethyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 088_E2 | (4R*,9R)-N-(3-chloro-4-fluorophenyl)-4-(fluoromethyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 089_E1 | (4S*,9R)-N-(5-bromo-2,4-difluorophenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 089_E2 | (4R*,9R)-N-(5-bromo-2,4-difluorophenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |

TABLE 7-continued

Activity in BDNA-assay (EC$_{50}$)

| Compound ID | Compound Name | DNA EC$_{50}$ (nM) |
|---|---|---|
| 090_E1 | (4S*,9R)-N-(5-chloro-2,4-difluorophenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 090_E2 | (4R*,9R)-N-(5-chloro-2,4-difluorophenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 091_E1 | (4S*,9R)-N-(3-chloro-2,4-difluorophenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 091_E2 | (4R*,9R)-N-(3-chloro-2,4-difluorophenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 092_E1 | (4S*,9R)-N-(3-bromo-2,4-difluorophenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 092_E2 | (4R*,9R)-N-(3-bromo-2,4-difluorophenyl)-4-(hydroxymethyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 093_D1 | (4S*,9R)-N-(3-chloro-4-fluorophenyl)-4-((dimethylamino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 093_D2 | (4R*,9R)-N-(3-chloro-4-fluorophenyl)-4-((dimethylamino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 094_D1 | (4S*,9R)-N-(3-bromo-4-fluorophenyl)-4-((dimethylamino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 094_D2 | (4R*,9R)-N-(3-bromo-4-fluorophenyl)-4-((dimethylamino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 095_D1 | (4S*,9R)-N-(2-bromo-3-fluoropyridin-4-yl)-4-((dimethylamino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide | B |
| 095_D2 | (4R*,9R)-N-(2-bromo-3-fluoropyridin-4-yl)-4-((dimethylamino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide | B |
| 096_D1 | (4S*,9R)-N-(3-cyano-4-fluorophenyl)-4-((dimethylamino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide | B |
| 096_D2 | (4R*,9R)-N-(3-cyano-4-fluorophenyl)-4-((dimethylamino)methyl)-2,9-dimethyl-1-oxo-1,4,5,8,9,11-hexahydropyrido[4',3':3,4]pyrazolo[5,1d]-[1,2,5]oxadiazepine-10(2H)-carboxamide | A |
| 097_D1 | (4S*,9R)-4-((dimethylamino)methyl)-N-(4-fluoro-3-methylphenyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 097_D2 | (4R*,9R)-4-((dimethylamino)methyl)-N-(4-fluoro-3-methylphenyl)-2,9-dimethyl-1-oxo-1,4,5,8,9,11-hexahydropyrido[4',3':3,4]pyrazolo[5,1d]-[1,2,5]oxadiazepine-10(2H)-carboxamide | A |
| 098_D1 | (4S*,9R)-4-((dimethylamino)methyl)-N-(4-fluoro-3-(trifluoromethyl)phenyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 098_D2 | (4R*,9R)-4-((dimethylamino)methyl)-N-(4-fluoro-3-(trifluoromethyl)phenyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |

TABLE 7-continued

Activity in BDNA-assay (EC$_{50}$)

| Compound ID | Compound Name | DNA EC$_{50}$ (nM) |
|---|---|---|
| 099_D1 | (4S*,9R)-N-(5-chloro-2,4-difluorophenyl)-4-((dimethylamino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide | B |
| 099_D2 | (4R*,9R)-N-(5-chloro-2,4-difluorophenyl)-4-((dimethylamino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide | B |
| 100_D1 | (4S*,9R)-N-(5-bromo-2,4-difluorophenyl)-4-((dimethylamino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide | B |
| 100_D2 | (4R*,9R)-N-(5-bromo-2,4-difluorophenyl)-4-((dimethylamino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 101 | N-(3-chloro-4-fluoro-phenyl)-4-(ethoxymethyl)-2-methyl-1-oxo-5,8,9,11-tetrahydro-4H-pyrido[2,3]pyrazolo[2,4-d][1,2,5]oxadiazepine-10-carboxamide | A |
| 102 | 4-(allyloxymethyl)-N-(3-chloro-4-fluoro-phenyl)-2-methyl-1-oxo-5,8,9,11-tetrahydro-4H-pyrido[2,3]pyrazolo[2,4-d][1,2,5]oxadiazepine-10-carboxamide | A |
| 103 | N-(3-chloro-4-fluoro-phenyl)-2-methyl-1-oxo-4-(propoxymethyl)-5,8,9,11-tetrahydro-4H-pyrido[2,3]pyrazolo[2,4-d][1,2,5]oxadiazepine-10-carboxamide | A |
| 104 | N-(3-chloro-4-fluoro-phenyl)-4-(cyclopropylmethoxymethyl)-2-methyl-1-oxo-5,8,9,11-tetrahydro-4H-pyrido[2,3]pyrazolo[2,4-d][1,2,5]oxadiazepine-10-carboxamide | A |
| 105 | N-(3-chloro-4-fluoro-phenyl)-4-(2,2-difluoroethoxymethyl)-2-methyl-1-oxo-5,8,9,11-tetrahydro-4H-pyrido[2,3]pyrazolo[2,4-d][1,2,5]oxadiazepine-10-carboxamide | A |
| 106 | N-(3-chloro-4-fluoro-phenyl)-2-methyl-1-oxo-4-(2,2,2-trifluoroethoxymethyl)-5,8,9,11-tetrahydro-4H-pyrido[2,3]pyrazolo[2,4-d][1,2,5]oxadiazepine-10-carboxamide | A |
| 107 | N-(3-chloro-4-fluoro-phenyl)-4-(hydroxymethyl)-1-oxo-2-(trideuteriomethyl)-5,8,9,11-tetrahydro-4H-pyrido[2,3]pyrazolo[2,4-d][1,2,5]oxadiazepine-10-carboxamide | A |
| 108_D1 | (4S*,9R)-N-(5-bromo-2,4-difluorophenyl)-4-((2,2-difluoroethoxy)methyl)-2,9-dimethyl-1-oxo-1,4,5,8,9,11-hexahydropyrido[4',3':3,4]pyrazolo[5,1-d][1,2,5]oxadiazepine-10(2H)-carboxamide | B |
| 108_D2 | (4R*,9R)-N-(5-bromo-2,4-difluorophenyl)-4-((2,2-difluoroethoxy)methyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 109_D1 | (4S*,9S*)-N-(3-chloro-4-fluorophenyl)-9-ethyl-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide | B |
| 109_D2 | (4S*,9R*)-N-(3-chloro-4-fluorophenyl)-9-ethyl-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide | B |
| 109_D3 | (4R*,9R*)-N-(3-chloro-4-fluorophenyl)-9-ethyl-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide | C |
| 109_D4 | (4R*,9S*)-N-(3-chloro-4-fluorophenyl)-9-ethyl-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide | B |
| 110_D1 | (4S*,9R)-N10-(3-chloro-2,4-difluorophenyl)-N4,2,9-trimethyl-1-oxo-1,4,5,8,9,11-hexahydropyrido[4',3':3,4]pyrazolo[5,1-d][1,2,5]oxadiazepine-4,10(2H)-dicarboxamide | C |

TABLE 7-continued

Activity in BDNA-assay (EC$_{50}$)

| Compound ID | Compound Name | DNA EC$_{50}$ (nM) |
|---|---|---|
| 110_D2 | (4R*,9R)-N10-(3-chloro-2,4-difluorophenyl)-N4,2,9-trimethyl-1-oxo-1,4,5,8,9,11-hexahydropyrido[4',3':3,4]pyrazolo[5,1-d][1,2,5]oxadiazepine-4,10(2H)-dicarboxamide | A |
| 111_D1 | (4S*,9R)-N10-(5-chloro-2,4-difluorophenyl)-N4,2,9-trimethyl-1-oxo-1,4,5,8,9,11-hexahydropyrido[4',3':3,4]pyrazolo[5,1-d][1,2,5]oxadiazepine-4,10(2H)-dicarboxamide | D |
| 111_D2 | (4R*,9R)-N10-(5-chloro-2,4-difluorophenyl)-N4,2,9-trimethyl-1-oxo-1,4,5,8,9,11-hexahydropyrido[4',3':3,4]pyrazolo[5,1-d][1,2,5]oxadiazepine-4,10(2H)-dicarboxamide | A |
| 112_D1 | (4S*,9R)-N10-(3-cyano-4-fluorophenyl)-N4,2,9-trimethyl-1-oxo-1,4,5,8,9,11-hexahydropyrido[4',3':3,4]pyrazolo[5,1-d][1,2,5]oxadiazepine-4,10(2H)-dicarboxamide | D |
| 112_D2 | (4R*,9R)-N10-(3-cyano-4-fluorophenyl)-N4,2,9-trimethyl-1-oxo-1,4,5,8,9,11-hexahydropyrido[4',3':3,4]pyrazolo[5,1-d][1,2,5]oxadiazepine-4,10(2H)-dicarboxamide | A |
| 113 | 4-(aminomethyl)-N-(3-chloro-4-fluoro-phenyl)-2-methyl-1-oxo-5,8,9,11-tetrahydro-4H-pyrido[2,3]pyrazolo[2,4-d][1,2,5]oxadiazepine-10-carboxamide | A |
| 114_E1 | (S*)-4-(aminomethyl)-N-(3-cyano-4-fluoro-phenyl)-2-methyl-1-oxo-5,8,9,11-tetrahydro-4H-pyrido[2,3]pyrazolo[2,4-d][1,2,5]oxadiazepine-10-carboxamide | A |
| 115_D1 | (4S*,9R)-4-(aminomethyl)-N-(3-cyano-4-fluorophenyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 115_D2 | (4R*,9R)-4-(aminomethyl)-N-(3-cyano-4-fluorophenyl)-2,9-dimethyl-1-oxo-1,4,5,8,9,11-hexahydropyrido[4',3':3,4]pyrazolo[5,1-d][1,2,5]oxadiazepine-10(2H)-carboxamide | N/A |
| 116_D1 | (4S*,9R)-4-(aminomethyl)-N-(4-fluoro-3-(trifluoromethyl)phenyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 116_D2 | (4R*,9R)-4-(aminomethyl)-N-(4-fluoro-3-(trifluoromethyl)phenyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 117_D1 | (4S*,9R)-4-(aminomethyl)-N-(3-bromo-4-fluorophenyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 117_D2 | (4R*,9R)-4-(aminomethyl)-N-(3-bromo-4-fluorophenyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 118 | N10-(3-chloro-2,4-difluorophenyl)-N4,2-dimethyl-1-oxo-1,4,5,8,9,11-hexahydropyrido[4',3':3,4]pyrazolo[5,1-d][1,2,5]oxadiazepine-4,10(2H)-dicarboxamide | A |
| 119 | N10-(5-chloro-2,4-difluorophenyl)-N4,2-dimethyl-1-oxo-1,4,5,8,9,11-hexahydropyrido[4',3':3,4]pyrazolo[5,1-d][1,2,5]oxadiazepine-4,10(2H)-dicarboxamide | B |
| 120 | N10-(3-cyano-4-fluorophenyl)-N4,2-dimethyl-1-oxo-1,4,5,8,9,11-hexahydropyrido[4',3':3,4]pyrazolo[5,1-d][1,2,5]oxadiazepine-4,10(2H)-dicarboxamide | B |
| 121_D1 | (4S*,9R)-N-(3-chloro-4-fluorophenyl)-4-((2,2-difluoroethoxy)methyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 121_D2 | (4R*,9R)-N-(3-chloro-4-fluorophenyl)-4-((2,2-difluoroethoxy)methyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 122_D1 | (4S*,9R)-N-(3-bromo-4-fluorophenyl)-4-((2,2-difluoroethoxy)methyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |

TABLE 7-continued

Activity in BDNA-assay (EC$_{50}$)

| Compound ID | Compound Name | DNA EC$_{50}$ (nM) |
|---|---|---|
| 122_D2 | (4R*,9R)-N-(3-bromo-4-fluorophenyl)-4-((2,2-difluoroethoxy)methyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 123_D1 | (4S*,9R)-N-(2-bromo-3-fluoropyridin-4-yl)-4-((2,2-difluoroethoxy)methyl)-2,9-dimethyl-1-oxo-1,4,5,8,9,11-hexahydropyrido[4',3':3,4]pyrazolo[5,1-d][1,2,5]oxadiazepine-10(2H)-carboxamide | B |
| 123_D2 | (4R*,9R)-N-(2-bromo-3-fluoropyridin-4-yl)-4-((2,2-difluoroethoxy)methyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 124_D1 | (4S*,9R)-N-(3-cyano-4-fluorophenyl)-4-((2,2-difluoroethoxy)methyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 124_D2 | (4R*,9R)-N-(3-cyano-4-fluorophenyl)-4-((2,2-difluoroethoxy)methyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 125_D1 | (4S*,9R)-4-42,2-difluoroethoxy)methyl)-N-(4-fluoro-3-methylphenyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 125_D2 | (4R*,9R)-44(2,2-difluoroethoxy)methyl)-N-(4-fluoro-3-methylphenyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 126_D1 | (4S*,9R)-4-42,2-difluoroethoxy)methyl)-N-(4-fluoro-3-(trifluoromethyl)phenyl)-2,9-dimethyl-1-oxo-1,4,5,8,9,11-hexahydropyrido[4',3':3,4]pyrazolo[5,1-d][1,2,5]oxadiazepine-10(2H)-carboxamide | B |
| 126_D2 | (4R*,9R)-4-42,2-difluoroethoxy)methyl)-N-(4-fluoro-3-(trifluoromethyl)phenyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 127_D1 | (4S*,9R)-N-(5-chloro-2,4-difluorophenyl)-4-42,2-difluoroethoxy)methyl)-2,9-dimethyl-1-oxo-1,4,5,8,9,11-hexahydropyrido[4',3':3,4]pyrazolo[5,1-d][1,2,5]oxadiazepine-10(2H)-carboxamide | B |
| 127_D2 | (4R*,9R)-N-(5-chloro-2,4-difluorophenyl)-4-((2,2-difluoroethoxy)methyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 128 | N-(3-chloro-4-fluoro-phenyl)-2-methyl-1-oxo-4-(trifluoromethoxymethyl)-5,8,9,11-tetrahydro-4H-pyrido[2,3]pyrazolo[2,4-d][1,2,5]oxadiazepine-10-carboxamide | A |
| 129 | N-(3-chloro-4-fluorophenyl)-4-(ethylsulfonamidomethyl)-2-methyl-1-oxo-1,4,5,8,9,11-hexahydropyrido[4',3':3,4]pyrazolo[5,1-d][1,2,5]oxadiazepine-10(2H)-carboxamide | A |
| 130 | N-(3-chloro-4-fluorophenyl)-2-methyl-1-oxo-4-(((2,2,2-trifluoroethyl)sulfonamido)methyl)-1,4,5,8,9,11-hexahydropyrido[4',3':3,4]pyrazolo[5,1-d][1,2,5]oxadiazepine-10(2H)-carboxamide | A |
| 131 | N-(3-chloro-4-fluorophenyl)-4-(3,3-difluoroazetidine-1-carbonyl)-2-methyl-1-oxo-1,4,5,8,9,11-hexahydropyrido[4',3':3,4]pyrazolo[5,1-d][1,2,5]oxadiazepine-10(2H)-carboxamide | A |
| 132 | N-(3-chloro-4-fluorophenyl)-4-(3 3-difluoropyrrolidine-1-carbonyl)-2-methyl-1-oxo-1,4,5,8,9,11-hexahydropyrido[4',3':3,4]pyrazolo[5,1-d][1,2,5]oxadiazepine-10(2H)-carboxamide | A |
| 133 | N10-(3-chloro-4-fluorophenyl)-N4,2-dimethyl-1-oxo-N4-(2,2,2-trifluoroethyl)-1,4,5,8,9,11-hexahydropyrido[4',3':3,4]pyrazolo[5,1-d][1,2,5]oxadiazepine-4,10(2H)-dicarboxamide | A |
| 134 | N10-(3-chloro-4-fluorophenyl)-N4-(2,2-difluoroethyl)-N4,2-dimethyl-1-oxo-1,4,5,8,9,11-hexahydropyrido[4',3':3,4]pyrazolo[5,1-d][1,2,5]oxadiazepine-4,10(2H)-dicarboxamide | A |

TABLE 7-continued

Activity in BDNA-assay (EC$_{50}$)

| Compound ID | Compound Name | DNA EC$_{50}$ (nM) |
|---|---|---|
| 135 | N10-(3-chloro-4-fluorophenyl)-2-methyl-1-oxo-N4-(2,2,2-trifluoroethyl)-1,4,5,8,9,11-hexahydropyrido[4',3':3,4]pyrazolo[5,1-d][1,2,5]oxadiazepine-4,10(2H)-dicarboxamide | A |
| 136 | N10-(3-chloro-4-fluorophenyl)-N4-(2,2-difluoroethyl)-2-methyl-1-oxo-1,4,5,8,9,11-hexahydropyrido[4',3':3,4]pyrazolo[5,1-d][1,2,5]oxadiazepine-4,10(2H)-dicarboxamide | A |
| 137_E1 | (S*)-N-(3-chloro-2,4,5-trifluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide | A |
| 138_E1 | (S*)-N-(3-chloro-2,6-difluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide | B |
| 139_E1 | (S*)-N-(5-chloro-2-fluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide | A |
| 140_E1 | (S*)-N-(5-bromo-2,3-difluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide | A |
| 141_E1 | (S*)-N-(5-bromo-2-fluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide | A |
| 142_E1 | (S*)-N-(2,4-difluoro-3-methylphenyl)-4-(hydroxymethyl)-2-methyl-1-oxo-1,4,5,8,9,11-hexahydropyrido[4',3':3,4]pyrazolo[5,1d]-[1,2,5]oxadiazepine-10(2H)-carboxamide | A |
| 143_E1 | (S*)-N-(2,4-difluoro-5-methylphenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide | A |
| 144_E1 | (S*)-4-(hydroxymethyl)-2-methyl-1-oxo-N-(2,4,5-trifluoro-3-methylphenyl)-1,4,5,8,9,11-hexahydropyrido[4',3':3,4]pyrazolo[5,1-d][1,2,5]oxadiazepine-10(2H)-carboxamide | A |
| 145_E1 | (S*)-N-(5-cyano-2-fluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide | D |
| 146_E1 | (S*)-N-(3-cyano-2-fluorophenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide | A |
| 147_E1 | (S*)-N-(2,4-difluoro-5-(trifluoromethyl)phenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide | A |
| 148_E1 | (S*)-N-(2-fluoro-5-(trifluoromethyl)phenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide | B |
| 149_E1 | (S*)-N-(2,4-difluoro-3-(trifluoromethyl)phenyl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide | A |
| 150_E1 | (S*)-N-(2-bromo-5-fluoropyridin-4-yl)-4-(hydroxymethyl)-2-methyl-1-oxo-1,4,5,8,9,11-hexahydropyrido[4',3':3,4]pyrazolo[5,1-d][1,2,5]oxadiazepine-10(2H)-carboxamide | A |
| 151_E1 | (S*)-4-(hydroxymethyl)-2-methyl-1-oxo-N-(2,3,4,5-tetrafluorophenyl)-1,4,5,8,9,11-hexahydropyrido[4',3':3,4]pyrazolo[5,1-d][1,2,5]oxadiazepine-10(2H)-carboxamide | A |
| 152_D1 | (4S*,9R)-N10-(3-chloro-2,4-difluorophenyl)-N4-(2,2-difluoroethyl)-N4,2,9-trimethyl-1-oxo-1,4,5,8,9,11-hexahydropyrido[4',3':3,4]pyrazolo[5,1-d][1,2,5]oxadiazepine-4,10(2H)-dicarboxamide | A |

TABLE 7-continued

Activity in BDNA-assay (EC$_{50}$)

| Compound ID | Compound Name | DNA EC$_{50}$ (nM) |
|---|---|---|
| 152_D2 | (4R*,9R)-N10-(3-chloro-2,4-difluorophenyl)-N4-(2,2-difluoroethyl)-N4,2,9-trimethyl-1-oxo-1,4,5,8,9,11-hexahydropyrido[4',3':3,4]pyrazolo[5,1-d][1,2,5]oxadiazepine-4,10(2H)-dicarboxamide | A |
| 153_D1 | (4S*,9R)-N10-(3-cyano-2,4-difluorophenyl)-N4-(2,2-difluoroethyl)-N4,2,9-trimethyl-1-oxo-1,4,5,8,9,11-hexahydropyrido[4',3':3,4]pyrazolo[5,1-d][1,2,5]oxadiazepine-4,10(2H)-dicarboxamide | B |
| 153_D2 | (4R*,9R)-N10-(3-cyano-2,4-difluorophenyl)-N4-(2,2-difluoroethyl)-N4,2,9-trimethyl-1-oxo-1,4,5,8,9,11-hexahydropyrido[4',3':3,4]pyrazolo[5,1-d][1,2,5]oxadiazepine-4,10(2H)-dicarboxamide | A |
| 154_D1 | (4S*,9R)-N10-(5-chloro-2,4-difluorophenyl)-N4-(2,2-difluoroethyl)-N4,2,9-trimethyl-1-oxo-1,4,5,8,9,11-hexahydropyrido[4',3':3,4]pyrazolo[5,1-d][1,2,5]oxadiazepine-4,10(2H)-dicarboxamide | C |
| 154_D2 | (4R*,9R)-N10-(5-chloro-2,4-difluorophenyl)-N4-(2,2-difluoroethyl)-N4,2,9-trimethyl-1-oxo-1,4,5,8,9,11-hexahydropyrido[4',3':3,4]pyrazolo[5,1-d][1,2,5]oxadiazepine-4,10(2H)-dicarboxamide | A |
| 155_D1 | (4S*,9R)-N10-(3-cyano-4-fluorophenyl)-N4-(2,2-difluoroethyl)-N4,2,9-trimethyl-1-oxo-1,4,5,8,9,11-hexahydropyrido[4',3':3,4]pyrazolo[5,1-d][1,2,5]oxadiazepine-4,10(2H)-dicarboxamide | C |
| 155_D2 | (4R*,9R)-N10-(3-cyano-4-fluorophenyl)-N4-(2,2-difluoroethyl)-N4,2,9-trimethyl-1-oxo-1,4,5,8,9,11-hexahydropyrido[4',3':3,4]pyrazolo[5,1-d][1,2,5]oxadiazepine-4,10(2H)-dicarboxamide | A |
| 156_D1 | (4S*,9R)-N10-(3-cyano-2,4-difluorophenyl)-N4,2,9-trimethyl-1-oxo-1,4,5,8,9,11-hexahydropyrido[4',3':3,4]pyrazolo[5,1-d][1,2,5]oxadiazepine-4,10(2H)-dicarboxamide | D |
| 156_D2 | (4R*,9R)-N10-(3-cyano-2,4-difluorophenyl)-N4,2,9-trimethyl-1-oxo-1,4,5,8,9,11-hexahydropyrido[4',3':3,4]pyrazolo[5,1-d][1,2,5]oxadiazepine-4,10(2H)-dicarboxamide | A |
| 157_D1 | (4S*,9R)-N-[2-fluoro-5-(trifluoromethyl)phenyl]-4-(hydroxymethyl)-2,9-dimethyl-1-oxo-5,8,9,11-tetrahydro-4H-pyrido[2,3]pyrazolo[2,4-d][1,2,5]oxadiazepine-10-carboxamide | A |
| 157_D2 | (4R*,9R)-N-[2-fluoro-5-(trifluoromethyl)phenyl]-4-(hydroxymethyl)-2,9-dimethyl-1-oxo-5,8,9,11-tetrahydro-4H-pyrido[2,3]pyrazolo[2,4-d][1,2,5]oxadiazepine-10-carboxamide | A |
| 158 | N10-(3-chloro-2,4-difluorophenyl)-N4-(2,2-difluoroethyl)-N4,2-dimethyl-1-oxo-1,4,5,8,9,11-hexahydropyrido[4',3':3,4]pyrazolo[5,1-d][1,2,5]oxadiazepine-4,10(2H)-dicarboxamide | A |
| 159 | N10-(5-chloro-2,4-difluorophenyl)-N4-(2,2-difluoroethyl)-N4,2-dimethyl-1-oxo-1,4,5,8,9,11-hexahydropyrido[4',3':3,4]pyrazolo[5,1-d][1,2,5]oxadiazepine-4,10(2H)-dicarboxamide | A |
| 160 | N10-(3-cyano-4-fluorophenyl)-N4-(2,2-difluoroethyl)-N4,2-dimethyl-1-oxo-1,4,5,8,9,11-hexahydropyrido[4',3':3,4]pyrazolo[5,1-d][1,2,5]oxadiazepine-4,10(2H)-dicarboxamide | A |
| 161 | N10-(3-cyano-2,4-difluorophenyl)-N4-(2,2-difluoroethyl)-N4,2-dimethyl-1-oxo-1,4,5,8,9,11-hexahydropyrido[4',3':3,4]pyrazolo[5,1-d][1,2,5]oxadiazepine-4,10(2H)-dicarboxamide | A |
| 162 | 4-(acetamidomethyl)-N-(3-chloro-4-fluorophenyl)-2-methyl-1-oxo-1,4,5,8,9,11-hexahydropyrido[4',3':3,4]pyrazolo[5,1-d][1,2,5]oxadiazepine-10(2H)-carboxamide | A |
| 163 | N-(3-chloro-4-fluorophenyl)-2-methyl-1-oxo-4-((2,2,2-trifluoroacetamido)methyl)-1,4,5,8,9,11-hexahydropyrido[4',3':3,4]pyrazolo[5,1-d][1,2,5]oxadiazepine-10(2H)-carboxamide | A |
| 164 | N-(3-chloro-4-fluorophenyl)-2-methyl-1-oxo-4-(((trifluoromethyl)sulfonamido)methyl)-1,4,5,8,9,11-hexahydropyrido[4',3':3,4]pyrazolo[5,1-d][1,2,5]oxadiazepine-10(2H)-carboxamide | B |

TABLE 7-continued

Activity in BDNA-assay (EC$_{50}$)

| Compound ID | Compound Name | DNA EC$_{50}$ (nM) |
|---|---|---|
| 165 | N-(3-chloro-4-fluorophenyl)-2-methyl-4-(methylsulfonamidomethyl)-1-oxo-1,4,5,8,9,11-hexahydropyrido[4',3':3,4]pyrazolo[5,1-d][1,2,5]oxadiazepine-10(2H)-carboxamide | A |
| 166 | methyl ((10-((3-chloro-4-fluorophenyl)carbamoyl)-2-methyl-1-oxo-1,2,4,5,8,9,10,11-octahydropyrido[4',3':3,4]pyrazolo[5,1-d][1,2,5]oxadiazepin-4-yl)methyl)carbamate | A |
| 167_E1 | (S*)-4-(acetamidomethyl)-N-(3-cyano-2,4-difluorophenyl)-2-methyl-1-oxo-1,4,5,8,9,11-hexahydropyrido[4',3':3,4]pyrazolo[5,1-d][1,2,5]oxadiazepine-10(2H)-carboxamide | A |
| 168_E1 | (S*)-4-(acetamidomethyl)-N-(3-cyano-4-fluorophenyl)-2-methyl-1-oxo-1,4,5,8,9,11-hexahydropyrido[4',3':3,4]pyrazolo[5,1-d][1,2,5]oxadiazepine-10(2H)-carboxamide | A |
| 169_E1 | (S*)-4-(acetamidomethyl)-N-(3-chloro-2,4-difluorophenyl)-2-methyl-1-oxo-1,4,5,8,9,11-hexahydropyrido[4',3':3,4]pyrazolo[5,1-d][1,2,5]oxadiazepine-10(2H)-carboxamide | A |
| 170_E1 | (S*)-4-(acetamidomethyl)-N-(3-bromo-2,4-difluorophenyl)-2-methyl-1-oxo-1,4,5,8,9,11-hexahydropyrido[4',3':3,4]pyrazolo[5,1-d][1,2,5]oxadiazepine-10(2H)-carboxamide | A |
| 171_E1 | (S*)-4-(acetamidomethyl)-N-(3-bromo-4-fluorophenyl)-2-methyl-1-oxo-1,4,5,8,9,11-hexahydropyrido[4',3':3,4]pyrazolo[5,1-d][1,2,5]oxadiazepine-10(2H)-carboxamide | A |
| 172_E1 | (S*)-4-(acetamidomethyl)-N-(2,4-difluoro-3-(trifluoromethyl)phenyl)-2-methyl-1-oxo-1,4,5,8,9,11-hexahydropyrido[4',3':3,4]pyrazolo[5,1-d][1,2,5]oxadiazepine-10(2H)-carboxamide | A |
| 173_E1 | (S*)-4-(acetamidomethyl)-N-(5-chloro-2,4-difluorophenyl)-2-methyl-1-oxo-1,4,5,8,9,11-hexahydropyrido[4',3':3,4]pyrazolo[5,1-d][1,2,5]oxadiazepine-10(2H)-carboxamide | A |
| 174_E1 | (S*)-4-(acetamidomethyl)-N-(5-bromo-2,4-difluorophenyl)-2-methyl-1-oxo-1,4,5,8,9,11-hexahydropyrido[4',3':3,4]pyrazolo[5,1-d][1,2,5]oxadiazepine-10(2H)-carboxamide | A |
| 175_E1 | (S*)-4-(acetamidomethyl)-N-(4-fluoro-3-(trifluoromethyl)phenyl)-2-methyl-1-oxo-1,4,5,8,9,11-hexahydropyrido[4',3':3,4]pyrazolo[5,1-d][1,2,5]oxadiazepine-10(2H)-carboxamide | A |
| 176_D1 | (4S*,9R)-4-(acetamidomethyl)-N-(3-cyano-4-fluorophenyl)-2,9-dimethyl-1-oxo-1,4,5,8,9,11-hexahydropyrido[4',3':3,4]pyrazolo[5,1-d][1,2,5]oxadiazepine-10(2H)-carboxamide | B |
| 176_D2 | (4R*,9R)-4-(acetamidomethyl)-N-(3-cyano-4-fluorophenyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 177_D1 | (4S*,9R)-4-(acetamidomethyl)-N-(4-fluoro-3-(trifluoromethyl)phenyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 177_D2 | (4R*,9R)-4-(acetamidomethyl)-N-(4-fluoro-3-(trifluoromethyl)phenyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 178_D1 | (4S*,9R)-N-(3-cyano-4-fluorophenyl)-2,9-dimethyl-4-(methylsulfonamidomethyl)-1-oxo-1,4,5,8,9,11-hexahydropyrido[4',3':3,4]pyrazolo[5,1-d][1,2,5]oxadiazepine-10(2H)-carboxamide | B |
| 178_D2 | (4R*,9R)-N-(3-cyano-4-fluorophenyl)-2,9-dimethyl-4-(methylsulfonamidomethyl)-1-oxo-1,4,5,8,9,11-hexahydropyrido[4',3':3,4]pyrazolo[5,1-d][1,2,5]oxadiazepine-10(2H)-carboxamide | A |
| 179_D1 | (4S*,9R)-N-(4-fluoro-3-(trifluoromethyl)phenyl)-2,9-dimethyl-4-(methylsulfonamidomethyl)-1-oxo-1,4,5,8,9,11-hexahydropyrido[4',3':3,4]pyrazolo[5,1-d][1,2,5]oxadiazepine-10(2H)-carboxamide | A |

TABLE 7-continued

Activity in BDNA-assay (EC$_{50}$)

| Compound ID | Compound Name | DNA EC$_{50}$ (nM) |
|---|---|---|
| 179_D2 | (4R*,9R)-N-(4-fluoro-3-(trifluoromethyl)phenyl)-2,9-dimethyl-4-(methylsulfonamidomethyl)-1-oxo-1,4,5,8,9,11-hexahydropyrido[4',3':3,4]pyrazolo[5,1-d][1,2,5]oxadiazepine-10(2H)-carboxamide | A |
| 180_D1 | methyl (((4S*,9R)-10-((3-cyano-4-fluorophenyl)carbamoyl)-2,9-dimethyl-1-oxo-1,2,4,5,8,9,10,11-octahydropyrido[4',3':3,4]pyrazolo[5,1-d][1,2,5]oxadiazepin-4-yl)methyl)carbamate | A |
| 180_D2 | methyl (((4R*,9R)-10-((3-cyano-4-fluorophenyl)carbamoyl)-2,9-dimethyl-1-oxo-1,2,4,5,8,9,10,11-octahydropyrido[4',3':3,4]pyrazolo[5,1-d][1,2,5]oxadiazepin-4-yl)methyl)carbamate | A |
| 181_D1 | methyl (((4S*,9R)-10-((4-fluoro-3-(trifluoromethyl)phenyl)carbamoyl)-2,9-dimethyl-1-oxo-1,2,4,5,8,9,10,11-octahydropyrido[4',3':3,4]pyrazolo[5,1-d][1,2,5]oxadiazepin-4-yl)methyl)carbamate | A |
| 181_D2 | methyl (((4R*,9R)-10-((4-fluoro-3-(trifluoromethyl)phenyl)carbamoyl)-2,9-dimethyl-1-oxo-1,2,4,5,8,9,10,11-octahydropyrido[4',3':3,4]pyrazolo[5,1-d][1,2,5]oxadiazepin-4-yl)methyl)carbamate | A |
| 182_D1 | (4S*,9R)-4-(((2,2-difluoroethyl)amino)methyl)-N-(4-fluoro-3-(trifluoromethyl)phenyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 182_D2 | (4R*,9R)-4-(((2,2-difluoroethyl)amino)methyl)-N-(4-fluoro-3-(trifluoromethyl)phenyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 183_D1 | (4S*,9R)-N-(3-cyano-4-fluorophenyl)-4-(((2,2-difluoroethyl)amino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 183_D2 | (4R*,9R)-N-(3-cyano-4-fluorophenyl)-4-(((2,2-difluoroethyl)amino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 184_D1 | (4S*,9R)-N-(3-bromo-4-fluorophenyl)-4-(((2,2-difluoroethyl)amino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 184_D2 | (4R*,9R)-N-(3-bromo-4-fluorophenyl)-4-(((2,2-difluoroethyl)amino)methyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 185_D1 | (4S*,9R)-4-(((2,2-difluoroethyl)amino)methyl)-N-(4-fluoro-3-methylphenyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 185_D2 | (4R*,9R)-44(2,2-difluoroethyl)amino)methyl)-N-(4-fluoro-3-methylphenyl)-2,9-dimethyl-1-oxo-1,4,5,8,9,11-hexahydropyrido[4',3':3,4]pyrazolo[5,1-d][1,2,5]oxadiazepine-10(2H)-carboxamide | A |
| 186_E1 | (S*)-N-(3-cyano-2,4-difluorophenyl)-4-(((2,2-difluoroethyl)amino)methyl)-2-methyl-1-oxo-1,4,5,8,9,11-hexahydropyrido[4',3':3,4]pyrazolo[5,1-d][1,2,5]oxadiazepine-10(2H)-carboxamide | A |
| 187_E1 | (S*)-N-(3-cyano-4-fluorophenyl)-4-(((2,2-difluoroethyl)amino)methyl)-2-methyl-1-oxo-1,4,5,8,9,11-hexahydropyrido[4',3':3,4]pyrazolo[5,1-d][1,2,5]oxadiazepine-10(2H)-carboxamide | A |
| 188_E1 | (S*)-N-(3-chloro-2,4-difluorophenyl)-4-(((2,2-difluoroethyl)amino)methyl)-2-methyl-1-oxo-1,4,5,8,9,11-hexahydropyrido[4',3':3,4]pyrazolo[5,1-d][1,2,5]oxadiazepine-10(2H)-carboxamide | A |
| 189_E1 | (S*)-N-(3-bromo-2,4-difluorophenyl)-4-(((2,2-difluoroethyl)amino)methyl)-2-methyl-1-oxo-1,4,5,8,9,11-hexahydropyrido[4',3':3,4]pyrazolo[5,1-d][1,2,5]oxadiazepine-10(2H)-carboxamide | A |
| 190_E1 | (S*)-N-(3-bromo-4-fluorophenyl)-4-(((2,2-difluoroethyl)amino)methyl)-2-methyl-1-oxo-1,4,5,8,9,11-hexahydropyrido[4',3':3,4]pyrazolo[5,1-d][1,2,5]oxadiazepine-10(2H)-carboxamide | A |

TABLE 7-continued

Activity in BDNA-assay (EC$_{50}$)

| Compound ID | Compound Name | DNA EC$_{50}$ (nM) |
|---|---|---|
| 191_E1 | (S*)-N-(2,4-difluoro-3-(trifluoromethyl)phenyl)-4-(((2,2-difluoroethyl)amino)methyl)-2-methyl-1-oxo-1,4,5,8,9,11-hexahydropyrido[4',3':3,4]pyrazolo[5,1-d][1,2,5]oxadiazepine-10(2H)-carboxamide | A |
| 192_E1 | (S*)-N-(5-chloro-2,4-difluorophenyl)-4-(((2,2-difluoroethyl)amino)methyl)-2-methyl-1-oxo-1,4,5,8,9,11-hexahydropyrido[4',3':3,4]pyrazolo[5,1-d][1,2,5]oxadiazepine-10(2H)-carboxamide | A |
| 193_E1 | (S*)-N-(5-bromo-2,4-difluorophenyl)-4-(((2,2-difluoroethyl)amino)methyl)-2-methyl-1-oxo-1,4,5,8,9,11-hexahydropyrido[4',3':3,4]pyrazolo[5,1-d][1,2,5]oxadiazepine-10(2H)-carboxamide | A |
| 194_E1 | (S*)-44(2,2-difluoroethyl)amino)methyl)-N-(4-fluoro-3-(trifluoromethyl)phenyl)-2-methyl-1-oxo-1,4,5,8,9,11-hexahydropyrido[4',3':3,4]pyrazolo[5,1-d][1,2,5]oxadiazepine-10(2H)-carboxamide | A |
| 195 | N10-(3-cyano-2,4-difluorophenyl)-N4,2-dimethyl-1-oxo-1,4,5,8,9,11-hexahydropyrido[4',3':3,4]pyrazolo[5,1-d][1,2,5]oxadiazepine-4,10(2H)-dicarboxamide | A |
| 196 | N-(3-chloro-4-fluoro-phenyl)-2-methyl-1-oxo-4-[(2-oxopyrrolidin-1-yl)methyl]-5,8,9,11-tetrahydro-4H-pyrido[2,3]pyrazolo[2,4-d][1,2,5]oxadiazepine-10-carboxamide | N/A |
| 197 | N-(3-chloro-4-fluorophenyl)-2-methyl-1-oxo-4-(propionamidomethyl)-1,4,5,8,9,11-hexahydropyrido[4',3':3,4]pyrazolo[5,1-d][1,2,5]oxadiazepine-10(2H)-carboxamide | A |
| 198 | N-(3-chloro-4-fluorophenyl)-4-(cyclopropanecarboxamidomethyl)-2-methyl-1-oxo-1,4,5,8,9,11-hexahydropyrido[4',3':3,4]pyrazolo[5,1-d][1,2,5]oxadiazepine-10(2H)-carboxamide | A |
| 199 | N-(3-chloro-4-fluorophenyl)-2-methyl-1-oxo-4-((3,3,3-trifluoropropanamido)methyl)-1,4,5,8,9,11-hexahydropyrido[4',3':3,4]pyrazolo[5,1-d][1,2,5]oxadiazepine-10(2H)-carboxamide | A |
| 200 | N-(3-chloro-4-fluorophenyl)-4-(isobutyramidomethyl)-2-methyl-1-oxo-1,4,5,8,9,11-hexahydropyrido[4',3':3,4]pyrazolo[5,1-d][1,2,5]oxadiazepine-10(2H)-carboxamide | A |
| 201 | N-(3-chloro-4-fluorophenyl)-2-methyl-1-oxo-4-(pivalamidomethyl)-1,4,5,8,9,11-hexahydropyrido[4',3':3,4]pyrazolo[5,1-d][1,2,5]oxadiazepine-10(2H)-carboxamide | A |
| 202 | ethyl ((10-((3-chloro-4-fluorophenyl)carbamoyl)-2-methyl-1-oxo-1,2,4,5,8,9,10,11-octahydropyrido[4',3':3,4]pyrazolo[5,1-d][1,2,5]oxadiazepin-4-yl)methyl)carbamate | A |
| 203 | cyclopropyl ((1043-chloro-4-fluorophenyl)carbamoyl)-2-methyl-1-oxo-1,2,4,5,8,9,10,11-octahydropyrido[4',3':3,4]pyrazolo[5,1-d][1,2,5]oxadiazepin-4-yl)methyl)carbamate | A |
| 204 | N-(3-chloro-4-fluorophenyl)-4-((3,3-dimethylureido)methyl)-2-methyl-1-oxo-1,4,5,8,9,11-hexahydropyrido[4',3':3,4]pyrazolo[5,1-d][1,2,5]oxadiazepine-10(2H)-carboxamide | A |
| 205 | N-(3-chloro-4-fluorophenyl)-4-((2-cyanoacetamido)methyl)-2-methyl-1-oxo-1,4,5,8,9,11-hexahydropyrido[4',3':3,4]pyrazolo[5,1-d][1,2,5]oxadiazepine-10(2H)-carboxamide | A |
| 206 | N-(3-chloro-4-fluorophenyl)-4-((2-hydroxyacetamido)methyl)-2-methyl-1-oxo-1,4,5,8,9,11-hexahydropyrido[4',3':3,4]pyrazolo[5,1-d][1,2,5]oxadiazepine-10(2H)-carboxamide | A |
| 207 | 2,2,2-trifluoroethyl ((10-((3-chloro-4-fluorophenyl)carbamoyl)-2-methyl-1-oxo-1,2,4,5,8,9,10,11-octahydropyrido[4',3':3,4]pyrazolo[5,1-d][1,2,5]oxadiazepin-4-yl)methyl)carbamate | A |
| 208 | N-(3-chloro-4-fluorophenyl)-4-(ethylsulfonamidomethyl)-2-methyl-1-oxo-1,4,5,8,9,11-hexahydropyrido[4',3':3,4]pyrazolo[5,1-d][1,2,5]oxadiazepine-10(2H)-carboxamide | A |
| 209 | N-(3-chloro-4-fluoro-phenyl)-4-(hydroxymethyl)-2-methyl-1-oxo-4,5,8,9,10,11-hexahydro-[1,2,5]oxadiazepino[5,4-b+indazole-10-carboxamide | C |

TABLE 7-continued

Activity in BDNA-assay (EC$_{50}$)

| Compound ID | Compound Name | DNA EC$_{50}$ (nM) |
|---|---|---|
| 210 | (4S*,9R)-N-(3-cyano-4-fluorophenyl)-2,9-dimethyl-1-oxo-442,2,2-trifluoroethoxy)methyl)-1,4,5,8,9,11-hexahydropyrido[4',3':3,4]pyrazolo[5,1-d][1,2,5]oxadiazepine-10(2H)-carboxamide | A |
| 211 | (S*)-N-(3-cyano-4-fluorophenyl)-442,2-difluoroethoxy)methyl)-2-methyl-1-oxo-1,4,5,8,9,11-hexahydropyrido[4',3':3,4]pyrazolo[5,1-d][1,2,5]oxadiazepine-10(2H)-carboxamide | A |
| 212 | (S*)-4((2,2-difluoroethoxy)methyl)-N-(4-fluoro-3-(trifluoromethyl)phenyl)-2-methyl-1-oxo-1,4,5,8,9,11-hexahydropyrido[4',3':3,4]pyrazolo[5,1-d][1,2,5]oxadiazepine-10(2H)-carboxamide | A |
| 213 | (R)-N-(3-cyano-4-fluorophenyl)-2,4,4,9-tetramethyl-1-oxo-1,4,5,8,9,11-hexahydropyrido[4',3':3,4]pyrazolo[5,1-d][1,2,5]oxadiazepine-10(2H)-carboxamide | A |
| 214 | (R)-N-(4-fluoro-3-(trifluoromethyl)phenyl)-2,4,4,9-tetramethyl-1-oxo-1,4,5,8,9,11-hexahydropyrido[4',3':3,4]pyrazolo[5,1-d][1,2,5]oxadiazepine-10(2H)-carboxamide | A |
| 216 | N-(3-chloro-4-fluorophenyl)-2-methyl-1-oxo-1,2,3,4,5,8,9,11-octahydro-10H-pyrido[4',3':3,4]pyrazolo[5,1-d][1,2,5]triazepine-10-carboxamide | B |
| 217 | N-(3-chloro-4-fluorophenyl)-2,3-dimethyl-1-oxo-1,2,3,4,5,8,9,11-octahydro-10H-pyrido[4',3':3,4]pyrazolo[5,1-d][1,2,5]triazepine-10-carboxamide | A |
| 218 | (R)-3-allyl-N-(3-cyano-4-fluorophenyl)-2,9-dimethyl-1-oxo-1,2,3,4,5,8,9,11-octahydro-10H-pyrido[4',3':3,4]pyrazolo[5,1-d][1,2,5]triazepine-10-carboxamide | A |
| 219 | (R)-N-(3-cyano-4-fluorophenyl)-3-(2,2-difluoroethyl)-2,9-dimethyl-1-oxo-1,2,3,4,5,8,9,11-octahydro-10H-pyrido[4',3':3,4]pyrazolo[5,1-d][1,2,5]triazepine-10-carboxamide | A |
| 220 | (R)-N-(3-cyano-4-fluorophenyl)-3-(2-hydroxyethyl)-2,9-dimethyl-1-oxo-1,2,3,4,5,8,9,11-octahydro-10H-pyrido[4',3':3,4]pyrazolo[5,1-d][1,2,5]triazepine-10-carboxamide | B |
| 221 | (R)-N-(3-cyano-4-fluorophenyl)-2,9-dimethyl-1-oxo-3-propyl-1,2,3,4,5,8,9,11-octahydro-10H-pyrido[4',3':3,4]pyrazolo[5,1-d][1,2,5]triazepine-10-carboxamide | A |
| 222 | (R)-N-(3-cyano-4-fluorophenyl)-3-(3-hydroxypropyl)-2,9-dimethyl-1-oxo-1,2,3,4,5,8,9,11-octahydro-10H-pyrido[4',3':3,4]pyrazolo[5,1-d][1,2,5]triazepine-10-carboxamide | B |
| 223 | (9R)-N-(3-cyano-4-fluorophenyl)-3-(2-hydroxypropyl)-2,9-dimethyl-1-oxo-1,2,3,4,5,8,9,11-octahydro-10H-pyrido[4',3':3,4]pyrazolo[5,1-d][1,2,5]triazepine-10-carboxamide | B |
| 224 | (R)-N-(3-cyano-4-fluorophenyl)-2,3,9-trimethyl-1-oxo-1,2,3,4,5,8,9,11-octahydro-10H-pyrido[4',3':3,4]pyrazolo[5,1-d][1,2,5]triazepine-10-carboxamide | A |
| 225 | (R)-N-(4-fluoro-3-(trifluoromethyl)phenyl)-2,3,9-trimethyl-1-oxo-1,2,3,4,5,8,9,11-octahydro-10H-pyrido[4',3':3,4]pyrazolo[5,1-d][1,2,5]triazepine-10-carboxamide | A |
| 226 | N-(3-chloro-4-fluorophenyl)-4-hydroxy-2-methyl-1-oxo-4-(trifluoromethyl)-1,2,3,4,5,8,9,11-octahydro-10H-pyrido[4',3':3,4]pyrazolo[5,1-d][1,2,5]triazepine-10-carboxamide | D |
| 227 | N-(3-chloro-4-fluorophenyl)-4-(hydroxymethyl)-2-methyl-1-oxo-1,2,5,8,9,11-hexahydro-10H-pyrido[4',3':3,4]pyrazolo[5,1-d][1,2,5]triazepine-10-carboxamide | A |
| 228 | N-(3-cyano-4-fluorophenyl)-4-(hydroxymethyl)-2-methyl-1-oxo-1,2,5,8,9,11-hexahydro-10H-pyrido[4',3':3,4]pyrazolo[5,1-d][1,2,5]triazepine-10-carboxamide | A |
| 229 | N-(3-chloro-4-fluorophenyl)-4-(1-hydroxypropyl)-2-methyl-1-oxo-1,2,5,8,9,11-hexahydro-10H-pyrido[4',3':3,4]pyrazolo[5,1-d][1,2,5]triazepine-10-carboxamide | B |

TABLE 7-continued

Activity in BDNA-assay ($EC_{50}$)

| Compound ID | Compound Name | DNA $EC_{50}$ (nM) |
|---|---|---|
| 230 | N-(3-chloro-4-fluorophenyl)-4-(1-hydroxyethyl)-2-methyl-1-oxo-1,2,5,8,9,11-hexahydro-10H-pyrido[4',3':3,4]pyrazolo[5,1-d][1,2,5]triazepine-10-carboxamide | A |
| 231 | N-(3-chloro-4-fluorophenyl)-4-(cyclopropyl(hydroxy)methyl)-2-methyl-1-oxo-1,2,5,8,9,11-hexahydro-10H-pyrido[4',3':3,4]pyrazolo[5,1-d][1,2,5]triazepine-10-carboxamide | B |
| 232 | N-(3-chloro-4-fluorophenyl)-2,4-dimethyl-1-oxo-1,2,5,8,9,11-hexahydro-10H-pyrido[4',3':3,4]pyrazolo[5,1-d][1,2,5]triazepine-10-carboxamide | A |
| 233 | (R)-N-(3-cyano-4-fluorophenyl)-4-(hydroxymethyl)-2,9-dimethyl-1-oxo-1,2,5,8,9,11-hexahydro-10H-pyrido[4',3':3,4]pyrazolo[5,1-d][1,2,5]triazepine-10-carboxamide | A |
| 234 | (R)-N-(3-bromo-4-fluorophenyl)-4-(hydroxymethyl)-2,9-dimethyl-1-oxo-1,2,5,8,9,11-hexahydro-10H-pyrido[4',3':3,4]pyrazolo[5,1-d][1,2,5]triazepine-10-carboxamide | A |
| 235 | (R)-N-(3-chloro-4-fluorophenyl)-4-(hydroxymethyl)-2,9-dimethyl-1-oxo-1,2,5,8,9,11-hexahydro-10H-pyrido[4',3':3,4]pyrazolo[5,1-d][1,2,5]triazepine-10-carboxamide | A |
| 236 | (R)-N-(3-bromo-4-fluorophenyl)-4-((2,2-difluoroethoxy)methyl)-2,9-dimethyl-1-oxo-1,2,5,8,9,11-hexahydro-10H-pyrido[4',3':3,4]pyrazolo[5,1-d][1,2,5]triazepine-10-carboxamide | A |
| 237 | (R)-N-(3-cyano-4-fluorophenyl)-4-((2,2-difluoroethoxy)methyl)-2,9-dimethyl-1-oxo-1,2,5,8,9,11-hexahydro-10H-pyrido[4',3':3,4]pyrazolo[5,1-d][1,2,5]triazepine-10-carboxamide | A |
| 238 | (R)-4-((2,2-difluoroethoxy)methyl)-N-(4-fluoro-3-(trifluoromethyl)phenyl)-2,9-dimethyl-1-oxo-1,2,5,8,9,11-hexahydro-10H-pyrido[4',3':3,4]pyrazolo[5,1-d][1,2,5]triazepine-10-carboxamide | B |

*Pure but unknown enantiomer or diastereomer.

Example 3: Crystalline Form of Intermediate 18 Analogue

The crystalline form compound 215, which is the iodobenzoic acid analogue of Intermediate 18, is described herein.

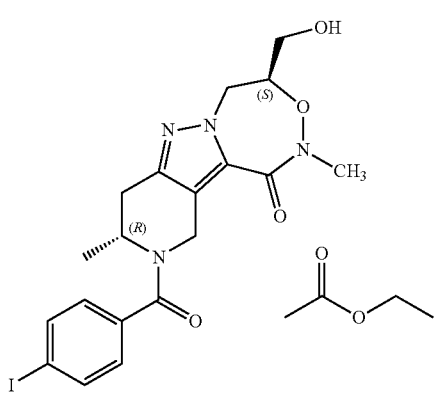

The X-ray crystal structure is shown in FIG. 1. Table 8 also shows crystal data and structure refinement for this intermediate.

TABLE 8

| Crystal data and structure refinement. | |
|---|---|
| Empirical formula | C23 H29 I N4 O6 |
| Formula weight | 584.40 |
| Temperature | 173(2) K |
| Wavelength | 1.54178 Å |
| Crystal system, space group | Monoclinic, P 21 |
| Unit cell dimensions | a = 5.2409(7) Å alpha = 90 deg. |
| | b = 19.141(2) Å beta = 99.804(6) deg. |
| | c = 12.9592(15) Å gamma = 90 deg. |
| Volume | 1281.0(3) Å^3 |
| Z, Calculated density | 2, 1.515 Mg/m^3 |
| Absorption coefficient | 10.196 mm^-1 |
| F(000) | 592 |
| Crystal size | 0.25 × 0.10 × 0.08 mm |
| Theta range for data collection | 3.46 to 67.23 deg. |
| Limiting indices | −5 <= h <= 6, −22 <= k <= 22, −15 <= l <= 15 |
| Reflections collected/unique | 9564/4208 [R(int) = 0.0479] |
| Completeness to theta = 67.23 | 97.4% |
| Absorption correction | Semi-empirical from equivalents |
| Max. and min. transmission | 0.3182 and 0.1437 |
| Refinement method | Full-matrix least-squares on F^2 |
| Data/restraints/parameters | 4208/1/311 |
| Goodness-of-fit on F^2 | 1.087 |
| Final R indices [I > 2sigma(I)] | R1 = 0.0456, wR2 = 0.1152 |
| R indices (all data) | R1 = 0.0523, wR2 = 0.1222 |
| Absolute structure parameter | 0.078(9) |
| Largest diff. peak and hole | 0.931 and −0.569 e.Å^−3 |

Table 9 also shows atomic coordinates (×10⁴) and equivalent isotropic displacement parameters (A²×10³) for the intermediate.

TABLE 9

Atomic coordinates and equivalent isotropic displacement parameters.

| | x | y | z | U(eq) |
|---|---|---|---|---|
| I(1) | 2937(1) | 5453(1) | −515(1) | 50(1) |
| O(1) | 8677(10) | 4897(2) | 4622(4) | 48(1) |
| O(2) | 8496(10) | 3521(2) | 6400(4) | 46(1) |
| O(3) | 12572(11) | 2866(3) | 7830(5) | 57(1) |
| O(4) | −1079(9) | 6970(2) | 3889(4) | 46(1) |
| N(1) | 6070(10) | 4702(3) | 7026(4) | 37(1) |
| N(2) | 4327(11) | 5136(3) | 7358(4) | 40(1) |
| N(3) | 2310(10) | 6353(3) | 4757(4) | 38(1) |
| N(4) | 9283(13) | 3932(3) | 5604(5) | 49(1) |
| C(1) | 9483(14) | 3805(4) | 7432(6) | 46(2) |
| C(2) | 7211(14) | 4172(3) | 7782(5) | 43(1) |
| C(3) | 3569(11) | 5571(3) | 6568(4) | 35(1) |
| C(4) | 1694(12) | 6154(3) | 6567(5) | 39(1) |
| C(5) | 2121(14) | 6704(3) | 5762(5) | 40(1) |
| C(6) | 4451(13) | 5851(3) | 4740(5) | 40(1) |
| C(7) | 4851(9) | 5429(4) | 5724(4) | 34(1) |
| C(8) | 6436(12) | 4862(3) | 6034(5) | 35(1) |
| C(9) | 8225(13) | 4557(3) | 5371(5) | 37(1) |
| C(10) | 10442(15) | 3215(4) | 8132(6) | 50(2) |
| C(11) | 11166(16) | 3614(4) | 5079(6) | 52(2) |
| C(12) | 712(12) | 6552(3) | 3879(5) | 36(1) |
| C(13) | 1240(12) | 6265(3) | 2862(5) | 35(1) |
| C(14) | 3170(15) | 6560(4) | 2406(6) | 49(2) |
| C(15) | 3618(15) | 6325(4) | 1444(6) | 50(2) |
| C(16) | 2130(14) | 5808(4) | 930(5) | 44(2) |
| C(17) | 236(14) | 5506(6) | 1390(5) | 51(2) |
| C(18) | −282(15) | 5735(4) | 2335(6) | 49(2) |
| C(19) | 4496(15) | 7147(4) | 6121(7) | 54(2) |
| O(1') | −1840(30) | 3792(6) | 473(10) | 152(4) |
| O(2') | −3660(40) | 3365(8) | 1631(11) | 175(6) |
| C(1') | −640(100) | 2470(14) | 770(30) | 340(30) |
| C(2') | −2150(90) | 3320(20) | 969(15) | 340(30) |
| C(3') | −4410(30) | 4042(6) | 1973(13) | 110(4) |
| C(4') | −5960(40) | 3988(9) | 2697(16) | 138(6) |

As can be seen, the stereo configuration of the Intermediate 18 analogue is 4S, 9R. Accordingly, the stereo configuration of compounds derived from Intermediate 18 is known.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:
1. A compound of Formula IA:

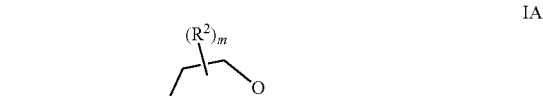

IA or a pharmaceutically acceptable salt thereof, wherein
A is N or C(H);
R¹ is H, $C_1$-$C_6$-alkyl, $C_1$-$C_6$-alkenyl, or $C_1$-$C_6$-alkyl-OH;
R² is, at each occurrence, independently selected from —OH, halo, $C_1$-$C_6$-alkyl, $C_1$-$C_6$-alkenyl, $C_0$-$C_6$-alkyl-$C_3$-$C_6$-cycloalkyl, $C_0$-$C_6$-alkyl-4-5 membered heterocyclyl, $C_0$-$C_6$-alkyl-OR⁶, $C_0$-$C_6$-alkyl-N(R⁷)₂, $C_0$-$C_6$-alkyl-SR⁸, $C_0$-$C_6$-alkyl-S(O)R⁸, $C_0$-$C_6$-alkyl-S(O)₂R⁸, $C_0$-$C_6$-alkyl-C(O)OR⁹, $C_0$-$C_6$-alkyl-OC(O)R⁹, $C_0$-$C_6$-alkyl-OC(O)OR⁹, $C_0$-$C_6$-alkyl-OC(O)N(R⁷)₂, and $C_0$-$C_6$-alkyl-C(O)N(R⁷)₂, and wherein alkyl, cycloalkyl, and heterocyclyl are optionally substituted with 1, 2, or 3 groups, each independently selected from —OH and halo;
R³ is, at each occurrence, independently selected from —OH, halo, $C_1$-$C_6$-alkyl, $C_1$-$C_6$-haloalkyl, —O—$C_1$-$C_6$-alkyl, and $C_1$-$C_6$-alkyl-OH;
R⁴ is selected from $(CR^aR^b)_p$-6-membered heteroaryl, $(CR^aR^b)_p$—$C_6$-$C_{12}$-aryl, $(CR^aR^b)_p$—$C_3$-$C_7$-cycloalkyl, and $C_0$-$C_6$-alkyl-4-5 membered heterocyclyl, wherein the heteroaryl contains one to four heteroatoms, and wherein heteroaryl, aryl, cycloalkyl, and heterocyclyl are optionally substituted with 1, 2, 3, or 4 groups, each independently selected from —OH, halo, —CN, —SF₅, $C_1$-$C_6$-alkyl, $C_1$-$C_6$-haloalkyl, —O—$C_1$-$C_6$-alkyl, and $C_1$-$C_6$-alkyl-OH;
R⁵ is selected from H, $C_1$-$C_6$-alkyl, and $C_1$-$C_6$-alkyl-OH;
R⁶ is selected from H, $C_1$-$C_6$-alkyl, $C_1$-$C_6$-haloalkyl, $C_1$-$C_6$-alkenyl, and $C_0$-$C_6$-alkyl-$C_3$-$C_6$-cycloalkyl;
R⁷ is selected from H, $C_1$-$C_6$-alkyl, $C_1$-$C_6$-haloalkyl, $C_1$-$C_6$-alkyl-OR¹⁰, —C(O)$C_1$-$C_6$-alkyl, —C(O)$C_1$-$C_6$-haloalkyl, —C(O)$C_1$-$C_6$-alkyl-OR¹⁰, —C(O)$C_1$-$C_6$-alkyl-CN, —C(O)$C_3$-$C_7$-cycloalkyl, —C(O)O—$C_1$-$C_6$-alkyl, —C(O)O—$C_1$-$C_6$-haloalkyl, —C(O)O—$C_3$-$C_7$-cycloalkyl, —C(O)N(R¹⁰)₂, —S(O)₂$C_1$-$C_6$-alkyl, —S(O)₂$C_1$-$C_6$-haloalkyl, and —S(O)₂$C_3$-$C_7$-cycloalkyl; or
wherein two R⁷ groups, together with the N to which they are attached, form a 4-5 membered heterocycle, wherein the heterocycle is further independently and optionally substituted with 1 or 2 oxo or halogen substituents;
R⁸ is selected from H and $C_1$-$C_6$-alkyl;
R⁹ is selected from H and $C_1$-$C_6$-alkyl;
R¹⁰ is selected from H and $C_1$-$C_6$-alkyl;
R^a is, at each occurrence, independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH;

$R^b$ is, at each occurrence, independently selected from H and $C_1$-$C_6$-alkyl;

m is 0, 1, 2, 3, or 4;

n is 0, 1, 2, 3, or 4; and p is 0, 1, 2, 3, or 4.

2. The compound of claim 1, wherein A is N.

3. The compound of claim 1, wherein $R^1$ is $C_1$-$C_6$-alkyl, or $C_1$-$C_6$-alkenyl.

4. The compound of claim 1, wherein $R^1$ is —CH$_3$, —CH$_2$CH$_3$, —CH$_2$CH$_2$CH$_3$, —CH$_2$CH=CH$_2$, or -CD$_3$.

5. The compound of claim 1, wherein:

m is 1 or 2; and each $R^2$ is independently selected from the group consisting of $C_1$-$C_6$-alkyl, $C_1$-$C_6$-haloalkyl, $C_0$-$C_6$-alkyl-OR$^6$, $C_1$-$C_6$-alkyl-N(R$^7$)$_2$, $C_0$-$C_6$-alkyl-SR$^8$, $C_0$-$C_6$-alkyl-S(O)R$^8$, $C_0$-$C_6$-alkyl-S(O)$_2$R$^8$, $C_0$-$C_6$-alkyl-C(O)OR$^9$, $C_0$-$C_6$-alkyl-OC(O)R$^9$, $C_0$-$C_6$-alkyl-OC(O)OR$^9$, $C_0$-$C_6$-alkyl-OC(O)N(R$^7$)$_2$, and $C_0$-$C_6$-alkyl-C(O)N(R$^7$)$_2$.

6. The compound of claim 1, wherein n is 0, 1, or 2; and each $R^3$ is independently $C_1$-$C_8$-alkyl.

7. The compound of claim 1, having the structure of Formula II:

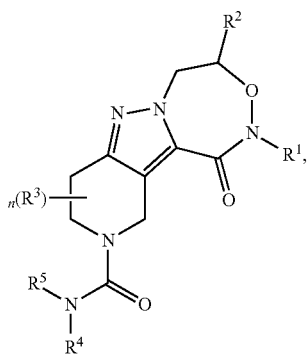

II or a pharmaceutically acceptable salt thereof.

8. The compound of claim 1, wherein the $R^3$ is in the position:

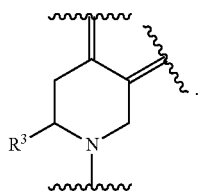

9. The compound of claim 1, wherein $R^2$ is selected from the group consisting of —CH$_3$, —CH$_2$OH, —CH$_2$F, —CH$_2$OCH$_3$, —CH$_2$OCH$_2$CH$_3$, —CH$_2$OCH$_2$CH$_2$CH$_3$, —CH$_2$OCH$_2$-cyclopropyl, —CH$_2$OCH$_2$CHF$_2$, —CH$_2$OCH$_2$CF$_3$, —CH$_2$OCH$_2$CH=CH$_2$, —CH$_2$SCH$_3$, —CH$_2$S(O)CH$_3$, —CH$_2$—S(O)$_2$CH$_3$, —CH$_2$OC(O)OCH$_3$, —CH$_2$OC(O)OCH(CH$_3$)$_2$, —CH$_2$OC(O)OC(CH$_3$)$_3$, —CH$_2$OC(O)OCH$_2$CH$_3$, —CH$_2$OC(O)CH$_3$, —CH$_2$OC(O)C(CH$_3$)$_3$, —C(O)OH, —C(O)OCH$_3$, —CH$_2$OC(O)NH$_2$, —CH$_2$OC(O)N(CH$_3$)$_2$, —C(O)NH$_2$, —C(O)NHCH$_3$, —C(O)N(CH$_3$)$_2$, —CH$_2$N(CH$_3$)$_2$, —CH$_2$OCF$_3$, —C(O)-3,3-difluoroazetidine, —C(O)-3,3-difluoropyrrolidine, —C(O)N(CH$_3$)(CH$_2$CHF$_2$), —C(O)N(CH$_3$)(CH$_2$CF$_3$), —C(O)N(H)(CH$_2$CHF$_2$), —C(O)N(H)(CH$_3$), —C(O)N(H)(CH$_2$CF$_3$), —CH$_2$N(H)(C(O)CH$_3$), —CH$_2$N(H)(C(O)CF$_3$), —CH$_2$N(H)(C(O)OCH$_3$), —CH$_2$N(H)(S(O)$_2$CH$_3$), —CH$_2$N(H)(S(O)$_2$CF$_3$), —CH$_2$-pyrrolidin-2-one, —CH$_2$N(H)(C(O)CH$_2$CH$_3$), —CH$_2$N(H)(C(O)-cyclopropyl), —CH$_2$N(H)(C(O)CH$_2$CF$_3$), —CH$_2$N(H)(C(O)CH(CH$_3$)$_2$), —CH$_2$N(H)(C(O)C(CH$_3$)$_3$), —CH$_2$N(H)(C(O)OCH$_2$CH$_3$), —CH$_2$N(H)(C(O)O-cyclopropyl), —CH$_2$N(H)(C(O)N(CH$_3$)$_2$), —CH$_2$N(H)(C(O)CH$_2$CN), —CH$_2$N(H)(C(O)CH$_2$OH), —CH$_2$N(H)(C(O)OCH$_2$CF$_3$), —CH$_2$N(H)(S(O)$_2$CH$_2$CH$_3$), —CH$_2$N(H)(S(O)$_2$CH$_2$CF$_3$), and —CH$_2$N(H)(S(O)$_2$-cyclopropyl).

10. The compound of claim 1, wherein $R^4$ is 6-membered heteroaryl, $C_6$-aryl, or $C_3$-$C_7$-cycloalkyl, any of which is optionally substituted with 1, 2, or 3 groups, each independently selected from —OH, halo, —CN, —SF$_5$, $C_1$-$C_6$-alkyl, and $C_1$-$C_6$-haloalkyl; and wherein the heteroaryl contains one to four heteroatoms.

11. The compound of claim 1, wherein $R^4$ is phenyl, pyridinyl, or cyclohexyl, wherein $R^4$ is optionally substituted with 1, 2, or 3 groups, each independently selected from —F, —Br, —Cl, —I, —CN, —CH$_3$, —CH$_2$CH$_3$, —CF$_3$, —CHF$_2$, and —SF$_5$.

12. The compound of claim 1, wherein $R^4$ is selected from the group consisting of:

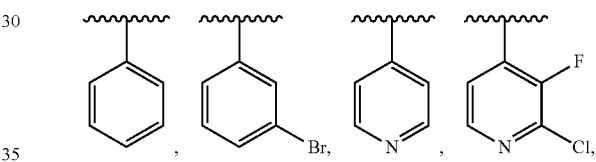

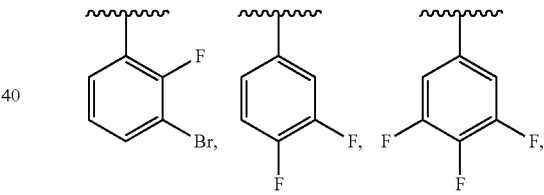

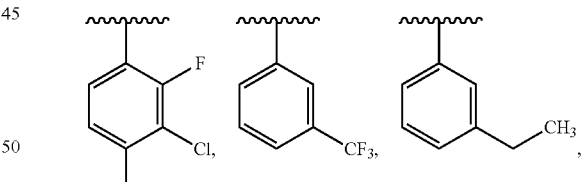

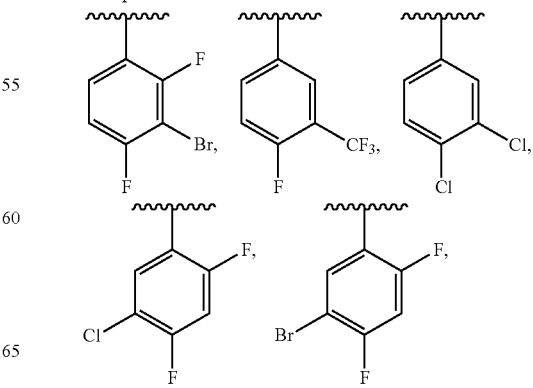

-continued

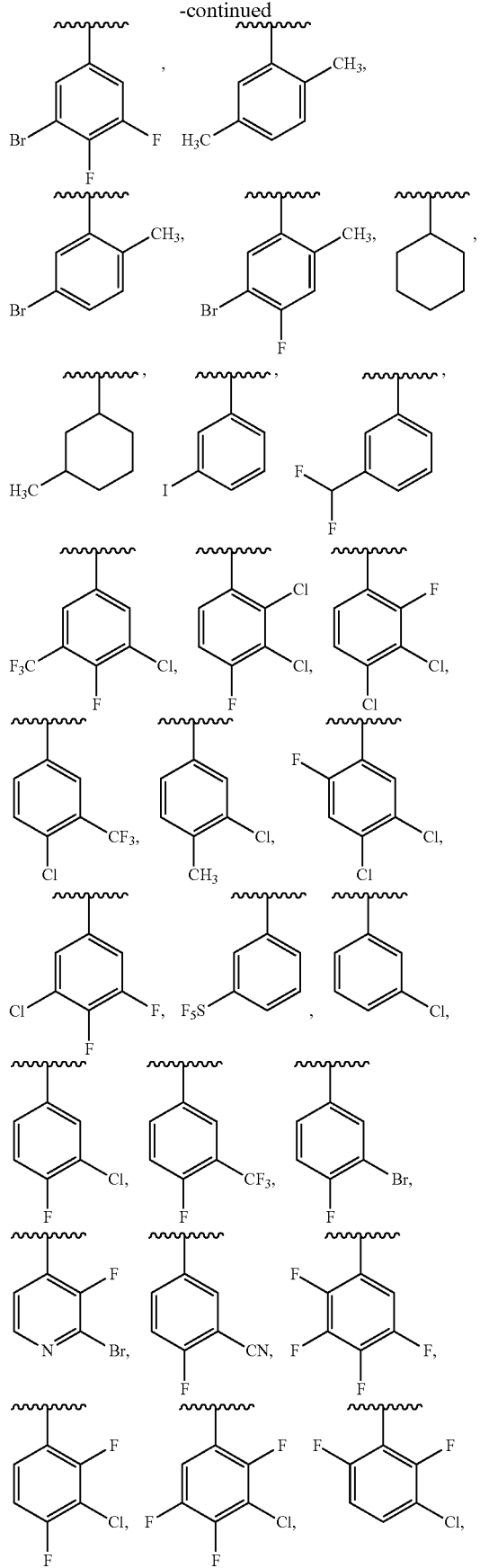
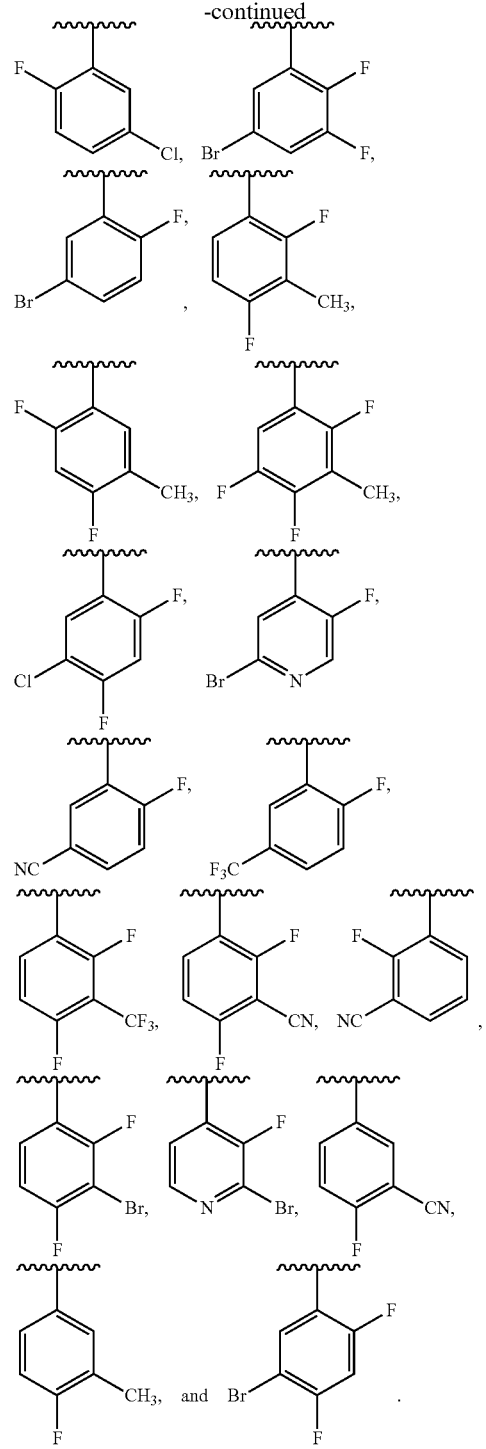

13. The compound of claim 1, wherein $R^5$ is H.
14. The compound of claim 1, wherein
$R^1$ is $C_1$-$C_6$-alkyl;
$R^2$ is, at each occurrence, independently selected from —$CH_3$, —$CH_2OH$, —$CH_2F$, —$CH_2OCH_3$, —$CH_2OCH_2CH_3$, —$CH_2OCH_2CH_2CH_3$, —$CH_2OCH_2$-cyclopropyl, —$CH_2OCH_2CHF_2$, —$CH_2OCH_2CF_3$, —$CH_2OCH_2CH=CH_2$, —$CH_2SCH_3$, —$CH_2S(O)CH_3$, —$CH_2$—$S(O)_2CH_3$, —$CH_2OC(O)OCH_3$, —$CH_2OC(O)OCH(CH_3)_2$, —$CH_2OC(O)OC(CH_3)_3$, —$CH_2OC(O)OCH_2CH_3$,—$CH_2OC(O)CH_3$, —CH$_2$OC(O)C(CH$_3$)$_3$, —C(O)OH, —C(O)OCH$_3$, —CH$_2$OC(O)NH$_2$, —CH$_2$OC(O)N(CH$_3$)$_2$, —C(O)NH$_2$, —C(O)NHCH$_3$, —C(O)N(CH$_3$)$_2$, and —CH$_2$N(CH$_3$)$_2$;

R$^3$ is, at each occurrence, independently C$_1$-C$_6$-alkyl;

R$^4$ is selected from (CR$^a$R$^b$)$_p$-6-membered heteroaryl and (CR$^a$R$^b$)$_p$—C$_6$-C$_{12}$-aryl, wherein the heteroaryl contains one to four heteroatoms, and wherein the heteroaryl or aryl is optionally substituted with 1, 2, 3, or 4 groups, each independently selected from halo, —CN, —SF$_5$, C$_1$-C$_6$-alkyl, and C$_1$-C$_6$-haloalkyl;

R$^5$ is H;

m is 0, 1, or 2;

n is 0, 1, or 2; and p is 0.

15. The compound of claim 1, wherein
R$^1$ is CH$_3$;
R$^2$ is, at each occurrence, independently selected from —CH$_3$, —CH$_2$OH, —CH$_2$F, —CH$_2$OCH$_3$, —CH$_2$OCH$_2$CH$_3$, —CH$_2$OCH$_2$CH$_2$CH$_3$, —CH$_2$OCH$_2$-cyclopropyl, —CH$_2$OCH$_2$CHF$_2$, —CH$_2$OCH$_2$CF$_3$, —CH$_2$OCH$_2$CH=CH$_2$, —CH$_2$SCH$_3$, —CH$_2$S(O)CH$_3$, —CH$_2$—S(O)$_2$CH$_3$, —CH$_2$OC(O)OCH$_3$, —CH$_2$OC(O)OCH(CH$_3$)$_2$, —CH$_2$OC(O)OCH$_2$CH$_3$, —CH$_2$OC(O)CH$_3$, —CH$_2$OC(O)C(CH$_3$)$_3$, —C(O)OH, —C(O)OCH$_3$, —CH$_2$OC(O)NH$_2$, —CH$_2$OC(O)N(CH$_3$)$_2$, —C(O)NH$_2$, —C(O)NHCH$_3$, —C(O)N(CH$_3$)$_2$, and —CH$_2$N(CH$_3$)$_2$;
R$^3$ is CH$_3$;
R$^4$ is phenyl, pyridinyl, or cyclohexyl, each optionally substituted with 1, 2, or 3 substituents, each independently selected from the group consisting of —F, —Br, —Cl, —CN, —CH$_3$, and —CF$_3$;
R$^5$ is H;
m is 1;
n is 0 or 1; and
p is 0.

16. The compound of claim 1, wherein n is 1 and R$^3$ is methyl.

17. The compound of claim 1, wherein R$^4$ is

[structure: phenyl with Cl and F substituents]

18. A compound of Formula III:

[structure III]

or a pharmaceutically acceptable salt thereof, wherein
----- is a single or double bond;

X is N—R$^c$;

R$^1$ is H, C$_1$-C$_6$-alkyl, C$_1$-C$_6$-alkenyl, or C$_1$-C$_6$-alkyl-OH;

R$^2$ is, at each occurrence, independently selected from —OH, halo, C$_1$-C$_6$-alkyl, C$_1$-C$_6$-alkenyl, C$_0$-C$_6$-alkyl-C$_3$-C$_6$-cycloalkyl, C$_0$-C$_6$-alkyl-4-5 membered heterocyclyl, C$_0$-C$_6$-alkyl-OR$^6$, C$_0$-C$_6$-alkyl-N(R$^7$)$_2$, C$_0$-C$_6$-alkyl-SR$^8$, C$_0$-C$_6$-alkyl-S(O)R$^8$, C$_0$-C$_6$-alkyl-S(O)$_2$R$^8$, C$_0$-C$_6$-alkyl-C(O)OR$^9$, C$_0$-C$_6$-alkyl-OC(O)R$^9$, C$_0$-C$_6$-alkyl-OC(O)OR$^9$, C$_0$-C$_6$-alkyl-OC(O)N(R$^7$)$_2$, and C$_0$-C$_6$-alkyl-C(O)N(R$^7$)$_2$, and wherein alkyl, cycloalkyl, and heterocyclyl are optionally substituted with 1, 2, or 3 groups, each independently selected from —OH and halo;

R$^3$ is, at each occurrence, independently selected from —OH, halo, C$_1$-C$_6$-alkyl, C$_1$-C$_6$-haloalkyl, —O—C$_1$-C$_6$-alkyl, and C$_1$-C$_6$-alkyl-OH;

R$^4$ is selected from (CR$^a$R$^b$)$_p$-6-membered heteroaryl, (CR$^a$R$^b$)$_p$—C$_6$-C$_{12}$-aryl, (CR$^a$R$^b$)$_p$—C$_3$-C$_7$-cycloalkyl, and C$_0$-C$_6$-alkyl-4-5 membered heterocyclyl, wherein the heteroaryl contains one to four heteroatoms, and wherein heteroaryl, aryl, cycloalkyl, and heterocyclyl are optionally substituted with 1, 2, 3, or 4 groups, each independently selected from —OH, halo, —CN, —SF$_5$, C$_1$-C$_6$-alkyl, C$_1$-C$_6$-haloalkyl, —O—C$_1$-C$_6$-alkyl, and C$_1$-C$_6$-alkyl-OH;

R$^5$ is selected from H, C$_1$-C$_6$-alkyl, and C$_1$-C$_6$-alkyl-OH;

R$^6$ is selected from H, C$_1$-C$_6$-alkyl, C$_1$-C$_6$-haloalkyl, C$_1$-C$_6$-alkenyl, and C$_0$-C$_6$-alkyl-C$_3$-C$_6$-cycloalkyl;

R$^7$ is selected from H, C$_1$-C$_6$-alkyl, C$_1$-C$_6$-haloalkyl, C$_1$-C$_6$-alkyl-OR$^{10}$, —C(O)C$_1$-C$_6$-alkyl, —C(O)C$_1$-C$_6$-haloalkyl, —C(O)C$_1$-C$_6$-alkyl-OR$^{10}$, —C(O)C$_1$-C$_6$-alkyl-CN, —C(O)C$_3$-C$_7$-cycloalkyl, —C(O)O—C$_1$-C$_6$-alkyl, —C(O)O—C$_1$-C$_6$-haloalkyl, —C(O)O—C$_3$-C$_7$-cycloalkyl, —C(O)N(R$^{10}$)$_2$, —S(O)$_2$C$_1$-C$_6$-alkyl, —S(O)$_2$C$_1$-C$_6$-haloalkyl, and —S(O)$_2$C$_3$-C$_7$-cycloalkyl;

or wherein two R$^7$ groups together with the N to which they are attached form a 4-5 membered heterocycle, and wherein the heterocycle is further independently and optionally substituted with 1 or 2 oxo or halogen substituents;

R$^8$ is selected from H and C$_1$-C$_6$-alkyl;

R$^9$ is selected from H and C$_1$-C$_6$-alkyl;

R$^{10}$ is selected from H and C$_1$-C$_6$-alkyl;

R$^a$ is, at each occurrence, independently selected from H, —OH, halo, C$_1$-C$_6$-alkyl, C$_1$-C$_6$-haloalkyl, —O—C$_1$-C$_6$-alkyl, and C$_1$-C$_6$-alkyl-OH;

R$^b$ is, at each occurrence, independently selected from H and C$_1$-C$_6$-alkyl;

R$^c$ is absent, H, C$_1$-C$_6$-alkyl, C$_1$-C$_6$-alkenyl, C$_1$-C$_6$-haloalkyl, or C$_1$-C$_6$-alkyl-OH;

m is 0, 1, 2, 3, or 4;

n is 0, 1, 2, 3, or 4; and p is 0, 1, 2, 3, or 4.

19. The compound of claim 18, wherein n is 0, 1, or 2; and each R$^3$ is independently C$_1$-C$_6$-alkyl.

20. The compound of claim 18, wherein R$^4$ is phenyl, pyridinyl, or cyclohexyl, wherein R$^4$ is optionally substituted with 1, 2, or 3 groups, each independently selected from —F, —Br, —Cl, —I, —CN, —CH$_3$, —CH$_2$CH$_3$, —CF$_3$, —CHF$_2$, and —SF$_5$.

21. The compound of claim 18, wherein
R¹ is $CH_3$;
R² is selected from the group consisting of: H, $C_{1-4}$haloalkyl, OH, $C_{1-4}$alkyl, $CH_2OH$, $CH(OH)CH_3$, $CH(OH)CH_2CH_3$, $CH(OH)$cyclopropyl, and $CH_2OCH_2CHF_2$;
R³ is H or $CH_3$;
R⁴ is selected from

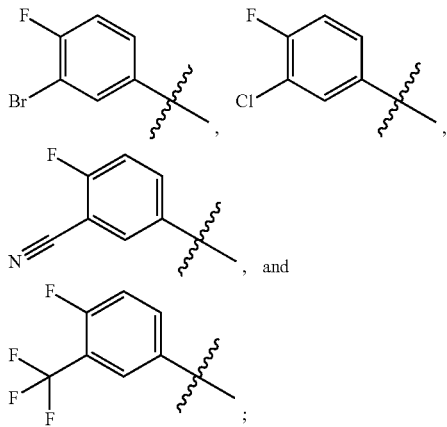

R⁵ is H;
$R^c$ is absent, H, $C_{1-4}$alkyl, $CH_2CH=CH_2$, $CH_3CHF_2$, $CH_2CH_2OH$, $CH_2CH_2CH_2OH$, or $CH_2CH(OH)CH_3$;
m is 0, 1, or 2; and
n is 0 or 1.

22. A pharmaceutical composition comprising a compound of claim 1, or a pharmaceutically acceptable salt thereof, together with a pharmaceutically acceptable carrier.

23. A method of treating an HBV infection in an individual in need thereof, comprising administering to the individual a therapeutically effective amount of a compound of claim 1.

24. The method of claim 23, further comprising administering to the individual at least one additional therapeutic agent selected from the group consisting of an HBV polymerase inhibitor, immunomodulatory agents, interferon, viral entry inhibitor, viral maturation inhibitor, capsid assembly modulator, reverse transcriptase inhibitor, a cyclophilin/TNF inhibitor, a TLR-agonist, an HBV vaccine, and any combination thereof.

* * * * *